United States Patent
Rountree et al.

(10) Patent No.: US 11,807,646 B2
(45) Date of Patent: Nov. 7, 2023

(54) 4-HYDROXYPIPERIDINE DERIVATIVES AND THEIR USE AS INHIBITORS OF UBIQUITIN SPECIFIC PROTEASE 19 (USP19)

(71) Applicant: ALMAC DISCOVERY LIMITED, Craigavon (GB)

(72) Inventors: James Samuel Shane Rountree, Craigavon (GB); Steven Kristopher Whitehead, Craigavon (GB); Adam Piotr Treder, Craigavon (GB); Lauren Emma Proctor, Craigavon (GB); Steven David Shepherd, Craigavon (GB); Frank Burkamp, Craigavon (GB); Joana Rita Castro Costa, Craigavon (GB); Colin O'Dowd, Craigavon (GB); Timothy Harrison, Craigavon (GB)

(73) Assignee: ALMAC DISCOVERY LIMITED, Craigavon (GB)

(*) Notice: Subject to any disclaimer, the term of this patent is extended or adjusted under 35 U.S.C. 154(b) by 47 days.

(21) Appl. No.: 16/965,403

(22) PCT Filed: Jan. 31, 2019

(86) PCT No.: PCT/GB2019/050271
§ 371 (c)(1),
(2) Date: Jul. 28, 2020

(87) PCT Pub. No.: WO2019/150119
PCT Pub. Date: Aug. 8, 2019

(65) Prior Publication Data
US 2021/0070773 A1 Mar. 11, 2021

(30) Foreign Application Priority Data
Jan. 31, 2018 (GB) .................................. 1801562

(51) Int. Cl.
| | |
|---|---|
| C07D 401/06 | (2006.01) |
| C07D 401/14 | (2006.01) |
| C07D 498/04 | (2006.01) |
| C07D 405/14 | (2006.01) |
| C07D 409/14 | (2006.01) |
| C07D 413/06 | (2006.01) |
| C07D 413/14 | (2006.01) |
| C07D 417/14 | (2006.01) |
| C07D 471/04 | (2006.01) |
| C07D 487/04 | (2006.01) |
| C07D 491/048 | (2006.01) |
| C07D 491/107 | (2006.01) |
| C07D 495/04 | (2006.01) |

(52) U.S. Cl.
CPC ......... *C07D 498/04* (2013.01); *C07D 401/06* (2013.01); *C07D 401/14* (2013.01); *C07D 405/14* (2013.01); *C07D 409/14* (2013.01); *C07D 413/06* (2013.01); *C07D 413/14* (2013.01); *C07D 417/14* (2013.01); *C07D 471/04* (2013.01); *C07D 487/04* (2013.01); *C07D 491/048* (2013.01); *C07D 491/107* (2013.01); *C07D 495/04* (2013.01)

(58) Field of Classification Search
CPC ............................ C07D 401/06; C07D 401/14
See application file for complete search history.

(56) References Cited

U.S. PATENT DOCUMENTS

| | | | | |
|---|---|---|---|---|
| 10,766,903 | B2 * | 9/2020 | O'Dowd | ............... C07D 401/14 |
| 11,053,213 | B2 * | 7/2021 | Hewitt | ................. C07D 409/14 |
| 2016/0185785 | A1 | 6/2016 | Ioannidis et al. | |
| 2016/0185786 | A1 | 6/2016 | Ioannidis et al. | |
| 2022/0002264 | A1 * | 1/2022 | Hewitt | .................... A61P 25/16 |

(Continued)

FOREIGN PATENT DOCUMENTS

| | | | |
|---|---|---|---|
| EP | 2565186 A1 | 3/2013 | |
| WO | 1998/03507 A1 | 1/1998 | |
| WO | WO 2006/021656 | 3/2006 | |

(Continued)

OTHER PUBLICATIONS

PubChem CID 131750081, National Center for Biotechnology Information. PubChem Compound Summary for CID 131750081. https://pubchem.ncbi.nlm.nih.gov/compound/131750081. Accessed Dec. 3, 2021, create date Nov. 15, 2017. (Year: 2017).*
Chemical Abstracts Registry No. 2127242-00-4, indexed in the Registry file on Sep. 14, 2017. (Year: 2017).*
Chemical Abstracts Registry No. 2125660-99-1, indexed in the Registry file on Sep. 6, 2017. (Year: 2017).*
Chemical Abstracts Registry No. 2127012-06-8, indexed in the Registry file on Sep. 13, 2017. (Year: 2017).*

(Continued)

*Primary Examiner* — Laura L Stockton
(74) *Attorney, Agent, or Firm* — Brian C. Trinque; Nicole Sassu; Lathrop GPM LLP

(57) ABSTRACT

Inhibitors of ubiquitin specific protease 19 (USP19) of Formula (I) are provided, together with pharmaceutical compositions comprising said inhibitors, and methods of use thereof. The compounds can be used in in the treatment of muscular atrophy, obesity, insulin resistance or type II diabetes or in reducing the loss of muscle mass.

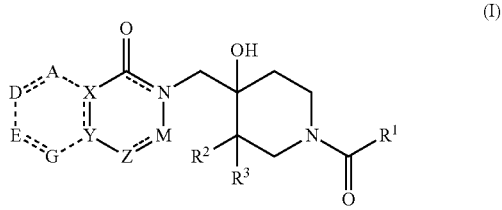

15 Claims, No Drawings

(56) References Cited

U.S. PATENT DOCUMENTS

2022/0033397 A1* 2/2022 Rountree ............. C07D 487/04

FOREIGN PATENT DOCUMENTS

| WO | 2016/126926 A1 | 8/2016 |
| WO | 2016/126929 A1 | 8/2016 |
| WO | 2016/126935 A1 | 8/2016 |
| WO | 2017/212010 A1 | 12/2017 |
| WO | 2017/212012 A1 | 12/2017 |
| WO | 2018/020242 A1 | 2/2018 |
| WO | 2018/073602 A1 | 4/2018 |

OTHER PUBLICATIONS

Chemical Abstracts Registry No. 2127012-74-0, indexed in the Registry file on Sep. 13, 2017. (Year: 2017).*

Chemical Abstracts Registry No. 1263281-24-8, indexed in the Registry file on Feb. 21, 2011. (Year: 2011).*

Gavory G et al: "Discovery and characterization of highly potent and selective allosteric USP7 inhibitors", Nature Chemical Biology, vol. 14, No. 2, Dec. 4, 2017, pp. 118-125, DOI: 10.1038/nchembio. 2528.

Turnbull A P et al: "Molecular basis of USP7 inhibition by selective small-molecule inhibitors", Nature, vol. 550, No. 7677, Oct. 18, 2017, pp. 481-486, DOI: 10.1038/Nature 4451.

O'Dowd C R et al: "Identification and Structure-Guided Development of Pyrimidinone Based USP7 Inhibitors", ACS Medicinal Chemistry Letters, vol. 9, No. 3, Feb. 21, 2018, pp. 238-243, XP055565198, ISSN: 1948-5875, DOI: 10.1021/acsmedchemlett. 7b00512 compounds.

International Preliminary Report on Patentability for PCT/GB2019/050271, dated Aug. 4, 2020, pp. 1-10.

Lamberto et al. "Structure-guided development of a potent and selective noncovalent active site inhibitor of USP7", *Cell Chemical Biology* 24(12):1490-1500, doi: 10.1016/j.chembiol.2017.09.003 (Dec. 2017).

* cited by examiner

4-HYDROXYPIPERIDINE DERIVATIVES AND THEIR USE AS INHIBITORS OF UBIQUITIN SPECIFIC PROTEASE 19 (USP19)

FIELD OF INVENTION

The present invention concerns inhibitors of ubiquitin specific protease 19 (USP19) and methods of use thereof.

BACKGROUND

Over the past decade, protein ubiquitination has emerged as an important post-translational modification with roles in a plethora of cellular processes including amongst others proteolysis, gene expression, DNA repair, immune response, metabolism or cell cycle regulation. Dysregulation of the Ubiquitin Proteasome System (UPS) has also been implicated in the pathogenesis of multiple human diseases including but not limited to cancer (Hoeller D. et al., Nat. Rev. Cancer (2006), 6, 776-788), viral infection (Gao et al., Can. J. Physiol., Pharmacol. (2006), 84, 5-14), metabolic or neurodegenerative disorders (Loosdregt J. et al., Immunity (2013), 39, 259-271; Rubinsztein D., et al., Nature (2006), 443, 780-786) as well as immune and inflammatory-related medical conditions (Wang J. et al., J. Cell Immunol. (2006), 3, 255-261; Corn J. et al., Nat. Struct. & Mol. Biol. (2014), 21, 297-300; Nicholson B. et al., Cell Biochem. Biophys. (2011), 60, 61-68).

The approval and clinical success of the proteasome inhibitors Velcade® (bortezomib) or Kyprolis® (carfilzomib) for the treatment of mantel cell lymphoma (AML) and multiple myeloma (MM) have validated the UPS as a cancer target amenable for pharmacological intervention. Although effective, their clinical utility has however been severely limited due to poor selectivity and acute toxicity issues. By inhibiting the 26S proteasome, the current proteasome inhibitors indiscriminately impair proteolysis in both cancer and normal cells and are characterized by a low therapeutic index. To circumvent this issue, a promising alternative approach may be to target the UPS upstream of the proteasome. Interfering with the ubiquitin (Ub) conjugation/deconjugation machinery, for instance at the level of the Ubiquitin Specific Proteases (USPs), would allow for the development of improved therapeutics with enhanced specificity and reduced toxicity profiles.

USPs are the largest subfamily of the deubiquitinating enzymes (DUBs) family with over 60 family members reported to date (Komander D. et al., Nat. Rev. Mol. (2009), 10, 550-563; Clague M. et al., Physiol. Rev. (2013), 93, 1289-1315). USPs are typically cysteine proteases that catalyze the removal of Ub from specific target substrates thus preventing their induced degradation by the proteasome, or regulating their activation and/or subcellular localization (Colland F. et al., Biochimie (2008), 90, 270-283; Nicholson B. et al., Cell Biochem. Biophys. (2011), 60, 61-68). It is now well established that USPs regulate the stability and activation of numerous proteins involved in the pathogenesis of human diseases including both oncogenes and tumor suppressors. As such, USPs represent an emerging and attractive target class for pharmacological intervention.

Amongst all USPs, USP19 is an important member due to its association with a number of important pathways with implications for pathological conditions including but not restricted to cancer, neurodegeneration and degenerative diseases as well as antiviral immune response. USP19 expresses as multiple isoforms varying in length from 71.09 kDa (isoform 2) to 156.03 kDa (isoform 5) with the canonical sequence (isoform 1) of 145.65 kDa in size (uniprot.org). The cellular localization of USP19 may be cytosolic or bound to the endoplasmic reticulum (Lee J. et al., J. Biol. Chem. (2014), 289, 3510-3507; Lee J. et al., Nat. Cell Biol. (2016), 18, 765-776). Localized to the endoplasmic reticulum, USP19 is a key component of the endoplasmic reticulum-associated degradation (ERAD) pathway (Hassink B. et al., EMBO J. (2009), 10, 755-761; Lee J. et al., J. Biol. Chem. (2014), 289, 3510-3507; Lee J. et al., Nat. Cell Biol. (2016), 18, 765-776). In particular, USP19 is involved in the latter steps of the protein quality-control machinery rescuing ERAD substrates that have been retro-translocated to the cytosol. USP19 has also been demonstrated to regulate the stability of the E3 ligases MARCH6 and HRD1 (Nakamura N. et al., Exp. Cell Res. (2014), 328, 207-216; Harada K. et al., Int. J. Mol. Sci. (2016), 17, E1829). In addition, USP19 has recently been implicated in the stabilization of multiple and potentially important protein substrates. For instance, USP19 interacts with SIAH proteins to rescue HIF1α from degradation under hypoxic conditions (Altun M. et al., J. Biol. Chem. (2012), 287, 1962-1969; Velasco K. et al., Biochem. Biophys. Res. Commun. (2013), 433, 390-395). USP19 also stabilizes the KPC1 ubiquitin ligase which is involved in the regulation of the p27$^{Kip1}$ cyclin-dependent kinase inhibitor (Lu Y. et al., Mol. Cell Biol. (2009), 29, 547-558). Knockout of USP19 by RNAi leads to p27$^{Kip1}$ accumulation and inhibition of cell proliferation (Lu L. et al., PLoS ONE (2011), 6,e15936). USP19 was also found to interact with the inhibitors of apoptosis (IAPs) including c-IAP1 and c-IAP2 (Mei Y. et al., J. Biol. Chem. (2011), 286, 35380-35387). Knockdown of USP19 decreases the total levels of these c-IAPs whilst overexpression increases the levels of both BIRC2/cIAP1 and BIRC3/cIAP2. Knockdown of USP19 also enhances TNFα-induced caspase activation and apoptosis in a BIRC2/c-IAP1 and BIRC3/c-IAP2 dependent manner. In addition to some direct involvement in regulating hypoxia response and ER stress, USP19 has also been implicated recently as a positive regulator of autophagy and negative regulator of type I interferon signaling (IFN, antiviral immune response) by deubiquitinating Beclin-1. USP19 was found to stabilize Beclin-1 at the post-translational level by removing the K11-linked ubiquitin chains of Beclin-1 at Lysine 437 (Jin S. et al., EMBO J. (2016), 35, 866-880). USP19 negatively regulates type I IFN signaling pathway, by blocking RIG-I-MAVS interaction in a Beclin-1 dependent manner. Depletion of either USP19 or Beclin-1 inhibits autophagic flux and promotes type I IFN signaling as well as cellular antiviral immunity (Jin S. et al., EMBO J. (2016), 35, 866-880; Cui J. et al., Autophagy (2016), 12, 1210-1211). Recent findings also indicate USP19 may negatively affect the cellular antiviral type I IFN signaling by regulating the TRAF3 substrate (Gu Z. et al., Future Microbiol. (2017), 12, 767-779). USP19 has also been recently implicated in the Wnt signaling pathway by stabilizing the coreceptor LRP6 (Perrody E. et al., eLife (2016), 5, e19083) and in the DNA repair processes, most particularly chromosomal stability and integrity, by regulating the HDAC1 and HDAC2 proteins (Wu M. et al., Oncotarget (2017), 8, 2197-2208).

In addition to cancer and associated conditions, USP19 has been linked in gene knock out studies to muscle-wasting syndromes and other skeletal muscle atrophy disorders (Wing S., Int. J. Biochem. Cell Biol. (2013), 45, 2130-2135; Wing S. et al., Int. J. Biochem. Cell Biol. (2016), 79, 426-468; Wiles B. et al., Mol. Biol. Cell (2015), 26, 913-923; Combaret L. et al., Am. J. Physiol. Endocrinol. Metab.

(2005), 288, E693-700), each of which is incorporated herein by reference). Muscle wasting associated with conditions such as cachexia is known to impair quality of life and response to therapy, which increase morbidity and mortality of cancer patients. Muscle wasting is also associated with other serious illnesses such as HIV/AIDS, heart failure, rheumatoid arthritis and chronic obstructive pulmonary disease (Wiles B. et al., *Mol. Biol. Cell* (2015), 26, 913-923). Muscle wasting is also a prominent feature of aging.

Beyond the above pathological conditions, USP19 may also have implications in the pathogenesis of degenerative diseases including but not restricted to Parkinson's disease and other prion-like transmission disorders by regulating important substrates such as α-synuclein or polyglutamine-containing proteins, Ataxin3, Huntington (He W. et al., *PLoS ONE* (2016), 11, e0147515; Bieri G. et al., *Neurobiol Dis.* (2018), 109B, 219-225). The regulation of coronin 2A (CORO2A) through the activity of USP19 has been shown to affect the transcriptional repression activity of the retinoic acid receptor (RAR), suggesting that USP19 may also be involved in the regulation of RAR-mediated adipogenesis (Lim K. et al., *Oncotarget* (2016), 7, 34759-34772).

The established and ever growing connections between USP19 and numerous proteins involved in human pathologies indicate that small molecule inhibitors of USP19 may have broad therapeutic applications beneficial to human health. Insofar as is known however, no inhibitors targeting USP19 have been reported and the identification of such inhibitors with drug-like potential therefore remains of prime importance and high priority.

SUMMARY OF INVENTION

In a first aspect is provided a compound of formula (I):

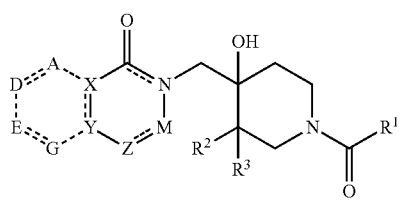

(I)

wherein $R^1$ is optionally substituted C1-C6 alkyl, optionally substituted C4-C10 alkylcycloalkyl, optionally substituted C6-C10 alkylaryl, optionally substituted C5-C8 aryl, optionally substituted C3-C8 heteroaryl, optionally substituted C3-C8 heterocycloalkyl, $NR^aR^b$, $NR^aCH2R^b$, $OR^a$, or $OCH2R^a$, wherein $R^a$ and $R^b$ are independently selected from H, C1-C6 alkyl, CF3, optionally substituted C3-C6 cycloalkyl, optionally substituted C5-C8 aryl, optionally substituted C6-C9 arylalkyl, and optionally substituted C2-C8 heteroaryl, or wherein $R^1$ is $NR^aR^b$ and $R^a$ and $R^b$ together form an optionally substituted C2-C9 heterocycle together with the N to which they are attached;

$R^2$ and $R^3$ are independently selected from H, and C1-C6 alkyl, or together form a C3-C6 cycloalkyl or heterocycloalkyl with the carbon to which they attached;

X is absent, C, $CR^{4a}$, $CR^{4a}R^{4b}$, N, $NR^{4a}$, or C=O, wherein $R^{4a}$ and $R^{4b}$ are independently selected from H, optionally substituted C1-C6 alkyl or halo;

or wherein $R^{4a}$ and $R^{4b}$ together form a C3-C6 cycloalkyl or C3-C6 heterocycloalkyl including the carbon to which they are attached;

Y is C, $CR^5$, $CR^5R^6$, N, $NR^5$, or O, wherein $R^5$ and $R^6$ are independently selected from H, halo, optionally substituted C1-C6 alkyl, optionally substituted C3-C6 cycloalkyl, optionally substituted C5-C8 aryl, optionally substituted C6-C9 arylalkyl, optionally substituted C3-C8 heteroaryl, CH2OH, NR'R", NS(O)R'R", SO2R', COR', C(O)R', C(O)OR', C(O)NR'R", OR', wherein R' and R" are independently selected from H, C1-C6 alkyl, C5-C8 aryl, C6-C9 arylalkyl, and C3-C8 heteroaryl, or wherein $R^5$ and $R^6$ together form a C3-C6 cycloalkyl or C3-C6 heterocycloalkyl including the carbon to which they are attached;

Z is N, $NR^7$, C, $CR^7$, $CR^7R^8$, or C=O, wherein $R^7$ and $R^8$ are independently selected from H, halo, C1-C6 alkyl, C2-C6 alkene, C2-C6 alkyne, C3-C6 cycloalkyl, optionally substituted C3-C6 heterocycloalkyl, C5-C8 aryl, C6-C9 arylalkyl, C3-C8 heteroaryl, CN, $C(O)OR^c$, $CONR^cR^d$, $NR^cR^d$, $NS(O)R^cR^d$, $S(O)(R^c)NR^d$, $SOR^c$, $SO2R^c$, and $SR^c$, wherein $R^c$ and $R^d$ are independently H, C1-C6 alkyl, C5-C6 aryl, C6-C9 arylalkyl, C3-C6 heteroaryl, CN, COOH, or COCH3 or $R^c$ and $R^d$ together form an optionally substituted C3-C7 heterocycle together with the heteroatom to which they are attached;

or wherein $R^7$ and $R^8$ together form a C3-C6 cycloalkyl or C3-C6 heterocycloalkyl including the carbon to which they are attached;

M is absent, C, $CR^{13}$ or $CR^{13}R^{14}$, wherein $R^{13}$ and $R^{14}$ are independently selected from H, and C1-C6 alkyl, or wherein $R^{13}$ and $R^{14}$ together form a C3-C6 cycloalkyl or C3-C6 heterocycloalkyl together with the carbon to which they are attached; and A is $CR^9$, $CHR^9$, N, $NR^9$, S, or O, D is $CR^9$, $CHR^9$, N or $NR^9$, G is absent, $CR^9$, $CHR^9$, or N, wherein $R^9$ is selected from H, halo, C1-C6 alkyl, CF3, and OR*, wherein R* is an optionally substituted C1-C6 alkyl, optionally substituted C1-C6 cycloalkyl or optionally substituted heterocycloalkyl, E is $CR^{10}$, $CHR^{10}$, N, $NR^{10}$, S, or O, wherein $R^{10}$ is selected from H, halo, C1-C6 alkyl, C3-C6 cycloalkyl, C5-C8 aryl, C6-C9 arylalkyl, C4-C8 heteroaryl, $SR^x$, $OR^x$, $NR^xR^y$, and $NS(O)R^xR^y$, $S(O)(R^x)NR^y$, wherein $R^x$ and $R^y$ are independently selected from H, C1-C6 alkyl, CF3, C3-C6 cycloalkyl, C5-C8 aryl, C6-C9 arylalkyl, C4-C8 heteroaryl, COOH, amido, cyano, C2-C6 alkene, C2-C6 alkyne, or wherein $R^x$ and $R^y$ together form an optionally substituted C4-C6 heterocycloalkyl together with the nitrogen to which they are attached;

or A, D, E and G are all absent, and X, Y, Z and M are defined above, and optionally wherein both X and M are absent, or optionally wherein Y and Z together form an optionally substituted C5-C6 aryl or C5-C6 heteroaryl fused ring or Z and M together form an optionally substituted C5-C6 aryl or C5-C6 heteroaryl fused ring;

or a stereoisomer, tautomer, hydrate, N-oxide derivative or pharmaceutically acceptable salt thereof.

In a second aspect is provided a compound according to formula (Ia):

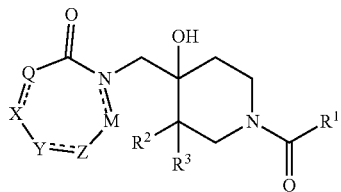

wherein Q is selected from $CR^{11}$, $CR^{11}R^{12}$, $NR^{11}$ or O, where $R^{11}$ and $R^{12}$ are independently selected from H, OH, C1-C6 alkyl, CF3, C3-C6 cycloalkyl, optionally substituted C5-C8 aryl, C4-C8 heteroaryl, or wherein $R^{11}$ and $R^{12}$ together form an optionally substituted C3-C5 carbocycle together with the C to which they are attached, and wherein each of X, Y, Z and M are present and as defined above, wherein the ring QXYZM is aliphatic or aromatic, preferably aliphatic;

and wherein $R^1$, $R^2$, and $R^3$ are as defined above;

or a stereoisomer, tautomer, hydrate, N-oxide derivative or pharmaceutically acceptable salt thereof.

In a third aspect is provided a pharmaceutical composition comprising a compound according to the first or second aspect, or a stereoisomer, tautomer, hydrate, N-oxide derivative or pharmaceutically acceptable salt thereof, and a pharmaceutically acceptable carrier or diluent.

USP19 has been associated with a number of diseases and conditions including (but not limited to) cancer and neoplastic conditions. Knockout of USP19 by RNAi leads to $p27^{Kip1}$ accumulation and inhibition of cell proliferation (Lu Y. et al., *PLoS ONE* (2011), 6, e15936). USP19 was also found to interact with the inhibitors of apoptosis (IAPs) including c-IAP1 and c-IAP2 (Mei Y. et al., *J. Biol. Chem.* (2011), 286, 35380-35387). Knockdown of USP19 decreases the total levels of these c-IAPs whilst overexpression increases the levels of both BIRC2/cIAP1 and BIRC3/cIAP2. Knockdown of USP19 also enhances TNFα-induced caspase activation and apoptosis in a BIRC2/c-IAP1 and BIRC3/c-IAP2 dependent manner. USP19 has also been recently implicated in the Wnt signaling pathway by stabilizing the coreceptor LRP6 (Perrody E. et al., *eLife* (2016), 5, e19083) and in the DNA repair processes, most particularly chromosomal stability and integrity, by regulating the HDAC1 and HDAC2 proteins (Wu M. et al., *Oncotarget* (2017), 8, 2197-2208).

In vivo studies have also demonstrated that mice lacking the USP19 gene (USP19 KO mice) exhibited a decrease in fat mass when fed a high-fat diet (Coyne E. et al., *Diabetologia* (2019), 62, 136-146, which is incorporated herein by reference). USP19 KO mice also exhibited greater glucose tolerance and higher insulin sensitivity when fed a high-fat diet.

USP19 is also implicated in muscular atrophy, muscle-wasting syndromes and other skeletal muscle atrophy disorders (Wing S., *Int. J. Biochem. Cell Biol.* (2013), 45, 2130-2135; Wing S. et al., *Int. J. Biochem. Cell Biol.* (2016), 79, 426-468; Wiles B. et al., *Mol. Biol. Cell* (2015), 26, 913-923; Combaret L. et al., *Am. J. Physiol. Endocrinol. Metab.* (2005), 288, E693-700). This was supported for instance by studies which demonstrated that USP19-silencing induced the expression of myofibrillar proteins and promoted myogenesis (Sundaram P. et al., *Am. J. Physiol. Endocrinol. Metab.* (2009), 297, E1283-90; Ogawa M. et al., *J. Biol. Chem.* (2011), 286, 41455-41465; Ogawa M. et al., *J. Endocrinol.* (2015), 225, 135-145).

Knockout studies have demonstrated that mice lacking the USP19 gene were resistant to muscle wasting in response to both glucocorticoids, a common systemic cause of muscle atrophy, as well as in response to denervation, a model of disuse atrophy (Bedard N. et al., *FASEB J.* (2015), 29, 3889-3898, which is incorporated herein by reference).

The compounds according to the invention are able to selectively inhibit USP19 activity. The compounds of the invention are therefore suitable for use in methods of treatment. Indications suitable for treatment with compounds of the invention include: the treatment and prevention of cancer and neoplastic conditions; immunological and inflammatory conditions for example by promoting antiviral immune response; treatment and prevention of muscular atrophy, for example cachexia and sarcopenia; treatment and prevention of obesity; treatment and prevention of insulin resistance, for example diabetes; treatment and prevention of neurodegenerative diseases including Parkinson's disease and other prion-based disorders.

Therefore, in a further aspect, is provided a compound according to the first or second aspect, or a pharmaceutical composition according to the third aspect, for use in therapy.

In a further aspect, is provided a compound according to the first or second aspect or a pharmaceutical composition according to the third aspect for use in a method of treating or preventing cancer. In certain preferred embodiments the cancer to be treated is breast cancer or neuroblastoma.

In a further aspect is provided a compound according to the first or second aspect or a pharmaceutical composition according to the third aspect for use in a method of treating or preventing muscular atrophy, optionally cachexia or sarcopenia.

In a further aspect is provided a compound according to the first or second aspect or a pharmaceutical composition according to the third aspect for use in a method of treating or preventing obesity.

In a further aspect is provided a compound according to the first or second aspect or a pharmaceutical composition according to the third aspect for use in a method of treating or preventing insulin resistance.

In a further aspect is provided a compound according to the first or second aspect or a pharmaceutical composition according to the third aspect for use in a method of treating or preventing type II diabetes.

In a further aspect is provided a compound according to the first or second aspect or a pharmaceutical composition according to the third aspect for use in a method of treating or preventing Parkinson's Disease.

In a further aspect is provided a method of treating cancer comprising administering to a subject an effective amount of a compound according to the first or second aspect or a pharmaceutical composition according to the third aspect.

In a further aspect is provided a method of treating muscular atrophy comprising administering to a subject an effective amount of a compound according to the first or second aspect or a pharmaceutical composition according to the third aspect.

In a further aspect is provided a method of treating Parkinson's Disease comprising administering to a subject an effective amount of a compound according to the first or second aspect or a pharmaceutical composition according to the third aspect.

The compounds may be used as monotherapy or as combination therapy with radiation and/or additional therapeutic agents.

Other preferred embodiments of the compounds provided herein appear throughout the specification and in particular in the examples. Particularly preferred are those named compounds having greater activity as tested. Compounds having higher activity are more preferred over those having lower activity.

Each aspect or embodiment as defined herein may be combined with any other aspect(s) or embodiment(s) unless clearly indicated to the contrary. In particular any feature indicated as being preferred or advantageous may be combined with any other feature or features indicated as being preferred or advantageous.

DETAILED DESCRIPTION OF THE INVENTION

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedence over any dictionary or extrinsic definition.

As used in the specification and the appended claims, unless specified to the contrary, the following terms have the meaning indicated:

The term "alkyl group" (alone or in combination with another term(s)) means a straight- or branched-chain saturated hydrocarbon substituent typically containing 1 to 15 carbon atoms, such as 1 to 10, 1 to 8, 1 to 6, or 1 to 4 carbon atoms. A "$C_n$ alkyl" group refers to an aliphatic group containing n carbon atoms. For example, a $C_1$-$C_{10}$ alkyl group contains 1, 2, 3, 4, 5, 6, 7, 8, 9 or 10 carbon atoms. Attachment to the alkyl group occurs through a carbon atom. Examples of such substituents include methyl, ethyl, n-propyl, isopropyl, n-butyl, isobutyl, sec-butyl, tert-butyl, pentyl (branched or unbranched), hexyl (branched or unbranched), heptyl (branched or unbranched), octyl (branched or unbranched), nonyl (branched or unbranched), and decyl (branched or unbranched).

The term "alkenyl group" (alone or in combination with another term(s)) means a straight- or branched-chain hydrocarbon substituent containing one or more double bonds and typically 2 to 15 carbon atoms; such as 2 to 10, 2 to 8, 2 to 6 or 2 to 4 carbon atoms. Examples of such substituents include ethenyl (vinyl), 1-propenyl, 3-propenyl, 1,4-pentadienyl, 1,4-butadienyl, 1-butenyl, 2-butenyl, 3-butenyl, pentenyl and hexenyl.

The term "alkynyl group" (alone or in combination with another term(s)) means a straight- or branched-chain hydrocarbon substituent containing one or more triple bonds and typically 2 to 15 carbon atoms; such as 2 to 10, 2 to 8, 2 to 6 or 2 to 4 carbon atoms. Examples of such substituents include ethynyl, 1-propynyl, 3-propynyl, 1-butynyl, 3-butynyl and 4-butynyl.

The term "heteroalkyl group" (alone or in combination with another term(s)) means a straight- or branched-chain saturated hydrocarbyl substituent typically containing 1 to 15 atoms, such as 1 to 10, 1 to 8, 1 to 6, or 1 to 4 atoms, wherein at least one of the atoms is a heteroatom (i.e. oxygen, nitrogen, or sulfur), with the remaining atoms being carbon atoms.

A "$C_n$ heteroalkyl" group refers to an aliphatic group containing n carbon atoms and one or more heteroatoms, for example one heteroatom. For example, a $C_1$-$C_{10}$ heteroalkyl group contains 1, 2, 3, 4, 5, 6, 7, 8, 9 or 10 carbon atoms in addition to one or more heteroatoms, for example one heteroatom. Attachment to the heteroalkyl group occurs through a carbon atom or through a heteroatom.

The term "heteroalkenyl group" (alone or in combination with another term(s)) means a straight- or branched-chain hydrocarbon substituent containing one or more carbon-carbon double bonds and typically 2 to 15 atoms; such as 2 to 10, 2 to 8, 2 to 6 or 2 to 4 atoms, wherein at least one of the atoms is a heteroatom (i.e. oxygen, nitrogen, or sulfur), with the remaining atoms being carbon atoms. A "$C_n$ heteroalkenyl" group refers to an aliphatic group containing n carbon atoms and one or more heteroatoms, for example one heteroatom. For example, a $C_2$-$C_{10}$ heteroalkenyl group contains 2, 3, 4, 5, 6, 7, 8, 9 or 10 carbon atoms in addition to one or more heteroatoms, for example one heteroatom. Attachment to the heteroalkenyl group occurs through a carbon atom or through a heteroatom.

The term "heteroalkynyl group" (alone or in combination with another term(s)) means a straight- or branched-chain hydrocarbon substituent containing one or more carbon-carbon triple bonds and typically 2 to 15 carbon atoms; such as 2 to 10, 2 to 8, 2 to 6 or 2 to 4 carbon atoms, wherein at least one of the atoms is a heteroatom (i.e. oxygen, nitrogen, or sulfur), with the remaining atoms being carbon atoms. A "$C_n$ heteroalkynyl" group refers to an aliphatic group containing n carbon atoms and one or more heteroatoms, for example one heteroatom. For example, a $C_2$-$C_{10}$ heteroalkynyl group contains 1, 2, 3, 4, 5, 6, 7, 8, 9 or 10 carbon atoms in addition to one or more heteroatoms, for example one heteroatom. Attachment to the heteroalkynyl group occurs through a carbon atom or through a heteroatom.

The term "carbocyclyl group" (alone or in combination with another term(s)) means a saturated cyclic (i.e. "cycloalkyl"), partially saturated cyclic (i.e. "cycloalkenyl"), or completely unsaturated (i.e. "aryl") hydrocarbon substituent containing from 3 to 14 carbon ring atoms ("ring atoms" are the atoms bound together to form the ring or rings of a cyclic substituent). A carbocyclyl may be a single-ring (monocyclic) or polycyclic ring structure.

A carbocyclyl may be a single ring structure, which typically contains 3 to 8 ring atoms, more typically 3 to 7 ring atoms, and more typically 5 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, and phenyl. A carbocyclyl may alternatively be polycyclic (i.e. may contain more than one ring). Examples of polycyclic carbocyclyls include bridged, fused, and spirocyclic carbocyclyls. In a spirocyclic carbocyclyl, one atom is common to two different rings. An example of a spirocyclic carbocyclyl is spiropentanyl. In a bridged carbocyclyl, the rings share at least two common non-adjacent atoms. Examples of bridged carbocyclyls include bicyclo[2.2.1]heptanyl, bicyclo[2.2.1]hept-2-enyl, and adamantanyl. In a fused-ring carbocyclyl system, two or more rings may be fused together, such that two rings share one common bond. Examples of two- or three-fused ring carbocyclyls include naphthalenyl, tetrahydronaphthalenyl (tetralinyl), indenyl, indanyl (dihydroindenyl), anthracenyl, phenanthrenyl, and decalinyl.

The term "cycloalkyl group" (alone or in combination with another term(s)) means a saturated cyclic hydrocarbon substituent containing 3 to 14 carbon ring atoms. A cycloalkyl may be a single carbon ring, which typically contains 3 to 8 carbon ring atoms and more typically 3 to 6 ring atoms.

It is understood that attachment to a cycloalkyl group is via a ring atom of the cycloalkyl group. Examples of single-ring cycloalkyls include cyclopropyl, cyclobutyl, cyclopentyl, and cyclohexyl. A cycloalkyl may alternatively be polycyclic or contain more than one ring. Polycyclic cycloalkyls include bridged, fused, and spirocyclic cycloalkyls.

The term "alkylcycloalkyl" refers to a cycloalkyl substituent attached via an alkyl chain. Examples of an alkylcycloalkyl substituent include cyclohexylethane, where the cyclohexane is attached via an ethane linker. Other examples include cyclopropylethane, cyclobutylethane, cyclopentylethane, cycloheptylethane, cyclohexylmethane. In a "$C_n$" alkylcycloalkyl, $C_n$ includes the carbon atoms in the alkyl chain and in the cycloalkyl ring. For example, cyclohexylethane is a C8 alkylcycloalkyl.

The term "aryl group" (alone or in combination with another term(s)) means an aromatic carbocyclyl containing from 5 to 14 carbon ring atoms, optionally 5 to 8, 5 to 7, optionally 5 to 6 carbon ring atoms. A "$C_n$ aryl" group refers to an aromatic group containing n carbon atoms. For example, a $C_6$-$C_{10}$ aryl group contains 6, 7, 8, 9 or 10 carbon atoms. Attachment to the aryl group occurs through a carbon atom. An aryl group may be monocyclic or polycyclic (i.e. may contain more than one ring). In the case of polycyclic aromatic rings, only one ring in the polycyclic system is required to be unsaturated while the remaining ring(s) may be saturated, partially saturated or unsaturated. Attachment to the aryl group occurs through a carbon atom contained in the ring. Examples of aryl groups include phenyl, naphthyl, acridinyl, indenyl, indanyl, and tetrahydronapthyl.

The term "arylalkyl" refers to an aryl substituent attached via an alkyl chain. Examples of an arylalkyl substituent include benzyl and phenylethane/ethylbenzene, where the ethane chain links to a phenyl group to the point of attachment. In a "$C_n$" arylalkyl, $C_n$ includes the carbon atoms in the alkyl chain and in the aryl group. For example, ethylbenzene is a C8 arylalkyl.

The term "heterocyclyl group" (alone or in combination with another term(s)) means a saturated (i.e. "heterocycloalkyl"), partially saturated (i.e. "heterocycloalkenyl"), or completely unsaturated (i.e. "heteroaryl") ring structure containing a total of 3 to 14 ring atoms, wherein at least one of the ring atoms is a heteroatom (i.e. oxygen, nitrogen, or sulfur), with the remaining ring atoms being carbon atoms. A heterocyclyl group may, for example, contain one, two, three, four or five heteroatoms. Attachment to the heterocyclyl group may occur through a carbon atom and/or one or more heteroatoms that are contained in the ring. A heterocyclyl may be a single-ring (monocyclic) or polycyclic ring structure.

A heterocyclyl group may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl(furazanyl) or 1,3,4-oxadiazolyl), oxatriazolyl, dioxazolyl oxathiolyl, pyranyl, dihydropyranyl, tetrahydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl) or pyrazinyl (1,4-diazinyl)), piperazinyl, triazinyl (including 1,3,5-triazinyl,1,2,4-triazinyl and 1,2,3-triazinyl)), oxazinyl (including 1,2-oxazinyl, 1,3-oxazinyl or 1,4-oxazinyl)), oxadiazinyl (including 1,2,3-oxadiazinyl, 1,2,4-oxadiazinyl, 1,4,2-oxadiazinyl or 1,3,5-oxadiazinyl)), morpholinyl, azepinyl, oxepinyl, thiepinyl, and diazepinyl.

A heterocyclyl group may alternatively be polycyclic (i.e. may contain more than one ring). Examples of polycyclic heterocyclyl groups include bridged, fused, and spirocyclic heterocyclyl groups. In a spirocyclic heterocyclyl group, one atom is common to two different rings. In a bridged heterocyclyl group, the rings share at least two common non-adjacent atoms. In a fused-ring heterocyclyl group, two or more rings may be fused together, such that two rings share one common bond. Examples of fused ring heterocyclyl groups containing two or three rings include indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyl groups include benzo-fused heterocyclyl groups, such as indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), and benzisoxazinyl (including 1,2-benzisoxazinyl or 1,4-benzisoxazinyl).

The term "heterocycloalkyl group" (alone or in combination with another term(s)) means a saturated heterocyclyl. A "$C_n$ heterocycloalkyl" group refers to a cyclic aliphatic group containing n carbon atoms in addition to at least one heteroatom, for example nitrogen. For example, a $C_1$-$C_{10}$ heterocycloalkyl group contains 1, 2, 3, 4, 5, 6, 7, 8, 9 or 10 carbon ring atoms in addition to the at least one heteroatom. Attachment to the heterocycloalkyl group occurs through a carbon atom or one of the at least one heteroatoms.

The term "alkylheterocycloalkyl" refers to a heterocycloalkyl substituent attached via an alkyl chain. In a "$C_n$" alkylheterocycloalkyl, $C_n$ includes the carbon atoms in the alkyl chain and in the heterocycloalkyl ring. For example, ethylpiperidine is a C7 alkylheterocycloalkyl.

The term "heteroaryl group" (alone or in combination with another term(s)) means an aromatic heterocyclyl containing from 5 to 14 ring atoms. A "$C_n$ heteroaryl" group refers to an aromatic group containing n carbon atoms and at least one heteroatom. For example, a $C_2$-$C_{10}$ aryl group contains 2, 3, 4, 5, 6, 7, 8, 9 or 10 carbon atoms in addition to at least one heteroatom. Attachment to the heteroaryl group occurs through a carbon atom or through a heteroatom. A heteroaryl group may be monocyclic or polycyclic. A heteroaryl may be a single ring or 2 or 3 fused rings. Examples of monocyclic heteroaryl groups include 6-membered rings such as pyridyl, pyrazinyl, pyrimidinyl, pyridazinyl, and 1,3,5-, 1,2,4- or 1,2,3-triazinyl; 5-membered rings such as imidazolyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl. Polycyclic heteroaryl groups may be 2 or 3 fused rings. Examples of polycyclic heteroaryl groups include 6/5-membered fused ring groups such as benzothiofuranyl, benzisoxazolyl, benzoxazolyl, and purinyl; and 6/6-membered fused ring groups such as benzopyranyl, quinolinyl, isoquinolinyl, cinnolinyl, quinazolinyl, and benzoxazinyl. In the case of polycyclic heteroaryl groups, only one ring in the polycyclic system is required to be unsaturated while the remaining ring(s) may be saturated, partially saturated or unsaturated.

A nitrogen-containing heteroaryl group is a heteroaryl group in which at least one of the one or more heteroatoms in the ring is nitrogen.

The term "heteroarylalkyl" refers to a heteroaryl substituent attached via an alkyl chain. Examples of a heteroarylalkyl substituent include ethylpyridine, where the ethane chain links a pyridine group to the point of attachment.

The term "amino group" refers to the —$NR_mR_n$ group. The amino group can be optionally substituted. In an unsubstituted amino group, R' and R" are hydrogen. In a substituted amino group $R_m$ and $R_n$ each independently may be, but are not limited to, hydrogen, an alkyl, heteroalkyl, cycloalkyl, heterocycloalkyl, alkylcycloalkyl, alkylheterocycloalkyl, alkoxy, sulfonyl, alkenyl, alkanoyl, aryl, arylalkyl, or a heteroaryl group, provided $R_m$ and $R_n$ are not both hydrogen. In a substituted amino group $R_m$ and $R_n$ may cyclise to form a cyclic amino group, e.g. a pyrrolidine group or a piperidine group. Such a cyclic amino group may incorporate other heteroatoms, for example to form a piperazine or morpholine group. Such a cyclic amino group may be optionally substituted, e.g. with an amino group, a hydroxyl group or an oxo group.

The term "aminoalkyl" group refers to the —$RNR_mR_n$ group, wherein R is an alkyl chain as defined above and $NR_mR_n$ is an optionally substituted amino group as defined above. "$C_n$ aminoalkyl" group refers to a group containing n carbon atoms. For example, a $C_1$-$C_{10}$ aminoalkyl group contains 1, 2, 3, 4, 5, 6, 7, 8, 9 or 10 carbon atoms. When the amino group of the aminoalkyl group is a substituted amino group, the number of carbon atoms includes any carbon atoms in the substituent groups. Attachment to the aminoalkyl group occurs through a carbon atom of the R alkyl group. Examples of aminoalkyl substituents include methylamine, ethylamine, methylaminomethyl, dimethylaminomethyl, methylaminoethyl, dimethylaminoethyl, methylpyrrolidine, and ethylpyrrolidine The term "amido group" refers to the —C(═O)—NR— group. Attachment may be through the carbon or nitrogen atom. For example, the amido group may be attached as a substituent via the carbon atom only, in which case the nitrogen atom has two R groups attached (—C(═O)—$NR_2$). The amido group may be attached by the nitrogen atom only, in which case the carbon atom has an R group attached (—NR—C(═O)R).

The term sulfoximine refers to sulfoximine substituents that are either S-linked or N-linked—that is, attachment may be through the sulfur or nitrogen atom. For example, the sulfoximine group may be attached as a substituent via the sulfur atom, in which case the sulfur has a single R group in addition to the oxo group and the sulfur-bound nitrogen atom has one R group attached—that is the group is —S(O)(R)NR'. By way of further example, the sulfoximine group may be attached as a substituent via the nitrogen atom, in which case the sulfur atom has two attached R groups in addition to the oxo group—that is, the group is —NS(O)RR'. In unsubstituted sulfoximine groups, each of R and R' are H. Alternatively, the sulfoximine group may be substituted at one or both of R and R', for example to form a dimethyl sulfoximine, where both R and R' are methyl.

The term "ether" refers to an —O-alkyl group or an -alkyl-O-alkyl group, for example a methoxy group, a methoxymethyl group or an ethoxyethyl group. The alkyl chain(s) of an ether can be linear, branched or cyclic chains. The ether group can be optionally substituted (a "substituted ether") with one or more substituents. A $C_n$ ether refers to an ether group having n carbons in all alkyl chains of the ether group. For example, a CH(CH3)-O—C6H11 ether is a $C_8$ ether group.

The term "alkoxy group" refers to an —O-alkyl group. The alkoxy group can refer to linear, branched, or cyclic, saturated or unsaturated oxy-hydrocarbon chains, including, for example, methoxyl, ethoxyl, propoxyl, isopropoxyl, butoxyl, t-butoxyl and pentoxyl. The alkoxy group can be optionally substituted (a "substituted alkoxy") with one or more alkoxy group substituents.

The term "aryloxy group" refers to an —O-aryl group, for example a phenoxy group. An aryloxy substituent may itself be optionally substituted, for example with a halogen.

The term "alkylester" refers to a —C(O)OR group, where R is an alkyl group as defined herein. An example of an alkylester is ethyl methanoate—i.e. R is an ethyl group.

The term "hydroxyl" refers to an —OH group.

The term "oxo group" refers to the (═O) group, i.e. a substituent oxygen atom connected to another atom by a double bond. For example, a carbonyl group (—C(═O)—) is a carbon atom connected by a double bond to an oxygen atom, i.e. an oxo group attached to a carbon atom. Examples of carbonyl substituents include aldehydes (—C(═O)H), acetyl (—C(═O)CH3) and carboxyl/carboxylic acid groups (—C(═O)OH).

The term "halo" refers to a substituent selected from chlorine, fluorine, bromine and iodine. Preferably, the halo substituent is selected from chlorine and fluorine.

An alkyl, alkenyl, alkynyl, carbocyclyl (including cycloalkyl, cycloalkenyl and aryl), heterocyclyl (including heterocycloalkyl, heterocyloalkenyl, heteroaryl, nitrogen-containing heterocyclyl), amino, amido, ester, ether, alkoxy, sulfoximine, or sulfonamide group can be optionally substituted with one or more substituents, which can be the same or different. A substituent can be attached through a carbon atom and/or a heteroatom in the alkyl, alkenyl, alkynyl, carbocyclyl (including cycloalkyl, cycloalkenyl and aryl), heterocyclyl (including heterocycloalkyl, heterocyloalkenyl, heteroaryl, nitrogen-containing heterocyclyl, nitrogen-containing heteroaryl), amino, amido, ester, ether, alkoxy, sulfoximine, or sulfonamide group. The term "substituent" (or "radical") includes but is not limited to alkyl, substituted alkyl, heteroalkyl, substituted heteroalkyl, aralkyl, substituted aralkyl, alkenyl, substituted alkenyl, alkynyl, substituted alkynyl, halo, hydroxyl, cyano, amino, amido, alkylamino, arylamino, carbocyclyl, cycloalkyl, substituted cycloalkyl, heterocycloalkyl, substituted heterocycloalkyl, cycloalkenyl, substituted cycloalkenyl, aryl, substituted aryl, heteroaryl, substituted heteroaryl, nitro, thio, alkanoyl, hydroxyl, aryloxyl, alkoxyl, alkylthio, arylthio, aralkyloxyl, aralkylthio, carboxyl, alkoxycarbonyl, oxo, alkylsulfonyl, arylsulfonyl and sulfoximinyl.

In certain aspects, the substituent is alkyl, substituted alkyl, heteroalkyl, substituted heteroalkyl, alkenyl, substituted alkenyl, alkynyl, substituted alkynyl, halo, hydroxyl, cyano, amino, amido, alkylamino, arylamino, carbocyclyl, cycloalkyl, substituted cycloalkyl, heterocycloalkyl, substituted heterocycloalkyl, cycloalkenyl, substituted cycloalkenyl, aryl, substituted aryl, heteroaryl, substituted heteroaryl, nitro, thio, alkanoyl, hydroxyl, aryloxyl, alkoxyl, alkylthio, arylthio, aralkyloxyl, aralkylthio, carboxyl, alkoxycarbonyl, oxo, alkylsulfonyl and arylsulfonyl.

If a group, for example an alkyl group, is "optionally substituted", it is understood that the group has one or more substituents attached (substituted) or does not have any substituents attached (unsubstituted).

If a group is substituted with a further optionally substituted group, it is understood that the first substituent may itself be either unsubstituted or substituted.

For completeness, it is also noted that certain chemical formulae used herein define delocalized systems. This definition is known in the art as a definition of aromaticity and may indicate the presence of, for example, a planar mono-, di- or tri-cyclic system that contains (4n+2) electrons where n is an integer. In other words, these systems may display Hückel aromaticity.

In whatever aspect, the compounds of the present invention may possess some aspect of stereochemistry. For example, the compounds may possess chiral centres and/or planes and/or axes of symmetry. As such, the compounds may be provided as single stereoisomers, single diastereomers, mixtures of stereoisomers or as racemic mixtures, unless otherwise specified. Stereoisomers are known in the art to be molecules that have the same molecular formula and sequence of bonded atoms, but which differ in their spatial orientations of their atoms and/or groups.

In addition, the compounds of the present invention may exhibit tautomerism. Each tautomeric form is intended to fall within the scope of the invention.

In addition, the compounds of the present invention may be provided as a pro-drug. Pro-drugs are transformed, generally in vivo, from one form to the active forms of the drugs described herein.

In addition, it will be understood that the elements described herein may be the common isotope or an isotope other than the common isotope. For example, a hydrogen atom may be $^1$H, $^2$H (deuterium) or $^3$H (tritium).

In addition, the compounds of the present invention may be provided in the form of their pharmaceutically acceptable salts or as co-crystals.

The term "pharmaceutically acceptable salt" refers to ionic compounds formed by the addition of an acid to a base. The term refers to such salts that are considered in the art as being suitable for use in contact with a patient, for example in vivo and pharmaceutically acceptable salts are generally chosen for their non-toxic, non-irritant characteristics.

The term "co-crystal" refers to a multi-component molecular crystal, which may comprise non-ionic interactions.

Pharmaceutically acceptable salts and co-crystals may be prepared by ion exchange chromatography or by reacting the free base or acidic form of a compound with stoichiometric amounts or with an excess of the desired salt-forming inorganic or organic acid or base in one or more suitable solvents, or by mixing the compound with another pharmaceutically acceptable compound capable of forming a co-crystal.

Salts known in the art to be generally suitable for use in contact with a patient include salts derived from inorganic and/or organic acids, including the hydrobromide, hydrochloride, sulfate, bisulfate, nitrate, acetate, oxalate, oleate, palmitate, stearate, laurate, benzoate, lactate, phosphate, tosylate, citrate, maleate, fumarate, succinate and tartrate. These may include cations based on the alkali and alkaline earth metals, such as sodium, potassium, calcium and magnesium, as well as ammonium, tetramethylammonium, tetraethylammonium. Further reference is made to the number of literature sources that survey suitable pharmaceutically acceptable salts, for example the handbook of pharmaceutical salts published by IUPAC.

In addition, the compounds of the present invention may sometimes exist as zwitterions, which are considered as part of the invention.

As used herein, a USP19 inhibitor refers to a compound which acts on USP19 so as to decrease the activity of the enzyme. Examples of USP19 inhibitors are exemplified compounds herein. Preferably a USP19 inhibitor exhibits an $IC_{50}$ of less than 5 μM, preferably less than 0.5 μM.

As used herein, "obesity" refers to the medical condition characterized by excess body fat. Obesity can be characterized by, for example, a body mass index (BMI) of greater than 30. Treatment of obesity may be indicated by, for example, the reduction of body fat, in percentage and/or absolute mass terms. Treatment of obesity may also be exemplified by a reduction in the rate of body fat accumulation by a subject compared to before treatment.

As used herein, "insulin resistance" refers to the medical condition characterized by an abnormally weak response to insulin. Since insulin resistance is typically not treated by exogenous insulin treatment, the resistance is typically to insulin produced by the body of the subject, though the subject may also be resistant to exogenous insulin. "Insulin resistance" encompasses the conditions "prediabetes" and Type II diabetes. Insulin resistance may be indicated, for example, by a glucose tolerance test (GTT) glycaemia of 7.8 mmol/L or greater. Type II diabetes is typically diagnosed following a glucose tolerance test (GTT) glycaemia of 11.1 mmol/L or greater.

Treatment of insulin resistance may be indicated by an improvement (i.e. reduction) in the subject's GTT glycaemia compared to before treatment. Treatment may also be indicated by a reduction in the subject's blood sugar concentration under normal conditions compared to before treatment.

As used herein, "muscular atrophy" and "muscle-wasting" are used interchangeably to refer to decrease in muscle mass in a subject, including in the context of cachexia or sarcopenia, for example. Muscular atrophy can be as a result of temporary or permanent disability, temporary or permanent immobilization of a limb, extended bedrest, cachexia (for example as a result of cancer, heart failure, or COPD), or sarcopenia.

Treatment of muscular atrophy may be characterized as the slowing of the rate of atrophy—that is, treatment results in less muscle mass lost over a given period of time. Preferably, successful treatment results in no loss of muscle mass.

Accordingly, in a first aspect is provided a compound of formula (I):

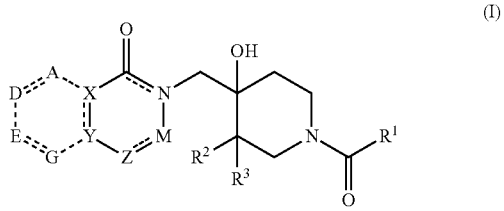

(I)

wherein $R^1$ is optionally substituted C1-C6 alkyl, optionally substituted C4-C10 alkylcycloalkyl, optionally substituted C6-C10 alkylaryl, optionally substituted C5-C8 aryl, optionally substituted C3-C8 heteroaryl, optionally substituted C3-C8 heterocycloalkyl, $NR^aR^b$, $NR^aCH2R^b$, $OR^a$, or $OCH2R^a$, wherein $R^a$ and $R^b$ are independently selected from H, C1-C6 alkyl, CF3, optionally substituted C3-C6 cycloalkyl, optionally substituted C5-C8 aryl, optionally substituted C6-C9 arylalkyl, and optionally substituted C2-C8 heteroaryl optionally C4-C8 heteroaryl,
or wherein $R^1$ is $NR^aR^b$ and $R^a$ and $R^b$ together form an optionally substituted C2-C9 heterocycle together with the N to which they are attached, optionally a C3-C5 heterocycle;

$R^2$ and $R^3$ are independently selected from H, and C1-C6 alkyl, or together form a C3-C6 cycloalkyl or heterocycloalkyl with the carbon to which they attached;

X is absent, C, $CR^{4a}$, $CR^{4a}R^{4b}$, N, $NR^{4a}$, or C=O,
wherein $R^{4a}$ and $R^{4b}$ are independently selected from H, optionally substituted C1-C6 alkyl or halo;
or wherein $R^{4a}$ and $R^{4b}$ together form a C3-C6 cycloalkyl or C3-C6 heterocycloalkyl including the carbon to which they are attached;

Y is C, $CR^5$, $CR^5R^6$, N, $NR^5$, or O,
wherein $R^5$ and $R^6$ are independently selected from H, halo, optionally substituted C1-C6 alkyl, optionally substituted C3-C6 cycloalkyl, optionally substituted C5-C8 aryl, optionally substituted C6-C9 arylalkyl, optionally substituted C3-C8 heteroaryl, CH2OH, NR'R", NS(O)R'R", SO2R', C(O)R', COR', C(O)OR', C(O)NR'R', OR', wherein R' and R" are independently selected from H, C1-C6 alkyl, C5-C8 aryl, C6-C9 arylalkyl, and C3-C8 heteroaryl,
or wherein $R^5$ and $R^6$ together form a C3-C6 cycloalkyl or C3-C6 heterocycloalkyl including the carbon to which they are attached;

Z is N, $NR^7$, C, $CR^7$, $CR^7R^8$, or C=O,
wherein $R^7$ and $R^8$ are independently selected from H, halo, C1-C6 alkyl, C2-C6 alkene, C2-C6 alkyne, C3-C6 cycloalkyl, optionally substituted C3-C6 heterocycloalkyl, C5-C8 aryl, C6-C9 arylalkyl, C3-C8 heteroaryl, CN, $COOR^c$, $CONR^cR^d$, $NR^cR^d$, NS(O)$R^cR^d$, S(O)($R^c$)$NR^d$, $SOR^c$, $SO2R^c$, and $SR^c$, wherein $R^c$ and $R^d$ are independently H, C1-C6 alkyl, C5-C6 aryl, C6-C9 arylalkyl, C3-C6 heteroaryl, CN, COOH, or COCH3 or $R^c$ and $R^d$ together form an optionally substituted C3-C7 heterocycle together with the heteroatom to which they are attached;
or wherein $R^7$ and $R^8$ together form a C3-C6 cycloalkyl or C3-C6 heterocycloalkyl including the carbon to which they are attached;

M is absent, C, $CR^{13}$ or $CR^{13}R^{14}$, wherein $R^{13}$ and $R^{14}$ are independently selected from H, and C1-C6 alkyl, or wherein $R^{13}$ and $R^{14}$ together form a C3-C6 cycloalkyl or C3-C6 heterocycloalkyl together with the carbon to which they are attached; and A is $CR^9$, $CHR^9$, N, $NR^9$, S, or O,
D is $CR^9$, $CHR^9$, N or $NR^9$,
G is absent, $CR^9$, $CHR^9$, or N,
wherein $R^9$ is selected from H, halo, C1-C6 alkyl, CF3, and OR*, wherein R* is an optionally substituted C1-C6 alkyl, optionally substituted C1-C6 cycloalkyl or optionally substituted heterocycloalkyl, E is $CR^{10}$, $CHR^{10}$, N, $NR^{10}$, S, or O,
wherein $R^{10}$ is selected from H, halo, C1-C6 alkyl, C3-C6 cycloalkyl, C5-C8 aryl, C6-C9 arylalkyl, C4-C8 heteroaryl, $SR^x$, $OR^x$, $NR^xR^y$, and NS(O)$R^xR^y$, S(O)($R^x$)$NR^y$, wherein $R^x$ and $R^y$ are independently selected from H, C1-C6 alkyl, CF3, C3-C6 cycloalkyl, C5-C8 aryl, C6-C9 arylalkyl, C4-C8 heteroaryl, COOH, amido, cyano, C2-C6 alkene, C2-C6 alkyne, or wherein $R^x$ and $R^y$ together form an optionally substituted C4-C6 heterocycloalkyl together with the nitrogen to which they are attached;
or A, D, E and G are all absent, and X, Y, Z and M are as defined above, and
optionally wherein both X and M are absent, or
optionally wherein Y and Z together form an optionally substituted C5-C6 aryl or C5-C6 heteroaryl fused ring or Z and M together form an optionally substituted C5-C6 aryl or C5-C6 heteroaryl fused ring; or a stereoisomer, tautomer, hydrate, N-oxide derivative or pharmaceutically acceptable salt thereof.

In further aspect is provided a compound of formula (Ia):

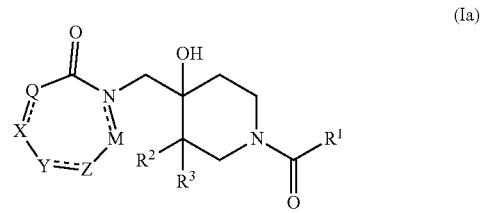

(Ia)

wherein Q is selected from $CR^{11}$, $CR^{11}R^{12}$, $NR^{11}$ or O, where $R^{11}$ and $R^{12}$ are independently selected from H, OH, C1-C6 alkyl, CF3, C3-C6 cycloalkyl, optionally substituted C5-C8 aryl, C4-C8 heteroaryl, or wherein $R^{11}$ and $R^{12}$ together form an optionally substituted C3-C5 carbocycle together with the C to which they are attached,
and wherein each of X, Y, Z and M are present and as defined in relation to formula (I), wherein the ring QXYZM is aliphatic or aromatic, preferably aliphatic;
and wherein $R^1$, $R^2$, and $R^3$ are as defined in relation to formula (I);
or a stereoisomer, tautomer, hydrate, N-oxide derivative or pharmaceutically acceptable salt thereof.

For the avoidance of doubt, in formula (I), if any of positions A, D, E or G are present, each of the other positions A, D and E (and optionally G) are also present to form a fused ring system.

For the avoidance of doubt, when one of positions X, M or G are absent, the remaining members of the ring form a 5 membered ring. In those embodiments in which X and M are absent, the remaining members form a 4 membered ring. For example, if M is absent, the atom at ring position Z is bound to the ring nitrogen.

Dotted lines in formulas (I) and (Ia) indicate optional bonds. That is, the dotted lines indicate the ring including positions X, Y, Z, M (and Q) can be aliphatic (for example saturated or partially unsaturated) or aromatic. Similarly, in formula (I) dotted lines indicate that, when present, the ring including positions A, D, E and optionally G can be aliphatic (for example saturated or partially unsaturated) or aromatic.

In certain embodiments of the compounds of formula (I) or (Ia) for each group that is optionally substituted, each of the one or more optional substituents is independently selected from C1-C4 alkyl, halo, CF3, hydroxyl, NH2, NO2, CH2OH, CH2OCH3, phenyl, benzyl, and oxo.

In certain preferred embodiments of the compound of formula (I) or formula (Ia), $R^1$ is optionally substituted ethylbenzene, optionally substituted ethylcyclohexyl, optionally substituted ethylcyclobutyl or optionally substituted trifluoropropyl. In certain preferred such embodiments, each optional substituent is selected from methyl, OH and CH2OH.

In certain preferred embodiments, R$^1$ is:

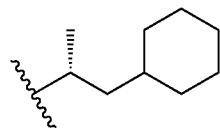 [SMILES: *[C@H](C)CC1CCCCC1]

In certain preferred embodiments, R$^1$ is:

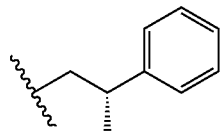

In certain preferred embodiments, R$^1$ is:

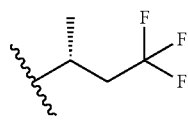

In certain preferred embodiments, R$^1$ is:

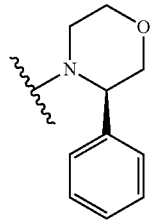

In certain preferred embodiments, R$^1$ is:

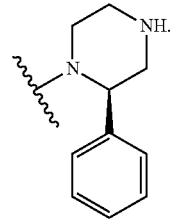 [SMILES: *N1CCNC[C@H]1c1ccccc1]

In certain preferred embodiments of the compound of formula (I) or (Ia), R$^1$ is NR$^a$R$^b$ or NR$^a$CH2R$^b$, wherein R$^a$ and R$^b$ are independently selected from H, methyl, ethyl, propyl, CF3, optionally substituted cyclopropyl, optionally substituted cyclobutyl, optionally substituted cyclopentyl, optionally substituted cyclohexyl, optionally substituted phenyl, optionally substituted benzyl, optionally substituted pyridinyl, pyrazole, imidazole, furan, benzodioxol, optionally substituted oxadiazole, thiazole, and thiophene, wherein the optionally substituents are independently selected from halo, methyl, cyclopropyl and CN, optionally wherein R$^1$ is NR$^a$CH2R$^b$ and the methylene group is substituted with CF3; or wherein R$^1$ is NR$^a$R$^b$ and R$^a$ and R$^b$ together form an optionally substituted C3-C9 heterocycle together with the N to which they are attached.

In certain embodiments, R$^1$ is NR$^a$R$^b$ and R$^a$ and R$^b$ form a heterocycle together with the N to which they are attached, wherein the heterocycle is selected from pyrrolidinyl, pyrimidinyl, morpholino, piperazinyl, and thiomorpholino, wherein the heterocycle is optionally substituted with one or more substituents independently selected from CH2CF3, oxo, thiophene, and phenyl optionally substituted with F or CF3.

In certain preferred embodiments, R$^1$ forms a morpholino group substituted with phenyl or fluoro-substituted phenyl. In preferred such embodiments where the compound is chiral at the phenyl substituent, the compound is the R enantiomer.

In certain preferred embodiments, R$^1$ forms a piperazinyl group substituted with phenyl.

In certain embodiments where R$^1$ is NR$^a$R$^b$ and R$^a$ and R$^b$ form a heterocycle, the heterocycle is optionally substituted with one or more of OH, CH2OH, CH2OCH3, methyl, ethyl, propyl, CF3, phenyl, or benzyl.

In certain preferred embodiments, R$^1$ is NR$^a$CH2R$^b$, wherein R$^a$ is H or methyl and R$^b$ is selected from cyclobutyl optionally substituted with F, cyclohexyl, phenyl optionally substituted with F, furan and thiophene, optionally wherein the methylene group is substituted with CF3.

In certain preferred such embodiments, R$^b$ is phenyl or fluoro-substituted phenyl.

In certain preferred embodiments of the compound of formula (I) or formula (Ia), R$^1$ is OR$^a$ or OCH2R$^a$, wherein R$^a$ is selected from H, C1-C6 alkyl, CF3, cyclopropyl, cyclobutyl, cyclopentyl, cyclohexyl, phenyl, benzyl, pyridinyl, pyrazole, imidazole, each optionally substituted with NO2, methyl, OH or CF3.

In certain preferred embodiments of the compound according to formula (I) or (Ia), R$^2$ and R$^3$ are independently selected from H, methyl and ethyl, or together form optionally substituted cyclopropyl, optionally substituted cyclobutyl, optionally substituted cyclopentyl, optionally substituted cyclohexyl, optionally substituted pyrrolidine, optionally substituted tetrahydropyran or optionally substituted tetrahydrofuran together with the carbon to which they attached.

In certain such embodiments, R$^2$ and R$^3$ are independently selected from H, and methyl.

In certain preferred embodiments, R$^2$ and R$^3$ together form cyclohexyl, cyclopentyl, or cyclobutyl together with the carbon to which they attached. Preferably R$^2$ and R$^3$ together form cyclopentyl. Alternatively preferably R$^2$ and R$^3$ together form cyclohexyl.

In certain embodiments is provided a compound of formula (I), wherein:

X is CR$^{4a}$, wherein R$^{4a}$ is independently selected from H, optionally substituted C1-C6 alkyl or halo, preferably H or C1-C6 alkyl;

Y is N;

Z is CR$^7$, wherein R$^7$ is selected from H, halo, C1-C6 alkyl, C2-C6 alkene, C2-C6 alkyne, C3-C6 cycloalkyl, optionally substituted C3-C6 heterocycloalkyl, C5-C8 aryl, C6-C9 arylalkyl, C3-C8 heteroaryl, CN, COOR$^c$, CONR$^c$R$^d$, NR$^c$R$^d$, NS(O)R$^c$R$^d$, S(O)(R$^c$)NR$^d$, SOR$^c$, SO2R$^c$, and SR$^c$, wherein R$^c$ and R$^d$ are independently H, C1-C6 alkyl, C3-C6 cycloalkyl, C5-C6 aryl, C6-C9 arylalkyl, C3-C6 heteroaryl, CN, COOH, or COCH3, or R$^c$ and R$^d$ together form an optionally substituted C3-C7 heterocycle together with the heteroatom to which they are attached;

M is CH or C—CH3;

and the ring including X, Y and Z is aromatic, and A, D, E and G are all absent.

In certain preferred such embodiments, Z is CR$^7$ and R$^7$ is selected from H, methyl, cyclopropyl, phenyl, pyridine, pyrazole, indazole, imidazole, Cl, Br, COOH, COOCH3, C(O)NR$^c$R$^d$, NR$^c$R$^d$, wherein R$^c$R$^d$ are selected from methyl, or wherein R$^c$ and R$^d$ together form an optionally substituted piperazine, morpholine or optionally substituted pyrrolidine together with the N to which they are attached.

In certain preferred embodiments, R$^7$ is Cl, Br or C(O)OCH3, or R$^7$ is CONR$^c$R$^d$ and R$^c$ and R$^d$ are each methyl, or R$^c$ and R$^d$ form a piperazinyl ring together with the N to which they are attached.

In certain embodiments,

X is CR$^{4a}$, wherein R$^{4a}$ is selected from H, optionally substituted C1-C6 alkyl and halo, optionally wherein R$^{4a}$ is H or C1-C6 alkyl;

Y is CR$^5$;

Z is N or CR$^7$;

M is CH or C—CH3;

wherein the ring including X, Y and Z is aromatic, and A, D, E and G are all absent, and R$^5$ is selected from H, halo, optionally substituted C1-C6 alkyl, optionally substituted C3-C6 cycloalkyl, optionally substituted C5-C8 aryl, optionally substituted C6-C9 arylalkyl, optionally substituted C3-C8 heteroaryl, CH2OH, NR'R', NS(O)R'R", SO2R', C(O)R', COR', C(O)OR', C(O)NR'R", OR', wherein R' and R" are independently selected from H, C1-C6 alkyl, C5-C8 aryl, C6-C9 arylalkyl, and C3-C8 heteroaryl, and R$^7$ is selected from H, halo, C1-C6 alkyl, C2-C6 alkene, C2-C6 alkyne, C3-C6 cycloalkyl, optionally substituted C3-C6 heterocycloalkyl, C5-C8 aryl, C6-C9 arylalkyl, C3-C8 heteroaryl, CN, C(O)OR$^c$, CONR$^c$R$^d$, NR$^c$R$^d$, NS(O)R$^c$R$^d$, S(O)(R$^c$)NR$^d$, SOR$^c$, SO2R$^c$, and SR$^c$, wherein R$^c$ and R$^d$ are independently H, C1-C6 alkyl, C3-C6 cycloalkyl, C5-C6 aryl, C6-C9 arylalkyl, C3-C6 heteroaryl, CN, COOH, or COCH3 or R$^c$ and R$^d$ together form an optionally substituted C3-C7 heterocycle together with the heteroatom to which they are attached.

In certain preferred such embodiments R$^{4a}$ is H, R$^5$ is Cl or phenyl optionally substituted with fluoro, and Z is N or CR$^7$.

In certain preferred such embodiments, R$^7$ is dimethyl amide.

In certain embodiments is provided a compound of formula (I) wherein the ring including X, Y and Z is aliphatic, wherein A, D, E and G are all absent and wherein:

X is absent, CR$^{4a}$R$^{4b}$, NR$^{4a}$, or C=O, wherein R$^{4a}$ and R$^{4b}$ are H, optionally substituted C1-C6 alkyl or halo, or wherein R$^{4a}$ and R$^{4b}$ together form a C3-6 cycloalkyl or C3-C6 heterocycloalkyl including the carbon to which they are attached;

Y is O, CR$^5$R$^6$, or NR$^5$, wherein R$^5$ and R$^6$ are independently selected from H, halo, optionally substituted C1-C6 alkyl, optionally substituted C3-C6 cycloalkyl, optionally substituted C5-C8 aryl, optionally substituted C6-C9 arylalkyl, optionally substituted C3-C8 heteroaryl, CH2OH, NR'R', NS(O)R'R", COR', COOR', C(O)NR'R", OR', wherein R' and R" are independently selected from C1-C6 alkyl, C5-C8 aryl, C6-C9 arylalkyl, and C3-C8 heteroaryl, or wherein R$^5$ and R$^6$ together form a C3-C6 cycloalkyl including the carbon to which they are attached;

Z is CR$^7$R$^8$, wherein R$^7$ and R$^8$ are independently selected from H, halo, C1-C6 alkyl, C2-C6 alkene, C2-C6 alkyne, C3-C6 cycloalkyl, optionally substituted C3-C6 heterocycloalkyl, C5-C8 aryl, C6-C9 arylalkyl, C3-C8 heteroaryl, CN, COOR$^c$, CONR$^c$R$^d$, NR$^c$R$^d$, wherein R$^c$ and R$^d$ are independently selected from H, C1-C6 alkyl, and C3-C6 cycloalkyl or R$^c$ and R$^d$ together form an optionally substituted C3-C7 heterocycle together with the heteroatom to which they are attached, or wherein R$^7$ and R$^8$ together form a C3-6 cycloalkyl or C3-C6 heterocycloalkyl including the carbon to which they are attached;

M is absent, CH2, or Z and M together form part of an optionally substituted phenyl or pyridine ring;

or M is absent and Y and Z together form a fused phenyl or heteroaryl ring, or M and X are both absent and Z is CHR$^7$, wherein R$^7$ is selected from H, halo, C1-C6 alkyl, C2-C6 alkene, C2-C6 alkyne, C3-C6 cycloalkyl, optionally substituted C3-C6 heterocycloalkyl, C5-C8 aryl, C6-C9 arylalkyl, C3-C8 heteroaryl, CN, COOR$^c$, CONR$^c$R$^d$, NR$^c$R$^d$, wherein R$^c$ and R$^d$ are independently H, C1-C6 alkyl or R$^c$ and R$^d$ together form an optionally substituted C3-C7 heterocycle together with the heteroatom to which they are attached.

In certain preferred such embodiments:

X is CR$^{4a}$R$^{4b}$ and R$^{4a}$ is selected from H, C1-C6 alkyl or halo, and R$^{4b}$ is H;

Y is O or CR$^5$R$^6$ where R$^5$ and R$^6$ are independently selected from H, halo, optionally substituted C1-C6 alkyl, optionally substituted phenyl, benzyl, pyridinyl, CH2OH, C(O)R', COR', C(O)OR', C(O)NR'R", and SO2R', wherein R' and R" are independently selected from methyl, ethyl, propyl, butyl, phenyl, and benzyl, or wherein R$^5$ and R$^6$ together form cyclohexyl, including the carbon to which they are attached;

Z is CR$^7$R$^8$ and R$^7$ is selected from H, C1-C6 alkyl, phenyl, and CONR$^c$R$^d$, wherein R$^c$ and R$^d$ are independently H, methyl or R$^c$ and R$^d$ together form an optionally substituted pyrrolidine together with the nitrogen to which they are attached, and R$^8$ is H.

In certain preferred such embodiments:

X is CR$^{4a}$R$^{4b}$ and R$^{4a}$ and R$^{4b}$ are both H;

Y is O or CR$^5$R$^6$, wherein R$^5$ is phenyl or C(O)NR'R", wherein R' and R" are both methyl, and R$^6$ is H; and Z is CR$^7$R$^8$, wherein R$^7$ is phenyl or C(O)NR$^c$R$^d$, wherein R$^c$ and R$^d$ are both methyl.

In certain preferred embodiments of the compound of formula (I) the ring including X, Y and Z is aliphatic, and:

A, D, E and G are each C or N and form a fused aryl or heteroaryl ring with the aliphatic ring including X, Y and Z in the case of a 5-membered ring (where M is absent) and X, Y, Z and M in the case of a 6-membered ring, X is C Y is C Z is NR$^7$, CR$^7$R$^8$ or C=O, wherein R$^7$ and R$^8$ are independently selected from H, halo, C1-C6 alkyl, C2-C6 alkene, C2-C6 alkyne, C3-C6 cycloalkyl, optionally substituted C3-C6 heterocycloalkyl, C5-C8 aryl, C6-C9 arylalkyl, C3-C8 heteroaryl, CN, COOR$^c$, CONR$^c$R$^d$, NR$^c$R$^d$, NS(O)R$^c$R$^d$, S(O)(R$^c$)NR$^d$, SOR$^c$, SO2R$^c$, and SR$^c$, wherein R$^c$ and R$^d$ are independently H, C1-C6 alkyl, C5-C6 aryl, C6-C9 arylalkyl, C3-C6 heteroaryl, CN, COOH, or COCH3, or R$^c$ and R$^d$ together form an optionally substituted C3-C7 heterocycle together with the heteroatom to which they are attached, or wherein R$^7$ and R$^8$ together form a C3-C6 cycloalkyl or C3-C6 heterocycloalkyl including the carbon to which they are attached;

and M is absent or CR$^{13}$R$^{14}$, wherein R$^{13}$ and R$^{14}$ are independently selected from H, and C1-C6 alkyl, or wherein R$^{13}$ and R$^{14}$ together form a C3-C6 cycloalkyl together with the carbon to which they are attached.

In certain preferred such embodiments, M is absent and Z is CR$^7$R$^8$ and wherein R$^7$ and R$^8$ are H.

In certain preferred such embodiments, A, D and E are C, and G is C or N.

In certain preferred embodiments of the compound of formula (I):

X is C or N

Y is C or N

Z is N, NR$^7$ or CR$^7$, wherein R$^7$ is selected from H, halo, C1-C6 alkyl, C2-C6 alkene, C2-C6 alkyne, C3-C6 cycloalkyl, optionally substituted C3-C6 heterocycloalkyl, C5-C8 aryl, C6-C9 arylalkyl, C3-C8 heteroaryl, CN, COOR$^c$, CONR$^c$R$^d$, NR$^c$R$^d$, NS(O)R$^c$R$^d$, S(O)(R$^c$)NR$^d$, SOR$^c$, SO2R$^c$, and SR$^c$, wherein R$^c$ and R$^d$ are independently H, C1-C6 alkyl, C5-C6 aryl, C6-C9 arylalkyl, C3-C6 heteroaryl, CN, COOH, or COCH3, or R$^c$ and R$^d$ together form an optionally substituted C3-C7 heterocycle together with the heteroatom to which they are attached;

M is absent, CH or C—CH3,

A is CR$^9$, CHR$^9$, N, NR$^9$, S, or O,

D is CR$^9$, CHR$^9$, N or NR$^9$,

G is absent, CR$^9$, CHR$^9$, or N, wherein R$^9$ is independently selected from H, halo, C1-C6 alkyl, CF3, and OR*, wherein R* is an optionally substituted C1-C6 alkyl, optionally substituted C1-C6 cycloalkyl or optionally substituted heterocycloalkyl, and E is CR$^{10}$, CHR$^{10}$, N, NR$^{10}$, S, or O, wherein R$^{10}$ is selected from H, halo, C1-C6 alkyl, C3-C6 cycloalkyl, C5-C8 aryl, C6-C9 arylalkyl, C4-C8 heteroaryl, SR$^x$, OR$^x$, NR$^x$R$^y$, and NS(O)R$^x$R$^y$, S(O)(R$^x$)NR$^y$, wherein R$^x$ and R$^y$ are independently selected from H, C1-C6 alkyl, CF3, C3-C6 cycloalkyl, C5-C8 aryl, C6-C9 arylalkyl, C4-C8 heteroaryl, COOH, amido, cyano, C2-C6 alkene, C2-C6 alkyne, or wherein R$^x$ and R$^y$ together form an optionally substituted C4-C6 heterocycloalkyl together with the nitrogen to which they are attached.

In certain preferred such embodiments Z is N, or CR$^7$, wherein R$^7$ is selected from H, C1-C6 alkyl, CN or C(O)NR$^c$R$^d$, wherein R$^c$ and R$^d$ are independently H, methyl, or together form an optionally substituted piperidine, piperazine or morpholine ring together with the nitrogen to which they are attached.

In certain preferred such embodiments:

E is CR$^{10}$, CHR$^{10}$, N, NR$^{10}$, S, or O, wherein R$^{10}$ is selected from H, F, Cl, Br, methyl, ethyl, cyclopropyl, cyclobutyl, cyclopentyl, cyclohexyl, SR$^x$, OR$^x$, NR$^x$R$^y$, and NS(O)(CH3)2, wherein R$^x$ and R$^y$ are independently selected from H, methyl, ethyl, CF3, cyclopropyl, cyclobutyl, cyclopentyl, cyclohexyl, COOH, amido, cyano, or wherein R$^x$ and R$^y$ together form a piperidine, piperazine or morpholine together with the nitrogen to which they are attached, optionally substituted with methyl.

In certain preferred embodiments:

A, M, X and Y are C, E is CR$^{10}$,

D is N,

G is C or N, and

Z is C or N, such that the rings including A, D, E, G, X, Y, Z and M form a fused aromatic ring system In certain preferred embodiments:

M is absent,

A, X and Y are C, D and G are N,

E is CR$^{10}$, and Z is NR$^7$, and the ring including A, D, E, G, X, and Y, forms an aromatic ring fused to the ring including X, Y and Z, wherein R$^7$ is H or C1-C6 alkyl, optionally wherein R7 is methyl.

In certain preferred embodiments E is CR$^{10}$, wherein R$^{10}$ is H or SR$^x$, wherein R$^x$ is C1-C6 alkyl. Preferably R$^x$ is methyl.

In certain preferred embodiments:

X, Y, M, A and G are C,

Z is N, D is CR$^9$ and E is CR$^{10}$, such that the rings including A, D, E, G, X, Y, Z and M form a fused aromatic ring system, wherein R$^9$ is halo, preferably F or Cl, and R$^{10}$ is H or halo, optionally F or Cl.

In certain preferred embodiments:

G is absent, A is C, D and Z are N, and E is NR$^{10}$, such that the rings including A, D, E, X, Y, Z and M form a fused aromatic ring system, wherein R$^{10}$ is selected from H, ethyl, phenyl and benzyl.

In preferred such embodiments, R$^2$ is not H, and R$^3$ is not H. This embodiment is particularly advantageous because it improves selectivity for USP19 inhibition compared to other USPs. In certain preferred such embodiments, R$^2$ and R$^3$ are both CH3, or together form a C3-C6 cycloalkyl together with the carbon to which they are attached. In certain preferred embodiments, R$^2$ and R$^3$ form cyclopentyl together with the carbon to which they are attached.

In certain preferred embodiments of the compound of formula (I):

X is CR$^4$, wherein R$^4$ is independently selected from H, C1-C6 alkyl or halo;

Y is CR$^5$, wherein R$^5$ is selected from H, halo, C1-C6 alkyl, C3-C6 cycloalkyl, optionally halo-substituted phenyl, optionally halo-substituted benzyl, pyridinyl, pyrazole, imidazole, CH2OH, NR'R', COR', C(O)OR', C(O)NR'R", OR', wherein R' and R" are independently selected from C1-C6 alkyl, and phenyl, benzyl, pyridinyl, pyrazole, imidazole;

Z is CR$^7$, wherein R$^7$ is selected from H, halo, C1-C6 alkyl, C2-C6 alkene, C2-C6 alkyne, C3-C6 cycloalkyl, optionally substituted C3-C6 heterocycloalkyl, C5-C8 aryl, C6-C9 arylalkyl, C3-C8 heteroaryl, CN, COOR$^c$, CONR$^c$R$^d$, NR$^c$R$^d$, NS(O)R$^c$R$^d$, S(O)(R$^c$)NR$^d$, SOR$^c$, SO2R$^c$, and SR$^c$, wherein R$^c$ and R$^d$ are independently H, C1-C6 alkyl, C5-C6 aryl, C6-C9 arylalkyl, C3-C6 heteroaryl, CN, COOH, or COCH3, or R$^c$ and R$^d$ together form an optionally substituted C3-C7 heterocycle together with the heteroatom to which they are attached;

M is CH; and the ring including X, Y and Z is aromatic, and A, D, E and G are all absent.

In certain preferred embodiments, the compound is a compound according to formula (Ia)

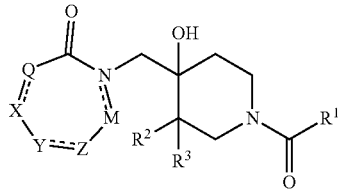

wherein the ring including QXYZM is aliphatic;
wherein Q is selected from CHR[11], where R[11] is selected from H, OH, C1-C6 alkyl, CF3, C3-C6 cycloalkyl, C5-C8 aryl, or C4-C8 heteroaryl;
X is CHR[4a], wherein R[4a] is selected from H, C1-C6 alkyl or halo, preferably wherein R[4a] is methyl;
Y is CR[5]R[6] wherein R[5] and R[6] are independently selected from H, halo, C1-C6 alkyl, C3-C6 cycloalkyl, C5-C8 aryl, C3-C8 heteroaryl, CH2OH, NR'R", and OR', wherein R' and R" are independently selected from H and C1-C6 alkyl; preferably wherein Y is CH2;
Z is CR[7]R[8], wherein R[7] and R[8] are independently selected from H, halo, C1-C6 alkyl, C2-C6 alkene, C2-C6 alkyne, C3-C6 cycloalkyl, optionally substituted C3-C6 heterocycloalkyl, C5-C8 aryl, C6-C9 arylalkyl, C3-C8 heteroaryl, CN, COOR[c], CONR[c]R[d], NR[c]R[d], NS(O)R[c]R[d], S(O)(R[c])NR[d], SOR[c], SO2R[c], and SR[c], wherein R[c] and R[d] are independently H, C1-C6 alkyl or R[c] and R[d] together form an optionally substituted C3-C7 heterocycle together with the heteroatom to which they are attached,
or wherein R[7] and R[8] together form a C3-C6 cycloalkyl or C3-C6 heterocycloalkyl including the carbon to which they are attached;
M is CR[13]R[14], wherein R[13] and R[14] are independently selected from H, and C1-C6 alkyl, or wherein R[13] and R[14] together form a C3-C6 cycloalkyl together with the carbon to which they are attached; preferably wherein M is CH2 or CHCH3; and
wherein R[1], R[2], and R[3] are as defined elsewhere herein.

In certain preferred such embodiments, the ring including QXYZM is aliphatic, Q is CH2, X is CHCH3, Y is CH2, Z is CHCH3 and M is CH2.

In certain preferred embodiments of the compound of formula (I) or formula (Ia):
Z is CR[7] or CHR[7] and R[7] is selected from NS(O)R[c]R[d], S(O)(R[c])NR[d], SO2R[c], and SR[c], wherein R[c] is selected from H, and methyl and wherein R[d] is H, C1-C6 alkyl, C5-C6 aryl, C6-C9 arylalkyl, C3-C6 heteroaryl, CN, COOH, or COCH3. In certain preferred embodiments, R[d] is H or methyl.

In certain preferred such embodiments, A, D, E and G are absent, X is CH and Y is CR[5], wherein R[5] is phenyl or halo, optionally Cl.

In certain embodiments of the compounds provided herein, the compound is chiral at the tertiary alcohol position of Formula (I) and (Ia). In preferred embodiments, the compound is in the (R)-configuration. In alternative preferred embodiments, the compound is in the (S)-configuration.

In certain embodiments is provided a compound selected from:
1-((1-((R)-3-Cyclohexyl-2-methylpropanoyl)-4-hydroxy-3,3-dimethylpiperidin-4-yl)methyl)pyrazin-2(1H)-one
1-((1-((R)-3-Cyclohexyl-2-methylpropanoyl)-4-hydroxy-3,3-dimethylpiperidin-4-yl)methyl)-5-phenylpyrazin-2(1H)-one
1-((7-((R)-3-Cyclohexyl-2-methylpropanoyl)-10-hydroxy-7-azaspiro[4.5]decan-10-yl)methyl)pyrazin-2(1H)-one
1-((7-((R)-3-Cyclobutyl-2-methylpropanoyl)-10-hydroxy-7-azaspiro[4.5]decan-10-yl)methyl)pyrazin-2(1H)-one
1-((10-Hydroxy-7-((R)-4,4,4-trifluoro-2-methylbutanoyl)-7-azaspiro[4.5]decan-10-yl)methyl)pyrazin-2(1H)-one
5-Chloro-1-((7-((R)-3-cyclohexyl-2-methylpropanoyl)-10-hydroxy-7-azaspiro[4.5]decan-10-yl)methyl)pyrazin-2(1H)-one
5-Bromo-1-((7-((R)-3-cyclohexyl-2-methylpropanoyl)-10-hydroxy-7-azaspiro[4.5]decan-10-yl)methyl)pyrazin-2(1H)-one
Methyl 4-((7-((R)-3-cyclohexyl-2-methylpropanoyl)-10-hydroxy-7-azaspiro[4.5]decan-10-yl)methyl)-5-oxo-4,5-dihydropyrazine-2-carboxylate
4-((7-((R)-3-Cyclohexyl-2-methylpropanoyl)-10-hydroxy-7-azaspiro[4.5]decan-10-yl)methyl)-5-oxo-4,5-dihydropyrazine-2-carboxylic acid
4-((7-((R)-3-Cyclohexyl-2-methylpropanoyl)-10-hydroxy-7-azaspiro[4.5]decan-10-yl)methyl)-N,N-dimethyl-5-oxo-4,5-dihydropyrazine-2-carboxamide
1-((7-((R)-3-Cyclohexyl-2-methylpropanoyl)-10-hydroxy-7-azaspiro[4.5]decan-10-yl)methyl)-5-(piperazine-1-carbonyl)pyrazin-2(1H)-one
1-((1-((R)-3-Cyclohexyl-2-methylpropanoyl)-4-hydroxy-3,3-dimethylpiperidin-4-yl)methyl)-5-(pyridin-3-yl)pyrazin-2(1H)-one
1-((1-((R)-3-Cyclohexyl-2-methylpropanoyl)-4-hydroxy-3,3-dimethylpiperidin-4-yl)methyl)-5-(2-oxopyrrolidin-1-yl)pyrazin-2(1H)-one
1-((1-((R)-3-Cyclohexyl-2-methylpropanoyl)-4-hydroxy-3,3-dimethylpiperidin-4-yl)methyl)-5-(pyridin-4-yl)pyrazin-2(1H)-one
1-((1-((R)-3-Cyclohexyl-2-methylpropanoyl)-4-hydroxy-3,3-dimethylpiperidin-4-yl)methyl)-5-(1H-indazol-1-yl)pyrazin-2(1H)-one
1-((1-((R)-3-Cyclohexyl-2-methylpropanoyl)-4-hydroxy-3,3-dimethylpiperidin-4-yl)methyl)-5-(2H-indazol-2-yl)pyrazin-2(1H)-one
1-((1-((R)-3-Cyclohexyl-2-methylpropanoyl)-4-hydroxy-3,3-dimethylpiperidin-4-yl)methyl)-5-(1H-pyrazol-5-yl)pyrazin-2(1H)-one
1-((1-((R)-3-Cyclohexyl-2-methylpropanoyl)-4-hydroxy-3,3-dimethylpiperidin-4-yl)methyl)-5-(1H-pyrazol-1-yl)pyrazin-2(1H)-one
1-((7-((R)-3-Cyclohexyl-2-methylpropanoyl)-10-hydroxy-7-azaspiro[4.5]decan-10-yl)methyl)-5-(pyridin-3-yl)pyrazin-2(1H)-one
1-((7-((R)-3-Cyclohexyl-2-methylpropanoyl)-10-hydroxy-7-azaspiro[4.5]decan-10-yl)methyl)-5-(pyridin-4-yl)pyrazin-2(1H)-one
1-((1-((R)-3-Cyclohexyl-2-methylpropanoyl)-4-hydroxy-3,3-dimethylpiperidin-4-yl)methyl)-5-methylpyrazin-2(1H)-one
1-((1-((R)-3-Cyclohexyl-2-methylpropanoyl)-4-hydroxy-3,3-dimethylpiperidin-4-yl)methyl)-5-cyclopropylpyrazin-2(1H)-one
1-((1-((R)-3-Cyclohexyl-2-methylpropanoyl)-4-hydroxy-3,3-dimethylpiperidin-4-yl)methyl)-5-(pyridin-2-yl)pyrazin-2(1H)-one
(R)-4-(2-Fluorophenyl)-1-((4-hydroxy-1-(3-phenylbutanoyl)piperidin-4-yl)methyl)piperazin-2-one 1-(((R)-1-((S)-3-Cyclohexyl-2-(hydroxymethyl)propanoyl)-4-hydroxy-3,3-dimethylpiperidin-4-yl)methyl)-N,N-dimethyl-6-oxo-4-phenylpiperidine-3-carboxamide
1-(((S)-1-((S)-3-Cyclohexyl-2-(hydroxymethyl)propanoyl)-4-hydroxy-3,3-dimethylpiperidin-4-yl)methyl)-N,N-dimethyl-6-oxo-4-phenylpiperidine-3-carboxamide
2-((1-((R)-3-Cyclohexyl-2-methylpropanoyl)-4-hydroxy-3,3-dimethylpiperidin-4-yl)methyl)isoindolin-1-one
(4S)-1-((1-((R)-3-Cyclohexyl-2-methylpropanoyl)-4-hydroxy-3,3-dimethylpiperidin-4-yl)methyl)-4-phenylpyrrolidin-2-one
(4R)-1-((1-((R)-3-Cyclohexyl-2-methylpropanoyl)-4-hydroxy-3,3-dimethylpiperidin-4-yl)methyl)-4-phenylpyrrolidin-2-one
4-Benzyl-1-((1-((R)-3-cyclohexyl-2-methylpropanoyl)-4-hydroxy-3,3-dimethylpiperidin-4-yl)methyl)pyrrolidin-2-one
4-((7-((R)-3-Cyclohexyl-2-methylpropanoyl)-10-hydroxy-7-azaspiro[4.5]decan-10-yl)methyl)morpholin-3-one
4-((10-Hydroxy-7-((R)-4,4,4-trifluoro-2-methylbutanoyl)-7-azaspiro[4.5]decan-10-yl)methyl)morpholin-3-one
1-((7((R)-3-Cyclohexyl-2-methylpropanoyl)-10-hydroxy-7-azaspiro[4.5]decan-10-yl)methyl)-3-propyl-1,3-dihydro-2H-benzo[d]imidazol-2-one
1-((7-((R)-3-Cyclohexyl-2-methylpropanoyl)-10-hydroxy-7-azaspiro[4.5]decan-10-yl)methyl)-4-(hydroxymethyl)pyrrolidin-2-one
4-((7-((R)-3-Cyclohexyl-2-methylpropanoyl)-10-hydroxy-7-azaspiro[4.5]decan-10-yl)methyl)-2H-pyrido[3,2-b][1,4]oxazin-3(4H)-one
1-((7-((R)-3-Cyclohexyl-2-methylpropanoyl)-10-hydroxy-7-azaspiro[4.5]decan-10-yl)methyl)indoline-2,3-dione
8-Amino-4-((7-((R)-3-cyclohexyl-2-methylpropanoyl)-10-hydroxy-7-azaspiro[4.5]decan-10-yl)methyl)-2H-benzo[b][1,4]oxazin-3(4H)-one
tert-Butyl 4-((7-((R)-3-cyclohexyl-2-methylpropanoyl)-10-hydroxy-7-azaspiro[4.5]decan-10-yl)methyl)-3-oxopiperazine-1-carboxylate
1-((7-((R)-3-Cyclohexyl-2-methylpropanoyl)-10-hydroxy-7-azaspiro[4.5]decan-10-yl)methyl)piperazin-2-one
(4S)-1-((7-((R)-3-Cyclohexyl-2-methylpropanoyl)-10-hydroxy-7-azaspiro[4.5]decan-10-yl)methyl)-4-phenylpyrrolidin-2-one
4-Benzyl-1-((7-((R)-3-cyclohexyl-2-methylpropanoyl)-10-hydroxy-7-azaspiro[4.5]decan-10-yl)methyl)pyrrolidin-2-one
2-((1-(3-Cyclohexyl-2-methylpropanoyl)-4-hydroxy-3,3-dimethylpiperidin-4-yl)methyl)isoindoline-1,3-dione
4-Benzyl-1-((1-(3-cyclohexyl-2-methylpropanoyl)-4-hydroxypiperidin-4-yl)methyl)pyrrolidin-2-one
4-Benzyl-1-((4-hydroxy-3,3-dimethyl-1-(3-phenylbutanoyl)piperidin-4-yl)methyl)pyrrolidin-2-one
4-Benzyl-1-((1-(3-cyclohexylpropanoyl)-4-hydroxy-3,3-dimethylpiperidin-4-yl)methyl)pyrrolidin-2-one
2-((1-(3-Cyclohexyl-2-methylpropanoyl)-4-hydroxy-3,3-dimethylpiperidin-4-yl)methyl)-2-azaspiro[4.5]decan-3-one
Benzyl 4-((7-((R)-3-cyclohexyl-2-methylpropanoyl)-10-hydroxy-7-azaspiro[4.5]decan-10-yl)methyl)-3-oxopiperazine-1-carboxylate
4-Acetyl-1-((7-((R)-3-cyclohexyl-2-methylpropanoyl)-10-hydroxy-7-azaspiro[4.5]decan-10-yl)methyl)piperazin-2-one
1-((7-((R)-3-Cyclohexyl-2-methylpropanoyl)-10-hydroxy-7-azaspiro[4.5]decan-10-yl)methyl)-4-(methylsulfonyl)piperazin-2-one
1-((7((R)-3-Cyclohexyl-2-methylpropanoyl)-10-hydroxy-7-azaspiro[4.5]decan-10-yl)methyl)-4-phenylpiperazin-2-one
2-((1-((R)-3-Cyclohexyl-2-methylpropanoyl)-4-hydroxy-3,3-dimethylpiperidin-4-yl)methyl)-[1,2,4]triazolo[4,3-a]pyridin-3(2H)-one
3-((7-((R)-3-Cyclohexyl-2-methylpropanoyl)-10-hydroxy-7-azaspiro[4.5]decan-10-yl)methyl)-6,7-dimethoxyquinazolin-4(3H)-one
3-((7-((R)-3-Cyclohexyl-2-methylpropanoyl)-10-hydroxy-7-azaspiro[4.5]decan-10-yl)methyl)-3,7-dihydro-4H-pyrrolo[2,3-d]pyrimidin-4-one
2-((7-((R)-3-Cyclohexyl-2-methylpropanoyl)-10-hydroxy-7-azaspiro[4.5]decan-10-yl)methyl)-1-methyl-6-(methylthio)-1,2-dihydro-3H-pyrazolo[3,4-d]pyrimidin-3-one
6-((7-((R)-3-Cyclohexyl-2-methylpropanoyl)-10-hydroxy-7-azaspiro[4.5]decan-10-yl)methyl)-2-(methylthio)pyrido[4,3-d]pyrimidin-5(6H)-one
6-((10-Hydroxy-7-((R)-4,4,4-trifluoro-2-methylbutanoyl)-7-azaspiro[4.5]decan-10-yl)methyl)-2-(methylthio)pyrido[4,3-d]pyrimidin-5(6H)-one
6-((10-Hydroxy-7-((R)-4,4,4-trifluoro-2-methylbutanoyl)-7-azaspiro[4.5]decan-10-yl)methyl)-2-(methylamino)pyrido[4,3-d]pyrimidin-5(6H)-one
2-(Dimethylamino)-6-((10-hydroxy-7-((R)-4,4,4-trifluoro-2-methylbutanoyl)-7-azaspiro[4.5]decan-10-yl)methyl)pyrido[4,3-d]pyrimidin-5(6H)-one
6-((10-Hydroxy-7-((R)-4,4,4-trifluoro-2-methylbutanoyl)-7-azaspiro[4.5]decan-10-yl)methyl)-2-methoxypyrido[4,3-d]pyrimidin-5(6H)-one
6-((10-Hydroxy-7-((R)-4,4,4-trifluoro-2-methylbutanoyl)-7-azaspiro[4.5]decan-10-yl)methyl)-2-morpholinopyrido[4,3-d]pyrimidin-5(6H)-one
6-((10-Hydroxy-7-((R)-4,4,4-trifluoro-2-methylbutanoyl)-7-azaspiro[4.5]decan-10-yl)methyl)-2-(4-methylpiperazin-1-yl)pyrido[4,3-d]pyrimidin-5(6H)-one
2-((Dimethyl(oxo)-$\lambda^6$-sulfaneylidene)amino)-6-((10-hydroxy-7-((R)-4,4,4-trifluoro-2-methylbutanoyl)-7-azaspiro[4.5]decan-10-yl)methyl)pyrido[4,3-d]pyrimidin-5(6H)-one
6-((10-Hydroxy-7-((R)-4,4,4-trifluoro-2-methylbutanoyl)-7-azaspiro[4.5]decan-10-yl)methyl)-2-(piperazin-1-yl)pyrido[4,3-d]pyrimidin-5(6H)-one
2-((10-Hydroxy-7-((R)-4,4,4-trifluoro-2-methylbutanoyl)-7-azaspiro[4.5]decan-10-yl)methyl)-1-methyl-6-(methylthio)-1,2-dihydro-3H-pyrazolo[3,4-d]pyrimidin-3-one
1-(((R)-1-((R)-3-Cyclohexyl-2-methylpropanoyl)-4-hydroxy-3,3-dimethylpiperidin-4-yl)methyl)-5-((dimethyl(oxo)-$\lambda^6$-sulfaneylidene)amino)-4-(2-fluorophenyl)pyridin-2(1H)-one
1-(((S)-1-((R)-3-Cyclohexyl-2-methylpropanoyl)-4-hydroxy-3,3-dimethylpiperidin-4-yl)methyl)-5-((dimethyl(oxo)-$\lambda^6$-sulfaneylidene)amino)-4-(2-fluorophenyl)pyridin-2(1H)-one
4-Chloro-1-((1-((R)-3-cyclohexyl-2-methylpropanoyl)-4-hydroxy-3,3-dimethylpiperidin-4-yl)methyl)-5-(S-methylsulfonimidoyl)pyridin-2(1H)-one
1-((1-((R)-3-Cyclohexyl-2-methylpropanoyl)-4-hydroxy-3,3-dimethylpiperidin-4-yl)methyl)-5-(S-methylsulfonimidoyl)-4-phenylpyridin-2(1H)-one
4-Chloro-1-((7-((R)-3-cyclohexyl-2-methylpropanoyl)-10-hydroxy-7-azaspiro[4.5]decan-10-yl)methyl)-5-((dimethyl(oxo)-$\lambda^6$-sulfaneylidene)amino)pyridin-2(1H)-one
4-Chloro-1-((7-((R)-3-cyclohexyl-2-methylpropanoyl)-10-hydroxy-7-azaspiro[4.5]decan-10-yl)methyl)-5-(methylsulfinyl)pyridin-2(1H)-one 4-Chloro-1-((7-((R)-3-cyclohexyl-2-methylpropanoyl)-10-hydroxy-7-azaspiro[4.5]decan-10-yl)methyl)-5-(S-methylsulfonimidoyl)pyridin-2(1H)-one 1-((7-((R)-3-Cyclohexyl-2-methylpropanoyl)-10-hydroxy-7-azaspiro[4.5]decan-10-yl)methyl)-5-((dimethyl(oxo)-$\lambda^6$-sulfaneylidene)amino)-4-phenylpyridin-2(1H)-one 1-((7-((R)-3-Cyclohexyl-2-methylpropanoyl)-10-hydroxy-7-azaspiro[4.5]decan-10-yl)methyl)-4-((dimethyl(oxo)-$\lambda^6$-sulfaneylidene)amino)-5-phenylpyridin-2(1H)-one 1-((7-((R)-3-Cyclohexyl-2-methylpropanoyl)-10-hydroxy-7-azaspiro[4.5]decan-10-yl)methyl)-5-(S-methylsulfonimidoyl)-4-phenylpyridin-2(1H)-one 5-((Dimethyl(oxo)-$\lambda^6$-sulfaneylidene)amino)-1-((10-hydroxy-7-((R)-4,4,4-trifluoro-2-methylbutanoyl)-7-azaspiro[4.5]decan-10-yl)methyl)-4-phenylpyridin-2(1H)-one 4-Chloro-1-((7-((R)-3-cyclohexyl-2-methylpropanoyl)-10-hydroxy-7-azaspiro[4.5]decan-10-yl)methyl)-5-(methylthio)pyridin-2(1H)-one 4-Chloro-1-((7-((R)-3-cyclohexyl-2-methylpropanoyl)-10-hydroxy-7-azaspiro[4.5]decan-10-yl)methyl)-5-(methylsulfonyl)pyridin-2(1H)-one 1-((7-((R)-3-Cyclohexyl-2-methylpropanoyl)-10-hydroxy-7-azaspiro[4.5]decan-10-yl)methyl)-5-(methylthio)-4-phenylpyridin-2(1H)-one 1-((7-((R)-3-Cyclohexyl-2-methylpropanoyl)-10-hydroxy-7-azaspiro[4.5]decan-10-yl)methyl)-5-(methylsulfinyl)-4-phenylpyridin-2(1H)-one 1-((7-((R)-3-Cyclohexyl-2-methylpropanoyl)-10-hydroxy-7-azaspiro[4.5]decan-10-yl)methyl)-5-(methylsulfonyl)-4-phenylpyridin-2(1H)-one N-Benzyl-4-((4-(2-fluorophenyl)-6-oxopyrimidin-1(6H)-yl)methyl)-4-hydroxy-N-methylpiperidine-1-carboxamide N-(Cyclohexylmethyl)-10-((5-(dimethylcarbamoyl)-2-oxo-4-phenylpyridin-1(2H)-yl)methyl)-10-hydroxy-N-methyl-7-azaspiro[4.5]decane-7-carboxamide 4-Nitrophenyl 10-((5-(dimethylcarbamoyl)-2-oxo-4-phenylpyridin-1(2H)-yl)methyl)-10-hydroxy-7-azaspiro[4.5]decane-7-carboxylate Isobutyl 10-((5-(dimethylcarbamoyl)-2-oxo-4-phenylpyridin-1(2H)-yl)methyl)-10-hydroxy-7-azaspiro[4.5]decane-7-carboxylate N-Benzyl-10-((5-(dimethylcarbamoyl)-2-oxo-4-phenylpyridin-1(2H)-yl)methyl)-10-hydroxy-7-azaspiro[4.5]decane-7-carboxamide 10-((5-(Dimethylcarbamoyl)-2-oxo-4-phenylpyridin-1(2H)-yl)methyl)-10-hydroxy-N,N-dimethyl-7-azaspiro[4.5]decane-7-carboxamide N-Benzyl-10-((5-(dimethylcarbamoyl)-2-oxo-4-phenylpyridin-1(2H)-yl)methyl)-10-hydroxy-N-methyl-7-azaspiro[4.5]decane-7-carboxamide 1-((10-Hydroxy-7-(3-(trifluoromethyl)pyrrolidine-1-carbonyl)-7-azaspiro[4.5]decan-10-yl)methyl)-N,N-dimethyl-6-oxo-4-phenyl-1,6-dihydropyridine-3-carboxamide N-Cyclohexyl-10-((5-(dimethylcarbamoyl)-2-oxo-4-phenylpyridin-1(2H)-yl)methyl)-10-hydroxy-N-methyl-7-azaspiro[4.5]decane-7-carboxamide 1-((10-Hydroxy-7-((R)-3-phenylmorpholine-4-carbonyl)-7-azaspiro[4.5]decan-10-yl)methyl)pyrazin-2(1H)-one 1-((10-Hydroxy-7-((R)-2-phenylpiperazine-1-carbonyl)-7-azaspiro[4.5]decan-10-yl)methyl)pyrazin-2(1H)-one 1-((10-Hydroxy-7-((R)-2-phenylpiperazine-1-carbonyl)-7-azaspiro[4.5]decan-10-yl)methyl)-5-methylpyrazin-2(1H)-one 1-((10-Hydroxy-7-((R)-2-phenylpiperazine-1-carbonyl)-7-azaspiro[4.5]decan-10-yl)methyl)-3-methylpyrazin-2(1H)-one (6R)-4-((10-Hydroxy-7-((R)-4,4,4-trifluoro-2-methylbutanoyl)-7-azaspiro[4.5]decan-10-yl)methyl)-6-methylmorpholin-3-one 6-Cyclopropyl-4-((10-hydroxy-7-((R)-4,4,4-trifluoro-2-methylbutanoyl)-7-azaspiro[4.5]decan-10-yl)methyl)morpholin-3-one 4-((10-Hydroxy-7-((R)-4,4,4-trifluoro-2-methylbutanoyl)-7-azaspiro[4.5]decan-10-yl)methyl)-7-oxa-4-azaspiro[2.5]octan-5-one 4-((10-Hydroxy-7-((R)-4,4,4-trifluoro-2-methylbutanoyl)-7-azaspiro[4.5]decan-10-yl)methyl)-6-methylmorpholin-3-one 1-((10-Hydroxy-7-((R)-4,4,4-trifluoro-2-methylbutanoyl)-7-azaspiro[4.5]decan-10-yl)methyl)-4-(methoxymethyl)piperidin-2-one 1-((10-Hydroxy-7-((R)-4,4,4-trifluoro-2-methylbutanoyl)-7-azaspiro[4.5]decan-10-yl)methyl)-4,6-dimethylazepan-2-one 4-Ethyl-1-((10-hydroxy-7-((R)-4,4,4-trifluoro-2-methylbutanoyl)-7-azaspiro[4.5]decan-10-yl)methyl)piperidin-2-one 1-((10-Hydroxy-7-((R)-4,4,4-trifluoro-2-methylbutanoyl)-7-azaspiro[4.5]decan-10-yl)methyl)-4-phenylazetidin-2-one 6-((7-((R)-3-Cyclohexyl-2-methylpropanoyl)-10-hydroxy-7-azaspiro[4.5]decan-10-yl)methyl)-5,6-dihydro-7H-pyrrolo[3,4-b]pyridin-7-one 6-((7-((R)-3-Cyclohexyl-2-methylpropanoyl)-10-hydroxy-7-azaspiro[4.5]decan-10-yl)methyl)-6,7-dihydro-5H-pyrrolo[3,4-b]pyridin-5-one 6-((10-Hydroxy-7-((R)-4,4,4-trifluoro-2-methylbutanoyl)-7-azaspiro[4.5]decan-10-yl)methyl)-6,7-dihydro-5H-pyrrolo[3,4-b]pyridin-5-one 2-((7-((R)-3-Cyclohexyl-2-methylpropanoyl)-10-hydroxy-7-azaspiro[4.5]decan-10-yl)methyl)isoindolin-1-one 2-((10-Hydroxy-7-((R)-4,4,4-trifluoro-2-methylbutanoyl)-7-azaspiro[4.5]decan-10-yl)methyl)-2,3-dihydro-1H-pyrrolo[3,4-c]pyridin-1-one 10-((4-Benzoyl-2-oxopiperazin-1-yl)methyl)-N-benzyl-10-hydroxy-7-azaspiro[4.5]decane-7-carboxamide 4-Benzoyl-1-((10-hydroxy-7-((R)-4,4,4-trifluoro-2-methylbutanoyl)-7-azaspiro[4.5]decan-10-yl)methyl)piperazin-2-one N-Benzyl-10-hydroxy-10-((2-oxo-4-phenylpiperazin-1-yl)methyl)-7-azaspiro[4.5]decane-7-carboxamide 1-((10-Hydroxy-7-((R)-4,4,4-trifluoro-2-methylbutanoyl)-7-azaspiro[4.5]decan-10-yl)methyl)-4-phenylpiperazin-2-one 10-((4-Acetyl-2-oxopiperazin-1-yl)methyl)-N-benzyl-10-hydroxy-7-azaspiro[4.5]decane-7-carboxamide 4-Acetyl-1-((10-hydroxy-7-((R)-4,4,4-trifluoro-2-methylbutanoyl)-7-azaspiro[4.5]decan-10-yl)methyl)piperazin-2-one 1-((10-Hydroxy-7-((R)-4,4,4-trifluoro-2-methylbutanoyl)-7-azaspiro[4.5]decan-10-yl)methyl)-4-(pyridin-2-yl)piperazin-2-one 1-((7-((R)-3-Cyclohexyl-2-methylpropanoyl)-10-hydroxy-7-azaspiro[4.5]decan-10-yl)methyl)-4-methylpiperazin-2-one N-Benzyl-10-((4-(4,4-dimethylcyclohexyl)-2-oxopiperazin-1-yl)methyl)-10-hydroxy-7-azaspiro[4.5]decane-7-carboxamide 4-(4,4-Dimethylcyclohexyl)-1-((10-hydroxy-7-((R)-4,4,4-trifluoro-2-methylbutanoyl)-7-azaspiro[4.5]decan-10-yl)methyl)piperazin-2-one 4-((10-Hydroxy-7-((R)-3-phenylmorpholine-4-carbonyl)-7-azaspiro[4.5]decan-10-yl)methyl)morpholin-3-one 4-((10-Hydroxy-7-((R)-2-phenylpiperazine-1-carbonyl)-7-azaspiro[4.5]decan-10-yl)methyl)morpholin-3-one 7-((10-Hydroxy-7-((R)-2-phenylpiperazine-1-carbonyl)-7-azaspiro[4.5]decan-10-yl)methyl)-7,8-dihydroimidazo[1,2-a]pyrazin-6(5H)-one 3-((7-((R)-3-Cyclohexyl-2-methylpropanoyl)-10-hydroxy-7-azaspiro[4.5]decan-10-yl)methyl)-2-methylquinazolin-4(3H)-one 2-((7-((R)-3-Cyclohexyl-2-methylpropanoyl)-10-hydroxy-7-azaspiro[4.5]decan-10-yl)methyl)-7-fluoroisoquinolin-1(2H)-one 2-((10-Hydroxy-7-((R)-4,4,4-trifluoro-2-methylbutanoyl)-7-azaspiro[4.5]decan-10-yl)methyl)-7-methoxyisoquinolin-1(2H)-one 3-((10-Hydroxy-7-((R)-4,4,4-trifluoro-2-methylbutanoyl)-7-azaspiro[4.5]decan-10-yl)methyl)thieno[2,3-d]pyrimidin-4(3H)-one 5-((7((R)-3-Cyclohexyl-2-methylpropanoyl)-10-hydroxy-7-azaspiro[4.5]decan-10-yl)methyl)-1-ethyl-1,5-dihydro-4H-pyrazolo[3,4-d]pyrimidin-4-one 3-((7-((R)-3-Cyclohexyl-2-methylpropanoyl)-10-hydroxy-7-azaspiro[4.5]decan-10-yl)methyl)-8-methylquinazolin-4(3H)-one 2-((10-Hydroxy-7-((R)-4,4,4-trifluoro-2-methylbutanoyl)-7-azaspiro[4.5]decan-10-yl)methyl)-6-(trifluoromethyl)isoquinolin-1(2H)-one 2-((7-((R)-3-Cyclohexyl-2-methylpropanoyl)-10-hydroxy-7-azaspiro[4.5]decan-10-yl)methyl)-7-methoxyisoquinolin-1(2H)-one 3-((7-((R)-3-Cyclohexyl-2-methylpropanoyl)-10-hydroxy-7-azaspiro[4.5]decan-10-yl)methyl)quinazolin-4(3H)-one 7-Chloro-3-((7-((R)-3-cyclohexyl-2-methylpropanoyl)-10-hydroxy-7-azaspiro[4.5]decan-10-yl)methyl)quinazolin-4(3H)-one 2-((10-Hydroxy-7-((R)-4,4,4-trifluoro-2-methylbutanoyl)-7-azaspiro[4.5]decan-10-yl)methyl)-N,N-dimethyl-1-oxo-1,2-dihydroisoquinoline-4-carboxamide 3-((7-((R)-3-Cyclohexyl-2-methylpropanoyl)-10-hydroxy-7-azaspiro[4.5]decan-10-yl)methyl)-8-fluoroquinazolin-4(3H)-one 3-((7-((R)-3-Cyclohexyl-2-methylpropanoyl)-10-hydroxy-7-azaspiro[4.5]decan-10-yl)methyl)thieno[2,3-d]pyrimidin-4(3H)-one 3-((10-Hydroxy-7-((R)-4,4,4-trifluoro-2-methylbutanoyl)-7-azaspiro[4.5]decan-10-yl)methyl)-7-methoxyquinazolin-4(3H)-one 7-Chloro-3-((10-hydroxy-7-((R)-4,4,4-trifluoro-2-methylbutanoyl)-7-azaspiro[4.5]decan-10-yl)methyl)quinazolin-4(3H)-one 7-Fluoro-2-((10-hydroxy-7-((R)-4,4,4-trifluoro-2-methylbutanoyl)-7-azaspiro[4.5]decan-10-yl)methyl)isoquinolin-1(2H)-one 2-((10-Hydroxy-7-((R)-4,4,4-trifluoro-2-methylbutanoyl)-7-azaspiro[4.5]decan-10-yl)methyl)-2,7-naphthyridin-1(2H)-one 2-((7-((R)-3-Cyclohexyl-2-methylpropanoyl)-10-hydroxy-7-azaspiro[4.5]decan-10-yl)methyl)-2,7-naphthyridin-1(2H)-one 5-((7-((R)-3-Cyclohexyl-2-methylpropanoyl)-10-hydroxy-7-azaspiro[4.5]decan-10-yl)methyl)furo[3,2-c]pyridin-4(5H)-one 3-((7-((R)-3-Cyclohexyl-2-methylpropanoyl)-10-hydroxy-7-azaspiro[4.5]decan-10-yl)methyl)-7-methoxyquinazolin-4(3H)-one 2-((10-Hydroxy-7-((R)-4,4,4-trifluoro-2-methylbutanoyl)-7-azaspiro[4.5]decan-10-yl)methyl)-6,7-dimethoxyisoquinolin-1(2H)-one 1-Ethyl-5-((10-hydroxy-7-((R)-4,4,4-trifluoro-2-methylbutanoyl)-7-azaspiro[4.5]decan-10-yl)methyl)-1,5-dihydro-4H-pyrazolo[3,4-d]pyrimidin-4-one 5-((7-((R)-3-Cyclohexyl-2-methylpropanoyl)-10-hydroxy-7-azaspiro[4.5]decan-10-yl)methyl)thieno[3,2-c]pyridin-4(5H)-one 6-Chloro-3-((7-((R)-3-cyclohexyl-2-methylpropanoyl)-10-hydroxy-7-azaspiro[4.5]decan-10-yl)methyl)quinazolin-4(3H)-one 3-((7-((R)-3-Cyclohexyl-2-methylpropanoyl)-10-hydroxy-7-azaspiro[4.5]decan-10-yl)methyl)thieno[3,2-d]pyrimidin-4(3H)-one 2-((7-((R)-3-Cyclohexyl-2-methylpropanoyl)-10-hydroxy-7-azaspiro[4.5]decan-10-yl)methyl)-N,N-dimethyl-1-oxo-1,2-dihydroisoquinoline-4-carboxamide 2-((7-((R)-3-Cyclohexyl-2-methylpropanoyl)-10-hydroxy-7-azaspiro[4.5]decan-10-yl)methyl)-6,7-dimethoxyisoquinolin-1(2H)-one 6-Chloro-3-((10-hydroxy-7-((R)-4,4,4-trifluoro-2-methylbutanoyl)-7-azaspiro[4.5]decan-10-yl)methyl)quinazolin-4(3H)-one 6-Fluoro-3-((10-hydroxy-7-((R)-4,4,4-trifluoro-2-methylbutanoyl)-7-azaspiro[4.5]decan-10-yl)methyl)quinazolin-4(3H)-one 6-Chloro-7-fluoro-3-((10-hydroxy-7-((R)-4,4,4-trifluoro-2-methylbutanoyl)-7-azaspiro[4.5]decan-10-yl)methyl)quinazolin-4(3H)-one 6-((7-((R)-3-Cyclohexyl-2-methylpropanoyl)-10-hydroxy-7-azaspiro[4.5]decan-10-yl)methyl)pyrido[3,4-b]pyrazin-5(6H)-one 3-((7-((R)-3-Cyclohexyl-2-methylpropanoyl)-10-hydroxy-7-azaspiro[4.5]decan-10-yl)methyl)-6,7-difluoroquinazolin-4(3H)-one 5-((7-((R)-3-Cyclohexyl-2-methylpropanoyl)-10-hydroxy-7-azaspiro[4.5]decan-10-yl)methyl)-2-ethyl-2,5-dihydro-4H-pyrazolo[3,4-d]pyrimidin-4-one 3-((7-((R)-3-Cyclohexyl-2-methylpropanoyl)-10-hydroxy-7-azaspiro[4.5]decan-10-yl)methyl)-2-methylpyrido[3,4-d]pyrimidin-4(3H)-one 3-((7-((R)-3-Cyclohexyl-2-methylpropanoyl)-10-hydroxy-7-azaspiro[4.5]decan-10-yl)methyl)-6-fluoroquinazolin-4(3H)-one 6-Chloro-3-((7-((R)-3-cyclohexyl-2-methylpropanoyl)-10-hydroxy-7-azaspiro[4.5]decan-10-yl)methyl)-7-fluoroquinazolin-4(3H)-one 7-Fluoro-3-((10-hydroxy-7-((R)-4,4,4-trifluoro-2-methylbutanoyl)-7-azaspiro[4.5]decan-10-yl)methyl)quinazolin-4(3H)-one 3-((7-((R)-3-Cyclohexyl-2-methylpropanoyl)-10-hydroxy-7-azaspiro[4.5]decan-10-yl)methyl)pyrido[4,3-d]pyrimidin-4(3H)-one 6-((7-((R)-3-Cyclohexyl-2-methylpropanoyl)-10-hydroxy-7-azaspiro[4.5]decan-10-yl)methyl)pyrido[4,3-d]pyrimidin-5(6H)-one 6-((10-Hydroxy-7-((R)-4,4,4-trifluoro-2-methylbutanoyl)-7-azaspiro[4.5]decan-10-yl)methyl)pyrido[4,3-d]pyrimidin-5(6H)-one 3-((7-((R)-3-Cyclohexyl-2-methylpropanoyl)-10-hydroxy-7-azaspiro[4.5]decan-10-yl)methyl)-7-(methylthio)pyrimido[4,5-d]pyrimidin-4(3H)-one 3-((10-Hydroxy-7-((R)-4,4,4-trifluoro-2-methylbutanoyl)-7-azaspiro[4.5]decan-10-yl)methyl)-7-(methylthio)pyrimido[4,5-d]pyrimidin-4(3H)-one 3-((10-Hydroxy-7-((R)-4,4,4-trifluoro-2-methylbutanoyl)-7-azaspiro[4.5]decan-10-yl)methyl)-7-morpholinopyrimido[4,5-d]pyrimidin-4(3H)-one 3-((10-Hydroxy-7-((R)-4,4,4-trifluoro-2-methylbutanoyl)-7-azaspiro[4.5]decan-10-yl)methyl)-7-(4-methylpiperazin-1-yl)pyrimido[4,5-d]pyrimidin-4(3H)-one 6-Fluoro-3-((10-Hydroxy-7-((R)-3-phenylmorpholine-4-carbonyl)-7-azaspiro[4.5]decan-10-yl)methyl)quinazolin-4(3H)-one 6,7-Difluoro-3-((10-hydroxy-7-((R)-3-phenylmorpholine-4-carbonyl)-7-azaspiro[4.5]decan-10-yl)methyl)quinazolin-4(3H)-one 2-((10-Hydroxy-7-((R)-3-phenylmorpholine-4-carbonyl)-7-azaspiro[4.5]decan-10-yl)methyl)-2,7-naphthyridin-1(2H)-one 1-Benzyl-5-((10-hydroxy-7-((R)-3-phenylmorpholine-4-carbonyl)-7-azaspiro[4.5]decan-10-yl)methyl)-1,5-dihydro-4H-pyrazolo[3,4-d]pyrimidin-4-one 1-Benzyl-5-((10-hydroxy-7-((R)-4,4,4-trifluoro-2-methylbutanoyl)-7-azaspiro[4.5]decan-10-yl)methyl)-1,5-dihydro-4H-pyrazolo[3,4-d]pyrimidin-4-one 6-Fluoro-3-((10-hydroxy-7-((R)-2-phenylpiperazine-1-carbonyl)-7-azaspiro[4.5]decan-10-yl)methyl)quinazolin-4(3H)-one 6,7-Difluoro-3-((10-hydroxy-7-((R)-2-phenylpiperazine-1-carbonyl)-7-azaspiro[4.5]decan-10-yl)methyl)quinazolin-4(3H)-one 2-((10-Hydroxy-7-((R)-2-phenylpiperazine-1-carbonyl)-7-azaspiro[4.5]decan-10-yl)methyl)-2,7-naphthyridin-1(2H)-one 1-Benzyl-5-((10-hydroxy-7-((R)-2-phenylpiperazine-1-carbonyl)-7-azaspiro[4.5]decan-10-yl)methyl)-1,5-dihydro-4H-pyrazolo[3,4-d]pyrimidin-4-one 6-((7-((R)-3-Cyclohexyl-2-methylpropanoyl)-10-hydroxy-7-azaspiro[4.5]decan-10-yl)methyl)-2-methyl-2,6-dihydro-7H-pyrazolo[4,3-d]pyrimidin-7-one 2-((7-((R)-3-Cyclohexyl-2-methylpropanoyl)-10-hydroxy-7-azaspiro[4.5]decan-10-yl)methyl)-1-methyl-1,2-dihydro-3H-pyrazolo[3,4-d]pyrimidin-3-one 2-((10-Hydroxy-7-((R)-2-phenylpiperazine-1-carbonyl)-7-azaspiro[4.5]decan-10-yl)methyl)-1-methyl-1,2-dihydro-3H-pyrazolo[3,4-d]pyrimidin-3-one 5-((7-((R)-3-Cyclohexyl-2-methylpropanoyl)-10-hydroxy-7-azaspiro[4.5]decan-10-yl)methyl)-1-phenyl-1,5-dihydro-4H-pyrazolo[3,4-d]pyrimidin-4-one 5-((10-Hydroxy-7-((R)-4,4,4-trifluoro-2-methylbutanoyl)-7-azaspiro[4.5]decan-10-yl)methyl)-1-phenyl-1,5-dihydro-4H-pyrazolo[3,4-d]pyrimidin-4-one 5-((10-Hydroxy-7-((R)-2-phenylpiperazine-1-carbonyl)-7-azaspiro[4.5]decan-10-yl)methyl)-1-phenyl-1,5-dihydro-4H-pyrazolo[3,4-d]pyrimidin-4-one 6-((10-Hydroxy-7-((R)-2-phenylpiperazine-1-carbonyl)-7-azaspiro[4.5]decan-10-yl)methyl)-2-methyl-2,6-dihydro-7H-pyrazolo[4,3-d]pyrimidin-7-one 5-((10-Hydroxy-7-((R)-4,4,4-trifluoro-2-methylbutanoyl)-7-azaspiro[4.5]decan-10-yl)methyl)-1-methyl-1,5-dihydro-4H-pyrazolo[3,4-d]pyrimidin-4-one 1-Cyclopropyl-5-((10-hydroxy-7-((R)-4,4,4-trifluoro-2-methylbutanoyl)-7-azaspiro[4.5]decan-10-yl)methyl)-1,5-dihydro-4H-pyrazolo[3,4-d]pyrimidin-4-one 5-((10-Hydroxy-7-((R)-2-phenylpiperazine-1-carbonyl)-7-azaspiro[4.5]decan-10-yl)methyl)-1-methyl-1,5-dihydro-4H-pyrazolo[3,4-d]pyrimidin-4-one 1-Cyclopropyl-5-((10-hydroxy-7-((R)-2-phenylpiperazine-1-carbonyl)-7-azaspiro[4.5]decan-10-yl)methyl)-1,5-dihydro-4H-pyrazolo[3,4-d]pyrimidin-4-one 6-(((S)-10-Hydroxy-7-((R)-2-phenylpiperazine-1-carbonyl)-7-azaspiro[4.5]decan-10-yl)methyl)-2-(methylthio)pyrido[4,3-d]pyrimidin-5(6H)-one 6-(((S)-10-Hydroxy-7-((R)-2-phenylpiperazine-1-carbonyl)-7-azaspiro[4.5]decan-10-yl)methyl)pyrido[4,3-d]pyrimidin-5(6H)-one 1-((10-Hydroxy-7-((R)-2-phenylpiperazine-1-carbonyl)-7-azaspiro[4.5]decan-10-yl)methyl)-5-(methylthio)-4-phenylpyridin-2(1H)-one 1-((10-Hydroxy-7-((R)-2-phenylpiperazine-1-carbonyl)-7-azaspiro[4.5]decan-10-yl)methyl)-5-(methylsulfinyl)-4-phenylpyridin-2(1H)-one 1-((10-Hydroxy-7-((R)-2-phenylpiperazine-1-carbonyl)-7-azaspiro[4.5]decan-10-yl)methyl)-5-(methylsulfonyl)-4-phenylpyridin-2(1H)-one 1-((10-Hydroxy-7-((R)-2-phenylpiperazine-1-carbonyl)-7-azaspiro[4.5]decan-10-yl)methyl)-5-(S-methylsulfonimidoyl)-4-phenylpyridin-2(1H)-one 1-((10-Hydroxy-7-((R)-3-phenylmorpholine-4-carbonyl)-7-azaspiro[4.5]decan-10-yl)methyl)-5-(S-methylsulfonimidoyl)-4-phenylpyridin-2(1H)-one 5-((Dimethyl(oxo)-$\lambda^6$-sulfaneylidene)amino)-1-((10-hydroxy-7-((R)-2-phenylpiperazine-1-carbonyl)-7-azaspiro[4.5]decan-10-yl)methyl)-4-phenylpyridin-2(1H)-one N-Benzyl-10-hydroxy-10-((2-oxo-4-phenylpyridin-1(2H)-yl)methyl)-7-azaspiro[4.5]decane-7-carboxamide N-Benzyl-10-hydroxy-10-((6-oxo-4-phenylpyrimidin-1(6H)-yl)methyl)-7-azaspiro[4.5]decane-7-carboxamide N-Benzyl-8-((4-(2-fluorophenyl)-6-oxopyrimidin-1(6H)-yl)methyl)-8-hydroxy-5-azaspiro[2.5]octane-5-carboxamide N-Benzyl-4-((4-(2-fluorophenyl)-6-oxopyrimidin-1(6H)-yl)methyl)-4-hydroxy-3,3-dimethylpiperidine-1-carboxamide 10-Hydroxy-10-((6-oxo-4-phenylpyrimidin-1(6H)-yl)methyl)-N-(2,2,2-trifluoroethyl)-7-azaspiro[4.5]decane-7-carboxamide 10-Hydroxy-10-((6-oxo-4-phenylpyrimidin-1(6H)-yl)methyl)-N-(pyridin-2-ylmethyl)-7-azaspiro[4.5]decane-7-carboxamide N-Benzyl-10-((4-chloro-6-oxopyrimidin-1(6H)-yl)methyl)-10-hydroxy-7-azaspiro[4.5]decane-7-carboxamide 10-Hydroxy-10-((6-oxo-4-phenylpyrimidin-1(6H)-yl)methyl)-N-(pyridin-3-ylmethyl)-7-azaspiro[4.5]decane-7-carboxamide N-Benzyl-10-hydroxy-10-((6-oxo-4-(pyridin-3-yl)pyrimidin-1(6H)-yl)methyl)-7-azaspiro[4.5]decane-7-carboxamide N-Benzyl-10-hydroxy-10-((6-oxo-4-(pyridin-4-yl)pyrimidin-1(6H)-yl)methyl)-7-azaspiro[4.5]decane-7-carboxamide N-Benzyl-10-hydroxy-10-((6-oxo-4-(pyrrolidin-1-yl)pyrimidin-1(6H)-yl)methyl)-7-azaspiro[4.5]decane-7-carboxamide N-Benzyl-10-hydroxy-10-((4-morpholino-6-oxopyrimidin-1(6H)-yl)methyl)-7-azaspiro[4.5]decane-7-carboxamide N-Benzyl-10-hydroxy-10-((4-(1-methyl-1H-pyrazol-4-yl)-6-oxopyrimidin-1(6H)-yl)methyl)-7-azaspiro[4.5]decane-7-carboxamide N-Benzyl-10-hydroxy-10-((4-(1-methyl-1H-pyrazol-5-yl)-6-oxopyrimidin-1(6H)-yl)methyl)-7-azaspiro[4.5]decane-7-carboxamide 3-((10-Hydroxy-7-(2-(trifluoromethyl)pyrrolidine-1-carbonyl)-7-azaspiro[4.5]decan-10-yl)methyl)-6-phenylpyrimidin-4(3H)-one 3-((10-Hydroxy-7-((R)-2-methylpiperazine-1-carbonyl)-7-azaspiro[4.5]decan-10-yl)methyl)-6-phenylpyrimidin-4(3H)-one 3-((10-Hydroxy-7-(2-isopropylpiperazine-1-carbonyl)-7-azaspiro[4.5]decan-10-yl)methyl)-6-phenylpyrimidin-4(3H)-one
3-((7-(3-Azabicyclo[3.1.0]hexane-3-carbonyl)-10-hydroxy-7-azaspiro[4.5]decan-10-yl)methyl)-6-phenylpyrimidin-4(3H)-one
3-(((S)-10-Hydroxy-7-((S)-2-phenylpiperazine-1-carbonyl)-7-azaspiro[4.5]decan-10-yl)methyl)-6-phenylpyrimidin-4(3H)-one
3-(((S)-10-Hydroxy-7-((R)-3-phenylmorpholine-4-carbonyl)-7-azaspiro[4.5]decan-10-yl)methyl)-6-phenylpyrimidin-4(3H)-one
3-(((S)-10-Hydroxy-7-((S)-3-phenylmorpholine-4-carbonyl)-7-azaspiro[4.5]decan-10-yl)methyl)-6-phenylpyrimidin-4(3H)-one
3-(((S)-10-Hydroxy-7-((S)-2-phenylpyrrolidine-1-carbonyl)-7-azaspiro[4.5]decan-10-yl)methyl)-6-phenylpyrimidin-4(3H)-one
(S)-10-Hydroxy-10-((6-oxo-4-phenylpyrimidin-1(6H)-yl)methyl)-N-(thiophen-2-ylmethyl)-7-azaspiro[4.5]decane-7-carboxamide
(S)-N-(4-Cyanobenzyl)-10-hydroxy-10-((6-oxo-4-phenylpyrimidin-1(6H)-yl)methyl)-7-azaspiro[4.5]decane-7-carboxamide
(S)-N-(3-Fluorobenzyl)-10-hydroxy-10-((6-oxo-4-phenylpyrimidin-1(6H)-yl)methyl)-7-azaspiro[4.5]decane-7-carboxamide
(S)-N-(Benzo[d][1,3]dioxol-5-ylmethyl)-10-hydroxy-10-((6-oxo-4-phenylpyrimidin-1(6H)-yl)methyl)-7-azaspiro[4.5]decane-7-carboxamide
(S)-N-((5-Cyclopropyl-1,2,4-oxadiazol-3-yl)methyl)-10-hydroxy-10-((6-oxo-4-phenylpyrimidin-1(6H)-yl)methyl)-7-azaspiro[4.5]decane-7-carboxamide
(S)-N-(Furan-2-ylmethyl)-10-hydroxy-10-((6-oxo-4-phenylpyrimidin-1(6H)-yl)methyl)-7-azaspiro[4.5]decane-7-carboxamide
6-Chloro-3-(((S)-10-hydroxy-7-((R)-3-phenylmorpholine-4-carbonyl)-7-azaspiro[4.5]decan-10-yl)methyl)pyrimidin-4(3H)-one
(S)-3-((10-Hydroxy-7-(3-(trifluoromethyl)azetidine-1-carbonyl)-7-azaspiro[4.5]decan-10-yl)methyl)-6-phenylpyrimidin-4(3H)-one
6-Cyclopropyl-3-(((S)-10-hydroxy-7-((R)-3-phenylmorpholine-4-carbonyl)-7-azaspiro[4.5]decan-10-yl)methyl)pyrimidin-4(3H)-one
3-(((S)-10-Hydroxy-7-((R)-3-phenylmorpholine-4-carbonyl)-7-azaspiro[4.5]decan-10-yl)methyl)-6-(pyrrolidin-1-yl)pyrimidin-4(3H)-one
3-(((S)-10-Hydroxy-7-((R)-3-phenylmorpholine-4-carbonyl)-7-azaspiro[4.5]decan-10-yl)methyl)-6-(1-methyl-1H-pyrazol-5-yl)pyrimidin-4(3H)-one
3-(((S)-10-Hydroxy-7-((R)-3-phenylmorpholine-4-carbonyl)-7-azaspiro[4.5]decan-10-yl)methyl)-6-(1-methyl-1H-pyrazol-4-yl)pyrimidin-4(3H)-one
6-(Dimethylamino)-3-(((S)-10-hydroxy-7-((R)-3-phenylmorpholine-4-carbonyl)-7-azaspiro[4.5]decan-10-yl)methyl)pyrimidin-4(3H)-one
3-(((10S)-10-Hydroxy-7-(3-(trifluoromethyl)pyrrolidine-1-carbonyl)-7-azaspiro[4.5]decan-10-yl)methyl)-6-phenylpyrimidin-4(3H)-one
3-(((S)-7-((R)-3-(4-Fluorophenyl)morpholine-4-carbonyl)-10-hydroxy-7-azaspiro[4.5]decan-10-yl)methyl)-6-phenylpyrimidin-4(3H)-one
3-((7-(3-(Cyclopropylmethyl)morpholine-4-carbonyl)-10-hydroxy-7-azaspiro[4.5]decan-10-yl)methyl)-6-phenylpyrimidin-4(3H)-one
3-((7-(3-Cyclobutylmorpholine-4-carbonyl)-10-hydroxy-7-azaspiro[4.5]decan-10-yl)methyl)-6-phenylpyrimidin-4(3H)-one
3-((10-Hydroxy-7-(3-(methoxymethyl)morpholine-4-carbonyl)-7-azaspiro[4.5]decan-10-yl)methyl)-6-phenylpyrimidin-4(3H)-one
N-(Furan-3-ylmethyl)-10-hydroxy-N-methyl-10-((6-oxo-4-phenylpyrimidin-1(6H)-yl)methyl)-7-azaspiro[4.5]decane-7-carboxamide
3-((10-Hydroxy-7-(2-methylpyrrolidine-1-carbonyl)-7-azaspiro[4.5]decan-10-yl)methyl)-6-phenylpyrimidin-4(3H)-one
N-Cyclobutyl-10-hydroxy-N-methyl-10-((6-oxo-4-phenylpyrimidin-1(6H)-yl)methyl)-7-azaspiro[4.5]decane-7-carboxamide
3-((10-Hydroxy-7-(3-(thiophen-2-yl)morpholine-4-carbonyl)-7-azaspiro[4.5]decan-10-yl)methyl)-6-phenylpyrimidin-4(3H)-one
3-((10-Hydroxy-7-(6-oxa-1-azaspiro[3.4]octane-1-carbonyl)-7-azaspiro[4.5]decan-10-yl)methyl)-6-phenylpyrimidin-4(3H)-one
3-((7-(3-Cyclopropylpyrrolidine-1-carbonyl)-10-hydroxy-7-azaspiro[4.5]decan-10-yl)methyl)-6-phenylpyrimidin-4(3H)-one
10-Hydroxy-N-(isothiazol-5-ylmethyl)-N-methyl-10-((6-oxo-4-phenylpyrimidin-1(6H)-yl)methyl)-7-azaspiro[4.5]decane-7-carboxamide
N-((3-Fluorocyclobutyl)methyl)-10-hydroxy-N-methyl-10-((6-oxo-4-phenylpyrimidin-1(6H)-yl)methyl)-7-azaspiro[4.5]decane-7-carboxamide
3-((7-(2,2-Dimethylpyrrolidine-1-carbonyl)-10-hydroxy-7-azaspiro[4.5]decan-10-yl)methyl)-6-phenylpyrimidin-4(3H)-one
3-((7-(4-(Difluoromethyl)piperidine-1-carbonyl)-10-hydroxy-7-azaspiro[4.5]decan-10-yl)methyl)-6-phenylpyrimidin-4(3H)-one
N-(Furan-2-ylmethyl)-10-hydroxy-N-methyl-10-((6-oxo-4-phenylpyrimidin-1(6H)-yl)methyl)-7-azaspiro[4.5]decane-7-carboxamide
3-((7-(2-Oxa-5-azabicyclo[4.1.0]heptane-5-carbonyl)-10-hydroxy-7-azaspiro[4.5]decan-10-yl)methyl)-6-phenylpyrimidin-4(3H)-one
10-Hydroxy-N-methyl-10-((6-oxo-4-phenylpyrimidin-1(6H)-yl)methyl)-N-(pyridin-3-ylmethyl)-7-azaspiro[4.5]decane-7-carboxamide
3-((10-Hydroxy-7-(2-(pyridin-3-yl)pyrrolidine-1-carbonyl)-7-azaspiro[4.5]decan-10-yl)methyl)-6-phenylpyrimidin-4(3H)-one
3-((7-(3-(1H-Pyrrol-1-yl)pyrrolidine-1-carbonyl)-10-hydroxy-7-azaspiro[4.5]decan-10-yl)methyl)-6-phenylpyrimidin-4(3H)-one
N-(1-Cyclopropylethyl)-10-hydroxy-N-methyl-10-((6-oxo-4-phenylpyrimidin-1(6H)-yl)methyl)-7-azaspiro[4.5]decane-7-carboxamide
3-((7-(3-Cyclopropylmorpholine-4-carbonyl)-10-hydroxy-7-azaspiro[4.5]decan-10-yl)methyl)-6-phenylpyrimidin-4(3H)-one
3-((10-Hydroxy-7-(2-(pyridin-4-yl)pyrrolidine-1-carbonyl)-7-azaspiro[4.5]decan-10-yl)methyl)-6-phenylpyrimidin-4(3H)-one
3-((10-Hydroxy-7-(5-azaspiro[2.5]octane-5-carbonyl)-7-azaspiro[4.5]decan-10-yl)methyl)-6-phenylpyrimidin-4(3H)-one
N-(3-Cyanobenzyl)-10-hydroxy-N-methyl-10-((6-oxo-4-phenylpyrimidin-1(6H)-yl)methyl)-7-azaspiro[4.5]decane-7-carboxamide 3-((7-(3-Cyclopropylazetidine-1-carbonyl)-10-hydroxy-7-azaspiro[4.5]decan-10-yl)methyl)-6-phenylpyrimidin-4(3H)-one
3-((7-(2,2-Difluoromorpholine-4-carbonyl)-10-hydroxy-7-azaspiro[4.5]decan-10-yl)methyl)-6-phenylpyrimidin-4(3H)-one
N-(2-Fluorobenzyl)-10-hydroxy-10-((6-oxo-4-phenylpyrimidin-1(6H)-yl)methyl)-7-azaspiro[4.5]decane-7-carboxamide
N-(1-(Furan-3-yl)ethyl)-10-hydroxy-10-((6-oxo-4-phenylpyrimidin-1(6H)-yl)methyl)-7-azaspiro[4.5]decane-7-carboxamide
10-Hydroxy-N-((1-methylcyclopropyl)methyl)-10-((6-oxo-4-phenylpyrimidin-1(6H)-yl)methyl)-7-azaspiro[4.5]decane-7-carboxamide
N-(3-Cyanobenzyl)-10-hydroxy-10-((6-oxo-4-phenylpyrimidin-1(6H)-yl)methyl)-7-azaspiro[4.5]decane-7-carboxamide
N-(4-(Cyanomethyl)benzyl)-10-hydroxy-10-((6-oxo-4-phenylpyrimidin-1(6H)-yl)methyl)-7-azaspiro[4.5]decane-7-carboxamide
N-((5,6-Dihydro-2H-pyran-3-yl)methyl)-10-hydroxy-10-((6-oxo-4-phenylpyrimidin-1(6H)-yl)methyl)-7-azaspiro[4.5]decane-7-carboxamide
N-((1,3-Dihydroisobenzofuran-5-yl)methyl)-10-hydroxy-10-((6-oxo-4-phenylpyrimidin-1(6H)-yl)methyl)-7-azaspiro[4.5]decane-7-carboxamide
3-((10-Hydroxy-7-(4-oxa-1-azaspiro[5.5]undecane-1-carbonyl)-7-azaspiro[4.5]decan-10-yl)methyl)-6-phenylpyrimidin-4(3H)-one
3-((7-(3-(Difluoromethyl)pyrrolidine-1-carbonyl)-10-hydroxy-7-azaspiro[4.5]decan-10-yl)methyl)-6-phenylpyrimidin-4(3H)-one
3-((10-Hydroxy-7-(3-(trifluoromethyl)morpholine-4-carbonyl)-7-azaspiro[4.5]decan-10-yl)methyl)-6-phenylpyrimidin-4(3H)-one
3-((7-(2-Cyclopropylpyrrolidine-1-carbonyl)-10-hydroxy-7-azaspiro[4.5]decan-10-yl)methyl)-6-phenylpyrimidin-4(3H)-one
3-((10-Hydroxy-7-((S)-2-(isoxazol-3-yl)pyrrolidine-1-carbonyl)-7-azaspiro[4.5]decan-10-yl)methyl)-6-phenylpyrimidin-4(3H)-one
(2S)-1-(10-Hydroxy-10-((6-oxo-4-phenylpyrimidin-1(6H)-yl)methyl)-7-azaspiro[4.5]decane-7-carbonyl)-N,N-dimethylpyrrolidine-2-carboxamide
3-((10-Hydroxy-7-((S)-2-(thiophen-2-ylmethyl)pyrrolidine-1-carbonyl)-7-azaspiro[4.5]decan-10-yl)methyl)-6-phenylpyrimidin-4(3H)-one
3-((7-((S)-2-(1H-1,2,4-Triazol-5-yl)pyrrolidine-1-carbonyl)-10-hydroxy-7-azaspiro[4.5]decan-10-yl)methyl)-6-phenylpyrimidin-4(3H)-one
3-((10-Hydroxy-7-((S)-2-(5-methyl-1H-1,2,4-triazol-3-yl)pyrrolidine-1-carbonyl)-7-azaspiro[4.5]decan-10-yl)methyl)-6-phenylpyrimidin-4(3H)-one
3-((10-Hydroxy-7-((S)-2-(4-isopropyloxazol-2-yl)pyrrolidine-1-carbonyl)-7-azaspiro[4.5]decan-10-yl)methyl)-6-phenylpyrimidin-4(3H)-one
3-((10-Hydroxy-7-(2-(2-methoxyphenyl)piperazine-1-carbonyl)-7-azaspiro[4.5]decan-10-yl)methyl)-6-phenylpyrimidin-4(3H)-one
3-((10-Hydroxy-7-(2-(3-methoxyphenyl)piperazine-1-carbonyl)-7-azaspiro[4.5]decan-10-yl)methyl)-6-phenylpyrimidin-4(3H)-one
3-((10-Hydroxy-7-(2-(4-methoxyphenyl)piperazine-1-carbonyl)-7-azaspiro[4.5]decan-10-yl)methyl)-6-phenylpyrimidin-4(3H)-one
3-((10-Hydroxy-7-(2-(pyridin-3-yl)piperazine-1-carbonyl)-7-azaspiro[4.5]decan-10-yl)methyl)-6-phenylpyrimidin-4(3H)-one
3-((7-(2-Cyclopropylpiperazine-1-carbonyl)-10-hydroxy-7-azaspiro[4.5]decan-10-yl)methyl)-6-phenylpyrimidin-4(3H)-one
3-((7-(2-Cyclobutylpiperazine-1-carbonyl)-10-hydroxy-7-azaspiro[4.5]decan-10-yl)methyl)-6-phenylpyrimidin-4(3H)-one
3-((10-Hydroxy-7-(2-(methoxymethyl)piperazine-1-carbonyl)-7-azaspiro[4.5]decan-10-yl)methyl)-6-phenylpyrimidin-4(3H)-one
3-(((S)-10-Hydroxy-7-((R)-2-phenylpiperazine-1-carbonyl)-7-azaspiro[4.5]decan-10-yl)methyl)-6-phenylpyrimidin-4(3H)-one
3-(((S)-7-((R)-4-Acetyl-2-phenylpiperazine-1-carbonyl)-10-hydroxy-7-azaspiro[4.5]decan-10-yl)methyl)-6-phenylpyrimidin-4(3H)-one
2-((10-Hydroxy-7-((R)-3-phenylmorpholine-4-carbonyl)-7-azaspiro[4.5]decan-10-yl)methyl)-5-phenylpyridazin-3(2H)-one
3-(((S)-10-Hydroxy-7-((R)-4-methyl-2-phenylpiperazine-1-carbonyl)-7-azaspiro[4.5]decan-10-yl)methyl)-6-phenylpyrimidin-4(3H)-one
6-Chloro-3-(((S)-7-((R)-3-(4-fluorophenyl)morpholine-4-carbonyl)-10-hydroxy-7-azaspiro[4.5]decan-10-yl)methyl)pyrimidin-4(3H)-one
1-(((S)-4-Hydroxy-3,3-dimethyl-1-((R)-3-phenylmorpholine-4-carbonyl)piperidin-4-yl)methyl)-N,N-dimethyl-6-oxo-4-phenyl-1,6-dihydropyridine-3-carboxamide
3-(((S)-7-((R)-3-(4-Fluorophenyl)morpholine-4-carbonyl)-10-hydroxy-7-azaspiro[4.5]decan-10-yl)methyl)-6-(1-methyl-1H-pyrazol-5-yl)pyrimidin-4(3H)-one
3-(((S)-7-((R)-3-(4-Fluorophenyl)morpholine-4-carbonyl)-10-hydroxy-7-azaspiro[4.5]decan-10-yl)methyl)-6-(1-methyl-1H-pyrazol-4-yl)pyrimidin-4(3H)-one
1-(((S)-4-Hydroxy-3,3-dimethyl-1-((R)-3-phenylmorpholine-4-carbonyl)piperidin-4-yl)methyl)-4-phenylpyridin-2(1H)-one
1-(((S)-10-Hydroxy-7-((R)-2-phenylpiperazine-1-carbonyl)-7-azaspiro[4.5]decan-10-yl)methyl)-4-phenylpyridin-2(1H)-one
1-(((S)-4-Hydroxy-3,3-dimethyl-1-((R)-2-phenylpiperazine-1-carbonyl)piperidin-4-yl)methyl)-4-phenylpyridin-2(1H)-one
3-(((S)-10-Hydroxy-7-((R)-2-phenylpiperazine-1-carbonyl)-7-azaspiro[4.5]decan-10-yl)methyl)-6-(1-methyl-1H-pyrazol-5-yl)pyrimidin-4(3H)-one
3-(((S)-10-Hydroxy-7-((R)-2-phenylpiperazine-1-carbonyl)-7-azaspiro[4.5]decan-10-yl)methyl)-6-(pyrrolidin-1-yl)pyrimidin-4(3H)-one
3-(((S)-10-Hydroxy-7-((R)-2-phenylpiperazine-1-carbonyl)-7-azaspiro[4.5]decan-10-yl)methyl)-6-(1-methyl-1H-pyrazol-4-yl)pyrimidin-4(3H)-one
6-Cyclopropyl-3-(((S)-10-hydroxy-7-((R)-2-phenylpiperazine-1-carbonyl)-7-azaspiro[4.5]decan-10-yl)methyl)pyrimidin-4(3H)-one
3-(((S)-7-((R)-3-(1H-Benzo[d]imidazol-2-yl)morpholine-4-carbonyl)-10-hydroxy-7-azaspiro[4.5]decan-10-yl)methyl)-6-phenylpyrimidin-4(3H)-one
(S)-10-Hydroxy-10-((6-oxo-4-phenylpyrimidin-1(6H)-yl)methyl)-N-((R)-2,2,2-trifluoro-1-phenylethyl)-7-azaspiro[4.5]decane-7-carboxamide
(R)-3-((4-Hydroxy-1-(3-phenylmorpholine-4-carbonyl)piperidin-4-yl)methyl)-6-phenylpyrimidin-4(3H)-one 3-((5-Hydroxy-2-((R)-3-phenylmorpholine-4-carbonyl)-2-azaspiro[5.5]undecan-5-yl)methyl)-6-phenylpyrimidin-4(3H)-one (R)-3-((4-Hydroxy-1-(2-phenylpiperazine-1-carbonyl)piperidin-4-yl)methyl)-6-phenylpyrimidin-4(3H)-one 3-((5-Hydroxy-2-((R)-2-phenylpiperazine-1-carbonyl)-2-azaspiro[5.5]undecan-5-yl)methyl)-6-phenylpyrimidin-4(3H)-one (S)-3-((10-Hydroxy-7-(2-phenylpyrazolidine-1-carbonyl)-7-azaspiro[4.5]decan-10-yl)methyl)-6-phenylpyrimidin-4(3H)-one 3-(((S)-10-Hydroxy-7-((R)-2-phenylpiperazine-1-carbonyl)-7-azaspiro[4.5]decan-10-yl)methyl)-6-methylpyrimidin-4(3H)-one (S)-N-(2,3-Difluorobenzyl)-10-hydroxy-10-((6-oxo-4-phenylpyrimidin-1(6H)-yl)methyl)-7-azaspiro[4.5]decane-7-carboxamide (S)-N-(2,6-Difluorobenzyl)-10-hydroxy-10-((6-oxo-4-phenylpyrimidin-1(6H)-yl)methyl)-7-azaspiro[4.5]decane-7-carboxamide (S)-N-(2,4-Difluorobenzyl)-10-hydroxy-10-((6-oxo-4-phenylpyrimidin-1(6H)-yl)methyl)-7-azaspiro[4.5]decane-7-carboxamide (S)-N-(3,4-Difluorobenzyl)-10-hydroxy-10-((6-oxo-4-phenylpyrimidin-1(6H)-yl)methyl)-7-azaspiro[4.5]decane-7-carboxamide 3-((9-Hydroxy-6-((R)-3-phenylmorpholine-4-carbonyl)-6-azaspiro[3.5]nonan-9-yl)methyl)-6-phenylpyrimidin-4(3H)-one 3-((9-Hydroxy-6-((R)-2-phenylpiperazine-1-carbonyl)-6-azaspiro[3.5]nonan-9-yl)methyl)-6-phenylpyrimidin-4(3H)-one (S)-N-((3,3-Difluorocyclobutyl)methyl)-10-hydroxy-10-((6-oxo-4-phenylpyrimidin-1(6H)-yl)methyl)-7-azaspiro[4.5]decane-7-carboxamide (S)-N-(1,1,1,3,3,3-Hexafluoropropan-2-yl)-10-hydroxy-10-((6-oxo-4-phenylpyrimidin-1(6H)-yl)methyl)-7-azaspiro[4.5]decane-7-carboxamide (S)-10-Hydroxy-10-((2-oxo-4-phenylpyridin-1(2H)-yl)methyl)-N-((R)-2,2,2-trifluoro-1-phenylethyl)-7-azaspiro[4.5]decane-7-carboxamide 3-(((S)-4-Hydroxy-3,3-dimethyl-1-((R)-3-phenylmorpholine-4-carbonyl)piperidin-4-yl)methyl)-6-phenylpyrimidin-4(3H)-one (S)-N-((1-Fluorocyclopropyl)methyl)-10-hydroxy-10-((6-oxo-4-phenylpyrimidin-1(6H)-yl)methyl)-7-azaspiro[4.5]decane-7-carboxamide (S)-N-((1-Fluorocyclobutyl)methyl)-10-hydroxy-10-((6-oxo-4-phenylpyrimidin-1(6H)-yl)methyl)-7-azaspiro[4.5]decane-7-carboxamide (S)-N-(Cyclopropylmethyl)-10-hydroxy-N-methyl-10-((6-oxo-4-phenylpyrimidin-1(6H)-yl)methyl)-7-azaspiro[4.5]decane-7-carboxamide 6-(2-Fluorophenyl)-3-(((S)-10-hydroxy-7-((R)-2-phenylpiperazine-1-carbonyl)-7-azaspiro[4.5]decan-10-yl)methyl)pyrimidin-4(3H)-one 6-(3-Fluorophenyl)-3-(((S)-10-hydroxy-7-((R)-2-phenylpiperazine-1-carbonyl)-7-azaspiro[4.5]decan-10-yl)methyl)pyrimidin-4(3H)-one 6-(4-Fluorophenyl)-3-(((S)-10-hydroxy-7-((R)-2-phenylpiperazine-1-carbonyl)-7-azaspiro[4.5]decan-10-yl)methyl)pyrimidin-4(3H)-one 3-(((S)-10-Hydroxy-7-((R)-2-phenylpiperazine-1-carbonyl)-7-azaspiro[4.5]decan-10-yl)methyl)-6-(2-methoxyphenyl)pyrimidin-4(3H)-one 6-(Dimethylamino)-3-(((S)-10-hydroxy-7-((R)-2-phenylpiperazine-1-carbonyl)-7-azaspiro[4.5]decan-10-yl)methyl)pyrimidin-4(3H)-one 3-(((S)-10-Hydroxy-7-((R)-2-phenylpiperazine-1-carbonyl)-7-azaspiro[4.5]decan-10-yl)methyl)-6-(methylamino)pyrimidin-4(3H)-one 3-(((S)-7-((R)-2-(3-Fluorophenyl)piperazine-1-carbonyl)-10-hydroxy-7-azaspiro[4.5]decan-10-yl)methyl)-6-phenylpyrimidin-4(3H)-one 3-((5-Hydroxy-2-((R)-2-phenylpiperazine-1-carbonyl)-9-oxa-2-azaspiro[5.5]undecan-5-yl)methyl)-6-phenylpyrimidin-4(3H)-one 3-(((S)-4-Hydroxy-3,3-dimethyl-1-((R)-2-phenylpiperazine-1-carbonyl)piperidin-4-yl)methyl)-6-phenylpyrimidin-4(3H)-one 3-(((S)-10-Hydroxy-7-((R)-2-phenyl-4-(2,2,2-trifluoroethyl)piperazine-1-carbonyl)-7-azaspiro[4.5]decan-10-yl)methyl)-6-phenylpyrimidin-4(3H)-one 3-(((S)-10-Hydroxy-7-((R)-2-phenylpiperazine-1-carbonyl)-7-azaspiro[4.5]decan-10-yl)methyl)-6-methoxypyrimidin-4(3H)-one 3-((5-Hydroxy-2-((R)-3-phenylmorpholine-4-carbonyl)-9-oxa-2-azaspiro[5.5]undecan-5-yl)methyl)-6-phenylpyrimidin-4(3H)-one 4-Chloro-1-(((S)-10-hydroxy-7-((R)-2-phenylpiperazine-1-carbonyl)-7-azaspiro[4.5]decan-10-yl)methyl)pyridin-2(1H)-one 4-Cyclopropyl-1-(((S)-10-hydroxy-7-((R)-2-phenylpiperazine-1-carbonyl)-7-azaspiro[4.5]decan-10-yl)methyl)pyridin-2(1H)-one 1-(((S)-10-Hydroxy-7-((R)-2-phenylpiperazine-1-carbonyl)-7-azaspiro[4.5]decan-10-yl)methyl)-4-(1-methyl-1H-pyrazol-5-yl)pyridin-2(1H)-one 1-(((S)-10-Hydroxy-7-((R)-2-phenylpiperazine-1-carbonyl)-7-azaspiro[4.5]decan-10-yl)methyl)-4-(1-methyl-1H-pyrazol-4-yl)pyridin-2(1H)-one 1-(((S)-10-Hydroxy-7-((R)-2-phenylpiperazine-1-carbonyl)-7-azaspiro[4.5]decan-10-yl)methyl)-4-(pyrrolidin-1-yl)pyridin-2(1H)-one 5-Fluoro-1-((10-hydroxy-7-((R)-2-phenylpiperazine-1-carbonyl)-7-azaspiro[4.5]decan-10-yl)methyl)-4-phenylpyridin-2(1H)-one 3-Fluoro-1-((10-hydroxy-7-((R)-2-phenylpiperazine-1-carbonyl)-7-azaspiro[4.5]decan-10-yl)methyl)-4-phenylpyridin-2(1H)-one (S)-3-((10-Hydroxy-7-(3-phenylthiomorpholine-4-carbonyl)-7-azaspiro[4.5]decan-10-yl)methyl)-6-phenylpyrimidin-4(3H)-one 3-(((10S)-10-Hydroxy-7-(1-imino-1-oxido-3-phenyl-1$\lambda^6$-thiomorpholine-4-carbonyl)-7-azaspiro[4.5]decan-10-yl)methyl)-6-phenylpyrimidin-4(3H)-one (S)-3-((7-(1,1-Dioxido-3-phenylthiomorpholine-4-carbonyl)-10-hydroxy-7-azaspiro[4.5]decan-10-yl)methyl)-6-phenylpyrimidin-4(3H)-one 3-(((10S)-10-Hydroxy-7-(2-(4-(trifluoromethyl)phenyl)piperazine-1-carbonyl)-7-azaspiro[4.5]decan-10-yl)methyl)-6-phenylpyrimidin-4(3H)-one, and 3-(((10S)-10-Hydroxy-7-(1-oxido-3-phenylthiomorpholine-4-carbonyl)-7-azaspiro[4.5]decan-10-yl)methyl)-6-phenylpyrimidin-4(3H)-one, or a stereoisomer, tautomer, hydrate, N-oxide derivative or pharmaceutically acceptable salt thereof.

In a third aspect the present invention provides a pharmaceutical composition comprising a compound according to any embodiment of the first or second aspect, or a stereoisomer, tautomer, hydrate, N-oxide derivative or pharmaceutically acceptable salt thereof, and at least one pharmaceutically acceptable excipient.

Pharmaceutical compositions may be formulated according to their particular use and purpose by mixing, for example, excipient, binding agent, lubricant, disintegrating agent, coating material, emulsifier, suspending agent, solvent, stabilizer, absorption enhancer and/or ointment base. The composition may be suitable for oral, injectable, rectal or topical administration.

Suitable pharmaceutically acceptable excipients would be known by the person skilled in the art, for example: fats, water, physiological saline, alcohol (e.g. ethanol), glycerol, polyols, aqueous glucose solution, extending agent, disintegrating agent, binder, lubricant, wetting agent, stabilizer, emulsifier, dispersant, preservative, sweetener, colorant, seasoning agent or aromatizer, concentrating agent, diluent, buffer substance, solvent or solubilizing agent, chemical for achieving storage effect, salt for modifying osmotic pressure, coating agent or antioxidant, saccharides such as lactose or glucose; starch of corn, wheat or rice; fatty acids such as stearic acid; inorganic salts such as magnesium metasilicate aluminate or anhydrous calcium phosphate; synthetic polymers such as polyvinylpyrrolidone or polyalkylene glycol; alcohols such as stearyl alcohol or benzyl alcohol; synthetic cellulose derivatives such as methylcellulose, carboxymethylcellulose, ethylcellulose or hydroxypropylmethylcellulose; and other conventionally used additives such as gelatin, talc, plant oil and gum arabic.

For example, the pharmaceutical composition may be administered orally, such as in the form of tablets, coated tablets, hard or soft gelatine capsules, solutions, emulsions, or suspensions. Administration can also be carried out rectally, for example using suppositories, locally or percutaneously, for example using ointments, creams, gels or solution, or parenterally, for example using injectable solutions.

For the preparation of tablets, coated tablets or hard gelatine capsules, the compounds of the present invention may be admixed with pharmaceutically inert, inorganic or organic excipients. Examples of suitable excipients include lactose, mize starch or derivatives thereof, talc or stearic acid or salts thereof. Suitable excipients for use with soft gelatine capsules include, for example, vegetable oils, waxes, fats and semi-solid or liquid polyols.

For the preparation of solutions and syrups, excipients include, for example, water, polyols, saccharose, invert sugar and glucose.

For injectable solutions, excipients include, for example, water, alcohols, polyols, glycerine and vegetable oil.

For suppositories and for local and percutaneous application, excipients include, for example, natural or hardened oils, waxes, fats and semi-solid or liquid polyols.

The pharmaceutical compositions may also contain preserving agents, solublizing agents, stabilizing agents, wetting agents, emulsifiers, sweeteners, colorants, odorants, buffers, coating agents and/or antioxidants.

For combination therapies, the second drug may be provided in pharmaceutical composition with the present invention or may be provided separately.

Thus, a pharmaceutical formulation for oral administration may, for example, be granule, tablet, sugar-coated tablet, capsule, pill, suspension or emulsion. For parenteral injection for, for example, intravenous, intramuscular or subcutaneous use, a sterile aqueous solution may be provided that may contain other substances including, for example, salts and/or glucose to make to solution isotonic. The anti-cancer agent may also be administered in the form of a suppository or pessary, or may be applied topically in the form of a lotion, solution, cream, ointment or dusting powder.

In a further aspect the invention provides a compound, including a stereoisomer, tautomer, hydrate, N-oxide derivative or pharmaceutically acceptable salt thereof, for use in therapy.

In a further aspect the invention provides a pharmaceutical composition according to the third aspect for use in therapy.

In a further aspect the invention provides a compound according to any embodiment of the first or second aspect, including a stereoisomer, tautomer, hydrate, N-oxide derivative or pharmaceutically acceptable salt thereof, for use in the treatment and/or prevention of cancer.

In a further aspect the invention provides a pharmaceutical composition according to the third aspect for use in the treatment and/or prevention of cancer.

In a further aspect the invention provides a method of treating or preventing cancer comprising administering to a subject a compound, including a stereoisomer, tautomer, hydrate, N-oxide derivative or pharmaceutically acceptable salt thereof, according to any embodiment of the first or second aspect of the invention or a pharmaceutical composition according to any embodiment of the third aspect of the invention.

In a further aspect the invention provides a use of a compound, including a stereoisomer, tautomer, hydrate, N-oxide derivative or pharmaceutically acceptable salt thereof, according to any embodiment of the first or second aspect in the manufacture of a medicament for treating or preventing cancer.

Cancers or neoplastic conditions suitable to be treated with the compounds or compositions according to the invention include, for example: prostate cancer, colon cancer, breast cancer, lung cancer, kidney cancer, CNS cancers (e.g. neuroblastomas, glioblastomas), osteosarcoma, haematological malignancies (e.g. leukemia, multiple myeloma and mantle cell lymphoma). In certain preferred embodiments the cancer is associated with p53 dysregulation. In certain preferred embodiments, the cancer is selected from a haematological malignancy (e.g. mantle cell lymphoma, multiple myeloma), prostate cancer, a neuroblastoma, or a glioblastoma. In certain preferred embodiments, the cancer is neuroblastoma or breast cancer.

Gene knockout studies have described a possible association between USP19 and fat accumulation (Coyne et al., *Diabetologia* (2019), 62, 136-146, incorporated herein by reference).

Accordingly, in a further aspect is provided a compound according to the first or second aspect, including a pharmaceutically acceptable salt, tautomer, stereoisomer or N-oxide derivative thereof, for use in a method of treating obesity.

In a further aspect is provided a pharmaceutical composition according to the third aspect for use in a method of treating obesity.

Also provided in accordance with the invention is a method of treating obesity comprising administering to a subject in need thereof an effective amount of a compound, pharmaceutically acceptable salt, tautomer, stereoisomer or N-oxide derivative according to the first or second aspect, or an effective amount of a pharmaceutical composition according to the third aspect.

Gene knockout studies have described a possible association between USP19 and insulin sensitivity (Coyne et al., supra). Coyne et al. describe an improvement in insulin sensitivity in USP19 knockout mice.

Accordingly, in a further aspect of the invention is provided a compound as defined in relation to the first or second aspect of the invention, including a pharmaceutically acceptable salt, tautomer, stereoisomer or N-oxide derivative thereof, for use in a method of treating insulin resistance.

In a further aspect of the invention is provided a compound as defined in relation to the first or second aspect of the invention, including a pharmaceutically acceptable salt, tautomer, stereoisomer or N-oxide derivative thereof, for use in a method of treating type II diabetes.

In a further aspect of the invention is provided a pharmaceutical composition according to the third aspect for use in a method of treating insulin resistance.

In a further aspect of the invention is provided a pharmaceutical composition according to the third aspect for use in a method of treating type II diabetes.

Also provided in accordance with the invention is a method of treating insulin resistance comprising administering to a subject in need thereof an effective amount of a compound, pharmaceutically acceptable salt, tautomer, stereoisomer or N-oxide derivative as defined in relation to the first or second aspect of the invention, or an effective amount of a pharmaceutical composition comprising a compound, pharmaceutically acceptable salt, tautomer, stereoisomer or N-oxide derivative as defined in relation to the first or second aspect of the invention.

Also provided in accordance with the invention is a method of treating type II diabetes comprising administering to a subject in need thereof an effective amount of a compound, pharmaceutically acceptable salt, tautomer, stereoisomer or N-oxide derivative as defined in relation to the first or second aspect of the invention, or an effective amount of a pharmaceutical composition comprising a compound, pharmaceutically acceptable salt, tautomer, stereoisomer or N-oxide derivative as defined in relation to the first or second aspect of the invention.

In a further aspect is provided a compound as defined in relation to the first or second aspect of the invention, including a pharmaceutically acceptable salt, tautomer, stereoisomer or N-oxide derivative thereof, for use in a method of treating muscular atrophy.

In a further aspect the invention provides a compound as defined in relation to the first or second aspect, or a pharmaceutically acceptable salt, tautomer, stereoisomer or N-oxide derivative thereof, for use in a method of treating cachexia or sarcopenia.

In a further aspect of the invention is provided a pharmaceutical composition according to the third aspect for use in a method of treating muscular atrophy.

In a further aspect of the invention is provided a pharmaceutical composition according to the third aspect for use in a method of treating cachexia or sarcopenia.

Also provided in accordance with the invention is a method of treating muscular atrophy comprising administering to a subject in need thereof an effective amount of a compound, pharmaceutically acceptable salt, tautomer, stereoisomer or N-oxide derivative as defined in relation to the first or second aspect of the invention, or an effective amount of a pharmaceutical composition comprising a compound, pharmaceutically acceptable salt, tautomer, stereoisomer or N-oxide derivative as defined in relation to the first or second aspect of the invention.

Also provided in accordance with the invention is a method of treating cachexia or sarcopenia comprising administering to a subject in need thereof an effective amount of a compound, pharmaceutically acceptable salt, tautomer, stereoisomer or N-oxide derivative as defined in relation to the first or second aspect of the invention, or an effective amount of a pharmaceutical composition comprising a compound, pharmaceutically acceptable salt, tautomer, stereoisomer or N-oxide derivative as defined in relation to the first or second aspect of the invention.

Muscle atrophy, cachexia or sarcopenia may be associated with or induced by HIV infection/AIDS, heart failure, rheumatoid arthritis, chronic obstructive pulmonary disease (COPD), cystic fibrosis, multiple sclerosis, motor neuron disease (MND), Parkinson's disease, dementia, or cancer.

In a further aspect, the invention provides a compound or composition according to any embodiment of the first aspect or second aspect for use in the treatment and/or prevention of Parkinson's Disease. In a further aspect, the invention provides a method of treating or preventing Parkinson's Disease comprising administering an effective amount of a compound or pharmaceutical composition according to the invention to a subject. In a further aspect, the invention provides the use of a compound according to the invention in the manufacture of a medicament for the treatment of Parkinson's Disease.

The compound or composition of the invention may be used in monotherapy and/or a combination modality. Suitable agents to be used in such combination modalities with compounds or compositions according to the invention include one or more of anti-cancer agents, anti-inflammatory agents, immuno-modulatory agents, for example immunosuppressive agents, neurological agents, anti-diabetic agents, anti-viral agents, anti-bacterial agents and/or radiation therapy.

Agents used in combination with the compounds of the present invention may target the same or a similar biological pathway to that targeted by the compounds of the present invention or may act on a different or unrelated pathway.

Depending on the disease to be treated, a variety of combination partners may be coadministered with the compounds of the present invention. The second active ingredient may include, but is not restricted to: alkylating agents, including cyclophosphamide, ifosfamide, thiotepa, melphalan, chloroethylnitrosourea and bendamustine; platinum derivatives, including cisplatin, oxaliplatin, carboplatin and satraplatin; antimitotic agents, including vinca alkaloids (vincristine, vinorelbine and vinblastine), taxanes (paclitaxel, docetaxel), epothilones and inhibitors of mitotic kinases including aurora and polo kinases; topoisomerase inhibitors, including anthracyclines, epipodophyllotoxins, camptothecin and analogues of camptothecin; antimetabolites, including 5-fluorouracil, capecitabine, cytarabine, gemcitabine, 6-mercaptopurine, 6-thioguanine, fludarabine, methotrexate and premetrexed; protein kinase inhibitors, including imatinib, gefitinib, sorafenib, sunitinib, erlotinib, dasatinib, and lapatinib; proteosome inhibitors, including bortezomib; histone deacetylase inhibitors, including valproate and SAHA; antiangiogenic drugs, including bevacizumab; monoclonal antibodies, including trastuzumab, rituximab, alemtuzumab, tositumomab, cetuximab, panitumumab; conjugates of myoclonal antibodies, including Gemtuzumab ozogamicin, Ibritumomab tiuxetan; hormonal therapies, including antiestrogens (tamoxifen, raloxifen, anastrazole, letrozole, examestane) antiandrogens (Flutamide, Biclutamide) and Luteinisng Hormone Analogues or antagonists.

In regard to aspects of the invention relating to therapeutic use of compounds according to the invention, the compounds may be administered to the subject in need of treatment in an "effective amount". The term "effective amount" refers to the amount or dose of a compound which, upon single or multiple dose administration to a subject, provides therapeutic efficacy in the treatment of disease. Therapeutically effective amounts of a compound according to the invention can comprise an amount in the range of from about 0.1 mg/kg to about 20 mg/kg per single dose. A therapeutic effective amount for any individual patient can be determined by the healthcare professional by methods understood by the skilled person. The amount of compound administered at any given time point may be varied so that optimal amounts of the compound, whether employed alone or in combination with any other therapeutic agent, are administered during the course of treatment. It is also contemplated to administer compounds according to the invention, or pharmaceutical compositions comprising such compounds, in combination with any other cancer treatment, as a combination therapy.

For combination therapies, the second drug may be provided in pharmaceutical composition with the present invention or may be provided separately.

In regard to aspects of the invention relating to therapeutic use of compounds according to the invention, in preferred embodiments the subject to be treated is human.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

The foregoing detailed description has been provided by way of explanation and illustration, and is not intended to limit the scope of the appended claims. Many variations in the presently preferred embodiments illustrated herein will be apparent to one of ordinary skill in the art, and remain within the scope of the appended claims and their equivalents.

EXAMPLES

The present invention will now be described in relation to several examples.

The examples indicated below were synthesized according to the methods described subsequently. $IC_{50}$ values were determined as described below and are represented in the following table.

TABLE 1

| Example Number | USP19 $IC_{50}$ activity |
|---|---|
| 1 | *** |
| 2 | *** |
| 3 | *** |
| 4 | *** |
| 5 | ** |
| 6 | **** |
| 7 | **** |
| 8 | **** |
| 9 | *** |
| 10 | **** |
| 11 | **** |
| 12 | *** |
| 13 | *** |
| 14 | *** |
| 15 | **† |
| 16 | **† |
| 17 | *** |

TABLE 1-continued

USP19 inhibition by exemplified compounds.

| Example Number | USP19 $IC_{50}$ activity |
|---|---|
| 18 | *** |
| 19 | *** |
| 20 | *** |
| 21 | ** |
| 22 | *** |
| 23 | ** |
| 24 | * |
| 25 | ** |
| 26 | **** |
| 27 | ** |
| 28 | ** |
| 29 | ** |
| 30 | *** |
| 31 | **** |
| 32 | * |
| 33 | ** |
| 34 | ** |
| 35 | *** |
| 36 | ** |
| 37 | *** |
| 38 | **** |
| 39 | *** |
| 40 | *** |
| 41 | *** |
| 42 | * |
| 43 | ** |
| 44 | * |
| 45 | * |
| 46 | * |
| 47 | *** |
| 48 | **** |
| 49 | *** |
| 50 | **** |
| 51 | ** |
| 52 | *** |
| 53 | ** |
| 54 | **** |
| 55 | **** |
| 56 | **** |
| 57 | *** |
| 58 | *** |
| 59 | ** |
| 60 | *** |
| 61 | *** |
| 62 | *** |
| 63 | *** |
| 64 | *** |
| 65 | * |
| 66 | *** |
| 67 | *** |
| 68 | *** |
| 69 | *** |
| 70 | **** |
| 71 | **** |
| 72 | **** |
| 73 | *** |
| 74 | **** |
| 75 | **** |
| 76 | **** |
| 77 | **** |
| 78 | **** |
| 79 | **** |
| 80 | **** |
| 81 | * |
| 82 | **** |
| 83 | * |
| 84 | ** |
| 85 | **** |
| 86 | ** |
| 87 | **** |
| 88 | **** |
| 89 | ** |
| 90 | *** |
| 91 | *** |
| 92 | **** |

TABLE 1-continued

USP19 inhibition by exemplified compounds.

| Example Number | USP19 IC$_{50}$ activity |
|---|---|
| 93 | ** |
| 94 | * |
| 95 | * |
| 96 | * |
| 97 | * |
| 98 | ** |
| 99 | ** |
| 100 | ** |
| 101 | * |
| 102 | ** |
| 103 | *** |
| 104 | * |
| 105 | *** |
| 106 | * |
| 107 | ** |
| 108 | ** |
| 109 | **** |
| 110 | **** |
| 111 | ** |
| 112 | ** |
| 113 | **** |
| 114 | *** |
| 115 | *** |
| 116 | ** |
| 117 | *** |
| 118 | *** |
| 119 | *** |
| 120 | *** |
| 121 | *** |
| 122 | * |
| 123 | * |
| 124 | **** |
| 125 | *** |
| 126 | ** |
| 127 | *** |
| 128 | *** |
| 129 | *** |
| 130 | * |
| 131 | *** |
| 132 | *** |
| 133 | ** |
| 134 | ** |
| 135 | ** |
| 136 | ** |
| 137 | **** |
| 138 | ** |
| 139 | *** |
| 140 | * |
| 141 | ** |
| 142 | ** |
| 143 | **** |
| 144 | *** |
| 145 | *** |
| 146 | *** |
| 147 | *** |
| 148 | ** |
| 149 | ** |
| 150 | * |
| 151 | **** |
| 152 | * |
| 153 | *** |
| 154 | **** |
| 155 | **** |
| 156 | ** |
| 157 | *** |
| 158 | *** |
| 159 | ** |
| 160 | **** |
| 161 | *** |
| 162 | *** |
| 163 | *** |
| 164 | **** |
| 165 | **** |
| 166 | *** |
| 167 | *** |
| 168 | ** |
| 169 | **** |
| 170 | **** |
| 171 | **** |
| 172 | **** |
| 173 | ** |
| 174 | ** |
| 175 | ** |
| 176 | **** |
| 177 | ** |
| 178 | **** |
| 179 | ** |
| 180 | ** |
| 181 | ** |
| 182 | **** |
| 183 | **** |
| 184 | **** |
| 185 | **** |
| 186 | **** |
| 187 | **** |
| 188 | **** |
| 189 | **** |
| 190 | **** |
| 191 | **** |
| 192 | **** |
| 193 | **** |
| 194 | * |
| 195 | ** |
| 196 | ** |
| 197 | * |
| 198 | * |
| 199 | * |
| 200 | ** |
| 201 | *** |
| 202 | ** |
| 203 | * |
| 204 | ** |
| 205 | *** |
| 206 | *** |
| 207 | * |
| 208 | * |
| 209 | * |
| 210 | **** |
| 211 | **** |
| 212 | * |
| 213 | **** |
| 214 | **** |
| 215 | * |
| 216 | **** |
| 217 | ** |
| 218 | ** |
| 219 | **** |
| 220 | **** |
| 221 | *** |
| 222 | **** |
| 223 | **** |
| 224 | **** |
| 225 | **** |
| 226 | **** |
| 227 | *** |
| 228 | **** |
| 229 | ** |
| 230 | * |
| 231 | ** |
| 232 | *** |
| 233 | ** |
| 234 | ** |
| 235 | **** |
| 236 | ** |
| 237 | ** |
| 238 | ** |
| 239 | ** |
| 240 | ** |
| 241 | ** |
| 242 | * |

TABLE 1-continued

USP19 inhibition by exemplified compounds.

| Example Number | USP19 IC$_{50}$ activity |
|---|---|
| 243 | ** |
| 244 | ** |
| 245 | *** |
| 246 | ** |
| 247 | ** |
| 248 | ** |
| 249 | *** |
| 250 | ** |
| 251 | *** |
| 252 | ** |
| 253 | ** |
| 254 | **** |
| 255 | *** |
| 256 | ** |
| 257 | ** |
| 258 | ** |
| 259 | ** |
| 260 | ** |
| 261 | ** |
| 262 | ** |
| 263 | ** |
| 264 | *** |
| 265 | *** |
| 266 | * |
| 267 | * |
| 268 | * |
| 269 | * |
| 270 | * |
| 271 | * |
| 272 | ** |
| 273 | ** |
| 274 | *** |
| 275 | ** |
| 276 | ** |
| 277 | * |
| 278 | **** |
| 279 | *** |
| 280 | **** |
| 281 | **** |
| 282 | **** |
| 283 | **** |
| 284 | **** |
| 285 | **** |
| 286 | **** |
| 287 | **** |
| 288 | **** |
| 289 | **** |
| 290 | **** |
| 291 | **** |
| 292 | **** |
| 293 | * |
| 294 | **** |
| 295 | *** |
| 296 | **** |
| 297 | **** |
| 298 | **** |
| 299 | *** |
| 300 | **** |
| 301 | **** |
| 302 | **** |
| 303 | **** |
| 304 | **** |
| 305 | **** |
| 306 | **** |
| 307 | **** |
| 308 | *** |
| 309 | **** |
| 310 | **** |
| 311 | *** |
| 312 | ** |
| 313 | *** |
| 314 | **** |
| 315 | **** |
| 316 | **** |
| 317 | **** |
| 318 | **** |
| 319 | **** |
| 320 | **** |
| 321 | **** |
| 322 | **** |
| 323 | **** |
| 324 | **** |
| 325 | **** |
| 326 | **** |
| 327 | **** |
| 328 | **** |
| 329 | **** |
| 330 | **** |
| 331 | **** |
| 332 | *** |
| 333 | **** |
| 334 | **** |
| 335 | **** |
| 336 | **** |
| 337 | **** |

†For Examples 15 and 16, the activity stated reflects of the 2:1 mixture of the Examples that was isolated during their preparation.

The USP19 inhibitory activities are classified as the following:

| | **** | *** | ** | * |
|---|---|---|---|---|
| USP19 IC$_{50}$ [μM] | IC$_{50}$ < 0.5 | 0.5 ≤ IC$_{50}$ < 5 | 5 ≤ IC$_{50}$ < 50 | 50 ≤ IC$_{50}$ < 250 |

USP19 activity was determined in a fluorescence polarization (FP) homogeneous assay using the isopeptide Ubiquitin-Lys-TAMRA substrate (either AUB-101, Almac Sciences Scotland Limited, or U-558, Boston Biochem, both of which gave identical results). Full-length USP19 was purchased from Boston Biochem (E-576). Unless otherwise stated, all other reagents were purchased from Sigma. Enzymatic reactions were conducted in black flat bottom polystyrene 384-well plates (Nunc) and 30 μL total volume. USP19 (2.5 nM, 10 μL) was incubated in assay buffer (50 mM HEPES (pH 7.4), 150 mM NaCl, 5 mM DTT, 0.05% BSA (w/v), 0.05% CHAPS) in the presence or absence of inhibitor (10 μL). Inhibitors were stored as 10 mM DMSO stocks in an inert environment (low humidity, dark, low oxygen, room temperature) using the Storage Pod System and serial dilutions were prepared in buffer just prior to the assay (from 200 μM to 2 pM, 8-18 data point curve). Following incubation at rt for 30 min, the enzymatic reactions were initiated by dispensing the Ub substrate (500 nM, 10 μL). FP was measured every 15 min over a period of 90 min (within the linear range of the assay) using a Synergy 4 plate reader (BioTek) exciting at 530 nm and measuring the amount of parallel and perpendicular light at 575 nm. The FP signal was subsequently normalized to the no compound control. Data were plotted and fitted, and the concentrations resulting in 50% inhibition (IC$_{50}$) were calculated using the non-linear regression curve fitting model using GraphPad (Prism). IC$_{50}$ values for the inhibitors of the invention are compiled in Table 1 and represent the average of at least two duplicate experiments.

Experimental Section

Abbreviations and Acronyms aq: aqueous; dba: dibenzylideneacetone; Bn: benzyl; Boc: tert-butyloxycarbonyl; br: broad; DBU: 1,8-diazabicyclo[5.4.0]undec-7-ene; CDI: carbonyldiimidazole; DCM: dichloromethane; d: doublet (spectral); DIPEA: diisopropylethylamine; DMA: N,N-dimethylacetamide; DMAP: 4-dimethylaminopyridine; DME: dimethoxyethane; DMF: N,N-dimethylformamide; DMSO: dimethylsulfoxide; dppf: 1,1'-bis(diphenylphosphino)ferrocene; Eaton's reagent: phosphorus pentoxide, 7.7 wt % in methanesulfonic acid; EDC: N-(3-dimethylaminopropyl)-N'-ethylcarbodiimide hydrochloride; equiv.: equivalents; EtOAc: ethyl acetate; Ex.: Example; PE: petroleum ether 40/60; ESI: electrospray ionisation; h: hour(s); HATU: N-[dimethylamino)-1H-1,2,3-triazolo-[4,5-b]pyridin-1-ylmethylene]-N-methylmethanaminium hexafluorophosphate N-oxide; hept: heptet (spectral); HPLC: high pressure liquid chromatography; IPA: 2-propanol; LC: liquid chromatography; LCMS: liquid chromatography mass spectrometry; M: molar; m/z: mass-to-charge ratio; mCPBA: 3-chloroperbenzoic acid; MeCN: acetonitrile; MeOH: methanol; min: minute(s); MS: mass spectrometry; m: multiplet (spectral); NaHMDS: sodium bis(trimethylsilyl)amide; NMP: N-methyl-2-pyrrolidone; NMR: nuclear magnetic resonance; p: pentet (spectral); Ph: phenyl; ppm: parts per million; q: quartet (spectral); quint: quintet (spectral); RBF: round-bottom flask; $R_T$: retention time; rt: room temperature; s: singlet; SM: starting material; TFA: trifluoroacetic acid; THF: tetrahydrofuran; t: triplet; UV: ultraviolet; v/v: volume per unit volume; wt %: weight percent; w/v: weight per unit volume; w/w: weight per unit weight; Xantphos: 4,5-bis(diphenylphosphino)-9,9-dimethylxanthene; XPhos: 2-dicyclohexylphosphino-2',4',6'-triisopropylbiphenyl.

General Experimental Conditions

Solvents and Reagents

Common organic solvents that were used in reactions (e.g. THF, DMF, DCM, and MeOH) were purchased anhydrous from Sigma-Aldrich® in Sure/Seal™ bottles and were handled appropriately under nitrogen. Water was deionised using an Elga PURELAB Option-Q. All other solvents used (i.e. for work-up procedures and purification) were generally HPLC grade and were used as supplied from various commercial sources. Unless otherwise stated, all starting materials used were purchased from commercial suppliers and used as supplied.

Microwave Synthesis

Microwave experiments were carried out using a Biotage Initiator™ Eight instrument. The system gives good reproducibility and control at temperature ranges from 60-250° C. and pressures of up to a maximum of 20 bar.

Flash Chromatography

Purification of compounds by flash chromatography was achieved using a Biotage Isolera Four system. Unless otherwise stated, Biotage KP-Sil SNAP cartridge columns (10-340 g) or Grace GraceResolv cartridge columns (4-330 g) were used along with the stated solvent system and an appropriate solvent gradient depending on compound polarity. In the case of more polar and basic compounds, Biotage KP-NH SNAP cartridge columns (11 g) were used.

NMR Spectroscopy $^1$H NMR spectra were recorded at ambient temperature using a Bruker Avance (300 MHz), Bruker Avance III (400 MHz) or Bruker Ascend (500 MHz) spectrometer. All chemical shifts (δ) are expressed in ppm. Residual solvent signals were used as an internal standard and the characteristic solvent peaks were corrected to the reference data outlined in *J. Org. Chem.*, 1997, 62, p7512-7515; in other cases, NMR solvents contained tetramethylsilane, which was used as an internal standard.

Liquid Chromatography Mass Spectrometry (LCMS)

Liquid Chromatography Mass Spectrometry (LCMS) experiments to determine retention times ($R_T$) and associated mass ions were performed using the following methods:

Method A: The system consisted of an Agilent Technologies 6130 quadrupole mass spectrometer linked to an Agilent Technologies 1290 Infinity LC system with UV diode array detector and autosampler. The spectrometer consisted of an electrospray ionization source operating in positive and negative ion mode. LCMS experiments were performed on each sample submitted using the following conditions: LC Column: Agilent Eclipse Plus C18 RRHD, 1.8 µm, 50×2.1 mm maintained at 40° C. Mobile phases: A) 0.1% (v/v) formic acid in water; B) 0.1% (v/v) formic acid in acetonitrile.

| Gradient Time (min) | Flow (mL/min) | % A | % B |
| --- | --- | --- | --- |
| 0.00 | 0.5 | 80 | 20 |
| 1.80 | 0.5 | 0 | 100 |
| 2.20 | 0.5 | 0 | 100 |
| 2.50 | 0.5 | 80 | 20 |
| 3.00 | 0.5 | 80 | 20 |

Method B: The system consisted of an Agilent Technologies 6140 single quadrupole mass spectrometer linked to an Agilent Technologies 1290 Infinity LC system with UV diode array detector and autosampler. The spectrometer consisted of a multimode ionization source (electrospray and atmospheric pressure chemical ionizations) operating in positive and negative ion mode. LCMS experiments were performed on each sample submitted using the following conditions: LC Column: Zorbax Eclipse Plus C18 RRHD, 1.8 µm, 50×2.1 mm maintained at 40° C. Mobile phases: A) 0.1% (v/v) formic acid in water; B) 0.1% (v/v) formic acid in acetonitrile.

| Gradient Time (min) | Flow (mL/min) | % A | % B |
| --- | --- | --- | --- |
| 0.00 | 1.0 | 95 | 5 |
| 1.80 | 1.0 | 0 | 100 |
| 2.20 | 1.0 | 0 | 100 |
| 2.21 | 1.0 | 95 | 5 |
| 2.50 | 1.0 | 95 | 5 |

Method C: The system consisted of either an Agilent Technologies 1100 Series LC/MSD system with UV diode array detector and evaporative light scattering detector (DAD/ELSD) and Agilent LC/MSD VL (G1956A), SL (G1956B) mass spectrometer or an Agilent 1200 Series LC/MSD system with DAD/ELSD and Agilent LC/MSD SL (G6130A), SL (G6140A) mass spectrometer. All of the LCMS data were obtained using the atmospheric pressure chemical ionization mode with positive and negative ion mode switching with a scan range of m/z 80-1000. LCMS experiments were performed on each sample submitted using the following conditions: LC Column: Zorbax SB-C18 RRHD, 1.8 µm, 4.6×15 mm. Mobile phases: A) 0.1% (v/v) formic acid in water; B) 0.1% (v/v) formic acid in acetonitrile.

| Gradient Time (min) | Flow (mL/min) | % A | % B |
| --- | --- | --- | --- |
| 0.00 | 3.0 | 100 | 0 |
| 1.50 | 3.0 | 0 | 100 |
| 1.80 | 3.0 | 0 | 100 |
| 1.81 | 3.0 | 100 | 0 |

Preparative High Pressure Liquid Chromatography

The system consisted of an Agilent Technologies 6120 single quadrupole mass spectrometer linked to an Agilent Technologies 1200 Preparative LC system with multiple wavelength detector and autosampler. The mass spectrometer used a multimode ionization source (electrospray and atmospheric pressure chemical ionizations) operating in positive and negative ion mode. Fraction collection was mass-triggered (multimode positive and negative ion). Purification experiments, unless otherwise stated, were performed under basic conditions at an appropriate solvent gradient that was typically determined by the retention time found using the LCMS method. In cases where the basic conditions were unsuccessful, acidic conditions were employed.

Basic conditions: LC Column: Waters XBridge™ Prep C18 5 μm OBD™ 19×50 mm column at rt. Mobile phase: A) 0.1% (v/v) ammonium hydroxide in water; B) 0.1% (v/v) ammonium hydroxide in 95:5, acetonitrile/water. Total experiment time was ca. 10 min and a generic method is shown:

| Gradient Time (min) | Flow (mL/min) | % A | % B |
|---|---|---|---|
| 0.00 | 20.0 | 50 | 50 |
| 3.00 | 20.0 | 12 | 88 |
| 5.00 | 20.0 | 12 | 88 |
| 7.00 | 20.0 | 0 | 100 |
| 8.0 | 20.0 | 0 | 100 |
| 8.20 | 20.0 | 50 | 50 |

Chiral Separation of Stereoimers by Supercritical Fluid Chromatography (SFC)

The separation of mixtures of stereoisomers was performed using the following general procedure. The mixture of stereoisomers was dissolved to 50 mg/mL in methanol and purified by SFC under the stated conditions. Combined fractions of each of stereoisomer were evaporated to near dryness using a rotary evaporator, transferred into final vessels using DCM, which was removed under a stream of compressed air at 40° C., before being stored in a vacuum oven at 40° C. and 5 mbar for 16 h.

Chiral Separation of Stereoimers by HPLC

The separation of mixtures of stereoisomers was performed using the following general procedure. The mixture of stereoisomers was dissolved to 66 mg/mL in methanol and purified by HPLC under the stated conditions. Combined fractions of each of stereoisomer were evaporated to near dryness using a rotary evaporator, transferred into final vessels using MeOH, which was removed under a stream of compressed air at 35° C., before being stored in a vacuum oven at 35° C. and 5 mbar for 16 h.

Chiral Purity Analysis

After chiral separation of mixtures of stereoisomers, each stereoisomer was analyzed to determine chiral purity using the following analytical SFC or HPLC methods under the stated conditions.

Method A (SFC):

| Column Details | Amy-C (4.6 mm × 250 mm, 5 μm) |
|---|---|
| Column Temperature | 40° C. |
| Flow Rate | 4 mL/min |
| BPR | 125 BarG |
| Detector Wavelength | 210 – 400 nm |
| Injection Volume | 1 μL |
| Isocratic Conditions | 45:55 EtOH:CO$_2$ (0.2% v/v NH$_3$) |

Method B (HPLC):

| Column Details | Lux C4 (4.6 mm × 250 mm, 5 μm) |
|---|---|
| Column Temperature | Ambient |
| Flow Rate | 1 mL/min |
| Detector Wavelength | 220 nm |
| Injection Volume | 1 μL |
| Isocratic Conditions | MeOH |

Method C (SFC):

| Column Details | Lux A1 (4.6 mm × 250 mm, 5 μm) |
|---|---|
| Column Temperature | 40° C. |
| Flow Rate | 4 mL/min |
| Detector Wavelength | 210 – 400 nm |
| Injection Volume | 1 μL |
| BPR | 125 BarG |
| Isocratic Conditions | 20:80 IPA:CO$_2$ (0.1% v/v NH$_3$) |

Method D (SFC):

| Column Details | Chiralpak IG (4.6 mm × 250 mm, 5 μm) |
|---|---|
| Column Temperature | 40° C. |
| Flow Rate | 4 mL/min |
| Detector Wavelength | 210 – 400 nm |
| Injection Volume | 1 μL |
| BPR | 125 BarG |
| Isocratic Conditions | 50:50 MeOH:CO$_2$ |

Method E (HPLC):

| Column Details | Lux A1 (4.6 mm × 150 mm, 5 μm) |
|---|---|
| Column Temperature | Ambient |
| Flow Rate | 1 mL/min |
| Detector Wavelength | 254 nm |
| Injection Volume | 1 μL |
| Isocratic Conditions | MeOH |

Nomenclature

Unless otherwise indicated, the nomenclature of structures was determined using the 'Convert Structure to Name' function of ChemDraw Professional 15.1 or 17.1 (CambridgeSoft/PerkinElmer). In the cases of 'Example 25 and Example 26' and 'Example 65 and Example 66', the tertiary alcohol group has been tentatively assigned based on previous findings in which X-ray crystal structure data was obtained and the Flack parameter was determined which showed that the (S)-configuration at this chiral centre results in the more active stereoisomers. In addition for Examples 184, 185, 210-228, 278, 279, 281-294, 299-304, 307-320, 322-324, 326-337 that contain a spirocyclopentane group and a single stereoisomer at the tertiary alcohol position, the chiral centre was also assigned to be of (S)-configuration for these compounds by inference from the gem-dimethyl analogous series. However, it should be noted that for all of these Examples, it may be the case that they have been assigned with the incorrect configuration at the tertiary alcohol position due to an error in the determination of the X-ray crystallography data or in the strategy of inferring the stereochemistry from other compounds. Therefore, it is possible that these compounds have the opposite (R)-configuration at this position, although it is thought to be unlikely. Both (R)- and (S)-enantiomers are disclosed herein, with the most potent preferred. Example 320 also has a second chiral centre at the phenylpiperazine that has been assigned (R)-configuration by inferring from the corresponding Example 278 which was prepared from commercial enantiopure tert-butyl (R)-3-phenylpiperazine-1-carboxylate. In this case, the compounds with (S)-configuration at this centre are less potent.

General Procedures

General Procedure 1: Corey-Chaykovsky Epoxidation

To a suspension of trimethylsulfonium iodide (2.5 equiv.) in DMSO under an atmosphere of nitrogen at rt was portionwise added sodium hydride (60% dispersion in mineral oil, 2.5 equiv.). The resulting mixture was stirred for 2 h before a solution of ketone (1 equiv.) in DMSO was added slowly and the reaction mixture was heated to 50° C. After 16 h, the reaction mixture was cooled to rt and quenched by the addition of water. The resulting mixture was extracted using diethyl ether, the organic layer was dried ($MgSO_4$) and concentrated under reduced pressure to give the crude epoxide.

General Procedure 2: Epoxide Opening with a Nucleophile

The appropriate nucleophile (1 equiv.), the epoxide (1-3 equiv.) and a base (1-5 equiv.) were suspended in a solvent and the reaction mixture was heated under the stated conditions. The reaction was allowed to cool to rt, saturated $NH_4Cl_{(aq)}$ or water was added and the resulting mixture was extracted using DCM or EtOAc (×3). The combined organic extracts were dried (phase separator or $MgSO_4$), concentrated under reduced pressure and the remaining residue was purified by flash chromatography to give the product.

General Procedure 3: Boc Deprotection to Free Base

The Boc protected amine (1 equiv.) was dissolved in DCM and TFA was added. The reaction was stirred at rt for the stated time before being concentrated under reduced pressure. The remaining residue was dissolved in a mixture of MeOH and DCM and loaded onto a pre-equilibrated SCX-2 cartridge. The column was washed with a 1:1 mixture of DCM/MeOH and the basic compound was eluted using a 3:2 mixture of DCM/2 M $NH_3$ in MeOH. The ammoniacal fractions were concentrated to give the desired product.

General Procedure 4: HATU Coupling

The appropriate amine (1 equiv.), carboxylic acid (1.0-1.5 equiv.) and HATU (1-1.5 equiv.) were dissolved in DCM and DIPEA (1-4 equiv.) was added. The reaction was stirred for 1-24 h before being quenched by the addition of saturated $NaHCO_{3(aq)}$. The resulting mixture was extracted using DCM (×3) using a phase separator. The combined organic extracts were concentrated under reduced pressure and the remaining residue was purified by flash chromatography to give the product.

General Procedure 5: Suzuki Coupling

A reaction vial was charged with a mixture of the appropriate halide (1 equiv.), the organoboron reagent (1-3 equiv.), a Pd catalyst (0.05-0.1 equiv.) and an inorganic base (2-5 equiv.) in a mixture of water and 1,4-dioxane or toluene, as stated. The mixture was de-gassed by evacuating and refilling with $N_2$ three times or by bubbling $N_2$ through for 5-15 min, then the reaction tube was sealed. The reaction was heated under the indicated conditions for the indicated time and allowed to cool to rt. Water or saturated $NH_4Cl_{(aq)}$ was added and the resulting mixture was extracted using DCM (×3). The combined organic extracts were dried (phase separator), concentrated under reduced pressure and the remaining residue was purified by flash chromatography to give the product.

General Procedure 6: BioShake Epoxide Opening Library

To a solution of the appropriate amide (93.9 μmol, 1 equiv.) and potassium tert-butoxide (141 μmol, 1.5 equiv.) in DMF (0.4 mL) was added a solution of Epoxide 4 (93.9 μmol, 1.0 equiv.) in DMF (0.4 mL). The reaction mixture was heated to 80° C. and agitated for 16 h in a BioShake IQ heater-shaker. The reaction mixture was concentrated in vacuo (Genevac EZ-2) and the remaining residue was dissolved in DCM (0.7 mL), washed with water (0.7 mL) and passed through a parallel phase separator. In cases of no layer separation or not passing through the frit, the solution was concentrated in vacuo (Genevac EZ-2), dissolved in DMSO (0.5-1.0 mL) and passed through syringe filter before purification using preparative HPLC.

General Procedure 7: Epoxide Opening, N-Boc Deprotection and Amide Coupling Library The appropriate amide or heterocycle (3 mmol) was dissolved in DMSO (5 mL) and cesium carbonate (3.3 mmol) was added. The mixture was stirred at rt for 30 min then the appropriate epoxide (3 mmol) was added. The resulting mixture was stirred at 70° C. for 16 h, then cooled and poured into water. The mixture was extracted (EtOAc× 2) and the organic extracts were washed with water, dried ($Na_2SO_4$) and concentrated in vacuo. The residue was dissolved in a solution of 10% TFA in DCM (20 mL). The solution was stirred for 16 h then concentrated in vacuo. The remaining residue was dissolved in a solution of benzotriazole N-oxide (10% w/v) in DMF (8 mL). The resulting solution was divided into 1 mL portions. The appropriate carboxylic acid (0.45 mmol) was added to each, followed by trimethylamine (114 mg, 1.125 mmol) and EDC (144 mg, 0.75 mmol). The mixture was stirred for 16 h, then diluted with water and extracted using DCM. The organic extract was washed using water (×3) and concentrated in vacuo. The residue was purified by preparative HPLC and the appropriate fractions were concentrated under nitrogen flow at 70° C. to give the product.

General Procedure 8: Carbamoyl Chloride Formation

To a solution of the appropriate amine (1 equiv.) and pyridine or DIPEA (2-5 equiv.) in DCM or THF at 0° C. was added a solution of triphosgene (0.3-0.6 equiv.) in DCM or THF, respectively, at 0° C. The reaction was allowed to warm to rt and stirred for 1-24 h before being quenched with 0.5-1 M HCl and extracted with DCM (×3) using a phase separator. The combined organic phases were concentrated in vacuo to give the product that was used in the next step without further purification.

General Procedure 9: Urea Formation Using a Carbamoyl Chloride Intermediate

The appropriate carbamoyl chloride (1-2.0 equiv.), amine or amine·HCl salt (1-3 equiv.) and DIPEA (2-6 equiv.) were stirred in the stated solvent at rt for the indicated time before saturated $NaHCO_{3(aq)}$ was added. The resulting mixture was extracted with DCM (×3) using a phase separator, the combined organic phases were concentrated under reduced pressure and the residue was purified by flash chromatography to give the product.

General Procedure 10: Urea Formation Using a 4-Nitrophenyl Carbamate Intermediate A solution of the appropriate 4-nitrophenyl carbamate (1 equiv.) and amine (5 equiv.) in DMA was heated at 80° C. for the indicated time before the reaction mixture was concentrated in a Genevac EZ-2 evaporator (low+high BP, 70° C.) and the residue was purified by flash chromatography to give the product.

General Procedure 11: Epoxide Opening, N-Boc Deprotection and Amide Coupling Library 2

The nucleophile to be varied (3 mmol) was dissolved in DMSO (5 mL) followed by addition of potassium tert-butoxide (370 mg, 3.3 mmol). The resulting mixture was left at rt for 30 min before Epoxide 2 (640 mg, 3 mmol) was added. The reaction mixture was stirred at 70° C. for 16 h, cooled to rt and poured into water (30 mL). The mixture was extracted using EtOAc (2×20 mL), the organic phase was washed using water (2×20 mL), dried (Na$_2$SO$_4$) and concentrated under reduced pressure to dryness. The residue was dissolved in 1:9 TFA/DCM (20 mL). The solution was stirred overnight (16-18 h) at rt. The volatiles were removed under reduced pressure, and the residue was dissolved in 8 mL of a solution of benzotriazole N-oxide (100 g) in DMF (1 L). A portion of 1 mL was taken and placed in a separated reaction vial. Acid 1 or Acid 3 (0.45 mmol), triethylamine (114 mg, 1.13 mmol) and EDC (144 mg, 0.75 mmol) were added. The reaction mixture was stirred overnight (16-18 h) at rt, before dilution with water (3 mL) and the product was extracted using DCM (4 mL). The organic layer was washed using water (3×3 mL) and the combined organic phase was evaporated to dryness. The crude residue was purified using preparative HPLC to give the title compounds.

General Procedure 12: Epoxide Opening Library Using Epoxide 5

To a stirred solution containing the nucleophile to be varied (0.2-0.3 mmol, 1.2 equiv.) and cesium carbonate (60-100 mg, 1.0 equiv.) in DMSO (0.7 mL), Epoxide 5 (50-90 mg, 1.0 equiv.) was added. The reaction mixture was stirred in an oven at 115° C. After 16 h, the reaction mixture was cooled to rt, filtered and the filtrate was directly purified by preparative HPLC to give the title compounds.

General Procedure 13: Urea Library Synthesis Using Triphosgene

A 5% w/v solution of triphosgene (59.4 mg, 200 µmol) in chloroform (1.2 mL) was prepared and cooled to 5° C. After 30 min, the amine to be varied (147 µmol, 1 equiv.) in DMF (0.2-1.5 M stock solutions) was added and the reaction mixture was stirred at 5° C. After a further 30 min, triethylamine (1.5 equiv.) was added dropwise and the resulting solution was stirred at rt for 1 h. After cooling to 5° C., 3-((10-hydroxy-7-azaspiro[4.5]decan-10-yl)methyl)-6-phenylpyrimidin-4(3H)-one (50 mg, 147 µmol) and further triethylamine (1 equiv.) were added and the temperature was allowed to increase to rt. After 12 h, the volatiles were evaporated and the residue was purified by preparative HPLC.

General Procedure 14: Urea Library Synthesis Using bis(2,2,2-trifluoroethyl) carbonate To a solution of the amine to be varied (52.4 µmol, 1 equiv.) in DMF (8 mL) in a glass vial was added bis(2,2,2-trifluoroethyl) carbonate (26.0 mg, 115 µmol). The reaction mixture was heated in an oven at 90° C. for 4 h. The volatiles were evaporated and the residue was dissolved in DMF (1 mL). 3-((10-Hydroxy-7-azaspiro[4.5]decan-10-yl)methyl)-6-phenylpyrimidin-4(3H)-one (19.6 mg, 57.6 µmol) and DBU (2.39 mg, 15.7 µmol) were added and the reaction mixture was heated in an oven at 90° C. for 12 h. The volatiles were evaporated and the residue was purified by preparative HPLC.

General Procedure 15: Urea Library Synthesis Using Carbamoyl Chloride

Each well of a 96-well microtiter plate was charged with DMF stock solutions of 10-hydroxy-10-((6-oxo-4-phenylpyrimidin-1(6H)-yl)methyl)-7-azaspiro[4.5]decane-7-carbonyl chloride (77-100 mg, 0.249 mmol, 1 equiv.) and the amine to be varied (0.230-0.300 mmol, 1.2 equiv.). DIPEA (2.0 equiv.) was added and the reaction mixtures were stirred at rt. After 16 h, the temperature was increased to 80° C. for 2.5 h. The volatiles were evaporated to dryness and the residue was purified by preparative HPLC.

General Procedure 16: Urea Library Synthesis Using Carbamoyl Chloride, N-Boc Deprotection Each well of a 96-well microtiter plate was charged with DMF stock solutions of 10-hydroxy-10-((6-oxo-4-phenylpyrimidin-1(6H)-yl)methyl)-7-azaspiro[4.5]decane-7-carbonyl chloride (77-100 mg, 0.249 mmol, 1 equiv.) and the amine to be varied (0.230-0.300 mmol, 1.2 equiv.). DIPEA (2.0 equiv.) was added and the reaction mixtures were stirred at rt. After 16 h, the temperature was increased to 80° C. for 2.5 h. The volatiles were evaporated to dryness and 1:4 TFA/DCM (1 mL) was added. After 4 h, the votailes were evaporated to dryness and the residue was purified by preparative HPLC.

Acid 1: (R)-3-Cyclohexyl-2-methylpropanoic acid

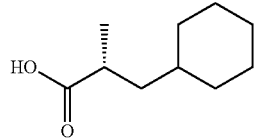

Step 1: 3-Cyclohexylpropanoyl chloride: 3-Cyclohexylpropanoic acid (2.19 mL, 12.8 mmol) was dissolved in anhydrous DCM (40 mL) and the mixture was cooled to 0° C. Thionyl chloride (1.88 mL, 25.6 mmol) was added. The colourless solution was heated to reflux for 1.75 h before the reaction was cooled to rt and stirred for a further 67.5 h. The mixture was concentrated and the yellow oil was dried by azeotropic distillation with toluene (2×10 mL) to give the crude title compound (2.3 g, quantitative) which was used without further purification. $^1$H NMR (400 MHz, CDCl$_3$): δ 2.90 (t, 2H), 1.76-1.47 (m, 7H), 1.33-1.07 (m, 4H), 0.96-0.84 (m, 2H).

Step 2: (R)-4-Benzyl-3-(3-cyclohexylpropanoyl)oxazolidin-2-one: (R)-4-Benzyloxazolidin-2-one (2.33 g, 13.2 mmol) was dissolved in anhydrous THF (40 mL) and the mixture was cooled to −78° C. n-Butyllithium (2.5 M in hexanes, 5.27 mL, 13.2 mmol) was added dropwise to form a colourless solution which was stirred at −78° C. for 1.5 h. 3-Cyclohexylpropanoyl chloride (2.3 g, 13.2 mmol) in THF (20 mL) was added dropwise. The mixture was stirred at −78° C. for 1 h then allowed to warm to rt and stirred for a further 18 h. Saturated ammonium chloride (aq) solution (14 mL) was added and the mixture was concentrated. The residue was partitioned between EtOAc (20 mL) and water (20 mL). The aqueous layer was extracted with EtOAc (3×20 mL) and the combined organic extracts were washed with brine (1×20 mL), dried over anhydrous magnesium sulfate and concentrated. The crude product was washed with ice cold cyclohexane to give the title compound (3.84 g, 93%). $^1$H NMR (400 MHz, CDCl$_3$): δ 7.38-7.18 (m, 5H), 4.72-4.63 (m, 1H), 4.24-4.13 (m, 2H), 3.30 (dd, 1H), 3.04-2.87 (m, 2H), 2.77 (dd, 1H), 1.80-1.52 (m, 7H), 1.37-1.08 (m, 4H), 1.00-0.87 (m, 2H).

Step 3: (R)-4-Benzyl-3-((R)-3-cyclohexyl-2-methylpropanoyl)oxazolidin-2-one: (R)-4-Benzyl-3-(3-cyclohexylpropanoyl)oxazolidin-2-one (2.50 g, 7.93 mmol) was dissolved in anhydrous THF (40 mL) and cooled to −78° C.

NaHMDS (1 M in THF, 8.72 mL, 8.72 mmol) was added dropwise and the yellow solution was stirred at −78° C. for 40 min. Iodomethane (2.48 mL, 39.6 mmol) was added dropwise and the reaction mixture was left to stir for 21 h. Brine (10 mL) was added dropwise and the temperature was allowed to increase to rt. The volatiles were removed in vacuo and the residue was partitioned between DCM and water. The biphasic mixture was separated and the aqueous layer was extracted using DCM (×3). The combined organic extracts were washed with brine, filtered (phase separator) and concentrated. The residue was purified by flash chromatography (0-10% EtOAc in PE) to give the title compound (1.66 g, 64%). $^1$H NMR (400 MHz, CDCl$_3$): δ 7.39-7.17 (m, 5H), 4.71-4.64 (m, 1H), 4.24-4.14 (m, 2H), 3.84 (m, 1H), 3.27 (dd, 1H), 2.76 (dd, 1H), 1.78-1.58 (br m, 6H), 1.32-1.08 (br m, 8H), 0.96-0.82 (br m, 2H).

Step 4: (R)-3-Cyclohexyl-2-methylpropanoic acid: A solution of lithium hydroxide (143 mg, 5.99 mmol) in water (3 mL) was added to hydrogen peroxide 30% w/w (3.06 mL, 29.9 mmol) at 0° C. and the solution was stirred. After 10 min, the resulting mixture was added dropwise to a solution of (R)-4-benzyl-3-((R)-3-cyclohexyl-2-methylpropanoyl)oxazolidin-2-one (990 mg, 2.99 mmol) in a mixture of water (10 mL) and THF (40 mL) at 0° C. and the solution was allowed to warm to rt over 2 h before stirring at rt for 14 h. Saturated sodium thiosulfate (aq) solution (35 mL) was added dropwise at 0° C. and the reaction mixture was stirred for 30 min. The solution was partitioned between DCM (50 mL) and water (50 mL) and the layers were separated. The aqueous layer was extracted with DCM (3×20 mL) and the organic layers were discarded. The aqueous layer was acidified with 2 M HCl$_{(aq)}$ to ~pH 2. The resulting solution was extracted with EtOAc (3×20 mL). The combined organic extracts were washed with water (3×20 mL), brine (2×20 mL), dried (MgSO$_4$) and concentrated to give the title compound (510 mg, 95%) which was used without further purification. $^1$H NMR (400 MHz, DMSO-d$_6$): δ 11.99 (s, 1H), 2.44-2.35 (m, 1H), 1.75-1.55 (br m, 5H), 1.53-1.43 (m, 1H), 1.30-1.07 (m, 5H), 1.04 (d, 3H), 0.91-0.77 (m, 2H).

Acid 2: (R)-3-Cyclobutyl-2-methylpropanoic acid

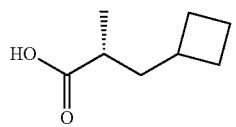

Step 1: (R)-4-Benzyl-3-(3-cyclobutylpropanoyl)oxazolidin-2-one: Pivaloyl chloride (1.2 mL, 9.75 mmol) and then triethylamine (1.41 mL, 10.1 mmol) were added to a suspension of 3-cyclobutylpropanoic acid (500 mg, 3.90 mmol), (R)-4-benzyloxazolidin-2-one (760 mg, 4.29 mmol) and lithium chloride (331 mg, 7.80 mmol) in THF (10 mL) at −20° C. After 30 min, the reaction was allowed to slowly warm to rt before being quenched by the addition of saturated NaHCO$_{3(aq)}$ (60 mL). The resulting mixture was extracted with DCM (3×30 mL) using a phase separator, the combined organic phases were concentrated in vacuo and the residue was purified by flash chromatography (0-30% EtOAc in cyclohexane) to give the title compound (966 mg, 86%) as a colourless viscous oil. $^1$H NMR (500 MHz, CDCl$_3$): δ 7.37-7.31 (m, 2H), 7.30-7.27 (m, 1H), 7.24-7.16 (m, 2H), 4.67 (ddt, J=10.5, 6.9, 3.2 Hz, 1H), 4.22-4.14 (m, 2H), 3.30 (dd, J=13.4, 3.4 Hz, 1H), 2.91-2.73 (m, 3H), 2.34 (hept, J=7.8 Hz, 1H), 2.12-2.03 (m, 2H), 1.92-1.72 (m, 4H), 1.69-1.60 (m, 2H).

Step 2: (R)-4-Benzyl-3-((R)-3-cyclobutyl-2-methylpropanoyl)oxazolidin-2-one: NaHMDS (1 M in THF, 1.91 mL, 1.91 mmol) was dropwise added to a solution of (R)-4-benzyl-3-(3-cyclobutylpropanoyl)oxazolidin-2-one (500 mg, 1.74 mmol) in THF (8.7 mL) at −78° C. and after 90 min, iodomethane (0.542 mL, 8.70 mmol) was added dropwise. The reaction was allowed to stir at −78° C. overnight before being allowed to slowly warm to rt. The reaction was quenched by the addition of saturated NH$_4$Cl$_{(aq)}$ (60 mL) and the resulting mixture was extracted with DCM (3×30 mL) using a phase separator. The combined organic phases were concentrated in vacuo and the residue was purified by flash chromatography (0-30% EtOAc in cyclohexane) to give the title compound (360 mg, 68%) as a viscous colourless oil. LCMS (Method A): R$_T$=1.91 min, m/z=302 [M+H]$^+$. $^1$H NMR (500 MHz, CDCl$_3$): δ 7.36-7.24 (m, 3H), 7.23-7.17 (m, 2H), 4.65 (ddt, J=10.3, 7.0, 3.1 Hz, 1H), 4.23-4.13 (m, 2H), 3.69 (h, J=6.9 Hz, 1H), 3.27 (dd, J=13.4, 3.3 Hz, 1H), 2.76 (dd, J=13.4, 9.6 Hz, 1H), 2.33 (hept, J=7.9 Hz, 1H), 2.01 (dddt, J=19.0, 11.7, 7.7, 3.9 Hz, 2H), 1.89-1.73 (m, 3H), 1.63 (tt, J=18.3, 9.0 Hz, 2H), 1.56-1.49 (m, 1H), 1.19 (d, J=6.8 Hz, 3H).

Step 3: (R)-3-Cyclobutyl-2-methylpropanoic acid: A 30% aqueous hydrogen peroxide solution (0.453 mL, 4.43 mmol) was added to a solution of (R)-4-benzyl-3-((R)-3-cyclobutyl-2-methylpropanoyl)oxazolidin-2-one (334 mg, 1.11 mmol) in THF (5.5 mL) and water (5.5 mL) at 0° C. After 5 min, lithium hydroxide (53 mg, 2.22 mmol) was added and the mixture was stirred for 2 h before the reaction was quenched by the addition of saturated sodium thiosulfate$_{(aq)}$ (2 mL). The reaction mixture was allowed to warm to rt, concentrated in vacuo to remove the THF and the resulting biphasic mixture was extracted using DCM (3×10 mL). The pH of the aqueous phase was adjusted to pH 2 by the addition of 2 M HCl$_{(aq)}$ and the mixture was extracted with diethyl ether (3×10 mL). The combined ethereal extractions were passed through a phase separator, carefully concentrated at 45° C. (no vacuum) and the residue was dried at 300 mbar (no heat) for 5 min to give the title compound (172 mg, 92%) as a very pale yellow oil containing 15% w/w diethyl ether. $^1$H NMR (500 MHz, CDCl$_3$): δ 2.45-2.30 (m, 2H), 2.05 (dtt, J=19.1, 7.9, 3.9 Hz, 2H), 1.91-1.74 (m, 3H), 1.67-1.48 (m, 3H), 1.18-1.10 (m, 3H).

Acid 3: (R)-4,4,4-Trifluoro-2-methylbutanoic acid

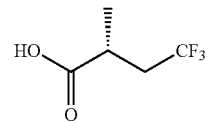

Step 1: (R)-4-Benzyl-3-(4,4,4-trifluorobutanoyl)oxazolidin-2-one: Pivaloyl chloride (6.50 mL, 52.8 mmol) and then triethylamine (7.65 mL, 54.9 mmol) were added to a suspension of 4,4,4-trifluorobutanoic acid (3.00 g, 21.1 mmol), (R)-4-benzyloxazolidin-2-one (3.74 g, 21.1 mmol) and lithium chloride (1.79 g, 42.2 mmol) in THF (50 mL) at −20° C. After 30 min, the reaction was allowed to slowly warm to rt before being quenched by the addition of saturated NaHCO$_{3(aq)}$ (60 mL). The resulting mixture was extracted with DCM (3×30 mL) using a phase separator, the combined organic phases were concentrated in vacuo, the residue was dissolved in DCM (75 mL) and washed with ~15% $NH_{3(aq)}$. The organic phase was passed through a phase separator, concentrated in vacuo and the residue was purified by flash chromatography (0-15% EtOAc in cyclohexane) to give the title compound (2.04 g, 32%) as pale yellow viscous oil. $^1$H NMR (500 MHz, $CDCl_3$): δ 7.37-7.32 (m, 2H), 7.32-7.27 (m, 1H), 7.23-7.18 (m, 2H), 4.69 (ddt, J=9.5, 7.3, 3.2 Hz, 1H), 4.28-4.18 (m, 2H), 3.34-3.15 (m, 3H), 2.78 (dd, J=13.4, 9.6 Hz, 1H), 2.64-2.47 (m, 2H).

Step 2: (R)-4-Benzyl-3-((R)-4,4,4-trifluoro-2-methylbutanoyl)oxazolidin-2-one: NaHMDS (1 M in THF, 3.07 mL, 3.07 mmol) was added dropwise to a solution of (R)-4-benzyl-3-(4,4,4-trifluorobutanoyl)oxazolidin-2-one (740 mg, 2.46 mmol) in THF (12 mL) at −78° C. and after 90 min, iodomethane (0.765 mL, 12.3 mmol) was added dropwise. The reaction was allowed to slowly warm to −20° C. and stirred at −20° C. overnight. The reaction was quenched at −20° C. by the addition of saturated $NH_4Cl_{(aq)}$ (50 mL) and water (50 mL). After warming to rt, the mixture was extracted with DCM (3×50 mL), the combined organic phases were passed through a phase separator, concentrated in vacuo and the residue was purified by flash chromatography (0-20% EtOAc in cyclohexane) to give the title compound (473 mg, 61%) as a pale yellow viscous oil. LCMS (Method A): $R_T$=1.59 min, m/z=316 $[M+H]^+$. $^1$H NMR (500 MHz, $CDCl_3$): δ 7.38-7.31 (m, 2H), 7.31-7.26 (m, 1H), 7.23-7.18 (m, 2H), 4.73-4.67 (m, 1H), 4.28-4.18 (m, 2H), 4.16-4.07 (m, 1H), 3.25 (dd, J=13.4, 3.4 Hz, 1H), 2.89-2.76 (m, 2H), 2.19 (dqd, J=15.5, 10.8, 4.8 Hz, 1H), 1.34 (d, J=7.0 Hz, 3H). $^{13}$C NMR (126 MHz, $CDCl_3$): δ 174.82, 152.97, 135.08, 129.57, 129.13, 127.62, 126.45 (q, J=276.9 Hz), 66.47, 55.44, 37.99, 36.62 (q, J=28.7 Hz), 32.52 (q, J=2.6 Hz), 18.56.

Step 3: (R)-4,4,4-Trifluoro-2-methylbutanoic acid: A 30% aqueous hydrogen peroxide solution (0.613 mL, 6.00 mmol) was added to a solution of (R)-4-benzyl-3-((R)-4,4,4-trifluoro-2-methylbutanoyl)oxazolidin-2-one (473 mg, 1.50 mmol) in THF (4 mL) and water (4 mL) at 0° C. After 5 min, lithium hydroxide (72 mg, 3.00 mmol) was added and the mixture was stirred for 70 min before the reaction was quenched by the addition of saturated sodium $thiosulfate_{(aq)}$ (2 mL). The reaction mixture was allowed to warm to rt, concentrated in vacuo to remove the THF and the resulting biphasic mixture was extracted with DCM (3×10 mL). The pH of the aqueous phase was adjusted to pH 2 by the addition of 2 M $HCl_{(aq)}$ and the mixture was extracted with DCM (3×10 mL). The combined acidic DCM extractions were passed through a phase separator, carefully concentrated at 50° C. (no vacuum) and the residue dried at 50 mbar (no heat) for 5 min to give the title compound (250 mg, quantitative) as a very pale yellow oil containing 8% w/w DCM. $^1$H NMR (500 MHz, $CDCl_3$): δ 10.96 (s, 1H), 2.84 (h, J=7.0 Hz, 1H), 2.69 (dqd, J=15.1, 10.9, 7.0 Hz, 1H), 2.18 (dqd, J=15.1, 10.6, 6.3 Hz, 1H), 1.35 (d, J=7.2 Hz, 3H).

Acid 4:
(S)-3-(Benzyloxy)-2-(cyclohexylmethyl)propanoic acid

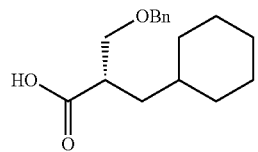 [SMILES: O=C(O)[C@H](COCc1ccccc1)CC1CCCCC1]

Step 1: (R)-4-Benzyl-3-((S)-3-(benzyloxy)-2-(cyclohexylmethyl)propanoyl)oxazolidin-2-one: Under $N_2$, to a ice cooled solution of (R)-4-benzyl-3-(3-cyclohexylpropanoyl)oxazolidin-2-one (Acid 1, Step 2) (200 mg, 0.634 mmol) in DCM (4 mL) was added titanium tetrachloride (76 μL, 0.698 mmol). The mixture was stirred at 0° C. for 10 min before triethylamine (97 μL, 0.698 mmol) was added. The reaction was stirred at 0° C. for 45 min before benzyl chloromethyl ether (0.106 mL, 0.761 mmol) was added. The reaction mixture was stirred at 0° C. for 2.5 h before being quenched with saturated $NH_4Cl_{(aq)}$ (50 mL). The mixture was extracted with DCM (3×50 mL) and the combined organic phases were washed with saturated $NH_4Cl_{(aq)}$ (50 mL). The organic phase was washed with brine (50 mL), passed through a phase separator, concentrated in vacuo and the residue was purified by flash chromatography (0-50% EtOAc in cyclohexane) to give the title compound (223 mg, 80%) as a very pale yellow oil. LCMS (Method A): $R_T$=2.21 min, m/z=436 $[M+H]^+$.

Step 2: (S)-3-(Benzyloxy)-2-(cyclohexylmethyl)propanoic acid: A 30% aqueous hydrogen peroxide solution (0.209 mL, 2.05 mmol) was added to a solution of (R)-4-benzyl-3-((S)-3-(benzyloxy)-2-(cyclohexylmethyl)propanoyl)oxazolidin-2-one (223 mg, 0.512 mmol) in THF (2.5 mL) and water (2.5 mL) at 0° C. and after 5 min lithium hydroxide (24.5 mg, 1.02 mmol) was added. After 2 h, the reaction was allowed to warm to rt and stirred for a further 16 h before the reaction was quenched by the addition of saturated sodium $thiosulfate_{(aq)}$ (2 mL). The reaction mixture was concentrated in vacuo without heating to remove the THF. The resulting biphasic mixture was diluted with water (2 mL) and extracted with DCM (3×5 mL). The aqueous phase was acidified to ~pH 2 by the addition of 2 M $HCl_{(aq)}$ and extracted with DCM (3×5 mL) using a phase separator. The DCM extractions under both basic and acidic conditions were combined, concentrated in vacuo and the residue was purified by flash chromatography (0-60% EtOAc in cyclohexane) to give the title compound (73 mg, 51%) as a pale yellow gum. LCMS (Method A): $R_T$=1.71 min, m/z=275 $[M-H]^-$. $^1$H NMR (500 MHz, $CDCl_3$): δ 7.46-7.07 (m, 5H), 4.55 (s, 1H), 3.63 (t, J=8.7 Hz, 1H), 3.56 (dd, J=9.3, 4.9 Hz, 1H), 2.83 (tt, J=8.7, 5.3 Hz, 1H), 1.77 (d, J=12.8 Hz, 1H), 1.73-1.50 (m, 5H), 1.39-1.03 (m, 6H), 0.97-0.78 (m, 2H).

Epoxide 1: tert-Butyl 4,4-dimethyl-1-oxa-6-azaspiro[2.5]octane-6-carboxylate

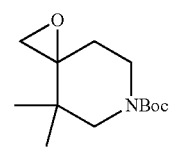 [SMILES: CC(C)(C)OC(=O)N1CCC2(CO2)C(C)(C)C1]

Prepared according to General Procedure 1 using trimethylsulfonium iodide (561 mg, 2.75 mmol), sodium hydride (60% dispersion in mineral oil, 110 mg, 2.75 mmol) and tert-butyl 3,3-dimethyl-4-oxopiperidine-1-carboxylate (250 mg, 1.10 mmol) in DMSO (2.6 mL) to give the title compound (290 mg, >100%) which was used without further purification. LCMS (Method B): $R_T$=1.47 min, m/z=142 $[M-Boc+H]^+$. $^1$H NMR (400 MHz, $CDCl_3$): δ 3.84-3.74 (m, 1H), 3.41-3.33 (m, 2H), 3.13 (d, 1H), 2.84 (d, 1H), 2.47 (d, 1H), 1.98-1.87 (m, 1H), 1.47 (s, 9H), 1.38 (d, 1H), 0.97 (s, 3H), 0.83 (s, 3H).

Epoxide 2: tert-Butyl 1-oxa-10-azadispiro[2.0.4⁴.4³]dodecane-10-carboxylate

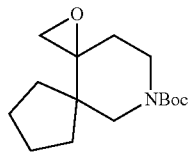 [SMILES: CC(C)(C)OC(=O)N1CCC2(CO2)C2(CCCC2)C1]

Step 1: tert-Butyl 10-oxo-7-azaspiro[4.5]decane-7-carboxylate: Potassium tert-butoxide (24.8 g, 221 mmol) was added portionwise to a solution of tert-butyl 4-oxopiperidine-1-carboxylate (20 g, 100 mmol) in toluene (200 mL) in a 3-necked 1 L RBF fitted with a reflux condenser under $N_2$ at rt. After 1 h, 1,4-dibromobutane (12.0 mL, 100 mmol) was added dropwise over 15 min and the reaction heated at reflux for 2 h. The reaction was allowed to cool to rt, diluted with 1:1 saturated $NH_4Cl_{(aq)}$/water (200 mL) and extracted with EtOAc (3×75 mL). The combined organic phases were washed with brine (100 mL), dried ($MgSO_4$) and concentrated in vacuo. The crude product was purified by flash chromatography (0-15% EtOAc in cyclohexane) to give the title compound (8.26 g, 32%) as a colourless solid. LCMS (Method A): $R_T$=1.52 min, m/z=198 [M-butene+H]⁺. ¹H NMR (500 MHz, CDCl₃): δ 3.70 (t, J=6.6 Hz, 2H), 3.45 (s, 2H), 2.48 (t, J=6.4 Hz, 2H), 1.97-1.88 (m, 2H), 1.72-1.62 (m, 4H), 1.52-1.43 (m, 2H), 1.49 (s, 9H).

Step 2: tert-Butyl 1-oxa-10-azadispiro[2.0.4⁴.4³]dodecane-10-carboxylate: To a suspension of trimethylsulfonium iodide (18.8 g, 92.1 mmol) in DMF (200 mL) at 0° C. under $N_2$ was added sodium hydride (60% dispersion in mineral oil, 3.68 g, 92.1 mmol) portionwise over 15 min. After stirring for 30 min, the mixture was allowed to warm to rt and stirred for further 1 h before a solution of tert-butyl 10-oxo-7-azaspiro[4.5]decane-7-carboxylate (15.6 g, 61.4 mmol) in DMF (100 mL) was added dropwise over 30 min using a pressure-equalized dropping funnel. The reaction mixture was stirred at rt for 2 days and slowly quenched by the addition of water (20 mL). The resulting mixture was concentrated in vacuo, water (600 mL) was added and the mixture extracted with EtOAc (3×200 mL). The combined organic phases were dried ($MgSO_4$), filtered and concentrated in vacuo. The crude product was purified by flash chromatography (0-20% EtOAc in cyclohexane) to give the title compound (14.0 g, 85%) as a colourless liquid. ¹H NMR (500 MHz, DMSO-$d_6$): δ 3.57 (s, 2H), 3.35-3.16 (m, 2H), 2.75 (d, J=4.5 Hz, 1H), 2.53 (d, J=4.5 Hz, 1H), 1.47 (s, 9H), 1.78-1.21 (m, 10H (signal overlaps with HDO)).

Epoxide 3: (R)-3-Phenyl-1-(1-oxa-6-azaspiro[2.5]octan-6-yl)butan-1-one

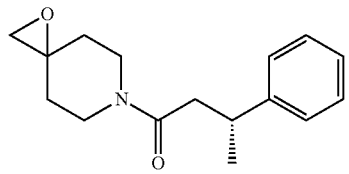 [SMILES: C[C@H](CC(=O)N1CCC2(CC1)CO2)c1ccccc1]

Step 1: (R)-1-(3-Phenylbutanoyl)piperidin-4-one: Piperidin-4-one hydrochloride (1.70 g, 12.6 mmol) was suspended in DCM (15 mL). EDC (2.89 g, 15.1 mmol) and DMAP (153 mg, 1.26 mmol) were added to the stirred suspension, followed by DIPEA (11 mL, 62.7 mmol). After 10 min, a solution of (R)-3-phenylbutanoic acid (2.47 g, 15.1 mmol) in DCM (10 mL) was added. After 20 h, a further portion of EDC (2.89 g, 15.1 mmol) was added. The reaction was stirred for a further 4 h then quenched by the addition of saturated ammonium bicarbonate (150 mL). The mixture was extracted with EtOAc (3×50 mL). The combined organic extracts were washed with water (50 mL) and brine (50 mL), dried over $MgSO_4$ and concentrated. The residue was purified by flash chromatography (0-60% EtOAc in PE) to give the title compound (2.93 g, 95%). LCMS (Method B): $R_T$=1.07 min, m/z=246 [M+H]⁺. ¹H NMR (300 MHz, CDCl₃): δ 7.44-7.13 (m, 5H), 4.30-4.03 (m, 1H), 3.77-3.58 (m, 1H), 3.46 (tdd, 2H), 3.11-2.93 (m, 2H), 2.82-2.61 (m, 4H), 1.86 (m, 1H), 1.77-1.62 (m, 1H), 1.54-1.33 (m, 2H).

Step 2: (R)-3-Phenyl-1-(1-oxa-6-azaspiro[2.5]octan-6-yl)butan-1-one: Prepared according to General Procedure 1 using trimethylsulfonium iodide (6.09 g, 29.9 mmol), sodium hydride (60% dispersion in mineral oil, 1.19 g, 29.9 mmol), and (R)-1-(3-phenylbutanoyl)piperidin-4-one (2.93 g, 11.9 mmol) in DMSO (15 mL) to give the title compound (2.68 g, 87%). LCMS (Method B): $R_T$=1.02 min, m/z=260 [M+H]⁺. ¹H NMR (300 MHz, CDCl₃): δ 7.43-7.14 (m, 5H), 4.30-3.95 (m, 1H), 3.69-3.18 (m, 4H), 2.84-2.47 (m, 4H), 1.87-1.66 (m, 2H), 1.51-1.31 (m, 2H), 1.37 (d, 3H).

Epoxide 4: (2R)-3-Cyclohexyl-1-(1-oxa-10-azadispiro[2.0.4⁴.4³]dodecan-10-yl)-2-methylpropan-1-one

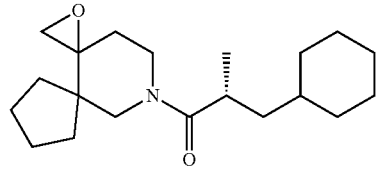 [SMILES: C[C@H](CC1CCCCC1)C(=O)N1CCC2(CO2)C2(CCCC2)C1]

Step 1: 7-Azaspiro[4.5]decan-10-one: To a stirred solution of tert-butyl 10-oxo-7-azaspiro[4.5]decane-7-carboxylate (3.68 g, 14.5 mmol) in DCM (30 mL) was added TFA (11.1 mL, 145 mmol) at rt. After 2 h, the solvents were removed in vacuo and the remaining residue was purified using 3×10 g pre-equilibrated SCX-2 cartridges (washed using 20% MeOH/DCM solution, eluted with 20% 7 M $NH_3$ MeOH/DCM solution). The basic fractions were concentrated in vacuo to afford the title compound (2.14 g, 96%) as a yellow oil. ¹H NMR (500 MHz, CDCl₃): δ 3.28 (s, 1H), 3.13 (t, 2H), 2.84 (s, 2H), 2.44 (t, 2H), 2.07-1.99 (m, 2H), 1.66-1.58 (m, 4H), 1.49-1.42 (m, 2H).

Step 2: (R)-7-(3-Cyclohexyl-2-methylpropanoyl)-7-azaspiro[4.5]decan-10-one: To a stirred solution of Acid 1 (2.8 g, 16.4 mmol) and DIPEA (9.54 mL, 54.8 mmol) in DCM (50 mL) was added HATU (7.81 g, 20.6 mmol) at rt. After 15 min, 7-azaspiro[4.5]decan-10-one (2.1 g, 13.7 mmol) was added. After 2.5 h, saturated $NaHCO_3$ (aq) solution and further DCM were added and the resulting biphasic solution was separated and extracted with DCM (×3). The combined organic phases were dried (phase separator), concentrated in vacuo, and the remaining residue was purified by flash chromatography (0-40% EtOAc in cyclohexane) to afford the title compound (3.15 g, 75%) as a yellow oil. LCMS (Method A): $R_T$=1.87 min, m/z=306 [M+H]⁺. ¹H NMR (500 MHz, CDCl₃): δ 3.97-3.42 (m, 4H), 2.96-2.84 (m, 1H), 2.57-2.46 (m, 2H), 2.04-1.84 (br m, 2H), 1.78-1.59 (br m, 10H), 1.52-1.44 (m, 2H), 1.34-1.07 (m, 8H), 0.96-0.81 (br m, 2H).

Step 3: (2R)-3-Cyclohexyl-1-(1-oxa-10-azadispiro[2.0.4⁴.4³]dodecan-10-yl)-2-methylpropan-1-one: To a stirred solution of trimethylsulfonium iodide (2.42 g, 11.9 mmol) in DMF (20 mL) at 0° C. was added sodium hydride (60% dispersion in mineral oil, 474 mg, 11.9 mmol) portionwise. The mixture was stirred for 50 min before a solution of (R)-7-(3-cyclohexyl-2-methylpropanoyl)-7-azaspiro[4.5]decan-10-one (2.41 g, 7.91 mmol) in DMF (10 mL) was added dropwise to afford a yellow solution. After 16 h, the reaction mixture was quenched with water and extracted into EtOAc (×2). The combined organic phases were washed using water (×3), saturated NaHCO₃(aq) and brine, and dried (phase separator). The solvents were removed in vacuo to afford the title compound (2.18 g, 86%). LCMS (Method A): $R_T$=2.00 min, m/z=320 [M+H]⁺. ¹H NMR (500 MHz, CDCl₃): δ 4.00-3.19 (m, 4H), 2.92-2.74 (m, 2H), 2.59-2.52 (m, 1H), 1.88-1.55 (br m, 11H), 1.51-1.29 (m, 4H), 1.28-1.06 (br m, 8H), 0.94-0.80 (br m, 3H).

Epoxide 5: (2R)-1-(1-Oxa-10-azadispiro[2.0.4⁴.4³]dodecan-10-yl)-4,4,4-trifluoro-2-methylbutan-1-one

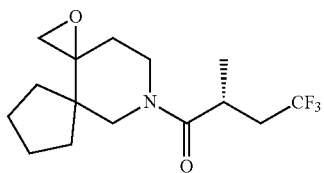 [SMILES: C[C@H](CC(F)(F)F)C(=O)N1CCC2(CO2)C2(CCCC2)C1]

The title compound was prepared according to the procedure for Epoxide 4 except that in Step 2, Acid 3 was used instead of Acid 1.

Example 1: 1-((1-((R)-3-Cyclohexyl-2-methylpropanoyl)-4-hydroxy-3,3-dimethylpiperidin-4-yl)methyl)pyrazin-2(1H)-one

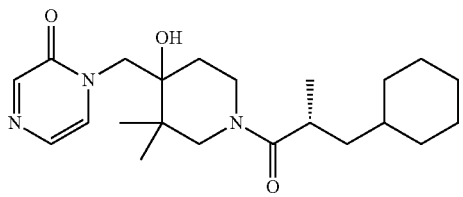 [SMILES: C[C@H](CC1CCCCC1)C(=O)N1CCC(O)(Cn2ccncc2=O)C(C)(C)C1]

Step 1: tert-Butyl 4-hydroxy-3,3-dimethyl-4-((2-oxopyrazin-1(2H)-yl)methyl)piperidine-1-carboxylate: Prepared according to General Procedure 2 using pyrazin-2(1H)-one (30 mg, 0.312 mmol), Epoxide 1 (98 mg, 0.406 mmol) and cesium carbonate (204 mg, 0.624 mmol) in NMP (1 mL), heated to 80° C. for 3 h to give the title compound (50 mg, 47%). LCMS (Method A): $R_T$=1.15 min, m/z=338 [M+H]⁺; 282 [M-butene+H]⁺.

Step 2: 1-((4-Hydroxy-3,3-dimethylpiperidin-4-yl)methyl)pyrazin-2(1H)-one: Prepared according to General Procedure 3 using tert-butyl 4-hydroxy-3,3-dimethyl-4-((2-oxopyrazin-1(2H)-yl)methyl)piperidine-1-carboxylate (50 mg, 0.148 mmol), DCM (1 mL) and TFA (0.5 mL), stirred at rt for 2 h to give the title compound (35 mg, quantitative). LCMS (Method A): $R_T$=0.37 min, m/z=238 [M+H]⁺.

Step 3: 1-((1-((R)-3-Cyclohexyl-2-methylpropanoyl)-4-hydroxy-3,3-dimethylpiperidin-4-yl)methyl)pyrazin-2(1H)-one: Prepared according to General Procedure 4 using 1-((4-hydroxy-3,3-dimethylpiperidin-4-yl)methyl)pyrazin-2(1H)-one (50 mg, 0.211 mmol), Acid 1 (43 mg, 0.253 mmol), HATU (120 mg, 0.316 mmol) and DIPEA (0.15 mL, 0.843 mmol) in DCM (3 mL) to give the title compound (32 mg, 37%). LCMS (Method B): $R_T$=1.29 min, m/z=390 [M+H]⁺. ¹H NMR (500 MHz, DMSO-d₆): δ 8.01 (s, 1H), 7.55 (dd, J=4.3, 1.3 Hz, 1H), 7.32 (d, J=4.3 Hz, 1H), 4.79 (d, J=1.0 Hz, 1H), 4.45-4.31 (m, 1H), 3.78-3.58 (m, 2H), 3.27-3.15 (m, 1H), 3.02-2.78 (m, 2H), 1.74-1.39 (m, 7H), 1.26-0.75 (m, 18H).

Example 2: 1-((1-((R)-3-Cyclohexyl-2-methylpropanoyl)-4-hydroxy-3,3-dimethylpiperidin-4-yl)methyl)-5-phenylpyrazin-2(1H)-one

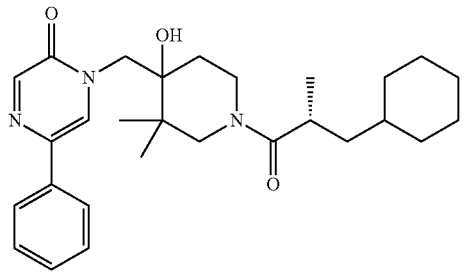

Step 1: tert-Butyl 4-((5-bromo-2-oxopyrazin-1(2H)-yl)methyl)-4-hydroxy-3,3-dimethylpiperidine-1-carboxylate: Prepared according to General Procedure 2 using 5-bromopyrazin-2(1H)-one (2.62 g, 15 mmol), Epoxide 1 (3.98 g, 16.5 mmol) and DIPEA (13.1 mL, 75 mmol) in NMP (30 mL), heated to 110° C. for 20 h to give the title compound (850 mg, 13%). LCMS (Method B): $R_T$=1.18 min, m/z=316, 318 [M-Boc+H]⁺.

Step 2: 5-Bromo-1-((4-hydroxy-3,3-dimethylpiperidin-4-yl)methyl)pyrazin-2(1H)-one: Prepared according to General Procedure 3 using tert-butyl 4-((5-bromo-2-oxopyrazin-1(2H)-yl)methyl)-4-hydroxy-3,3-dimethylpiperidine-1-carboxylate (850 mg, 2.04 mmol), DCM (10 mL) and TFA (5 mL), stirred at rt for 30 min to give the title compound (510 mg, 79%). LCMS (Method B): $R_T$=0.41 min, m/z=316, 318 [M+H]⁺.

Step 3: 5-Bromo-1-((1-((R)-3-cyclohexyl-2-methylpropanoyl)-4-hydroxy-3,3-dimethylpiperidin-4-yl)methyl)pyrazin-2(1H)-one: Prepared according to General Procedure 4 using 5-bromo-1-((4-hydroxy-3,3-dimethylpiperidin-4-yl)methyl)pyrazin-2(1H)-one (510 mg, 1.61 mol), Acid 1 (302 mg, 1.77 mmol), HATU (736 mg, 1.94 mmol) and DIPEA (0.85 mL, 4.84 mmol) in DCM (10 mL) to give the title compound (600 mg, 79%). LCMS (Method B): $R_T$=1.44 min, m/z=468, 470 [M+H]⁺.

Step 4: 1-((1-((R)-3-Cyclohexyl-2-methylpropanoyl)-4-hydroxy-3,3-dimethylpiperidin-4-yl)methyl)-5-phenylpyrazin-2(1H)-one: Prepared according to General Procedure 5 using 5-bromo-1-((1-((R)-3-cyclohexyl-2-methylpropanoyl)-4-hydroxy-3,3-dimethylpiperidin-4-yl)

methyl)pyrazin-2(1H)-one (40 mg, 85.4 µmol), phenylboronic acid (31.2 mg, 0.256 mmol), Pd(PPh₃)₄ (9.87 mg, 8.50 µmol) and K₃PO₄ (90.6 mg, 0.427 mmol) in 1,4-dioxane (0.5 mL) and water (0.2 mL). The reaction was heated under microwave irradiation at 120° C. for 15 min to give the title compound (29 mg, 69%). LCMS (Method A): R$_T$=1.79 min, m/z=466 [M+H]⁺. ¹H NMR (500 MHz, DMSO-d₆): δ 8.15 (s, 2H), 7.82 (d, J=7.7 Hz, 2H), 7.46 (t, J=7.6 Hz, 2H), 7.33 (t, J=7.3 Hz, 1H), 4.86 (s, 1H), 4.53-4.39 (m, 1H), 3.84-3.62 (m, 2H), 3.37-3.13 (m, 1H (signal obscured by HDO)), 3.03-2.75 (m, 2H), 1.78-1.38 (m, 7H), 1.31-0.73 (m, 18H).

Example 3: 1-((7-((R)-3-Cyclohexyl-2-methylpropanoyl)-10-hydroxy-7-azaspiro[4.5]decan-10-yl)methyl)pyrazin-2(1H)-one

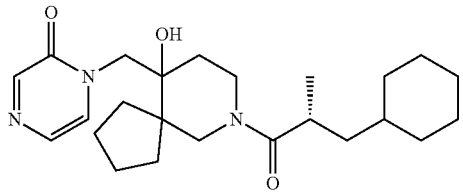 [SMILES: C[C@H](CC1CCCCC1)C(=O)N1CCC(O)(Cn2ccncc2=O)C2(CCCC2)C1]

Step 1: tert-Butyl 10-hydroxy-10-((2-oxopyrazin-1(2H)-yl)methyl)-7-azaspiro[4.5]decane-7-carboxylate: Prepared according to General Procedure 2 using pyrazin-2(1H)-one (100 mg, 1.04 mmol), Epoxide 2 (362 mg, 1.35 mmol) and cesium carbonate (678 mg, 2.08 mmol) in DMF (3 mL), heated to 80° C. for 2 h to give the title compound (120 mg, 31%). LCMS (Method A): R$_T$=1.61 min, m/z=364 [M+H]⁺; 308 [M-butene+H]⁺.

Step 2: 1-((10-Hydroxy-7-azaspiro[4.5]decan-10-yl)methyl)pyrazin-2(1H)-one: Prepared according to General Procedure 3 using tert-butyl 10-hydroxy-10-((2-oxopyrazin-1(2H)-yl)methyl)-7-azaspiro[4.5]decane-7-carboxylate (120 mg, 0.330 mmol), DCM (2 mL) and TFA (1 mL), stirred at rt for 1.5 h to give the title compound (80 mg, 92%). LCMS (Method A): R$_T$=0.29 min, m/z=264 [M+H]⁺.

Step 3: 1-((7-((R)-3-Cyclohexyl-2-methylpropanoyl)-10-hydroxy-7-azaspiro[4.5]decan-10-yl)methyl)pyrazin-2(1H)-one: Prepared according to General Procedure 4 using 1-((10-hydroxy-7-azaspiro[4.5]decan-10-yl)methyl)pyrazin-2(1H)-one (20 mg, 75.9 µmol), Acid 1 (15.5 mg, 91.1 µmol), HATU (43.3 mg, 0.114 mmol) and DIPEA (53 µL, 0.304 mmol) in DCM (1 mL) to give the title compound (21 mg, 64%). LCMS (Method A): R$_T$=1.40 min, m/z=416 [M+H]⁺. ¹H NMR (500 MHz, DMSO-d₆): δ 8.01 (d, J=1.1 Hz, 1H), 7.59 (dd, J=4.4, 1.4 Hz, 1H), 7.32 (d, J=4.3 Hz, 1H), 4.85-4.76 (m, 1H), 4.56 (td, J=26.0, 13.2 Hz, 1H), 3.71-3.10 (m, 5H), 2.93-2.78 (m, 1H), 1.98-1.80 (m, 1H), 1.72-1.03 (m, 20H), 0.94 (dt, J=11.1, 6.6 Hz, 3H), 0.90-0.75 (m, 2H).

Example 4: 1-((7-((R)-3-Cyclobutyl-2-methylpropanoyl)-10-hydroxy-7-azaspiro[4.5]decan-10-yl)methyl)pyrazin-2(1H)-one

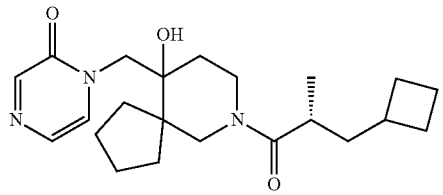 [SMILES: C[C@H](CC1CCC1)C(=O)N1CCC(O)(Cn2ccncc2=O)C2(CCCC2)C1]

Prepared according to General Procedure 4 using 1-((10-hydroxy-7-azaspiro[4.5]decan-10-yl)methyl)pyrazin-2(1H)-one (20 mg, 75.9 µmol), Acid 2 (13.0 mg, 91.1 µmol), HATU (43.3 mg, 0.114 mmol) and DIPEA (53 µL, 0.304 mmol) in DCM (1 mL) to give the title compound (16 mg, 53%). LCMS (Method A): R$_T$=1.20 min, m/z=388 [M+H]⁺. ¹H NMR (500 MHz, DMSO-d₆): δ 8.01 (dd, J=2.7, 1.1 Hz, 1H), 7.59 (d, J=3.7 Hz, 1H), 7.32 (d, J=4.2 Hz, 1H), 4.81 (dd, J=17.7, 3.2 Hz, 1H), 4.56 (td, J=14.2, 13.7, 5.2 Hz, 1H), 3.79-3.50 (m, 2H), 3.47-3.15 (m, 3H (signal obscured by HDO)), 2.76-2.62 (m, 1H (signal obscured by DMSO satellite)), 2.19 (dp, J=15.3, 7.8 Hz, 1H), 2.02-1.45 (m, 12H), 1.45-1.07 (m, 6H), 0.94 (dt, J=12.6, 7.3 Hz, 3H).

Example 5: 1-((10-Hydroxy-7-((R)-4,4,4-trifluoro-2-methylbutanoyl)-7-azaspiro[4.5]decan-10-yl)methyl)pyrazin-2(1H)-one

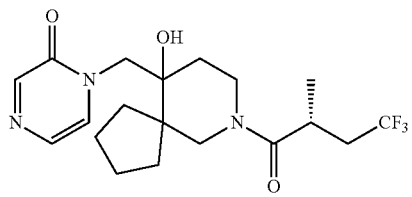 [SMILES: C[C@H](CC(F)(F)F)C(=O)N1CCC(O)(Cn2ccncc2=O)C2(CCCC2)C1]

Prepared according to General Procedure 4 using 1-((10-hydroxy-7-azaspiro[4.5]decan-10-yl)methyl)pyrazin-2(1H)-one (20 mg, 75.9 µmol), Acid 3 (14.2 mg, 91.1 µmol), HATU (43.3 mg, 0.114 mmol) and DIPEA (53 µL, 0.304 mmol) in DCM (1 mL) to give the title compound (18.5 mg, 57%). LCMS (Method A): R$_T$=1.00 min, m/z=402 [M+H]⁺. ¹H NMR (500 MHz, DMSO-d₆): δ 8.01 (d, J=1.1 Hz, 1H), 7.61-7.57 (m, 1H), 7.33 (dd, J=4.3, 2.2 Hz, 1H), 4.87-4.81 (m, 1H), 4.56 (dd, J=13.3, 6.4 Hz, 1H), 3.72-2.99 (m, 5H (signal obscured by HDO)), 2.80-2.65 (m, 1H), 2.25 (dqd, J=15.9, 11.7, 4.4 Hz, 1H), 2.02-1.81 (m, 1H), 1.77-1.47 (m, 5H), 1.47-1.03 (m, 8H).

Example 6: 5-Chloro-1-((7-((R)-3-cyclohexyl-2-methylpropanoyl)-10-hydroxy-7-azaspiro[4.5]decan-10-yl)methyl)pyrazin-2(1H)-one

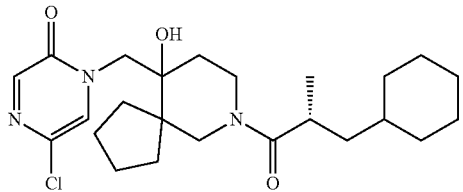

Step 1: tert-Butyl 10-((5-chloro-2-oxopyrazin-1(2H)-yl)methyl)-10-hydroxy-7-azaspiro[4.5]decane-7-carboxylate: Prepared according to General Procedure 2 using 5-chloropyrazin-2(1H)-one (120 mg, 0.919 mmol), Epoxide 2 (246 mg, 0.919 mmol) and DIPEA (0.803 mL, 4.60 mmol) in NMP (1.2 mL), heated to 110° C. for 18 h to give the title compound (36 mg, 9%). LCMS (Method A): $R_T$=1.41 min, m/z=342, 344 [M-butene+H]$^+$.

Step 2: 5-Chloro-1-((10-hydroxy-7-azaspiro[4.5]decan-10-yl)methyl)pyrazin-2(1H)-one: Prepared according to General Procedure 3 using tert-butyl 10-((5-chloro-2-oxopyrazin-1(2H)-yl)methyl)-10-hydroxy-7-azaspiro[4.5]decane-7-carboxylate (36 mg, 90.5 μmol), DCM (1 mL) and TFA (0.5 mL), stirred at rt for 30 min to give the title compound (21 mg, 78%). LCMS (Method A): $R_T$=0.35 min, m/z=298, 300 [M+H]$^+$.

Step 3: 5-Chloro-1-((7-((R)-3-cyclohexyl-2-methylpropanoyl)-10-hydroxy-7-azaspiro[4.5]decan-10-yl)methyl)pyrazin-2(1H)-one: Prepared according to General Procedure 4 using 5-chloro-1-((10-hydroxy-7-azaspiro[4.5]decan-10-yl)methyl)pyrazin-2(1H)-one (20 mg, 67.2 μmol), Acid 1 (13.7 mg, 80.6 μmol), HATU (38.3 mg, 0.101 mmol) and DIPEA (47 μL, 0.269 mmol) in DCM (1 mL) to give the title compound (27.3 mg, 87%). LCMS (Method B): $R_T$=1.66 min, m/z=450, 452 [M+H]$^+$. $^1$H NMR (500 MHz, DMSO-d$_6$): δ 7.90 (d, J=1.0 Hz, 1H), 7.82 (d, J=1.2 Hz, 1H), 4.84 (dd, J=15.7, 6.3 Hz, 1H), 4.61-4.47 (m, 1H), 3.71-3.49 (m, 2H), 3.47-3.06 (m, 3H (signal obscured by HDO)), 2.94-2.79 (m, 1H), 2.02-1.82 (m, 1H), 1.72-1.02 (m, 20H), 0.99-0.89 (m, 3H), 0.82 (s, 2H).

Example 7: 5-Bromo-1-((7-((R)-3-cyclohexyl-2-methylpropanoyl)-10-hydroxy-7-azaspiro[4.5]decan-10-yl)methyl)pyrazin-2(1H)-one

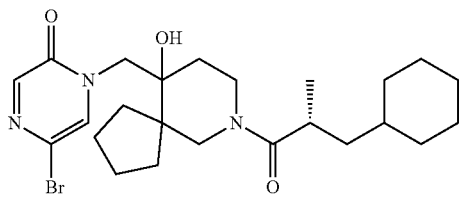 [SMILES: C[C@H](CC1CCCCC1)C(=O)N1CCC(O)(Cn2cc(Br)ncc2=O)C2(CCCC2)C1]

Step 1: tert-Butyl 10-((5-bromo-2-oxopyrazin-1(2H)-yl)methyl)-10-hydroxy-7-azaspiro[4.5]decane-7-carboxylate: Prepared according to General Procedure 2 using 5-bromopyrazin-2(1H)-one (140 mg, 0.800 mmol), Epoxide 2 (214 mg, 0.800 mmol) and DIPEA (0.700 mL, 4.00 mmol) in NMP (1.1 mL), heated to 110° C. for 18 h to give the title compound (34 mg, 9%). LCMS (Method A): $R_T$=1.45 min, m/z=386, 388 [M-butene+H]$^+$.

Step 2: 5-Bromo-1-((10-hydroxy-7-azaspiro[4.5]decan-10-yl)methyl)pyrazin-2(1H)-one: Prepared according to General Procedure 3 using tert-butyl 10-((5-bromo-2-oxopyrazin-1(2H)-yl)methyl)-10-hydroxy-7-azaspiro[4.5]decane-7-carboxylate (34 mg, 76.9 μmol), DCM (1 mL) and TFA (0.5 mL), stirred at rt for 30 min to give the title compound (21 mg, 79%). LCMS (Method A): $R_T$=0.39 min, m/z=342, 344 [M+H]$^+$.

Step 3: 5-Bromo-1-((7-((R)-3-cyclohexyl-2-methylpropanoyl)-10-hydroxy-7-azaspiro[4.5]decan-10-yl)methyl)pyrazin-2(1H)-one: Prepared according to General Procedure 4 using 5-bromo-1-((10-hydroxy-7-azaspiro[4.5]decan-10-yl)methyl)pyrazin-2(1H)-one (20 mg, 58.4 μmol), Acid 1 (11.9 mg, 70.1 μmol), HATU (33.3 mg, 87.7 μmol) and DIPEA (41 μL, 0.234 mmol) in DCM (1 mL) to give the title compound (23.7 mg, 78%). LCMS (Method B): $R_T$=1.67 min, m/z=494, 496 [M+H]$^+$. $^1$H NMR (500 MHz, DMSO-d$_6$): δ 7.89 (d, J=1.0 Hz, 1H), 7.87 (d, J=1.3 Hz, 1H), 4.84 (dd, J=16.1, 6.3 Hz, 1H), 4.60-4.46 (m, 1H), 3.71-3.15 (m, 5H (signal obscured by HDO)), 2.94-2.78 (m, 1H), 2.03-1.80 (m, 1H), 1.71-1.03 (m, 20H), 1.00-0.90 (m, 3H), 0.90-0.76 (m, 2H).

Example 8: Methyl 4-((7-((R)-3-cyclohexyl-2-methylpropanoyl)-10-hydroxy-7-azaspiro[4.5]decan-10-yl)methyl)-5-oxo-4,5-dihydropyrazine-2-carboxylate

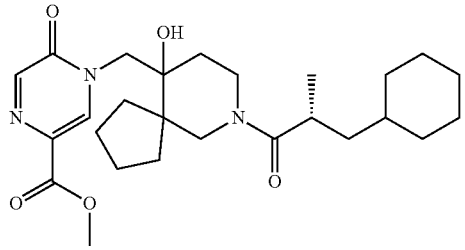 [SMILES: COC(=O)c1cn(CC2(O)CCN(C(=O)[C@H](C)CC3CCCCC3)CC23CCCC3)c(=O)cn1]

Step 1: tert-Butyl 10-hydroxy-10-((5-(methoxycarbonyl)-2-oxopyrazin-1(2H)-yl)methyl)-7-azaspiro[4.5]decane-7-carboxylate: Prepared according to General Procedure 2 using methyl 5-oxo-4,5-dihydropyrazine-2-carboxylate (100 mg, 0.649 mmol), Epoxide 2 (173 mg, 0.649 mmol) and DIPEA (0.567 mL, 3.24 mmol) in NMP (0.9 mL), heated to 110° C. for 18 h to give the title compound (108 mg, 39%). LCMS (Method A): $R_T$=1.25 min, m/z=422 [M+H]$^+$; 366 [M-butene+H]$^+$.

Step 2: Methyl 4-((10-hydroxy-7-azaspiro[4.5]decan-10-yl)methyl)-5-oxo-4,5-dihydropyrazine-2-carboxylate: Prepared according to General Procedure 3 using tert-butyl 10-hydroxy-10-((5-(methoxycarbonyl)-2-oxopyrazin-1(2H)-yl)methyl)-7-azaspiro[4.5]decane-7-carboxylate (108 mg, 0.256 mmol), DCM (2 mL) and TFA (1 mL), stirred at rt for 30 min to give the title compound (81 mg, quantitative). LCMS (Method A): $R_T$=0.31 min, m/z=322 [M+H]$^+$.

Step 3: Methyl 4-((7-((R)-3-cyclohexyl-2-methylpropanoyl)-10-hydroxy-7-azaspiro[4.5]decan-10-yl)methyl)-5-oxo-4,5-dihydropyrazine-2-carboxylate: Prepared according to General Procedure 4 using methyl 4-((10-hydroxy-7-azaspiro[4.5]decan-10-yl)methyl)-5-oxo-4,5-dihydropyrazine-2-carboxylate (81 mg, 0.252 mmol), Acid 1 (51.5 mg, 0.303 mmol), HATU (144 mg, 0.378 mmol) and DIPEA (0.176 mL, 1.01 mmol) in DCM (3 mL) to give the title compound (108 mg, 88%). LCMS (Method B): $R_T$=1.51 min, m/z=474 [M+H]⁺. ¹H NMR (500 MHz, DMSO-d₆): δ 8.44 (s, 1H), 8.04 (s, 1H), 4.91 (dd, J=12.1, 6.1 Hz, 1H), 4.68-4.54 (m, 1H), 3.82 (s, 3H), 3.70-3.50 (m, 2H), 3.47-3.17 (m, 2H (signal obscured by HDO)), 3.21 (q, J=12.1, 11.0 Hz, 1H), 2.95-2.79 (m, 1H), 2.03-1.83 (m, 1H), 1.74-1.02 (m, 20H), 0.94 (dt, J=14.7, 6.4 Hz, 3H), 0.90-0.75 (m, 2H).

Example 9: 4-((7-((R)-3-Cyclohexyl-2-methylpropanoyl)-10-hydroxy-7-azaspiro[4.5]decan-10-yl)methyl)-5-oxo-4,5-dihydropyrazine-2-carboxylic acid

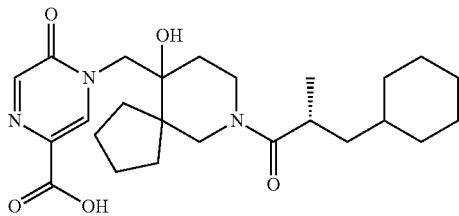 [SMILES: C[C@H](CC1CCCCC1)C(=O)N1CCC(O)(Cn2cc(C(=O)O)ncc2=O)C2(CCCC2)C1]

To a solution of methyl 4-((7-((R)-3-cyclohexyl-2-methylpropanoyl)-10-hydroxy-7-azaspiro[4.5]decan-10-yl)methyl)-5-oxo-4,5-dihydropyrazine-2-carboxylate (97 mg, 0.205 mmol) in EtOH (1 mL) was added and 2 M sodium hydroxide$_{(aq)}$ (1.00 mL, 4.00 mmol) and the resulting mixture was stirred at 50° C. for 3 h. The reaction was concentrated under reduced pressure and the crude product was partitioned between diethyl ether and water. The layers were separated and the aqueous phase was acidified with 2 M HCl$_{(aq)}$ until <pH 4. The aqueous suspension was extracted with EtOAc (×3), the combined organic phases were washed with brine, passed through a phase separator and concentrated under reduced pressure. The crude product was purified by flash chromatography (0-20% 0.1% v/v HCO₂H in MeOH in 0.1% v/v HCO₂H in EtOAc) to give the title compound (90 mg, 94%). LCMS (Method B): $R_T$=1.37 min, m/z=460 [M+H]⁺. ¹H NMR (500 MHz, DMSO-d₆): δ 12.86 (s, 1H), 8.39 (s, 1H), 8.02 (s, 1H), 4.90 (dd, J=13.6, 5.9 Hz, 1H), 4.60 (dt, J=25.1, 12.7 Hz, 1H), 3.72-3.06 (m, 5H (signal obscured by HDO)), 2.94-2.78 (m, 1H), 2.02-1.83 (m, 1H), 1.76-1.01 (m, 20H), 1.00-0.90 (m, 3H), 0.89-0.76 (m, 2H).

Example 10: 4-((7-((R)-3-Cyclohexyl-2-methylpropanoyl)-10-hydroxy-7-azaspiro[4.5]decan-10-yl)methyl)-N,N-dimethyl-5-oxo-4,5-dihydropyrazine-2-carboxamide

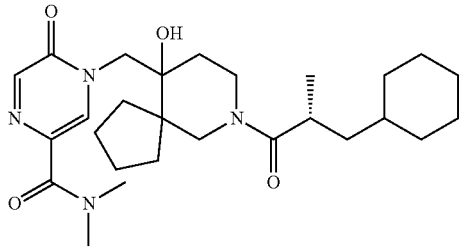 [SMILES: C[C@H](CC1CCCCC1)C(=O)N1CCC(O)(Cn2cc(C(=O)N(C)C)ncc2=O)C2(CCCC2)C1]

Prepared according to General Procedure 4 using 4-((7-((R)-3-cyclohexyl-2-methylpropanoyl)-10-hydroxy-7-azaspiro[4.5]decan-10-yl)methyl)-5-oxo-4,5-dihydropyrazine-2-carboxylic acid (30 mg, 65.3 µmol), dimethylamine (2 M in THF, 39.2 µL, 0.78.3 µmol), HATU (32.3 mg, 84.9 µmol) and DIPEA (32.4 µL, 0.196 mmol) in DCM (2 mL) to give the title compound (21.6 mg, 67%). LCMS (Method A): $R_T$=1.50 min, m/z=487 [M+H]⁺. ¹H NMR (500 MHz, DMSO-d₆): δ 8.06 (s, 1H), 7.97 (s, 1H), 4.85 (dd, J=14.4, 7.2 Hz, 1H), 4.60 (dt, J=27.1, 13.5 Hz, 1H), 3.71-2.78 (m, 12H (signal obscured by HDO)), 2.10-1.81 (m, 1H), 1.73-1.03 (m, 20H), 0.99-0.91 (m, 3H), 0.90-0.74 (m, 2H).

Example 11: 1-((7-((R)-3-Cyclohexyl-2-methylpropanoyl)-10-hydroxy-7-azaspiro[4.5]decan-10-yl)methyl)-5-(piperazine-1-carbonyl)pyrazin-2(1H)-one

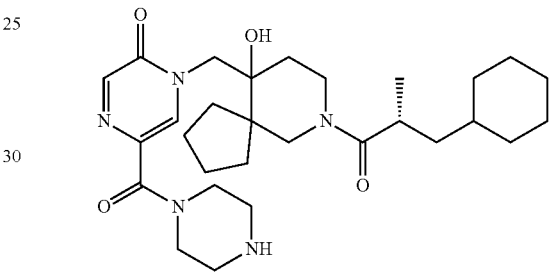

Step 1: tert-Butyl 4-(4-((7-((R)-3-cyclohexyl-2-methylpropanoyl)-10-hydroxy-7-azaspiro[4.5]decan-10-yl)methyl)-5-oxo-4,5-dihydropyrazine-2-carbonyl)piperazine-1-carboxylate: Prepared according to General Procedure 4 using 4-((7-((R)-3-cyclohexyl-2-methylpropanoyl)-10-hydroxy-7-azaspiro[4.5]decan-10-yl)methyl)-5-oxo-4,5-dihydropyrazine-2-carboxylic acid (30 mg, 65.3 µmol), tert-butyl piperazine-1-carboxylate (14.6 mg, 78.3 µmol), HATU (32.3 mg, 84.9 µmol) and DIPEA (34.2 µL, 0.196 mmol) in DCM (2 mL) to give the title compound (39 mg, 95%). LCMS (Method A): $R_T$=1.76 min, m/z=628 [M+H]⁺; 572 [M-butene+H]⁺.

Step 2: 1-((7-((R)-3-Cyclohexyl-2-methylpropanoyl)-10-hydroxy-7-azaspiro[4.5]decan-10-yl)methyl)-5-(piperazine-1-carbonyl)pyrazin-2(1H)-one: Prepared according to General Procedure 3 using tert-butyl 4-(4-((7-((R)-3-cyclohexyl-2-methylpropanoyl)-10-hydroxy-7-azaspiro[4.5]decan-10-yl)methyl)-5-oxo-4,5-dihydropyrazine-2-carbonyl)piperazine-1-carboxylate (45 mg, 71.7 µmol), DCM (1 mL) and TFA (0.5 mL). The crude product was purified by SCX-2 followed by flash chromatography (Biotage KP-NH, 0-20% MeOH in DCM) to give the title compound (12.2 mg, 32%). LCMS (Method A): $R_T$=1.09 min, m/z=528 [M+H]⁺. ¹H NMR (500 MHz, DMSO-d₆): δ 8.05 (s, 1H), 7.97 (s, 1H), 4.84 (dd, J=14.1, 7.5 Hz, 1H), 4.59 (dt, J=26.4, 13.3 Hz, 1H), 3.72-3.08 (m, 10H), 2.94-2.79 (m, 1H), 2.72 (t, J=5.0 Hz, 4H), 2.00-1.81 (m, 1H), 1.76-1.02 (m, 20H), 1.00-0.90 (m, 3H), 0.90-0.76 (m, 2H).

Example 12: 1-((1-((R)-3-Cyclohexyl-2-methylpropanoyl)-4-hydroxy-3,3-dimethylpiperidin-4-yl)methyl)-5-(pyridin-3-yl)pyrazin-2(1H)-one

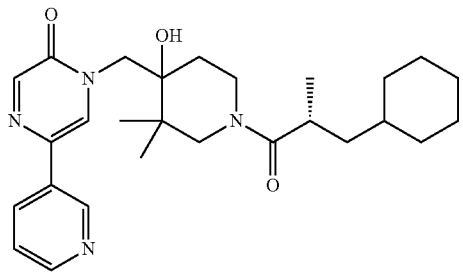

Prepared according to General Procedure 5 using 5-bromo-1-((1-((R)-3-cyclohexyl-2-methylpropanoyl)-4-hydroxy-3,3-dimethylpiperidin-4-yl)methyl)pyrazin-2(1H)-one (40 mg, 85.4 μmol), pyridin-3-ylboronic acid (31.5 mg, 0.256 mmol), Pd(PPh$_3$)$_4$ (9.87 mg, 8.50 μmol) and K$_3$PO$_4$ (90.6 mg, 0.427 mmol) in 1,4-dioxane (0.5 mL) and water (0.2 mL). The reaction was heated under microwave irradiation at 120° C. for 15 min to give the title compound (18 mg, 43%). LCMS (Method A): R$_T$=1.16 min, m/z=467 [M+H]$^+$. $^1$H NMR (500 MHz, DMSO-d$_6$): δ 9.03 (d, J=1.7 Hz, 1H), 8.53 (dd, J=4.7, 1.2 Hz, 1H), 8.26 (s, 1H), 8.20-8.14 (m, 2H), 7.48 (dd, J=8.0, 4.8 Hz, 1H), 4.84 (d, J=2.2 Hz, 1H), 4.54-4.38 (m, 1H), 3.84-3.63 (m, 2H), 3.36-3.13 (m, 1H (signal obscured by HDO)), 3.02-2.74 (m, 2H), 1.77-1.39 (m, 7H), 1.30-0.73 (m, 18H).

Example 13: 1-((1-((R)-3-Cyclohexyl-2-methylpropanoyl)-4-hydroxy-3,3-dimethylpiperidin-4-yl)methyl)-5-(2-oxopyrrolidin-1-yl)pyrazin-2(1H)-one

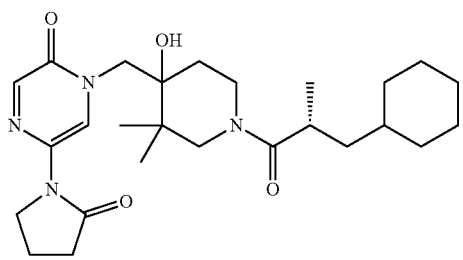 [SMILES: C[C@H](CC1CCCCC1)C(=O)N1CCC(O)(Cn2cc(N3CCCC3=O)ncc2=O)C(C)(C)C1]

A solution of Pd$_2$(dba)$_3$ (1.6 mg, 1.70 μmol) and XantPhos (3.0 mg, 5.10 μmol) in pre-degassed (bubbling nitrogen) 1,4-dioxane (0.8 mL) was added to a mixture of 5-bromo-1-((1-((R)-3-cyclohexyl-2-methylpropanoyl)-4-hydroxy-3,3-dimethylpiperidin-4-yl)methyl)pyrazin-2(1H)-one (40 mg, 85.4 μmol), pyrrolidin-2-one (7.8 μL, 0.103 mmol) and cesium carbonate (39.0 mg, 0.120 mmol). The reaction vessel was sealed and heated to 100° C. for 3 h. The reaction was allowed to cool to rt before being poured on to 1:1 water/brine. The resulting mixture was extracted with EtOAc (×3), the combined organic phases were passed through a phase separator and concentrated in vacuo. The crude material was purified by flash chromatography (0-100% EtOAc in cyclohexane) and further purified by preparative HPLC to give the title compound (4.6 mg, 11%). LCMS (Method A): R$_T$=1.66 min, m/z=473 [M+H]$^+$. $^1$H NMR (500 MHz, DMSO-d$_6$): δ 8.44-8.40 (m, 1H), 7.95 (s, 1H), 4.87 (s, 1H), 4.53-4.40 (m, 1H), 3.95-3.89 (m, 1H), 3.85-3.79 (m, 1H), 3.77-3.58 (m, 2H), 3.26-3.15 (m, 1H), 3.02-2.78 (m, 2H), 2.05 (pt, J=8.4, 3.4 Hz, 2H), 1.74-1.38 (m, 8H), 1.26-0.74 (m, 19H).

Example 14: 1-((1-((R)-3-Cyclohexyl-2-methylpropanoyl)-4-hydroxy-3,3-dimethylpiperidin-4-yl)methyl)-5-(pyridin-4-yl)pyrazin-2(1H)-one

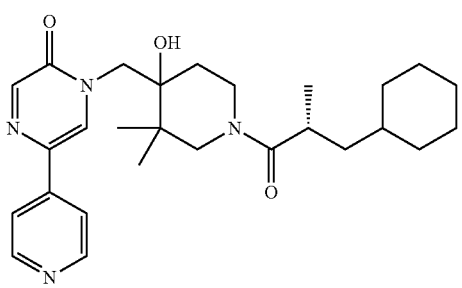 [SMILES: C[C@H](CC1CCCCC1)C(=O)N1CCC(O)(Cn2cc(-c3ccncc3)ncc2=O)C(C)(C)C1]

Prepared according to General Procedure 5 using 5-bromo-1-((1-((R)-3-cyclohexyl-2-methylpropanoyl)-4-hydroxy-3,3-dimethylpiperidin-4-yl)methyl)pyrazin-2(1H)-one (40 mg, 85.4 μmol), pyridin-4-ylboronic acid hydrate (36.1 mg, 0.256 mmol), Pd(PPh$_3$)$_4$ (9.9 mg, 8.50 μmol) and K$_3$PO$_4$ (90.6 mg, 0.427 mmol) in 1,4-dioxane (0.5 mL) and water (0.2 mL). The reaction was heated under microwave irradiation at 120° C. for 15 min to give the title compound (14.7 mg, 36%). LCMS (Method A): R$_T$=1.25 min, m/z=467 [M+H]$^+$. $^1$H NMR (500 MHz, DMSO-d$_6$): δ 8.62 (d, J=5.8 Hz, 2H), 8.40-8.35 (m, 1H), 8.18 (s, 1H), 7.79 (d, J=6.0 Hz, 2H), 4.87 (s, 1H), 4.54-4.40 (m, 1H), 3.84-3.64 (m, 2H), 3.36-3.11 (m, 1H (signal obscured by HDO)), 3.01-2.73 (m, 2H), 1.77-1.39 (m, 7H), 1.26-0.73 (m, 18H).

Example 15 and Example 16: 1-((1-((R)-3-Cyclohexyl-2-methylpropanoyl)-4-hydroxy-3,3-dimethylpiperidin-4-yl)methyl)-5-(1H-indazol-1-yl)pyrazin-2(1H)-one and 1-((1-((R)-3-Cyclohexyl-2-methylpropanoyl)-4-hydroxy-3,3-dimethylpiperidin-4-yl)methyl)-5-(2H-indazol-2-yl)pyrazin-2(1H)-one

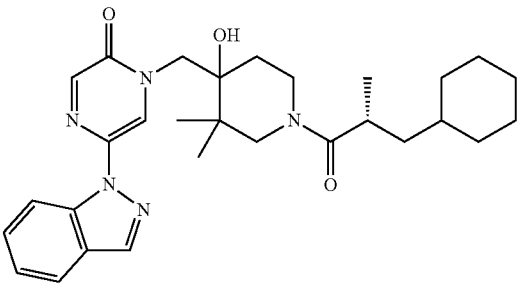

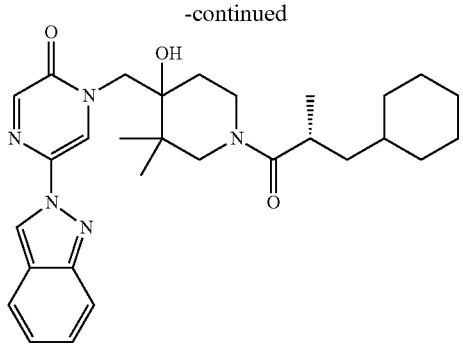

1,4-Dioxane (1.7 mL) and trans-N¹,N²-dimethylcyclohexane-1,2-diamine (13.5 µL, 85.4 µmol) were added to a vial containing 5-bromo-1-((1-((R)-3-cyclohexyl-2-methylpropanoyl)-4-hydroxy-3,3-dimethylpiperidin-4-yl)methyl)pyrazin-2(1H)-one (40 mg, 85.4 µmol), 1H-indazole (10.1 mg, 85.4 µmol), copper(I) iodide (16.3 mg, 85.4 µmol) and K$_2$CO$_3$ (23.6 mg, 0.171 mmol). The vial was flushed with N$_2$, sealed and the reaction was stirred at 100° C. for 16 h. The reaction was allowed to cool to rt and poured on to water (30 mL) and 28-30% ammonium hydroxide$_{(aq)}$ (4 mL). The resulting mixture was extracted with EtOAc (×3), the combined organic phases passed through a phase separator and concentrated under reduced pressure. The crude material was purified by flash chromatography (0-100% EtOAc in cyclohexane) and further purified by preparative HPLC to give a 2:1 mixture of the title compounds (4.7 mg, 10%). LCMS (Method A): R$_T$=2.12 min, m/z=506 [M+H]$^+$. This material was isolated as a mixture of regioisomers a and b in a 2:1 ratio: ¹H NMR (500 MHz, DMSO-d$_6$) δ 8.96 (s, 1H$_b$), 8.53-8.50 (m, 1H$_b$), 8.37 (s, 1H$_a$), 8.23-8.06 (m, 3H$_a$ and 1H$_b$), 7.88 (d, J=8.1 Hz, 1H$_a$), 7.79 (d, J=8.4 Hz, 1H$_b$), 7.69 (d, J=8.8 Hz, 1H$_b$), 7.52-7.48 (m, 1H$_a$), 7.35-7.31 (m, 1H$_b$), 7.30-7.25 (m, 1H$_a$), 7.13-7.09 (m, 1H$_b$), 5.01-4.98 (m, 1H$_b$), 4.94 (s, 1H$_a$), 4.62-2.78 (m, 7H$_a$ and 7H$_b$ (signals overlap with HDO)), 1.78-0.76 (m, 24H$_a$ and 24H$_b$).

Example 17: 1-((1-((R)-3-Cyclohexyl-2-methylpropanoyl)-4-hydroxy-3,3-dimethylpiperidin-4-yl)methyl)-5-(1H-pyrazol-5-yl)pyrazin-2(1H)-one

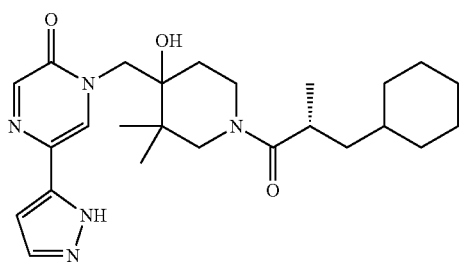 [SMILES: C[C@H](CC1CCCCC1)C(=O)N1CCC(O)(Cn2cc(-c3ccn[nH]3)ncc2=O)C(C)(C)C1]

Prepared according to General Procedure 5 using 5-bromo-1-((1-((R)-3-cyclohexyl-2-methylpropanoyl)-4-hydroxy-3,3-dimethylpiperidin-4-yl)methyl)pyrazin-2(1H)-one (50 mg, 0.107 mmol), (1H-pyrazol-5-yl)boronic acid (23.9 mg, 0.214 mmol), Pd(dppf)Cl$_2$·DCM (8.7 mg, 10.7 µmol) and sodium carbonate (33.9 mg, 0.320 mmol) in 1,4-dioxane (0.5 mL) and water (0.2 mL). The reaction was heated under microwave irradiation at 120° C. for 15 min to give the title compound (7.2 mg, 14%). LCMS (Method A): R$_T$=1.60 min, m/z=456 [M+H]$^+$. ¹H NMR (500 MHz, DMSO-d$_6$) δ 12.82 (s, 1H), 8.22-8.12 (m, 1H), 8.09 (s, 1H), 7.72 (s, 1H), 6.64-6.52 (m, 1H), 4.93 (s, 1H), 4.72-4.59 (m, 1H), 3.90-3.08 (m, 5H (signal overlaps with HDO)), 2.95-2.80 (m, 1H), 2.02-1.86 (m, 1H), 1.77-1.03 (m, 18H), 1.01-0.89 (m, 3H), 0.89-0.75 (m, 2H).

Example 18: 1-((1-((R)-3-Cyclohexyl-2-methylpropanoyl)-4-hydroxy-3,3-dimethylpiperidin-4-yl)methyl)-5-(1H-pyrazol-1-yl)pyrazin-2(1H)-one

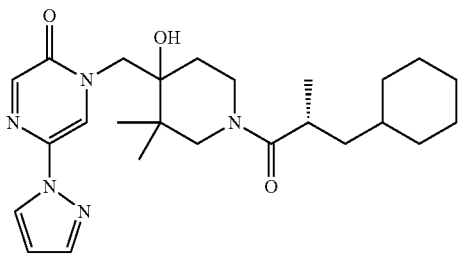 [SMILES: C[C@H](CC1CCCCC1)C(=O)N1CCC(O)(Cn2cc(-n3cccn3)ncc2=O)C(C)(C)C1]

Prepared similarly to Example 15 using 5-bromo-1-((1-((R)-3-cyclohexyl-2-methylpropanoyl)-4-hydroxy-3,3-dimethylpiperidin-4-yl)methyl)pyrazin-2(1H)-one (40 mg, 85.4 µmol), 1H-pyrazole (5.8 mg, 85.4 µmol), copper(I) iodide (16.3 mg, 85.4 µmol), trans-N¹,N²-dimethylcyclohexane-1,2-diamine (13.5 µL, 85.4 µmol) and K$_2$CO$_3$ (23.6 mg, 0.171 mmol) in 1,4-dioxane (1.7 mL) to give the title compound (0.9 mg, 2%). LCMS (Method A): R$_T$=1.57 min, m/z=456 [M+H]$^+$. ¹H NMR (500 MHz, DMSO-d$_6$): δ 8.31 (d, J=2.4 Hz, 1H), 8.17 (d, J=3.2 Hz, 1H), 8.03 (s, 1H), 7.74 (s, 1H), 6.53 (t, J=1.9 Hz, 1H), 4.93 (s, 1H), 4.56-4.44 (m, 1H), 3.80-3.61 (m, 2H), 3.36-3.14 (m, 1H (signal obscured by HDO)), 3.02-2.76 (m, 2H), 1.75-1.39 (m, 7H), 1.31-0.71 (m, 18H).

Example 19: 1-((7-((R)-3-Cyclohexyl-2-methylpropanoyl)-10-hydroxy-7-azaspiro[4.5]decan-10-yl)methyl)-5-(pyridin-3-yl)pyrazin-2(1H)-one

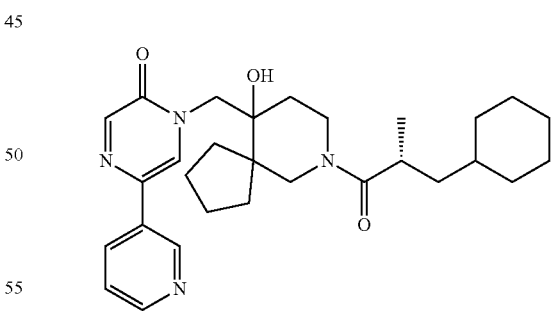

Prepared according to General Procedure 5 using 5-bromo-1-((7-((R)-3-cyclohexyl-2-methylpropanoyl)-10-hydroxy-7-azaspiro[4.5]decan-10-yl)methyl)pyrazin-2(1H)-one (10 mg, 20.2 µmol), pyridin-3-ylboronic acid (7.5 mg, 60.7 µmol), Pd(PPh$_3$)$_4$ (2.3 mg, 2.00 µmol) and K$_3$PO$_4$ (21.5 mg, 0.101 mmol) in 1,4-dioxane (0.125 mL) and water (0.05 mL). The reaction was heated under microwave irradiation at 120° C. for 15 min to give the title compound (3.8 mg, 37%). LCMS (Method B): R$_T$=1.19 min, m/z=493 [M+H]$^+$. ¹H NMR (500 MHz, DMSO-d$_6$): δ 9.04 (d, J=1.9

Hz, 1H), 8.53 (dd, J=4.7, 1.5 Hz, 1H), 8.29 (t, J=2.0 Hz, 1H), 8.21-8.14 (m, 2H), 7.48 (dd, J=8.0, 4.8 Hz, 1H), 4.91-4.81 (m, 1H), 4.72-4.55 (m, 1H), 3.75-3.53 (m, 2H), 3.48-3.03 (m, 3H (signal obscured by HDO)), 2.96-2.81 (m, 1H), 2.08-1.88 (m, 1H), 1.81-1.02 (m, 20H), 0.95 (dt, J=18.9, 6.1 Hz, 3H), 0.90-0.75 (m, 2H).

Example 20: 1-((7-((R)-3-Cyclohexyl-2-methylpropanoyl)-10-hydroxy-7-azaspiro[4.5]decan-10-yl)methyl)-5-(pyridin-4-yl)pyrazin-2(1H)-one

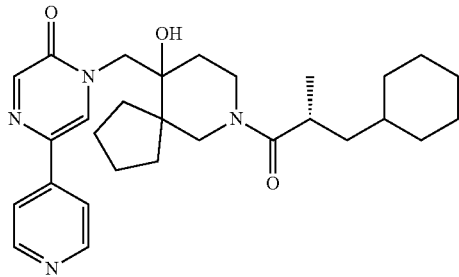 [SMILES: C[C@H](CC1CCCCC1)C(=O)N1CCC(O)(Cn2cc(-c3ccncc3)ncc2=O)C2(CCCC2)C1]

Prepared according to General Procedure 5 using 5-bromo-1-((7-((R)-3-cyclohexyl-2-methylpropanoyl)-10-hydroxy-7-azaspiro[4.5]decan-10-yl)methyl)pyrazin-2(1H)-one (10 mg, 20.2 μmol), pyridin-4-ylboronic acid monohydrate (8.6 mg, 60.7 μmol), Pd(PPh$_3$)$_4$ (2.3 mg, 2.00 μmol) and K$_3$PO$_4$ (21.5 mg, 0.101 mmol) in 1,4-dioxane (0.125 mL) and water (0.05 mL). The reaction was heated under microwave irradiation at 120° C. for 15 min to give the title compound (3.4 mg, 33%). LCMS (Method B): R$_T$=1.04 min, m/z=493 [M+H]$^+$. $^1$H NMR (500 MHz, DMSO-d$_6$): δ 8.64-8.59 (m, 2H), 8.41 (d, J=2.8 Hz, 1H), 8.18 (s, 1H), 7.80 (d, J=6.1 Hz, 2H), 4.87 (s, 1H), 4.71-4.56 (m, 1H), 3.74-3.54 (m, 2H), 3.47-3.05 (m, 3H (signal obscured by HDO)), 2.95-2.79 (m, 1H), 2.08-1.89 (m, 1H), 1.80-1.02 (m, 20H), 0.95 (dt, J=19.2, 6.2 Hz, 3H), 0.90-0.75 (m, 2H).

Example 21: 1-((1-((R)-3-Cyclohexyl-2-methylpropanoyl)-4-hydroxy-3,3-dimethylpiperidin-4-yl)methyl)-5-methylpyrazin-2(1H)-one

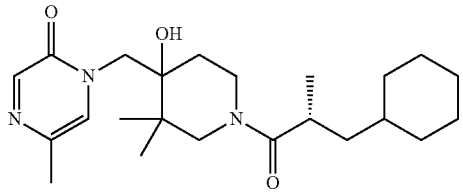 [SMILES: Cc1cn(CC2(O)CCN(C(=O)[C@H](C)CC3CCCCC3)CC2(C)C)c(=O)cn1]

Prepared according to General Procedure 5 using 5-chloro-1-((1-((R)-3-cyclohexyl-2-methylpropanoyl)-4-hydroxy-3,3-dimethylpiperidin-4-yl)methyl)pyrazin-2(1H)-one (100 mg, 0.236 mmol), trimethylboroxine (74 mg, 0.590 mmol), Pd(dppf)Cl$_2$·DCM (9.6 mg, 11.8 μmol) and K$_2$CO$_3$ (130 mg, 0.943 mmol) in 1,4-dioxane (0.95 mL). The reaction mixture was heated at 100° C. for 16 h to give the title compound (31.8 mg, 33%). LCMS (Method B): R$_T$=1.25 min, m/z=404 [M+H]$^+$. $^1$H NMR (500 MHz, DMSO-d$_6$): δ 7.96 (s, 1H), 7.40 (s, 1H), 4.82 (s, 1H), 4.41-4.26 (m, 1H), 3.78-3.54 (m, 2H), 3.32-3.15 (m, 2H (signal obscured by HDO)), 3.01-2.77 (m, 2H), 2.19 (s, 3H), 1.75-1.39 (m, 7H), 1.23-1.02 (m, 6H), 0.95 (ddd, J=28.3, 12.9, 5.9 Hz, 9H), 0.83 (p, J=11.7, 11.0 Hz, 2H).

Example 22: 1-((1-((R)-3-Cyclohexyl-2-methylpropanoyl)-4-hydroxy-3,3-dimethylpiperidin-4-yl)methyl)-5-cyclopropylpyrazin-2(1H)-one

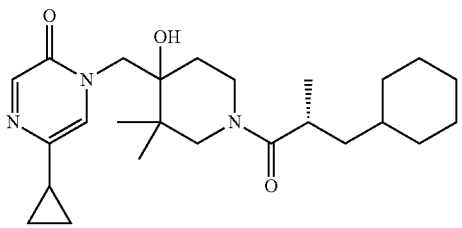 [SMILES: C[C@H](CC1CCCCC1)C(=O)N1CCC(O)(Cn2cc(C3CC3)ncc2=O)C(C)(C)C1]

Prepared according to General Procedure 5 using 5-chloro-1-((1-((R)-3-cyclohexyl-2-methylpropanoyl)-4-hydroxy-3,3-dimethylpiperidin-4-yl)methyl)pyrazin-2(1H)-one (100 mg, 0.236 mmol), cyclopropylboronic acid (81 mg, 0.943 mmol), Pd(dppf)Cl$_2$·DCM (9.6 mg, 11.8 μmol) and K$_2$CO$_3$ (196 mg, 1.41 mmol) in 1,4-dioxane (0.75 mL) and water (0.25 mL). The reaction was heated under microwave irradiation at 120° C. for 15 min to give the title compound (9.1 mg, 9%). LCMS (Method B): R$_T$=1.41 min, m/z=430 [M+H]$^+$. $^1$H NMR (500 MHz, DMSO-d$_6$) δ 7.96-7.90 (m, 1H), 7.49-7.44 (m, 1H), 4.87-4.81 (m, 1H), 4.41-4.27 (m, 1.2H), 4.03 (dd, J=39.8, 13.0 Hz, 0.8H), 3.80-3.54 (m, 2.6H), 3.34-3.14 (m, 1H (signal overlaps with HDO)), 3.02-2.76 (m, 2.4H), 1.87 (tt, J=8.6, 4.9 Hz, 1H), 1.74-1.40 (m, 7H), 1.22-0.76 (m, 18H), 0.74-0.66 (m, 2H).

Example 23: 1-((1-((R)-3-Cyclohexyl-2-methylpropanoyl)-4-hydroxy-3,3-dimethylpiperidin-4-yl)methyl)-5-(pyridin-2-yl)pyrazin-2(1H)-one

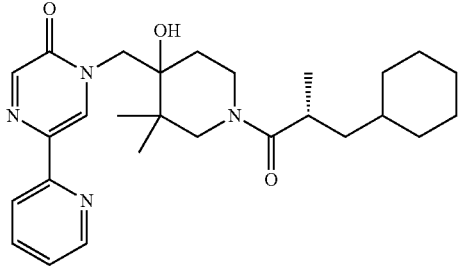

Step 1: tert-Butyl 4-((5-chloro-2-oxopyrazin-1(2H)-yl)methyl)-4-hydroxy-3,3-dimethylpiperidine-1-carboxylate: Prepared according to General Procedure 2 using 5-chloropyrazin-2(1H)-one (1.96 g, 15 mmol), Epoxide 1 (3.98 g, 16.5 mmol) and DIPEA (13.1 mL, 75 mmol) in NMP (30 mL), heated to 110° C. for 20 h to give the title compound (1.00 g, 18%). LCMS (Method A): R$_T$=1.31 min, m/z=316, 318 [M-butene+H]$^+$.

Step 2: 5-Chloro-1-((4-hydroxy-3,3-dimethylpiperidin-4-yl)methyl)pyrazin-2(1H)-one: Prepared according to General Procedure 3 using tert-butyl 4-((5-chloro-2-oxopyrazin-1(2H)-yl)methyl)-4-hydroxy-3,3-dimethylpiperidine-1- carboxylate (1.00 g, 2.69 mmol), DCM (10 mL) and TFA (5 mL), stirred at rt for 30 min to give the title compound (540 mg, 73%). LCMS (Method A): $R_T$=0.31 min, m/z=272, 274 [M+H]$^+$.

Step 3: 5-Chloro-1-((1-((R)-3-cyclohexyl-2-methylpropanoyl)-4-hydroxy-3,3-dimethylpiperidin-4-yl)methyl)pyrazin-2(1H)-one: Prepared according to General Procedure 4 using 5-chloro-1-((4-hydroxy-3,3-dimethylpiperidin-4-yl)methyl)pyrazin-2(1H)-one (540 mg, 1.99 mmol), Acid 1 (372 mg, 2.19 mmol), HATU (907 mg, 2.38 mmol) and DIPEA (1.04 mL, 5.96 mmol) in DCM (10 mL) to give the title compound (730 mg, 86%). LCMS (Method A): $R_T$=1.61 min, m/z=424, 426 [M+H]$^+$.

Step 4: 1-((1-((R)-3-Cyclohexyl-2-methylpropanoyl)-4-hydroxy-3,3-dimethylpiperidin-4-yl)methyl)-5-(pyridin-2-yl)pyrazin-2(1H)-one: A suspension of 5-chloro-1-((1-((R)-3-cyclohexyl-2-methylpropanoyl)-4-hydroxy-3,3-dimethylpiperidin-4-yl)methyl)pyrazin-2(1H)-one (50 mg, 0.118 mmol), CsF (53.7 mg, 0.354 mmol) and copper(I) iodide (1.1 mg, 5.90 μmol) in DME (1.18 mL) in a reaction vial was purged of O$_2$ by bubbling N$_2$ through the mixture for 5 min before 2-(tributylstannyl)pyridine (46 μL, 0.142 mmol) and Pd(PPh$_3$)$_4$ (6.8 mg, 5.90 μmol) were added. The reaction vial was sealed and the reaction was heated under microwave irradiation at 120° C. for 30 min. The reaction mixture was purified directly by flash chromatography (0-80% EtOAc in cyclohexane) and further purified by preparative HPLC to give the title compound (4.2 mg, 7%). LCMS (Method B): $R_T$=1.31 min, m/z=467 [M+H]$^+$. $^1$H NMR (500 MHz, DMSO-d$_6$): δ 8.61-8.54 (m, 2H), 8.14 (s, 1H), 8.05 (d, J=8.0 Hz, 1H), 7.89 (td, J=7.8, 1.6 Hz, 1H), 7.33 (dd, J=7.1, 5.1 Hz, 1H), 4.94 (s, 1H), 4.59-4.47 (m, 1H), 3.81-3.60 (m, 2H), 3.35-3.15 (m, 1H (signal obscured by HDO)), 3.04-2.77 (m, 2H), 1.76-1.39 (m, 7H), 1.28-0.73 (m, 18H).

Example 24: (R)-4-(2-Fluorophenyl)-1-((4-hydroxy-1-(3-phenylbutanoyl)piperidin-4-yl)methyl)piperazin-2-one

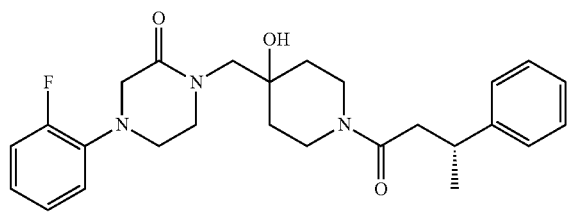 [SMILES: C[C@H](CC(=O)N1CCC(O)(CN2CCN(c3ccccc3F)CC2=O)CC1)c1ccccc1]

Step 1: tert-Butyl (R)-4-((4-hydroxy-1-(3-phenylbutanoyl)piperidin-4-yl)methyl)-3-oxopiperazine-1-carboxylate: tert-Butyl 3-oxopiperazine-1-carboxylate (64 mg, 0.318 mmol) was dissolved in DMF (1.0 mL) and sodium hydride (55% dispersion in mineral oil, 15.1 mg, 0.347 mmol) was added. The mixture was stirred at rt for 10 min Epoxide 3 (75 mg, 0.289 mmol) was added as a solution in DMF (1.0 mL) and the mixture was stirred at rt for 16 h. The temperature was increased to 80° C. After 3 h, further portions of tert-butyl 3-oxopiperazine-1-carboxylate (150 mg, 0.749 mmol) and sodium hydride (60% dispersion in mineral oil, 30 mg, 0.694 mmol) were added and the mixture was stirred at 100° C. After a further 3 h, the mixture was cooled, concentrated in vacuo, the residue was partitioned between EtOAc and water, and extracted using EtOAc (×2). The combined organic phases were washed with brine, dried over MgSO$_4$ and concentrated in vacuo. The residue was purified by flash chromatography (10-100% EtOAc in cyclohexane; then 0-20% MeOH in EtOAc) to give the title compound (27.0 mg, 20%). LCMS (Method A): $R_T$=1.26 min, m/z=460 [M+H]$^+$.

Step 2: (R)-1-((4-Hydroxy-1-(3-phenylbutanoyl)piperidin-4-yl)methyl)piperazin-2-one: tert-Butyl (R)-4-((4-hydroxy-1-(3-phenylbutanoyl)piperidin-4-yl)methyl)-3-oxopiperazine-1-carboxylate (27 mg, 58.7 μmol) was dissolved in DCM (1 mL) and TFA (1 mL) was added. The mixture was stirred at rt for 20 min then concentrated in vacuo. The residue was dissolved in MeOH and added to a pre-equilibrated 2 g SCX-2 cartridge. The column was washed with MeOH then eluted using 2 M NH$_3$ in MeOH and the ammoniacal fractions were concentrated to give the title compound (21 mg, 99%). LCMS (Method A): $R_T$=0.249 min, m/z=360 [M+H]$^+$.

Step 3: (R)-4-(2-Fluorophenyl)-1-((4-hydroxy-1-(3-phenylbutanoyl)piperidin-4-yl)methyl)piperazin-2-one: 1-Bromo-2-fluorobenzene (10 μL, 91.8 μmol) and (R)-1-((4-hydroxy-1-(3-phenylbutanoyl)piperidin-4-yl)methyl)piperazin-2-one (21 mg, 58.4 μmol) were dissolved in toluene (1.0 mL). Cesium carbonate (50 mg, 0.153 mmol) was added, followed by XPhos (5.8 mg, 12.0 μmol) and the mixture was degassed. Pd$_2$(dba)$_3$ (5.6 mg, 6.12 μmol) was added and the mixture was stirred at 110° C. for 16 h. The mixture was concentrated and the residue was purified by flash chromatography twice (10-100% EtOAc in cyclohexane; then 0-20% MeOH in EtOAc; followed Biotage KP-NH column, 0-100% EtOAc in cyclohexane; then 0-15% MeOH in EtOAc) to give the title compound (3.5 mg, 13%). LCMS (Method A): $R_T$=1.35 min, m/z=454 [M+H]$^+$. $^1$H NMR (300 MHz, CDCl$_3$): 7.24-7.35 (m, presumed 6H, partially obscured by solvent signal), 7.10 (m, 2H), 6.96 (m, 1H), 4.48 (m, 1H), 3.84 (m, 1H), 3.55 (m, 3H), 3.40 (m, 4H), 2.99 (m, 1H), 2.63 (m, 1H), 2.51 (m, 1H), 1.55 (m, presumed 2H, partially obscured by water signal), 1.40 (m, 4H), 1.25 (m, 3H), 0.85 (m, 1H), 0.71 (m, 1H).

Example 25 and Example 26: 1-(((R)-1-((S)-3-Cyclohexyl-2-(hydroxymethyl)propanoyl)-4-hydroxy-3,3-dimethylpiperidin-4-yl)methyl)-N,N-dimethyl-6-oxo-4-phenylpiperidine-3-carboxamide and 1-(((S)-1-((S)-3-Cyclohexyl-2-(hydroxymethyl)propanoyl)-4-hydroxy-3,3-dimethylpiperidin-4-yl)methyl)-N,N-dimethyl-6-oxo-4-phenylpiperidine-3-carboxamide

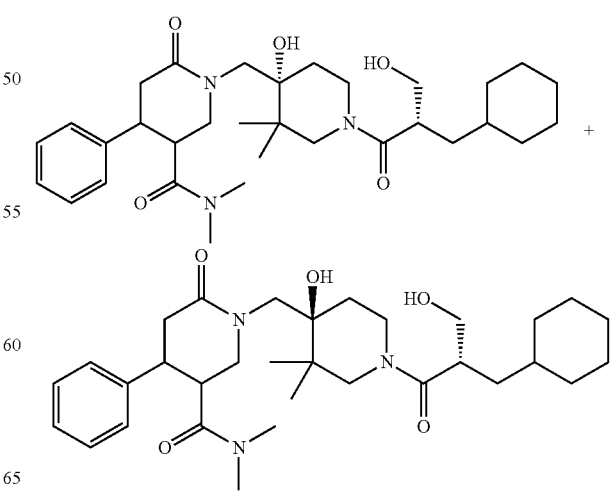

Step 1: Ethyl 4-chloro-6-oxo-1,6-dihydropyridine-3-carboxylate: A mixture of ethyl 4,6-dichloronicotinate (25.0 g, 114 mmol) and sodium acetate (46.6 g, 568 mmol) in acetic acid (325 mL) was heated at reflux for 3 days. The reaction mixture was allowed to cool to rt, diluted with water (650 mL) and the resulting precipitate isolated by filtration. The precipitate was washed with water (6×100 mL) and dried in a vacuum oven at 50° C. to give title compound (18.7 g, 81%) as a light beige solid. LCMS (Method A): $R_T$=0.73 min, m/z=202, 204 [M+H]$^+$. $^1$H NMR (500 MHz, DMSO-$d_6$): δ 12.40 (br. s, 1H), 8.11 (s, 1H), 6.55 (s, 1H), 4.22 (q, J=7.1 Hz, 2H), 1.27 (t, J=7.1 Hz, 3H).

Step 2: Ethyl 6-oxo-4-phenyl-1,6-dihydropyridine-3-carboxylate: Prepared according to General Procedure 5 using ethyl 4-chloro-6-oxo-1,6-dihydropyridine-3-carboxylate (2.00 g, 9.92 mmol), phenylboronic acid (1.81 g, 14.9 mmol), Pd(dppf)Cl$_2$·DCM (420 mg, 0.496 mmol) and sodium carbonate (2.10 g, 19.8 mmol) in 1,4-dioxane (60 mL) and water (12 mL) under microwave irradiation at 120° C. for 30 min to give the title compound (1.77 g, 73%). LCMS (Method A): $R_T$=0.91 min, m/z=244 [M+H]$^+$.

Step 3: Ethyl 1-((1-(tert-butoxycarbonyl)-4-hydroxy-3,3-dimethylpiperidin-4-yl)methyl)-6-oxo-4-phenyl-1,6-dihydropyridine-3-carboxylate: Prepared according to General Procedure 2 using ethyl 6-oxo-4-phenyl-1,6-dihydropyridine-3-carboxylate (1.77 g, 7.28 mmol), Epoxide 1 (1.93 g, 8.00 mmol) and cesium carbonate (3.56 g, 10.9 mmol) in DMF (30 mL) heated to 80° C. for 24 h to give the title compound (2.15 g, 61%). LCMS (Method A): $R_T$=1.75 min, m/z=485 [M+H]$^+$.

Step 4: 1-((1-(tert-Butoxycarbonyl)-4-hydroxy-3,3-dimethylpiperidin-4-yl)methyl)-6-oxo-4-phenyl-1,6-dihydropyridine-3-carboxylic acid: To a stirred solution of ethyl 1-((1-(tert-butoxycarbonyl)-4-hydroxy-3,3-dimethylpiperidin-4-yl)methyl)-6-oxo-4-phenyl-1,6-dihydropyridine-3-carboxylate (1.00 g, 2.06 mmol) in THF (10 mL) and water (2 mL) was added 4 M sodium hydroxide$_{(aq)}$ (2.58 mL, 10.3 mmol). The reaction mixture was heated to 60° C. and stirred overnight at this temperature. The solution was allowed to cool to rt and the solvent volume reduced under reduced pressure. The mixture was acidified with 2 M HCl$_{(aq)}$ and extracted with EtOAc (×3). The combined organic phases were washed with brine, dried over MgSO$_4$, filtered and concentrated under reduced pressure to afford the title compound (937 mg, 99%). LCMS (Method A): $R_T$=1.31 min, m/z=457 [M+H]$^+$.

Step 5: tert-Butyl 4-((5-(dimethylcarbamoyl)-2-oxo-4-phenylpyridin-1(2H)-yl)methyl)-4-hydroxy-3,3-dimethylpiperidine-1-carboxylate: Prepared according to General Procedure 4 using 1-((1-(tert-butoxycarbonyl)-4-hydroxy-3,3-dimethylpiperidin-4-yl)methyl)-6-oxo-4-phenyl-1,6-dihydropyridine-3-carboxylic acid (274 mg, 0.600 mmol), dimethylamine (2 M in THF, 0.360 mL, 0.720 mmol), HATU (274 mg, 0.720 mmol), DIPEA (0.419 mL, 2.40 mmol) and in DCM (12 mL) at rt for 90 min to give the title compound (284 mg, 97%). LCMS (Method A): $R_T$=1.20 min, m/z=484 [M+H]$^+$.

Step 6: 1-((4-Hydroxy-3,3-dimethylpiperidin-4-yl)methyl)-N,N-dimethyl-6-oxo-4-phenyl-1,6-dihydropyridine-3-carboxamide: A solution of tert-butyl 4-((5-(dimethylcarbamoyl)-2-oxo-4-phenylpyridin-1(2H)-yl)methyl)-4-hydroxy-3,3-dimethylpiperidine-1-carboxylate (284 mg, 0.587 mmol) in TFA (3 mL) and DCM (6 mL) was stirred for 10 min before the reaction mixture was purified using a 5 g SCX-2 cartridge (pre-equilibrated with and then washed using 1:1 DCM/MeOH before being eluted with 1:1 DCM/7 M in NH$_3$ in MeOH). The basic eluents were concentrated under reduced pressure to give the title compound (199 mg, 88%) as a colourless solid. LCMS (Method A): $R_T$=0.39 min, m/z=384 [M+H]$^+$.

Step 7: 1-((1-((S)-3-(Benzyloxy)-2-(cyclohexylmethyl)propanoyl)-4-hydroxy-3,3-dimethylpiperidin-4-yl)methyl)-N,N-dimethyl-6-oxo-4-phenyl-1,6-dihydropyridine-3-carboxamide: Prepared according to General Procedure 4 using 1-((4-hydroxy-3,3-dimethylpiperidin-4-yl)methyl)-N,N-dimethyl-6-oxo-4-phenyl-1,6-dihydropyridine-3-carboxamide (65 mg, 0.155 mmol), Acid 4 (43 mg, 0.155 mmol), HATU (65 mg, 0.170 mmol), DIPEA (0.108 mL, 0.619 mmol) and DCM (3 mL) to give the title compound (57 mg, 56%) as a colourless solid after lyophilisation. LCMS (Method A): $R_T$=1.73, 1.76 min (2 diastereoisomers), m/z=642 [M+H]$^+$. $^1$H NMR (500 MHz, DMSO-$d_6$): δ 7.87-7.69 (m, 1H), 7.61-7.08 (m, 10H), 6.51-6.39 (m, 1H), 4.95-4.84 (m, 1H), 4.53-4.30 (m, 3H), 4.20-3.99 (m, 1H), 3.93-3.63 (m, 3H), 3.59-3.38 (m, 2H), 3.25-3.12 (m, 1H), 3.06-2.81 (m, 1H), 2.75 (s, 3H), 2.62 (s, 3H), 1.77-1.48 (m, 6H), 1.49-1.33 (m, 1H), 1.23-1.06 (m, 7H), 1.00-0.74 (m, 7H).

Step 8: 1-(((R)-1-((S)-3-Cyclohexyl-2-(hydroxymethyl)propanoyl)-4-hydroxy-3,3-dimethylpiperidin-4-yl)methyl)-N,N-dimethyl-6-oxo-4-phenylpiperidine-3-carboxamide and 1-(((S)-1-((S)-3-cyclohexyl-2-(hydroxymethyl)propanoyl)-4-hydroxy-3,3-dimethylpiperidin-4-yl)methyl)-N,N-dimethyl-6-oxo-4-phenylpiperidine-3-carboxamide: A solution of 1-((1-((S)-3-(benzyloxy)-2-(cyclohexylmethyl)propanoyl)-4-hydroxy-3,3-dimethylpiperidin-4-yl)methyl)-N,N-dimethyl-6-oxo-4-phenyl-1,6-dihydropyridine-3-carboxamide (52 mg, 81.0 μmol) in MeOH (5 mL) was reduced using an H-Cube® (1 mLmin$^{-1}$, 60° C., full H$_2$). The resulting solution was concentrated under reduced pressure and the residue was purified by flash chromatography (0-10% MeOH in DCM) to give a mixture of products which were further purified by preparative HPLC to give 1-(((R)-1-((S)-3-cyclohexyl-2-(hydroxymethyl)propanoyl)-4-hydroxy-3,3-dimethylpiperidin-4-yl)methyl)-N,N-dimethyl-6-oxo-4-phenylpiperidine-3-carboxamide (3.4 mg, 7%) and 1-(((S)-1-((S)-3-cyclohexyl-2-(hydroxymethyl)propanoyl)-4-hydroxy-3,3-dimethylpiperidin-4-yl)methyl)-N,N-dimethyl-6-oxo-4-phenylpiperidine-3-carboxamide (2.7 mg, 6%) both as colourless solids after lyophilisation. 1-(((R)-1-((S)-3-Cyclohexyl-2-(hydroxymethyl)propanoyl)-4-hydroxy-3,3-dimethylpiperidin-4-yl)methyl)-N,N-dimethyl-6-oxo-4-phenylpiperidine-3-carboxamide: LCMS (Method A): $R_T$=1.27 min, m/z=556 [M+H]$^+$. $^1$H NMR (500 MHz, DMSO-$d_6$): δ 7.33-7.18 (m, 3H), 7.11-7.02 (m, 2H), 4.79 (s, 0.4H), 4.68 (s, 0.6H), 4.56 (t, J=5.5 Hz, 0.6H), 4.49 (t, J=5.7 Hz, 0.4H), 4.01-3.93 (m, 0.6H), 3.89-3.80 (m, 1H), 3.80-3.69 (m, 1.4H), 3.69-3.47 (m, 4H), 3.47-3.36 (m, 2H), 3.24-3.11 (m, 2H), 3.09-3.00 (m, 1H), 3.01-2.80 (m, 2H), 2.80-2.71 (m, 1H), 2.72-2.57 (m, 6H), 1.74-1.50 (m, 5H), 1.50-1.32 (m, 2H), 1.31-1.20 (m, 2H), 1.20-1.01 (m, 5H), 0.98-0.78 (m, 7H). 1-(((S)-1-((S)-3-Cyclohexyl-2-(hydroxymethyl)propanoyl)-4-hydroxy-3,3-dimethylpiperidin-4-yl)methyl)-N,N-dimethyl-6-oxo-4-phenylpiperidine-3-carboxamide: LCMS (Method A): $R_T$=1.29 min, m/z=556 [M+H]$^+$. $^1$H NMR (500 MHz, DMSO-$d_6$): δ 7.33-7.20 (m, 3H), 7.12-7.04 (m, 2H), 4.81 (s, 0.4H), 4.68 (s, 0.6H), 4.60-4.53 (m, 1H), 4.21-4.14 (m, 0.6H), 3.85-3.74 (m, 1.4H), 3.68-3.49 (m, 4H), 3.47-3.35 (m, 3H), 3.28-3.22 (m, 1H), 3.22-3.15 (m, 1H), 3.07-2.96 (m, 2H), 2.94-2.81 (m, 1H), 2.80-2.72 (m, 1H), 2.72-2.65 (m, 6H), 1.79-0.74 (m, 21H).

Example 27: 2-((1-((R)-3-Cyclohexyl-2-methylpropanoyl)-4-hydroxy-3,3-dimethylpiperidin-4-yl)methyl)isoindolin-1-one

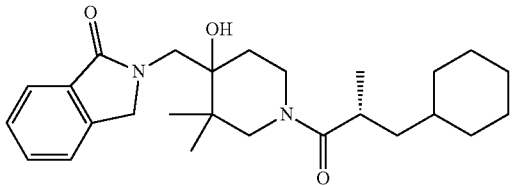 [SMILES: C[C@H](CC1CCCCC1)C(=O)N1CCC(O)(CN2Cc3ccccc3C2=O)C(C)(C)C1]

Step 1: tert-Butyl 4-hydroxy-3,3-dimethyl-4-((1-oxoisoindolin-2-yl)methyl)piperidine-1-carboxylate: Prepared according to General Procedure 2 using isoindolin-1-one (100 mg, 0.751 mmol), Epoxide 1 (235 mg, 0.976 mmol) and cesium carbonate (489 mg, 1.50 mmol) in DMF (2 mL), heated to 80° C. for 16 h to give the title compound (35 mg, 12%). LCMS (Method A): $R_T$=1.34 min, m/z=375 [M+H]$^+$.

Step 2: 2-((4-Hydroxy-3,3-dimethylpiperidin-4-yl)methyl)isoindolin-1-one: Prepared according to General Procedure 3 using tert-butyl 4-hydroxy-3,3-dimethyl-4-((1-oxoisoindolin-2-yl)methyl)piperidine-1-carboxylate (35 mg, 93.5 µmol), DCM (1 mL) and TFA (0.5 mL), stirred at rt for 30 min to give the title compound (22 mg, 85%). LCMS (Method A): $R_T$=0.37 min, m/z=275 [M+H]$^+$.

Step 3: 2-((1-((R)-3-Cyclohexyl-2-methylpropanoyl)-4-hydroxy-3,3-dimethylpiperidin-4-yl)methyl)isoindolin-1-one: Prepared according to General Procedure 4 using 2-((4-hydroxy-3,3-dimethylpiperidin-4-yl)methyl)isoindolin-1-one (22 mg, 80.2 µmol), Acid 1 (16.4 mg, 96.2 µmol), HATU (45.7 mg, 0.120 mmol) and DIPEA (56 µL, 0.321 mmol) in DCM (2 mL) to give the title compound (16.8 mg, 46%). LCMS (Method A): $R_T$=1.57 min, m/z=427 [M+H]$^+$. $^1$H NMR (500 MHz, DMSO-d$_6$): δ 7.68 (dd, J=7.7, 2.3 Hz, 1H), 7.63-7.57 (m, 2H), 7.48 (ddd, J=8.0, 5.7, 2.7 Hz, 1H), 4.81 (ddd, J=18.2, 13.1, 2.5 Hz, 1H), 4.72-4.66 (m, 1H), 4.54-4.46 (m, 1H), 3.97-3.59 (m, 2H), 3.51-3.08 (m, 3H (signal obscured by HDO)), 3.01-2.85 (m, 1H), 1.75-1.31 (m, 8H), 1.26-0.75 (m, 17H).

Example 28: (4S)-1-((1-((R)-3-Cyclohexyl-2-methylpropanoyl)-4-hydroxy-3,3-dimethylpiperidin-4-yl)methyl)-4-phenylpyrrolidin-2-one

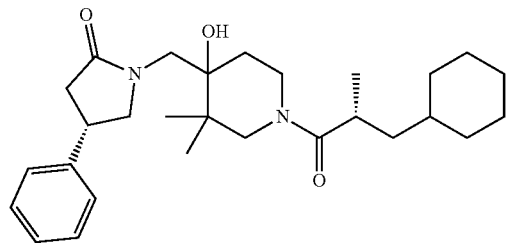 [SMILES: C[C@H](CC1CCCCC1)C(=O)N1CCC(O)(CN2C[C@H](c3ccccc3)CC2=O)C(C)(C)C1]

Step 1: tert-Butyl 4-hydroxy-3,3-dimethyl-4-(((S)-2-oxo-4-phenylpyrrolidin-1-yl)methyl)piperidine-1-carboxylate: Sodium hydride (60% dispersion in mineral oil, 27.3 mg, 0.682 mmol) was added to a solution of (S)-4-phenylpyrrolidin-2-one (100 mg, 0.620 mmol) in DMF (1.5 mL) at rt and the resulting mixture was stirred for 30 min. A solution of Epoxide 1 (180 mg, 0.744 mmol) in DMF (0.5 mL) was added and the reaction was stirred at 80° C. for 3 h. The reaction mixture was allowed to cool to rt, poured on to 1:1 water/brine and extracted with EtOAc (×3). The combined organic phases were passed through a phase separator and concentrated in vacuo. The crude material was purified by flash chromatography (0-100% EtOAc in cyclohexane, then 0-20% MeOH in EtOAc) to give the title compound (160 mg, 64%). LCMS (Method A): $R_T$=1.55 min, m/z=403 [M+H]$^+$; 347 [M-butene+H]$^+$.

Step 2: (4S)-1-((4-Hydroxy-3,3-dimethylpiperidin-4-yl)methyl)-4-phenylpyrrolidin-2-one: Prepared according to General Procedure 3 using tert-butyl 4-hydroxy-3,3-dimethyl-4-(((S)-2-oxo-4-phenylpyrrolidin-1-yl)methyl)piperidine-1-carboxylate (160 mg, 0.398 mmol), DCM (3 mL) and TFA (1.5 mL), stirring at rt for 30 min to give the title compound (92 mg, 76%). LCMS (Method A): $R_T$=0.58 min, m/z=303 [M+H]$^+$.

Step 3: (4S)-1-((1-((R)-3-Cyclohexyl-2-methylpropanoyl)-4-hydroxy-3,3-dimethylpiperidin-4-yl)methyl)-4-phenylpyrrolidin-2-one: Prepared according to General Procedure 4 using (4S)-1-((4-hydroxy-3,3-dimethylpiperidin-4-yl)methyl)-4-phenylpyrrolidin-2-one (20 mg, 66.1 µmol), Acid 1 (13.5 mg, 79.4 µmol), HATU (37.7 mg, 99.2 µmol) and DIPEA (46.2 µL, 0.264 mmol) in DCM (2 mL) to give the title compound (9.9 mg, 29%) as a colourless solid. LCMS (Method A): $R_T$=1.68 min, m/z=455 [M+H]$^+$. $^1$H NMR (500 MHz, DMSO-d$_6$): δ 7.37-7.21 (m, 5H), 4.59-4.50 (m, 1H), 3.80-3.50 (m, 4H), 3.46-2.86 (m, 6H (signal obscured by HDO)), 2.73-2.33 (m, 1H (signal obscured by DMSO and satellites)), 1.74-1.32 (m, 8H), 1.31-1.02 (m, 6H), 1.01-0.76 (m, 11H).

Example 29: (4R)-1-((1-((R)-3-Cyclohexyl-2-methylpropanoyl)-4-hydroxy-3,3-dimethylpiperidin-4-yl)methyl)-4-phenylpyrrolidin-2-one

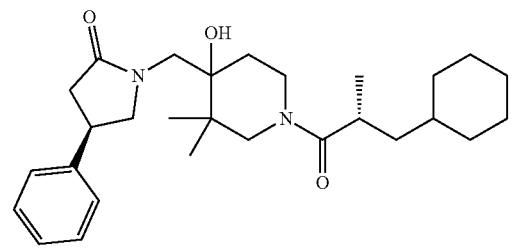 [SMILES: C[C@H](CC1CCCCC1)C(=O)N1CCC(O)(CN2C[C@@H](c3ccccc3)CC2=O)C(C)(C)C1]

Step 1: tert-Butyl 4-hydroxy-3,3-dimethyl-4-(((R)-2-oxo-4-phenylpyrrolidin-1-yl)methyl)piperidine-1-carboxylate: Sodium hydride (60% dispersion in mineral oil, 27.3 mg, 0.682 mmol) was added to a solution of (R)-4-phenylpyrrolidin-2-one (100 mg, 0.620 mmol) in DMF (1.5 mL) at rt and the resulting mixture was stirred for 30 min. A solution of Epoxide 1 (180 mg, 0.744 mmol) in DMF (0.5 mL) was added and the reaction was stirred at 80° C. for 2 h. The reaction mixture was allowed to cool to rt, poured on to 1:1 water/brine and extracted with EtOAc (×3). The combined organic phases were passed through a phase separator and concentrated in vacuo. The crude material was purified by flash chromatography (0-100% EtOAc in cyclohexane) to give the title compound (120 mg, 48%). LCMS (Method A): $R_T$=1.53 min, m/z=403 [M+H]$^+$; 347 [M-butene+H]$^+$.

Step 2: (4R)-1-((4-Hydroxy-3,3-dimethylpiperidin-4-yl)methyl)-4-phenylpyrrolidin-2-one: Prepared according to General Procedure 3 using tert-butyl 4-hydroxy-3,3-dimethyl-4-(((R)-2-oxo-4-phenylpyrrolidin-1-yl)methyl)piperidine-1-carboxylate (120 mg, 0.298 mmol), DCM (3 mL) and TFA (1.5 mL), stirring at rt for 30 min to give the title compound (80 mg, 88%). LCMS (Method A): $R_T$=0.49 min, m/z=303 [M+H]$^+$.

Step 3: (4R)-1-((1-((R)-3-Cyclohexyl-2-methylpropanoyl)-4-hydroxy-3,3-dimethylpiperidin-4-yl)methyl)-4-phenylpyrrolidin-2-one: Prepared according to General Procedure 4 using (4R)-1-((4-hydroxy-3,3-dimethylpiperidin-4-yl)methyl)-4-phenylpyrrolidin-2-one (80 mg, 0.265 mmol), Acid 1 (49.5 mg, 0.291 mmol), HATU (121 mg, 0.317 mmol) and DIPEA (139 μL, 0.794 mmol) in DCM (4 mL) to give the title compound (111 mg, 87%). LCMS (Method A): $R_T$=1.83 min, m/z=455 [M+H]$^+$. $^1$H NMR (500 MHz, DMSO-d$_6$): δ 7.37-7.27 (m, 4H), 7.27-7.22 (m, 1H), 4.59-4.50 (m, 1H), 3.80-3.52 (m, 4H), 3.45-2.85 (m, 6H (signal obscured by HDO)), 2.73-2.59 (m, 1H (signal obscured by DMSO satellite)), 2.47-2.35 (m, 1H (signal obscured by DMSO+satellite)), 1.73-1.34 (m, 8H), 1.23-1.02 (m, 5H), 0.99-0.77 (m, 11H).

Example 30: 4-Benzyl-1-((1-((R)-3-cyclohexyl-2-methylpropanoyl)-4-hydroxy-3,3-dimethylpiperidin-4-yl)methyl)pyrrolidin-2-one

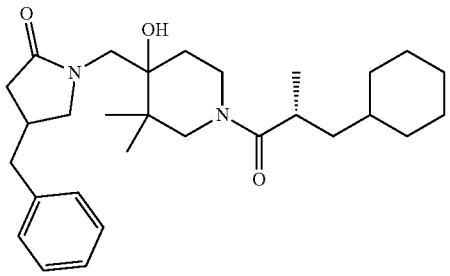 [SMILES: C[C@H](CC1CCCCC1)C(=O)N1CCC(O)(CN2CC(Cc3ccccc3)CC2=O)C(C)(C)C1]

Step 1: tert-Butyl 4-((4-benzyl-2-oxopyrrolidin-1-yl)methyl)-4-hydroxy-3,3-dimethylpiperidine-1-carboxylate: Sodium hydride (60% dispersion in mineral oil, 25.1 mg, 0.628 mmol) was added to a solution of 4-benzylpyrrolidin-2-one (100 mg, 0.571 mmol) in DMF (2.5 mL) at rt and the resulting mixture was stirred for 30 min. A solution of Epoxide 1 (165 mg, 0.685 mmol) in DMF (0.5 mL) was added and the reaction was stirred at 80° C. for 16 h. The reaction mixture was allowed to cool to rt, poured on to 1:1 water/brine and extracted with EtOAc (×3). The combined organic phases were passed through a phase separator and concentrated in vacuo. The crude material was purified by flash chromatography (0-100% EtOAc in cyclohexane) to give the title compound (62 mg, 26%). LCMS (Method A): $R_T$=1.54 min, m/z=417 [M+H]$^+$; 361 [M-butene+H]$^+$.

Step 2: 4-Benzyl-1-((4-hydroxy-3,3-dimethylpiperidin-4-yl)methyl)pyrrolidin-2-one: Prepared according to General Procedure 3 using tert-butyl 4-((4-benzyl-2-oxopyrrolidin-1-yl)methyl)-4-hydroxy-3,3-dimethylpiperidine-1-carboxylate (60 mg, 0.144 mmol), DCM (2 mL) and TFA (1 mL), stirring at rt for 30 min to give the title compound (31 mg, 68%). LCMS (Method A): $R_T$=0.31 min, m/z=317 [M+H]$^+$.

Step 3: 4-Benzyl-1-((1-((R)-3-cyclohexyl-2-methylpropanoyl)-4-hydroxy-3,3-dimethylpiperidin-4-yl)methyl)pyrrolidin-2-one: Prepared according to General Procedure 4 using 4-benzyl-1-((4-hydroxy-3,3-dimethylpiperidin-4-yl)methyl)pyrrolidin-2-one (30 mg, 94.8 μmol), Acid 1 (19.4 mg, 0.114 mmol), HATU (54.1 mg, 0.142 mmol) and DIPEA (66.2 μL, 0.379 mmol) in DCM (2.5 mL) to give the title compound (32.8 mg, 69%). LCMS (Method A): $R_T$=1.74 min, m/z=469 [M+H]$^+$. $^1$H NMR (500 MHz, DMSO-d$_6$): δ 7.33-7.26 (m, 2H), 7.25-7.17 (m, 3H), 4.52-4.47 (m, 1H), 3.75-2.83 (m, 8H (signal obscured by HDO)), 2.78-2.55 (m, 4H (signal obscured by DMSO satellite)), 2.41-2.27 (m, 1H (signal obscured by DMSO satellite)), 2.05 (ddd, J=33.3, 15.6, 6.8 Hz, 1H), 1.71-1.02 (m, 13H), 0.99-0.75 (m, 11H).

Example 31: 4-((7-((R)-3-Cyclohexyl-2-methylpropanoyl)-10-hydroxy-7-azaspiro[4.5]decan-10-yl)methyl)morpholin-3-one

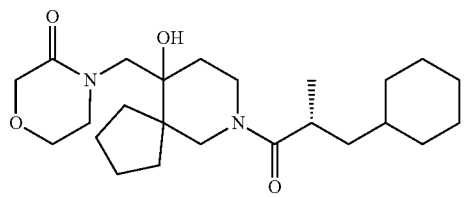 [SMILES: C[C@H](CC1CCCCC1)C(=O)N1CCC(O)(CN2CCOCC2=O)C2(CCCC2)C1]

Step 1: tert-Butyl 10-hydroxy-10-((3-oxomorpholino)methyl)-7-azaspiro[4.5]decane-7-carboxylate: Cesium carbonate (121 mg, 0.371 mmol) was added to a stirred solution of morpholin-3-one (25.0 mg, 0.247 mmol) and Epoxide 2 (72.7 mg, 0.272 mmol) in DMF (1.0 mL) in a 4 mL vial. The vessel was sealed and was heated to 100° C. After 2 h, the reaction mixture was partitioned between 1:1 brine/water and EtOAc, the layers were separated, the aqueous phases was further extracted with EtOAc (×3), the combined organic extracts were dried (phase separator), the solvents were removed in vacuo and the remaining residue was purified by flash chromatography (0-100% EtOAc in cyclohexane) to give the title compound (46.0 mg, 50%) as a white solid.

Step 2: 4-((10-Hydroxy-7-azaspiro[4.5]decan-10-yl)methyl)morpholin-3-one hydrochloride: 4 M HCl in 1,4-dioxane (1.0 mL, 28.8 mmol) was added to tert-butyl 10-hydroxy-10-((3-oxomorpholino)methyl)-7-azaspiro[4.5]decane-7-carboxylate (44.0 mg, 0.119 mmol) and stirred at rt. After 30 min, the solvents were removed in vacuo to give the crude title compound (46.2 mg, >100%) as a colourless gum that was carried through to the next step without further purification.

Step 3: 4-((7-((R)-3-Cyclohexyl-2-methylpropanoyl)-10-hydroxy-7-azaspiro[4.5]decan-10-yl)methyl)morpholin-3-one: Prepared according to General Procedure 4 using 4-((10-hydroxy-7-azaspiro[4.5]decan-10-yl)methyl)morpholin-3-one hydrochloride (18.3 mg, 60.0 μmol), Acid 1 (10.2 mg, 60.0 μmol), HATU (27.4 mg, 72.0 μmol), DIPEA (31 μL, 180 μmol) and DCM (0.5 mL) to give the title compound (22.9 mg, 90%) as a white solid after lyophilisation. LCMS (Method A): $R_T$=1.69 min, m/z=421 [M+H]$^+$. $^1$H NMR (500 MHz, DMSO-d$_6$): δ 4.74-4.60 (m, 1H), 4.20-3.95 (m, 3H), 3.88-2.77 (m, 9H, overlapping solvent peak), 1.93-0.75 (m, 27H).

Example 32: 4-((10-Hydroxy-7-((R)-4,4-trifluoro-2-methylbutanoyl)-7-azaspiro[4.5]decan-10-yl)methyl)morpholin-3-one

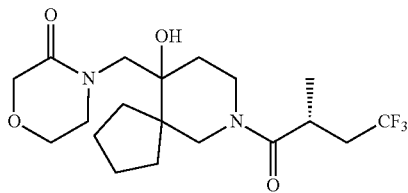 [SMILES: C[C@H](CC(F)(F)F)C(=O)N1CCC(O)(CN2CCOCC2=O)C2(CCCC2)C1]

Prepared according to General Procedure 4 using 4-((10-hydroxy-7-azaspiro[4.5]decan-10-yl)methyl)morpholin-3-one hydrochloride (18.3 mg, 60.0 μmol), Acid 3 (9.4 mg, 60.0 μmol), HATU (27.4 mg, 72.0 μmol), DIPEA (31 μL, 180 μmol) and DCM (0.5 mL) to give the title compound (20.6 mg, 84%) as a white solid after lyophilisation. LCMS (Method A): $R_T$=1.21 min, m/z=407 [M+H]$^+$. $^1$H NMR (500 MHz, DMSO-d$_6$): δ 4.80-4.60 (m, 1H), 4.24-3.90 (m, 3H), 3.88-3.59 (m, 4H), 3.55-2.87 (m, 5H, overlapping solvent peak), 2.83-2.66 (m, 1H), 2.32-2.18 (m, 1H), 1.96-0.70 (m, 14H).

The following table of Examples were prepared using parallel synthesis according to General Procedure 6, except Example 39 that resulted from the N-Boc deprotection of Example 38 using General Procedure 3.

| Ex. | Structure | Name | LCMS (Method A): $R_T$, m/z | $^1$H NMR (500 MHz, DMSO-d$_6$): |
|---|---|---|---|---|
| 33 | 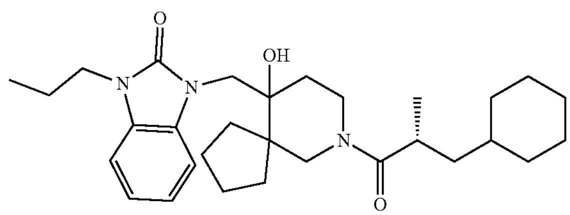 [SMILES: CCCn1c(=O)n(CC2(O)CCN(C(=O)[C@H](C)CC3CCCCC3)CC23CCCC3)c2ccccc21] | 1-((7-((R)-3-Cyclohexyl-2-methylpropanoyl)-10-hydroxy-7-azaspiro[4.5]decan-10-yl)methyl)-3-propyl-1,3-dihydro-2H-benzo[d]imidazol-2-one | 2.20 min, 496 [M + H]$^+$ | |
| 34 | 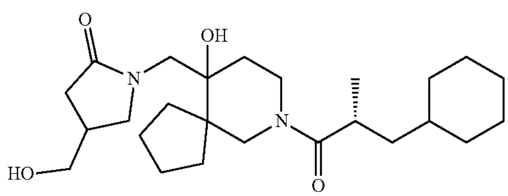 [SMILES: C[C@H](CC1CCCCC1)C(=O)N1CCC(O)(CN2CC(CO)CC2=O)C2(CCCC2)C1] | 1-((7-((R)-3-Cyclohexyl-2-methylpropanoyl)-10-hydroxy-7-azaspiro[4.5]decan-10-yl)methyl)-4-(hydroxymethyl)pyrrolidin-2-one | 1.47 min, 435 [M + H]$^+$ | δ 4.80-4.40 (m, 2H), 3.87-2.73 (m, 9H), 2.40-0.7 (m, 31H). |
| 35 | 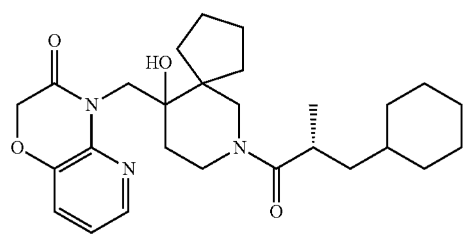 [SMILES: C[C@H](CC1CCCCC1)C(=O)N1CCC(O)(CN2C(=O)COc3cccnc32)C2(CCCC2)C1] | 4-((7-((R)-3-Cyclohexyl-2-methylpropanoyl)-10-hydroxy-7-azaspiro[4.5]decan-10-yl)methyl)-2H-pyrido[3,2-b][1,4]oxazin-3(4H)-one | 1.63 min, 470 [M + H]$^+$ | |
| 36 | 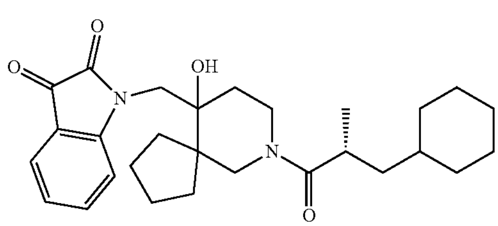 [SMILES: C[C@H](CC1CCCCC1)C(=O)N1CCC(O)(CN2C(=O)C(=O)c3ccccc32)C2(CCCC2)C1] | 1-((7-((R)-3-Cyclohexyl-2-methylpropanoyl)-10-hydroxy-7-azaspiro[4.5]decan-10-yl)methyl)indoline-2,3-dione | 2.04 min, 467 [M + H]$^+$ | |
| 37 | 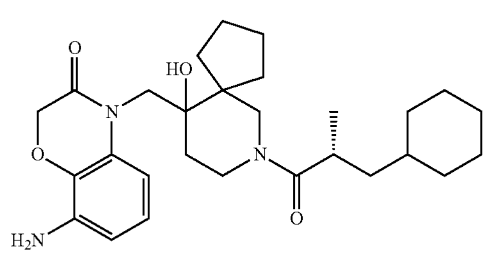 [SMILES: C[C@H](CC1CCCCC1)C(=O)N1CCC(O)(CN2C(=O)COc3c(N)cccc32)C2(CCCC2)C1] | 8-Amino-4-((7-((R)-3-cyclohexyl-2-methylpropanoyl)-10-hydroxy-7-azaspiro[4.5]decan-10-yl)methyl)-2H-benzo[b][1,4]oxazin-3(4H)-one | 1.93 min, 484 [M + H]$^+$ | |

| Ex. | Structure | Name | LCMS (Method A): $R_T$, m/z | $^1$H NMR (500 MHz, DMSO-$d_6$): |
|---|---|---|---|---|
| 38 | 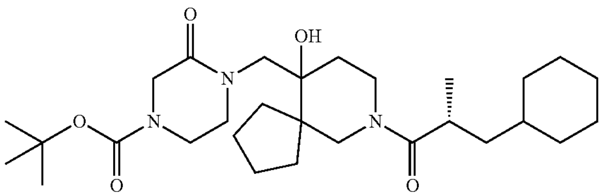 [SMILES: C[C@H](CC1CCCCC1)C(=O)N1CCC(O)(CN2CCN(C(=O)OC(C)(C)C)CC2=O)C2(CCCC2)C1] | tert-Butyl 4-((7-((R)-3-cyclohexyl-2-methylpropanoyl)-10-hydroxy-7-azaspiro[4.5]decan-10-yl)methyl)-3-oxopiperazine-1-carboxylate | 1.97 min, 520 [M + H]$^+$ | |
| 39 | 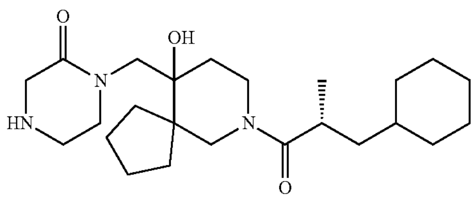 [SMILES: C[C@H](CC1CCCCC1)C(=O)N1CCC(O)(CN2CCNCC2=O)C2(CCCC2)C1] | 1-((7-((R)-3-Cyclohexyl-2-methylpropanoyl)-10-hydroxy-7-azaspiro[4.5]decan-10-yl)methyl)piperazin-2-one | 1.25 min, 420 [M + H]$^+$ | δ 4.80 (d, 0.5H), 4.72 (s, 1H), 4.03 (d, 0.5H), 3.98-3.93 (m, 0.5H), 3.89-3.81 (m, 0.5H), 3.70-3.56 (m, 2H), 3.52-2.76 (m, 10H (signal overlaps with HDO)), 1.86-1.75 (m, 1H), 1.68-1.34 (m, 14H), 1.18-1.04 (m, 6H), 0.97-0.91 (m, 3H), 0.87-0.78 (m, 2H). |
| 40 | 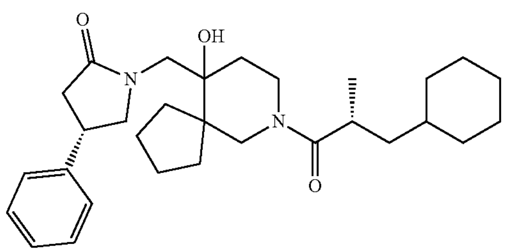 [SMILES: C[C@H](CC1CCCCC1)C(=O)N1CCC(O)(CN2C[C@H](c3ccccc3)CC2=O)C2(CCCC2)C1] | (4S)-1-((7-((R)-3-Cyclohexyl-2-methylpropanoyl)-10-hydroxy-7-azaspiro[4.5]decan-10-yl)methyl)-4-phenylpyrrolidin-2-one | 1.96 min, 481 [M + H]$^+$ | |
| 41 | 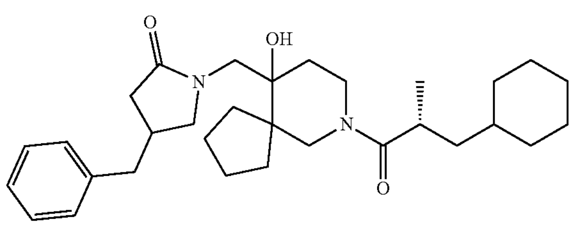 [SMILES: C[C@H](CC1CCCCC1)C(=O)N1CCC(O)(CN2CC(Cc3ccccc3)CC2=O)C2(CCCC2)C1] | 4-Benzyl-1-((7-((R)-3-cyclohexyl-2-methylpropanoyl)-10-hydroxy-7-azaspiro[4.5]decan-10-yl)methyl)pyrrolidin-2-one | 2.04 min, 495 [M + H]$^+$ | δ 7.33-7.28 (m, 2H), 7.26-7.19 (m, 3H), 4.60-4.44 (m, 1H), 3.90-2.99 (m, 6H), 2.97-2.55 (m, 5H), 2.44-2.28 (m, 1H), 2.17-1.99 (m, 1H), 1.90-1.70 (m, 1H), 1.70-1.01 (m, 21H), 1.00-0.74 (m, 5H) |

The following table of Examples were prepared using parallel synthesis according to General Procedure 7:

| Example | Structure | Name | LCMS (Method C): $R_T$, m/z |
|---|---|---|---|
| 42 | 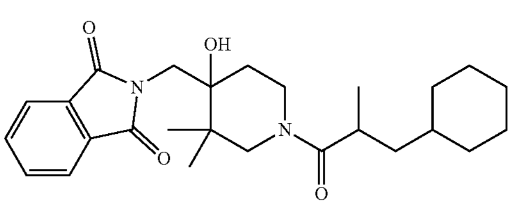 [SMILES: CC(CC1CCCCC1)C(=O)N1CCC(O)(CN2C(=O)c3ccccc3C2=O)C(C)(C)C1] | 2-((1-(3-Cyclohexyl-2-methylpropanoyl)-4-hydroxy-3,3-dimethylpiperidin-4-yl)methyl)isoindoline-1,3-dione | 1.33 min, 441 [M + H]$^+$ |

| Example | Structure | Name | LCMS (Method C): $R_T$, m/z |
|---|---|---|---|
| 43 | 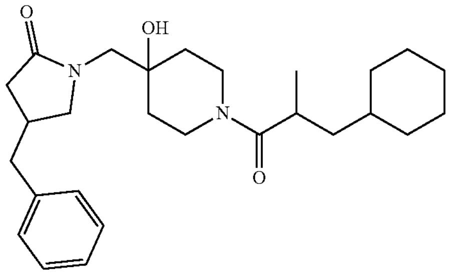 [SMILES: CC(CC1CCCCC1)C(=O)N1CCC(O)(CN2CC(Cc3ccccc3)CC2=O)CC1] | 4-Benzyl-1-((1-(3-cyclohexyl-2-methylpropanoyl)-4-hydroxypiperidin-4-yl)methyl)pyrrolidin-2-one | 1.42 min, 441 [M + H]+ |
| 44 | 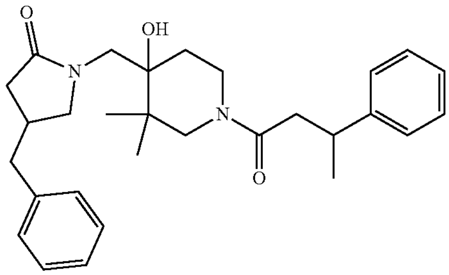 [SMILES: CC(CC(=O)N1CCC(O)(CN2CC(Cc3ccccc3)CC2=O)C(C)(C)C1)c1ccccc1] | 4-Benzyl-1-((4-hydroxy-3,3-dimethyl-1-(3-phenylbutanoyl)piperidin-4-yl)methyl)pyrrolidin-2-one | 1.48 min, 463 [M + H]+ |
| 45 | 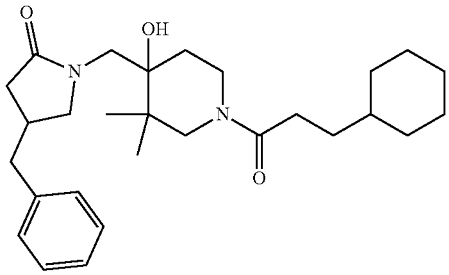 [SMILES: CC1(C)CN(C(=O)CCC2CCCCC2)CCC1(O)CN1CC(Cc2ccccc2)CC1=O] | 4-Benzyl-1-((1-(3-cyclohexylpropanoyl)-4-hydroxy-3,3-dimethylpiperidin-4-yl)methyl)pyrrolidin-2-one | 1.59 min, 455 [M + H]+ |
| 46 | 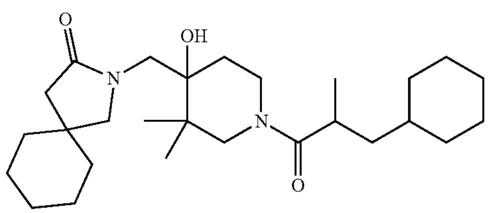 [SMILES: CC(CC1CCCCC1)C(=O)N1CCC(O)(CN2CC3(CCCCC3)CC2=O)C(C)(C)C1] | 2-((1-(3-Cyclohexyl-2-methylpropanoyl)-4-hydroxy-3,3-dimethylpiperidin-4-yl)methyl)-2-azaspiro[4.5]decan-3-one | 1.56 min, 447 [M + H]+ |

Example 47: Benzyl 4-((7-((R)-3-cyclohexyl-2-methylpropanoyl)-10-hydroxy-7-azaspiro[4.5]decan-10-yl)methyl)-3-oxopiperazine-1-carboxylate

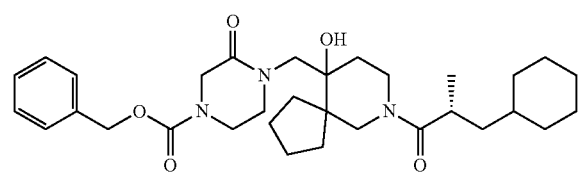 [SMILES: C[C@H](CC1CCCCC1)C(=O)N1CCC(O)(CN2CCN(C(=O)OCc3ccccc3)CC2=O)C2(CCCC2)C1]

Step 1: tert-Butyl 10-((4-((benzyloxy)carbonyl)-2-oxopiperazin-1-yl)methyl)-10-hydroxy-7-azaspiro[4.5]decane-7-carboxylate: Prepared according to General Procedure 2 using benzyl 3-oxopiperazine-1-carboxylate (117 mg, 0.500 mmol), Epoxide 2 (134 mg, 0.500 mmol), potassium tert-butoxide (67 mg, 0.600 mmol) and DMF (1 mL) at 80° C. for 19.5 h to give the title compound (24.5 mg, 9%) as a very pale yellow solid. LCMS (Method A): $R_T$=1.62 min, m/z=446 [M-butene+H]+. $^1$H NMR (500 MHz, DMSO-d$_6$): δ 7.47-7.25 (m, 5H), 5.11 (s, 2H), 4.56 (s, 1H), 4.12-3.91 (m, 4H), 3.74-3.69 (m, 1H), 3.66-3.45 (m, 4H), 3.41-3.36 (m, 1H), 3.11-3.05 (m, 1H), 2.93 (d, J=14.0 Hz, 1H), 1.83-1.77 (m, 1H), 1.67-1.44 (m, 6H), 1.43-1.21 (m, 11H), 1.12-1.06 (m, 1H).

Step 2: Benzyl 4-((10-hydroxy-7-azaspiro[4.5]decan-10-yl)methyl)-3-oxopiperazine-1-carboxylate: A solution of tert-butyl 10-((4-((benzyloxy)carbonyl)-2-oxopiperazin-1-yl)methyl)-10-hydroxy-7-azaspiro[4.5]decane-7-carboxylate (37 mg, 74.2 μmol) in TFA (0.5 mL) and DCM (1 mL) was stirred for 10 min before the reaction mixture was purified using a 2 g SCX-2 cartridge (pre-equilibrated with and then washed using 1:1 DCM/MeOH before being eluted with 1:1 DCM/7 M in NH$_3$ in MeOH). The basic eluents were concentrated under reduced pressure to give the title compound (26.6 mg, 89%) as colourless solid. LCMS (Method A): $R_T$=0.72 min, m/z=402 [M+H]$^+$.

Step 3: Benzyl 4-((7-((R)-3-cyclohexyl-2-methylpropanoyl)-10-hydroxy-7-azaspiro[4.5]decan-10-yl)methyl)-3-oxopiperazine-1-carboxylate: Prepared according to General Procedure 4 using benzyl 4-((10-hydroxy-7-azaspiro[4.5]decan-10-yl)methyl)-3-oxopiperazine-1-carboxylate (26.6 mg, 66.3 µmol), Acid 1 (12.4 mg, 72.9 µmol), HATU (27.7 mg, 0.0729 mmol) and DIPEA (46 µL, 0.265 mmol) in DCM (1.3 mL) to give the title compound (37 mg, quantitative) as a colourless solid after lyophilisation. LCMS (Method A): $R_T$=1.83 min, m/z=554 [M+H]$^+$. $^1$H NMR (500 MHz, DMSO-d$_6$): δ 7.54-7.22 (m, 5H), 5.11 (s, 2H), 4.66-4.56 (m, 1H), 4.17-3.93 (m, 3H), 3.78-3.69 (m, 1H), 3.67-3.06 (m, 6H (signal overlaps with HDO)), 3.03-2.75 (m, 3H), 1.91-1.02 (m, 21H), 1.01-0.90 (m, 3H), 0.88-0.77 (m, 2H).

Example 48: 4-Acetyl-1-((7-((R)-3-cyclohexyl-2-methylpropanoyl)-10-hydroxy-7-azaspiro[4.5]decan-10-yl)methyl)piperazin-2-one

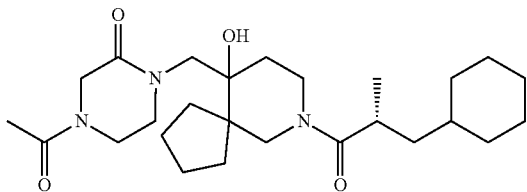 [SMILES: CC(=O)N1CCN(CC2(O)CCN(C(=O)[C@H](C)CC3CCCCC3)CC23CCCC3)C(=O)C1]

To a solution of 1-((7-((R)-3-cyclohexyl-2-methylpropanoyl)-10-hydroxy-7-azaspiro[4.5]decan-10-yl)methyl)piperazin-2-one (5 mg, 11.9 µmol) and triethylamine (17 µL, 0.119 mmol) in DCM (0.5 mL) was added acetic anhydride (6 µL, 59.6 µmol). After 30 min, the reaction mixture was diluted with saturated NaHCO$_{3(aq)}$ (5 mL) and the resulting mixture was extracted with DCM (3×4 mL) using a phase separator. The combined organic phases were concentrated under reduced pressure and the residue was purified by flash chromatography (0-10% MeOH in DCM) to give the title compound (4 mg, 69%) as a beige solid after lyophilisation. LCMS (Method A): $R_T$=1.42 min, m/z=462 [M+H]$^+$. $^1$H NMR (500 MHz, DMSO-d$_6$): δ 4.67-4.56 (m, 1H), 4.20-3.92 (m, 3H), 3.83-2.77 (m, 10H (signal overlaps with HDO)), 2.03 (s, 1.5H), 2.00 (s, 1.5H), 1.89-1.76 (m, 1H), 1.66-1.21 (m, 15H), 1.21-1.03 (m, 5H), 1.02-0.88 (m, 3H), 0.87-0.79 (m, 2H).

Example 49: 1-((7-((R)-3-Cyclohexyl-2-methylpropanoyl)-10-hydroxy-7-azaspiro[4.5]decan-10-yl)methyl)-4-(methylsulfonyl)piperazin-2-one

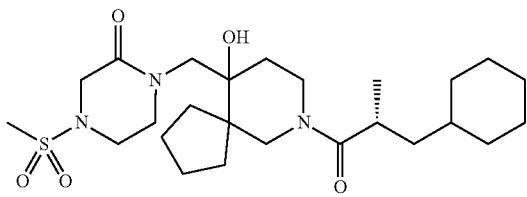 [SMILES: C[C@H](CC1CCCCC1)C(=O)N1CCC(O)(CN2CCN(S(C)(=O)=O)CC2=O)C2(CCCC2)C1]

A solution of triethylamine (0.2 M in DCM, 0.200 mL, 40 µmol) was added to a solution of 1-((7-((R)-3-cyclohexyl-2-methylpropanoyl)-10-hydroxy-7-azaspiro[4.5]decan-10-yl)methyl)piperazin-2-one (14 mg, 33.4 µmol) and methanesulfonyl chloride (0.2 M in DCM, 0.200 mL, 40.0 µmol) in DCM (0.33 mL) at rt. After 70 min, the reaction mixture was diluted with saturated NaHCO$_{3(aq)}$ (5 mL) and the resulting mixture was extracted with DCM (3×5 mL) using a phase separator. The combined organic phases were concentrated under reduced pressure and the residue was purified by flash chromatography (0-10% MeOH in DCM) to give the title compound (8.9 mg, 50%) as a colourless solid after lyophilisation. LCMS (Method A): $R_T$=1.44 min, m/z=498 [M+H]$^+$. $^1$H NMR (500 MHz, DMSO-d$_6$): δ 4.69-4.59 (m, 1H), 4.22-4.02 (m, 1H), 3.89-3.73 (m, 3H), 3.69-3.08 (m, 7H (signals overlap with HDO)), 2.99 (s, 3H), 2.97-2.74 (m, 2H), 1.90-1.02 (m, 21H), 0.99-0.89 (m, 3H), 0.88-0.77 (m, 2H).

Example 50: 1-((7-((R)-3-Cyclohexyl-2-methylpropanoyl)-10-hydroxy-7-azaspiro[4.5]decan-10-yl)methyl)-4-phenylpiperazin-2-one

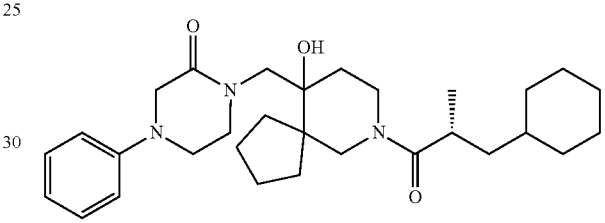

Step 1: 4-Phenylpiperazin-2-one: A solution of sodium nitrite (248 mg, 3.60 mmol) in water (2.25 mL) was added dropwise to a solution of 4-(4-aminophenyl)-2-piperazinone (574 mg, 3.00 mmol) in 50% sulfuric acid$_{(aq)}$ (2.25 mL) at 0° C. After stirring for 30 min, a solution of sodium hypophosphite monohydrate (636 mg, 6.00 mmol) in water (2.25 mL) was added and the reaction was stirred at 0° C. for 30 min before being allowed to warm to rt. After 4 h, the reaction was diluted with water (10 mL) and saturated NaHCO$_{3(aq)}$ was added until gas evolution ceased (pH ~8). The resulting mixture was extracted with EtOAc (×3), the combined organic phases were passed through a phase separator and concentrated under reduced pressure. The crude material was purified by flash chromatography (0-100% EtOAc in cyclohexane; then 0-20% MeOH in EtOAc) to give the title compound (59 mg, 11%) as a yellow solid. LCMS (Method B): $R_T$=0.72 min, m/z=177 [M+H]$^+$. $^1$H NMR (500 MHz, DMSO-d$_6$): δ 8.00 (s, 1H), 7.28-7.18 (m, 2H), 6.91 (d, J=8.2 Hz, 2H), 6.78 (t, J=7.3 Hz, 1H), 3.69 (s, 2H), 3.42-3.37 (m, 2H), 3.32-3.29 (m, 2H).

Step 2: 1-((7-((R)-3-Cyclohexyl-2-methylpropanoyl)-10-hydroxy-7-azaspiro[4.5]decan-10-yl)methyl)-4-phenylpiperazin-2-one: Sodium hydride (60% dispersion in mineral oil, 7.5 mg, 0.187 mmol) was added to a solution of 4-phenylpiperazin-2-one (30 mg, 0.170 mmol) in DMF (0.4 mL) at rt and the resulting mixture was stirred for 30 min. A solution of Epoxide 4 (65 mg, 0.204 mmol) in DMF (0.2 mL) was added and the reaction was stirred at 80° C. for 20 h. The reaction mixture was allowed to cool to rt, poured on to 1:1 water/brine and extracted with EtOAc (×3). The combined organic phases were passed through a phase separator and concentrated under reduced pressure. The crude material was purified by flash chromatography (0-100% EtOAc in cyclohexane) and preparative HPLC to give the title compound (16.4 mg, 19%) as a colourless solid after lyophilisation. LCMS (Method B): $R_T$=1.66 min, m/z=496 [M+H]$^+$. $^1$H NMR (500 MHz, DMSO-$d_6$): δ 7.23 (t, J=7.7 Hz, 2H), 6.91 (d, J=8.1 Hz, 2H), 6.79 (t, J=7.3 Hz, 1H), 4.75-4.64 (m, 1H), 4.23-2.78 (m, 13H (signal overlaps with HDO)), 1.92-1.76 (m, 1H), 1.68-1.05 (m, 20H), 1.01-0.90 (m, 3H), 0.89-0.77 (m, 2H).

Example 51: 2-((1-((R)-3-Cyclohexyl-2-methylpropanoyl)-4-hydroxy-3,3-dimethylpiperidin-4-yl)methyl)-[1,2,4]triazolo[4,3-a]pyridin-3(2H)-one

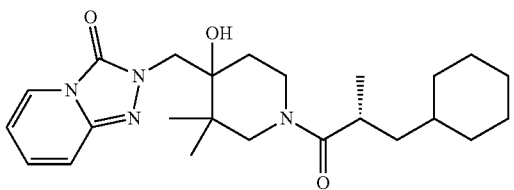 [SMILES: C[C@H](CC1CCCCC1)C(=O)N1CCC(O)(Cn2nc3ccccn3c2=O)C(C)(C)C1]

Step 1: tert-Butyl 4-hydroxy-3,3-dimethyl-4-((3-oxo-[1,2,4]triazolo[4,3-a]pyridin-2(3H)-yl)methyl)piperidine-1-carboxylate: Prepared according to General Procedure 2 using [1,2,4]triazolo[4,3-a]pyridin-3(2H)-one (50 mg, 0.370 mmol), Epoxide 1 (116 mg, 0.481 mmol) and cesium carbonate (241 mg, 0.740 mmol) in NMP (1 mL), heated to 80° C. for 3 h to give the title compound (50 mg, 35%). LCMS (Method A): $R_T$=1.51 min, m/z=377 [M+H]$^+$; 321 [M-butene+H]$^+$.

Step 2: 2-((4-Hydroxy-3,3-dimethylpiperidin-4-yl)methyl)-[1,2,4]triazolo[4,3-a]pyridin-3(2H)-one: Prepared according to General Procedure 3 using tert-butyl 4-hydroxy-3,3-dimethyl-4-((3-oxo-[1,2,4]triazolo[4,3-a]pyridin-2(3H)-yl)methyl)piperidine-1-carboxylate (50 mg, 0.133 mmol), DCM (1 mL) and TFA (0.5 mL), stirred at rt for 30 min to give the title compound (35 mg, 95%). LCMS (Method A): $R_T$=0.35 min, m/z=277 [M+H]$^+$.

Step 3: 2-((1-((R)-3-Cyclohexyl-2-methylpropanoyl)-4-hydroxy-3,3-dimethylpiperidin-4-yl)methyl)-[1,2,4]triazolo[4,3-a]pyridin-3(2H)-one: Prepared according to General Procedure 4 using 2-((4-hydroxy-3,3-dimethylpiperidin-4-yl)methyl)-[1,2,4]triazolo[4,3-a]pyridin-3(2H)-one (30 mg, 0.109 mmol), Acid 1 (22.2 mg, 0.130 mmol), HATU (62 mg, 0.163 mmol) and DIPEA (76 μL, 0.434 mmol) in DCM (2 mL) to give the title compound (44.6 mg, 93%). LCMS (Method B): $R_T$=1.43 min, m/z=429 [M+H]$^+$. $^1$H NMR (500 MHz, DMSO-$d_6$): δ 7.84 (dt, J=7.0, 1.3 Hz, 1H), 7.22 (dd, J=5.1, 1.3 Hz, 2H), 6.61 (td, J=6.0, 5.0, 1.9 Hz, 1H), 4.45 (d, J=12.0 Hz, 1H), 4.08-4.00 (m, 1H), 3.96-3.86 (m, 1H), 3.81-3.62 (m, 1H), 3.34-3.17 (m, 2H (signal obscured by HDO)), 3.00-2.78 (m, 2H), 1.81-1.40 (m, 8H), 1.22-1.02 (m, 5H), 1.02-0.88 (m, 9H), 0.88-0.75 (m, 2H).

The following table of Examples were prepared using parallel synthesis according to General Procedure 6:

| Ex. | Structure | Name | LCMS (Method A): $R_T$, m/z | $^1$H NMR (500 MHz, DMSO-$d_6$): |
|---|---|---|---|---|
| 52 | 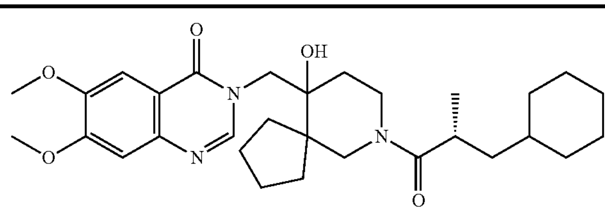 | 3-((7-((R)-3-Cyclohexyl-2-methylpropanoyl)-10-hydroxy-7-azaspiro[4.5]decan-10-yl)methyl)-6,7-dimethoxyquinazolin-4(3H)-one | 1.80 min, 526 [M + H]$^+$ | δ 8.23-8.18 (m, 1H), 7.48 (s, 1H), 7.15 (s, 1H), 4.87-4.73 (m, 1H), 4.70-4.55 (m, 1H), 3.91 (s, 3H), 3.88 (s, 3H), 3.75-3.62 (m, 2H), 3.57-3.21 (m, 3H (signal overlaps with HDO)), 2.93-2.81 (m, 1H), 2.04-1.86 (m, 1H), 1.76-1.02 (m, 20H), 0.99-0.89 (m, 3H), 0.88-0.75 (m, 2H). |
| 53 | 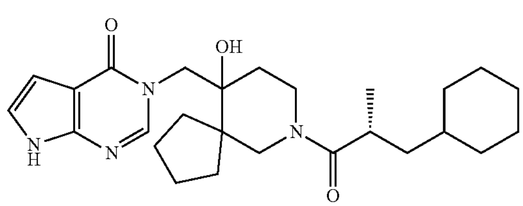 [SMILES: C[C@H](CC1CCCCC1)C(=O)N1CCC(O)(Cn2cnc3[nH]ccc3c2=O)C2(CCCC2)C1] | 3-((7-((R)-3-Cyclohexyl-2-methylpropanoyl)-10-hydroxy-7-azaspiro[4.5]decan-10-yl)methyl)-3,7-dihydro-4H-pyrrolo[2,3-d]pyrimidin-4-one | 1.66 min, 455 [M + H]$^+$ | |
| 54 | 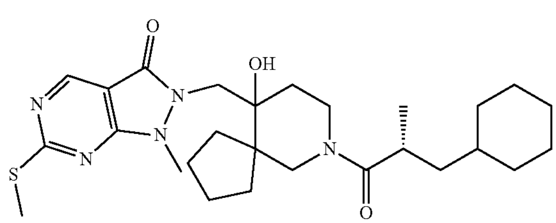 [SMILES: CSc1ncc2c(=O)n(CC3(O)CCN(C(=O)[C@H](C)CC4CCCCC4)CC34CCCC4)n(C)c2n1] | 2-((7-((R)-3-Cyclohexyl-2-methylpropanoyl)-10-hydroxy-7-azaspiro[4.5]decan-10-yl)methyl)-1-methyl-6-(methylthio)-1,2-dihydro-3H-pyrazolo[3,4-d]pyrimidin-3-one | 1.93 min, 516 [M + H]$^+$ | δ 8.90-8.75 (m, 1H), 4.84-4.73 (m, 1H), 4.36-4.15 (m, 1H), 3.92-3.06 (m, 8H (signals overlap with HDO)), 2.94-2.77 (m, 1H), 2.57 (s, 3H), 1.99-1.83 (m, 1H), 1.71-1.03 (m, 20H), 0.99-0.89 (m, 3H), 0.88-0.76 (m, 2H). |

Example 55: 6-((7-((R)-3-Cyclohexyl-2-methylpropanoyl)-10-hydroxy-7-azaspiro[4.5]decan-10-yl)methyl)-2-(methylthio)pyrido[4,3-d]pyrimidin-5(6H)-one

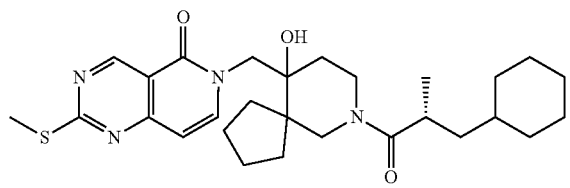 [SMILES: CSc1ncc2c(=O)n(CC3(O)CCN(C(=O)[C@H](C)CC4CCCCC4)CC34CCCC4)ccc2n1]

Step 1: tert-Butyl 10-hydroxy-10-((2-(methylthio)-5-oxopyrido[4,3-d]pyrimidin-6(5H)-yl)methyl)-7-azaspiro[4.5]decane-7-carboxylate: A solution of 2-(methylthio)pyrido[4,3-d]pyrimidin-5(6H)-one (97 mg, 0.500 mmol), Epoxide 2 (134 mg, 0.500 mmol) and DBU (90 µL, 0.600 mmol) in NMP (1 mL) was stirred at 70° C. for 20 h. The reaction mixture was allowed to cool to rt before being purified directly by flash chromatography (0-60% EtOAc in cyclohexane) to give the title compound (160 mg, 69%) as very pale yellow solid. LCMS (Method A): $R_T$=1.72 min, m/z=461 [M+H]$^+$. $^1$H NMR (500 MHz, DMSO-d$_6$): δ 9.23 (s, 1H), 7.92 (d, J=7.6 Hz, 1H), 6.52 (d, J=7.6 Hz, 1H), 4.68 (s, 1H), 4.63 (d, J=13.7 Hz, 1H), 3.61 (d, J=13.7 Hz, 1H), 3.59-3.52 (m, 1H), 3.27-3.16 (m, 3H), 2.59 (s, 3H), 1.95-1.88 (m, 1H), 1.70-1.51 (m, 5H), 1.41-1.33 (m, 2H), 1.39 (s, 9H), 1.21-1.12 (m, 2H).

Step 2: 6-((10-Hydroxy-7-azaspiro[4.5]decan-10-yl)methyl)-2-(methylthio)pyrido[4,3-d]pyrimidin-5(6H)-one: A solution of tert-butyl 10-hydroxy-10-((2-(methylthio)-5-oxopyrido[4,3-d]pyrimidin-6(5H)-yl)methyl)-7-azaspiro[4.5]decane-7-carboxylate (111 mg, 0.241 mmol) in TFA (1.2 mL) and DCM (2.4 mL) was stirred for 10 min before the reaction mixture was purified using a 2 g SCX-2 cartridge (pre-equilibrated with and then washed using 1:1 DCM/MeOH before being eluted with 1:1 DCM/7 M in NH$_3$ in MeOH). The basic eluents were concentrated under reduced pressure to give the title compound (85 mg, 97%) as light yellow solid. LCMS (Method B): $R_T$=0.65 min, m/z=361 [M+H]$^+$.

Step 3: 6-((7-((R)-3-Cyclohexyl-2-methylpropanoyl)-10-hydroxy-7-azaspiro[4.5]decan-10-yl)methyl)-2-(methylthio)pyrido[4,3-d]pyrimidin-5(6H)-one: Prepared according to General Procedure 4 using 6-((10-hydroxy-7-azaspiro[4.5]decan-10-yl)methyl)-2-(methylthio)pyrido[4,3-d]pyrimidin-5(6H)-one (20 mg, 55.5 µmol), Acid 1 (10.4 mg, 61.0 µmol), HATU (23 mg, 61.0 µmol), DIPEA (39 µL, 0.222 mmol) and DCM (1.1 mL) to give the title compound (25.4 mg, 87%) as colourless solid after lyophilisation. LCMS (Method B): $R_T$=1.63 min, m/z=513 [M+H]$^+$. $^1$H NMR (500 MHz, DMSO-d$_6$): δ 9.27-9.18 (m, 1H), 7.96-7.90 (m, 1H), 6.53 (d, J=7.6 Hz, 1H), 4.77-4.57 (m, 3H), 3.90-3.83 (m, 0.3H), 3.72-3.18 (m, 4.1H (signal overlaps with HDO)), 3.15-3.07 (m, 0.3H), 2.94-2.80 (m, 1H), 2.59 (s, 3H), 2.02-1.84 (m, 1H), 1.74-1.02 (m, 20H), 1.01-0.90 (m, 3H), 0.90-0.75 (m, 2H).

Example 56: 6-((10-Hydroxy-7-((R)-4,4,4-trifluoro-2-methylbutanoyl)-7-azaspiro[4.5]decan-10-yl)methyl)-2-(methylthio)pyrido[4,3-d]pyrimidin-5(6H)-one

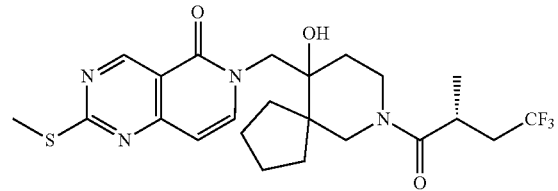 [SMILES: CSc1ncc2c(=O)n(CC3(O)CCN(C(=O)[C@H](C)CC(F)(F)F)CC34CCCC4)ccc2n1]

Prepared according to General Procedure 4 using 6-((10-hydroxy-7-azaspiro[4.5]decan-10-yl)methyl)-2-(methylthio)pyrido[4,3-d]pyrimidin-5(6H)-one (20 mg, 55.5 µmol), Acid 3 (9.5 mg, 61.0 µmol), HATU (23 mg, 61.0 µmol), DIPEA (39 µL, 0.222 mmol) and DCM (1.1 mL) to give the title compound (25.7 mg, 91%) as colourless solid after lyophilisation. LCMS (Method B): $R_T$=1.32 min, m/z=499 [M+H]$^+$. $^1$H NMR (500 MHz, DMSO-d$_6$): δ 9.30-9.18 (m, 1H), 7.95-7.89 (m, 1H), 6.56-6.50 (m, 1H), 4.80-4.71 (m, 1H), 4.70-4.63 (m, 0.7H), 4.59-4.51 (m, 0.3H), 4.00-3.92 (m, 0.3H), 3.75-2.96 (m, 4.7H (signal overlaps with HDO)), 2.83-2.66 (m, 1H), 2.60 (s, 3H), 2.31-2.19 (m, 1H), 2.05-1.86 (m, 1H), 1.83-1.12 (m, 10H), 1.12-1.01 (m, 3H).

Example 57: 6-((10-Hydroxy-7-((R)-4,4,4-trifluoro-2-methylbutanoyl)-7-azaspiro[4.5]decan-10-yl)methyl)-2-(methylamino)pyrido[4,3-d]pyrimidin-5(6H)-one

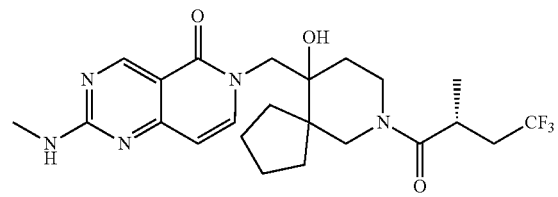

mCPBA (<77% pure) (9.1 mg, 40.6 µmol) in DCM (0.25 mL) was added to a stirred solution of 6-((10-hydroxy-7-((R)-4,4,4-trifluoro-2-methylbutanoyl)-7-azaspiro[4.5]decan-10-yl)methyl)-2-(methylthio)pyrido[4,3-d]pyrimidin-5(6H)-one (15 mg, 30.1 µmol) in toluene (1.0 mL) at rt in a 4 mL vial. The vessel was sealed and after 15 min, 2 M methylamine in THF (15 µL, 30.1 µmol) and DIPEA (16 µL, 90.3 µmol) were added successively. After 1 h, the reaction mixture was purified directly by flash chromatography (0-100%, EtOAc in cyclohexane) and freeze-dried to give the title compound (10.4 mg, 72%) as a white solid. LCMS (Method A): $R_T$=1.15 min, m/z=482 [M+H]$^+$. $^1$H NMR (500 MHz, DMSO-d$_6$): δ 9.10-8.91 (m, 1H), 7.85-7.60 (m, 2H), 6.33-6.10 (m, 1H), 4.84-4.71 (m, 1H), 4.68-4.40 (m, 1H), 4.02-2.96 (m, 4H, overlapping solvent peak), 2.94-2.83 (m, 3H), 2.82-2.62 (m, 1H, overlapping solvent peak), 2.33-2.18 (m, 1H), 2.05-0.70 (m, 15H).

Example 58: 2-(Dimethylamino)-6-((10-hydroxy-7-((R)-4,4,4-trifluoro-2-methylbutanoyl)-7-azaspiro[4.5]decan-10-yl)methyl)pyrido[4,3-d]pyrimidin-5(6H)-one

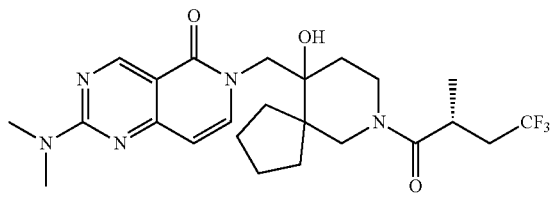 [SMILES: C[C@H](CC(F)(F)F)C(=O)N1CCC(O)(Cn2ccc3nc(N(C)C)ncc3c2=O)C2(CCCC2)C1]

Prepared according to the procedure for Example 57 except using 2 M dimethylamine in THF (0.02 mL, 30.1 μmol) as the nucleophile source and using a Biotage KP-NH column for flash chromatography to give the title compound (11.7 mg, 78%) as a white solid. LCMS (Method A): $R_T$=1.44 min, m/z=496 [M+H]$^+$. $^1$H NMR (500 MHz, DMSO-$d_6$): δ 9.07-9.02 (m, 1H), 7.76-7.69 (m, 1H), 6.27 (d, 1H), 4.82-4.71 (m, 1H), 4.66-4.41 (m, 1H), 4.00-2.97 (m, 10H, overlapping solvent peak), 2.84-2.61 (m, 1H, overlapping solvent peak), 2.32-2.17 (m, 1H), 2.05-0.67 (m, 15H).

Example 59: 6-((10-Hydroxy-7-((R)-4,4,4-trifluoro-2-methylbutanoyl)-7-azaspiro[4.5]decan-10-yl)methyl)-2-methoxypyrido[4,3-d]pyrimidin-5(6H)-one

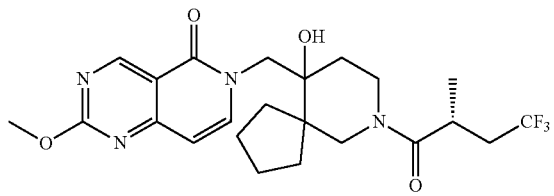 [SMILES: COc1ncc2c(=O)n(CC3(O)CCN(C(=O)[C@H](C)CC(F)(F)F)CC34CCCC4)ccc2n1]

Prepared according to the procedure for Example 57 except using sodium methoxide in MeOH, 25-30% w/w (6.5 mg, 30.1 μmol) as the nucleophile source and using a Biotage KP-NH column for flash chromatography to give the title compound (8.7 mg, 60%) as a white solid. LCMS (Method A): $R_T$=1.28 min, m/z=483 [M+H]$^+$. $^1$H NMR (500 MHz, DMSO-$d_6$): δ 9.32-9.26 (m, 1H), 7.95-7.88 (m, 1H), 6.55-6.49 (m, 1H), 4.82-4.51 (m, 2H), 4.02 (s, 3H), 4.01-2.96 (m, 4H, overlapping solvent peak), 2.84-2.61 (m, 1H, overlapping solvent peak), 2.32-2.18 (m, 1H), 2.06-1.85 (m, 1H), 1.81-0.75 (m, 14H).

Example 60: 6-((10-Hydroxy-7-((R)-4,4,4-trifluoro-2-methylbutanoyl)-7-azaspiro[4.5]decan-10-yl)methyl)-2-morpholinopyrido[4,3-d]pyrimidin-5(6H)-one

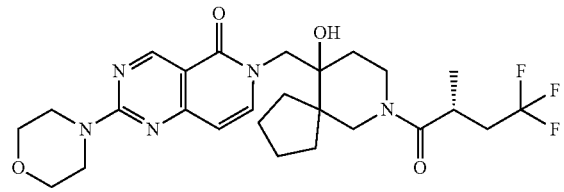 [SMILES: C[C@H](CC(F)(F)F)C(=O)N1CCC(O)(Cn2ccc3nc(N4CCOCC4)ncc3c2=O)C2(CCCC2)C1]

Prepared according to the procedure for Example 57 except using morpholine (2.6 mg, 30.1 μmol) as the nucleophile and using a Biotage KP-NH column for flash chromatography to give the title compound (12.5 mg, 77%) as a white solid. LCMS (Method A): $R_T$=1.48 min, m/z=538 [M+H]$^+$. $^1$H NMR (500 MHz, DMSO-$d_6$): δ 9.10-9.05 (m, 1H), 7.79-7.71 (m, 1H), 6.27 (d, 1H), 4.82-4.70 (m, 1H), 4.69-4.42 (m, 1H), 4.01-2.88 (m, 12H, overlapping solvent peak), 2.84-2.62 (m, 1H, overlapping solvent peak), 2.32-2.18 (m, 1H), 2.05-1.84 (m, 1H), 1.81-0.76 (m, 14H).

Example 61: 6-((10-Hydroxy-7-((R)-4,4,4-trifluoro-2-methylbutanoyl)-7-azaspiro[4.5]decan-10-yl)methyl)-2-(4-methylpiperazin-1-yl)pyrido[4,3-d]pyrimidin-5(6H)-one

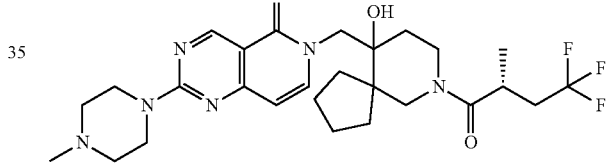

Prepared according to the procedure for Example 57 except using 1-methylpiperazine (3.0 mg, 30.1 μmol) as the nucleophile and using a Biotage KP-NH column for flash chromatography to give the title compound (13.0 mg, 77%) as a white solid. LCMS (Method B): $R_T$=0.85 min, m/z=551 [M+H]$^+$. $^1$H NMR (500 MHz, DMSO-$d_6$): δ 9.08-9.03 (m, 1H), 7.79-7.70 (m, 1H), 6.26 (d, 1H), 4.82-4.71 (m, 1H), 4.68-4.42 (m, 1H), 4.03-2.88 (m, 8H, overlapping solvent peak), 2.86-2.62 (m, 1H, overlapping solvent peak), 2.42-2.13 (m, 8H, overlapping solvent peak), 2.05-1.82 (m, 1H), 1.81-0.77 (m, 14H).

Example 62: 2-((Dimethyl(oxo)-λ$^6$-sulfaneylidene)amino)-6-((10-hydroxy-7-((R)-4,4,4-trifluoro-2-methylbutanoyl)-7-azaspiro[4.5]decan-10-yl)methyl)pyrido[4,3-d]pyrimidin-5(6H)-one

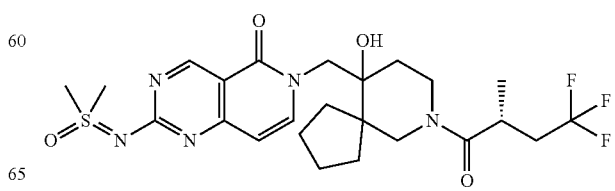

Prepared according to the procedure for Example 57 except using S,S-dimethylsulfoximine (2.8 mg, 30.1 μmol) as the nucleophile and using a Biotage KP-NH column for flash chromatography to give the title compound (8.3 mg, 51%) as a white solid. LCMS (Method B): $R_T$=0.95 min, m/z=544 [M+H]$^+$. $^1$H NMR (500 MHz, DMSO-d$_6$): δ 9.18-9.12 (m, 1H), 7.84-7.74 (m, 1H), 6.38 (d, 1H), 4.81-4.46 (m, 2H), 4.01-2.90 (m, 10H, overlapping solvent peak), 2.84-2.62 (m, 1H, overlapping solvent peak), 2.33-2.18 (m, 1H), 2.05-1.83 (m, 1H), 1.81-0.72 (m, 14H).

Example 63: 6-((10-Hydroxy-7-((R)-4,4,4-trifluoro-2-methylbutanoyl)-7-azaspiro[4.5]decan-10-yl)methyl)-2-(piperazin-1-yl)pyrido[4,3-d]pyrimidin-5(6H)-one

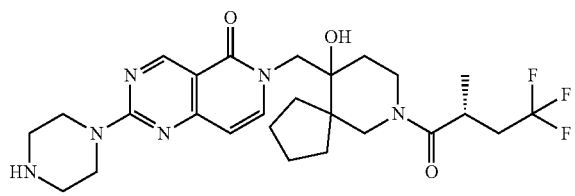 [SMILES: C[C@H](CC(F)(F)F)C(=O)N1CCC(O)(Cn2ccc3nc(N4CCNCC4)ncc3c2=O)C2(CCCC2)C1]

Step 1: tert-Butyl 4-(6-((10-hydroxy-7-((R)-4,4,4-trifluoro-2-methylbutanoyl)-7-azaspiro[4.5]decan-10-yl)methyl)-5-oxo-5,6-dihydropyrido[4,3-d]pyrimidin-2-yl)piperazine-1-carboxylate: Prepared according to the procedure for Example 57 except using tert-butyl piperazine-1-carboxylate (5.6 mg, 30.1 μmol) as the nucleophile and using a Biotage KP-NH column for flash chromatography to give the title compound (13.5 mg, 70%) as a white solid. LCMS (Method A): $R_T$=1.83 min, m/z=637 [M+H]$^+$.

Step 2: 6-((10-Hydroxy-7-((R)-4,4,4-trifluoro-2-methylbutanoyl)-7-azaspiro[4.5]decan-10-yl)methyl)-2-(piperazin-1-yl)pyrido[4,3-d]pyrimidin-5(6H)-one: A solution of tert-butyl 4-(6-((10-hydroxy-7-((R)-4,4,4-trifluoro-2-methylbutanoyl)-7-azaspiro[4.5]decan-10-yl)methyl)-5-oxo-5,6-dihydropyrido[4,3-d]pyrimidin-2-yl)piperazine-1-carboxylate (13.5 mg, 21.2 μmol) in TFA (1.0 mL) and DCM (1.0 mL) was stirred at rt. After 30 min, the solvents were removed in vacuo and the remaining residue was partitioned between saturated sodium bicarbonate (aq) solution and DCM, separated, extracted (DCM×3), dried (phase separator), and the solvents were removed in vacuo. The remaining residue was loaded onto a Biotage KP-NH cartridge, purified by flash chromatography (0-100% EtOAc in cyclohexane; then 0-5% MeOH in EtOAc) and freeze-dried to give the title compound (9.1 mg, 79%) as an off-white solid. LCMS (Method B): $R_T$=0.83 min, m/z=537 [M+H]$^+$. $^1$H NMR (500 MHz, DMSO-d$_6$): δ 9.07-9.02 (m, 1H), 7.79-7.68 (m, 1H), 6.24 (d, 1H), 4.82-4.71 (m, 1H), 4.68-4.41 (m, 1H), 4.01-2.86 (m, 9H, overlapping solvent peak), 2.83-2.62 (m, 5H, overlapping solvent peak), 2.33-2.17 (m, 1H, overlapping solvent peak), 2.03-1.83 (m, 1H), 1.80-0.76 (m, 14H).

Example 64: 2-((10-Hydroxy-7-((R)-4,4,4-trifluoro-2-methylbutanoyl)-7-azaspiro[4.5]decan-10-yl)methyl)-1-methyl-6-(methylthio)-1,2-dihydro-3H-pyrazolo[3,4-d]pyrimidin-3-one

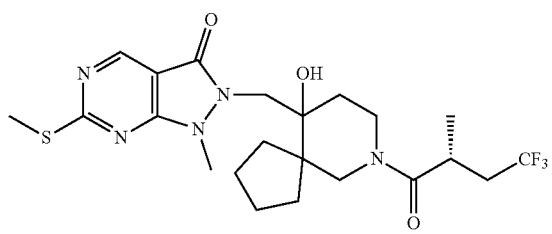 [SMILES: CSc1ncc2c(=O)n(CC3(O)CCN(C(=O)[C@H](C)CC(F)(F)F)CC34CCCC4)n(C)c2n1]

Step 1: tert-Butyl 10-hydroxy-10-((1-methyl-6-(methylthio)-3-oxo-1,3-dihydro-2H-pyrazolo[3,4-d]pyrimidin-2-yl)methyl)-7-azaspiro[4.5]decane-7-carboxylate: Prepared according to General Procedure 2 using 1-methyl-6-(methylthio)-1,2-dihydro-3H-pyrazolo[3,4-d]pyrimidin-3-one (WO 2003029209) (59 mg, 0.300 mmol), Epoxide 2 (80 mg, 0.300 mmol), cesium carbonate (108 mg, 0.330 mmol) and DMF (2 mL) at 80° C. for 3 days and at 100° C. for 5 days to give the title compound (11.7 mg, 8%) as a very pale yellow solid. LCMS (Method A): $R_T$=1.52 min, m/z=464 [M+H]$^+$. $^1$H NMR (500 MHz, DMSO-d$_6$): δ 8.82 (s, 1H), 4.73 (s, 1H), 4.27 (d, J=15.3 Hz, 1H), 3.77 (d, J=15.3 Hz, 1H), 3.62 (s, 3H), 3.60-3.53 (m, 1H), 3.25-3.13 (m, 3H), 2.57 (s, 3H), 1.93-1.86 (m, 1H), 1.75-1.48 (m, 6H), 1.42-1.36 (m, 1H), 1.39 (s, 9H), 1.29-1.25 (m, 1H), 1.20-1.12 (m, 1H).

Step 2: 2-((10-Hydroxy-7-azaspiro[4.5]decan-10-yl)methyl)-1-methyl-6-(methylthio)-1,2-dihydro-3H-pyrazolo[3,4-d]pyrimidin-3-one: A solution of tert-butyl 10-hydroxy-10-((1-methyl-6-(methylthio)-3-oxo-1,3-dihydro-2H-pyrazolo[3,4-d]pyrimidin-2-yl)methyl)-7-azaspiro[4.5]decane-7-carboxylate (11.7 mg, 25.2 μmol) in TFA (0.125 mL) and DCM (0.250 mL) was stirred for 20 min before the reaction mixture was purified using a 2 g SCX-2 cartridge (pre-equilibrated with and then washed using 1:1 DCM/MeOH before being eluted with 1:1 DCM/7 M in NH$_3$ in MeOH). The basic eluents were concentrated under reduced pressure to give the title compound (9 mg, quantitative) as a colourless solid. LCMS (Method A): $R_T$=0.61 min, m/z=364 [M+H]$^+$.

Step 3: 2-((10-Hydroxy-7-((R)-4,4,4-trifluoro-2-methylbutanoyl)-7-azaspiro[4.5]decan-10-yl)methyl)-1-methyl-6-(methylthio)-1,2-dihydro-3H-pyrazolo[3,4-d]pyrimidin-3-one: Prepared according to General Procedure 4 using 2-((10-hydroxy-7-azaspiro[4.5]decan-10-yl)methyl)-1-methyl-6-(methylthio)-1,2-dihydro-3H-pyrazolo[3,4-d]pyrimidin-3-one (5.6 mg, 15.4 μmol), Acid 3 (3.6 mg, 23.1 μmol), HATU (8.8 mg, 23.1 μmol), DIPEA (11 μL, 61.6 μmol) and DCM (0.5 mL) to give the title compound (6 mg, 72%) as an off-white solid after lyophilisation. LCMS (Method B): $R_T$=1.19 min, m/z=502 [M+H]$^+$. $^1$H NMR (500 MHz, DMSO-d$_6$): δ 8.82 (s, 1H), 4.85-4.75 (m, 1H), 4.42-2.95 (m, 9H (signals overlap with HDO)), 2.80-2.65 (m, 1H), 2.57 (s, 3H), 2.33-2.18 (m, 1.5H), 2.04-1.95 (m, 0.5H), 1.94-1.85 (m, 1H), 1.67-1.46 (m, 5H), 1.44-1.24 (m, 3H), 1.21-1.13 (m, 1H), 1.12-1.02 (m, 3H).

Example 65 and Example 66: 1-(((R)-1-((R)-3-Cyclohexyl-2-methylpropanoyl)-4-hydroxy-3,3-dimethylpiperidin-4-yl)methyl)-5-((dimethyl(oxo)-λ⁶-sulfaneylidene)amino)-4-(2-fluorophenyl)pyridin-2(1H)-one and 1-(((S)-1-((R)-3-Cyclohexyl-2-methylpropanoyl)-4-hydroxy-3,3-dimethylpiperidin-4-yl)methyl)-5-((dimethyl(oxo)-λ⁶-sulfaneylidene)amino)-4-(2-fluorophenyl)pyridin-2(1H)-one

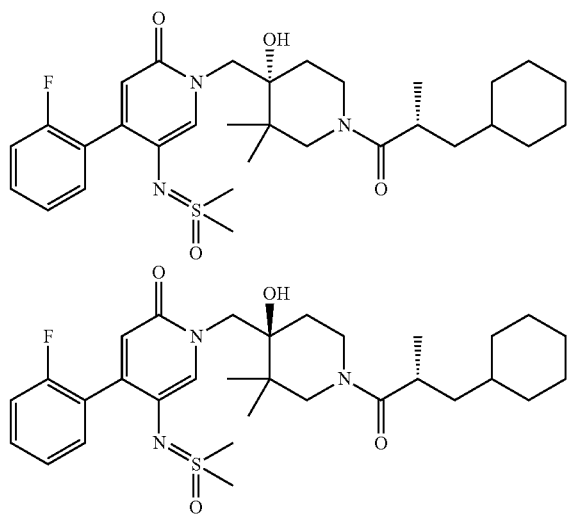

Step 1: 5-Bromo-4-(2-fluorophenyl)pyridin-2(1H)-one: A solution of 5-bromo-2-chloro-4-(2-fluorophenyl)pyridine (3.10 g, 10.8 mmol) (prepared according to *Eur. J. Org. Chem.*, 2013, p2316-2324) and sodium hydroxide (3.03 g, 75.7 mmol) in 1,4-dioxane (36 mL) and water (36 mL) was heated at 130° C. under microwave irradiation for 30 min. The resulting mixture was acidified to pH 2 by the addition of 2 M HCl$_{(aq)}$ and extracted with EtOAc (3×30 mL). The combined organic phases were washed with 1:1 water/brine (30 mL), dried over MgSO$_4$, filtered and concentrated under reduce pressure before a minimum of 1:1 DCM/diethyl ether was added and the product isolated by filtrated to give the title compound (2.50 g, 86%) as a yellow solid. This material was used without further purification. LCMS (Method B): R$_T$=1.18 min, m/z=268, 270 [M+H]⁺.

Step 2: tert-Butyl 4-((5-bromo-4-(2-fluorophenyl)-2-oxopyridin-1(2H)-yl)methyl)-4-hydroxy-3,3-dimethylpiperidine-1-carboxylate: Prepared according to General Procedure 2 using 5-bromo-4-(2-fluorophenyl)pyridin-2(1H)-one (594 mg, 2.22 mmol), Epoxide 1 (1.07 g, 4.43 mmol), cesium carbonate (794 mg, 2.44 mmol) and DMF (7.5 mL) at 90° C. for 16 h to give the title compound (459 mg, 40%) as a pale yellow solid. LCMS (Method A): R$_T$=1.66 min, m/z=509, 511 [M+H]⁺.

Step 3: 5-Bromo-4-(2-fluorophenyl)-1-((4-hydroxy-3,3-dimethylpiperidin-4-yl)methyl)pyridin-2(1H)-one: A solution of tert-butyl 4-((5-bromo-4-(2-fluorophenyl)-2-oxopyridin-1(2H)-yl)methyl)-4-hydroxy-3,3-dimethylpiperidine-1-carboxylate (69 mg, 0.136 mmol) was stirred in TFA (1 mL) and DCM (2 mL) for 20 min before the reaction mixture was purified using a 2 g SCX-2 cartridge (pre-equilibrated with and then washed using 1:1 DCM/MeOH before being eluted with 1:1 DCM/7 M in NH$_3$ in MeOH). The basic eluents were concentrated under reduced pressure to give the title compound (56 mg, quantitative) as a colourless solid. LCMS (Method A): R$_T$=0.70 min, m/z=409, 411 [M+H]⁺.

Step 4: 5-Bromo-1-((1-((R)-3-cyclohexyl-2-methylpropanoyl)-4-hydroxy-3,3-dimethylpiperidin-4-yl)methyl)-4-(2-fluorophenyl)pyridin-2(1H)-one: Prepared according to General Procedure 4 using 5-bromo-4-(2-fluorophenyl)-1-((4-hydroxy-3,3-dimethylpiperidin-4-yl)methyl)pyridin-2(1H)-one (56 mg, 0.137 mmol), Acid 1 (26 mg, 0.151 mmol), HATU (57 mg, 0.151 mmol), DIPEA (96 µL, 0.547 mmol) and DCM (3 mL) to give the title compound (68 mg, 88%) as a colourless solid after lyophilisation. LCMS (Method A): R$_T$=1.84, 1.85 min (2 diastereoisomers), m/z=561, 563 [M+H]⁺. ¹H NMR (500 MHz, DMSO-d$_6$): δ 8.10-8.02 (m, 1H), 7.57-7.47 (m, 1H), 7.40-7.25 (m, 3H), 4.96-4.87 (m, 1H), 4.55-4.39 (m, 1H), 4.18-3.97 (m, 0.4H), 3.82-3.56 (m, 2.6H), 3.27-3.19 (m, 1H), 3.07-2.79 (m, 2H), 1.75-1.55 (m, 7H), 1.55-1.41 (m, 1H), 1.24-1.06 (m, 6H), 1.02 (d, J=4.5 Hz, 1H), 1.00-0.90 (m, 8H), 0.88-0.77 (m, 2H).

Step 5: 1-(((R)-1-((R)-3-Cyclohexyl-2-methylpropanoyl)-4-hydroxy-3,3-dimethylpiperidin-4-yl)methyl)-5-((dimethyl(oxo)-λ⁶-sulfaneylidene)amino)-4-(2-fluorophenyl)pyridin-2(1H)-one and 1-(((S)-1-((R)-3-cyclohexyl-2-methylpropanoyl)-4-hydroxy-3,3-dimethylpiperidin-4-yl)methyl)-5-((dimethyl(oxo)-λ⁶-sulfaneylidene)amino)-4-(2-fluorophenyl)pyridin-2(1H)-one: A suspension of 5-bromo-1-((1-((R)-3-cyclohexyl-2-methylpropanoyl)-4-hydroxy-3,3-dimethylpiperidin-4-yl)methyl)-4-(2-fluorophenyl)pyridin-2(1H)-one (30.5 mg, 54.3 µmol), S,S-dimethylsulfoximine (5 mg, 54.3 µmol), Pd$_2$(dba)$_3$ (2.5 mg, 2.72 µmol), Xantphos (3.5 mg, 5.97 µmol) and cesium carbonate (53 mg, 0.163 mmol) in 1,4-dioxane (0.5 mL) in a sealed reaction vial was degassed by bubbling through N$_2$ for 5 min. The reaction was stirred at 100° C. for 16 h before being allowed to cool to rt. The reaction mixture was diluted with saturated NH$_4$Cl$_{(aq)}$ (15 mL) and extracted with DCM (3×10 mL) using a phase separator. The combined organic phases were concentrated under reduced pressure and the residue was purified by flash chromatography (0-10% MeOH in DCM) to give impure product. This material was further purified by preparative HPLC to give 1-(((R)-1-((R)-3-cyclohexyl-2-methylpropanoyl)-4-hydroxy-3,3-dimethylpiperidin-4-yl)methyl)-5-((dimethyl(oxo)-λ⁶-sulfaneylidene)amino)-4-(2-fluorophenyl)pyridin-2(1H)-one (7.7 mg, 24%) and 1-(((S)-1-((R)-3-cyclohexyl-2-methylpropanoyl)-4-hydroxy-3,3-dimethylpiperidin-4-yl)methyl)-5-((dimethyl(oxo)-λ⁶-sulfaneylidene)amino)-4-(2-fluorophenyl)pyridin-2(1H)-one (7.6 mg, 24%) both as colourless solids after lyophilisation. 1-(((R)-1-((R)-3-Cyclohexyl-2-methylpropanoyl)-4-hydroxy-3,3-dimethylpiperidin-4-yl)methyl)-5-((dimethyl(oxo)-λ⁶-sulfaneylidene)amino)-4-(2-fluorophenyl)pyridin-2(1H)-one: LCMS (Method A): R$_T$=1.42 min, m/z=574 [M+H]⁺. ¹H NMR (500 MHz, DMSO-d$_6$): δ 7.47-7.28 (m, 3H), 7.27-7.16 (m, 2H), 6.36-6.29 (m, 1H), 5.26-5.15 (m, 1H), 4.41-4.30 (m, 1H), 4.06-3.66 (m, 3H), 3.34-3.20 (m, 2H (signal overlaps with HDO)), 3.03 (s, 3H), 2.97 (s, 3H), 2.96-2.85 (m, 1H), 1.79-1.35 (m, 7H), 1.32-0.68 (m, 17H). 1-(((S)-1-((R)-3-Cyclohexyl-2-methylpropanoyl)-4-hydroxy-3,3-dimethylpiperidin-4-yl)methyl)-5-((dimethyl (oxo)-λ⁶-sulfaneylidene)amino)-4-(2-fluorophenyl)pyridin-2(1H)-one: LCMS (Method A): R$_T$=1.43 min, m/z=574 [M+H]⁺. ¹H NMR (500 MHz, DMSO-d$_6$): δ 7.46-7.31 (m, 3H), 7.27-7.17 (m, 2H), 6.35 (s, 0.5H), 6.33 (s, 0.5H), 5.24 (s, 0.5H), 5.16 (s, 0.5H), 4.44 (d, J=13.4 Hz, 0.5H), 4.28 (d, J=13.4 Hz, 0.5H), 4.11 (d, J=12.8 Hz, 0.5H), 3.94 (d, J=13.5 Hz, 0.5H), 3.81-3.73

(m, 1H), 3.58 (d, J=12.8 Hz, 0.5H), 3.37-3.21 (m, 2.5H (signal overlaps with HDO signal)), 3.03 (s, 3H), 2.97 (s, 3H), 2.96-2.85 (m, 1H), 1.79-1.54 (m, 6H), 1.52-1.43 (m, 1H), 1.31-0.78 (m, 17H).

Example 67: 4-Chloro-1-((1-((R)-3-cyclohexyl-2-methylpropanoyl)-4-hydroxy-3,3-dimethylpiperidin-4-yl)methyl)-5-(S-methylsulfonimidoyl)pyridin-2(1H)-one

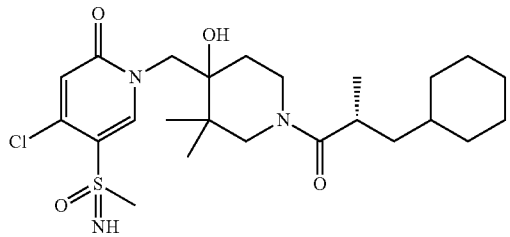 [SMILES: C[C@H](CC1CCCCC1)C(=O)N1CCC(O)(Cn2cc(S(C)(=N)=O)c(Cl)cc2=O)C(C)(C)C1]

Step 1: 4-Chloro-5-(methylthio)pyridin-2-amine: A suspension of 4-chloro-5-iodopyridin-2-amine (2.54 g, 10.0 mmol), sodium thiomethoxide (1.40 g, 20.0 mmol), copper (I) iodide (190 mg, 1.00 mmol), potassium carbonate (2.76 g, 20.0 mmol) and ethylene glycol (1.12 mL, 20.0 mmol) in IPA (3 mL) was stirred at 80° C. under an $N_2$ atmosphere for 19 h. The reaction mixture was allowed to cool to rt, filtered through Celite® and the solids were washed using MeOH (3×20 mL). The combined filtrates were concentrated under reduce pressure and water (30 mL) was added to the residue. The resulting suspension was extracted with DCM (3×20 mL) using a phase separator. The combined organic phases were concentrated under reduced pressure and the residue was purified by flash chromatography (20%; then 30%; then 40% EtOAc in cyclohexane (isocratic)) to give the title compound (779 mg, 44%) as an off-white crystalline solid. LCMS (Method A): $R_T$=0.41 min, m/z=175, 177 [M+H]$^+$. $^1$H NMR (500 MHz, DMSO-d$_6$): δ 8.01 (s, 1H), 6.59 (s, 1H), 6.34 (s, 2H), 2.32 (s, 3H).

Step 2: 4-Chloro-5-(methylsulfinyl)pyridin-2(1H)-one: A solution of sodium nitrite (923 mg, 13.4 mmol) in water (9 mL) was added to a solution of 4-chloro-5-(methylthio)pyridin-2-amine (779 mg, 4.46 mmol) in 75% sulfuric acid$_{(aq)}$ (25.4 mL, 267 mmol) at 0° C. After 1 h, 28-30% ammonium hydroxide$_{(aq)}$ (~10 mL) was added, no precipitate formed so further 28-30% ammonium hydroxide$_{(aq)}$ (~10 mL) was added. No precipitate formed so the mixture was extracted with EtOAc (3×20 mL), the aqueous phase was left standing for 3 days and a crystalline solid appeared. The aqueous phase was diluted with water (~20 mL) and the mixture cooled in an ice bath. The precipitate was collected by filtration before being washed with water (20 mL) and dried in a vacuum oven at 50° C. to give the title compound (395 mg, 46%) as yellow needles. LCMS (Method A): $R_T$=0.30 min, m/z=190, 192 [M−H]$^-$. $^1$H NMR (500 MHz, DMSO-d$_6$): δ 12.30 (s, 1H), 7.65 (s, 1H), 6.64 (s, 1H), 2.84 (s, 3H).

Step 3: tert-Butyl 4-((4-chloro-5-(methylsulfinyl)-2-oxopyridin-1(2H)-yl)methyl)-4-hydroxy-3,3-dimethylpiperidine-1-carboxylate: Prepared according to General Procedure 2 using 4-chloro-5-(methylsulfinyl)pyridin-2(1H)-one (96 mg, 0.500 mmol), Epoxide 1 (241 mg, 1.00 mmol), DIPEA (0.437 mL, 2.50 mmol) and NMP (1 mL) at 90° C. for 89 h to give the title compound (66 mg, 30%) as an orange solid. LCMS (Method A): $R_T$=1.18 min, m/z=377, 379 [M-butene+H]$^+$. $^1$H NMR (500 MHz, DMSO-d$_6$): δ 7.99 (s, 1H), 6.76-6.66 (m, 1H), 4.84-4.74 (m, 1H), 4.56-4.45 (m, 1H), 3.77-3.61 (m, 2H), 3.27-3.15 (m, 1H), 3.13-2.90 (m, 2H), 2.89-2.81 (m, 3H), 1.63-1.51 (m, 1H), 1.47-1.31 (m, 9H), 1.11-1.03 (m, 1H), 0.98 (s, 3H), 0.96-0.88 (m, 3H).

Step 4: 4-Chloro-1-((1-((R)-3-cyclohexyl-2-methylpropanoyl)-4-hydroxy-3,3-dimethylpiperidin-4-yl)methyl)-5-(methylsulfinyl)pyridin-2(1H)-one: To a solution of tert-butyl 4-((4-chloro-5-(methylsulfinyl)-2-oxopyridin-1(2H)-yl)methyl)-4-hydroxy-3,3-dimethylpiperidine-1-carboxylate (63 mg, 0.146 mmol) in 1,4-dioxane (1.5 mL) was added 4 M HCl in 1,4-dioxane (0.218 mL, 0.873 mmol). After stirring at rt for 3.5 h, further 4 M HCl in 1,4-dioxane (0.218 mL, 0.873 mmol) was added and the reaction stirred for a further 2 h. The reaction mixture was concentrated under reduced pressure and to the residue was added Acid 1 (25 mg, 0.146 mmol), HATU (56 mg, 0.146 mmol), DCM (3 mL) and DIPEA (102 μL, 0.585 mmol). The reaction mixture was stirred at rt for 15.5 h before being diluted with saturated NaHCO$_{3(aq)}$ (15 mL) and the resulting mixture was extracted with DCM (3×10 mL) using a phase separator. The combined organic phases were concentrated under reduced pressure and the residue was purified by flash chromatography (0-100% EtOAc in cyclohexane; then 0-20% MeOH in EtOAc) to give the title compound (22 mg, 30%) as a pale yellow gum. LCMS (Method B): $R_T$=1.27 min, m/z=485, 487 [M+H]$^+$.

Step 5: 4-Chloro-1-((1-((R)-3-cyclohexyl-2-methylpropanoyl)-4-hydroxy-3,3-dimethylpiperidin-4-yl)methyl)-5-(S-methylsulfonimidoyl)pyridin-2(1H)-one: A mixture of 4-chloro-1-((1-((R)-3-cyclohexyl-2-methylpropanoyl)-4-hydroxy-3,3-dimethylpiperidin-4-yl)methyl)-5-(methylsulfinyl)pyridin-2(1H)-one (22 mg, 44.9 μmol), sodium azide (12 mg, 0.180 mmol) and Eaton's reagent (0.5 mL) was heated at 50° C. for 25 min. The reaction mixture was allowed to cool to rt and diluted with DCM (~5 mL) before being poured into saturated NaHCO$_{3(aq)}$ (30 mL). The resulting mixture was extracted with DCM (3×10 mL) using a phase separator, the combined organic phases were concentrated under reduced pressure and the residue was purified by flash chromatography (0-20% MeOH in DCM) to give the title compound (7.3 mg, 29%) as a light beige foam. LCMS (Method A): $R_T$=1.42 min, m/z=500, 502 [M+H]$^+$. $^1$H NMR (500 MHz, DMSO-d$_6$): δ 8.44-8.39 (m, 1H), 6.75-6.69 (m, 1H), 4.90-4.82 (m, 1H), 4.61-2.75 (m, 11H (signals overlap with HDO)), 1.78-1.38 (m, 8H), 1.20-0.76 (m, 16H).

Example 68: 1-((1-((R)-3-Cyclohexyl-2-methylpropanoyl)-4-hydroxy-3,3-dimethylpiperidin-4-yl)methyl)-5-(S-methylsulfonimidoyl)-4-phenylpyridin-2(1H)-one

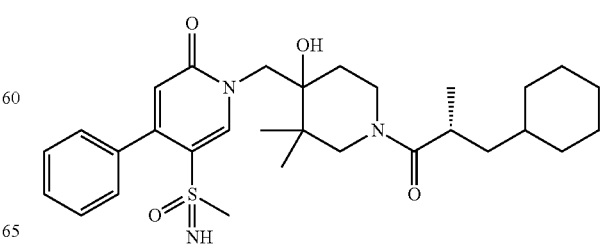

Prepared according to General Procedure 5 using 4-chloro-1-((1-((R)-3-cyclohexyl-2-methylpropanoyl)-4-hydroxy-3,3-dimethylpiperidin-4-yl)methyl)-5-(S-methylsulfonimidoyl)pyridin-2(1H)-one (6 mg, 12.0 μmol), phenylboronic acid (4.4 mg, 36.0 μmol), Pd(dppf)Cl$_2$·DCM (1 mg, 1.20 μmol), sodium carbonate (5.1 mg, 48.0 μmol), 1,4-dioxane (0.36 mL) and water (0.12 mL) for 1 h at 130° C. under microwave irradiation to give, after purification by preparative HPLC, the title compound (1.2 mg, 18%) as a light beige solid. LCMS (Method A): R$_T$=1.60 min, m/z=542 [M+H]$^+$. $^1$H NMR (500 MHz, DMSO-d$_6$): δ 8.50-8.45 (m, 1H), 7.58-7.46 (m, 1H), 7.45-7.37 (m, 4H), 6.23-6.18 (m, 1H), 4.93 (s, 1H), 4.65-4.53 (m, 1H), 4.11-3.97 (m, 1H), 3.84-3.59 (m, 3H), 3.09-2.83 (m, 3H), 2.80-2.66 (m, 3H), 1.81-1.39 (m, 8H), 1.30-0.90 (m, 14H), 0.89-0.77 (m, 2H).

Example 69: 4-Chloro-1-((7-((R)-3-cyclohexyl-2-methylpropanoyl)-10-hydroxy-7-azaspiro[4.5]decan-10-yl)methyl)-5-((dimethyl(oxo)-λ$^6$-sulfaneylidene)amino)pyridin-2(1H)-one

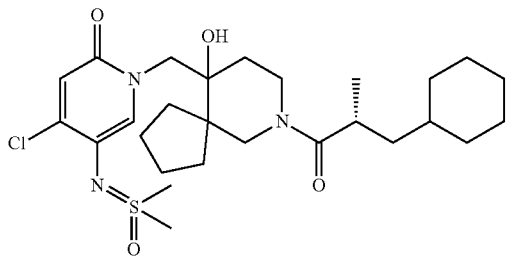 [SMILES: C[C@H](CC1CCCCC1)C(=O)N1CCC(O)(Cn2cc(N=S(C)(C)=O)c(Cl)cc2=O)C2(CCCC2)C1]

Step 1: tert-Butyl 10-((5-bromo-4-chloro-2-oxopyridin-1(2H)-yl)methyl)-10-hydroxy-7-azaspiro[4.5]decane-7-carboxylate: Potassium tert-butoxide (231 mg, 2.06 mmol) was added to a stirred solution of 5-bromo-4-chloropyridin-2(1H)-one (390 mg, 1.87 mmol) and Epoxide 2 (1.00 g, 3.74 mmol) in DMSO (5.0 mL) under nitrogen in a RBF fitted with a condenser. The reaction mixture was heated to 60° C. After 24 h, the reaction mixture was allowed to cool to rt, diluted with saturated NH$_4$Cl$_{(aq)}$ solution and extracted using EtOAc (×3). The combined organic phases were dried (phase separator), the solvents were removed in vacuo and the remaining residue was purified by flash chromatography (0-50% EtOAc in cyclohexane) to give the title compound (263 mg, 30%). LCMS (Method A): R$_T$=1.67 min, m/z=475 [M+H]$^+$.

Step 2: tert-Butyl 10-((4-chloro-5-((dimethyl(oxo)-λ$^6$-sulfaneylidene)amino)-2-oxopyridin-1(2H)-yl)methyl)-10-hydroxy-7-azaspiro[4.5]decane-7-carboxylate: Pd$_2$(dba)$_3$ (25.3 mg, 0.0277 mmol) and Xantphos (35.2 mg, 0.0609 mmol) were added to a pre-degassed stirred suspension of tert-butyl 10-((5-bromo-4-chloro-2-oxopyridin-1(2H)-yl)methyl)-10-hydroxy-7-azaspiro[4.5]decane-7-carboxylate (263 mg, 0.553 mmol), S,S-dimethylsulfoximine (51.6 mg, 0.553 mmol) and cesium carbonate (541 mg, 1.66 mmol) in 1,4-dioxane (2.6 mL) under nitrogen. The temperature was increased to 100° C. After 18 h, analysis by LCMS showed a 1:1 product mixture of sulfoximine products (ca. 40%) and residual starting material (ca. 60%). Further Pd$_2$(dba)$_3$ (25.3 mg, 0.0277 mmol) and Xantphos (35.2 mg, 0.0609 mmol) were added. After a further 2 h, the temperature was increased to 110° C. After a further 2 h, further S,S-dimethylsulfoximine (25.8 mg, 0.277 mmol) was added. After a further 1 h, analysis by LCMS showed that the reaction had stalled. The reaction mixture was cooled to rt, diluted with saturated NH$_4$Cl$_{(aq)}$ and extracted using DCM (×3). The combined organic phase was dried (phase separator), the solvents were removed in vacuo and the residue was purified by flash chromatography (0-100% EtOAc in cyclohexane; then 0-5% MeOH in EtOAc). The pure fraction was concentrated to give the title compound (3.3 mg, 1%) as a yellow gum. The other fractions containing the title compound also contained tert-butyl 10-((5-bromo-4-((dimethyl(oxo)-λ$^6$-sulfaneylidene)amino)-2-oxopyridin-1(2H)-yl)methyl)-10-hydroxy-7-azaspiro[4.5]decane-7-carboxylate, which resulted in the poor recovery of pure title compound. LCMS (Method A): R$_T$=1.16 min, m/z=488 [M+H]$^+$.

Step 3: 4-Chloro-5-((dimethyl(oxo)-λ$^6$-sulfaneylidene)amino)-1-((10-hydroxy-7-azaspiro[4.5]decan-10-yl)methyl)pyridin-2(1H)-one hydrochloride: 4 M HCl in 1,4-dioxane (0.22 mL, 6.42 mmol) was added to tert-butyl 10-((4-chloro-5-((dimethyl(oxo)-λ$^6$-sulfaneylidene)amino)-2-oxopyridin-1(2H)-yl)methyl)-10-hydroxy-7-azaspiro[4.5]decane-7-carboxylate (3.3 mg, 6.8 μmol) at rt. After 15 min, the solvents were removed in vacuo to give the crude title compound (3.6 mg, >100%) as a yellow solid that was carried through to the next step without further purification. LCMS (Method A): R$_T$=0.30 min, m/z=388 [M–Cl]$^+$.

Step 4: 4-Chloro-1-((7-((R)-3-cyclohexyl-2-methylpropanoyl)-10-hydroxy-7-azaspiro[4.5]decan-10-yl)methyl)-5-((dimethyl(oxo)-λ$^6$-sulfaneylidene)amino)pyridin-2(1H)-one: Prepared according to General Procedure 4 using 4-chloro-5-((dimethyl(oxo)-λ$^6$-sulfaneylidene)amino)-1-((10-hydroxy-7-azaspiro[4.5]decan-10-yl)methyl)pyridin-2(1H)-one hydrochloride (crude, assumed 2.9 mg, 6.8 μmol), Acid 1 (1.2 mg, 6.8 μmol), HATU (3.1 mg, 8.2 μmol), DIPEA (4 μL, 20.4 μmol) and DCM (0.5 mL) to give the title compound (1.1 mg, 25%) as an off-white solid after lyophilisation. LCMS (Method A): R$_T$=1.40 min, m/z=540 [M+H]$^+$. $^1$H NMR (500 MHz, DMSO-d$_6$): δ 7.47-7.43 (m, 1H), 6.62-6.57 (m, 1H), 5.01-4.91 (m, 1H), 4.61-4.42 (m, 1H), 3.71-3.10 (m, 10H, overlapping solvent peak), 2.91-2.79 (m, 1H), 1.97-1.80 (m, 1H), 1.73-0.72 (m, 26H).

Example 70: 4-Chloro-1-((7-((R)-3-cyclohexyl-2-methylpropanoyl)-10-hydroxy-7-azaspiro[4.5]decan-10-yl)methyl)-5-(methylsulfinyl)pyridin-2(1H)-one

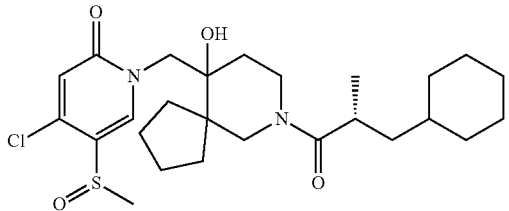 [SMILES: C[C@H](CC1CCCCC1)C(=O)N1CCC(O)(Cn2cc(S(C)=O)c(Cl)cc2=O)C2(CCCC2)C1]

Step 1: tert-Butyl 10-((4-chloro-5-(methylsufinyl)-2-oxopyridin-1(2H)-yl)methyl)-10-hydroxy-7-azaspiro[4.5]decane-7-carboxylate: A solution of 4-chloro-5-(methylsulfinyl)pyridin-2(1H)-one (122 mg, 0.637 mmol), Epoxide 2 (170 mg, 0.637 mmol) and DBU (0.115 mL, 0.764 mmol) in NMP (1.25 mL) was heated at 70° C. for 47 h. The reaction mixture was allowed to cool to rt before being purified directly by flash chromatography (0-50% EtOAc in cyclohexane) to give the title compound (114 mg, 39%) as a yellow gum. LCMS (Method A): $R_T$=1.45 min, m/z=403, 405 [M-butene+H]$^+$.

Step 2: 4-Chloro-1-((10-hydroxy-7-azaspiro[4.5]decan-10-yl)methyl)-5-(methylsufinyl)pyridin-2(1H)-one: A solution of tert-butyl 10-((4-chloro-5-(methylsulfinyl)-2-oxopyridin-1(2H)-yl)methyl)-10-hydroxy-7-azaspiro[4.5]decane-7-carboxylate (106 mg, 0.231 mmol) in TFA (0.7 mL) and DCM (2.1 mL) was stirred for 10 min before the reaction mixture was purified using a 2 g SCX-2 cartridge (pre-equilibrated with and then washed using 1:1 DCM/MeOH before being eluted with 1:1 DCM/7 M in NH$_3$ in MeOH). The basic eluents were concentrated under reduced pressure to give the title compound (70.6 mg, 85%) as a light yellow solid. LCMS (Method A): $R_T$=0.40 min, m/z=359, 361 [M+H]$^+$.

Step 3: 4-Chloro-1-((7-((R)-3-cyclohexyl-2-methylpropanoyl)-10-hydroxy-7-azaspiro[4.5]decan-10-yl)methyl)-5-(methylsufinyl)pyridin-2(1H)-one: Prepared according to General Procedure 4 using 4-chloro-1-((10-hydroxy-7-azaspiro[4.5]decan-10-yl)methyl)-5-(methylsulfinyl)pyridin-2(1H)-one (75 mg, 0.209 mmol), Acid 1 (39 mg, 0.230 mmol), HATU (87 mg, 0.230 mmol), DIPEA (0.146 mL, 0.836 mmol) and DCM (4.2 mL) to give the title compound (50.4 mg, 45%) as a pale yellow solid. LCMS (Method B): $R_T$=1.34 min, m/z=511, 513 [M+H]$^+$. $^1$H NMR (500 MHz, DMSO-d$_6$): δ 8.09-8.01 (m, 1H), 6.76-6.69 (m, 1H), 4.90-4.83 (m, 1H), 4.80-4.58 (m, 2H), 3.89-3.07 (m, 4H (signal overlaps with HDO)), 2.98-2.75 (m, 4H), 2.01-1.80 (m, 2H), 1.78-1.00 (m, 20H), 0.98-0.91 (m, 2H), 0.89-0.75 (m, 2H).

Example 71: 4-Chloro-1-((7-((R)-3-cyclohexyl-2-methylpropanoyl)-10-hydroxy-7-azaspiro[4.5]decan-10-yl)methyl)-5-(S-methylsulfonimidoyl)pyridin-2(1H)-one

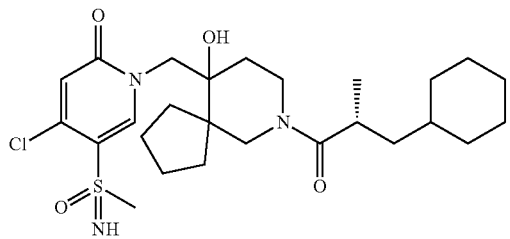 [SMILES: C[C@H](CC1CCCCC1)C(=O)N1CCC(O)(Cn2cc(S(C)(=N)=O)c(Cl)cc2=O)C2(CCCC2)C1]

A mixture of 4-chloro-1-((7-((R)-3-cyclohexyl-2-methylpropanoyl)-10-hydroxy-7-azaspiro[4.5]decan-10-yl)methyl)-5-(methylsulfinyl)pyridin-2(1H)-one (49 mg, 95.9 μmol), sodium azide (25 mg, 0.384 mmol) and Eaton's reagent (0.5 mL) was heated at 50° C. for 25 min. The reaction mixture was allowed to cool to rt and diluted with DCM (5 mL) before being poured into saturated NaHCO$_{3(aq)}$ (30 mL). The resulting mixture was extracted with DCM (3×10 mL) using a phase separator, the combined organic phases were concentrated under reduced pressure and the residue was purified by flash chromatography (0-100% EtOAc in cyclohexane; then 0-15% MeOH in EtOAc) to give the title compound (28 mg, 55%) as beige solid. LCMS (Method B): $R_T$=1.31 min, m/z=526, 528 [M+H]$^+$. $^1$H NMR (500 MHz, DMSO-d$_6$): δ 8.50-8.41 (m, 1H), 6.76-6.67 (m, 1H), 4.94-4.84 (m, 1H), 4.79-2.78 (m, 11H (signals overlap with HDO)), 1.93-1.83 (m, 1H), 1.79-1.28 (m, 13H), 1.28-1.01 (m, 7H), 1.01-0.89 (m, 3H), 0.88-0.78 (m, 2H).

Example 72: 1-((7-((R)-3-Cyclohexyl-2-methylpropanoyl)-10-hydroxy-7-azaspiro[4.5]decan-10-yl)methyl)-5-((dimethyl(oxo)-λ$^6$-sulfaneylidene)amino)-4-phenylpyridin-2(1H)-one

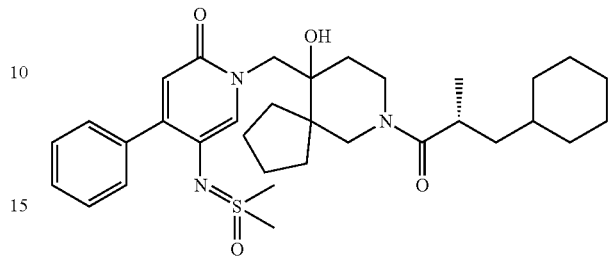

Step 1: tert-Butyl 10-((4-chloro-5-((dimethyl(oxo)-λ$^6$-sulfaneylidene)amino)-2-oxopyridin-1(2H)-yl)methyl)-10-hydroxy-7-azaspiro[4.5]decane-7-carboxylate and tert-butyl 10-((5-bromo-4-((dimethyl(oxo)-λ$^6$-sulfaneylidene)amino)-2-oxopyridin-1(2H)-yl)methyl)-10-hydroxy-7-azaspiro[4.5]decane-7-carboxylate: Pd$_2$(dba)$_3$ (18.3 mg, 20.0 μmol) and Xantphos (25.4 mg, 43.9 μmol) were added to a pre-degassed stirred suspension of tert-butyl 10-((5-bromo-4-chloro-2-oxopyridin-1(2H)-yl)methyl)-10-hydroxy-7-azaspiro[4.5]decane-7-carboxylate (190 mg, 0.399 mmol), S,S-dimethylsulfoximine (37.2 mg, 0.399 mmol) and cesium carbonate (390 mg, 1.20 mmol) in 1,4-dioxane (4.0 mL) in a RBF under nitrogen. The temperature was increased to 100° C. After 1 h, LCMS showed significant residual starting material (ca. 27%) and conversion to both chloro- (ca. 28%) and bromo-products (ca. 17%). After 2 h, LCMS showed residual starting material (ca. 20%), chloro-product (ca. 34%) and bromo-product (ca. 21%). After 3 h, the reaction appeared to stall and therefore was allowed to cool to rt, diluted with saturated NH$_4$Cl$_{(aq)}$ and was extracted using DCM (×3). The combined organic phase was dried (phase separator), the solvents were removed in vacuo and the residue was purified by flash chromatography (0-100% EtOAc in cyclohexane; then 0-5% MeOH in EtOAc) to give the mixture of title compounds (68.8 mg, beige solid, ca. 2:1, tert-butyl 10-((4-chloro-5-((dimethyl(oxo)-λ$^6$-sulfaneylidene)amino)-2-oxopyridin-1(2H)-yl)methyl)-10-hydroxy-7-azaspiro[4.5]decane-7-carboxylate/tert-butyl 10-((5-bromo-4-((dimethyl(oxo)-λ$^6$-sulfaneylidene)amino)-2-oxopyridin-1(2H)-yl)methyl)-10-hydroxy-7-azaspiro[4.5]decane-7-carboxylate by LCMS Method B) as a beige solid that was carried through to the next step without further purification. LCMS (Method B): $R_T$=1.07 min, m/z=488 [M+H]$^+$ and $R_T$=1.20 min, m/z=532, 534 [M+H]$^+$.

Step 2: tert-Butyl 10-((5-((dimethyl(oxo)-λ$^6$-sulfaneylidene)amino)-2-oxo-4-phenylpyridin-1(2H)-yl)methyl)-10-hydroxy-7-azaspiro[4.5]decane-7-carboxylate: Pd(dppf)Cl$_2$·DCM (6.0 mg, 7.0 μmol) was added to a pre-degassed (bubbling nitrogen for 15 min) suspension of the 2:1 mixture of tert-butyl 10-((4-chloro-5-((dimethyl(oxo)-λ$^6$-sulfaneylidene)amino)-2-oxopyridin-1(2H)-yl)methyl)-10-hydroxy-7-azaspiro[4.5]decane-7-carboxylate and tert-butyl 10-((5-bromo-4-((dimethyl(oxo)-λ$^6$-sulfaneylidene)amino)-2-oxopyridin-1(2H)-yl)methyl)-10-hydroxy-7-azaspiro[4.5]decane-7-carboxylate (68.8 mg, 0.141 mmol), phenylboronic acid (25.8 mg, 0.212 mmol) and sodium carbonate (29.9 mg, 0.282 mmol) in 1,4-dioxane (1.0 mL)/water (0.25 mL) in a sealed 2-5 mL microwave vial. The vessel was sealed and the reaction mixture was heated using microwave irradiation at 120° C. for 30 min. Due to incomplete reaction, the reaction was rerun under the same conditions. Due to incomplete reaction, further Pd(dppf)Cl$_2$·DCM (6.0 mg, 7.0 µmol) was added and the reaction was rerun under the same conditions. Due to incomplete reaction, further phenylboronic acid (25.8 mg, 0.212 mmol) and Pd(dppf)Cl$_2$·DCM (6.0 mg, 7.0 µmol) were added and the reaction was rerun under the same conditions. The reaction mixture was diluted with water and the mixture was extracted using EtOAc (×3), dried (phase separator), the solvents were removed in vacuo, and the remaining residue was purified by flash chromatography (0-100% EtOAc in cyclohexane; then 0-5% MeOH in EtOAc) to give the title compound (27.2 mg, 36%) as a pale yellow solid. LCMS (Method B): R$_T$=1.21 min, m/z=530 [M+H]$^+$. tert-Butyl 10-((4-((dimethyl(oxo)-λ$^6$-sulfaneylidene)amino)-2-oxo-5-phenylpyridin-1(2H)-yl)methyl)-10-hydroxy-7-azaspiro[4.5]decane-7-carboxylate (18.9 mg, 25%) was also isolated as a pale yellow solid. LCMS (Method B): R$_T$=1.32 min, m/z=530 [M+H]$^+$.

Step 3: 5-((Dimethyl(oxo)-λ$^6$-sulfaneylidene)amino)-1-((10-hydroxy-7-azaspiro[4.5]decan-10-yl)methyl)-4-phenylpyridin-2(1H)-one hydrochloride: 4 M HCl in 1,4-dioxane (0.5 mL, 14.4 mmol) was added to tert-butyl 10-((5-((dimethyl(oxo)-λ$^6$-sulfaneylidene)amino)-2-oxo-4-phenylpyridin-1(2H)-yl)methyl)-10-hydroxy-7-azaspiro[4.5]decane-7-carboxylate (12.5 mg, 23.6 µmol) and stirred. After 1 h, the solvents were removed in vacuo and the residue was dried in a vacuum oven overnight to give the crude title compound (13.6 mg, >100%) as a pale yellow solid that was carried through to the next step without further purification. LCMS (Method B): R$_T$=0.61 min, m/z=430 [M−Cl]$^+$.

Step 4: 1-((7-((R)-3-Cyclohexyl-2-methylpropanoyl)-10-hydroxy-7-azaspiro[4.5]decan-10-yl)methyl)-5-((dimethyl(oxo)-λ$^6$-sulfaneylidene)amino)-4-phenylpyridin-2(1H)-one: Prepared according to General Procedure 4 using 5-((dimethyl(oxo)-λ$^6$-sulfaneylidene)amino)-1-((10-hydroxy-7-azaspiro[4.5]decan-10-yl)methyl)-4-phenylpyridin-2(1H)-one hydrochloride (crude, assumed 11.0 mg, 23.6 µmol), Acid 1 (4.0 mg, 23.6 µmol), HATU (10.8 mg, 28.3 µmol), DIPEA (12.4 µL, 70.8 µmol) and DCM (0.5 mL) to give the title compound (9.3 mg, 66%) as a very pale yellow solid after lyophilisation. LCMS (Method A): R$_T$=1.58 min, m/z=582 [M+H]$^+$. $^1$H NMR (500 MHz, DMSO-d$_6$): 7.59-7.48 (m, 2H), 7.46-7.34 (m, 4H), 6.40-6.34 (m, 1H), 5.38-5.18 (m, 1H), 4.62-4.37 (m, 1H), 3.94-3.61 (m, 2H), 3.58-3.10 (m, 2H, overlapping solvent peak), 3.05 (s, 3H), 2.99-2.80 (m, 4H), 2.02-1.82 (m, 1H), 1.80-0.65 (m, 26H).

Example 73: 1-((7-((R)-3-Cyclohexyl-2-methylpropanoyl)-10-hydroxy-7-azaspiro[4.5]decan-10-yl)methyl)-4-((dimethyl(oxo)-λ$^6$-sulfaneylidene)amino)-5-phenylpyridin-2(1H)-one

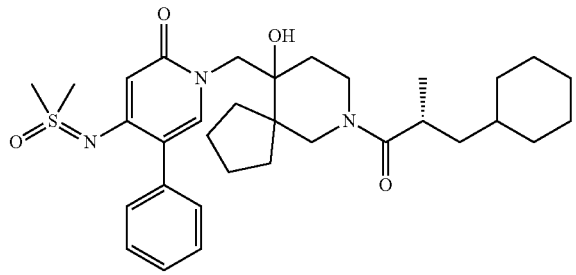 [SMILES: C[C@H](CC1CCCCC1)C(=O)N1CCC(O)(Cn2cc(-c3ccccc3)c(N=S(C)(C)=O)cc2=O)C2(CCCC2)C1]

Step 1: 4-((Dimethyl(oxo)-λ$^6$-sulfaneylidene)amino)-1-((10-hydroxy-7-azaspiro[4.5]decan-10-yl)methyl)-5-phenylpyridin-2(1H)-one hydrochloride: 4 M HCl in 1,4-dioxane (0.5 mL, 14.4 mmol) was added to tert-butyl 10-((4-((dimethyl(oxo)-λ$^6$-sulfaneylidene)amino)-2-oxo-5-phenylpyridin-1(2H)-yl)methyl)-10-hydroxy-7-azaspiro[4.5]decane-7-carboxylate (6.8 mg, 12.8 µmol) and stirred. After 30 min, the solvents were removed in vacuo and the residue was dried in a vacuum oven overnight to give the crude title compound (7.2 mg, >100%) as a pale yellow solid that was carried through to the next step without further purification. LCMS (Method B): R$_T$=0.68 min, m/z=430 [M−Cl]$^+$.

Step 2: 1-((7-((R)-3-Cyclohexyl-2-methylpropanoyl)-10-hydroxy-7-azaspiro[4.5]decan-10-yl)methyl)-4-((dimethyl(oxo)-λ$^6$-sulfaneylidene)amino)-5-phenylpyridin-2(1H)-one: Prepared according to General Procedure 4 using 4-((dimethyl(oxo)-λ$^6$-sulfaneylidene)amino)-1-((10-hydroxy-7-azaspiro[4.5]decan-10-yl)methyl)-5-phenylpyridin-2(1H)-one hydrochloride (crude, assumed 6.0 mg, 12.8 µmol), Acid 1 (2.2 mg, 12.8 µmol), HATU (5.8 mg, 15.4 µmol), DIPEA (6.7 µL, 38.4 µmol) and DCM (0.5 mL) to give the title compound (4.5 mg, 54%) as a white solid after lyophilisation. LCMS (Method A): R$_T$=1.69 min, m/z=582 [M+H]$^+$. $^1$H NMR (500 MHz, DMSO-d$_6$): 7.65 (s, 1H), 7.51-7.44 (m, 2H), 7.35 (t, 2H), 7.26 (t, 1H), 6.04-6.01 (m, 1H), 5.53-5.29 (m, 1H), 4.50-4.25 (m, 1H), 3.97-3.03 (m, 10H, overlapping solvent peak), 2.94-2.80 (m, 1H), 2.02-0.76 (m, 27H).

Example 74: 1-((7-((R)-3-Cyclohexyl-2-methylpropanoyl)-10-hydroxy-7-azaspiro[4.5]decan-10-yl)methyl)-5-(S-methylsulfonimidoyl)-4-phenylpyridin-2(1H)-one

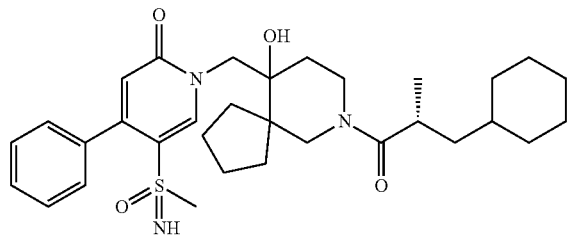 [SMILES: C[C@H](CC1CCCCC1)C(=O)N1CCC(O)(Cn2cc(S(C)(=N)=O)c(-c3ccccc3)cc2=O)C2(CCCC2)C1]

Prepared according to General Procedure 5 using 4-chloro-1-((7-((R)-3-cyclohexyl-2-methylpropanoyl)-10-hydroxy-7-azaspiro[4.5]decan-10-yl)methyl)-5-(S-methylsulfonimidoyl)pyridin-2(1H)-one (27 mg, 50.6 µmol), phenylboronic acid (18.5 mg, 0.152 mmol), Pd(dppf)Cl$_2$·DCM (4.3 mg, 5.06 µmol), sodium carbonate (21 mg, 0.202 mmol) in 1,4-dioxane (0.75 mL) and water (0.25 mL) for 1 h at 130° C. under microwave irradiation to give, after purification by preparative HPLC, the title compound (10.1 mg, 34%) as an off-white solid after lyophilisation. LCMS (Method B): R$_T$=1.34, 1.37 min (diastereoisomers), m/z=568 [M+H]$^+$. $^1$H NMR (500 MHz, DMSO-d$_6$): δ 8.54-8.48 (m, 1H), 7.52-7.33 (m, 5H), 6.24-6.18 (m, 1H), 4.97-4.91 (m, 1H), 4.83-3.13 (m, 8H (signal overlap with HDO)), 2.73-2.66 (m, 3H), 1.96-1.84 (m, 1H), 1.78-1.25 (m, 14H), 1.22-1.03 (m, 6H), 1.00-0.90 (m, 3H), 0.88-0.79 (m, 2H).

Example 75: 5-((Dimethyl(oxo)-λ⁶-sulfaneylidene)
amino)-1-((10-hydroxy-7-((R)-4,4,4-trifluoro-2-
methylbutanoyl)-7-azaspiro[4.5]decan-10-yl)
methyl)-4-phenylpyridin-2(1H)-one

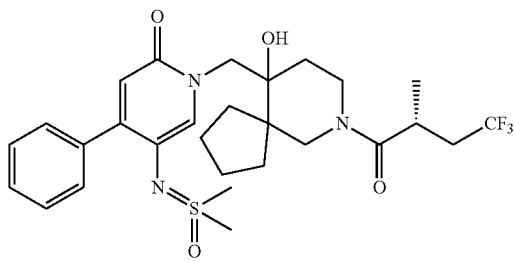 [SMILES: C[C@H](CC(F)(F)F)C(=O)N1CCC(O)(Cn2cc(N=S(C)(C)=O)c(-c3ccccc3)cc2=O)C2(CCCC2)C1]

Prepared according to General Procedure 4 using 5-((dimethyl(oxo)-λ⁶-sulfaneylidene)amino)-1-((10-hydroxy-7-azaspiro[4.5]decan-10-yl)methyl)-4-phenylpyridin-2(1H)-one hydrochloride (Example 72, Step 3) (crude, assumed 11.3 mg, 24.2 μmol), Acid 3 (3.8 mg, 24.2 μmol), HATU (11.0 mg, 29.0 μmol), DIPEA (12.7 μL, 72.6 μmol) and DCM (0.5 mL) to give the title compound (6.8 mg, 49%) as a white solid after lyophilisation. LCMS (Method A): $R_T$=1.19 min, m/z=568 [M+H]⁺. ¹H NMR (500 MHz, DMSO-$d_6$): 7.59-7.50 (m, 2H), 7.47-7.35 (m, 4H), 6.40-6.35 (m, 1H), 5.38-5.18 (m, 1H), 4.63-4.33 (m, 1H), 4.03-3.00 (m, 7H, overlapping solvent peak), 2.96 (s, 3H), 2.83-2.66 (m, 1H), 2.33-2.19 (m, 1H), 2.04-0.77 (m, 15H).

Example 76: 4-Chloro-1-((7-((R)-3-cyclohexyl-2-methylpropanoyl)-10-hydroxy-7-azaspiro[4.5]decan-10-yl)methyl)-5-(methylthio)pyridin-2(1H)-one

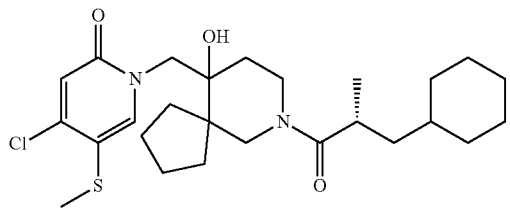 [SMILES: CSc1cn(CC2(O)CCN(C(=O)[C@H](C)CC3CCCCC3)CC23CCCC3)c(=O)cc1Cl]

Step 1: 4-Chloro-5-(methylthio)pyridin-2(1H)-one: To a solution of 4-chloro-5-(methylthio)pyridin-2-amine (450 mg, 2.58 mmol) in DMF (14.7 mL) was added water (1 drop) and tert-butyl nitrite (0.613 mL, 5.15 mmol). The reaction was stirred at rt for 16 h before being poured in to water and the resulting mixture extracted with DCM (×3) using a phase separator. The combined organic phases were concentrated under reduced pressure and the residue was purified by flash chromatography (0-100% EtOAc in cyclohexane; then 0-20% MeOH in EtOAc) to give the title compound (300 mg, 66%) as a yellow solid. LCMS (Method B): $R_T$=0.72 min, m/z=176, 178 [M+H]⁺. ¹H NMR (500 MHz, DMSO-$d_6$): δ 12.04 (s, 1H), 7.60 (s, 1H), 6.61 (s, 1H), 2.32 (s, 3H).

Step 2: tert-Butyl 10-((4-chloro-5-(methylthio)-2-oxopyridin-1(2H)-yl)methyl)-10-hydroxy-7-azaspiro[4.5]decane-7-carboxylate: A solution of 4-chloro-5-(methylthio)pyridin-2(1H)-one (800 mg, 4.55 mmol), Epoxide 2 (1.34 g, 5.01 mmol) and DBU (0.893 mL, 5.92 mmol) in NMP (11 mL) was stirred at 110° C. for 16 h. The reaction mixture was allowed to cool to rt before being purified directly by flash chromatography (0-25% EtOAc in cyclohexane) to give the title compound (680 mg, 33%) as a colourless solid. LCMS (Method A): $R_T$=1.81 min, m/z=443, 445 [M+H]⁺. ¹H NMR (500 MHz, DMSO-$d_6$): δ 7.93 (s, 1H), 6.70 (s, 1H), 4.77 (s, 1H), 4.56 (d, J=13.4 Hz, 1H), 3.59 (d, J=13.5 Hz, 1H), 3.56-3.50 (m, 1H), 3.26-3.12 (m, 3H), 2.34 (s, 3H), 1.92-1.85 (m, 1H), 1.69-1.48 (m, 5H), 1.38 (s, 9H), 1.36-1.22 (m, 2H), 1.17-1.08 (m, 2H).

Step 3: 4-Chloro-1-((10-hydroxy-7-azaspiro[4.5]decan-10-yl)methyl)-5-(methylthio)pyridin-2(1H)-one: Prepared according to General Procedure 3 using tert-butyl 10-((4-chloro-5-(methylthio)-2-oxopyridin-1(2H)-yl)methyl)-10-hydroxy-7-azaspiro[4.5]decane-7-carboxylate (740 mg, 1.67 mmol), DCM (10 mL) and TFA (4 mL), stirred at rt for 2 h to give the title compound (450 mg, 78%) as a clear glassy solid. LCMS (Method B): $R_T$=0.68 min, m/z=343, 345 [M+H]⁺.

Step 4: 4-Chloro-1-((7-((R)-3-cyclohexyl-2-methylpropanoyl)-10-hydroxy-7-azaspiro[4.5]decan-10-yl)methyl)-5-(methylthio)pyridin-2(1H)-one: Prepared according to General Procedure 4 using 4-chloro-1-((10-hydroxy-7-azaspiro[4.5]decan-10-yl)methyl)-5-(methylthio)pyridin-2(1H)-one (450 mg, 1.31 mmol), Acid 1 (246 mg, 1.44 mmol), HATU (599 mg, 1.57 mmol) and DIPEA (0.688 mL, 3.94 mmol) in DCM (15 mL) to give the title compound (450 mg, 69%) as a colourless solid. LCMS (Method B): $R_T$=1.68 min, m/z=495, 497 [M+H]⁺. ¹H NMR (500 MHz, DMSO-$d_6$): δ 7.96-7.92 (m, 1H), 6.74-6.66 (m, 1H), 4.85-4.78 (m, 1H), 4.65-4.51 (m, 1H), 3.91-3.05 (m, 5H, signal overlaps with HDO)), 2.93-2.80 (m, 1H), 2.35 (s, 3H), 2.00-1.82 (m, 1H), 1.71-1.27 (m, 13H), 1.23-1.02 (m, 7H), 0.99-0.88 (m, 3H), 0.89-0.75 (m, 2H).

Example 77: 4-Chloro-1-((7-((R)-3-cyclohexyl-2-methylpropanoyl)-10-hydroxy-7-azaspiro[4.5]decan-10-yl)methyl)-5-(methylsulfonyl)pyridin-2(1H)-one

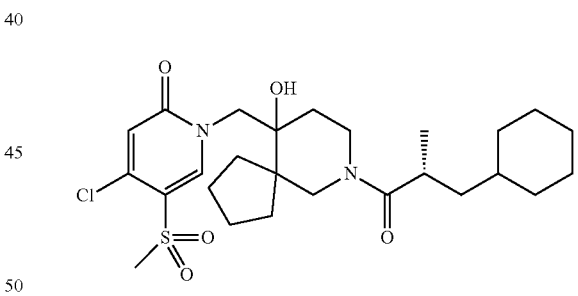

To a solution of 4-chloro-1-((7-((R)-3-cyclohexyl-2-methylpropanoyl)-10-hydroxy-7-azaspiro[4.5]decan-10-yl)methyl)-5-(methylthio)pyridin-2(1H)-one (50 mg, 0.101 mmol) in DCM (7 mL) at 0° C. was added mCPBA (<77% pure) (91 mg, 0.404 mmol). The reaction was allowed to warm to rt and stirred for 20 h. The reaction mixture was concentrated under reduced pressure and the residue was purified by flash chromatography (0-100% EtOAc in cyclohexane) to give the title compound (39.7 mg, 74%) as a colourless solid after lyophilisation. LCMS (Method B): $R_T$=1.47, 1.48 min (diastereoisomers), m/z=527, 529 [M+H]⁺. ¹H NMR (500 MHz, DMSO-$d_6$: δ 8.48-8.41 (m, 1H), 6.88-6.73 (m, 1H), 4.98-4.91 (m, 1H), 4.74-4.62 (m, 1H), 3.87-3.06 (m, 8H (signal overlaps with HDO)), 2.94-2.78 (m, 1H), 2.00-1.83 (m, 1H), 1.75-1.02 (m, 20H), 1.01-0.88 (m, 3H), 0.88-0.74 (m, 2H).

Example 78: 1-((7-((R)-3-Cyclohexyl-2-methylpropanoyl)-10-hydroxy-7-azaspiro[4.5]decan-10-yl)methyl)-5-(methylthio)-4-phenylpyridin-2(1H)-one

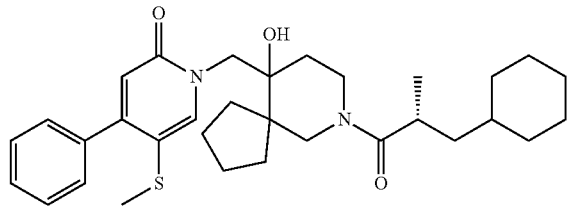 [SMILES: CSc1cn(CC2(O)CCN(C(=O)[C@H](C)CC3CCCCC3)CC23CCCC3)c(=O)cc1-c1ccccc1]

Prepared according to General Procedure 5 using 4-chloro-1-((7-((R)-3-cyclohexyl-2-methylpropanoyl)-10-hydroxy-7-azaspiro[4.5]decan-10-yl)methyl)-5-(methylthio)pyridin-2(1H)-one (100 mg, 0.202 mmol), phenylboronic acid (37 mg, 0.303 mmol), Pd(dppf)Cl$_2$·DCM (10.2 mg, 10.1 µmol), sodium carbonate (32 mg, 0.303 mmol), 1,4-dioxane (0.9 mL) and water (0.3 mL) for 15 min at 120° C., then 15 min at 130° C. under microwave irradiation to give the title compound (82 mg, 76%). LCMS (Method B): $R_T$=1.75, 1.76 min (diastereoisomers), m/z=537 [M+H]$^+$. $^1$H NMR (500 MHz, DMSO-d$_6$): δ 7.90-7.83 (m, 1H), 7.60-7.28 (m, 5H), 6.38-6.31 (m, 1H), 5.03-4.92 (m, 1H), 4.70-4.52 (m, 1H), 3.94-3.08 (m, 5H (signal overlaps with HDO)), 2.95-2.82 (m, 1H), 2.07 (s, 3H), 1.97-1.85 (m, 1H), 1.80-1.03 (m, 20H), 1.01-0.89 (m, 3H), 0.88-0.77 (m, 2H).

Example 79: 1-((7-((R)-3-Cyclohexyl-2-methylpropanoyl)-10-hydroxy-7-azaspiro[4.5]decan-10-yl)methyl)-5-(methylsulfinyl)-4-phenylpyridin-2(1H)-one

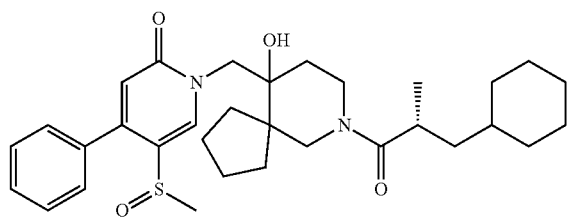 [SMILES: C[C@H](CC1CCCCC1)C(=O)N1CCC(O)(Cn2cc(S(C)=O)c(-c3ccccc3)cc2=O)C2(CCCC2)C1]

mCPBA (<77% pure) (34.7 mg, 0.155 mmol) was added to a solution of 1-((7-((R)-3-cyclohexyl-2-methylpropanoyl)-10-hydroxy-7-azaspiro[4.5]decan-10-yl)methyl)-5-(methylthio)-4-phenylpyridin-2(1H)-one (83.0 mg, 0.155 mmol) in DCM (7 mL) at rt and stirred for 1 h. The reaction was concentrated in vacuo and the crude product purified by flash chromatography (0-100% EtOAc in cyclohexane, 0-20% MeOH in EtOAc) to give the title compound (49.4 mg, 57%). LCMS (Method B): $R_T$=1.51 min, m/z=553 [M+H]$^+$. $^1$H NMR (500 MHz, DMSO-d$_6$) δ 8.24-8.14 (m, 1H), 7.54-7.44 (m, 5H), 6.39 (t, J=4.5 Hz, 1H), 4.98-4.90 (m, 1H), 4.86-4.66 (m, 1H), 3.92-3.62 (m, 2H), 3.58-3.13 (m, 3H (signal obscured by HDO)), 2.95-2.80 (m, 1H), 2.40 (m, 3H), 2.05-1.85 (m, 1H), 1.81-1.03 (m, 20H), 0.95 (dq, J=11.9, 6.4, 5.3 Hz, 3H), 0.91-0.75 (m, 2H).

Example 80: 1-((7-((R)-3-Cyclohexyl-2-methylpropanoyl)-10-hydroxy-7-azaspiro[4.5]decan-10-yl)methyl)-5-(methylsulfonyl)-4-phenylpyridin-2(1H)-one

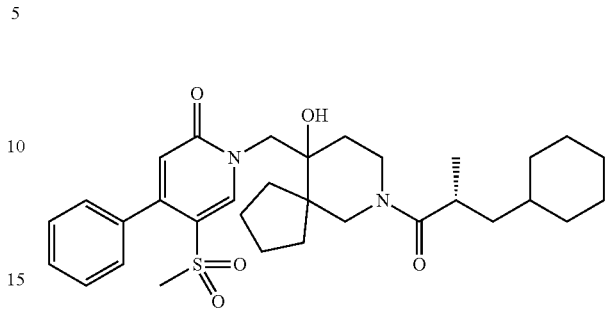

To a solution of 1-((7-((R)-3-cyclohexyl-2-methylpropanoyl)-10-hydroxy-7-azaspiro[4.5]decan-10-yl)methyl)-5-(methylthio)-4-phenylpyridin-2(1H)-one (65 mg, 0.121 mmol) in DCM (7 mL) at 0° C. was added mCPBA (<77% pure) (40.7 mg, 0.182 mmol). The reaction was allowed to warm to rt and stirred for 20 h. The reaction mixture was concentrated under reduced pressure and the residue purified by flash chromatography (0-100% EtOAc in cyclohexane; then 0-20% MeOH in EtOAc) to give the title compound (37.9 mg, 55%) as a colourless solid after lyophilisation. LCMS (Method B): $R_T$=1.58 min, m/z=569 [M+H]$^+$. $^1$H NMR (500 MHz, DMSO-d$_6$): δ 8.53-8.46 (m, 1H), 7.60-7.23 (m, 5H), 6.34-6.21 (m, 1H), 5.03-4.95 (m, 1H), 4.86-4.69 (m, 1H), 3.89-3.15 (m, 5H (signal overlaps with HDO)), 2.95-2.80 (m, 1H), 2.75 (s, 3H), 2.02-1.87 (m, 1H), 1.78-1.03 (m, 20H), 1.00-0.90 (m, 3H), 0.89-0.75 (m, 2H).

Example 81: N-Benzyl-4-((4-(2-fluorophenyl)-6-oxopyrimidin-1(6H)-yl)methyl)-4-hydroxy-N-methylpiperidine-1-carboxamide

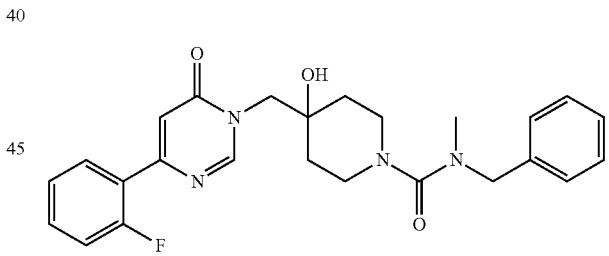

Step 1: tert-Butyl 4-((4-chloro-6-oxopyrimidin-1(6H)-yl)methyl)-4-hydroxypiperidine-1-carboxylate: Prepared according to General Procedure 2 using 6-chloropyrimidin-4(3H)-one (3.18 g, 24.4 mmol), tert-butyl 1-oxa-6-azaspiro[2.5]octane-6-carboxylate (5.2 g, 24.4 mmol) and DIPEA (6.39 mL, 36.6 mmol) in DMF (32 mL). The crude product was triturated with a mixture of cyclohexane and EtOAc and the residual solvents were removed in vacuo to give the title compound (3.70 g, 44%). LCMS (Method B): $R_T$=1.01 min, m/z=244 [M+H-Boc]$^+$. $^1$H NMR (400 MHz, CDCl$_3$): δ 8.08 (s, 1H), 6.57 (s, 1H), 4.0 (br d, 4H), 3.15 (br t, 2H), 2.78 (s, 1H), 1.69-1.59 (m, 1H), 1.54-1.49 (m, 1H), 1.46 (m, 11H).

Step 2: tert-Butyl 4-((4-(2-fluorophenyl)-6-oxopyrimidin-1(6H)-yl)methyl)-4-hydroxypiperidine-1-carboxylate: Prepared according to General Procedure 5 using tert-butyl 4-((4-chloro-6-oxopyrimidin-1(6H)-yl)methyl)-4-hydroxypiperidine-1-carboxylate (1 g, 2.91 mmol), (2-fluorophenyl)boronic acid (0.61 g, 4.36 mmol), sodium carbonate (0.617 g, 5.82 mmol), 1,4-dioxane (12 mL), water (4.8 mL) and Pd(Ph$_3$P)$_4$ (0.168 g, 0.145 mmol). The reaction was heated in a microwave at 150° C. for 15 min. The crude product was triturated with diethyl ether to give the title compound (1.71 g, 73%). LCMS (Method B): R$_T$=1.22 min, m/z=304 [M-Boc+H]$^+$. $^1$H NMR (400 MHz, CDCl$_3$): δ 8.19 (s, 1H), 8.05 (td, 1H), 7.44 (qd, 1H), 7.29 (d, 1H), 7.17 (dd, 1H), 7.11 (s, 1H), 4.0 (br d, 4H), 3.56 (s, 1H), 3.22-3.07 (m, 2H), 1.56-1.67 (m, 4H), 1.46 (s, 9H).

Step 3: 6-(2-Fluorophenyl)-3-((4-hydroxypiperidin-4-yl)methyl)pyrimidin-4(3H)-one: A solution of tert-butyl 4-((4-(2-fluorophenyl)-6-oxopyrimidin-1(6H)-yl)methyl)-4-hydroxypiperidine-1-carboxylate (2.60 g, 6.44 mmol) in DCM (10 mL) and TFA (10 mL) was stirred at rt for 30 min. The reaction mixture was concentrated under reduced pressure the residue was dissolved in MeOH (10 mL) and the resulting solution was purified using a 2×10 g SCX-2 cartridges in parallel (pre-equilibrated with and then washed using MeOH before being eluted with 2 M in NH$_3$ in MeOH). The basic eluents were concentrated under reduced pressure to give the title compound (1.9 g, 97%) as a pale yellow solid. LCMS (Method B): R$_T$=0.58 min, m/z=304 [M+H]$^+$.

Step 4: N-Benzyl-N-methyl-1H-imidazole-1-carboxamide: CDI (130 mg, 0.805 mmol) was added portionwise to an ice cold solution of N-benzylmethylamine (79.9 µL, 0.619 mmol) in water (3.0 mL). After 30 min, the reaction mixture was extracted using EtOAc (×3), the combined organic phase was dried (MgSO$_4$), the solvents were removed in vacuo, and the remaining residue was purified by flash chromatography (0-100% EtOAc in cyclohexane) to afford the title compound (81 mg, 61%) as a white solid. LCMS (Method B): R$_T$=0.57 min, m/z=216 [M+H]$^+$. $^1$H NMR (400 MHz, CDCl$_3$): δ 7.95-7.91 (m, 1H), 7.45-7.32 (m, 3H), 7.32-7.24 (m, 3H), 7.10-7.05 (m, 1H), 4.65 (s, 2H), 3.05 (s, 3H).

Step 5: 1-(Benzyl(methyl)carbamoyl)-3-methyl-1H-imidazol-3-ium iodide: Iodomethane (69.4 µL, 1.11 mmol) was added dropwise to an ice cold solution of N-benzyl-N-methyl-1H-imidazole-1-carboxamide (40 mg, 0.186 mmol) in acetonitrile (1.5 mL). The temperature was allowed to increase to rt. After 2 days, the solvents were removed in vacuo and the crude title compound was carried through to the next step without any further purification. LCMS (Method B): R$_T$=0.84 min, m/z=230 [M−I]$^+$.

Step 6: N-Benzyl-4-((4-(2-fluorophenyl)-6-oxopyrimidin-1(6H)-yl)methyl)-4-hydroxy-N-methylpiperidine-1-carboxamide: The crude 1-(benzyl(methyl)carbamoyl)-3-methyl-1H-imidazol-3-ium iodide material (assumed 66.4 mg, 0.186 mmol) was dissolved in DCM (2.0 mL) and 6-(2-fluorophenyl)-3-((4-hydroxypiperidin-4-yl)methyl)pyrimidin-4(3H)-one (0.188 g, 0.619 mmol) and triethylamine (0.086 mL, 0.619 mmol) were added and the resulting mixture was stirred at rt. After 2 days, the reaction mixture was quenched using 1 M HCl (aq) solution, the layers were separated, and the aqueous phase was extracted (DCM×2), and the combined organic phases was dried (phase separator). The solvents were removed in vacuo and the remaining residue was purified by flash chromatography (Biotage KP-NH, 0-100% EtOAc in cyclohexane) to afford the title compound (3.0 mg, 4%) as a white solid. LCMS (Method B): R$_T$=1.17 min, m/z=451 [M+H]$^+$. $^1$H NMR (400 MHz, CDCl$_3$): δ 8.12 (s, 1H), 7.99 (td, 1H), 7.42-7.34 (m, 1H), 7.31-7.23 (m, 2H), 7.23-7.15 (m, 4H, overlapping solvent peak), 7.10 (ddd, 1H), 7.04 (s, 1H), 4.32 (s, 2H), 4.00 (s, 2H), 3.55-3.45 (m, 3H), 3.24-3.12 (m, 2H), 2.68 (s, 3H), 1.66 (br td, 2H), 1.58-1.49 (m, 2H).

Example 82: N-(Cyclohexylmethyl)-10-((5-(dimethylcarbamoyl)-2-oxo-4-phenylpyridin-1(2H)-yl)methyl)-10-hydroxy-N-methyl-7-azaspiro[4.5]decane-7-carboxamide

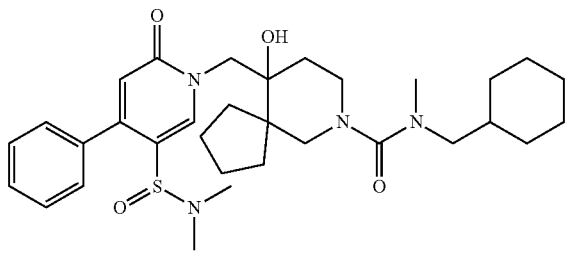 [SMILES: CN(CC1CCCCC1)C(=O)N1CCC(O)(Cn2cc(S(=O)N(C)C)c(-c3ccccc3)cc2=O)C2(CCCC2)C1]

Step 1: tert-Butyl 10-((4-chloro-5-(ethoxycarbonyl)-2-oxopyridin-1(2H)-yl)methyl)-10-hydroxy-7-azaspiro[4.5]decane-7-carboxylate: Prepared according to General Procedure 2 using ethyl 4-chloro-6-oxo-1,6-dihydropyridine-3-carboxylate (1.06 g, 5.24 mmol), Epoxide 2 (1.75 g, 5.24 mmol) and cesium carbonate (2.56 g, 7.85 mmol) in DMF (20 mL). The reaction was stirred at 80° C. for 16 h to give the title compound (1.02 g, 41%). LCMS (Method A): R$_T$=1.66 min, m/z=413, 415 [M-butene+H]$^+$.

Step 2: tert-Butyl 10-((5-(ethoxycarbonyl)-2-oxo-4-phenylpyridin-1(2H)-yl)methyl)-10-hydroxy-7-azaspiro[4.5]decane-7-carboxylate: Prepared according to General Procedure 5 using tert-butyl 10-((4-chloro-5-(ethoxycarbonyl)-2-oxopyridin-1(2H)-yl)methyl)-10-hydroxy-7-azaspiro[4.5]decane-7-carboxylate (1.02 g, 2.18 mmol), phenylboronic acid (398 mg, 3.26 mmol), Pd(dppf)Cl$_2$·DCM (186 mg, 0.218 mmol), sodium carbonate (576 mg, 5.44 mmol), 1,4-dioxane (9 mL) and water (3 mL). The reaction was heated under microwave irradiation at 150° C. for 15 min to give the title compound (1.02 g, 91%). LCMS (Method A): R$_T$=1.77 min, m/z=511 [M+H]$^+$.

Step 3: 1-((7-(tert-Butoxycarbonyl)-10-hydroxy-7-azaspiro[4.5]decan-10-yl)methyl)-6-oxo-4-phenyl-1,6-dihydropyridine-3-carboxylic acid: To a solution of tert-butyl 10-((5-(ethoxycarbonyl)-2-oxo-4-phenylpyridin-1(2H)-yl)methyl)-10-hydroxy-7-azaspiro[4.5]decane-7-carboxylate (1.24 g, 2.43 mmol) in ethanol (9 mL) was added 2 M sodium hydroxide$_{(aq)}$ (9 mL). The resulting mixture was stirred at 55° C. for 3 h. The reaction was concentrated under reduced pressure and the residue taken up in water (10 mL). The aqueous phase was washed with diethyl ether (10 mL) and 2 M HCl$_{(aq)}$ added to the aqueous phase until pH <4. The resulting precipitate was collected by filtration to give the title compound (900 mg, 76%). LCMS (Method A): R$_T$=1.42 min, m/z=483 [M+H]$^+$.

Step 4: tert-Butyl 10-((5-(dimethylcarbamoyl)-2-oxo-4-phenylpyridin-1(2H)-yl)methyl)-10-hydroxy-7-azaspiro[4.5]decane-7-carboxylate: Prepared according to General Procedure 4 using 1-((7-(tert-butoxycarbonyl)-10-hydroxy-7-azaspiro[4.5]decan-10-yl)methyl)-6-oxo-4-phenyl-1,6-dihydropyridine-3-carboxylic acid (1.00 g, 2.07 mmol), dimethylamine (2 M in THF, 1.55 mL, 3.11 mmol), HATU (867 mg, 2.28 mmol) and DIPEA (1.09 mL, 6.22 mmol) in DCM (20 mL) to give the title compound (1.00 g, 94%). LCMS (Method A): R$_T$=1.39 min, m/z=510 [M+H]$^+$.

Step 5: 1-((10-Hydroxy-7-azaspiro[4.5]decan-10-yl)methyl)-N,N-dimethyl-6-oxo-4-phenyl-1,6-dihydropyridine-3-carboxamide: Prepared according to General Procedure 3 using tert-butyl 10-((5-(dimethylcarbamoyl)-2-oxo-4-phenylpyridin-1(2H)-yl)methyl)-10-hydroxy-7-azaspiro[4.5]decane-7-carboxylate (1.00 g, 1.95 mmol), DCM (20 mL) and TFA (10 mL) to give the title compound (560 mg, 70%). LCMS (Method A): R$_T$=0.49 min, m/z=410 [M+H]$^+$.

Step 6: 4-Nitrophenyl (cyclohexylmethyl)(methyl)carbamate: To a stirred suspension of 1-cyclohexyl-N-methylmethanamine hydrochloride (82 mg, 0.500 mmol) and 4-nitrophenyl chloroformate (302 mg, 1.50 mmol) in DCM (5 mL) at 0° C. was added pyridine (0.162 mL, 2.00 mmol). The reaction was allowed to slowly warm to rt and stirred for 16 h before saturated NH$_4$Cl$_{(aq)}$ (30 mL) was added. The resulting mixture was extracted with DCM (3×20 mL) using a phase separator, the combined organic phases concentrated under reduced pressure and the residue was purified by flash chromatography (10-60% EtOAc in cyclohexane) to give the title compound (120 mg, 82%) as a colourless oil that solidified upon standing. LCMS (Method A): R$_T$=1.82 min, m/z=293 [M+H]$^+$. $^1$H NMR (500 MHz, DMSO-d$_6$): δ 8.30-8.23 (m, 2H), 7.45-7.36 (m, 2H), 3.27 (d, J=7.0 Hz, 1H), 3.15 (d, J=7.0 Hz, 1H), 3.05 (s, 1.5H (rotomer)), 2.93 (s, 1.5H (rotomer)), 1.76-1.58 (m, 6H), 1.29-1.10 (m, 3H), 1.03-0.87 (m, 2H).

Step 7: N-(Cyclohexylmethyl)-10-((5-(dimethylcarbamoyl)-2-oxo-4-phenylpyridin-1(2H)-yl)methyl)-10-hydroxy-N-methyl-7-azaspiro[4.5]decane-7-carboxamide: A solution of 1-((10-hydroxy-7-azaspiro[4.5]decan-10-yl)methyl)-N,N-dimethyl-6-oxo-4-phenyl-1,6-dihydropyridine-3-carboxamide (30 mg, 73.3 μmol) and 4-nitrophenyl (cyclohexylmethyl)(methyl)carbamate (43 mg, 0.147 mmol) in MeOH (0.7 mL) was heated under microwave radiation at 120° C. for 15 min and subsequently at 150° C. for 1 h. To this mixture was added DMAP (1.8 mg, 14.7 μmol) and the reaction was heated under microwave radiation at 165° C. for 24 h. The reaction mixture was concentrated under reduced pressure and the residue was purified by flash chromatography (0-100% EtOAc in cyclohexane; then 0-20% MeOH in EtOAc; then 2$^{nd}$ column, 0-15% MeOH in DCM) to give the title compound (10.1 mg, 22%) as yellow solid after lyophilisation. LCMS (Method B): R$_T$=1.38 min, m/z=563 [M+H]$^+$. $^1$H NMR (500 MHz, DMSO-d$_6$): δ 7.84 (s, 1H), 7.48-7.41 (m, 3H), 7.41-7.34 (m, 2H), 6.45 (s, 1H), 4.83 (s, 1H), 4.63 (d, J=13.5 Hz, 1H), 3.67 (d, J=13.5 Hz, 1H), 3.35-3.24 (m, 1H (signal overlaps with HDO)), 3.14-3.03 (m, 2H), 3.02-2.87 (m, 3H), 2.75 (s, 3H), 2.72 (s, 3H), 2.62 (s, 3H), 1.94-1.88 (m, 1H), 1.70-1.39 (m, 12H), 1.27-1.09 (m, 6H), 0.87-0.77 (m, 2H).

Example 83: 4-Nitrophenyl 10-((5-(dimethylcarbamoyl)-2-oxo-4-phenylpyridin-1(2H)-yl)methyl)-10-hydroxy-7-azaspiro[4.5]decane-7-carboxylate

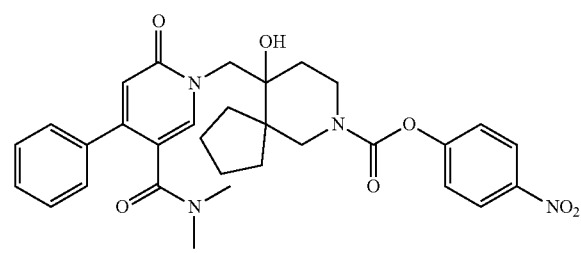 [SMILES: CN(C)C(=O)c1cn(CC2(O)CCN(C(=O)Oc3ccc([N+](=O)[O-])cc3)CC23CCCC3)c(=O)cc1-c1ccccc1]

To suspension of 1-((10-hydroxy-7-azaspiro[4.5]decan-10-yl)methyl)-N,N-dimethyl-6-oxo-4-phenyl-1,6-dihydropyridine-3-carboxamide (402 mg, 0.982 mmol) and 4-nitrophenyl chloroformate (594 mg, 2.94 mmol) in DCM (10 mL) was added pyridine (0.238 mL, 2.94 mmol) and after stirring at rt for 16 h the reaction mixture was purified directly by flash chromatography (0-100% EtOAc in cyclohexane) to give the title compound (345 mg, 61%) as an off-white solid. LCMS (Method B): R$_T$=1.28 min, m/z=575 [M+H]$^+$. $^1$H NMR (500 MHz, DMSO-d$_6$): δ 8.40-8.20 (m, 2H), 7.85 (s, 1H), 7.69-6.94 (m, 7H), 6.47 (s, 1H), 5.03 (d, J=6.1 Hz, 1H), 4.73-4.56 (m, 1H), 3.95-3.66 (m, 2H), 3.58-3.31 (m, 3H), 2.76 (s, 3H), 2.64 (s, 3H), 2.03-1.96 (m, 1H), 1.85-1.20 (m, 9H).

Example 84: Isobutyl 10-((5-(dimethylcarbamoyl)-2-oxo-4-phenylpyridin-1(2H)-yl)methyl)-10-hydroxy-7-azaspiro[4.5]decane-7-carboxylate

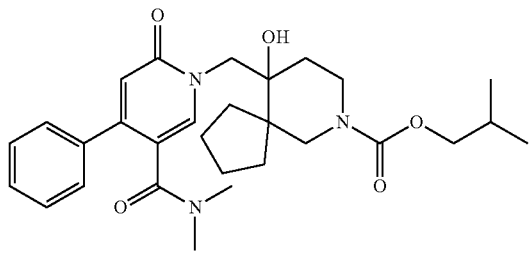 [SMILES: CC(C)COC(=O)N1CCC(O)(Cn2cc(C(=O)N(C)C)c(-c3ccccc3)cc2=O)C2(CCCC2)C1]

A solution of 1-((10-hydroxy-7-azaspiro[4.5]decan-10-yl)methyl)-N,N-dimethyl-6-oxo-4-phenyl-1,6-dihydropyridine-3-carboxamide (20 mg, 48.8 μmol), isobutyl chloroformate (12.7 μL, 97.7 μmol) and DIPEA (25.6 μL, 0.147 mmol) in DCM (0.5 mL) was stirred for 15 min before the reaction mixture was diluted with saturated NaHCO$_{3(aq)}$ (15 mL) and the resulting mixture was extracted with DCM (3×10 mL) using a phase separator. The combined organic phases were concentrated under reduced pressure and the residue was purified by flash chromatography (0-100% EtOAc in cyclohexane) to give the title compound (19.4 mg, 76%) as colourless solid after lyophilisation. LCMS (Method B): R$_T$=1.28 min, m/z=510 [M+H]$^+$. $^1$H NMR (500 MHz, DMSO-d$_6$): δ 7.83 (s, 1H), 7.46-7.41 (m, 3H), 7.40-7.35 (m, 2H), 6.45 (s, 1H), 4.92 (s, 1H), 4.60 (d, J=13.5 Hz, 1H), 3.83-3.73 (m, 2H), 3.70 (d, J=13.5 Hz, 1H), 3.67-3.60 (m, 1H), 3.35-3.21 (m, 3H (signal overlaps with HDO)), 2.75 (s, 3H), 2.62 (s, 3H), 1.96-1.89 (m, 1H), 1.88-1.81 (m, 1H), 1.72-1.50 (m, 5H), 1.45-1.33 (m, 2H), 1.27-1.21 (m, 1H), 1.20-1.13 (m, 1H), 0.89 (d, J=6.7 Hz, 6H).

Example 85: N-Benzyl-10-((5-(dimethylcarbamoyl)-2-oxo-4-phenylpyridin-1(2H)-yl)methyl)-10-hydroxy-7-azaspiro[4.5]decane-7-carboxamide

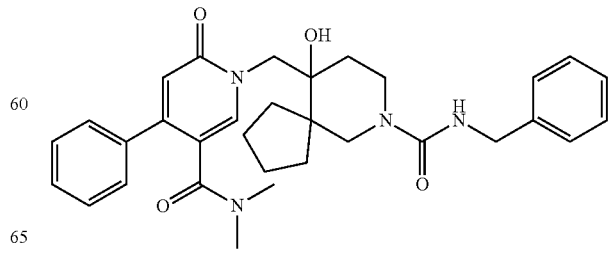

A solution of 4-nitrophenyl 10-((5-(dimethylcarbamoyl)-2-oxo-4-phenylpyridin-1(2H)-yl)methyl)-10-hydroxy-7-azaspiro[4.5]decane-7-carboxylate (20 mg, 34.8 µmol) and benzylamine (4.5 mg, 41.8 µmol) in DMF (0.35 mL) was stirred at 80° C. for 102 h. The reaction mixture was allowed to cool to rt before being diluted with DMF (~0.4 mL) and was purified by preparative HPLC to give the title compound (2.5 mg, 13%) as a colourless solid after lyophilisation. LCMS (Method B): $R_T$=1.10 min, m/z=543 [M+H]$^+$. $^1$H NMR (500 MHz, DMSO-d$_6$): δ 7.84 (s, 1H), 7.47-7.41 (m, 3H), 7.41-7.35 (m, 2H), 7.32-7.27 (m, 2H), 7.26-7.22 (m, 2H), 7.22-7.17 (m, 1H), 6.97 (t, J=5.9 Hz, 1H), 6.45 (s, 1H), 4.84 (s, 1H), 4.61 (d, J=13.5 Hz, 1H), 4.23 (d, J=5.7 Hz, 2H), 3.68 (d, J=13.5 Hz, 1H), 3.57 (dd, J=13.3, 6.3 Hz, 1H), 3.28-3.23 (m, 2H), 3.19 (d, J=13.1 Hz, 1H), 2.75 (s, 3H), 2.63 (s, 3H), 1.93-1.85 (m, 1H), 1.71-1.58 (m, 4H), 1.56-1.48 (m, 1H), 1.44-1.36 (m, 2H), 1.24-1.14 (m, 2H).

Example 86: 10-((5-(Dimethylcarbamoyl)-2-oxo-4-phenylpyridin-1(2H)-yl)methyl)-10-hydroxy-N,N-dimethyl-7-azaspiro[4.5]decane-7-carboxamide

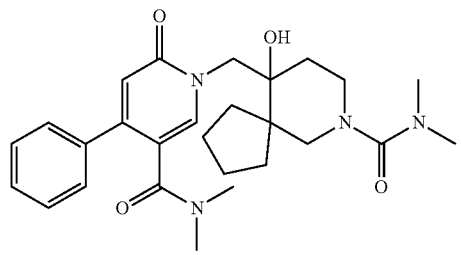 [SMILES: CN(C)C(=O)c1cn(CC2(O)CCN(C(=O)N(C)C)CC23CCCC3)c(=O)cc1-c1ccccc1]

Isolated as a by-product in the formation of Example 85 due to reaction of 4-nitrophenyl 10-((5-(dimethylcarbamoyl)-2-oxo-4-phenylpyridin-1(2H)-yl)methyl)-10-hydroxy-7-azaspiro[4.5]decane-7-carboxylate with DMF. The title compound (5 mg, 27%) was isolated as a colourless solid after lyophilisation. LCMS (Method B): $R_T$=0.96 min, m/z=481 [M+H]$^+$. $^1$H NMR (500 MHz, DMSO-d$_6$): δ 7.84 (s, 1H), 7.48-7.41 (m, 3H), 7.41-7.34 (m, 2H), 6.45 (s, 1H), 4.84 (s, 1H), 4.62 (d, J=13.4 Hz, 1H), 3.68 (d, J=13.5 Hz, 1H), 3.37-3.23 (m, 1H (signal overlaps with HDO)), 3.15-3.05 (m, 2H), 2.95 (d, J=13.0 Hz, 1H), 2.75 (s, 3H), 2.70 (s, 6H), 2.63 (s, 3H), 1.96-1.87 (m, 1H), 1.72-1.39 (m, 7H), 1.29-1.16 (m, 2H).

Example 87: N-Benzyl-10-((5-(dimethylcarbamoyl)-2-oxo-4-phenylpyridin-1(2H)-yl)methyl)-10-hydroxy-N-methyl-7-azaspiro[4.5]decane-7-carboxamide

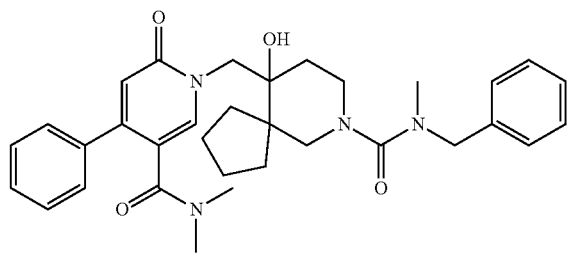 [SMILES: CN(C)C(=O)c1cn(CC2(O)CCN(C(=O)N(C)Cc3ccccc3)CC23CCCC3)c(=O)cc1-c1ccccc1]

A solution of 4-nitrophenyl 10-((5-(dimethylcarbamoyl)-2-oxo-4-phenylpyridin-1(2H)-yl)methyl)-10-hydroxy-7-azaspiro[4.5]decane-7-carboxylate (20 mg, 34.8 µmol) and N-benzylmethylamine (9 µL, 69.6 µmol) in DMA (0.35 mL) was heated at 80° C. for 147 h. The reaction mixture was allowed to cool to rt before being diluted with DMF (0.4 mL) and the resulting solution was purified by preparative HPLC to give title compound (6.3 mg, 32%) as a colourless solid after lyophilisation. LCMS (Method B): $R_T$=1.23 min, m/z=557 [M+H]$^+$. $^1$H NMR (500 MHz, DMSO-d$_6$): δ 7.84 (s, 1H), 7.47-7.40 (m, 3H), 7.41-7.31 (m, 4H), 7.28-7.21 (m, 3H), 6.44 (s, 1H), 4.86 (s, 1H), 4.62 (d, J=13.4 Hz, 1H), 4.31, 4.27 (ABq, J$_{AB}$=16 Hz, 2H), 3.67 (d, J=13.5 Hz, 1H), 3.45-3.36 (m, 1H), 3.23-3.09 (m, 2H), 2.99 (d, J=13.0 Hz, 1H), 2.75 (s, 3H), 2.65 (s, 3H), 2.62 (s, 3H), 1.96-1.86 (m, 1H), 1.74-1.65 (m, 1H), 1.64-1.44 (m, 5H), 1.44-1.36 (m, 1H), 1.30-1.22 (m, 1H), 1.22-1.13 (m, 1H).

Example 88: 1-((10-Hydroxy-7-(3-(trifluoromethyl)pyrrolidine-1-carbonyl)-7-azaspiro[4.5]decan-10-yl)methyl)-N,N-dimethyl-6-oxo-4-phenyl-1,6-dihydropyridine-3-carboxamide

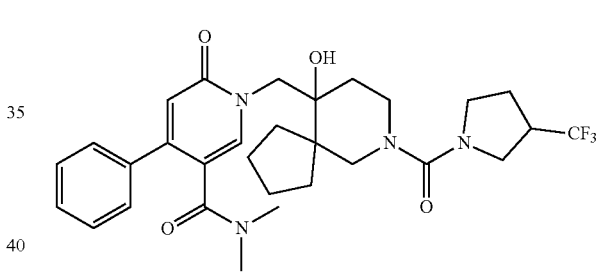

A solution of 4-nitrophenyl 10-((5-(dimethylcarbamoyl)-2-oxo-4-phenylpyridin-1(2H)-yl)methyl)-10-hydroxy-7-azaspiro[4.5]decane-7-carboxylate (26 mg, 45.2 µmol) and 3-(trifluoromethyl)pyrrolidine hydrochloride (16 mg, 90.5 µmol) in DMA (0.45 mL) was heated at 80° C. for 50 min before DIPEA (15.8 µL, 90.5 µmol) was added and the resulting solution was stirred at 80° C. for a further 144 h. The reaction mixture was allowed to cool to rt before being diluted with DMF (0.4 mL) and the resulting solution was purified by preparative HPLC to give title compound (16.7 mg, 63%) as a pale beige solid after lyophilisation. LCMS (Method B): $R_T$=1.17 min, m/z=575 [M+H]$^+$. $^1$H NMR (500 MHz, DMSO-d$_6$): δ 7.84 (s, 1H), 7.47-7.41 (m, 3H), 7.40-7.35 (m, 2H), 6.45 (s, 1H), 4.86 (s, 1H), 4.62 (d, J=13.5 Hz, 1H), 3.68 (d, J=13.5 Hz, 1H), 3.57-3.45 (m, 1H), 3.45-3.30 (m, 4H), 3.21-3.09 (m, 3H), 3.06-2.98 (m, 1H), 2.75 (s, 3H), 2.63 (s, 3H), 2.12-2.02 (m, 1H), 1.95-1.81 (m, 2H), 1.73-1.50 (m, 5H), 1.49-1.39 (m, 2H), 1.30-1.16 (m, 2H).

Example 89: N-Cyclohexyl-10-((5-(dimethylcarbamoyl)-2-oxo-4-phenylpyridin-1(2H)-yl)methyl)-10-hydroxy-N-methyl-7-azaspiro[4.5]decane-7-carboxamide

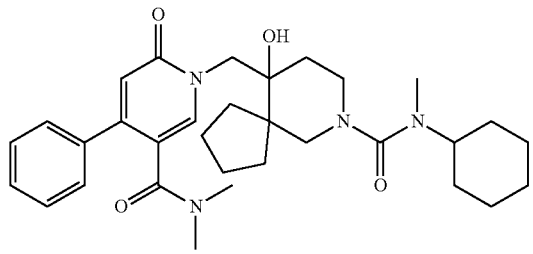 [SMILES: CN(C)C(=O)c1cn(CC2(O)CCN(C(=O)N(C)C3CCCCC3)CC23CCCC3)c(=O)cc1-c1ccccc1]

A solution of 4-nitrophenyl 10-((5-(dimethylcarbamoyl)-2-oxo-4-phenylpyridin-1(2H)-yl)methyl)-10-hydroxy-7-azaspiro[4.5]decane-7-carboxylate (20 mg, 34.8 μmol) and N-methylcyclohexylamine (16.8 μL, 0.139 mmol) in DMA (0.35 mL) was heated at 80° C. for 64 h. The reaction mixture was allowed to cool to rt before being diluted with DMF (0.7 mL) and the resulting solution was purified by preparative HPLC to give title compound (6.6 mg, 34%) as a colourless solid after lyophilisation. LCMS (Method B): $R_T$=1.31 min, m/z=549 [M+H]$^+$. $^1$H NMR (500 MHz, DMSO-d$_6$): δ 7.84 (s, 1H), 7.49-7.41 (m, 3H), 7.41-7.35 (m, 2H), 6.45 (s, 1H), 4.84 (s, 1H), 4.63 (d, J=13.4 Hz, 1H), 3.67 (d, J=13.5 Hz, 1H), 3.37 (tt, J=11.8, 3.6 Hz, 1H), 3.33-3.25 (m, 1H (signal overlaps with HDO)), 3.14-3.05 (m, 2H), 2.91 (d, J=13.1 Hz, 1H), 2.75 (s, 3H), 2.63 (s, 3H), 2.59 (s, 3H), 1.95-1.86 (m, 1H), 1.79-1.72 (m, 2H), 1.72-1.65 (m, 1H), 1.66-1.51 (m, 7H), 1.51-1.36 (m, 4H), 1.29-1.14 (m, 4H), 1.10-1.01 (m, 1H).

Example 90: 1-((10-Hydroxy-7-((R)-3-phenylmorpholine-4-carbonyl)-7-azaspiro[4.5]decan-10-yl)methyl)pyrazin-2(1H)-one

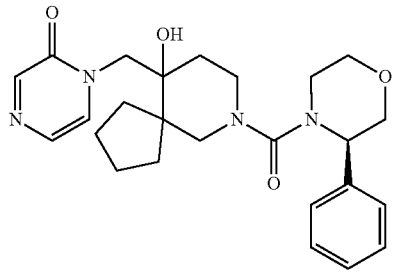 [SMILES: O=C(N1CCC(O)(Cn2ccncc2=O)C2(CCCC2)C1)N1CCOC[C@H]1c1ccccc1]

Step 1: (R)-3-Phenylmorpholine-4-carbonyl chloride: Prepared according to General Procedure 8 using (R)-3-phenylmorpholine (50 mg, 0.306 mmol), triphosgene (45.5 mg, 0.153 mmol), DIPEA (161 μL, 0.919 mmol) and THF (1.5 mL), stirred at 0° C. for 30 min, warmed to rt and stirred at rt for 2 h to give the title compound (65 mg, 94%). Material was taken on without further purification. LCMS (Method A): $R_T$=1.32 min, m/z=226, 228 [M+H]$^+$.

Step 2: 1-((10-Hydroxy-7-((R)-3-phenylmorpholine-4-carbonyl)-7-azaspiro[4.5]decan-10-yl)methyl)pyrazin-2(1H)-one: Prepared according to General Procedure 9 using 1-((10-hydroxy-7-azaspiro[4.5]decan-10-yl)methyl)pyrazin-2(1H)-one (15 mg, 57.0 μmol), (R)-3-phenylmorpholine-4-carbonyl chloride (15.4 mg, 68.4 μmol) and DIPEA (39.8 μL, 0.228 mmol) in DCM (1 mL) to give the title compound (13.0 mg, 47%). LCMS (Method A): $R_T$=1.02 min, m/z=453 [M+H]$^+$. $^1$H NMR (500 MHz, DMSO-d$_6$): δ 8.01 (d, J=3.6 Hz, 1H), 7.58 (t, J=4.3 Hz, 1H), 7.31 (t, J=6.5 Hz, 5H), 7.23 (qd, J=6.5, 1.7 Hz, 1H), 4.76 (d, J=7.9 Hz, 1H), 4.61-4.47 (m, 1H), 4.39 (dt, J=15.9, 4.8 Hz, 1H), 3.79-3.64 (m, 4H), 3.61-3.47 (m, 2H), 3.40-2.95 (m, 5H (signal obscured by HDO)), 1.89-1.77 (m, 1H), 1.64-1.14 (m, 8H), 1.13-1.02 (m, 1H).

Example 91: 1-((10-Hydroxy-7-((R)-2-phenylpiperazine-1-carbonyl)-7-azaspiro[4.5]decan-10-yl)methyl)pyrazin-2(1H)-one

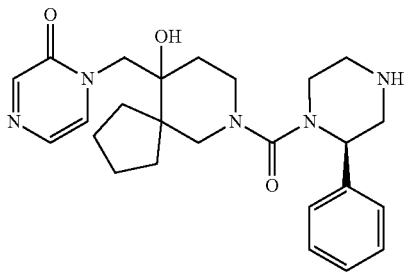 [SMILES: O=C(N1CCC(O)(Cn2ccncc2=O)C2(CCCC2)C1)N1CCNC[C@H]1c1ccccc1]

Step 1: tert-Butyl (R)-4-(chlorocarbonyl)-3-phenylpiperazine-1-carboxylate: Prepared according to General Procedure 8 using tert-butyl (R)-3-phenylpiperazine-1-carboxylate (500 mg, 1.91 mmol), triphosgene (283 mg, 0.953 mmol), DIPEA (1.0 mL, 5.72 mmol) and THF (14 mL), stirred at 0° C. for 30 min, warmed to rt and stirred at rt for 1 h to give the title compound (620 mg, quantitative). Material was taken on without further purification.

Step 2: tert-Butyl (3R)-4-(10-hydroxy-10-((2-oxopyrazin-1(2H)-yl)methyl)-7-azaspiro[4.5]decane-7-carbonyl)-3-phenylpiperazine-1-carboxylate: Prepared according to General Procedure 9 using 1-((10-hydroxy-7-azaspiro[4.5]decan-10-yl)methyl)pyrazin-2(1H)-one (25 mg, 94.9 μmol), tert-butyl (R)-4-(chlorocarbonyl)-3-phenylpiperazine-1-carboxylate (37.0 mg, 0.114 mmol), DIPEA (66.3 μL, 0.380 mmol) and DCM (2 mL), stirring at rt for 1 h to give the title compound (37 mg, 70%). LCMS (Method A): $R_T$=1.36 min, m/z=552 [M+H]$^+$; 496 [M-butene+H]$^+$.

Step 3: 1-((10-Hydroxy-7-((R)-2-phenylpiperazine-1-carbonyl)-7-azaspiro[4.5]decan-10-yl)methyl)pyrazin-2(1H)-one: Prepared according to General Procedure 3 using tert-butyl (3R)-4-(10-hydroxy-10-((2-oxopyrazin-1(2H)-yl)methyl)-7-azaspiro[4.5]decane-7-carbonyl)-3-phenylpiperazine-1-carboxylate (25 mg, 45.3 μmol), TFA (1 mL) and DCM (2 mL), stirred at rt for 40 min to give the title compound (22.5 mg, quantitative). LCMS (Method B): $R_T$=0.52 min, m/z=452 [M+H]$^+$. $^1$H NMR (500 MHz, DMSO-d$_6$): δ 8.01 (d, J=2.9 Hz, 1H), 7.58 (t, J=3.5 Hz, 1H), 7.33-7.24 (m, 5H), 7.19 (td, J=7.8, 7.0, 3.8 Hz, 1H), 4.74 (d, J=5.7 Hz, 1H), 4.54 (dd, J=25.9, 13.3 Hz, 1H), 4.29 (dt, J=15.6, 5.3 Hz, 1H), 3.58-3.47 (m, 2H), 3.26-2.85 (m, 7H), 2.77 (q, J=5.4 Hz, 2H), 1.82 (dq, J=13.2, 6.9 Hz, 1H), 1.64-1.14 (m, 8H), 1.07 (ddt, J=20.2, 13.4, 6.2 Hz, 1H). NH signal not observed.

Example 92: 1-((10-Hydroxy-7-((R)-2-phenylpiperazine-1-carbonyl)-7-azaspiro[4.5]decan-10-yl)methyl)-5-methylpyrazin-2(1H)-one

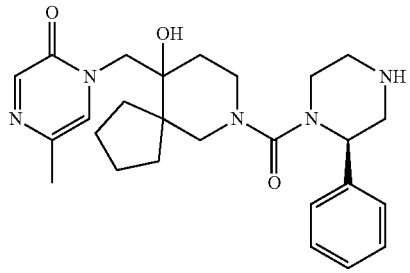 [SMILES: Cc1cn(CC2(O)CCN(C(=O)N3CCNC[C@H]3c3ccccc3)CC23CCCC3)c(=O)cn1]

Step 1: tert-Butyl 10-hydroxy-10-((5-methyl-2-oxopyrazin-1(2H)-yl)methyl)-7-azaspiro[4.5]decane-7-carboxylate: Prepared according to General Procedure 2 using 5-methylpyrazin-2-ol (55.1 mg, 0.500 mmol), Epoxide 2 (160 mg, 0.600 mmol) and cesium carbonate (179 mg, 0.550 mmol) in DMF (2.5 mL) at 90° C. for 21 h 15 min to give the title compound (60.9 mg, 32%) as a pale yellow foam. LCMS (Method A): $R_T$=1.23 min, m/z=378 [M+H]$^+$.

Step 2: 1-((10-Hydroxy-7-azaspiro[4.5]decan-10-yl)methyl)-5-methylpyrazin-2(1H)-one: A solution of tert-butyl 10-hydroxy-10-((5-methyl-2-oxopyrazin-1(2H)-yl)methyl)-7-azaspiro[4.5]decane-7-carboxylate (60.9 mg, 0.161 mmol) in TFA (0.8 mL) and DCM (1.6 mL) was stirred at rt for 15 min before the reaction mixture was loaded on to a 2 g SCX-2 cartridge that was pre-equilibrated with 1:1 DCM/MeOH. The cartridge was washed with 1:1 DCM/MeOH (60 mL) before the product was eluted with 1:1 DCM/7 M NH$_3$ in MeOH (30 mL). The basic eluents were concentrated under reduced pressure to give the title compound (41.2 mg, 92%) as a yellow foam. LCMS (Method A): $R_T$=0.23 min, m/z=278 [M+H]$^+$.

Step 3: tert-Butyl (3R)-4-(10-hydroxy-10-((5-methyl-2-oxopyrazin-1(2H)-yl)methyl)-7-azaspiro[4.5]decane-7-carbonyl)-3-phenylpiperazine-1-carboxylate: To a solution triphosgene (5.4 mg, 0.0180 mmol) in MeCN (0.36 mL) at 0° C. was added pyridine (17 μL, 0.210 mmol). After 20 min, a solution of tert-butyl (R)-3-phenylpiperazine-1-carboxylate (14.2 mg, 0.0541 mmol) in MeCN (0.36 mL) was added and the reaction mixture was stirred at 0° C. for a further 15 min before being allowed to warm to rt. After stirring for 2 h, 1-((10-hydroxy-7-azaspiro[4.5]decan-10-yl)methyl)-5-methylpyrazin-2(1H)-one (10 mg, 0.0361 mmol) and DIPEA (32 μL, 0.180 mmol) were added. The reaction was stirred at rt for 2 h 30 min before saturated NaHCO$_{3(aq)}$ (15 mL) was added and the resulting mixture was extracted with DCM (3×10 mL) using a phase separator. The combined organic phases were concentrated under reduced pressure and the residue was purified by flash chromatography (0-100% EtOAc in cyclohexane; then 0-10% MeOH in EtOAc) to give title compound (17.5 mg, 85%) as an off-white foam. LCMS (Method A): $R_T$=1.42 min, m/z=566 [M+H]$^+$.

Step 4: 1-((10-Hydroxy-7-((R)-2-phenylpiperazine-1-carbonyl)-7-azaspiro[4.5]decan-10-yl)methyl)-5-methylpyrazin-2(1H)-one: A solution of tert-butyl (3R)-4-(10-hydroxy-10-((5-methyl-2-oxopyrazin-1(2H)-yl)methyl)-7-azaspiro[4.5]decane-7-carbonyl)-3-phenylpiperazine-1-carboxylate (17.5 mg, 0.0309 mmol) in TFA (0.25 mL) and DCM (0.5 mL) was stirred at rt for 20 min before the reaction mixture was concentrated under reduced pressure. To the TFA salt, were added DCM (1 mL) and triethylamine (1 mL) and the resulting solution was directly purified by flash chromatography (Biotage KP-NH 11 g cartridge, 0-100% EtOAc in cyclohexane; then 0-20% MeOH in EtOAc) to give the title compound (11.6 mg, 75%) as a colourless solid after lyophilisation. LCMS (Method B): $R_T$=0.65, 0.67 min (2 diastereoisomers), m/z=466 [M+H]$^+$. $^1$H NMR (500 MHz, DMSO-d$_6$): δ 7.96 (d, J=0.9 Hz, 0.5H), 7.96 (d, J=0.9 Hz, 0.5H), 7.45-7.40 (m, 1H), 7.33-7.23 (m, 4H), 7.22-7.15 (m, 1H), 4.77 (s, 0.5H), 4.76 (s, 0.5H), 4.51 (d, J=13.3 Hz, 0.5H), 4.46 (d, J=13.3 Hz, 0.5H), 4.30 (t, J=5.2 Hz, 0.5H), 4.27 (t, J=5.2 Hz, 0.5H), 3.58-3.42 (m, 2H), 3.35-2.84 (m, 7H (signals overlap with HDO)), 2.82-2.70 (m, 2H), 2.19 (s, 3H), 1.87-1.76 (m, 1H), 1.61-1.34 (m, 6H), 1.30-1.17 (m, 2H), 1.11-0.99 (m, 1H). NH not visible.

Example 93: 1-((10-Hydroxy-7-((R)-2-phenylpiperazine-1-carbonyl)-7-azaspiro[4.5]decan-10-yl)methyl)-3-methylpyrazin-2(1H)-one

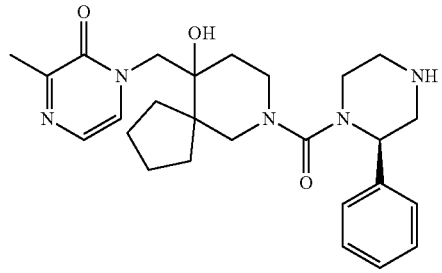 [SMILES: Cc1nccn(CC2(O)CCN(C(=O)N3CCNC[C@H]3c3ccccc3)CC23CCCC3)c1=O]

Step 1: tert-Butyl 10-hydroxy-10-((3-methyl-2-oxopyrazin-1(2H)-yl)methyl)-7-azaspiro[4.5]decane-7-carboxylate: Prepared according to General Procedure 2 using 3-methylpyrazin-2-ol (55.1 mg, 0.500 mmol), Epoxide 2 (160 mg, 0.600 mmol) and cesium carbonate (179 mg, 0.550 mmol) in DMF (2.5 mL) at 90° C. for 21 h 15 min to give the title compound (121 mg, 63%) as a pale yellow foam. LCMS (Method A): $R_T$=1.25 min, m/z=378 [M+H]$^+$.

Step 2: 1-((10-Hydroxy-7-azaspiro[4.5]decan-10-yl)methyl)-3-methylpyrazin-2(1H)-one: A solution of tert-butyl 10-hydroxy-10-((3-methyl-2-oxopyrazin-1(2H)-yl)methyl)-7-azaspiro[4.5]decane-7-carboxylate (121 mg, 0.319 mmol) in TFA (1.6 mL) and DCM (3.2 mL) was stirred at rt for 15 min before the reaction mixture was loaded on to a 2 g SCX-2 cartridge that was pre-equilibrated with 1:1 DCM/MeOH. The cartridge was washed with 1:1 DCM/MeOH (60 mL) before the product was eluted with 1:1 DCM/7 M NH$_3$ in MeOH (30 mL). The basic eluents were concentrated under reduced pressure to give the title compound (82.9 mg, 93%) as a dark yellow foam. LCMS (Method A): $R_T$=0.23 min, m/z=278 [M+H]$^+$.

Step 3: tert-Butyl (3R)-4-(10-hydroxy-10-((3-methyl-2-oxopyrazin-1(2H)-yl)methyl)-7-azaspiro[4.5]decane-7-carbonyl)-3-phenylpiperazine-1-carboxylate: To a solution of triphosgene (5.4 mg, 0.0180 mmol) in MeCN (0.36 mL) at 0° C. was added pyridine (17 μL, 0.210 mmol). After 20 min, a solution of tert-butyl (R)-3-phenylpiperazine-1-carboxylate (14.2 mg, 0.0541 mmol) in MeCN (0.36 mL) was added and the reaction mixture was stirred at 0° C. for a further 15 min before being allowed to warm to rt. After stirring for 3 h, 1-((10-hydroxy-7-azaspiro[4.5]decan-10-yl)methyl)-3-methylpyrazin-2(1H)-one (10 mg, 0.0361 mmol)

and DIPEA (32 μL, 0.180 mmol) were added. The reaction was stirred at rt for 16 h before saturated NaHCO$_{3(aq)}$ (15 mL) was added and the resulting mixture was extracted with DCM (3×10 mL) using a phase separator. The combined organic phases were concentrated under reduced pressure and the residue was purified by flash chromatography (0-100% EtOAc in cyclohexane; then 0-10% MeOH in EtOAc) to give title compound (15.7 mg, 77%) as an off-white foam. LCMS (Method A): R$_T$=1.43 min, m/z=566 [M+H]$^+$.

Step 4: 1-((10-Hydroxy-7-((R)-2-phenylpiperazine-1-carbonyl)-7-azaspiro[4.5]decan-10-yl)methyl)-3-methylpyrazin-2(1H)-one: A solution of tert-butyl (3R)-4-(10-hydroxy-10-((3-methyl-2-oxopyrazin-1(2H)-yl)methyl)-7-azaspiro[4.5]decane-7-carbonyl)-3-phenylpiperazine-1-carboxylate (15.7 mg, 0.0278 mmol) in TFA (0.25 mL) and DCM (0.5 mL) was stirred at rt for 20 min before the reaction mixture was concentrated under reduced pressure.

To the TFA salt, were added DCM (1 mL) and triethylamine (1 mL) and the resulting solution was directly purified by flash chromatography (Biotage KP-NH 11 g cartridge, 0-100% EtOAc in cyclohexane; then 0-20% MeOH in EtOAc) to give the title compound (11.5 mg, 83%) as colourless solid after lyophilisation. LCMS (Method B): R$_T$=0.65, 0.67 min (2 diastereoisomers), m/z=466 [M+H]$^+$.
$^1$H NMR (500 MHz, DMSO-d$_6$): δ 7.46 (d, J=4.2 Hz, 0.5H), 7.45 (d, J=4.2 Hz, 0.5H), 7.36-7.24 (m, 4H), 7.22-7.16 (m, 1H), 7.15 (d, J=4.4 Hz, 1H), 4.72 (s, 0.5H), 4.71 (s, 0.5H), 4.54 (d, J=13.3 Hz, 0.5H), 4.48 (d, J=13.3 Hz, 0.5H), 4.31 (t, J=5.2 Hz, 0.5H), 4.26 (t, J=5.2 Hz, 0.5H), 3.60-3.48 (m, 2H), 3.36-2.86 (m, 7H (signals overlap with HDO)), 2.81-2.70 (m, 2H), 2.30 (s, 1.5H), 2.29 (s, 1.5H), 1.87-1.77 (m, 1H), 1.61-1.36 (m, 6H), 1.31-1.16 (m, 2H), 1.13-1.00 (m, 1H). NH not visible.

The following table contains Examples that were prepared using parallel synthesis according to General Procedure 11 or General Procedure 12, as indicated.

| Example (General Procedure) | Structure | Name | LCMS (Method C): R$_T$, m/z |
|---|---|---|---|
| 94 (11) | 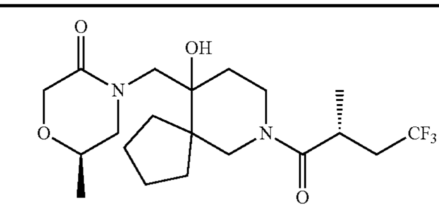 | (6R)-4-((10-Hydroxy-7-((R)-4,4,4-trifluoro-2-methylbutanoyl)-7-azaspiro[4.5]decan-10-yl)methyl)-6-methylmorpholin-3-one | 1.19 min, 421 [M + H]$^+$ |
| 95 (11) | 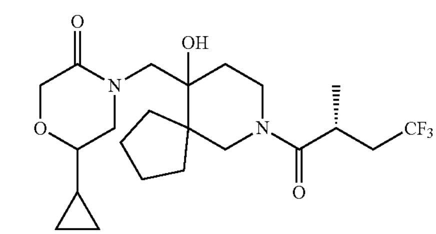 [SMILES: C[C@H](CC(F)(F)F)C(=O)N1CCC(O)(CN2CC(C3CC3)OCC2=O)C2(CCCC2)C1] | 6-Cyclopropyl-4-((10-hydroxy-7-((R)-4,4,4-trifluoro-2-methylbutanoyl)-7-azaspiro[4.5]decan-10-yl)methyl)morpholin-3-one | 1.27 min, 447 [M + H]$^+$ |
| 96 (11) | 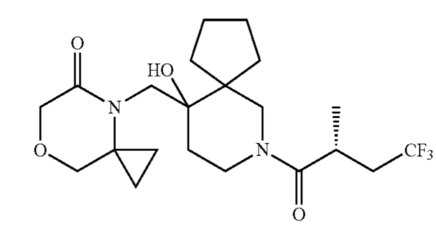 [SMILES: C[C@H](CC(F)(F)F)C(=O)N1CCC(O)(CN2C(=O)COCC23CC3)C2(CCCC2)C1] | 4-((10-Hydroxy-7-((R)-4,4,4-trifluoro-2-methylbutanoyl)-7-azaspiro[4.5]decan-10-yl)methyl)-7-oxa-4-azaspiro[2.5]octan-5-one | 1.31 min, 433 [M + H]$^+$ |
| 97 (11) | 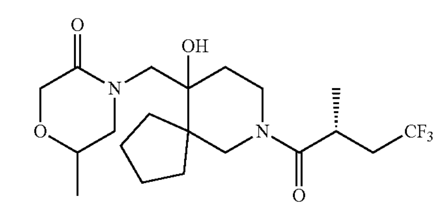 [SMILES: CC1CN(CC2(O)CCN(C(=O)[C@H](C)CC(F)(F)F)CC23CCCC3)C(=O)CO1] | 4-((10-Hydroxy-7-((R)-4,4,4-trifluoro-2-methylbutanoyl)-7-azaspiro[4.5]decan-10-yl)methyl)-6-methylmorpholin-3-one | 1.19 min, 421 [M + H]$^+$ |
| 98 (12) | 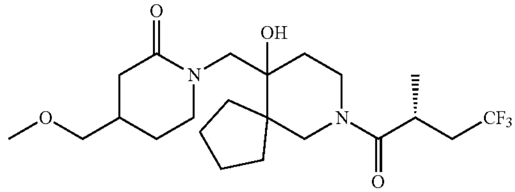 [SMILES: COCC1CCN(CC2(O)CCN(C(=O)[C@H](C)CC(F)(F)F)CC23CCCC3)C(=O)C1] | 1-((10-Hydroxy-7-((R)-4,4,4-trifluoro-2-methylbutanoyl)-7-azaspiro[4.5]decan-10-yl)methyl)-4-(methoxymethyl)piperidin-2-one | 1.24 min, 449 [M + H]$^+$ |

-continued

| Example (General Procedure) | Structure | Name | LCMS (Method C): $R_T$, m/z |
|---|---|---|---|
| 99 (12) | 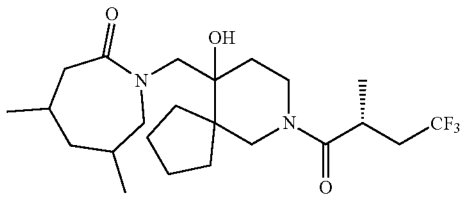 [SMILES: CC1CC(=O)N(CC2(O)CCN(C(=O)[C@H](C)CC(F)(F)F)CC23CCCC3)CC(C)C1] | 1-((10-Hydroxy-7-((R)-4,4,4-trifluoro-2-methylbutanoyl)-7-azaspiro[4.5]decan-10-yl)methyl)-4,6-dimethylazepan-2-one | 1.46 min, 447 [M + H]+ |
| 100 (12) | 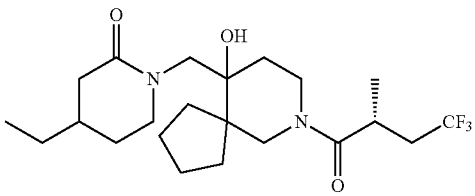 [SMILES: CCC1CCN(CC2(O)CCN(C(=O)[C@H](C)CC(F)(F)F)CC23CCCC3)C(=O)C1] | 4-Ethyl-1-((10-hydroxy-7-((R)-4,4,4-trifluoro-2-methylbutanoyl)-7-azaspiro[4.5]decan-10-yl)methyl)piperidin-2-one | 1.39 min, 433 [M + H]+ |
| 101 (12) | 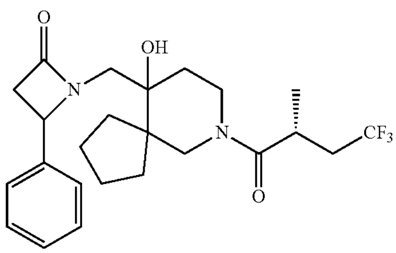 [SMILES: C[C@H](CC(F)(F)F)C(=O)N1CCC(O)(CN2C(=O)CC2c2ccccc2)C2(CCCC2)C1] | 1-((10-Hydroxy-7-((R)-4,4,4-trifluoro-2-methylbutanoyl)-7-azaspiro[4.5]decan-10-yl)methyl)-4-phenylazetidin-2-one | 1.41 min, 453 [M + H]+ |
| 102 (11) | 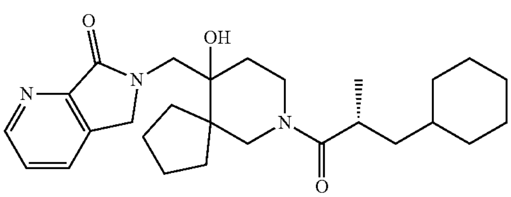 [SMILES: C[C@H](CC1CCCCC1)C(=O)N1CCC(O)(CN2Cc3cccnc3C2=O)C2(CCCC2)C1] | 6-((7-((R)-3-Cyclohexyl-2-methylpropanoyl)-10-hydroxy-7-azaspiro[4.5]decan-10-yl)methyl)-5,6-dihydro-7H-pyrrolo[3,4-b]pyridin-7-one | 1.48 min, 454 [M + H]+ |
| 103 (11) | 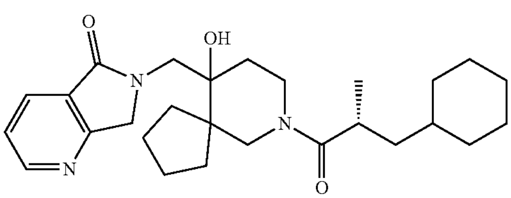 [SMILES: C[C@H](CC1CCCCC1)C(=O)N1CCC(O)(CN2Cc3ncccc3C2=O)C2(CCCC2)C1] | 6-((7-((R)-3-Cyclohexyl-2-methylpropanoyl)-10-hydroxy-7-azaspiro[4.5]decan-10-yl)methyl)-6,7-dihydro-5H-pyrrolo[3,4-b]pyridin-5-one | 1.48 min, 454 [M + H]+ |
| 104 (12) | 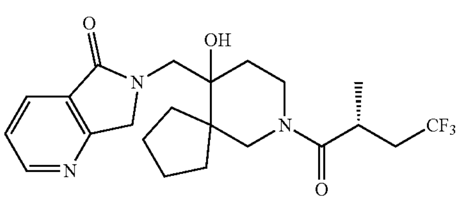 [SMILES: C[C@H](CC(F)(F)F)C(=O)N1CCC(O)(CN2Cc3ncccc3C2=O)C2(CCCC2)C1] | 6-((10-Hydroxy-7-((R)-4,4,4-trifluoro-2-methylbutanoyl)-7-azaspiro[4.5]decan-10-yl)methyl)-6,7-dihydro-5H-pyrrolo[3,4-b]pyridin-5-one | 1.26 min, 440 [M + H]+ |
| 105 (11) | 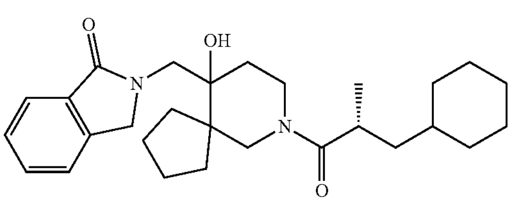 [SMILES: C[C@H](CC1CCCCC1)C(=O)N1CCC(O)(CN2Cc3ccccc3C2=O)C2(CCCC2)C1] | 2-((7-((R)-3-Cyclohexyl-2-methylpropanoyl)-10-hydroxy-7-azaspiro[4.5]decan-10-yl)methyl)isoindolin-1-one | 1.62 min, 453 [M + H]+ |

| Example (General Procedure) | Structure | Name | LCMS (Method C): $R_T$, m/z |
|---|---|---|---|
| 106 (12) | 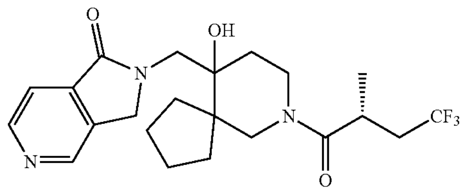 [SMILES: C[C@H](CC(F)(F)F)C(=O)N1CCC(O)(CN2Cc3cnccc3C2=O)C2(CCCC2)C1] | 2-((10-Hydroxy-7-((R)-4,4,4-trifluoro-2-methylbutanoyl)-7-azaspiro[4.5]decan-10-yl)methyl)-2,3-dihydro-1H-pyrrolo[3,4-c]pyridin-1-one | 1.19 min, 440 [M + H]+ |

Example 107: 10-((4-Benzoyl-2-oxopiperazin-1-yl)methyl)-N-benzyl-10-hydroxy-7-azaspiro[4.5]decane-7-carboxamide

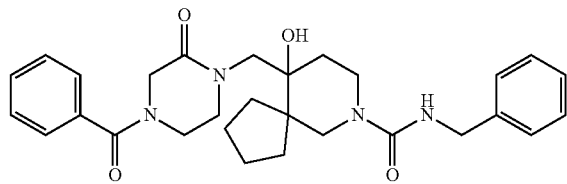 [SMILES: O=C1CN(C(=O)c2ccccc2)CCN1CC1(O)CCN(C(=O)NCc2ccccc2)CC12CCCC2]

Step 1: tert-Butyl 10-((4-benzyl-2-oxopiperazin-1-yl)methyl)-10-hydroxy-7-azaspiro[4.5]decane-7-carboxylate: Prepared according to General Procedure 2 using 4-benzylpiperazin-2-one (1.00 g, 5.3 mmol), Epoxide 2 (1.55 g, 5.8 mmol) and potassium tert-butoxide (0.65 g, 5.8 mmol) in DMSO (10 mL), heated to 75° C. for 3 days to give the title compound (1.55 g, 64%). LCMS (Method C): $R_T$=1.25 min, m/z=402 [M-butene+H]+.

Step 2: tert-Butyl 10-hydroxy-10-((2-oxopiperazin-1-yl)methyl)-7-azaspiro[4.5]decane-7-carboxylate: To a pre-degassed (backfilling with nitrogen) stirred solution of tert-butyl 10-((4-benzyl-2-oxopiperazin-1-yl)methyl)-10-hydroxy-7-azaspiro[4.5]decane-7-carboxylate (1.35 g, 2.95 mmol) in methanol (60 mL) was added 10% w/w Pd—C (0.13 g). The reaction mixture was evacuated and hydrogenated under atmospheric pressure. After 24 h, the reaction mixture was filtered over Celite®, the solvents were removed in vacuo and the remaining residue was purified by flash chromatography to give the title compound (0.30 g, 27%). LCMS (Method C): $R_T$=1.06 min, m/z=312 [M-butene+H]+.

Step 3: tert-Butyl 10-((4-benzoyl-2-oxopiperazin-1-yl)methyl)-10-hydroxy-7-azaspiro[4.5]decane-7-carboxylate: Prepared according to General procedure 4 using tert-butyl 10-hydroxy-10-((2-oxopiperazin-1-yl)methyl)-7-azaspiro[4.5]decane-7-carboxylate (30 mg, 0.0816 mmol), benzoic acid (10 mg, 0.0816 mmol), HATU (31 mg, 0.0816 mmol) and DIPEA (57 µL, 0.327 mmol) in DCM (1.6 mL) to give the title compound (31.8 mg, 82%) as colourless gum. LCMS (Method A): $R_T$=1.35 min, m/z=472 [M+H]+.

Step 4: 4-Benzoyl-1-((10-hydroxy-7-azaspiro[4.5]decan-10-yl)methyl)piperazin-2-one: A solution of tert-butyl 10-((4-benzoyl-2-oxopiperazin-1-yl)methyl)-10-hydroxy-7-azaspiro[4.5]decane-7-carboxylate (31.8 mg, 0.0674 mmol) in TFA (0.5 mL) and DCM (1 mL) was stirred for 10 min before the reaction mixture was loaded on to a 2 g SCX-2 cartridge that was pre-equilibrated with 1:1 DCM/MeOH. The cartridge was washed with DCM/MeOH (~50 mL) before the product was eluted with 1:1 DCM/7 M NH3 in MeOH (~30 mL). The basic eluents were concentrated under reduced pressure to give the title compound (28.3 mg, 113%) as colourless glass. This material was used without further purification. LCMS (Method A): $R_T$=0.38 min, m/z=372 [M+H]+.

Step 5: 10-((4-Benzoyl-2-oxopiperazin-1-yl)methyl)-N-benzyl-10-hydroxy-7-azaspiro[4.5]decane-7-carboxamide: A solution of 4-benzoyl-1-((10-hydroxy-7-azaspiro[4.5]decan-10-yl)methyl)piperazin-2-one (13.3 mg, 0.0358 mmol) and benzyl isocyanate (6.6 µL, 0.0537 mmol) in DCM (0.36 mL) was stirred at rt for 16 h before the reaction mixture was purified directly by flash chromatography (0%; then 2%; then 4%; then 6%; then 8% MeOH in DCM (isocratic)) to give the title compound (13.3 mg, 72%) as colourless solid after lyophilisation. LCMS (Method B): $R_T$=1.13 min, m/z=505 [M+H]+. 1H NMR (500 MHz, DMSO-d6): δ 7.56-7.38 (m, 5H), 7.32-7.25 (m, 2H), 7.25-7.14 (m, 3H), 6.94 (t, J=5.8 Hz, 1H), 4.52 (s, 1H), 4.28-3.95 (m, 5H), 3.91-3.35 (m, 6H), 3.22 (d, J=13.0 Hz, 1H), 3.08 (d, J=13.1 Hz, 1H), 2.94 (d, J=13.9 Hz, 1H), 1.84-1.76 (m, 1H), 1.64-1.50 (m, 4H), 1.50-1.35 (m, 3H), 1.35-1.28 (m, 1H), 1.17-1.08 (m, 1H).

Example 108: 4-Benzoyl-1-((10-hydroxy-7-((R)-4,4,4-trifluoro-2-methylbutanoyl)-7-azaspiro[4.5]decan-10-yl)methyl)piperazin-2-one

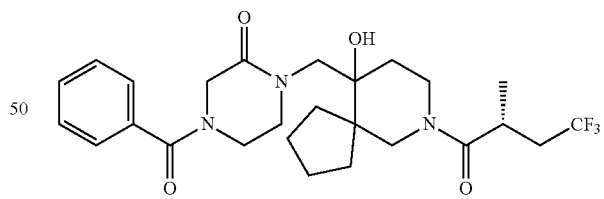

Prepared according to General procedure 4 using 4-benzoyl-1-((10-hydroxy-7-azaspiro[4.5]decan-10-yl)methyl)piperazin-2-one (15 mg, 0.0404 mmol), Acid 3 (6.3 mg, 0.0404 mmol), HATU (15.4 mg, 0.0404 mmol) and DIPEA (28 µL, 0.162 mmol) in DCM (0.81 mL) to give the title compound (18.2 mg, 81%) as a colourless solid after lyophilisation. LCMS (Method B): $R_T$=1.19 min, m/z=510 [M+H]+. 1H NMR (500 MHz, DMSO-d6): δ 7.65-7.35 (m, 5H), 4.70-4.60 (m, 1H), 4.30-3.83 (m, 4H), 3.81-3.71 (m, 1H), 3.70-3.54 (m, 2H), 3.50-3.38 (m, 2H), 3.21-3.02 (m, 2H), 2.93 (d, J=13.9 Hz, 1H), 2.79-2.65 (m, 1H), 2.31-2.17 (m, 1H), 1.92-1.77 (m, 1H), 1.69-1.00 (m, 13H).

Example 109: N-Benzyl-10-hydroxy-10-((2-oxo-4-phenylpiperazin-1-yl)methyl)-7-azaspiro[4.5]decane-7-carboxamide

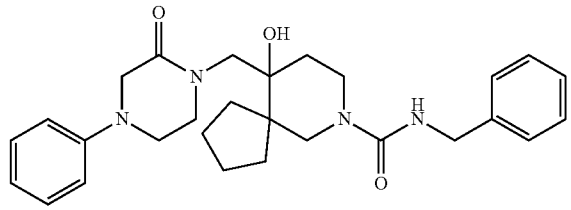 [SMILES: O=C1CN(c2ccccc2)CCN1CC1(O)CCN(C(=O)NCc2ccccc2)CC12CCCC2]

Step 1: tert-Butyl 10-hydroxy-10-((2-oxo-4-phenylpiperazin-1-yl)methyl)-7-azaspiro[4.5]decane-7-carboxylate: A 0.5-2 mL microwave vial was charged with $Pd_2(dba)_3$ (7.5 mg, 8.2 µmol), XPhos (7.8 mg, 16.3 µmol), tert-butyl 10-hydroxy-10-((2-oxopiperazin-1-yl)methyl)-7-azaspiro[4.5]decane-7-carboxylate (30 mg, 0.0816 mmol), $Cs_2CO_3$ (32 mg, 0.0980 mmol) and bromobenzene (15.4 mg, 0.0980 mmol) before the vial was capped and purged of $O_2$ by evacuating and refilling the vessel with $N_2$ three times via needles pierced through the septa; toluene (0.81 mL) was added and the vial was purged of $O_2$ through evacuating and refilling the vessel with $N_2$ three more times. The reaction was heated at 110° C. (oil bath) for 16 h. Upon cooling to rt, the reaction mixture was diluted with 1:1 water/saturated $NH_4Cl_{(aq)}$ (15 mL) and the resulting mixture was extracted with DCM (3×10 mL) using a phase separator. The combined organic phases were concentrated under reduced pressure and the residue was purified by flash chromatography (0-100% EtOAc in cyclohexane) to give the title compound (23.6 mg, 65%) as an off-white solid. LCMS (Method A): $R_T$=1.64 min, m/z=444 [M+H]$^+$.

Step 2: 1-((10-Hydroxy-7-azaspiro[4.5]decan-10-yl)methyl)-4-phenylpiperazin-2-one: A solution of tert-butyl 10-hydroxy-10-((2-oxo-4-phenylpiperazin-1-yl)methyl)-7-azaspiro[4.5]decane-7-carboxylate (23.6 mg, 0.0532 mmol) in TFA (0.5 mL) and DCM (1 mL) was stirred for 10 min before the reaction mixture was loaded on to a 2 g SCX-2 cartridge that was pre-equilibrated with 1:1 DCM/MeOH. The cartridge was washed with DCM/MeOH (~50 mL) before the product was eluted with 1:1 DCM/7 M $NH_3$ in MeOH (~30 mL). The basic eluents were concentrated under reduced pressure to give the title compound (21.4 mg, 117%) as an off-white solid. This material was used without further purification. LCMS (Method A): $R_T$=0.64 min, m/z=344 [M+H]$^+$.

Step 3: N-Benzyl-10-hydroxy-10-((2-oxo-4-phenylpiperazin-1-yl)methyl)-7-azaspiro[4.5]decane-7-carboxamide: A solution of 1-((10-hydroxy-7-azaspiro[4.5]decan-10-yl)methyl)-4-phenylpiperazin-2-one (11.1 mg, 0.0323 mmol) and benzyl isocyanate (6 µL, 0.0485 mmol) in DCM (0.33 mL) was stirred at rt for 16 h before the reaction mixture was purified directly by flash chromatography (0%; then 2%; then 4% MeOH in DCM (isocratic)) to give the title compound (12.5 mg, 78%) as a colourless solid after lyophilisation. LCMS (Method B): $R_T$=1.32 min, m/z=477 [M+H]$^+$. $^1$H NMR (500 MHz, DMSO-$d_6$): δ 7.29 (t, J=7.5 Hz, 2H), 7.26-7.11 (m, 5H), 6.97-6.88 (m, 3H), 6.78 (t, J=7.3 Hz, 1H), 4.58 (s, 1H), 4.23 (d, J=5.8 Hz, 2H), 4.11 (d, J=14.0 Hz, 1H), 3.89-3.80 (m, 2H), 3.78 (d, J=16.9 Hz, 1H), 3.55-3.38 (m, 4H), 3.36-3.30 (m, 1H), 3.24 (d, J=13.0 Hz, 1H), 3.09 (d, J=13.0 Hz, 1H), 3.00 (d, J=14.0 Hz, 1H), 1.85-1.78 (m, 1H), 1.65-1.54 (m, 4H), 1.52-1.41 (m, 2H), 1.40-1.28 (m, 2H), 1.18-1.10 (m, 1H).

Example 110: 1-((10-Hydroxy-7-((R)-4,4,4-trifluoro-2-methylbutanoyl)-7-azaspiro[4.5]decan-10-yl)methyl)-4-phenylpiperazin-2-one

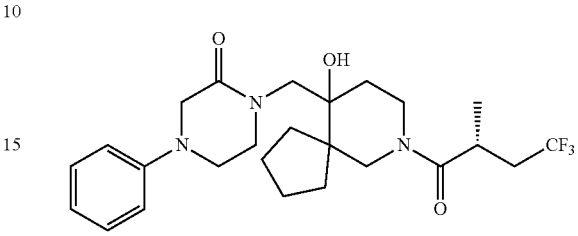

Prepared according to General procedure 4 using 1-((10-hydroxy-7-azaspiro[4.5]decan-10-yl)methyl)-4-phenylpiperazin-2-one (10.3 mg, 0.0300 mmol), Acid 3 (4.7 mg, 0.0300 mmol), HATU (11.4 mg, 0.0300 mmol) and DIPEA (21 µL, 0.120 mmol) in DCM (0.6 mL) to give the title compound (10.8 mg, 72%) as a colourless solid after lyophilisation. LCMS (Method B): $R_T$=1.41 min, m/z=482 [M+H]$^+$. $^1$H NMR (500 MHz, DMSO-$d_6$): δ 7.23 (t, J=7.7 Hz, 2H), 6.92 (d, J=8.2 Hz, 2H), 6.79 (t, J=7.3 Hz, 1H), 4.79-4.65 (m, 1H), 4.25-2.95 (m, 12H (signals overlap with HDO)), 2.78-2.67 (m, 1H), 2.31-2.19 (m, 1H), 1.94-1.78 (m, 1H), 1.73-1.03 (m, 13H).

Example 111: 10-((4-Acetyl-2-oxopiperazin-1-yl)methyl)-N-benzyl-10-hydroxy-7-azaspiro[4.5]decane-7-carboxamide

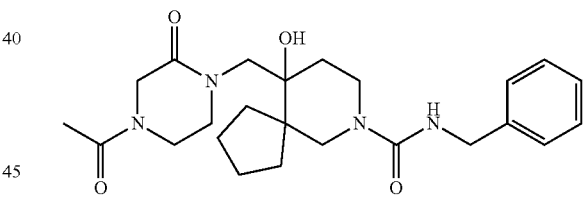

Step 1: tert-Butyl 10-((4-acetyl-2-oxopiperazin-1-yl)methyl)-10-hydroxy-7-azaspiro[4.5]decane-7-carboxylate: Acetic anhydride (39 µL, 0.408 mmol) was added to a solution of tert-butyl 10-hydroxy-10-((2-oxopiperazin-1-yl)methyl)-7-azaspiro[4.5]decane-7-carboxylate (30 mg, 0.0816 mmol) and triethylamine (0.114 mL, 0.816 mmol) in DCM (0.81 mL). After 15 min, the reaction mixture was diluted with saturated $NaHCO_{3(aq)}$ (7 mL) and the mixture extracted with DCM (3×5 mL) using a phase separator. The combined organic phases were concentrated under reduced pressure to give the title compound (33 mg, 98%) as a colourless gum. LCMS (Method A; 220 nm): $R_T$=1.06 min, m/z=410 [M+H]$^+$.

Step 2: 4-Acetyl-1-((10-hydroxy-7-azaspiro[4.5]decan-10-yl)methyl)piperazin-2-one: A solution of tert-butyl 10-((4-acetyl-2-oxopiperazin-1-yl)methyl)-10-hydroxy-7-azaspiro[4.5]decane-7-carboxylate (33 mg, 0.0806 mmol) in TFA (0.5 mL) and DCM (1 mL) was stirred for 15 min before the reaction mixture was loaded on to a 2 g SCX-2 cartridge that was pre-equilibrated with 1:1 DCM/MeOH.

The cartridge was washed with DCM/MeOH (~50 mL) before the product was eluted with 1:1 DCM/7 M NH₃ in MeOH (~30 mL). The basic eluents were concentrated under reduced pressure to give the title compound (21.7 mg, 87%) as an off-white foam. This material was used with further purification. LCMS (Method A; 220 nm): $R_T$=0.28 min, m/z=310 [M+H]⁺.

Step 3: 10-((4-Acetyl-2-oxopiperazin-1-yl)methyl)-N-benzyl-10-hydroxy-7-azaspiro[4.5]decane-7-carboxamide: A solution of 4-acetyl-1-((10-hydroxy-7-azaspiro[4.5]decan-10-yl)methyl)piperazin-2-one (11.2 mg, 0.0362 mmol) and benzyl isocyanate (6.7 μL, 0.0543 mmol) in DCM (0.36 mL) was stirred at rt for 45 min before benzyl isocyanate (3.4 μL, 0.0272 mmol) was added and the reaction was stirred for 2 h before the reaction mixture was purified directly by flash chromatography (0%; then 3%; then 6%; then 10% MeOH in DCM (isocratic)) to give the title compound (11.9 mg, 72%) as colourless solid after lyophilisation. LCMS (Method B): $R_T$=0.94 min, m/z=443 [M+H]⁺. ¹H NMR (500 MHz, DMSO-d₆): δ 7.36-7.26 (m, 2H), 7.27-7.11 (m, 3H), 6.94 (t, J=5.8 Hz, 1H), 4.51 (s, 0.4H), 4.50 (s, 0.6H), 4.28-4.17 (m, 2H), 4.18-3.86 (m, 3H), 3.81-3.30 (m, 6H), 3.22 (d, J=13.0 Hz, 1H), 3.08 (d, J=13.0 Hz, 1H), 2.93 (d, J=13.9 Hz, 1H), 2.03 (s, 1.8H), 2.00 (s, 1.2H), 1.85-1.76 (m, 1H), 1.65-1.26 (m, 8H), 1.18-1.07 (m, 1H).

Example 112: 4-Acetyl-1-((10-hydroxy-7-((R)-4,4,4-trifluoro-2-methylbutanoyl)-7-azaspiro[4.5]decan-10-yl)methyl)piperazin-2-one

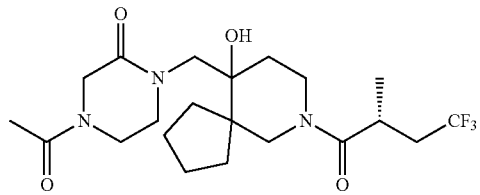 [SMILES: CC(=O)N1CCN(CC2(O)CCN(C(=O)[C@H](C)CC(F)(F)F)CC23CCCC3)C(=O)C1]

Prepared according to General procedure 4 using 4-acetyl-1-((10-hydroxy-7-azaspiro[4.5]decan-10-yl)methyl)piperazin-2-one (10.5 mg, 0.0339 mmol), Acid 3 (5.3 mg, 0.0339 mmol), HATU (12.9 mg, 0.0339 mmol) and DIPEA (23.7 μL, 0.136 mmol) in DCM (0.68 mL) to give the title compound (14.5 mg, 93%) as a colourless solid after lyophilisation. LCMS (Method B): $R_T$=0.99 min, m/z=448 [M+H]⁺. ¹H NMR (500 MHz, DMSO-d₆): δ 4.71-4.58 (m, 1H), 4.19-3.92 (m, 3H), 3.80-3.24 (m, 6H (signals overlap with HDO)), 3.21-3.01 (m, 2H), 2.98-2.86 (m, 1H), 2.80-2.65 (m, 1H), 2.32-2.17 (m, 1H), 2.03 (s, 1.7H), 2.00 (s, 1.3H), 1.92-1.76 (m, 1H), 1.71-1.03 (m, 13H).

Example 113: 1-((10-Hydroxy-7-((R)-4,4,4-trifluoro-2-methylbutanoyl)-7-azaspiro[4.5]decan-10-yl)methyl)-4-(pyridin-2-yl)piperazin-2-one

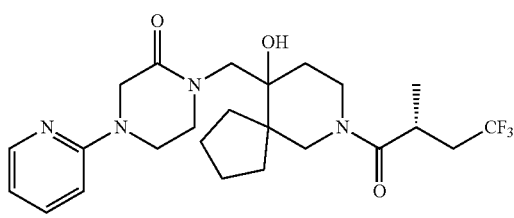 [SMILES: C[C@H](CC(F)(F)F)C(=O)N1CCC(O)(CN2CCN(c3ccccn3)CC2=O)C2(CCCC2)C1]

Step 1: tert-Butyl 10-hydroxy-10-((2-oxo-4-(pyridin-2-yl)piperazin-1-yl)methyl)-7-azaspiro[4.5]decane-7-carboxylate: A 0.5-2 mL microwave vial was charged with Pd₂(dba)₃ (7.5 mg, 8.2 μmol), XPhos (7.8 mg, 16.3 μmol), tert-butyl 10-hydroxy-10-((2-oxopiperazin-1-yl)methyl)-7-azaspiro[4.5]decane-7-carboxylate (30 mg, 0.0816 mmol), Cs₂CO₃ (32 mg, 0.0980 mmol) and 2-bromopyridine (15.5 mg, 0.0980 mmol) before the vial was capped and purged of O₂ by evacuating and refilling the vessel with N₂ three times via needles pierced through the septa; toluene (0.81 mL) was added and the vial was purged of O₂ through evacuating and refilling the vessel with N₂ three more times. The reaction was heated at 110° C. (oil bath) for 17 h before being heated under microwave irradiation at 140° C. for 15 min and subsequently at 160° C. for 2 h. Upon cooling to rt, the reaction mixture was diluted with 1:1 water/saturated NH₄Cl $_{(aq)}$ (15 mL) and the resulting mixture was extracted with DCM (3×10 mL) using a phase separator. The combined organic phases were concentrated under reduced pressure and the residue was purified by flash chromatography (0-100% EtOAc in cyclohexane) to give the title compound (3.8 mg, 10%) as a dark yellow film. LCMS (Method A): $R_T$=0.95 min, m/z=445 [M+H]⁺.

Step 2: 1-((10-Hydroxy-7-((R)-4,4,4-trifluoro-2-methylbutanoyl)-7-azaspiro[4.5]decan-10-yl)methyl)-4-(pyridin-2-yl)piperazin-2-one: A solution of tert-butyl 10-hydroxy-10-((2-oxo-4-(pyridin-2-yl)piperazin-1-yl)methyl)-7-azaspiro[4.5]decane-7-carboxylate (7 mg, 0.0157 mmol) and 4 M HCl in 1,4-dioxane (42 μL, 1.2 mmol) in DCM (0.3 mL) was stirred at rt for 24 h before the reaction mixture was concentrated under reduced pressure. To the residue was added Acid 3 (3.7 mg, 0.0236 mmol), HATU (9 mg, 0.0236 mmol) and DCM (0.3 mL) before DIPEA (11 μL, 0.0630 mmol) was added. After stirring for 2 h the reaction mixture was diluted with saturated NaHCO₃$_{(aq)}$ (15 mL) and the resulting mixture was extracted with DCM (3×10 mL) using a phase separator. The combined organic phases were concentrated under reduced pressure and the residue was purified by flash chromatography (Biotage KP-NH 11 g cartridge, 0-100% EtOAc in cyclohexane; then Buchi FlashPure silica 12 g cartridge, 0-100% EtOAc in cyclohexane, then 0-10% MeOH in EtOAc) to give the title compound (4.4 mg, 53%) as a colourless solid after lyophilisation. LCMS (Method A): $R_T$=0.79 min, m/z=483 [M+H]⁺. ¹H NMR (500 MHz, DMSO-d₆): δ 8.16-8.09 (m, 1H), 7.60-7.53 (m, 1H), 6.83-6.77 (m, 1H), 6.70-6.64 (m, 1H), 4.76-4.64 (m, 1H), 4.24-2.93 (m, 12H (signals overlap with HDO)), 2.81-2.65 (m, 1H), 2.31-2.19 (m, 1H), 1.94-1.76 (m, 1H), 1.72-1.25 (m, 9H), 1.18-1.03 (m, 4H).

Example 114: 1-((7-((R)-3-Cyclohexyl-2-methylpropanoyl)-10-hydroxy-7-azaspiro[4.5]decan-10-yl)methyl)-4-methylpiperazin-2-one

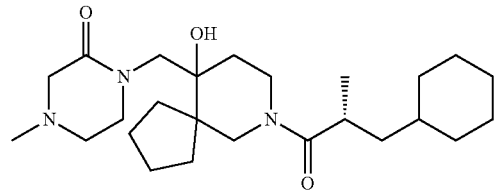 [SMILES: C[C@H](CC1CCCCC1)C(=O)N1CCC(O)(CN2CCN(C)CC2=O)C2(CCCC2)C1]

Step 1: tert-Butyl 10-hydroxy-10-((4-methyl-2-oxopiperazin-1-yl)methyl)-7-azaspiro[4.5]decane-7-carboxylate:

tert-Butyl 10-hydroxy-10-((2-oxopiperazin-1-yl)methyl)-7-azaspiro[4.5]decane-7-carboxylate (59 mg, 0.160 mmol) was dissolved in MeOH (3 mL) and 37% formaldehyde in water solution (64 µL, 0.319 mmol) was added followed by NaBH(OAc)$_3$ (169 mg, 0.798 mmol). The reaction mixture was stirred for 1 h at rt before the volatiles were evaporated under reduced pressure and the residue taken up in DCM and washed with 1 M NaOH$_{(aq)}$. The organic layer was separated and the aqueous phase was extracted using DCM (×2). The organic layers were combined, dried (phase separator) and evaporated under reduced pressure to give the title product (60 mg, 98%) as a clear glass. LCMS (Method A): R$_T$=0.77 min, m/z=382 [M+H]$^+$.

Step 2: 1-((10-Hydroxy-7-azaspiro[4.5]decan-10-yl)methyl)-4-methylpiperazin-2-one: Prepared according to General Procedure 3 using tert-butyl 10-hydroxy-10-((4-methyl-2-oxopiperazin-1-yl)methyl)-7-azaspiro[4.5]decane-7-carboxylate (52 mg, 0.137 mmol), DCM (2 mL) and TFA (1 mL), stirred at rt for 1 h to give the crude product. The material was purified by flash chromatography (0-10% MeOH in DCM; then 0-50% of a stock solution of 20% 7N NH$_3$/MeOH in DCM) to give the title compound (35 mg, 90%) as a clear glass. LCMS (Method A): R$_T$=0.28 min, m/z=282 [M+H]$^+$.

Step 3: 1-((7-((R)-3-Cyclohexyl-2-methylpropanoyl)-10-hydroxy-7-azaspiro[4.5]decan-10-yl)methyl)-4-methylpiperazin-2-one: Prepared according to General Procedure 4 using 1-((10-hydroxy-7-azaspiro[4.5]decan-10-yl)methyl)-4-methylpiperazin-2-one (11.5 mg, 0.041 mmol), Acid 1 (7.0 mg, 0.041 mmol), HATU (16 mg, 0.041 mmol) and DIPEA (29 µL, 0.164 mmol) in DCM (0.5 mL) to give the title compound (7 mg, 41%) as a white solid. LCMS (Method A): R$_T$=0.95 min, m/z=434 [M+H]$^+$. $^1$H NMR (500 MHz, DMSO-d$_6$): δ 4.80-4.62 (m, 1H), 4.10-3.96 (m, 1H), 3.94-3.78 (m, 0.5H), 3.75-3.55 (m, 2H), 3.52-3.32 (m, 2H), 3.26-3.14 (m, 2H), 3.13-2.77 (m, 4.5H), 2.61-2.53 (m, 2H), 2.21 (s, 3H), 1.90-1.74 (m, 1H), 1.69-1.03 (m, 19H), 0.98-0.90 (m, 3H), 0.88-0.77 (m, 2H).

Example 115: N-Benzyl-10-((4-(4,4-dimethylcyclohexyl)-2-oxopiperazin-1-yl)methyl)-10-hydroxy-7-azaspiro[4.5]decane-7-carboxamide

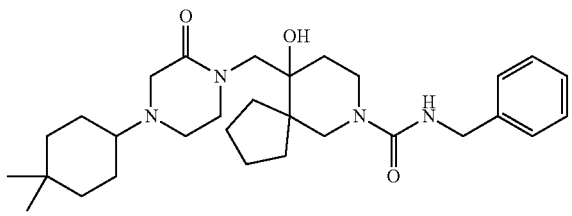 [SMILES: CC1(C)CCC(N2CCN(CC3(O)CCN(C(=O)NCc4ccccc4)CC34CCCC4)C(=O)C2)CC1]

Step 1: tert-Butyl 10-((4-(4,4-dimethylcyclohexyl)-2-oxopiperazin-1-yl)methyl)-10-hydroxy-7-azaspiro[4.5]decane-7-carboxylate: tert-Butyl 10-hydroxy-10-((2-oxopiperazin-1-yl)methyl)-7-azaspiro[4.5]decane-7-carboxylate (50 mg, 0.136 mmol) was dissolved in MeOH (3 mL) and 4,4-dimethylcyclohexan-1-one (36 µL, 0.951 mmol) was added followed by NaHB(OAc)$_3$ (144 mg, 0.680 mmol). The reaction mixture was stirred overnight at rt before the reaction mixture was loaded onto a pre-washed SCX-2 column and washed with 20% MeOH in DCM. The product was then eluted with 20% 7N NH$_3$ in MeOH/DCM and the product containing fractions were concentrated to afford the crude product. The material was further purified by flash chromatography (0-20% MeOH in DCM, then 0-10% of a stock solution of 20% 7N NH$_3$/MeOH in DCM) to give the title compound (29 mg, 45%) as a clear glass. LCMS (Method A): R$_T$=1.10 min, m/z=478 [M+H]$^+$.

Step 2: 4-(4,4-Dimethylcyclohexyl)-1-((10-hydroxy-7-azaspiro[4.5]decan-10-yl)methyl)piperazin-2-one: Prepared according to General Procedure 3 using tert-butyl 10-((4-(4,4-dimethylcyclohexyl)-2-oxopiperazin-1-yl)methyl)-10-hydroxy-7-azaspiro[4.5]decane-7-carboxylate (29 mg, 0.062 mmol), DCM (1 mL) and TFA (0.5 mL), stirred at rt for 1 h to give the crude title compound (25 mg, >100%) as a clear glass. LCMS (Method A): R$_T$=0.35 min, m/z=378 [M+H]$^+$.

Step 3: N-Benzyl-10-((4-(4,4-dimethylcyclohexyl)-2-oxopiperazin-1-yl)methyl)-10-hydroxy-7-azaspiro[4.5]decane-7-carboxamide: To a solution of 4-(4,4-dimethylcyclohexyl)-1-((10-hydroxy-7-azaspiro[4.5]decan-10-yl)methyl)piperazin-2-one (12 mg, 0.033 mmol) in DCM (0.5 mL) was added benzylisocyanate (4 mg, 0.033 mmol) and the reaction was stirred at rt for 1 h. The reaction mixture was directly purified by flash chromatography (Biotage KP-NH cartridge, 0-100% EtOAc in cyclohexane) to give the title compound (10 mg, 58%) as a white solid after lyophilisation. LCMS (Method A): R$_T$=1.31 min, m/z=511 [M+H]$^+$. $^1$H NMR (500 MHz, DMSO-d$_6$): δ 7.24-7.19 (m, 2H), 7.18-7.10 (m, 3H), 6.88-6.83 (m, 1H), 4.56 (s, 1H), 4.19-4.12 (m, 2H), 3.91-3.83 (m, 1H), 3.61-3.54 (m, 1H), 3.47-3.39 (m, 1H), 3.18-3.10 (m, 2H), 3.09-2.99 (m, 3H), 2.94-2.88 (m, 1H), 2.69-2.62 (m, 1H), 2.61-2.55 (m, 1H), 2.14-2.06 (m, 1H), 1.76-1.68 (m, 1H), 1.57-1.44 (m, 6H), 1.44-1.15 (m, 9H), 1.13-1.01 (m, 3H), 0.84-0.77 (m, 6H).

Example 116: 4-(4,4-Dimethylcyclohexyl)-1-((10-hydroxy-7-((R)-4,4,4-trifluoro-2-methylbutanoyl)-7-azaspiro[4.5]decan-10-yl)methyl)piperazin-2-one

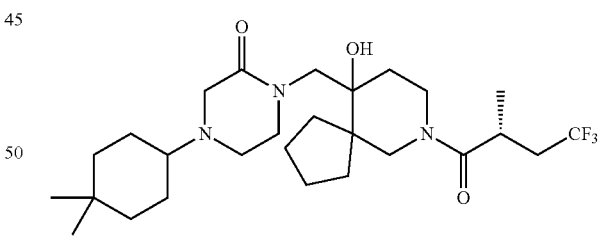

Prepared according to General Procedure 4 using 4-(4,4-dimethylcyclohexyl)-1-((10-hydroxy-7-azaspiro[4.5]decan-10-yl)methyl)piperazin-2-one (15 mg, 0.041 mmol), Acid 3 (6.4 mg, 0.041 mmol), HATU (16 mg, 0.041 mmol) and DIPEA (29 µL, 0.164 mmol) in DCM (0.5 mL) to give the title compound (10 mg, 47%). LCMS (Method A): R$_T$=1.09 min, m/z=516 [M+H]$^+$.

$^1$H NMR (500 MHz, DMSO-d$_6$): δ 4.85-4.69 (m, 1H), 4.10-3.90 (m, 1H), 3.84-3.56 (m, 2H), 3.55-3.31 (m, 2H), 3.27-3.02 (m, 4H), 3.00-2.92 (m, 1H), 2.79-2.61 (m, 3H), 2.32-2.12 (m, 2H), 1.91-1.74 (m, 1H), 1.69-1.03 (m, 21H), 0.92-0.84 (m, 6H).

Example 117: 4-((10-Hydroxy-7-((R)-3-phenylmorpholine-4-carbonyl)-7-azaspiro[4.5]decan-10-yl)methyl)morpholin-3-one

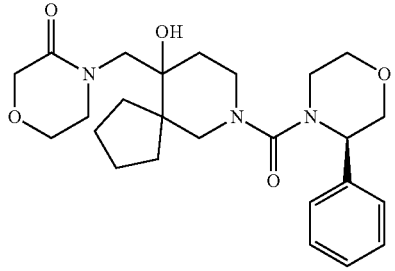 [SMILES: O=C1COCCN1CC1(O)CCN(C(=O)N2CCOC[C@H]2c2ccccc2)CC12CCCC2]

Prepared according to General Procedure 9 using 4-((10-hydroxy-7-azaspiro[4.5]decan-10-yl)methyl)morpholin-3-one (18 mg, 67.1 μmol), (R)-3-phenylmorpholine-4-carbonyl chloride (18.2 mg, 80.5 μmol) and DIPEA (46.9 μL, 0.268 mmol) in DCM (1.2 mL) to give the title compound (8.0 mg, 24%). LCMS (Method A): $R_T$=1.05 min, m/z=458 [M+H]$^+$. $^1$H NMR (500 MHz, DMSO-d$_6$): δ 7.31 (d, J=6.5 Hz, 4H), 7.23 (dt, J=8.6, 4.1 Hz, 1H), 4.62 (d, J=7.1 Hz, 1H), 4.38 (dt, J=13.8, 4.8 Hz, 1H), 4.14-3.99 (m, 3H), 3.87-3.64 (m, 7H), 3.60-3.38 (m, 2H), 3.33 (ddd, J=10.9, 7.8, 5.2 Hz, 1H), 3.21-3.07 (m, 2H), 3.06-2.85 (m, 3H), 1.77 (dq, J=13.9, 7.2 Hz, 1H), 1.61-1.37 (m, 7H), 1.23-1.13 (m, 1H), 1.03 (tt, J=13.6, 6.2 Hz, 1H).

Example 118: 4-((10-Hydroxy-7-((R)-2-phenylpiperazine-1-carbonyl)-7-azaspiro[4.5]decan-10-yl)methyl)morpholin-3-one

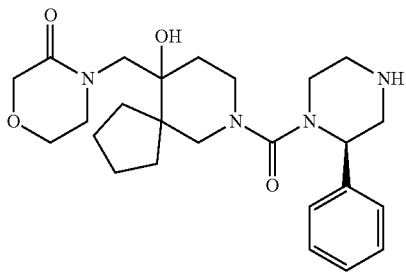 [SMILES: O=C1COCCN1CC1(O)CCN(C(=O)N2CCNC[C@H]2c2ccccc2)CC12CCCC2]

Step 1: tert-Butyl (3R)-4-(10-hydroxy-10-((3-oxomorpholino)methyl)-7-azaspiro[4.5]decane-7-carbonyl)-3-phenylpiperazine-1-carboxylate: Prepared according to General Procedure 9 using 4-((10-hydroxy-7-azaspiro[4.5]decan-10-yl)methyl)morpholin-3-one (30 mg, 0.112 mmol), tert-butyl (R)-4-(chlorocarbonyl)-3-phenylpiperazine-1-carboxylate (43.4 mg, 0.134 mmol), DIPEA (78.1 μL, 0.447 mmol) and DCM (2 mL), stirring at rt for 17 h to give the title compound (40 mg, 64%) as a colourless solid. LCMS (Method A): $R_T$=1.39 min, m/z=557 [M+H]$^+$; 501 [M-butene+H]$^+$.

Step 2: 4-((10-Hydroxy-7-((R)-2-phenylpiperazine-1-carbonyl)-7-azaspiro[4.5]decan-10-yl)methyl)morpholin-3-one: Prepared according to General Procedure 3 using tert-butyl (3R)-4-(10-hydroxy-10-((3-oxomorpholino)methyl)-7-azaspiro[4.5]decane-7-carbonyl)-3-phenylpiperazine-1-carboxylate carboxylate (40 mg, 71.9 μmol), TFA (1 mL) and DCM (2 mL), stirred at rt for 40 min to give the title compound (23.4 mg, 67%). LCMS (Method B): $R_T$=0.65 min, m/z=457 [M+H]$^+$. $^1$H NMR (500 MHz, DMSO-d$_6$): δ 7.31-7.24 (m, 4H), 7.18 (tt, J=5.6, 2.9 Hz, 1H), 4.60 (d, J=4.3 Hz, 1H), 4.28 (dt, J=14.7, 5.3 Hz, 1H), 4.13-3.99 (m, 3H), 3.86-3.70 (m, 3H), 3.57-3.44 (m, 1H), 3.44-3.24 (m, 2H (signal obscured by HDO)), 3.14 (dd, J=26.5, 12.8 Hz, 1H), 3.01 (dt, J=9.2, 5.9 Hz, 2H), 2.97-2.82 (m, 4H), 2.82-2.71 (m, 2H), 2.52 (s, 1H (signal obscured by DMSO)), 1.75 (dt, J=13.2, 6.6 Hz, 1H), 1.46 (dddd, J=25.1, 19.1, 13.0, 6.9 Hz, 7H), 1.27-1.11 (m, 1H), 1.03 (ddt, J=20.4, 13.2, 6.0 Hz, 1H).

Example 119: 7-((10-Hydroxy-7-((R)-2-phenylpiperazine-1-carbonyl)-7-azaspiro[4.5]decan-10-yl)methyl)-7,8-dihydroimidazo[1,2-a]pyrazin-6(5H)-one

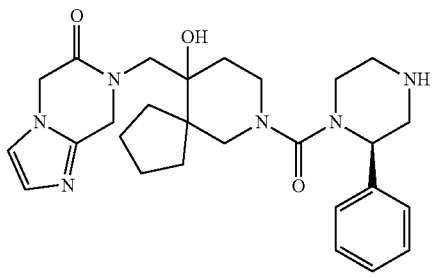 [SMILES: O=C1Cn2ccnc2CN1CC1(O)CCN(C(=O)N2CCNC[C@H]2c2ccccc2)CC12CCCC2]

Step 1: tert-Butyl 10-hydroxy-10-((6-oxo-5,6-dihydroimidazo[1,2-a]pyrazin-7(8H)-yl)methyl)-7-azaspiro[4.5]decane-7-carboxylate: Prepared according to General Procedure 2 using 7,8-dihydroimidazo[1,2-a]pyrazin-6(5H)-one (0.100 g, 0.7 mmol) [commercially available], Epoxide 2 (0.21 g, 0.8 mmol) and potassium tert-butoxide (0.09 g, 0.8 mmol) in DMSO (1 mL), heated to 75° C. for 3 days to give the title compound (0.045 g, 15%). LCMS (Method C): $R_T$=1.05 min, m/z=405 [M+H]$^+$.

Step 2: 7-((10-Hydroxy-7-azaspiro[4.5]decan-10-yl)methyl)-7,8-dihydroimidazo[1,2-a]pyrazin-6(5H)-one: Prepared according to General Procedure 3 using tert-butyl 10-hydroxy-10-((6-oxo-5,6-dihydroimidazo[1,2-a]pyrazin-7(8H)-yl)methyl)-7-azaspiro[4.5]decane-7-carboxylate (30 mg, 74.2 μmol), TFA (0.5 mL) and DCM (1 mL), stirred at rt for 1.5 h to give the title compound (20 mg, 88%). LCMS (Method B): $R_T$=0.19 min, m/z=305 [M+H]$^+$.

Step 3: tert-Butyl (3R)-4-(10-hydroxy-10-((6-oxo-5,6-dihydroimidazo[1,2-a]pyrazin-7(8H)-yl)methyl)-7-azaspiro[4.5]decane-7-carbonyl)-3-phenylpiperazine-1-carboxylate: Prepared according to General Procedure 9 using 7-((10-hydroxy-7-azaspiro[4.5]decan-10-yl)methyl)-7,8-dihydroimidazo[1,2-a]pyrazin-6(5H)-one (10 mg, 32.9 μmol), tert-butyl (R)-4-(chlorocarbonyl)-3-phenylpiperazine-1-carboxylate (12.8 mg, 39.4 μmol), DIPEA (23 μL, 0.131 mmol) and DCM (1 mL), stirring at rt for 2 h to give the title compound (15 mg, 77%). LCMS (Method B): $R_T$=0.97 min, m/z=593 [M+H]$^+$; 537 [M-butene+H]$^+$.

Step 4: 7-((10-Hydroxy-7-((R)-2-phenylpiperazine-1-carbonyl)-7-azaspiro[4.5]decan-10-yl)methyl)-7,8-dihydroimidazo[1,2-a]pyrazin-6(5H)-one: Prepared according to General Procedure 3 using tert-butyl (3R)-4-(10-hydroxy-10-((6-oxo-5,6-dihydroimidazo[1,2-a]pyrazin-7(8H)-yl) methyl)-7-azaspiro[4.5]decane-7-carbonyl)-3-phenylpiperazine-1-carboxylate (15 mg, 25.3 μmol), TFA (0.5 mL) and DCM (1 mL), stirred at rt for 1.5 h. The crude material was purified by flash chromatography and freeze-dried to give the title compound (11.9 mg, 93%) as a colourless solid. LCMS (Method B): R$_T$=0.46 min, m/z=493 [M+H]$^+$. $^1$H NMR (500 MHz, DMSO-d$_6$): δ 7.31-7.24 (m, 4H), 7.18 (ddt, J=8.2, 5.7, 3.2 Hz, 1H), 7.09 (d, J=1.2 Hz, 1H), 6.94 (d, J=1.2 Hz, 1H), 4.97 (dd, J=16.2, 10.0 Hz, 1H), 4.76 (dd, J=17.4, 5.8 Hz, 1H), 4.70-4.52 (m, 3H), 4.32-4.17 (m, 2H), 3.52 (d, J=14.3 Hz, 1H), 3.36 (s, 1H), 3.27-3.09 (m, 1H), 3.07-2.84 (m, 6H), 2.76 (td, J=8.6, 7.5, 3.9 Hz, 2H), 1.78 (dd, J=14.5, 8.1 Hz, 1H), 1.68-0.97 (m, 9H). NH signal not observed.

The following table of Examples was prepared using parallel synthesis according to General Procedure 11.

| Example | Structure | Name | LCMS (Method C): R$_T$, m/z |
|---|---|---|---|
| 120 | 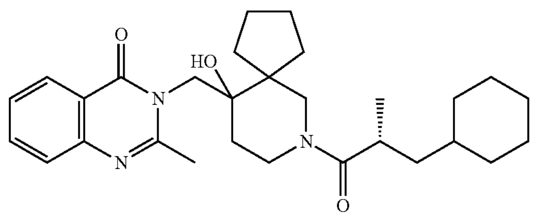 [SMILES: Cc1nc2ccccc2c(=O)n1CC1(O)CCN(C(=O)[C@H](C)CC2CCCCC2)CC12CCCC2] | 3-((7-((R)-3-Cyclohexyl-2-methylpropanoyl)-10-hydroxy-7-azaspiro[4.5]decan-10-yl)methyl)-2-methylquinazolin-4(3H)-one | 1.66 min, 480 [M + H]$^+$ |
| 121 | 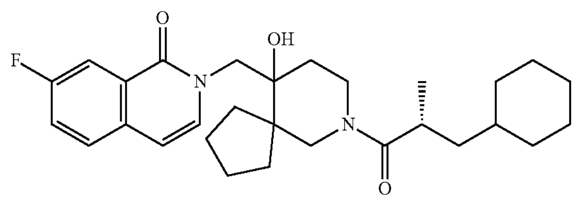 [SMILES: C[C@H](CC1CCCCC1)C(=O)N1CCC(O)(Cn2ccc3ccc(F)cc3c2=O)C2(CCCC2)C1] | 2-((7-((R)-3-Cyclohexyl-2-methylpropanoyl)-10-hydroxy-7-azaspiro[4.5]decan-10-yl)methyl)-7-fluoroisoquinolin-1(2H)-one | 1.74 min, 483 [M + H]$^+$ |
| 122 | 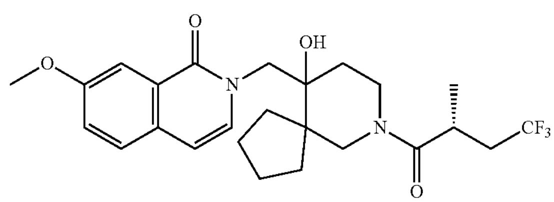 [SMILES: COc1ccc2ccn(CC3(O)CCN(C(=O)[C@H](C)CC(F)(F)F)CC34CCCC4)c(=O)c2c1] | 2-((10-Hydroxy-7-((R)-4,4,4-trifluoro-2-methylbutanoyl)-7-azaspiro[4.5]decan-10-yl)methyl)-7-methoxyisoquinolin-1(2H)-one | 1.53 min, 481 [M + H]$^+$ |
| 123 | 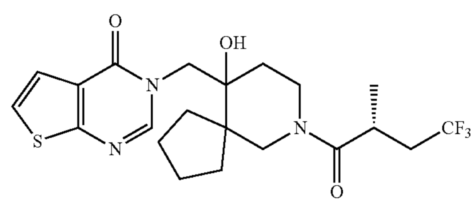 [SMILES: C[C@H](CC(F)(F)F)C(=O)N1CCC(O)(Cn2cnc3sccc3c2=O)C2(CCCC2)C1] | 3-((10-Hydroxy-7-((R)-4,4,4-trifluoro-2-methylbutanoyl)-7-azaspiro[4.5]decan-10-yl)methyl)thieno[2,3-d]pyrimidin-4(3H)-one | 1.36 min, 458 [M + H]$^+$ |
| 124 | 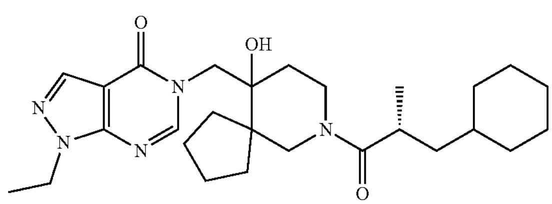 [SMILES: CCn1ncc2c(=O)n(CC3(O)CCN(C(=O)[C@H](C)CC4CCCCC4)CC34CCCC4)cnc21] | 5-((7-((R)-3-Cyclohexyl-2-methylpropanoyl)-10-hydroxy-7-azaspiro[4.5]decan-10-yl)methyl)-1-ethyl-1,5-dihydro-4H-pyrazolo[3,4-d]pyrimidin-4-one | 1.55 min, 484 [M + H]$^+$ |
| 125 | 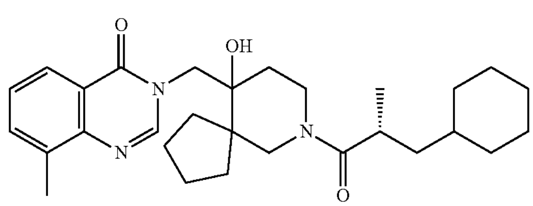 [SMILES: Cc1cccc2c(=O)n(CC3(O)CCN(C(=O)[C@H](C)CC4CCCCC4)CC34CCCC4)cnc12] | 3-((7-((R)-3-Cyclohexyl-2-methylpropanoyl)-10-hydroxy-7-azaspiro[4.5]decan-10-yl)methyl)-8-methylquinazolin-4(3H)-one | 1.67 min, 480 [M + H]$^+$ |

-continued

| Example | Structure | Name | LCMS (Method C): $R_T$, m/z |
|---|---|---|---|
| 126 | 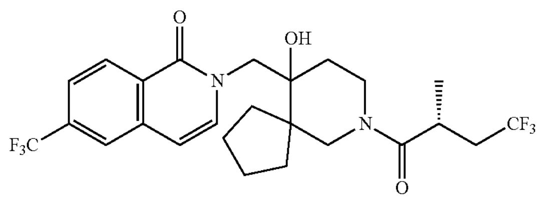 [SMILES: C[C@H](CC(F)(F)F)C(=O)N1CCC(O)(Cn2ccc3cc(C(F)(F)F)ccc3c2=O)C2(CCCC2)C1] | 2-((10-Hydroxy-7-((R)-4,4,4-trifluoro-2-methylbutanoyl)-7-azaspiro[4.5]decan-10-yl)methyl)-6-(trifluoromethyl)isoquinolin-1(2H)-one | 1.58 min, 519 [M + H]+ |
| 127 | 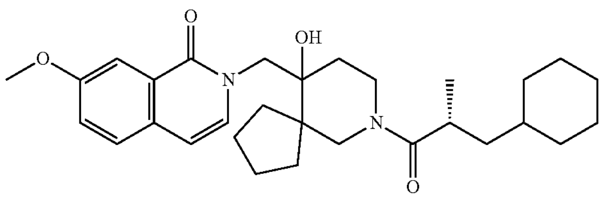 [SMILES: COc1ccc2ccn(CC3(O)CCN(C(=O)[C@H](C)CC4CCCCC4)CC34CCCC4)c(=O)c2c1] | 2-((7-((R)-3-Cyclohexyl-2-methylpropanoyl)-10-hydroxy-7-azaspiro[4.5]decan-10-yl)methyl)-7-methoxyisoquinolin-1(2H)-one | 1.70 min, 495 [M + H]+ |
| 128 | 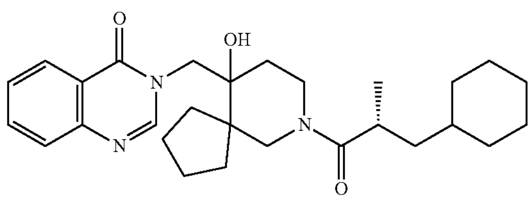 [SMILES: C[C@H](CC1CCCCC1)C(=O)N1CCC(O)(Cn2cnc3ccccc3c2=O)C2(CCCC2)C1] | 3-((7-((R)-3-Cyclohexyl-2-methylpropanoyl)-10-hydroxy-7-azaspiro[4.5]decan-10-yl)methyl)quinazolin-4(3H)-one | 1.59 min, 466 [M + H]+ |
| 129 | 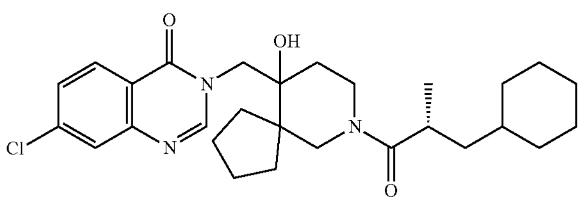 [SMILES: C[C@H](CC1CCCCC1)C(=O)N1CCC(O)(Cn2cnc3cc(Cl)ccc3c2=O)C2(CCCC2)C1] | 7-Chloro-3-((7-((R)-3-cyclohexyl-2-methylpropanoyl)-10-hydroxy-7-azaspiro[4.5]decan-10-yl)methyl)quinazolin-4(3H)-one | 1.71 min, 500 [M + H]+ |
| 130 | 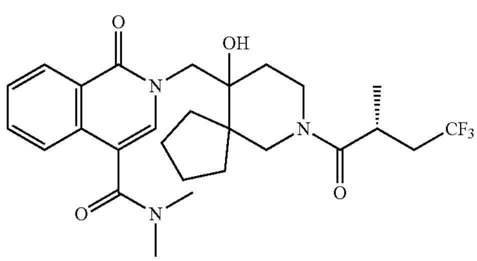 [SMILES: C[C@H](CC(F)(F)F)C(=O)N1CCC(O)(Cn2cc(C(=O)N(C)C)c3ccccc3c2=O)C2(CCCC2)C1] | 2-((10-Hydroxy-7-((R)-4,4,4-trifluoro-2-methylbutanoyl)-7-azaspiro[4.5]decan-10-yl)methyl)-N,N-dimethyl-1-oxo-1,2-dihydroisoquinoline-4-carboxamide | 1.37 min, 522 [M + H]+ |
| 131 | 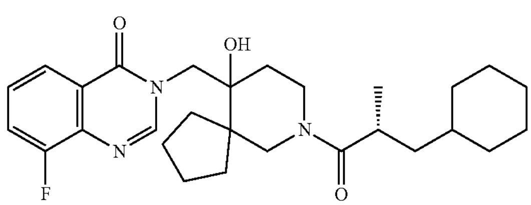 | 3-((7-((R)-3-Cyclohexyl-2-methylpropanoyl)-10-hydroxy-7-azaspiro[4.5]decan-10-yl)methyl)-8-fluoroquinazolin-4(3H)-one | 1.63 min, 484 [M + H]+ |
| 132 | 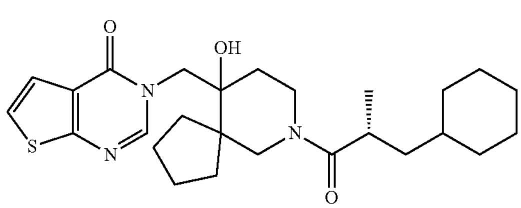 | 3-((7-((R)-3-Cyclohexyl-2-methylpropanoyl)-10-hydroxy-7-azaspiro[4.5]decan-10-yl)methyl)thieno[2,3-d]pyrimidin-4(3H)-one | 1.59 min, 472 [M + H]+ |

-continued

| Example | Structure | Name | LCMS (Method C): $R_T$, m/z |
|---|---|---|---|
| 133 | 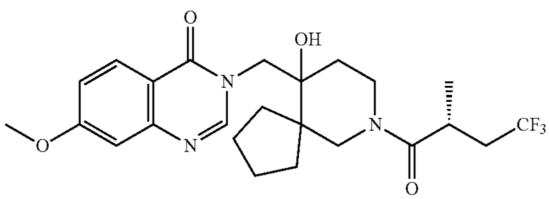 [SMILES: COc1ccc2c(=O)n(CC3(O)CCN(C(=O)[C@H](C)CC(F)(F)F)CC34CCCC4)cnc2c1] | 3-((10-Hydroxy-7-((R)-4,4,4-trifluoro-2-methylbutanoyl)-7-azaspiro[4.5]decan-10-yl)methyl)-7-methoxyquinazolin-4(3H)-one | 1.39 min, 482 [M + H]⁺ |
| 134 | 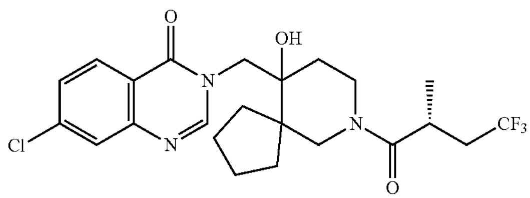 [SMILES: C[C@H](CC(F)(F)F)C(=O)N1CCC(O)(Cn2cnc3cc(Cl)ccc3c2=O)C2(CCCC2)C1] | 7-Chloro-3-((10-hydroxy-7-((R)-4,4,4-trifluoro-2-methylbutanoyl)-7-azaspiro[4.5]decan-10-yl)methyl)quinazolin-4(3H)-one | 1.47 min, 486 [M + H]⁺ |
| 135 | 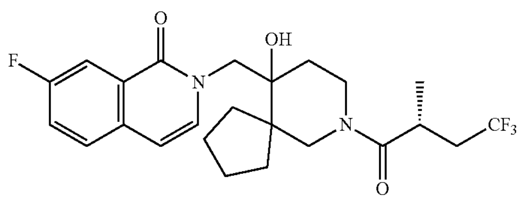 [SMILES: C[C@H](CC(F)(F)F)C(=O)N1CCC(O)(Cn2ccc3ccc(F)cc3c2=O)C2(CCCC2)C1] | 7-Fluoro-2-((10-hydroxy-7-((R)-4,4,4-trifluoro-2-methylbutanoyl)-7-azaspiro[4.5]decan-10-yl)methyl)isoquinolin-1(2H)-one | 1.53 min, 469 [M + H]⁺ |
| 136 | 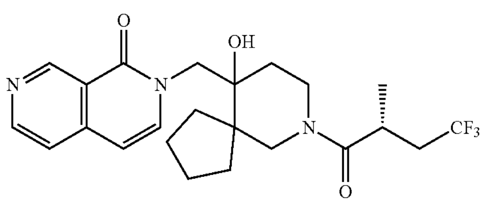 [SMILES: C[C@H](CC(F)(F)F)C(=O)N1CCC(O)(Cn2ccc3ccncc3c2=O)C2(CCCC2)C1] | 2-((10-Hydroxy-7-((R)-4,4,4-trifluoro-2-methylbutanoyl)-7-azaspiro[4.5]decan-10-yl)methyl)-2,7-naphthyridin-1(2H)-one | 1.19 min, 452 [M + H]⁺ |
| 137 | 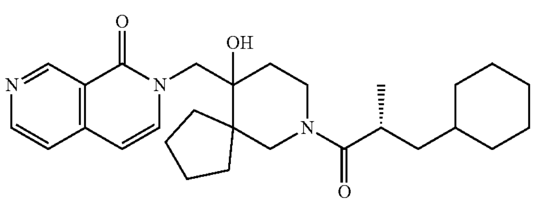 [SMILES: C[C@H](CC1CCCCC1)C(=O)N1CCC(O)(Cn2ccc3ccncc3c2=O)C2(CCCC2)C1] | 2-((7-((R)-3-Cyclohexyl-2-methylpropanoyl)-10-hydroxy-7-azaspiro[4.5]decan-10-yl)methyl)-2,7-naphthyridin-1(2H)-one | 1.47 min, 466 [M + H]⁺ |
| 138 | 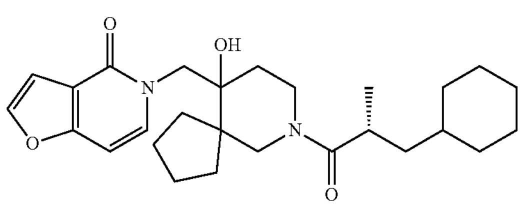 | 5-((7-((R)-3-Cyclohexyl-2-methylpropanoyl)-10-hydroxy-7-azaspiro[4.5]decan-10-yl)methyl)furo[3,2-c]pyridin-4(5H)-one | 1.60 min, 455 [M + H]⁺ |
| 139 | 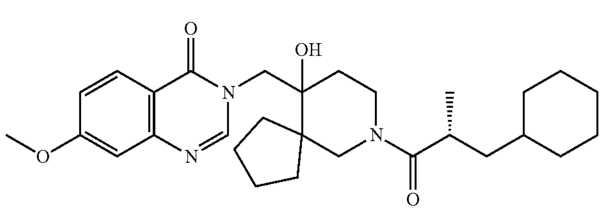 [SMILES: COc1ccc2c(=O)n(CC3(O)CCN(C(=O)[C@H](C)CC4CCCCC4)CC34CCCC4)cnc2c1] | 3-((7-((R)-3-Cyclohexyl-2-methylpropanoyl)-10-hydroxy-7-azaspiro[4.5]decan-10-yl)methyl)-7-methoxyquinazolin-4(3H)-one | 1.64 min, 496 [M + H]⁺ |

| Example | Structure | Name | LCMS (Method C): R$_T$, m/z |
|---|---|---|---|
| 140 | 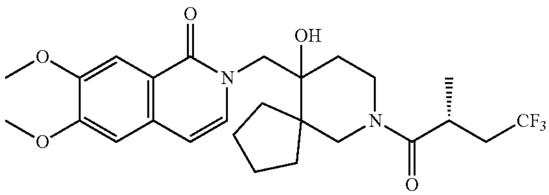 [SMILES: COc1cc2ccn(CC3(O)CCN(C(=O)[C@H](C)CC(F)(F)F)CC34CCCC4)c(=O)c2cc1OC] | 2-((10-Hydroxy-7-((R)-4,4,4-trifluoro-2-methylbutanoyl)-7-azaspiro[4.5]decan-10-yl)methyl)-6,7-dimethoxyisoquinolin-1(2H)-one | 1.44 min, 511 [M + H]$^+$ |
| 141 | 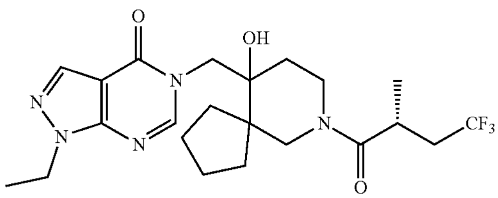 [SMILES: CCn1ncc2c(=O)n(CC3(O)CCN(C(=O)[C@H](C)CC(F)(F)F)CC34CCCC4)cnc21] | 1-Ethyl-5-((10-hydroxy-7-((R)-4,4,4-trifluoro-2-methylbutanoyl)-7-azaspiro[4.5]decan-10-yl)methyl)-1,5-dihydro-4H-pyrazolo[3,4-d]pyrimidin-4-one | 1.33 min, 470 [M + H]$^+$ |
| 142 | 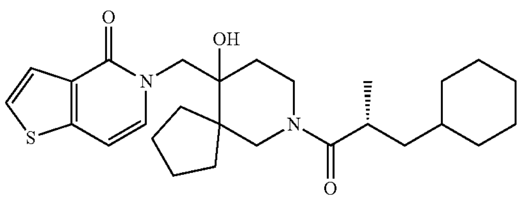 [SMILES: C[C@H](CC1CCCCC1)C(=O)N1CCC(O)(Cn2ccc3sccc3c2=O)C2(CCCC2)C1] | 5-((7-((R)-3-Cyclohexyl-2-methylpropanoyl)-10-hydroxy-7-azaspiro[4.5]decan-10-yl)methyl)thieno[3,2-c]pyridin-4(5H)-one | 1.64 min, 471 [M + H]$^+$ |
| 143 | 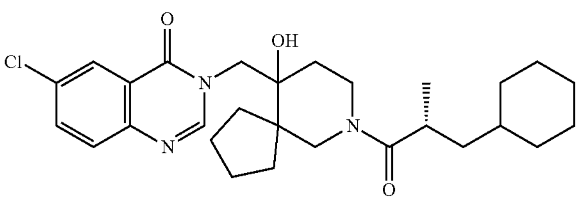 [SMILES: C[C@H](CC1CCCCC1)C(=O)N1CCC(O)(Cn2cnc3ccc(Cl)cc3c2=O)C2(CCCC2)C1] | 6-Chloro-3-((7-((R)-3-cyclohexyl-2-methylpropanoyl)-10-hydroxy-7-azaspiro[4.5]decan-10-yl)methyl)quinazolin-4(3H)-one | 1.73 min, 500 [M + H]$^+$ |
| 144 | 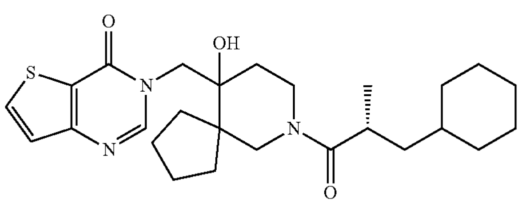 [SMILES: C[C@H](CC1CCCCC1)C(=O)N1CCC(O)(Cn2cnc3ccsc3c2=O)C2(CCCC2)C1] | 3-((7-((R)-3-Cyclohexyl-2-methylpropanoyl)-10-hydroxy-7-azaspiro[4.5]decan-10-yl)methyl)thieno[3,2-d]pyrimidin-4(3H)-one | 1.60 min, 472 [M + H]$^+$ |
| 145 | 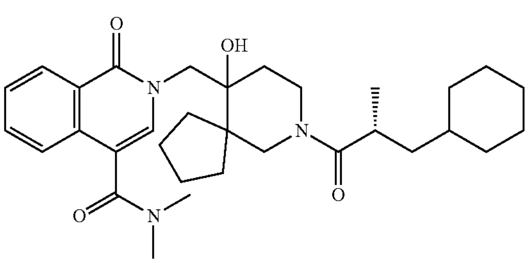 [SMILES: C[C@H](CC1CCCCC1)C(=O)N1CCC(O)(Cn2cc(C(=O)N(C)C)c3ccccc3c2=O)C2(CCCC2)C1] | 2-((7-((R)-3-Cyclohexyl-2-methylpropanoyl)-10-hydroxy-7-azaspiro[4.5]decan-10-yl)methyl)-N,N-dimethyl-1-oxo-1,2-dihydroisoquinoline-4-carboxamide | 1.59 min, 536 [M + H]$^+$ |
| 146 | 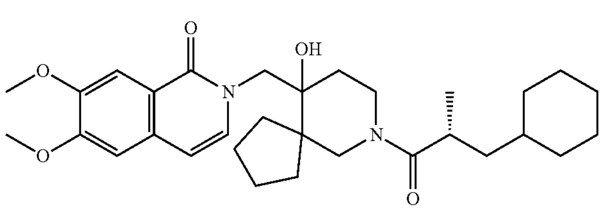 [SMILES: COc1cc2ccn(CC3(O)CCN(C(=O)[C@H](C)CC4CCCCC4)CC34CCCC4)c(=O)c2cc1OC] | 2-((7-((R)-3-Cyclohexyl-2-methylpropanoyl)-10-hydroxy-7-azaspiro[4.5]decan-10-yl)methyl)-6,7-dimethoxyisoquinolin-1(2H)-one | 1.68 min, 525 [M + H]$^+$ |

-continued

| Example | Structure | Name | LCMS (Method C): R_T, m/z |
|---|---|---|---|
| 147 | 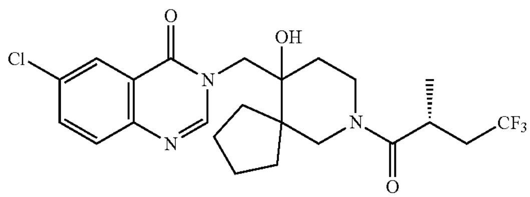 [SMILES: C[C@H](CC(F)(F)F)C(=O)N1CCC(O)(Cn2cnc3ccc(Cl)cc3c2=O)C2(CCCC2)C1] | 6-Chloro-3-((10-hydroxy-7-((R)-4,4,4-trifluoro-2-methylbutanoyl)-7-azaspiro[4.5]decan-10-yl)methyl)quinazolin-4(3H)-one | 1.49 min, 486 [M + H]+ |
| 148 | 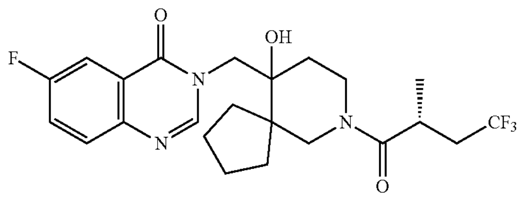 [SMILES: C[C@H](CC(F)(F)F)C(=O)N1CCC(O)(Cn2cnc3ccc(F)cc3c2=O)C2(CCCC2)C1] | 6-Fluoro-3-((10-hydroxy-7-((R)-4,4,4-trifluoro-2-methylbutanoyl)-7-azaspiro[4.5]decan-10-yl)methyl)quinazolin-4(3H)-one | 1.35 min, 470 [M + H]+ |
| 149 | 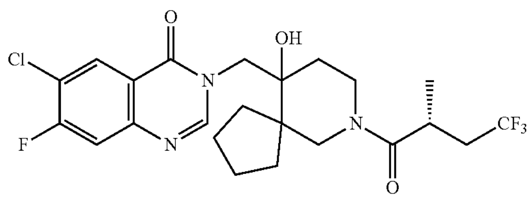 [SMILES: C[C@H](CC(F)(F)F)C(=O)N1CCC(O)(Cn2cnc3cc(F)c(Cl)cc3c2=O)C2(CCCC2)C1] | 6-Chloro-7-fluoro-3-((10-hydroxy-7-((R)-4,4,4-trifluoro-2-methylbutanoyl)-7-azaspiro[4.5]decan-10-yl)methyl)quinazolin-4(3H)-one | 1.50 min, 504 [M + H]+ |
| 150 | 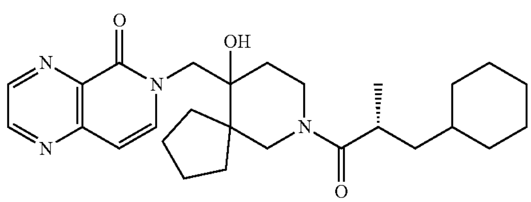 [SMILES: C[C@H](CC1CCCCC1)C(=O)N1CCC(O)(Cn2ccc3nccnc3c2=O)C2(CCCC2)C1] | 6-((7-((R)-3-Cyclohexyl-2-methylpropanoyl)-10-hydroxy-7-azaspiro[4.5]decan-10-yl)methyl)pyrido[3,4-b]pyrazin-5(6H)-one | 1.38 min, 467 [M + H]+ |
| 151 | 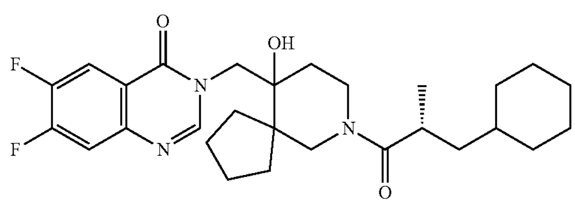 [SMILES: C[C@H](CC1CCCCC1)C(=O)N1CCC(O)(Cn2cnc3cc(F)c(F)cc3c2=O)C2(CCCC2)C1] | 3-((7-((R)-3-Cyclohexyl-2-methylpropanoyl)-10-hydroxy-7-azaspiro[4.5]decan-10-yl)methyl)-6,7-difluoroquinazolin-4(3H)-one | 1.69 min, 502 [M + H]+ |
| 152 | 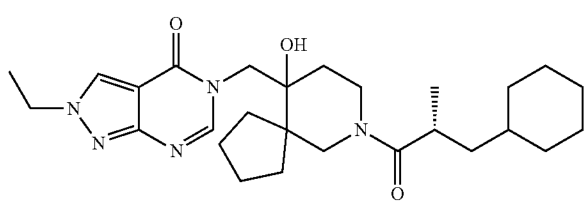 [SMILES: CCn1cc2c(=O)n(CC3(O)CCN(C(=O)[C@H](C)CC4CCCCC4)CC34CCCC4)cnc2n1] | 5-((7-((R)-3-Cyclohexyl-2-methylpropanoyl)-10-hydroxy-7-azaspiro[4.5]decan-10-yl)methyl)-2-ethyl-2,5-dihydro-4H-pyrazolo[3,4-d]pyrimidin-4-one | 1.58 min, 484 [M + H]+ |
| 153 | 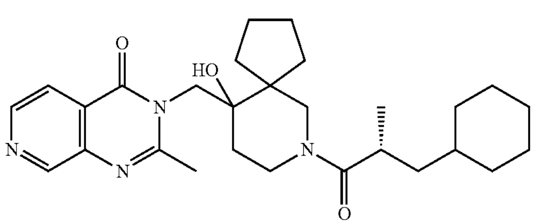 [SMILES: Cc1nc2cnccc2c(=O)n1CC1(O)CCN(C(=O)[C@H](C)CC2CCCCC2)CC12CCCC2] | 3-((7-((R)-3-Cyclohexyl-2-methylpropanoyl)-10-hydroxy-7-azaspiro[4.5]decan-10-yl)methyl)-2-methylpyrido[3,4-d]pyrimidin-4(3H)-one | 1.57 min, 481 [M + H]+ |

| Example | Structure | Name | LCMS (Method C): $R_T$, m/z |
|---|---|---|---|
| 154 | 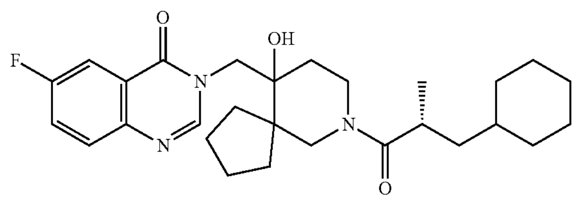 [SMILES: C[C@H](CC1CCCCC1)C(=O)N1CCC(O)(Cn2cnc3ccc(F)cc3c2=O)C2(CCCC2)C1] | 3-((7-((R)-3-Cyclohexyl-2-methylpropanoyl)-10-hydroxy-7-azaspiro[4.5]decan-10-yl)methyl)-6-fluoroquinazolin-4(3H)-one | 1.66 min, 484 [M + H]+ |
| 155 | 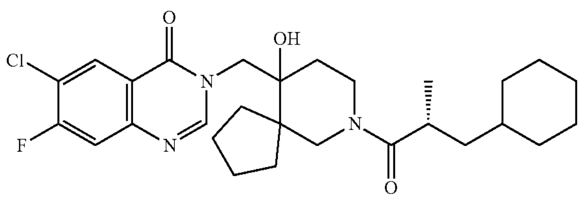 [SMILES: C[C@H](CC1CCCCC1)C(=O)N1CCC(O)(Cn2cnc3cc(F)c(Cl)cc3c2=O)C2(CCCC2)C1] | 6-Chloro-3-((7-((R)-3-cyclohexyl-2-methylpropanoyl)-10-hydroxy-7-azaspiro[4.5]decan-10-yl)methyl)-7-fluoroquinazolin-4(3H)-one | 1.62 min, 518 [M + H]+ |
| 156 | 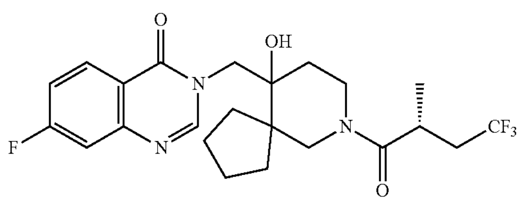 [SMILES: C[C@H](CC(F)(F)F)C(=O)N1CCC(O)(Cn2cnc3cc(F)ccc3c2=O)C2(CCCC2)C1] | 7-Fluoro-3-((10-hydroxy-7-((R)-4,4,4-trifluoro-2-methylbutanoyl)-7-azaspiro[4.5]decan-10-yl)methyl)quinazolin-4(3H)-one | 1.43 min, 470 [M + H]+ |

Example 157: 3-((7-((R)-3-Cyclohexyl-2-methylpropanoyl)-10-hydroxy-7-azaspiro[4.5]decan-10-yl)methyl)pyrido[4,3-d]pyrimidin-4(3H)-one

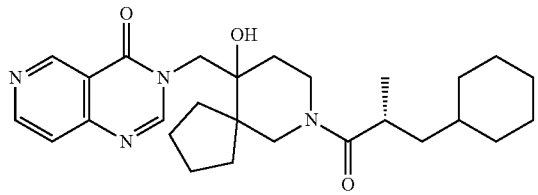

Step 1: tert-Butyl 10-hydroxy-10-((4-oxopyrido[4,3-d]pyrimidin-3(4H)-yl)methyl)-7-azaspiro[4.5]decane-7-carboxylate: Prepared according to General procedure 2 using pyrido[4,3-d]pyrimidin-4(3H)-one (73.6 mg, 0.500 mmol), Epoxide 2 (134 mg, 0.500 mmol), cesium carbonate (179 mg, 0.550 mmol) in DMF (2.5 mL), heated to 80° C. for 66 h to give the title compound (87 mg, 41%) as an off-white solid. LCMS (Method A): $R_T$=1.19 min, m/z=415 [M+H]+.
1H NMR (500 MHz, DMSO-d6): δ 9.33 (s, 1H), 8.84 (d, J=5.6 Hz, 1H), 8.45 (s, 1H), 7.60 (d, J=5.6 Hz, 1H), 4.77 (s, 1H), 4.61 (d, J=13.7 Hz, 1H), 3.69 (d, J=13.7 Hz, 1H), 3.61-3.48 (m, 1H), 3.27-3.14 (m, 3H), 2.00-1.89 (m, 1H), 1.73-1.51 (m, 5H), 1.46-1.33 (m, 2H), 1.39 (s, 9H), 1.28-1.21 (m, 1H), 1.19-1.11 (m, 1H).

Step 2: 3-((10-Hydroxy-7-azaspiro[4.5]decan-10-yl)methyl)pyrido[4,3-d]pyrimidin-4(3H)-one: A solution of tert-butyl 10-hydroxy-10-((4-oxopyrido[4,3-d]pyrimidin-3(4H)-yl)methyl)-7-azaspiro[4.5]decane-7-carboxylate (87 mg, 0.210 mmol) and 4 M HCl in 1,4-dioxane (1.05 mL, 4.20 mmol) in 1,4-dioxane (1 mL) was stirred at 50° C. for 45 min before 1,4-dioxane (1 mL) was added and the reaction was stirred at 50° C. for 90 min before the reaction mixture was allowed to cool to rt and DCM (2 mL) was added. The solids were collected by filtration, washed with DCM (3×2 mL) and dried in a vacuum oven at 50° C. The product was purified by flash chromatography (Biotage KP-NH 11 g cartridge, 0-100% DCM in cyclohexane; then 0-30% MeOH in DCM) to give the title compound (15 mg, 20%) as an off-white solid. LCMS (Method A): $R_T$=0.22 min, m/z=315 [M+H]+.

Step 3: 3-((7-((R)-3-Cyclohexyl-2-methylpropanoyl)-10-hydroxy-7-azaspiro[4.5]decan-10-yl)methyl)pyrido[4,3-d]pyrimidin-4(3H)-one: Prepared according to General procedure 4 using 3-((10-hydroxy-7-azaspiro[4.5]decan-10-yl)methyl)pyrido[4,3-d]pyrimidin-4(3H)-one (15 mg, 0.0477 mmol), Acid 1 (8.1 mg, 0.0477 mmol), HATU (18.1 mg, 0.0477 mmol) and DIPEA (33 μL, 0.191 mmol) in DCM (0.95 mL) to give the title compound (20.2 mg, 90%) as a colourless solid after lyophilisation. LCMS (Method B): $R_T$=1.30, 1.31 min (2 diastereoisomers), m/z=467 [M+H]+.
1H NMR (500 MHz, DMSO-d6): δ 9.33 (s, 1H), 8.85 (d, J=5.6 Hz, 1H), 8.47 (s, 1H), 7.61 (d, J=5.4 Hz, 1H), 4.87-4.79 (m, 1H), 4.72-4.53 (m, 1H), 3.93-3.53 (m, 3H), 3.49-3.15 (m, 2H (signals overlap with HDO)), 2.96-2.80 (m, 1H), 2.07-1.88 (m, 1H), 1.78-1.02 (m, 20H), 1.02-0.88 (m, 3H), 0.90-0.74 (m, 2H).

Example 158: 6-((7-((R)-3-Cyclohexyl-2-methyl-propanoyl)-10-hydroxy-7-azaspiro[4.5]decan-10-yl)methyl)pyrido[4,3-d]pyrimidin-5(6H)-one

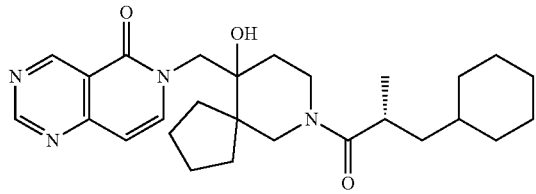

Step 1: tert-Butyl 10-hydroxy-10-((5-oxopyrido[4,3-d]pyrimidin-6(5H)-yl)methyl)-7-azaspiro[4.5]decane-7-carboxylate: Prepared according to General procedure 2 using pyrido[4,3-d]pyrimidin-5(6H)-one (2.00 g, 13.6 mmol), Epoxide 2 (5.45 g, 20.4 mmol), cesium carbonate (6.64 g, 20.4 mmol) in DMF (20 mL), heated to 80° C. for 24 h to give the title compound (4.20 g, 75%) that was used in the next step without further purification.

Step 2: 6-((10-Hydroxy-7-azaspiro[4.5]decan-10-yl)methyl)pyrido[4,3-d]pyrimidin-5(6H)-one: To a stirred solution of tert-butyl 10-hydroxy-10-((5-oxopyrido[4,3-d]pyrimidin-6(5H)-yl)methyl)-7-azaspiro[4.5]decane-7-carboxylate (4.14 g, 10 mmol) in DCM (100 mL) at 0° C. was added TFA (4.0 mL). After 24 h, the reaction mixture was evaporated to dryness, dissolved in water and basified to ca. pH 10 using sodium hydroxide (aq) solution. The reaction mixture was evaporated to dryness and the residue was triturated with hot isopropanol, the solvent was removed in vacuo and the remaining residue was purified by flash chromatography to give the title compound (1.10 g, 35%). LCMS (Method C): $R_T$=0.75 min, m/z=315 [M+H]$^+$.

Step 3: 6-((7-((R)-3-Cyclohexyl-2-methylpropanoyl)-10-hydroxy-7-azaspiro[4.5]decan-10-yl)methyl)pyrido[4,3-d]pyrimidin-5(6H)-one: DIPEA (0.033 mL, 0.191 mmol) was added to a stirred solution of 6-((10-hydroxy-7-azaspiro[4.5]decan-10-yl)methyl)pyrido[4,3-d]pyrimidin-5(6H)-one (20.0 mg, 0.0636 mmol), (R)-3-cyclohexyl-2-methylpropanoic acid (10.8 mg, 0.0636 mmol) and HATU (29.0 mg, 0.0763 mmol) and DCM (1.0 mL) at rt. After 2 h, the reaction mixture was partitioned between further DCM and saturated sodium bicarbonate (aq) solution. The resulting biphasic mixture was separated, extracted (×3), dried (phase separator), the solvents were removed in vacuo, and the remaining residue was purified by flash chromatography (Biotage KP-NH column, 0-100% EtOAc in cyclohexane; then 0-10% MeOH in EtOAc) and freeze-dried to give the title compound (17.5 mg, 59% yield) as a white solid. LCMS (Method A): $R_T$=1.50 min, m/z=467 [M+H]$^+$. $^1$H NMR (500 MHz, DMSO-d$_6$): δ 9.47 (s, 1H), 9.34 (s, 1H), 8.01-7.94 (m, 1H), 6.67 (d, 1H), 4.82-4.58 (m, 2H), 3.93-3.04 (m, 5H, overlapping with HDO), 2.95-2.79 (m, 1H), 2.05-1.85 (m, 1H), 1.82-0.72 (m, 25H).

Example 159: 6-((10-Hydroxy-7-((R)-4,4,4-trifluoro-2-methylbutanoyl)-7-azaspiro[4.5]decan-10-yl)methyl)pyrido[4,3-d]pyrimidin-5(6H)-one

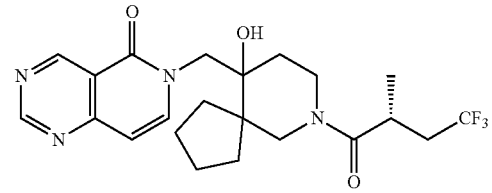 [SMILES: C[C@H](CC(F)(F)F)C(=O)N1CCC(O)(Cn2ccc3ncncc3c2=O)C2(CCCC2)C1]

DIPEA (0.03 mL, 0.1909 mmol) was added to a stirred solution of 6-((10-hydroxy-7-azaspiro[4.5]decan-10-yl)methyl)pyrido[4,3-d]pyrimidin-5(6H)-one (20.0 mg, 0.0636 mmol), (R)-4,4,4-trifluoro-2-methylbutanoic acid (9.9 mg, 0.0636 mmol) and HATU (29.0 mg, 0.0763 mmol) in DCM (1 mL) at rt. After 2 h, the reaction mixture was partitioned between further DCM and saturated sodium bicarbonate (aq) solution. The resulting biphasic mixture was separated, extracted (×3), dried (phase separator), the solvents were removed in vacuo, and the remaining residue was purified by flash chromatography (Biotage KP-NH column, 0-100% EtOAc in cyclohexane; then 0-10% MeOH in EtOAc) and freeze-dried to give the title compound (11.3 mg, 39%) as a white solid. LCMS (Method A): $R_T$=1.08 min, m/z=453 [M+H]$^+$. $^1$H NMR (500 MHz, DMSO-d$_6$): δ 9.49-9.44 (m, 1H), 9.36-9.30 (s, 1H), 8.00-7.93 (m, 1H), 6.72-6.63 (m, 1H), 4.83-4.54 (m, 2H), 4.01-2.93 (m, 5H, overlapping HDO peak), 2.84-2.62 (m, 1H, overlapping solvent peak), 2.33-2.18 (m, 1H), 2.08-1.85 (m, 1H), 1.82-0.77 (m, 13H).

Example 160: 3-((7-((R)-3-Cyclohexyl-2-methylpropanoyl)-10-hydroxy-7-azaspiro[4.5]decan-10-yl)methyl)-7-(methylthio)pyrimido[4,5-d]pyrimidin-4(3H)-one

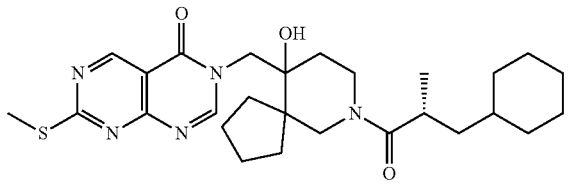

Step 1: tert-Butyl 10-hydroxy-10-((7-(methylthio)-4-oxopyrimido[4,5-d]pyrimidin-3(4H)-yl)methyl)-7-azaspiro[4.5]decane-7-carboxylate: A suspension of 7-(methylthio)pyrimido[4,5-d]pyrimidin-4(3H)-one (500 mg, 2.57 mmol), tert-butyl 1-oxa-10-azadispiro[2.0.4$^4$.4$^3$]dodecane-10-carboxylate (688 mg, 2.57 mmol) and DIPEA (2.25 mL, 12.9 mmol) in 1-methyl-2-pyrrolidinone (2.5 mL) was stirred at 100° C. After 20 h, the temperature was increased to 110° C. After a further 2 h, the reaction mixture was allowed to cool to rt, diluted with saturated ammonium chloride (15 mL) and the mixture extracted with DCM (3×10 mL) and dried using a phase separator. The combined organic phases were concentrated in vacuo and the remaining residue was purified by flash chromatography (0-100% EtOAc in cyclohexane) to give the title compound (1.06 g, 89%) as a pale yellow solid. LCMS (Method A): $R_T$=1.46 min, m/z=462 [M+H]$^+$.

Step 2: 3-((10-Hydroxy-7-azaspiro[4.5]decan-10-yl)methyl)-7-(methylthio)pyrimido[4,5-d]pyrimidin-4(3H)-one: A solution of tert-butyl 10-hydroxy-10-((7-(methylthio)-4-oxopyrimido[4,5-d]pyrimidin-3(4H)-yl)methyl)-7-azaspiro[4.5]decane-7-carboxylate (200 mg, 0.433 mmol) in TFA (2.0 mL, 26.0 mmol) and DCM (2 mL) was stirred at rt. After 30 min, the solvents were removed in vacuo and the remaining residue was partitioned between DCM and sodium bicarbonate (aq) solution, extracted (DCM×2), and the solvents were removed in vacuo. The remaining residue was purified by flash chromatography (Biotage KP-NH column, 0-100% EtOAc in cyclohexane) to give the title compound (11.7 mg, 7.5%). LCMS (Method A): $R_T$=0.43 min, m/z=362 [M+H]$^+$.

Step 3: 3-((7-((R)-3-Cyclohexyl-2-methylpropanoyl)-10-hydroxy-7-azaspiro[4.5]decan-10-yl)methyl)-7-(methylthio)pyrimido[4,5-d]pyrimidin-4(3H)-one: DIPEA (0.017 mL, 0.0971 mmol) was added to a stirred solution of 3-((10-hydroxy-7-azaspiro[4.5]decan-10-yl)methyl)-7-(methylthio)pyrimido[4,5-d]pyrimidin-4(3H)-one (11.7 mg, 0.0324 mmol), (R)-3-cyclohexyl-2-methylpropanoic acid (5.5 mg, 0.0324 mmol) and HATU (14.8 mg, 0.0388 mmol) and DCM (1 mL) at rt. After 30 min, the reaction mixture was partitioned between further DCM and saturated sodium bicarbonate (aq) solution. The resulting biphasic mixture was separated, extracted (×3), dried (phase separator), the solvents were removed in vacuo, and the remaining residue was purified by flash chromatography (0-100% EtOAc in cyclohexane; then 0-10% MeOH in EtOAc) and freeze-dried to give the title compound (5.6 mg, 30%) as a white solid. LCMS (Method A): $R_T$=1.67 min, m/z=514 [M+H]$^+$. $^1$H NMR (500 MHz, DMSO-$d_6$): δ 9.27 (m, 1H), 8.61 (m, 1H), 4.87-4.78 (m, 1H), 4.65-4.48 (m, 1H), 3.91-3.02 (m, 4H, overlapping with HDO), 2.96-2.79 (m, 1H), 2.61 (s, 3H), 2.08-0.74 (m, 27H).

Example 161: 3-((10-Hydroxy-7-((R)-4,4,4-trifluoro-2-methylbutanoyl)-7-azaspiro[4.5]decan-10-yl)methyl)-7-(methylthio)pyrimido[4,5-d]pyrimidin-4(3H)-one

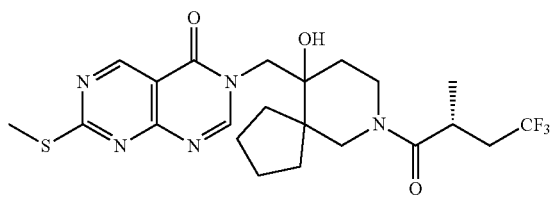 [SMILES: CSc1ncc2c(=O)n(CC3(O)CCN(C(=O)[C@H](C)CC(F)(F)F)CC34CCCC4)cnc2n1]

Step 1: 3-((10-Hydroxy-7-azaspiro[4.5]decan-10-yl)methyl)-7-(methylthio)pyrimido[4,5-d]pyrimidin-4(3H)-one hydrochloride: 4 M HCl in 1,4-dioxane (2.5 mL, 72.0 mmol) was added to tert-butyl 10-hydroxy-10-((7-(methylthio)-4-oxopyrimido[4,5-d]pyrimidin-3(4H)-yl)methyl)-7-azaspiro[4.5]decane-7-carboxylate (500 mg, 1.08 mmol) and stirred. After 30 min, the solvents were removed in vacuo and the remaining residue was dried in a vacuum oven to give the crude title compound (512 mg, >100%) as a pale orange solid that was carried through to the next step without further purification. LCMS (Method A): $R_T$=0.35 min, m/z=362 [M−Cl]$^+$.

Step 2: 3-((10-Hydroxy-7-((R)-4,4,4-trifluoro-2-methylbutanoyl)-7-azaspiro[4.5]decan-10-yl)methyl)-7-(methylthio)pyrimido[4,5-d]pyrimidin-4(3H)-one: DIPEA (0.76 mL, 4.33 mmol) was added to a stirred solution of crude 3-((10-hydroxy-7-azaspiro[4.5]decan-10-yl)methyl)-7-(methylthio)pyrimido[4,5-d]pyrimidin-4(3H)-one hydrochloride (assumed 431 mg, 1.08 mmol), (R)-4,4,4-trifluoro-2-methylbutanoic acid (169 mg, 1.08 mmol) and HATU (494 mg, 1.30 mmol) and DCM (10 mL) at rt. After 1 h, the reaction mixture was partitioned between further DCM and saturated sodium bicarbonate (aq) solution. The resulting biphasic mixture was separated, extracted (×3), dried (phase separator), the solvents were removed in vacuo, and the remaining residue was purified by flash chromatography (0-100% EtOAc in cyclohexane) and freeze-dried to give the title compound (136 mg, 23%) as a very pale yellow solid. LCMS (Method A): $R_T$=1.27 min, m/z=500 [M+H]$^+$. $^1$H NMR (500 MHz, DMSO-$d_6$): δ 9.29-9.25 (m, 1H), 8.63-8.57 (m, 1H), 4.90-4.80 (m, 1H), 4.56 (ddd, 1H), 4.01-2.89 (m, 4H, overlapping with HDO), 2.84-2.65 (m, 1H), 2.61 (s, 3H), 2.33-2.18 (m, 1H), 2.10-0.80 (m, 15H).

Example 162: 3-((10-Hydroxy-7-((R)-4,4,4-trifluoro-2-methylbutanoyl)-7-azaspiro[4.5]decan-10-yl)methyl)-7-morpholinopyrimido[4,5-d]pyrimidin-4(3H)-one

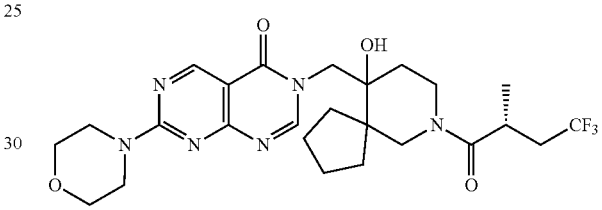

mCPBA (<77% pure) (9.1 mg, 0.0406 mmol) in DCM (0.25 mL) was added to a stirred solution of 3-((10-hydroxy-7-((R)-4,4,4-trifluoro-2-methylbutanoyl)-7-azaspiro[4.5]decan-10-yl)methyl)-7-(methylthio)pyrimido[4,5-d]pyrimidin-4(3H)-one (15.0 mg, 0.0301 mmol) in toluene (1.0 mL) in a 4 mL vial. The vessel was sealed and after 15 min, morpholine (0.0026 mL, 0.0301 mmol) and DIPEA (0.02 mL, 0.0903 mmol) were added, successively. After a further 30 min, the reaction mixture was loaded directly onto a column and was purified by flash chromatography (0-100%, EtOAc in cyclohexane) and freeze-dried to give the title compound (10.3 mg, 63%) as a white solid. LCMS (Method A): $R_T$=1.18 min, m/z=539 [M+H]$^+$. $^1$H NMR (500 MHz, DMSO-$d_6$): δ 9.09 (s, 1H), 8.44 (s, 1H), 4.88-4.77 (m, 1H), 4.52 (ddd, 1H), 4.05-2.90 (m, 12H, overlapping solvent peak), 2.84-2.60 (m, 1H, overlapping solvent peak), 2.33-2.18 (m, 1H), 2.09-1.86 (m, 1H), 1.80-0.76 (m, 14H).

Example 163: 3-((10-Hydroxy-7-((R)-4,4,4-trifluoro-2-methylbutanoyl)-7-azaspiro[4.5]decan-10-yl)methyl)-7-(4-methylpiperazin-1-yl)pyrimido[4,5-d]pyrimidin-4(3H)-one

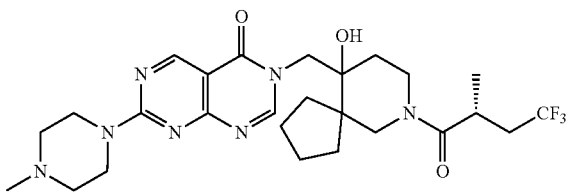 [SMILES: C[C@H](CC(F)(F)F)C(=O)N1CCC(O)(Cn2cnc3nc(N4CCN(C)CC4)ncc3c2=O)C2(CCCC2)C1]

mCPBA (<77% pure) (9.1 mg, 0.0406 mmol) in DCM (0.25 mL) was added to a stirred solution of 3-((10-hydroxy-7-((R)-4,4,4-trifluoro-2-methylbutanoyl)-7-azaspiro[4.5]decan-10-yl)methyl)-7-(methylthio)pyrimido[4,5-d]pyrimidin-4(3H)-one (15.0 mg, 0.0301 mmol) in toluene (1.0 mL) in a 4 mL vial. The vessel was sealed and after 15 min, 1-methylpiperazine (0.0033 mL, 0.0301 mmol) and DIPEA (0.0158 mL, 0.0903 mmol) were added, successively.

After a further 1 h, the reaction mixture was loaded directly onto a column and purified by flash chromatography (0-100% EtOAc in cyclohexane; then 0-20% MeOH in EtOAc) and freeze-dried to give the title compound (14.0 mg, 76%) as a white solid. LCMS (Method A): $R_T$=0.85 min, m/z=552 [M+H]$^+$. $^1$H NMR (500 MHz, DMSO-d$_6$): δ 9.07 (s, 1H), 8.43 (s, 1H), 4.88-4.77 (m, 1H), 4.52 (ddd, 1H), 4.08-2.94 (m, 8H, overlapping solvent peak), 2.84-2.61 (m, 1H, overlapping solvent peak), 2.42-2.15 (m, 8H, overlapping solvent peak), 2.10-1.85 (m, 1H), 1.80-0.75 (m, 14H).

Example 164: 6-Fluoro-3-((10-Hydroxy-7-((R)-3-phenylmorpholine-4-carbonyl)-7-azaspiro[4.5]decan-10-yl)methyl)quinazolin-4(3H)-one

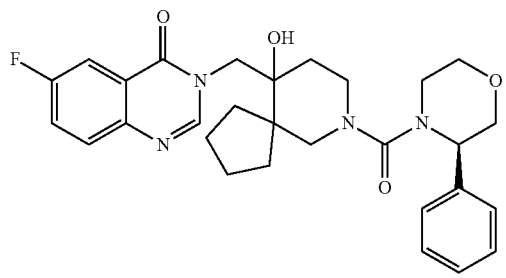 [SMILES: O=C(N1CCC(O)(Cn2cnc3ccc(F)cc3c2=O)C2(CCCC2)C1)N1CCOC[C@H]1c1ccccc1]

Step 1: tert-Butyl 10-(((6-fluoro-4-oxoquinazolin-3(4H)-yl)methyl)-10-hydroxy-7-azaspiro[4.5]decane-7-carboxylate: Prepared according to General procedure 2 using 6-fluoroquinazolin-4(3H)-one (0.20 g, 1.2 mmol), Epoxide 2 (0.49 g, 1.8 mmol), cesium carbonate (0.60 g, 1.8 mmol) in DMF (2 mL), heated to 80° C. for 24 h to give the title compound (0.42 g, 80%). LCMS (Method C): $R_T$=1.49 min, m/z=376 [M-butene+H]$^+$.

Step 2: 6-Fluoro-3-((10-hydroxy-7-azaspiro[4.5]decan-10-yl)methyl)quinazolin-4(3H)-one: Prepared according to General Procedure 3 using tert-butyl 10-((6-fluoro-4-oxoquinazolin-3(4H)-yl)methyl)-10-hydroxy-7-azaspiro[4.5]decane-7-carboxylate (60 mg, 0.139 mmol), TFA (1 mL) and DCM (2 mL), stirred at rt for 2 h to give the title compound (48 mg, quantitative). LCMS (Method A): $R_T$=0.61 min, m/z=332 [M+H]$^+$.

Step 3: 6-Fluoro-3-((10-Hydroxy-7-((R)-3-phenylmorpholine-4-carbonyl)-7-azaspiro[4.5]decan-10-yl)methyl)quinazolin-4(3H)-one: Prepared according to General Procedure 9 using 6-fluoro-3-((10-hydroxy-7-azaspiro[4.5]decan-10-yl)methyl)quinazolin-4(3H)-one (25 mg, 75.4 µmol), (R)-3-phenylmorpholine-4-carbonyl chloride (20.4 mg, 90.5 µmol) and DIPEA (53 µL, 0.302 mmol) in DCM (2 mL), stirring at rt for 1 h to give the title compound (22 mg, 55%) as a colourless solid. LCMS (Method A): $R_T$=1.38 min, m/z=521 [M+H]$^+$. $^1$H NMR (500 MHz, DMSO-d$_6$): δ 8.28 (d, J=3.4 Hz, 1H), 7.84 (td, J=8.8, 2.7 Hz, 1H), 7.80-7.69 (m, 2H), 7.36-7.20 (m, 5H), 4.75 (d, J=10.1 Hz, 1H), 4.61 (dd, J=30.4, 13.7 Hz, 1H), 4.39 (dt, J=23.3, 4.6 Hz, 1H), 3.79-3.64 (m, 5H), 3.58 (dq, J=13.5, 4.8 Hz, 1H), 3.40-2.96 (m, 5H (signal obscured by HDO)), 1.98-1.84 (m, 1H), 1.69-1.19 (m, 8H), 1.16-1.03 (m, 1H).

Example 165: 6,7-Difluoro-3-((10-hydroxy-7-((R)-3-phenylmorpholine-4-carbonyl)-7-azaspiro[4.5]decan-10-yl)methyl)quinazolin-4(3H)-one

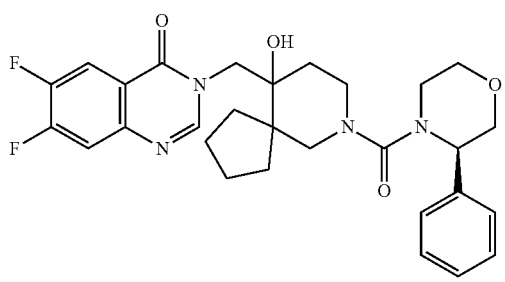 [SMILES: O=C(N1CCC(O)(Cn2cnc3cc(F)c(F)cc3c2=O)C2(CCCC2)C1)N1CCOC[C@H]1c1ccccc1]

Step 1: tert-Butyl 10-((6,7-difluoro-4-oxoquinazolin-3(4H)-yl)methyl)-10-hydroxy-7-azaspiro[4.5]decane-7-carboxylate: Prepared according to General procedure 2 using 6,7-difluoroquinazolin-4(3H)-one (0.20 g, 1.1 mmol), Epoxide 2 (0.44 g, 1.7 mmol), cesium carbonate (0.54 g, 1.7 mmol) in DMF (2 mL), heated to 80° C. for 24 h to give the title compound (0.22 g, 45%). LCMS (Method C): $R_T$=1.52 min, m/z=394 [M-butene+H]$^+$.

Step 2: 6,7-Difluoro-3-((10-hydroxy-7-azaspiro[4.5]decan-10-yl)methyl)quinazolin-4(3H)-one: Prepared according to General Procedure 3 using tert-butyl 10-((6,7-difluoro-4-oxoquinazolin-3(4H)-yl)methyl)-10-hydroxy-7-azaspiro[4.5]decane-7-carboxylate (60 mg, 0.134 mmol), TFA (1 mL) and DCM (2 mL), stirred at rt for 2 h to give the title compound (48 mg, quantitative). LCMS (Method A): $R_T$=0.70 min, m/z=350 [M+H]$^+$.

Step 3: 6,7-Difluoro-3-((10-hydroxy-7-((R)-3-phenylmorpholine-4-carbonyl)-7-azaspiro[4.5]decan-10-yl)methyl)quinazolin-4(3H)-one: Prepared according to General Procedure 9 using 6,7-difluoro-3-((10-hydroxy-7-azaspiro[4.5]decan-10-yl)methyl)quinazolin-4(3H)-one (25 mg, 71.6 µmol), (R)-3-phenylmorpholine-4-carbonyl chloride (19.4 mg, 85.9 µmol) and DIPEA (50 µL, 0.286 mmol) in DCM (2 mL), stirring at rt for 1 h to give the title compound (11.8 mg, 30%) as a colourless solid. LCMS (Method A): $R_T$=1.46 min, m/z=539 [M+H]$^+$. $^1$H NMR (500 MHz, DMSO-d$_6$): δ 8.31 (d, J=3.3 Hz, 1H), 8.09 (q, J=9.5 Hz, 1H), 7.78 (dd, J=11.2, 7.2 Hz, 1H), 7.36-7.19 (m, 5H), 4.76 (d, J=8.8 Hz, 1H), 4.60 (dd, J=30.7, 13.7 Hz, 1H), 4.39 (dt, J=23.0, 4.9 Hz, 1H), 3.80-3.62 (m, 5H), 3.57 (dd, J=12.8, 6.2 Hz, 1H), 3.40-2.96 (m, 5H (signal obscured by HDO)), 1.90 (ddt, J=19.3, 13.3, 6.5 Hz, 1H), 1.69-1.17 (m, 8H), 1.09 (d, J=6.8 Hz, 1H).

Example 166: 2-((10-Hydroxy-7-((R)-3-phenylmorpholine-4-carbonyl)-7-azaspiro[4.5]decan-10-yl)methyl)-2,7-naphthyridin-1(2H)-one

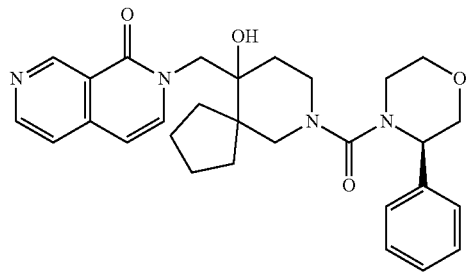 [SMILES: O=C(N1CCC(O)(Cn2ccc3ccncc3c2=O)C2(CCCC2)C1)N1CCOC[C@H]1c1ccccc1]

Step 1: tert-Butyl 10-hydroxy-10-((1-oxo-2,7-naphthyridin-2(1H)-yl)methyl)-7-azaspiro[4.5]decane-7-carboxylate: Prepared according to General procedure 2 using 2,7-naphthyridin-1(2H)-one (0.20 g, 1.4 mmol), Epoxide 2 (0.55 g, 2.1 mmol), cesium carbonate (0.67 g, 2.1 mmol) in DMF (2 mL), heated to 80° C. for 24 h to give the title compound (0.45 g, 80%). LCMS (Method C): $R_T$=1.24 min, m/z=414 [M+H]$^+$.

Step 2: 2-((10-Hydroxy-7-azaspiro[4.5]decan-10-yl)methyl)-2,7-naphthyridin-1(2H)-one: Prepared according to General Procedure 3 using tert-butyl 10-hydroxy-10-((1-oxo-2,7-naphthyridin-2(1H)-yl)methyl)-7-azasprio[4.5]decane-7-carboxylate (60 mg, 0.145 mmol), TFA (1 mL) and DCM (2 mL), stirred at rt for 2 h to give the title compound (50 mg, quantitative). LCMS (Method A): $R_T$=0.29 min, m/z=314 [M+H]$^+$.

Step 3: 2-((10-Hydroxy-7-((R)-3-phenylmorpholine-4-carbonyl)-7-azaspiro[4.5]decan-10-yl)methyl)-2,7-naphthyridin-1(2H)-one: Prepared according to General Procedure 9 using 2-((10-hydroxy-7-azaspiro[4.5]decan-10-yl)methyl)-2,7-naphthyridin-1(2H)-one (25 mg, 79.8 µmol), (R)-3-phenylmorpholine-4-carbonyl chloride (21.6 mg, 95.7 µmol) and DIPEA (56 µL, 0.319 mmol) in DCM (2 mL), stirring at rt for 1 h to give the title compound (21.3 mg, 51%) as an off-white solid. LCMS (Method A): $R_T$=0.96 min, m/z=503 [M+H]$^+$. $^1$H NMR (500 MHz, DMSO-$d_6$): δ 9.35 (d, J=7.7 Hz, 1H), 8.70 (dd, J=5.4, 1.6 Hz, 1H), 7.71 (dd, J=7.4, 6.1 Hz, 1H), 7.58 (d, J=5.4 Hz, 1H), 7.37-7.19 (m, 5H), 6.62 (d, J=7.4 Hz, 1H), 4.75-4.60 (m, 2H), 4.39 (dt, J=22.6, 5.0 Hz, 1H), 3.79-3.55 (m, 6H), 3.42-2.95 (m, 5H (signal obscured by HDO)), 1.88 (tt, J=13.7, 6.7 Hz, 1H), 1.69-1.17 (m, 8H), 1.09 (dq, J=13.3, 6.8 Hz, 1H).

Example 167: 1-Benzyl-5-((10-hydroxy-7-((R)-3-phenylmorpholine-4-carbonyl)-7-azaspiro[4.5]decan-10-yl)methyl)-1,5-dihydro-4H-pyrazolo[3,4-d]pyrimidin-4-one

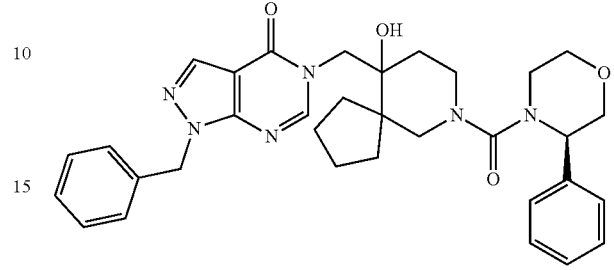

Step 1: tert-Butyl 10-((1-benzyl-4-oxo-1,4-dihydro-5H-pyrazolo[3,4-d]pyrimidin-5-yl)methyl)-10-hydroxy-7-azaspiro[4.5]decane-7-carboxylate: Prepared according to General procedure 2 using 1-benzyl-1,5-dihydro-4H-pyrazolo[3,4-d]pyrimidin-4-one (0.40 g, 1.8 mmol), Epoxide 2 (0.71 g, 2.7 mmol), cesium carbonate (0.86 g, 2.7 mmol) in DMF (4 mL), heated to 80° C. for 24 h to give the title compound (0.35 g, 40%). LCMS (Method C): $R_T$=1.57 min, m/z=494 [M+H]$^+$.

Step 2: 1-Benzyl-5-((10-hydroxy-7-azaspiro[4.5]decan-10-yl)methyl)-1,5-dihydro-4H-pyrazolo[3,4-d]pyrimidin-4-one: Prepared according to General Procedure 3 using tert-butyl 10-((1-benzyl-4-oxo-1,4-dihydro-5H-pyrazolo[3,4-d]pyrimidin-5-yl)methyl)-10-hydroxy-7-azaspiro[4.5]decane-7-carboxylate (70 mg, 0.142 mmol), TFA (1 mL) and DCM (2 mL), stirred at rt for 2 h to give the title compound (58 mg, quantitative). LCMS (Method A): $R_T$=0.80 min, m/z=394 [M+H]$^+$.

Step 3: 1-Benzyl-5-((10-hydroxy-7-((R)-3-phenylmorpholine-4-carbonyl)-7-azaspiro[4.5]decan-10-yl)methyl)-1,5-dihydro-4H-pyrazolo[3,4-d]pyrimidin-4-one: Prepared according to General Procedure 9 using 1-benzyl-5-((10-hydroxy-7-azaspiro[4.5]decan-10-yl)methyl)-1,5-dihydro-4H-pyrazolo[3,4-d]pyrimidin-4-one (19.9 mg, 50.6 µmol), (R)-3-phenylmorpholine-4-carbonyl chloride (13.7 mg, 60.7 µmol) and DIPEA (35 µL, 0.202 mmol) in DCM (1.5 mL), stirring at rt for 1 h to give the title compound (15.5 mg, 52%) as a colourless solid. LCMS (Method A): $R_T$=1.46 min, m/z=583 [M+H]$^+$. $^1$H NMR (500 MHz, DMSO-$d_6$): δ 8.30 (d, J=2.9 Hz, 1H), 8.12 (d, J=7.5 Hz, 1H), 7.37-7.18 (m, 10H), 5.50 (s, 2H), 4.72 (d, J=10.4 Hz, 1H), 4.61 (dd, J=30.0, 13.8 Hz, 1H), 4.38 (dt, J=23.6, 5.0 Hz, 1H), 3.79-3.53 (m, 6H), 3.42-2.95 (m, 5H (signal obscured by HDO)), 1.88 (ddd, J=26.1, 12.5, 6.9 Hz, 1H), 1.67-1.13 (m, 8H), 1.07 (dq, J=14.1, 8.4, 7.2 Hz, 1H).

Example 168: 1-Benzyl-5-((10-hydroxy-7-((R)-4,4,4-trifluoro-2-methylbutanoyl)-7-azaspiro[4.5]decan-10-yl)methyl)-1,5-dihydro-4H-pyrazolo[3,4-d]pyrimidin-4-one

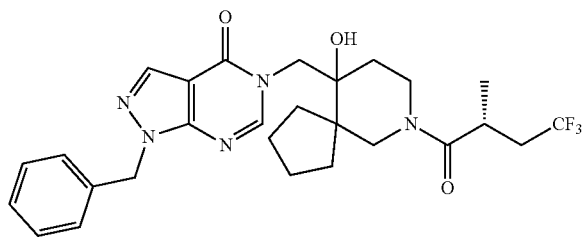 [SMILES: C[C@H](CC(F)(F)F)C(=O)N1CCC(O)(Cn2cnc3c(cnn3Cc3ccccc3)c2=O)C2(CCCC2)C1]

Prepared according to General Procedure 4 using 1-benzyl-5-((10-hydroxy-7-azaspiro[4.5]decan-10-yl)methyl)-1,5-dihydro-4H-pyrazolo[3,4-d]pyrimidin-4-one (20 mg, 50.8 µmol), Acid 3 (9.5 mg, 61.0 µmol), HATU (25.1 mg, 66.1 µmol) and DIPEA (27 µL, 0.153 mmol) in DCM (1 mL), stirred at rt for 1 h to give the title compound (15.6 mg, 57%) as a colourless solid. LCMS (Method A): $R_T$=1.45 min, m/z=532 [M+H]$^+$. $^1$H NMR (500 MHz, DMSO-d$_6$) δ 8.31 (d, J=4.3 Hz, 1H), 8.12 (d, J=2.7 Hz, 1H), 7.34 (dd, J=8.0, 6.5 Hz, 2H), 7.29 (td, J=8.3, 7.8, 4.0 Hz, 3H), 5.51 (s, 2H), 4.80 (d, J=14.2 Hz, 1H), 4.73-4.49 (m, 1H), 3.74-2.90 (m, 6H (signals overlaps with HDO signal)), 2.83-2.64 (m, 1H), 2.32-2.18 (m, 1H), 2.08-1.86 (m, 1H), 1.82-1.00 (m, 12H).

Example 169: 6-Fluoro-3-((10-hydroxy-7-((R)-2-phenylpiperazine-1-carbonyl)-7-azaspiro[4.5]decan-10-yl)methyl)quinazolin-4(3H)-one

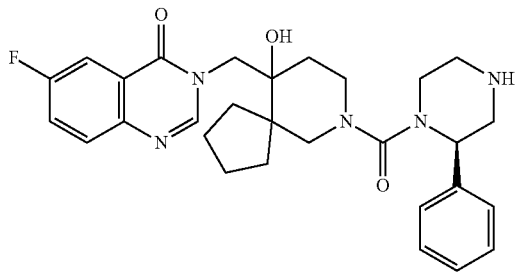 [SMILES: O=C(N1CCC(O)(Cn2cnc3ccc(F)cc3c2=O)C2(CCCC2)C1)N1CCNC[C@H]1c1ccccc1]

Step 1: tert-Butyl (3R)-4-(10-((6-fluoro-4-oxoquinazolin-3(4H)-yl)methyl)-10-hydroxy-7-azaspiro[4.5]decane-7-carbonyl)-3-phenylpiperazine-1-carboxylate: Prepared according to General Procedure 9 using 6-fluoro-3-((10-hydroxy-7-azaspiro[4.5]decan-10-yl)methyl)quinazolin-4(3H)-one (25 mg, 75.4 µmol), tert-butyl (R)-4-(chlorocarbonyl)-3-phenylpiperazine-1-carboxylate (29.4 mg, 90.5 µmol), DIPEA (53 µL, 0.302 mmol) and DCM (1 mL), stirring at rt for 17 h to give the title compound (19 mg, 40%). LCMS (Method A): $R_T$=1.68 min, m/z=620 [M+H]$^+$.

Step 2: 6-Fluoro-3-((10-hydroxy-7-((R)-2-phenylpiperazine-1-carbonyl)-7-azaspiro[4.5]decan-10-yl)methyl)quinazolin-4(3H)-one: Prepared according to General Procedure 3 using tert-butyl (3R)-4-(10-((6-fluoro-4-oxoquinazolin-3(4H)-yl)methyl)-10-hydroxy-7-azaspiro[4.5]decane-7-carbonyl)-3-phenylpiperazine-1-carboxylate (19 mg, 30.7 µmol), TFA (0.5 mL) and DCM (1 mL), stirred at rt for 1.5 h to give the title compound (14.7 mg, 91%) as a colourless solid. LCMS (Method A): $R_T$=0.86 min, m/z=520 [M+H]$^+$. $^1$H NMR (500 MHz, DMSO-d$_6$): δ 8.27 (d, J=2.4 Hz, 1H), 7.85 (ddd, J=9.2, 6.9, 2.9 Hz, 1H), 7.75 (ddd, J=18.1, 8.7, 4.0 Hz, 2H), 7.33-7.23 (m, 4H), 7.19 (ddd, J=13.1, 8.7, 5.3 Hz, 1H), 4.73 (d, J=7.6 Hz, 1H), 4.60 (dd, J=21.0, 13.7 Hz, 1H), 4.29 (dt, J=23.5, 5.3 Hz, 1H), 3.68 (t, J=14.2 Hz, 1H), 3.56 (dt, J=10.0, 5.2 Hz, 1H), 3.37-2.84 (m, 7H (signal obscured by HDO)), 2.77 (q, J=10.1, 7.4 Hz, 2H), 2.58-2.17 (br s, 1H (signal obscured by DMSO)), 1.97-1.83 (m, 1H), 1.69-1.18 (m, 8H), 1.16-1.01 (m, 1H).

Example 170: 6,7-Difluoro-3-((10-hydroxy-7-((R)-2-phenylpiperazine-1-carbonyl)-7-azaspiro[4.5]decan-10-yl)methyl)quinazolin-4(3H)-one

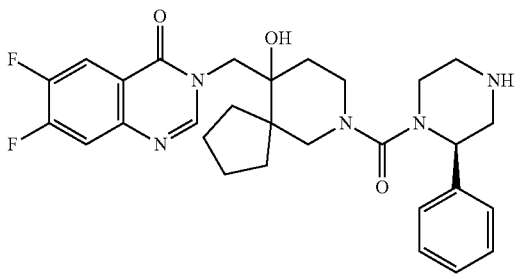 [SMILES: O=C(N1CCC(O)(Cn2cnc3cc(F)c(F)cc3c2=O)C2(CCCC2)C1)N1CCNC[C@H]1c1ccccc1]

Step 1: tert-Butyl (3R)-4-(10-((6,7-difluoro-4-oxoquinazolin-3(4H)-yl)methyl)-10-hydroxy-7-azaspiro[4.5]decane-7-carbonyl)-3-phenylpiperazine-1-carboxylate: Prepared according to General Procedure 9 using 6,7-difluoro-3-((10-hydroxy-7-azaspiro[4.5]decan-10-yl)methyl)quinazolin-4(3H)-one (25 mg, 71.6 µmol), tert-butyl (R)-4-(chlorocarbonyl)-3-phenylpiperazine-1-carboxylate (27.9 mg, 85.9 µmol), DIPEA (50 µL, 0.286 mmol) and DCM (1 mL), stirring at rt for 17 h to give the title compound (18 mg, 39%). LCMS (Method A): $R_T$=1.74 min, m/z=638 [M+H]$^+$; 582 [M-butene+H]$^+$.

Step 2: 6,7-Difluoro-3-((10-hydroxy-7-((R)-2-phenylpiperazine-1-carbonyl)-7-azaspiro[4.5]decan-10-yl)methyl)quinazolin-4(3H)-one: Prepared according to General Procedure 3 using tert-butyl (3R)-4-(10-((6,7-difluoro-4-oxoquinazolin-3(4H)-yl)methyl)-10-hydroxy-7-azaspiro[4.5]decane-7-carbonyl)-3-phenylpiperazine-1-carboxylate (18 mg, 28.2 µmol), TFA (0.5 mL) and DCM (1 mL), stirred at rt for 1.5 h to give the title compound (11.9 mg, 77%) as a colourless solid. LCMS (Method A): $R_T$=0.94 min, m/z=538 [M+H]$^+$. $^1$H NMR (500 MHz, DMSO-d$_6$): δ 8.31 (d, J=2.3 Hz, 1H), 8.09 (ddd, J=10.3, 8.6, 6.9 Hz, 1H), 7.78 (dd, J=11.3, 7.2 Hz, 1H), 7.38-7.23 (m, 4H), 7.23-7.14 (m, 1H), 4.74 (d, J=7.8 Hz, 1H), 4.59 (dd, J=20.5, 13.8 Hz, 1H), 4.29 (dt, J=23.0, 5.3 Hz, 1H), 3.67 (t, J=13.9 Hz, 1H), 3.55 (td, J=10.3, 9.7, 4.4 Hz, 1H), 3.37-2.85 (m, 7H (signal obscured by HDO)), 2.83-2.71 (m, 2H), 2.58-2.27 (br s, 1H (signal obscured by DMSO)), 1.89 (dq, J=14.1, 7.4 Hz, 1H), 1.68-1.17 (m, 8H), 1.08 (ddd, J=19.1, 13.2, 5.9 Hz, 1H).

161

Example 171: 2-((10-Hydroxy-7-((R)-2-phenylpiperazine-1-carbonyl)-7-azaspiro[4.5]decan-10-yl)methyl)-2,7-naphthyridin-1(2H)-one

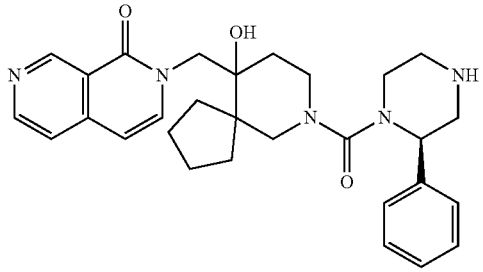 [SMILES: O=C(N1CCC(O)(Cn2ccc3ccncc3c2=O)C2(CCCC2)C1)N1CCNC[C@H]1c1ccccc1]

Step 1: tert-Butyl (3R)-4-(10-hydroxy-10-((1-oxo-2,7-naphthyridin-2(1H)-yl)methyl)-7-azaspiro[4.5]decane-7-carbonyl)-3-phenylpiperazine-1-carboxylate: Prepared according to General Procedure 9 using 2-((10-hydroxy-7-azaspiro[4.5]decan-10-yl)methyl)-2,7-naphthyridin-1(2H)-one (25 mg, 79.8 μmol), tert-butyl (R)-4-(chlorocarbonyl)-3-phenylpiperazine-1-carboxylate (31.1 mg, 95.7 μmol), DIPEA (56 μL, 0.319 mmol) and DCM (1 mL), stirring at rt for 17 h to give the title compound (40 mg, 83%). LCMS (Method A): $R_T$=1.36 min, m/z=602 [M+H]$^+$; 546 [M-butene+H]$^+$.

Step 2: 2-((10-Hydroxy-7-((R)-2-phenylpiperazine-1-carbonyl)-7-azaspiro[4.5]decan-10-yl)methyl)-2,7-naphthyridin-1(2H)-one: Prepared according to General Procedure 3 using tert-butyl (3R)-4-(10-hydroxy-10-((1-oxo-2,7-naphthyridin-2(1H)-yl)methyl)-7-azaspiro[4.5]decane-7-carbonyl)-3-phenylpiperazine-1-carboxylate (40 mg, 66.5 μmol), TFA (0.5 mL) and DCM (1 mL), stirred at rt for 1.5 h to give the title compound (24.9 mg, 73%). LCMS (Method A): $R_T$=0.56 min, m/z=502 [M+H]$^+$. $^1$H NMR (500 MHz, DMSO-d$_6$): δ 9.36 (d, J=6.5 Hz, 1H), 8.70 (d, J=5.4 Hz, 1H), 7.71 (dd, J=7.4, 4.4 Hz, 1H), 7.58 (d, J=5.5 Hz, 1H), 7.33-7.24 (m, 4H), 7.19 (dtt, J=8.6, 6.1, 3.1 Hz, 1H), 6.62 (d, J=7.4 Hz, 1H), 4.75-4.60 (m, 2H), 4.29 (dt, J=22.8, 5.3 Hz, 1H), 3.69-3.52 (m, 2H), 3.37-2.84 (m, 7H (signal obscured by HDO)), 2.77 (h, J=6.4 Hz, 2H), 2.57-2.21 (br s, 1H (signal obscured by DMSO)), 1.93-1.81 (m, 1H), 1.68-1.41 (m, 6H), 1.38-1.18 (m, 2H), 1.09 (td, J=13.8, 6.5 Hz, 1H).

Example 172: 1-Benzyl-5-((10-hydroxy-7-((R)-2-phenylpiperazine-1-carbonyl)-7-azaspiro[4.5]decan-10-yl)methyl)-1,5-dihydro-4H-pyrazolo[3,4-d]pyrimidin-4-one

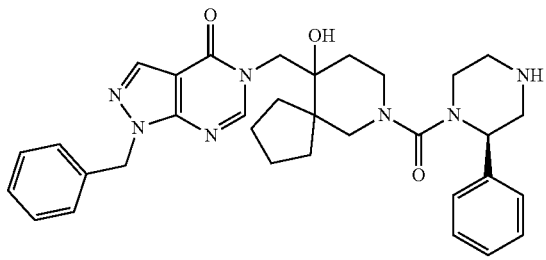 [SMILES: O=C(N1CCC(O)(Cn2cnc3c(cnn3Cc3ccccc3)c2=O)C2(CCCC2)C1)N1CCNC[C@H]1c1ccccc1]

Step 1: tert-Butyl (3R)-4-(10-((1-benzyl-4-oxo-1,4-dihydro-5H-pyrazolo[3,4-d]pyrimidin-5-yl)methyl)-10-hydroxy-7-azaspiro[4.5]decane-7-carbonyl)-3-phenylpiperazine-1-carboxylate: Prepared according to General Procedure 9 using 1-benzyl-5-((10-hydroxy-7-azaspiro[4.5]decan-10-yl)methyl)-1,5-dihydro-4H-pyrazolo[3,4-d]pyrimidin-4-one (20 mg, 50.6 μmol), tert-butyl (R)-4-(chlorocarbonyl)-3-phenylpiperazine-1-carboxylate (19.7 mg, 60.7 μmol), DIPEA (35 μL, 0.201 mmol) and DCM (1 mL), stirring at rt for 17 h to give the title compound (28 mg, 81%). LCMS (Method A): $R_T$=1.73 min, m/z=682 [M+H]$^+$; 626 [M-butene+H]$^+$.

Step 2: 1-Benzyl-5-((10-hydroxy-7-((R)-2-phenylpiperazine-1-carbonyl)-7-azaspiro[4.5]decan-10-yl)methyl)-1,5-dihydro-4H-pyrazolo[3,4-d]pyrimidin-4-one: Prepared according to General Procedure 3 using tert-butyl (3R)-4-(10-((1-benzyl-4-oxo-1,4-dihydro-5H-pyrazolo[3,4-d]pyrimidin-5-yl)methyl)-10-hydroxy-7-azaspiro[4.5]decane-7-carbonyl)-3-phenylpiperazine-1-carboxylate (28 mg, 41.1 μmol), TFA (0.5 mL) and DCM (1 mL), stirred at rt for 1.5 h to give the title compound (15.3 mg, 63%) as a colourless solid. LCMS (Method A): $R_T$=0.98 min, m/z=582 [M+H]$^+$. $^1$H NMR (500 MHz, DMSO-d$_6$): δ 8.30 (d, J=1.9 Hz, 1H), 8.12 (d, J=6.4 Hz, 1H), 7.34 (dd, J=8.0, 6.5 Hz, 2H), 7.28 (td, J=7.4, 6.7, 4.3 Hz, 7H), 7.18 (tdd, J=8.5, 6.7, 3.0 Hz, 1H), 5.50 (s, 2H), 4.70 (d, J=7.7 Hz, 1H), 4.60 (dd, J=20.6, 13.7 Hz, 1H), 4.28 (dt, J=24.6, 5.3 Hz, 1H), 3.68-3.50 (m, 2H), 3.37-2.84 (m, 7H (signal obscured by HDO)), 2.81-2.70 (m, 2H), 2.58-2.30 (br s, 1H (signal obscured by DMSO)), 1.86 (dt, J=13.5, 6.1 Hz, 1H), 1.67-1.00 (m, 9H).

Example 173: 6-((7-((R)-3-Cyclohexyl-2-methylpropanoyl)-10-hydroxy-7-azaspiro[4.5]decan-10-yl)methyl)-2-methyl-2,6-dihydro-7H-pyrazolo[4,3-d]pyrimidin-7-one

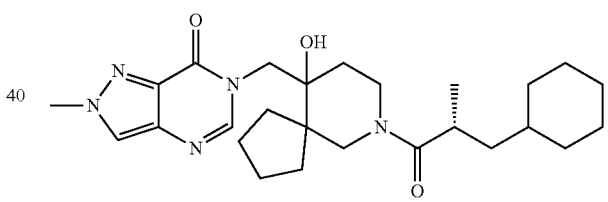

Step 1: tert-Butyl 10-hydroxy-10-((2-methyl-7-oxo-2,7-dihydro-6H-pyrazolo[4,3-d]pyrimidin-6-yl)methyl)-7-azaspiro[4.5]decane-7-carboxylate: Prepared according to General procedure 2 using 2-methyl-2,6-dihydro-7H-pyrazolo[4,3-d]pyrimidin-7-one (1.20 g, 8 mmol), Epoxide 2 (3.21 g, 12 mmol), cesium carbonate (3.91 g, 12 mmol) in DMF (12 mL), heated to 80° C. for 24 h to give the title compound (1.62 g, 49%). LCMS (Method C): $R_T$=1.31 min, m/z=362 [M-butene+H]$^+$.

Step 2: 6-((10-Hydroxy-7-azaspiro[4.5]decan-10-yl)methyl)-2-methyl-2,6-dihydro-7H-pyrazolo[4,3-d]pyrimidin-7-one: Prepared according to General Procedure 3 using tert-butyl 10-hydroxy-10-((2-methyl-7-oxo-2,7-dihydro-6H-pyrazolo[4,3-d]pyrimidin-6-yl)methyl)-7-azaspiro[4.5]decane-7-carboxylate (200 mg, 0.479 mmol), DCM (4 mL) and TFA (2 mL), stirred at rt for 20 min to give the title compound (142 mg, 93%). LCMS (Method B): $R_T$=0.47 min, m/z=318 [M+H]$^+$.

Step 3: 6-((7-((R)-3-Cyclohexyl-2-methylpropanoyl)-10-hydroxy-7-azaspiro[4.5]decan-10-yl)methyl)-2-methyl-2,6-dihydro-7H-pyrazolo[4,3-d]pyrimidin-7-one: Prepared according to General Procedure 4 using 6-((10-hydroxy-7- azaspiro[4.5]decan-10-yl)methyl)-2-methyl-2,6-dihydro-7H-pyrazolo[4,3-d]pyrimidin-7-one (20.0 mg, 0.063 mmol), Acid 1 (10.7 mg, 0.063 mmol), HATU (28.8 mg, 0.076 mmol) and DIPEA (33 μL, 0.189 mmol) in DCM (1 mL) to give the title compound (23.6 mg, 78%) as a white solid. LCMS (Method B): $R_T$=1.31 min, m/z=470 [M+H]$^+$. $^1$H NMR (500 MHz, DMSO-d$_6$): δ 8.30 (s, 1H), 8.02 (s, 1H), 4.76-4.71 (m, 1H), 4.68-4.54 (m, 1H), 4.08 (s, 3H), 3.72-3.52 (m, 2H), 3.46-3.17 (m, 2H), 2.93-2.81 (m, 1H), 2.03-1.85 (m, 1H), 1.72-1.33 (m 13H), 1.26-1.03 (m, 8H), 1.00-0.90 (m, 3H), 0.89-0.75 (m, 2H).

Example 174: 2-((7-((R)-3-Cyclohexyl-2-methyl-propanoyl)-10-hydroxy-7-azaspiro[4.5]decan-10-yl)methyl)-1-methyl-1,2-dihydro-3H-pyrazolo[3,4-d]pyrimidin-3-one

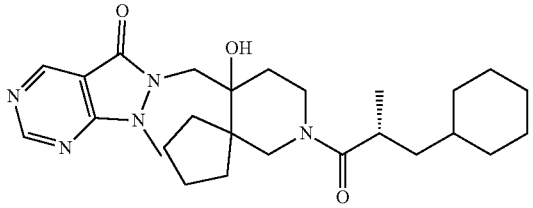 [SMILES: C[C@H](CC1CCCCC1)C(=O)N1CCC(O)(Cn2c(=O)c3cncnc3n2C)C2(CCCC2)C1]

Step 1: tert-Butyl 10-hydroxy-10-((1-methyl-3-oxo-1,3-dihydro-2H-pyrazolo[3,4-d]pyrimidin-2-yl)methyl)-7-azaspiro[4.5]decane-7-carboxylate: Prepared according to General procedure 2 using 1-methyl-1,2-dihydro-3H-pyrazolo[3,4-d]pyrimidin-3-one (0.14 g, 0.9 mmol), Epoxide 2 (0.37 g, 1.4 mmol), cesium carbonate (0.46 g, 1.4 mmol) in DMF (1.5 mL), heated to 80° C. for 24 h to give the title compound (0.22 g, 56%). LCMS (Method C): $R_T$=1.26 min, m/z=362 [M-butene+H]$^+$.

Step 2: 2-((10-Hydroxy-7-azaspiro[4.5]decan-10-yl)methyl)-1-methyl-1,2-dihydro-3H-pyrazolo[3,4-d]pyrimidin-3-one: Prepared according to General Procedure 3 using tert-butyl 10-hydroxy-10-((1-methyl-3-oxo-1,3-dihydro-2H-pyrazolo[3,4-d]pyrimidin-2-yl)methyl)-7-azaspiro[4.5]decane-7-carboxylate (120 mg, 0.287 mmol), TFA (1.5 mL) and DCM (3 mL), stirred at rt for 1.5 h to give the title compound (80 mg, 87%). LCMS (Method A): $R_T$=0.47 min, m/z=318 [M+H]$^+$.

Step 3: 2-((7-((R)-3-Cyclohexyl-2-methylpropanoyl)-10-hydroxy-7-azaspiro[4.5]decan-10-yl)methyl)-1-methyl-1,2-dihydro-3H-pyrazolo[3,4-d]pyrimidin-3-one: Prepared according to General Procedure 4 using 2-((10-hydroxy-7-azaspiro[4.5]decan-10-yl)methyl)-1-methyl-1,2-dihydro-3H-pyrazolo[3,4-d]pyrimidin-3-one (15 mg, 47.3 μmol), Acid 1 (9.7 mg, 56.7 μmol), HATU (23.4 mg, 61.4 μmol) and DIPEA (24.8 μL, 0.142 mmol) in DCM (1 mL), stirred at rt for 2 h to give the title compound (6 mg, 26%) as a colourless solid. LCMS (Method B): $R_T$=1.30 min, m/z=470 [M+H]$^+$. $^1$H NMR (500 MHz, DMSO-d$_6$): δ 8.30 (s, 1H), 8.02 (s, 1H), 4.77-4.70 (m, 1H), 4.68-4.54 (m, 1H), 4.08 (s, 3H), 3.72-3.51 (m, 2H), 3.47-3.31 (m, 2H), 3.27-3.04 (m, 1H), 2.87 (dp, J=21.8, 6.6 Hz, 1H), 1.93 (tdd, J=21.7, 18.0, 14.1, 5.7 Hz, 1H), 1.80-1.01 (m, 20H), 0.95 (dt, J=20.4, 6.7 Hz, 3H), 0.90-0.74 (m, 2H).

Example 175: 2-((10-Hydroxy-7-((R)-2-phenylpiperazine-1-carbonyl)-7-azaspiro[4.5]decan-10-yl)methyl)-1-methyl-1,2-dihydro-3H-pyrazolo[3,4-d]pyrimidin-3-one

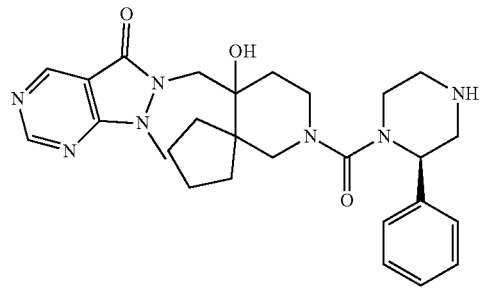 [SMILES: Cn1c2ncncc2c(=O)n1CC1(O)CCN(C(=O)N2CCNC[C@H]2c2ccccc2)CC12CCCC2]

Step 1: tert-Butyl (3R)-4-(10-hydroxy-10-((1-methyl-3-oxo-1,3-dihydro-2H-pyrazolo[3,4-d]pyrimidin-2-yl)methyl)-7-azaspiro[4.5]decane-7-carbonyl)-3-phenylpiperazine-1-carboxylate: Prepared according to General Procedure 9 using 2-((10-hydroxy-7-azaspiro[4.5]decan-10-yl)methyl)-1-methyl-1,2-dihydro-3H-pyrazolo[3,4-d]pyrimidin-3-one (15 mg, 47.3 μmol), tert-butyl (R)-4-(chlorocarbonyl)-3-phenylpiperazine-1-carboxylate (18.4 mg, 56.7 μmol), DIPEA (33 μL, 0.189 mmol) and DCM (1 mL), stirring at rt for 2 h to give the title compound (20 mg, 70%). LCMS (Method B): $R_T$=1.26 min, m/z=550 [M-butene+H]$^+$; 506 [M-Boc+H]$^+$.

Step 2: 2-((10-Hydroxy-7-((R)-2-phenylpiperazine-1-carbonyl)-7-azaspiro[4.5]decan-10-yl)methyl)-1-methyl-1,2-dihydro-3H-pyrazolo[3,4-d]pyrimidin-3-one: Prepared according to General Procedure 3 using tert-butyl (3R)-4-(10-hydroxy-10-((1-methyl-3-oxo-1,3-dihydro-2H-pyrazolo[3,4-d]pyrimidin-2-yl)methyl)-7-azaspiro[4.5]decane-7-carbonyl)-3-phenylpiperazine-1-carboxylate (20 mg, 33.0 μmol), TFA (0.5 mL) and DCM (1 mL), stirred at rt for 1.5 h to give the title compound (15 mg, 87%) as a colourless solid. LCMS (Method B): $R_T$=0.64 min, m/z=506 [M+H]$^+$. $^1$H NMR (500 MHz, DMSO-d$_6$): δ 8.30 (s, 1H), 8.01 (d, J=2.5 Hz, 1H), 7.33-7.24 (m, 4H), 7.19 (ddq, J=11.4, 5.4, 3.2, 2.4 Hz, 1H), 4.66 (d, J=5.4 Hz, 1H), 4.59 (dd, J=21.3, 13.9 Hz, 1H), 4.29 (dt, J=17.3, 5.2 Hz, 1H), 4.08 (d, J=1.6 Hz, 3H), 3.66-3.52 (m, 2H), 3.27-2.85 (m, 7H), 2.77 (dq, J=6.8, 4.4, 3.9 Hz, 2H), 1.92-1.81 (m, 1H), 1.69-1.00 (m, 9H). NH signal not observed.

Example 176: 5-((7-((R)-3-Cyclohexyl-2-methyl-propanoyl)-10-hydroxy-7-azaspiro[4.5]decan-10-yl)methyl)-1-phenyl-1,5-dihydro-4H-pyrazolo[3,4-d]pyrimidin-4-one

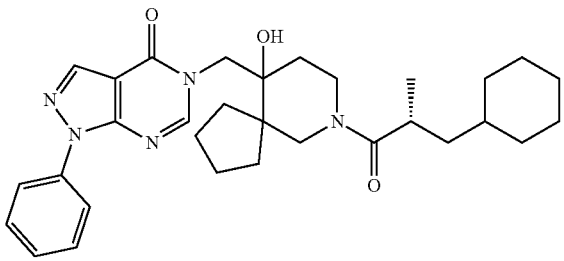 [SMILES: C[C@H](CC1CCCCC1)C(=O)N1CCC(O)(Cn2cnc3c(cnn3-c3ccccc3)c2=O)C2(CCCC2)C1]

Step 1: tert-Butyl 10-hydroxy-10-((4-oxo-1-phenyl-1,4-dihydro-5H-pyrazolo[3,4-d]pyrimidin-5-yl)methyl)-7-azaspiro[4.5]decane-7-carboxylate: Prepared according to General procedure 2 using 1-phenyl-1,5-dihydro-4H-pyrazolo[3,4-d]pyrimidin-4-one (0.10 g, 0.5 mmol), Epoxide 2 (0.19 g, 0.7 mmol), cesium carbonate (0.23 g, 0.7 mmol) in DMF (1.0 mL), heated to 80° C. for 24 h to give the title compound (0.16 g, 71%). LCMS (Method C): $R_T$=1.49 min, m/z=424 [M-butene+H]$^+$.

Step 2: 5-((10-Hydroxy-7-azaspiro[4.5]decan-10-yl)methyl)-1-phenyl-1,5-dihydro-4H-pyrazolo[3,4-d]pyrimidin-4-one: Prepared according to General Procedure 3 using tert-butyl 10-hydroxy-10-((4-oxo-1-phenyl-1,4-dihydro-5H-pyrazolo[3,4-d]pyrimidin-5-yl)methyl)-7-azaspiro[4.5]decane-7-carboxylate (110 mg, 0.229 mmol), DCM (2 mL) and TFA (1 mL), stirred at rt for 20 min to give the title compound (91.7 mg, 100%). LCMS (Method B): $R_T$=0.73 min, m/z=380 [M+H]$^+$.

Step 3: 5-((7-((R)-3-cyclohexyl-2-methylpropanoyl)-10-hydroxy-7-azaspiro[4.5]decan-10-yl)methyl)-1-phenyl-1,5-dihydro-4H-pyrazolo[3,4-d]pyrimidin-4-one: Prepared according to General Procedure 4 using 5-((10-hydroxy-7-azaspiro[4.5]decan-10-yl)methyl)-1-phenyl-1,5-dihydro-4H-pyrazolo[3,4-d]pyrimidin-4-one (20.0 mg, 0.063 mmol), Acid 1 (9.0 mg, 0.053 mmol), HATU (24.0 mg, 0.063 mmol) and DIPEA (28 μL, 0.158 mmol) in DCM (1 mL) to give the title compound (27.8 mg, 97%) as a white solid. LCMS (Method B): $R_T$=1.68 min, m/z=532 [M+H]$^+$. $^1$H NMR (500 MHz, DMSO-$d_6$): δ 8.41-8.35 (m, 2H), 8.06 (d, 2H), 7.59 (t, 2H), 7.42 (t, 1H), 4.81-4.75 (m, 1H), 4.74-4.59 (m, 1H), 3.79-3.54 (m, 2H), 3.48-3.37 (m, 1H), 3.27-3.01 (m, 1H), 2.95-2.80 (m, 1H), 2.07-1.87 (m, 1H), 1.77-1.02 (m, 21H), 1.00-0.91 (m, 3H), 0.90-0.74 (m, 2H).

Example 177: 5-((10-Hydroxy-7-((R)-4,4,4-trifluoro-2-methylbutanoyl)-7-azaspiro[4.5]decan-10-yl)methyl)-1-phenyl-1,5-dihydro-4H-pyrazolo[3,4-d]pyrimidin-4-one

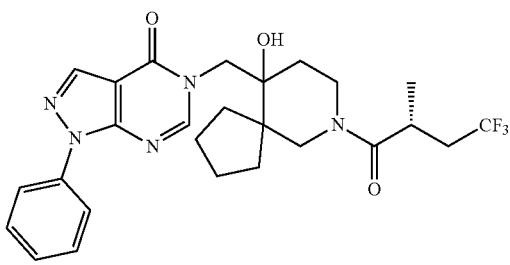 [SMILES: C[C@H](CC(F)(F)F)C(=O)N1CCC(O)(Cn2cnc3c(cnn3-c3ccccc3)c2=O)C2(CCCC2)C1]

Prepared according to General Procedure 4 using 5-((10-hydroxy-7-azaspiro[4.5]decan-10-yl)methyl)-1-phenyl-1,5-dihydro-4H-pyrazolo[3,4-d]pyrimidin-4-one (20.0 mg, 0.053 mmol), Acid 3 (8.2 mg, 0.053 mmol), HATU (24.0 mg, 0.063 mmol) and DIPEA (28 μL, 0.158 mmol) in DCM (1 mL) to give the title compound (23.1 mg, 84%) as a white solid. LCMS (Method B): $R_T$=1.38 min, m/z=518 [M+H]$^+$. $^1$H NMR (500 MHz, DMSO-$d_6$): δ 8.44-8.32 (m, 2H), 8.06 (d, 2H), 7.59 (t, 2H), 7.42 (t, 1H), 4.85-4.77 (m, 1H), 4.77-4.54 (m, 1H), 4.04-3.49 (m, 3H), 3.43-3.36 (m, 1H), 3.21-3.05 (m, 1H), 2.81-2.66 (m, 1H), 2.33-2.20 (m, 1H), 2.12-1.88 (m, 1H), 1.85-0.95 (m, 13H).

Example 178: 5-((10-Hydroxy-7-((R)-2-phenylpiperazine-1-carbonyl)-7-azaspiro[4.5]decan-10-yl)methyl)-1-phenyl-1,5-dihydro-4H-pyrazolo[3,4-d]pyrimidin-4-one

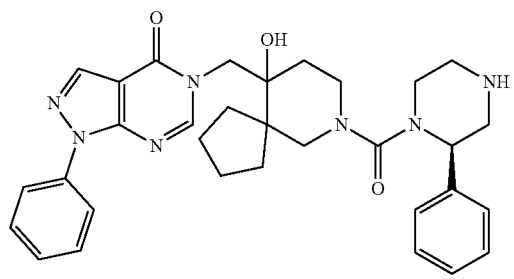 [SMILES: O=C(N1CCC(O)(Cn2cnc3c(cnn3-c3ccccc3)c2=O)C2(CCCC2)C1)N1CCNC[C@H]1c1ccccc1]

Step 1: tert-Butyl (3R)-4-(10-hydroxy-10-((4-oxo-1-phenyl-1,4-dihydro-5H-pyrazolo[3,4-d]pyrimidin-5-yl)methyl)-7-azaspiro[4.5]decane-7-carbonyl)-3-phenylpiperazine-1-carboxylate: To a stirring solution of 5-((10-hydroxy-7-azaspiro[4.5]decan-10-yl)methyl)-1-phenyl-1,5-dihydro-4H-pyrazolo[3,4-d]pyrimidin-4-one (30.0 mg, 0.079 mmol) and DIPEA (28 uL, 0.158 mmol) in anhydrous DCM (0.5 mL) was added tert-butyl (R)-4-(chlorocarbonyl)-3-phenylpiperazine-1-carboxylate (42.3 mg, 0.130 mmol) and the solution stirred for 72 h. The mixture was washed with saturated sodium hydrogen carbonate (aq) solution (2 mL). The aqueous phase was separated and extracted using DCM (2×2 mL). The combined organic fractions were dried (phase separator) and the solvents were removed in vacuo. The residue was purified by flash chromatography (0-50% EtOAc in cyclohexane) to give the title compound (38.9 mg, 74%). LCMS (Method B): $R_T$=1.61 min, m/z=612 [M-butene+H]$^+$.

Step 3: 5-((10-Hydroxy-7-((R)-2-phenylpiperazine-1-carbonyl)-7-azaspiro[4.5]decan-10-yl)methyl)-1-phenyl-1,5-dihydro-4H-pyrazolo[3,4-d]pyrimidin-4-one: Prepared according to General Procedure 3 using tert-butyl (3R)-4-(10-hydroxy-10-((4-oxo-1-phenyl-1,4-dihydro-5H-pyrazolo[3,4-d]pyrimidin-5-yl)methyl)-7-azaspiro[4.5]decane-7-carbonyl)-3-phenylpiperazine-1-carboxylate (32.9 mg, 0.049 mmol), DCM (1 mL) and TFA (0.25 mL) stirred at rt for 20 min to give the title compound (25.2 mg, 89%) as a white solid. LCMS (Method B): $R_T$=0.88 min, m/z=568 [M+H]$^+$. $^1$H NMR (500 MHz, DMSO-$d_6$): δ 8.40-8.34 (m, 2H), 8.06 (d, 2H), 7.58 (t, 2H), 7.42 (t, 1H), 7.34-7.24 (m, 4H), 7.24-7.16 (m, 1H), 4.71 (d, 1H), 4.64 (t, 1H), 4.30 (dt, 1H), 3.68 (t, 1H), 3.64-3.53 (m, 1H), 3.23-3.12 (m, 2H), 3.11-2.99 (m, 2H), 2.99-2.86 (m, 3H), 2.85-2.73 (m, 2H), 1.96-1.84 (m, 1H), 1.68-1.38 (m, 6H), 1.38-1.18 (m, 2H), 1.14-1.01 (m, 1H).

Example 179: 6-((10-Hydroxy-7-((R)-2-phenylpiperazine-1-carbonyl)-7-azaspiro[4.5]decan-10-yl)methyl)-2-methyl-2,6-dihydro-7H-pyrazolo[4,3-d]pyrimidin-7-one

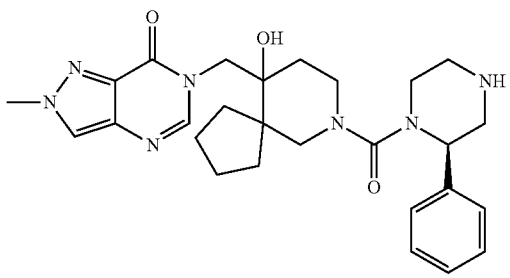 [SMILES: Cn1cc2ncn(CC3(O)CCN(C(=O)N4CCNC[C@H]4c4ccccc4)CC34CCCC4)c(=O)c2n1]

Step 1: tert-Butyl (3R)-4-(10-hydroxy-10-((2-methyl-7-oxo-2,7-dihydro-6H-pyrazolo[4,3-d]pyrimidin-6-yl)methyl)-7-azaspiro[4.5]decane-7-carbonyl)-3-phenylpiperazine-1-carboxylate: To a stirring solution of 6-((10-hydroxy-7-azaspiro[4.5]decan-10-yl)methyl)-2-methyl-2,6-dihydro-7H-pyrazolo[4,3-d]pyrimidin-7-one (30.0 mg, 0.095 mmol) and DIPEA (33 uL, 0.189 mmol) in anhydrous DCM (0.5 mL) was added tert-butyl (R)-4-(chlorocarbonyl)-3-phenylpiperazine-1-carboxylate (42.3 mg, 0.130 mmol) and the solution stirred for 6 days. The mixture was washed with saturated sodium hydrogen carbonate (aq) solution (2 mL). The aqueous was separated and extracted using DCM (2×2 mL). The combined organic fractions were dried (phase separator) and the solvents were removed in vacuo. The residue was purified by flash chromatography (0-100% EtOAc in cyclohexane; then 0-15% MeOH in EtOAc). The residue was further purified by flash chromatography (0-15% MeOH in DCM) to give the title compound (42.3 mg, 74%). LCMS (Method B): $R_T$=1.26 min, m/z=550 [M-butene+H]$^+$.

Step 2: 6-((10-Hydroxy-7-((R)-2-phenylpiperazine-1-carbonyl)-7-azaspiro[4.5]decan-10-yl)methyl)-2-methyl-2,6-dihydro-7H-pyrazolo[4,3-d]pyrimidin-7-one: Prepared according to General Procedure 3 using (3R)-4-(10-hydroxy-10-((2-methyl-7-oxo-2,7-dihydro-6H-pyrazolo[4,3-d]pyrimidin-6-yl)methyl)-7-azaspiro[4.5]decane-7-carbonyl)-3-phenylpiperazine-1-carboxylate (42.3 mg, 0.070 mmol), DCM (2 mL) and TFA (1 mL) stirred at rt for 20 min to give the title compound (31.8 mg, 88%) as a white solid. LCMS (Method B): $R_T$=0.63 min, m/z=506 [M+H]$^+$. $^1$H NMR (500 MHz, DMSO-d$_6$): δ 8.30 (s, 1H), 8.03-7.99 (m, 1H), 7.33-7.24 (m, 4H), 7.23-7.15 (m, 1H), 4.66 (d, 1H), 4.59 (t, 1H), 4.29 (dt, 1H), 4.12-4.04 (m, 3H), 3.66-3.52 (m, 2H), 3.22-3.10 (m, 2H), 3.10-2.99 (m, 2H), 2.99-2.87 (m, 3H), 2.84-2.72 (m, 2H), 1.93-1.80 (m, 1H), 1.68-1.28 (m, 7H), 1.28-1.14 (m, 2H), 1.13-1.00 (m, 1H).

Example 180: 5-((10-Hydroxy-7-((R)-4,4,4-trifluoro-2-methylbutanoyl)-7-azaspiro[4.5]decan-10-yl)methyl)-1-methyl-1,5-dihydro-4H-pyrazolo[3,4-d]pyrimidin-4-one

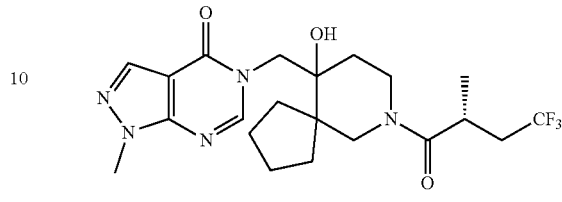

Step 1: tert-Butyl 10-hydroxy-10-((1-methyl-4-oxo-1,4-dihydro-5H-pyrazolo[3,4-d]pyrimidin-5-yl)methyl)-7-azaspiro[4.5]decane-7-carboxylate: Prepared according to General procedure 2 using 1-methyl-1,5-dihydro-4H-pyrazolo[3,4-d]pyrimidin-4-one (0.14 g, 0.9 mmol), Epoxide 2 (0.37 g, 1.4 mmol), cesium carbonate (0.46 g, 1.4 mmol) in DMF (1.5 mL), heated to 80° C. for 24 h to give the title compound (0.30 g, 77%). LCMS (Method C): $R_T$=1.31 min, m/z=362 [M-butene+H]$^+$.

Step 2: 5-((10-Hydroxy-7-azaspiro[4.5]decan-10-yl)methyl)-1-methyl-1,5-dihydro-4H-pyrazolo[3,4-d]pyrimidin-4-one: Prepared according to General Procedure 3 using tert-butyl 10-hydroxy-10-((1-methyl-4-oxo-1,4-dihydro-5H-pyrazolo[3,4-d]pyrimidin-5-yl)methyl)-7-azaspiro[4.5]decane-7-carboxylate (100 mg, 0.240 mmol), TFA (1 mL) and DCM (2 mL), stirred at rt for 1 h to give the title compound (70 mg, 92%). LCMS (Method B): $R_T$=0.52 min, m/z=318 [M+H]$^+$.

Step 3: 5-((10-Hydroxy-7-((R)-4,4,4-trifluoro-2-methylbutanoyl)-7-azaspiro[4.5]decan-10-yl)methyl)-1-methyl-1,5-dihydro-4H-pyrazolo[3,4-d]pyrimidin-4-one: Prepared according to General Procedure 4 using 5-((10-hydroxy-7-azaspiro[4.5]decan-10-yl)methyl)-1-methyl-1,5-dihydro-4H-pyrazolo[3,4-d]pyrimidin-4-one (22 mg, 69.3 μmol), Acid 3 (13.0 mg, 83.2 μmol), HATU (34.3 mg, 90.1 μmol) and DIPEA (37 μL, 0.208 mmol) in DCM (1 mL), stirred at rt for 45 min to give the title compound (18.4 mg, 57%) as a colourless solid. LCMS (Method B): $R_T$=1.05 min, m/z=456 [M+H]$^+$. $^1$H NMR (500 MHz, DMSO-d$_6$): δ 8.29 (d, J=3.8 Hz, 1H), 8.07 (d, J=2.9 Hz, 1H), 4.77 (dd, J=15.5, 6.8 Hz, 1H), 4.73-4.50 (m, 1H), 3.92 (d, J=1.7 Hz, 3H), 3.75-3.46 (m, 2H), 3.42-3.31 (m, 1H), 3.28-3.20 (m, 1H), 3.20-3.04 (m, 1H), 2.69 (s, 2H), 2.32-2.18 (m, 1H), 2.07-1.88 (m, 1H), 1.81-1.47 (m, 5H), 1.47-1.00 (m, 7H).

Example 181: 1-Cyclopropyl-5-((10-hydroxy-7-((R)-4,4,4-trifluoro-2-methylbutanoyl)-7-azaspiro[4.5]decan-10-yl)methyl)-1,5-dihydro-4H-pyrazolo[3,4-d]pyrimidin-4-one

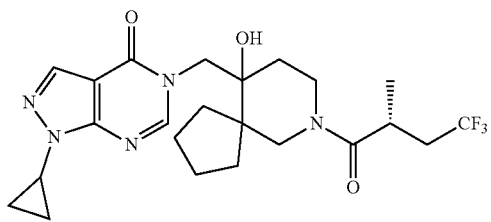 [SMILES: C[C@H](CC(F)(F)F)C(=O)N1CCC(O)(Cn2cnc3c(cnn3C3CC3)c2=O)C2(CCCC2)C1]

Step 1: tert-Butyl 10-((1-cyclopropyl-4-oxo-1,4-dihydro-5H-pyrazolo[3,4-d]pyrimidin-5-yl)methyl)-10-hydroxy-7-azaspiro[4.5]decane-7-carboxylate: Prepared according to General procedure 2 using 1-cyclopropyl-1,5-dihydro-4H-pyrazolo[3,4-d]pyrimidin-4-one (0.30 g, 1.7 mmol), Epoxide 2 (0.68 g, 2.6 mmol), cesium carbonate (0.83 g, 2.6 mmol) in DMF (3.0 mL), heated to 80° C. for 24 h to give the title compound (0.50 g, 66%). LCMS (Method C): $R_T$=1.46 min, m/z=388 [M-butene+H]$^+$.

Step 2: 1-Cyclopropyl-5-((10-hydroxy-7-azaspiro[4.5]decan-10-yl)methyl)-1,5-dihydro-4H-pyrazolo[3,4-d]pyrimidin-4-one: Prepared according to General Procedure 3 using tert-butyl 10-((1-cyclopropyl-4-oxo-1,4-dihydro-5H-pyrazolo[3,4-d]pyrimidin-5-yl)methyl)-10-hydroxy-7-azaspiro[4.5]decane-7-carboxylate (100 mg, 0.226 mmol), TFA (1 mL) and DCM (2 mL), stirred at rt for 1 h to give the title compound (58 mg, 75%). LCMS (Method B): $R_T$=0.60 min, m/z=344 [M+H]$^+$.

Step 3: 1-Cyclopropyl-5-((10-hydroxy-7-((R)-4,4,4-trifluoro-2-methylbutanoyl)-7-azaspiro[4.5]decan-10-yl)methyl)-1,5-dihydro-4H-pyrazolo[3,4-d]pyrimidin-4-one: Prepared according to General Procedure 4 using 1-cyclopropyl-5-((10-hydroxy-7-azaspiro[4.5]decan-10-yl)methyl)-1,5-dihydro-4H-pyrazolo[3,4-d]pyrimidin-4-one (21 mg, 61.1 µmol), Acid 3 (11.5 mg, 73.4 µmol), HATU (30.2 mg, 79.5 µmol) and DIPEA (32 µL, 0.183 mmol) in DCM (1 mL), stirred at rt for 45 min to give the title compound (17.4 mg, 58%) as a colourless solid. LCMS (Method B): $R_T$=1.15 min, m/z=482 [M+H]$^+$. $^1$H NMR (500 MHz, DMSO-d$_6$): δ 8.29 (d, J=3.9 Hz, 1H), 8.02 (d, J=3.4 Hz, 1H), 4.82-4.73 (m, 1H), 4.73-4.49 (m, 1H), 3.86 (tt, J=7.4, 3.8 Hz, 1H), 3.74-3.47 (m, 3H), 3.37 (ddd, J=21.2, 14.3, 9.4 Hz, 1H), 3.24 (d, J=21.8 Hz, 1H), 3.19-3.03 (m, 1H), 2.84-2.65 (m, 1H), 2.32-2.18 (m, 1H), 2.08-1.88 (m, 1H), 1.81-1.48 (m, 5H), 1.48-1.01 (m, 11H).

Example 182: 5-((10-Hydroxy-7-((R)-2-phenylpiperazine-1-carbonyl)-7-azaspiro[4.5]decan-10-yl)methyl)-1-methyl-1,5-dihydro-4H-pyrazolo[3,4-d]pyrimidin-4-one

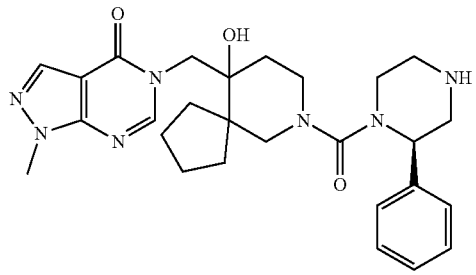 [SMILES: Cn1ncc2c(=O)n(CC3(O)CCN(C(=O)N4CCNC[C@H]4c4ccccc4)CC34CCCC4)cnc21]

Step 1: tert-Butyl (3R)-4-(10-hydroxy-10-((1-methyl-4-oxo-1,4-dihydro-5H-pyrazolo[3,4-d]pyrimidin-5-yl)methyl)-7-azaspiro[4.5]decane-7-carbonyl)-3-phenylpiperazine-1-carboxylate: Prepared according to General Procedure 9 using 5-((10-hydroxy-7-azaspiro[4.5]decan-10-yl)methyl)-1-methyl-1,5-dihydro-4H-pyrazolo[3,4-d]pyrimidin-4-one (24 mg, 75.1 µmol), tert-butyl (R)-4-(chlorocarbonyl)-3-phenylpiperazine-1-carboxylate (29.5 mg, 90.7 µmol), DIPEA (53 µL, 0.303 mmol) and DCM (1 mL), stirred at rt for 20 h to give the title compound (20 mg, 43%). LCMS (Method B): $R_T$=1.35 min, m/z=550 [M-butene+H]$^+$.

Step 2: 5-((10-Hydroxy-7-((R)-2-phenylpiperazine-1-carbonyl)-7-azaspiro[4.5]decan-10-yl)methyl)-1-methyl-1,5-dihydro-4H-pyrazolo[3,4-d]pyrimidin-4-one: Prepared according to General Procedure 3 using tert-butyl (3R)-4-(10-hydroxy-10-((1-methyl-4-oxo-1,4-dihydro-5H-pyrazolo[3,4-d]pyrimidin-5-yl)methyl)-7-azaspiro[4.5]decane-7-carbonyl)-3-phenylpiperazine-1-carboxylate (20 mg, 33.0 µmol), TFA (0.5 mL) and DCM (1 mL), stirred at rt for 45 min to give the title compound (16.2 mg, 93%) as a colourless solid. LCMS (Method B): $R_T$=0.71 min, m/z=506 [M+H]$^+$. $^1$H NMR (500 MHz, DMSO-d$_6$): δ 8.28 (d, J=1.8 Hz, 1H), 8.07 (d, J=5.9 Hz, 1H), 7.31-7.24 (m, 4H), 7.23-7.14 (m, 1H), 4.67 (d, J=5.7 Hz, 1H), 4.60 (dd, J=20.1, 13.8 Hz, 1H), 4.28 (dt, J=22.5, 5.2 Hz, 1H), 3.91 (s, 3H), 3.63 (t, J=14.4 Hz, 1H), 3.55 (dt, J=10.8, 5.3 Hz, 1H), 3.27-2.85 (m, 7H), 2.81-2.70 (m, 2H), 1.93-1.82 (m, 1H), 1.67-1.01 (m, 9H). NH signal not observed.

Example 183: 1-Cyclopropyl-5-((10-hydroxy-7-((R)-2-phenylpiperazine-1-carbonyl)-7-azaspiro[4.5]decan-10-yl)methyl)-1,5-dihydro-4H-pyrazolo[3,4-d]pyrimidin-4-one

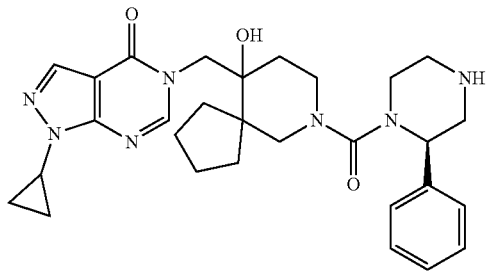 [SMILES: O=C(N1CCC(O)(Cn2cnc3c(cnn3C3CC3)c2=O)C2(CCCC2)C1)N1CCNC[C@H]1c1ccccc1]

Step 1: tert-Butyl (3R)-4-(10-((1-cyclopropyl-4-oxo-1,4-dihydro-5H-pyrazolo[3,4-d]pyrimidin-5-yl)methyl)-10-hydroxy-7-azaspiro[4.5]decane-7-carbonyl)-3-phenylpiperazine-1-carboxylate: Prepared according to General Procedure 9 using 1-cyclopropyl-5-((10-hydroxy-7-azaspiro[4.5]decan-10-yl)methyl)-1,5-dihydro-4H-pyrazolo[3,4-d]pyrimidin-4-one (21 mg, 60.8 µmol), tert-butyl (R)-4-(chlorocarbonyl)-3-phenylpiperazine-1-carboxylate (23.7 mg, 70.0 µmol), DIPEA (41 µL, 0.233 mmol) and DCM (1 mL), stirring at rt for 20 h to give the title compound (21 mg, 54%). LCMS (Method B): $R_T$=1.44 min, m/z=576 [M-butene+H]$^+$.

Step 2: 1-Cyclopropyl-5-((10-hydroxy-7-((R)-2-phenylpiperazine-1-carbonyl)-7-azaspiro[4.5]decan-10-yl)methyl)-1,5-dihydro-4H-pyrazolo[3,4-d]pyrimidin-4-one: Prepared according to General Procedure 3 using tert-butyl (3R)-4-(10-((1-cyclopropyl-4-oxo-1,4-dihydro-5H-pyrazolo[3,4-d]pyrimidin-5-yl)methyl)-10-hydroxy-7-azaspiro[4.5]decane-7-carbonyl)-3-phenylpiperazine-1-carboxylate (20 mg, 31.7 µmol), TFA (0.5 mL) and DCM (1 mL), stirred at rt for 45 min to give the title compound (16.5 mg, 96%) as a colourless solid. LCMS (Method B): $R_T$=0.77 min, m/z=532 [M+H]$^+$. $^1$H NMR (500 MHz, DMSO-d$_6$): δ 8.28 (d, J=1.9 Hz, 1H), 8.02 (d, J=6.0 Hz, 1H), 7.32-7.24 (m, 4H), 7.22-7.15 (m, 1H), 4.68 (d, J=6.6 Hz, 1H), 4.60 (dd, J=20.8, 13.8 Hz, 1H), 4.29 (dt, J=23.7, 5.2 Hz, 1H), 3.86 (tt, J=7.4, 3.8 Hz, 1H), 3.62 (t, J=14.5 Hz, 1H), 3.58-3.50 (m, 1H), 3.27-2.84 (m, 7H), 2.76 (dt, J=9.6, 5.5 Hz, 2H), 1.87 (dq, J=13.4, 6.4 Hz, 1H), 1.67-1.01 (m, 13H). NH signal not observed.

Example 184: 6-(((S)-10-Hydroxy-7-((R)-2-phenylpiperazine-1-carbonyl)-7-azaspiro[4.5]decan-10-yl)methyl)-2-(methylthio)pyrido[4,3-d]pyrimidin-5(6H)-one

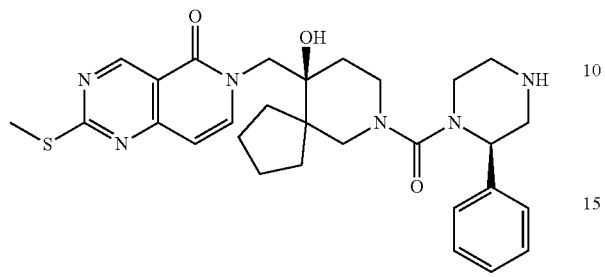

Step 1: tert-Butyl (S)-10-hydroxy-10-((2-(methylthio)-5-oxopyrido[4,3-d]pyrimidin-6(5H)-yl)methyl)-7-azaspiro[4.5]decane-7-carboxylate: tert-Butyl 10-hydroxy-10-((2-(methylthio)-5-oxopyrido[4,3-d]pyrimidin-6(5H)-yl)methyl)-7-azaspiro[4.5]decane-7-carboxylate (1.06 g) was resolved into the single stereoisomers by chiral supercritical fluid chromatography using an Amy-C (20 mm×250 mm, 5 μm) column with isocratic solvent conditions: 45:55 EtOH/$CO_2$. The first eluted material afforded tert-butyl (S)-10-hydroxy-10-((2-(methylthio)-5-oxopyrido[4,3-d]pyrimidin-6(5H)-yl)methyl)-7-azaspiro[4.5]decane-7-carboxylate (482 mg, 45% recovery). Chiral purity (Method A): $R_T$=1.66 min, 100% ee. The second eluted material afforded tert-butyl (R)-10-hydroxy-10-((2-(methylthio)-5-oxopyrido[4,3-d]pyrimidin-6(5H)-yl)methyl)-7-azaspiro[4.5]decane-7-carboxylate (465 mg, 44% recovery). Chiral purity (Method A): $R_T$=3.31 min, >99.9% ee.

Step 2: (S)-6-((10-Hydroxy-7-azaspiro[4.5]decan-10-yl)methyl)-2-(methylthio)pyrido[4,3-d]pyrimidin-5(6H)-one: Prepared according to General Procedure 3 using tert-butyl (S)-10-hydroxy-10-((2-(methylthio)-5-oxopyrido[4,3-d]pyrimidin-6(5H)-yl)methyl)-7-azaspiro[4.5]decane-7-carboxylate (230 mg, 0.499 mmol), TFA (3 mL) and DCM (6 mL), stirred at rt for 1 h to give the title compound (167 mg, 92%). LCMS (Method A): $R_T$=0.62 min, m/z=361 [M+H]$^+$.

Step 3: tert-Butyl (R)-4-((S)-10-hydroxy-10-((2-(methylthio)-5-oxopyrido[4,3-d]pyrimidin-6(5H)-yl)methyl)-7-azaspiro[4.5]decane-7-carbonyl)-3-phenylpiperazine-1-carboxylate: Prepared according to General Procedure 9 using (S)-6-((10-hydroxy-7-azaspiro[4.5]decan-10-yl)methyl)-2-(methylthio)pyrido[4,3-d]pyrimidin-5(6H)-one (50 mg, 0.137 mmol), tert-butyl (R)-4-(chlorocarbonyl)-3-phenylpiperazine-1-carboxylate (58.6 mg, 0.180 mmol), DIPEA (97 μL, 0.555 mmol) and DCM (1.5 mL), stirring at rt for 7 h to give the title compound (15 mg, 66%). LCMS (Method B): $R_T$=1.74 min, m/z=649 [M+H]$^+$; 593 [M-butene+H]$^+$.

Step 4: 6-(((S)-10-Hydroxy-7-((R)-2-phenylpiperazine-1-carbonyl)-7-azaspiro[4.5]decan-10-yl)methyl)-2-(methylthio)pyrido[4,3-d]pyrimidin-5(6H)-one: Prepared according to General Procedure 3 using tert-butyl (R)-4-((S)-10-hydroxy-10-((2-(methylthio)-5-oxopyrido[4,3-d]pyrimidin-6(5H)-yl)methyl)-7-azaspiro[4.5]decane-7-carbonyl)-3-phenylpiperazine-1-carboxylate (15 mg, 23.1 μmol), TFA (0.5 mL) and DCM (1 mL), stirred at rt for 1 h to give the title compound (11.4 mg, 88%) as a colourless solid. LCMS (Method A): $R_T$=0.76 min, m/z=549 [M+H]$^+$. $^1$H NMR (500 MHz, DMSO-$d_6$): δ 9.23 (s, 1H), 7.92 (d, J=7.6 Hz, 1H), 7.38-7.15 (m, 6H), 4.65 (s, 1H), 4.61 (d, J=13.6 Hz, 1H), 4.31 (t, J=5.2 Hz, 1H), 3.70-3.52 (m, 2H), 3.19 (d, J=13.0 Hz, 2H), 3.03 (td, J=10.7, 9.4, 5.4 Hz, 2H), 2.92 (dd, J=26.1, 5.5 Hz, 3H), 2.77 (t, J=5.1 Hz, 2H), 2.59 (s, 3H), 1.88 (dd, J=17.3, 11.2 Hz, 1H), 1.66-1.41 (m, 6H), 1.35-1.20 (m, 2H), 1.10-1.01 (m, 1H). NH signal not observed.

Example 185: 6-(((S)-10-Hydroxy-7-((R)-2-phenylpiperazine-1-carbonyl)-7-azaspiro[4.5]decan-10-yl)methyl)pyrido[4,3-d]pyrimidin-5(6H)-one

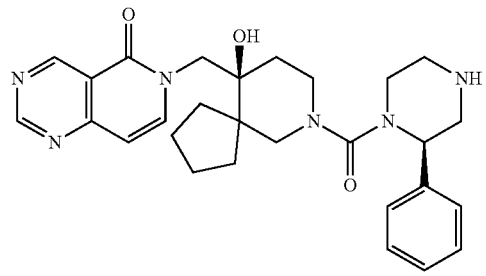 [SMILES: O=C(N1CC[C@@](O)(Cn2ccc3ncncc3c2=O)C2(CCCC2)C1)N1CCNC[C@H]1c1ccccc1]

Step 1: tert-Butyl (R)-4-((S)-10-hydroxy-10-((5-oxopyrido[4,3-d]pyrimidin-6(5H)-yl)methyl)-7-azaspiro[4.5]decane-7-carbonyl)-3-phenylpiperazine-1-carboxylate: To a stirring solution of tert-butyl (R)-4-((S)-10-hydroxy-10-((2-(methylthio)-5-oxopyrido[4,3-d]pyrimidin-6(5H)-yl)methyl)-7-azaspiro[4.5]decane-7-carbonyl)-3-phenylpiperazine-1-carboxylate (30 mg, 46.2 μmol) and 10% Pd/C (0.5 mg, 4.6 μmol) in dry THF (0.5 mL) at 0° C. under nitrogen was added triethylsilane (22 μL, 0.139 mmol). The resulting mixture was stirred at 0° C. for 2 h then warmed to rt and stirred for a further 18 h. The reaction mixture was purified directly by flash chromatography to give the title compound (14 mg, 50%). LCMS (Method B): $R_T$=1.32 min, m/z=547 [M-butene+H]$^+$.

Step 2: 6-(((S)-10-Hydroxy-7-((R)-2-phenylpiperazine-1-carbonyl)-7-azaspiro[4.5]decan-10-yl)methyl)pyrido[4,3-d]pyrimidin-5(6H)-one: Prepared according to General Procedure 3 using tert-butyl (R)-4-((S)-10-hydroxy-10-((5-oxopyrido[4,3-d]pyrimidin-6(5H)-yl)methyl)-7-azaspiro[4.5]decane-7-carbonyl)-3-phenylpiperazine-1-carboxylate (14 mg, 23.2 μmol), TFA (0.5 mL) and DCM (1 mL), stirred at rt for 0.5 h to give the title compound (10.9 mg, 90%) as a colourless solid. LCMS (Method B): $R_T$=0.67 min, m/z=503 [M+H]$^+$. $^1$H NMR (500 MHz, DMSO-$d_6$) δ 9.47 (s, 1H), 9.33 (s, 1H), 7.96 (d, J=7.6 Hz, 1H), 7.31-7.23 (m, 4H), 7.18 (tt, J=6.0, 2.2 Hz, 1H), 6.66 (d, J=7.6 Hz, 1H), 4.65 (d, J=12.6 Hz, 2H), 4.32 (t, J=5.2 Hz, 1H), 3.65 (d, J=13.7 Hz, 1H), 3.56 (dt, J=13.1, 5.0 Hz, 1H), 3.22 (dd, J=29.3, 14.3 Hz, 2H), 3.09-2.99 (m, 2H), 2.98-2.86 (m, 3H), 2.78 (t, J=5.1 Hz, 2H), 1.89 (dd, J=12.3, 6.1 Hz, 1H), 1.67-1.42 (m, 6H), 1.40-1.19 (m, 2H), 1.06 (dt, J=13.1, 6.4 Hz, 1H). NH signal not observed.

Example 186: 1-((10-Hydroxy-7-((R)-2-phenylpiperazine-1-carbonyl)-7-azaspiro[4.5]decan-10-yl)methyl)-5-(methylthio)-4-phenylpyridin-2(1H)-one

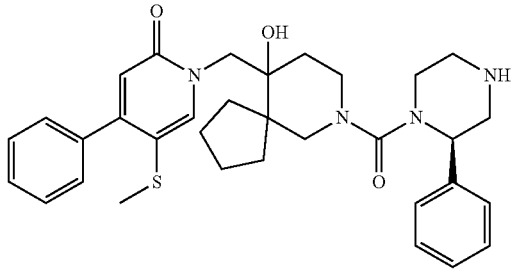 [SMILES: CSc1cn(CC2(O)CCN(C(=O)N3CCNC[C@H]3c3ccccc3)CC23CCCC3)c(=O)cc1-c1ccccc1]

Step 1: 5-(Methylthio)-4-phenylpyridin-2-amine: Prepared according to General Procedure 5 using 4-chloro-5-(methylthio)pyridin-2-amine (3.00 g, 17.2 mmol), phenylboronic acid (3.14 g, 25.8 mmol), sodium carbonate (3.64 g, 34.4 mmol) and Pd(dppf)Cl$_2$·DCM (0.707 g, 0.859 mmol) in 1,4-dioxane (26 mL) and water (9 mL), divided equally between 2×10-20 mL microwave vials. The reaction was heated under microwave irradiation at 120° C. for 3 h to give the title compound (2.65 g, 71%). LCMS (Method B): R$_T$=0.70 min, m/z=217 [M+H]$^+$.

Step 2: 5-(Methylthio)-4-phenylpyridin-2(1H)-one: To a solution of 5-(methylthio)-4-phenylpyridin-2-amine (2.6 g, 12.0 mmol) and water (0.24 mL, 13.2 mmol) in DMF (60 mL) was added tert-butyl nitrite (2.86 mL, 24.0 mmol). The resulting mixture was stirred at rt for 21 h. The reaction was quenched with water and extracted with DCM (×3) using a phase separator. The combined organic phase was concentrated in vacuo and the crude material was purified by flash chromatography to give the title compound (820 mg, 31%). LCMS (Method B): R$_T$=0.92 min, m/z=218 [M+H]$^+$.

Step 3: tert-Butyl 10-hydroxy-10-((5-(methylthio)-2-oxo-4-phenylpyridin-1(2H)-yl)methyl)-7-azaspiro[4.5]decane-7-carboxylate: Prepared according to General Procedure 2 using 5-(methylthio)-4-phenylpyridin-2(1H)-one (0.80 g, 3.68 mmol), Epoxide 2 (1.18 g, 4.42 mmol) and cesium carbonate (2.40 g, 7.36 mmol) in DMF (11 mL) at 80° C. for 17 h to give the title compound (1.26 g, 70%) as an off-white foam. LCMS (Method B): R$_T$=1.59 min, m/z=485 [M+H]$^+$; 429 [M-butene+H]$^+$.

Step 4: 1-((10-Hydroxy-7-azaspiro[4.5]decan-10-yl)methyl)-5-(methylthio)-4-phenylpyridin-2(1H)-one: Prepared according to General Procedure 3 using tert-butyl 10-hydroxy-10-((5-(methylthio)-2-oxo-4-phenylpyridin-1(2H)-yl)methyl)-7-azaspiro[4.5]decane-7-carboxylate (1.25 g, 2.58 mmol), TFA (10 mL) and DCM (20 mL), stirred at rt for 1 h to give the title compound (950 mg, 96%). LCMS (Method B): R$_T$=0.82 min, m/z=385 [M+H]$^+$.

Step 5: tert-Butyl (3R)-4-(10-hydroxy-10-((5-(methylthio)-2-oxo-4-phenylpyridin-1(2H)-yl)methyl)-7-azaspiro[4.5]decane-7-carbonyl)-3-phenylpiperazine-1-carboxylate: Prepared according to General Procedure 9 using 1-((10-hydroxy-7-azaspiro[4.5]decan-10-yl)methyl)-5-(methylthio)-4-phenylpyridin-2(1H)-one (200 mg, 0.520 mmol), tert-butyl (R)-4-(chlorocarbonyl)-3-phenylpiperazine-1-carboxylate (203 mg, 0.624 mmol), DIPEA (363 µL, 2.08 mmol) and DCM (5 mL), stirring at rt for 2 h to give the title compound (250 mg, 71%). LCMS (Method B): R$_T$=1.66 min, m/z=673 [M+H]$^+$; 617 [M-butene+H]$^+$.

Step 6: 1-((10-Hydroxy-7-((R)-2-phenylpiperazine-1-carbonyl)-7-azaspiro[4.5]decan-10-yl)methyl)-5-(methylthio)-4-phenylpyridin-2(1H)-one: Prepared according to General Procedure 3 using tert-butyl (3R)-4-(10-hydroxy-10-((5-(methylthio)-2-oxo-4-phenylpyridin-1(2H)-yl)methyl)-7-azaspiro[4.5]decane-7-carbonyl)-3-phenylpiperazine-1-carboxylate (20 mg, 29.7 µmol), TFA (0.5 mL) and DCM (1 mL), stirred at rt for 1 h to give the title compound (14.9 mg, 82%) as a colourless solid. LCMS (Method A): R$_T$=0.90 min, m/z=573 [M+H]$^+$. $^1$H NMR (500 MHz, DMSO-d$_6$): δ 7.86 (d, J=5.9 Hz, 1H), 7.45 (d, J=1.3 Hz, 5H), 7.31-7.16 (m, 5H), 6.34 (d, J=2.9 Hz, 1H), 4.89 (d, J=2.9 Hz, 1H), 4.60 (dd, J=30.1, 13.5 Hz, 1H), 4.30 (dt, J=20.8, 5.2 Hz, 1H), 3.64 (td, J=24.8, 23.8, 13.5 Hz, 2H), 3.38-2.85 (m, 7H (signal obscured by HDO)), 2.77 (t, J=4.9 Hz, 2H), 2.07 (s, 3H), 1.85 (dt, J=13.3, 7.7 Hz, 1H), 1.66-1.39 (m, 6H), 1.35-1.03 (m, 3H). NH signal not observed.

Example 187: 1-((10-Hydroxy-7-((R)-2-phenylpiperazine-1-carbonyl)-7-azaspiro[4.5]decan-10-yl)methyl)-5-(methylsulfinyl)-4-phenylpyridin-2(1H)-one

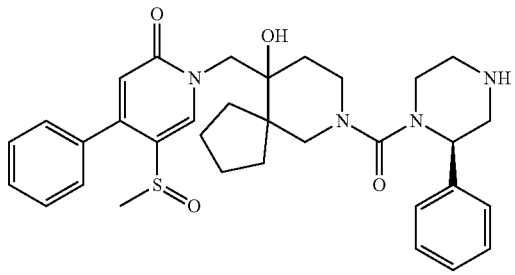 [SMILES: CS(=O)c1cn(CC2(O)CCN(C(=O)N3CCNC[C@H]3c3ccccc3)CC23CCCC3)c(=O)cc1-c1ccccc1]

Step 1: tert-Butyl (3R)-4-(10-hydroxy-10-((5-(methylsulfinyl)-2-oxo-4-phenylpyridin-1(2H)-yl)methyl)-7-azaspiro[4.5]decane-7-carbonyl)-3-phenylpiperazine-1-carboxylate: To a stirring solution of tert-butyl (3R)-4-(10-hydroxy-10-((5-(methylthio)-2-oxo-4-phenylpyridin-1(2H)-yl)methyl)-7-azaspiro[4.5]decane-7-carbonyl)-3-phenylpiperazine-1-carboxylate (30 mg, 44.6 µmol) in DCM (2 mL) at rt was added mCPBA (<77% pure) (12 mg, 53.5 µmol). The resulting reaction was stirred at rt for 17 h before purifying directly by flash chromatography to give the title compound (20 mg, 65%). LCMS (Method B): R$_T$=1.41 min, m/z=689 [M+H]$^+$; 633 [M-butene+H]$^+$.

Step 2: 1-((10-Hydroxy-7-((R)-2-phenylpiperazine-1-carbonyl)-7-azaspiro[4.5]decan-10-yl)methyl)-5-(methylsufinyl)-4-phenylpyridin-2(1H)-one: Prepared according to General Procedure 3 using tert-butyl (3R)-4-(10-hydroxy-10-((5-(methylsulfinyl)-2-oxo-4-phenylpyridin-1(2H)-yl)methyl)-7-azaspiro[4.5]decane-7-carbonyl)-3-phenylpiperazine-1-carboxylate (20 mg, 29.0 µmol), TFA (0.5 mL) and DCM (1 mL), stirred at rt for 1 h to give the title compound (16.1 mg, 93%) as a colourless solid. LCMS (Method A): R$_T$=0.73 min (solvent front), m/z=589 [M+H]$^+$. $^1$H NMR (500 MHz, DMSO-d$_6$): δ 8.18 (m, 1H), 7.54-7.44 (m, 5H), 7.33-7.25 (m, 4H), 7.19 (dtt, J=6.6, 4.6, 2.5 Hz, 1H), 6.38 (t, J=4.0 Hz, 1H), 4.89-4.84 (m, 1H), 4.75 (ddd, J=28.3, 21.3, 13.5 Hz, 1H), 4.36-4.24 (m, 1H), 3.75-3.52 (m, 2H), 3.40-2.86 (m, 7H (signal obscured by HDO)), 2.78 (q, J=5.2, 4.6 Hz, 2H), 2.45-2.32 (m, 3H (signal obscured by DMSO satellite)), 1.93-1.80 (m, 1H), 1.70-1.17 (m, 8H), 1.16-1.03 (m, 1H). NH signal not observed.

Example 188: 1-((10-Hydroxy-7-((R)-2-phenylpiperazine-1-carbonyl)-7-azaspiro[4.5]decan-10-yl)methyl)-5-(methylsulfonyl)-4-phenylpyridin-2(1H)-one

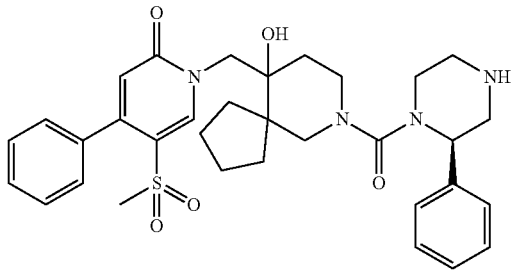 [SMILES: CS(=O)(=O)c1cn(CC2(O)CCN(C(=O)N3CCNC[C@H]3c3ccccc3)CC23CCCC3)c(=O)cc1-c1ccccc1]

Step 1: tert-Butyl (3R)-4-(10-hydroxy-10-((5-(methylsulfonyl)-2-oxo-4-phenylpyridin-1(2H)-yl)methyl)-7-azaspiro[4.5]decane-7-carbonyl)-3-phenylpiperazine-1-carboxylate: To a stirring solution of tert-butyl (3R)-4-(10-hydroxy-10-((5-(methylthio)-2-oxo-4-phenylpyridin-1(2H)-yl)methyl)-7-azaspiro[4.5]decane-7-carbonyl)-3-phenylpiperazine-1-carboxylate (30 mg, 44.6 µmol) in DCM (2 mL) at rt was added mCPBA (<77% pure) (24 mg, 0.107 mmol). The resulting reaction was stirred at rt for 17 h before purifying directly by flash chromatography to give the title compound (20 mg, 63%). LCMS (Method B): $R_T$=1.50 min, m/z=649 [M-butene+H]$^+$.

Step 2: 1-((10-Hydroxy-7-((R)-2-phenylpiperazine-1-carbonyl)-7-azaspiro[4.5]decan-10-yl)methyl)-5-(methylsulfonyl)-4-phenylpyridin-2(1H)-one: Prepared according to General Procedure 3 using tert-butyl (3R)-4-(10-hydroxy-10-((5-(methylsulfonyl)-2-oxo-4-phenylpyridin-1(2H)-yl)methyl)-7-azaspiro[4.5]decane-7-carbonyl)-3-phenylpiperazine-1-carboxylate (20 mg, 28.4 µmol), TFA (0.5 mL) and DCM (1 mL), stirred at rt for 1 h to give the title compound (17.7 mg, quantitative) as a colourless solid. LCMS (Method A): $R_T$=0.77 min, m/z=605 [M+H]$^+$. $^1$H NMR (500 MHz, DMSO-d$_6$): δ 8.48 (d, J=4.6 Hz, 1H), 7.49-7.41 (m, 5H), 7.32-7.25 (m, 4H), 7.19 (ddt, J=8.6, 6.1, 2.6 Hz, 1H), 6.29 (d, J=4.4 Hz, 1H), 4.92 (d, J=7.6 Hz, 1H), 4.76 (dd, J=20.6, 13.3 Hz, 1H), 4.30 (dt, J=23.5, 5.2 Hz, 1H), 3.68-3.52 (m, 2H), 3.40-2.86 (m, 7H (signal obscured by HDO)), 2.77 (t, J=5.3 Hz, 2H), 2.75 (s, 3H), 1.91-1.80 (m, 1H), 1.67-1.19 (m, 8H), 1.10 (ddt, J=27.5, 13.7, 6.1 Hz, 1H). NH signal not observed.

Example 189: 1-((10-Hydroxy-7-((R)-2-phenylpiperazine-1-carbonyl)-7-azaspiro[4.5]decan-10-yl)methyl)-5-(S-methylsulfonimidoyl)-4-phenylpyridin-2(1H)-one

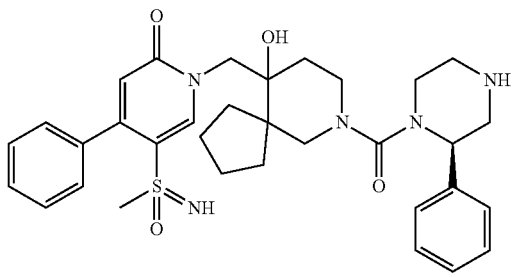 [SMILES: CS(=N)(=O)c1cn(CC2(O)CCN(C(=O)N3CCNC[C@H]3c3ccccc3)CC23CCCC3)c(=O)cc1-c1ccccc1]

Step 1: tert-Butyl (3R)-4-(10-hydroxy-10-((5-(S-methylsulfonimidoyl)-2-oxo-4-phenylpyridin-1(2H)-yl)methyl)-7-azaspiro[4.5]decane-7-carbonyl)-3-phenylpiperazine-1-carboxylate: A solution of tert-butyl (3R)-4-(10-hydroxy-10-((5-(methylthio)-2-oxo-4-phenylpyridin-1(2H)-yl)methyl)-7-azaspiro[4.5]decane-7-carbonyl)-3-phenylpiperazine-1-carboxylate (40 mg, 59.4 µmol), (diacetoxyiodo)benzene (47.9 mg, 0.149 mmol) and ammonium carbamate (9.3 mg, 0.119 mmol) in MeOH (0.25 mL) was stirred at rt for 1.75 h before purifying directly by flash chromatography to give the title compound (20 mg, 47%). LCMS (Method B): $R_T$=1.34 min, m/z=704 [M+H]$^+$; 648 [M-butene+H]$^+$.

Step 2: 1-((10-Hydroxy-7-((R)-2-phenylpiperazine-1-carbonyl)-7-azaspiro[4.5]decan-10-yl)methyl)-5-(S-methylsulfonimidoyl)-4-phenylpyridin-2(1H)-one: Prepared according to General Procedure 3 using tert-butyl (3R)-4-(10-hydroxy-10-((5-(S-methylsulfonimidoyl)-2-oxo-4-phenylpyridin-1(2H)-yl)methyl)-7-azaspiro[4.5]decane-7-carbonyl)-3-phenylpiperazine-1-carboxylate (20 mg, 28.4 µmol), TFA (0.5 mL) and DCM (1 mL), stirred at rt for 1 h to give the title compound (17.5 mg, 94%) as an off-white solid. LCMS (Method A): $R_T$=0.66 min, m/z=604 [M+H]$^+$. $^1$H NMR (500 MHz, DMSO-d$_6$): δ 8.50 (m, 1H), 7.42 (s, 5H), 7.33-7.25 (m, 4H), 7.20 (tq, J=6.1, 2.9, 2.5 Hz, 1H), 6.21 (dd, J=4.7, 1.9 Hz, 1H), 4.90-4.85 (m, 1H), 4.73 (td, J=17.6, 15.4, 7.7 Hz, 1H), 4.32 (dt, J=27.7, 5.0 Hz, 1H), 4.12-3.95 (m, 1H), 3.68-3.54 (m, 2H), 3.41-2.87 (m, 7H (signal obscured by HDO)), 2.85-2.74 (m, 2H), 2.70 (d, J=3.2 Hz, 3H), 1.87 (dd, J=20.0, 13.0 Hz, 1H), 1.67-1.17 (m, 8H), 1.17-1.02 (m, 1H). NH signal not observed.

Example 190: 1-((10-Hydroxy-7-((R)-3-phenylmorpholine-4-carbonyl)-7-azaspiro[4.5]decan-10-yl)methyl)-5-(S-methylsulfonimidoyl)-4-phenylpyridin-2(1H)-one

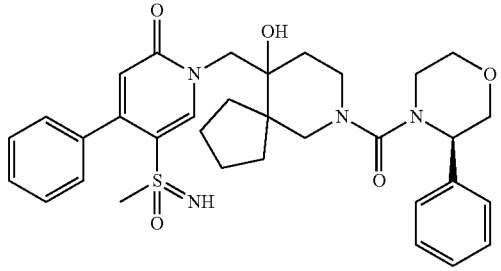 [SMILES: CS(=N)(=O)c1cn(CC2(O)CCN(C(=O)N3CCOC[C@H]3c3ccccc3)CC23CCCC3)c(=O)cc1-c1ccccc1]

Step 1: 1-((10-Hydroxy-7-((R)-3-phenylmorpholine-4-carbonyl)-7-azaspiro[4.5]decan-10-yl)methyl)-5-(methylthio)-4-phenylpyridin-2(1H)-one: Prepared according to General Procedure 9 using 1-((10-hydroxy-7-azaspiro[4.5]decan-10-yl)methyl)-5-(methylthio)-4-phenylpyridin-2(1H)-one (50 mg, 0.130 mmol), (R)-3-phenylmorpholine-4-carbonyl chloride (35.2 mg, 0.156 mol) and DIPEA (91 µL, 0.520 mmol) in DCM (1.5 mL), stirring at rt for 17 h to give the title compound (50 mg, 67%). LCMS (Method B): $R_T$=1.46 min, m/z=574 [M+H]$^+$.

Step 2: 1-((10-Hydroxy-7-((R)-3-phenylmorpholine-4-carbonyl)-7-azaspiro[4.5]decan-10-yl)methyl)-5-(S-methylsulfonimidoyl)-4-phenylpyridin-2(1H)-one: A solution of 1-((10-hydroxy-7-((R)-3-phenylmorpholine-4-carbonyl)-7-azaspiro[4.5]decan-10-yl)methyl)-5-(methylthio)-4-phenylpyridin-2(1H)-one (35 mg, 61.0 µmol), (diacetoxyiodo)benzene (49.1 mg, 0.153 mmol) and ammonium carbamate (9.5 mg, 0.122 mmol) in MeOH (0.3 mL) was stirred at rt for 45 min before purifying directly by flash chromatography to give the title compound (10.2 mg, 27%). LCMS (Method B): $R_T$=1.11 min, m/z=605 [M+H]$^+$. $^1$H NMR (400 MHz, DMSO-d$_6$): δ 8.50 (dd, J=6.0, 3.3 Hz, 1H), 7.42 (s, 5H), 7.36-7.27 (m, 4H), 7.24 (tt, J=6.1, 2.4 Hz, 1H), 6.24-6.17 (m, 1H), 4.94-4.87 (m, 1H), 4.75 (dd, J=24.3, 15.3 Hz, 1H), 4.45-4.34 (m, 1H), 4.06 (d, J=50.8 Hz, 1H), 3.81-3.52 (m, 6H), 3.47-2.96 (m, 5H (signal obscured by HDO)), 2.70 (d, J=2.3 Hz, 3H), 1.87 (dd, J=18.5, 8.3 Hz, 1H), 1.70-1.03 (m, 9H).

Example 191: 5-((Dimethyl(oxo)-λ$^6$-sulfaneylidene)amino)-1-((10-hydroxy-7-((R)-2-phenylpiperazine-1-carbonyl)-7-azaspiro[4.5]decan-10-yl)methyl)-4-phenylpyridin-2(1H)-one

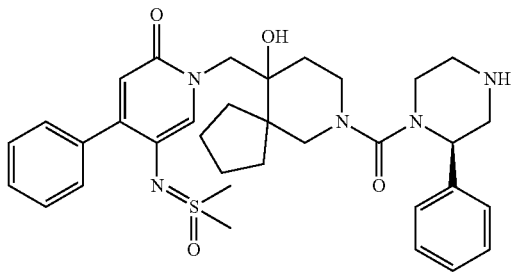 [SMILES: CS(C)(=O)=Nc1cn(CC2(O)CCN(C(=O)N3CCNC[C@H]3c3ccccc3)CC23CCCC3)c(=O)cc1-c1ccccc1]

Step 1: tert-Butyl (3R)-4-(10-((5-((dimethyl(oxo)-λ$^6$-sulfaneylidene)amino)-2-oxo-4-phenylpyridin-1(2H)-yl)methyl)-10-hydroxy-7-azaspiro[4.5]decane-7-carbonyl)-3-phenylpiperazine-1-carboxylate: Prepared according to General Procedure 9 using 5-((dimethyl(oxo)-λ$^6$-sulfaneylidene)amino)-1-((10-hydroxy-7-azaspiro[4.5]decan-10-yl)methyl)-4-phenylpyridin-2(1H)-one (20.0 mg, 0.0466 mmol), tert-butyl (R)-4-(chlorocarbonyl)-3-phenylpiperazine-1-carboxylate (22.7 mg, 0.0698 mmol), DIPEA (24.4 µL, 0.140 mmol) and DCM (1 mL), stirring at rt for 2 h to give the title compound (17.4 mg, 52%). LCMS (Method A): $R_T$=1.47 min, m/z=718 [M+H]$^+$.

Step 2: 5-((Dimethyl(oxo)-λ$^6$-sulfaneylidene)amino)-1-((10-hydroxy-7-((R)-2-phenylpiperazine-1-carbonyl)-7-azaspiro[4.5]decan-10-yl)methyl)-4-phenylpyridin-2(1H)-one: Prepared according to General Procedure 3 using tert-butyl (3R)-4-(10-((5-((dimethyl(oxo)-λ$^6$-sulfaneylidene)amino)-2-oxo-4-phenylpyridin-1(2H)-yl)methyl)-10-hydroxy-7-azaspiro[4.5]decane-7-carbonyl)-3-phenylpiperazine-1-carboxylate (17.4 mg, 24.2 µmol), TFA (0.5 mL) and DCM (1 mL), stirred at rt for 1 h to give the title compound (5.1 mg, 34%) as a pale yellow solid after lyophilisation. LCMS (Method B): $R_T$=0.78 min, m/z=618 [M+H]$^+$. $^1$H NMR (500 MHz, DMSO-d$_6$): δ 7.57-7.50 (m, 2H), 7.46-7.12 (m, 9H), 6.39-6.34 (m, 1H), 5.25-5.10 (m, 1H), 4.68-4.37 (m, 1H), 4.34-4.23 (m, 1H), 3.73 (br t, 1H), 3.63-2.98 (m, 11H, overlapping HDO peak), 2.98-2.92 (m, 3H), 2.89 (br t, 1H), 2.80-2.71 (m, 1H), 1.97-0.66 (m, 11H).

Example 192: N-Benzyl-10-hydroxy-10-((2-oxo-4-phenylpyridin-1(2H)-yl)methyl)-7-azaspiro[4.5]decane-7-carboxamide

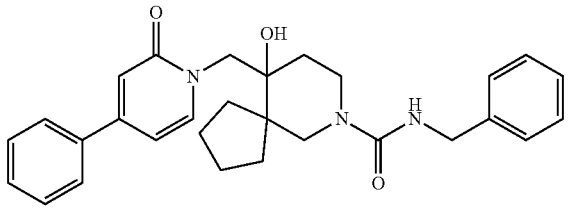 [SMILES: O=C(NCc1ccccc1)N1CCC(O)(Cn2ccc(-c3ccccc3)cc2=O)C2(CCCC2)C1]

Step 1: tert-Butyl 10-((4-chloro-2-oxopyridin-1(2H)-yl)methyl)-10-hydroxy-7-azaspiro[4.5]decane-7-carboxylate: Prepared according to General Procedure 2 using 4-chloropyridin-2(1H)-one (648 mg, 5.00 mmol), Epoxide 2 (1.34 g, 5.00 mmol) and cesium carbonate (1.79 g, 5.50 mmol) in DMF (25 mL) at 80° C. for 19 h 20 min to give the title compound (1.18 g, 59%) as a colourless solid. LCMS (Method A): $R_T$=1.49 min, m/z=397, 399 [M+H]$^+$. $^1$H NMR (500 MHz, DMSO-d$_6$): δ 7.72 (d, J=7.3 Hz, 1H), 6.55 (d, J=2.4 Hz, 1H), 6.38 (dd, J=7.3, 2.4 Hz, 1H), 4.76 (s, 1H), 4.53 (d, J=13.5 Hz, 1H), 3.59 (d, J=13.6 Hz, 1H), 3.56-3.50 (m, 1H), 3.26-3.09 (m, 3H), 1.91-1.82 (m, 1H), 1.69-1.48 (m, 5H), 1.38 (s, 9H), 1.45-1.23 (m, 2H), 1.18-1.08 (m, 2H).

Step 2: tert-Butyl 10-hydroxy-10-((2-oxo-4-phenylpyridin-1(2H)-yl)methyl)-7-azaspiro[4.5]decane-7-carboxylate: Prepared according to General Procedure 5 using tert-butyl 10-((4-chloro-2-oxopyridin-1(2H)-yl)methyl)-10-hydroxy-7-azaspiro[4.5]decane-7-carboxylate (155 mg, 0.390 mmol), phenylboronic acid (71.4 mg, 0.586 mmol), Pd(dppf)Cl$_2$·DCM (16.5 mg, 0.0195 mmol) and sodium carbonate (82.8 mg, 0.781 mmol) in 1,4-dioxane (1.5 mL) and water (0.5 mL) under microwave irradiation at 130° C. for 30 min to give the title compound (135 mg, 78%) as an off-white solid. LCMS (Method A): $R_T$=1.65 min, m/z=439 [M+H]$^+$.

Step 3: 1-((10-Hydroxy-7-azaspiro[4.5]decan-10-yl)methyl)-4-phenylpyridin-2(1H)-one: A solution of tert-butyl 10-hydroxy-10-((2-oxo-4-phenylpyridin-1(2H)-yl)methyl)-7-azaspiro[4.5]decane-7-carboxylate (135 mg, 0.307 mmol) in TFA (1 mL) and DCM (2 mL) was stirred at rt for 15 min before the reaction mixture was loaded on to a 2 g SCX-2 cartridge that was pre-equilibrated with 1:1 DCM/MeOH. The cartridge was washed with 1:1 DCM/MeOH (50 mL) before the product was eluted with 1:1 DCM/7 M NH$_3$ in MeOH (30 mL). The basic eluents were concentrated under reduced pressure to give the title compound (98 mg, 94%) as a colourless solid. LCMS (Method A): $R_T$=0.77 min, m/z=339 [M+H]$^+$.

Step 4: 4-Nitrophenyl 10-hydroxy-10-((2-oxo-4-phenylpyridin-1(2H)-yl)methyl)-7-azaspiro[4.5]decane-7-carboxylate: 4-Nitrophenyl chloroformate (175 mg, 0.869 mmol) was added in one portion to a solution of 1-((10-hydroxy-7-azaspiro[4.5]decan-10-yl)methyl)-4-phenylpyridin-2(1H)-one (98 mg, 0.290 mmol) and pyridine (70 µL, 0.869 mmol) in DCM (3 mL) at rt. After 16 h, the reaction mixture was purified directly by flash chromatography (0-100% EtOAc in cyclohexane) to give the title compound (127 mg, 87%) as an off-white solid. LCMS (Method A): $R_T$=1.61 min, m/z=504 [M+H]$^+$.

Step 5: N-Benzyl-10-hydroxy-10-((2-oxo-4-phenylpyridin-1(2H)-yl)methyl)-7-azaspiro[4.5]decane-7-carboxamide: Prepared according to General Procedure 10 using 4-nitrophenyl 10-hydroxy-10-((2-oxo-4-phenylpyridin-1(2H)-yl)methyl)-7-azaspiro[4.5]decane-7-carboxylate (20 mg, 0.0348 mmol) and benzylamine (19 μL, 0.174 mmol) in DMA (0.35 mL) for 18 h to give the title compound (13.5 mg, 80%) as a very light yellow solid after lyophilisation. LCMS (Method B): $R_T$=1.32 min, m/z=472 [M+H]$^+$. $^1$H NMR (500 MHz, DMSO-d$_6$): δ 7.79 (d, J=7.1 Hz, 1H), 7.77-7.71 (m, 2H), 7.53-7.44 (m, 3H), 7.32-7.26 (m, 2H), 7.26-7.22 (m, 2H), 7.22-7.17 (m, 1H), 6.96 (t, J=5.9 Hz, 1H), 6.72 (d, J=2.1 Hz, 1H), 6.64 (dd, J=7.2, 2.1 Hz, 1H), 4.96 (s, 1H), 4.53 (d, J=13.5 Hz, 1H), 4.23 (d, J=5.7 Hz, 2H), 3.75 (d, J=13.6 Hz, 1H), 3.62-3.53 (m, 1H), 3.27-3.18 (m, 3H), 1.94-1.86 (m, 1H), 1.72-1.58 (m, 4H), 1.57-1.49 (m, 1H), 1.45-1.36 (m, 2H), 1.23-1.14 (m, 2H).

Example 193: N-Benzyl-10-hydroxy-10-((6-oxo-4-phenylpyrimidin-1(6H)-yl)methyl)-7-azaspiro[4.5]decane-7-carboxamide

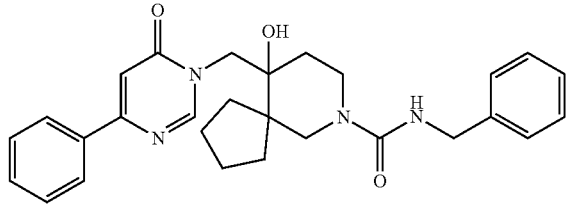 [SMILES: O=C(NCc1ccccc1)N1CCC(O)(Cn2cnc(-c3ccccc3)cc2=O)C2(CCCC2)C1]

Step 1: tert-Butyl 10-((4-chloro-6-oxopyrimidin-1(6H)-yl)methyl)-10-hydroxy-7-azaspiro[4.5]decane-7-carboxylate: Prepared according to General Procedure 2 using 6-chloropyrimidin-4(3H)-one (8.88 g, 68.0 mmol), Epoxide 2 (18.2 g, 68.0 mmol) and potassium tert-butoxide (8.40 g, 74.8 mmol) in NMP (68 mL) at 110° C. for 16 h to give the title compound (4.44 g, 16%) as a pale yellow solid. LCMS (Method A): $R_T$=1.41 min, m/z=342, 344 [M-butene+H]$^+$. $^1$H NMR (500 MHz, DMSO-d$_6$): δ 8.33 (s, 1H), 6.61 (s, 1H), 4.81 (s, 1H), 4.50 (d, J=13.5 Hz, 1H), 3.57 (d, J=13.5 Hz, 1H), 3.55-3.49 (m, 1H), 3.26-3.09 (m, 3H), 1.93-1.85 (m, 1H), 1.68-1.50 (m, 5H), 1.44-1.33 (m, 1H), 1.39 (s, 9H), 1.33-1.23 (m, 1H), 1.20-1.10 (m, 2H).

Step 2: tert-Butyl 10-hydroxy-10-((6-oxo-4-phenylpyrimidin-1(6H)-yl)methyl)-7-azaspiro[4.5]decane-7-carboxylate: Prepared according to General Procedure 5 using tert-butyl 10-((4-chloro-6-oxopyrimidin-1(6H)-yl)methyl)-10-hydroxy-7-azaspiro[4.5]decane-7-carboxylate (94 mg, 0.236 mmol), phenylboronic acid (43.2 mg, 0.354 mmol), Pd(dppf)Cl$_2$·DCM (10 mg, 0.0118 mmol) and sodium carbonate (50.1 mg, 0.473 mmol) in 1,4-dioxane (1.5 mL) and water (0.5 mL) under microwave irradiation at 130° C. for 30 min to give the title compound (48.2 mg, 46%) as a yellow solid. LCMS (Method A): $R_T$=1.61 min, m/z=440 [M+H]$^+$.

Step 3: 3-((10-Hydroxy-7-azaspiro[4.5]decan-10-yl)methyl)-6-phenylpyrimidin-4(3H)-one: A solution of tert-butyl 10-hydroxy-10-((6-oxo-4-phenylpyrimidin-1(6H)-yl)methyl)-7-azaspiro[4.5]decane-7-carboxylate (48 mg, 0.109 mmol) in TFA (1 mL) and DCM (2 mL) was stirred at rt for 10 min before the reaction mixture was loaded on to a 2 g SCX-2 cartridge that was pre-equilibrated with 1:1 DCM/MeOH. The cartridge was washed with 1:1 DCM/MeOH (50 mL) before the product was eluted with 1:1 DCM/7 M NH$_3$ in MeOH (30 mL). The basic eluents were concentrated under reduced pressure to give the title compound (33 mg, 89%) as a colourless solid. LCMS (Method A): $R_T$=0.77 min, m/z=340 [M+H]$^+$.

Step 4: 4-Nitrophenyl 10-hydroxy-10-((6-oxo-4-phenylpyrimidin-1(6H)-yl)methyl)-7-azaspiro[4.5]decane-7-carboxylate: 4-Nitrophenyl chloroformate (58.8 mg, 0.292 mmol) was added in one portion to a suspension of 3-((10-hydroxy-7-azaspiro[4.5]decan-10-yl)methyl)-6-phenylpyrimidin-4(3H)-one (33 mg, 0.0972 mmol) and pyridine (24 μL, 0.292 mmol) in DCM (1 mL) at rt. After 16 h, the reaction mixture was purified directly by flash chromatography (0-100% EtOAc in cyclohexane) to give the title compound (21 mg, 42%) as an off-white solid. LCMS (Method A): $R_T$=1.57 min, m/z=505 [M+H]$^+$.

Step 5: N-Benzyl-10-hydroxy-10-((6-oxo-4-phenylpyrimidin-1(6H)-yl)methyl)-7-azaspiro[4.5]decane-7-carboxamide: Prepared according to General Procedure 10 using 4-nitrophenyl 10-hydroxy-10-((6-oxo-4-phenylpyrimidin-1(6H)-yl)methyl)-7-azaspiro[4.5]decane-7-carboxylate (21 mg, 0.0416 mmol) and benzylamine (23 μL, 0.208 mmol) in DMA (0.42 mL) for 18 h to give the title compound (7 mg, 33%) as an off-white solid after lyophilisation. LCMS (Method B): $R_T$=1.30 min, m/z=473 [M+H]$^+$. $^1$H NMR (500 MHz, DMSO-d$_6$): δ 8.47 (s, 1H), 8.11-8.04 (m, 2H), 7.53-7.46 (m, 3H), 7.31-7.27 (m, 2H), 7.26-7.22 (m, 2H), 7.22-7.17 (m, 1H), 7.00-6.94 (m, 2H), 4.78 (s, 1H), 4.59 (d, J=13.6 Hz, 1H), 4.23 (d, J=5.6 Hz, 2H), 3.62 (d, J=13.6 Hz, 1H), 3.58-3.52 (m, 1H), 3.28-3.16 (m, 3H), 1.95-1.87 (m, 1H), 1.70-1.59 (m, 4H), 1.58-1.50 (m, 1H), 1.45-1.33 (m, 2H), 1.25-1.16 (m, 2H).

Example 194: N-Benzyl-8-((4-(2-fluorophenyl)-6-oxopyrimidin-1(6H)-yl)methyl)-8-hydroxy-5-azaspiro[2.5]octane-5-carboxamide

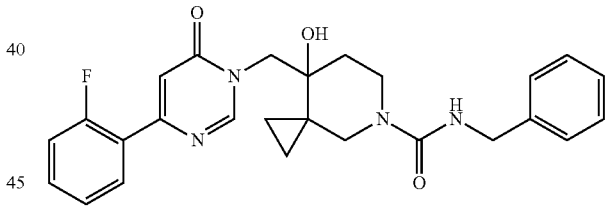

Step 1: 4-(2-Fluorophenyl)-6-methoxypyrimidine: 4,6-Dichloropyrimidine (5 g, 33.6 mmol) and (2-fluorophenyl)boronic acid (4.70 g, 33.6 mmol) were suspended in a mixture of toluene (100 mL) and MeOH (50 mL). Potassium carbonate (4.64, 33.6 mmol) was added and the mixture was degassed (bubbling N$_2$). Pd(PPh$_3$)$_4$ (0.97 g, 0.84 mmol) was added and the mixture was heated at 90° C. for 3 h. The mixture was cooled to rt and concentrated. The residue was diluted with water and extracted (EtOAc×2). The combined organic extracts were washed with brine, dried (MgSO$_4$) and concentrated. The residue was purified by flash chromatography (GraceResolv 80 g, 0-20% EtOAc in cyclohexane) to give the title compound (approx. 5.5 g) contaminated with 4-chloro-6-(2-fluorophenyl)pyrimidine (approx. 0.5 g) and 4,6-bis(2-fluorophenyl)pyrimidine (approx. 1.5 g). The product was used without further purification. LCMS (Method B): $R_T$=1.29 min, m/z=205 [M+H]$^+$.

Step 2: 6-(2-Fluorophenyl)pyrimidin-4(3H)-one: The crude material of 4-(2-fluorophenyl)-6-methoxypyrimidine from Step 1 (total mass: 7.5 g) was suspended in dilute hydrochloride acid (2 M in water, 30 mL, 60 mmol) and 1,4-dioxane (10 mL). The reaction was heated at 110° C. for 5 h. The mixture was cooled and basified with sodium hydroxide (aq). The mixture was extracted with Et$_2$O (×2) and the organic extracts were discarded. The aqueous layer was acidified with HCl (aq) and the resulting white precipitate was collected by filtration to give the title compound (3.99 g, 62% for two steps). LCMS (Method B): R$_T$=0.70 min, m/z=191 [M+H]$^+$.

Step 3: tert-Butyl 1-oxa-8-azadispiro[2.0.2⁴.4³]decane-8-carboxylate: To a stirred solution of trimethylsulfonium iodide (919 mg, 4.51 mmol) in dry DMSO (5.0 mL) at 0° C. was added sodium hydride (180 mg, 4.51 mmol) and the reaction mixture was stirred at rt. After 2 h, a solution of tert-butyl 8-oxo-5-azaspiro[2.5]octane-5-carboxylate (406 mg, 1.80 mmol) [commercially available] in DMSO (2.5 mL) was added and the reaction mixture was heated to 50° C. After a further 16 h, the mixture was cooled to rt and quenched with water before being extracted into diethyl ether (×3). The combined organic phase was washed with brine, dried (MgSO$_4$), the solvents were removed in vacuo, and the remaining residue was purified by flash chromatography (0-40% EtOAc in cyclohexane) to give the title compound (209 mg, 48%) as a colourless oil. LCMS (Method B): R$_T$=0.89 min, m/z=140 [M-Boc+H]$^+$.

Step 4: tert-Butyl 8-((4-(2-fluorophenyl)-6-oxopyrimidin-1(6H)-yl)methyl)-8-hydroxy-5-azaspiro[2.5]octane-5-carboxylate: A stirred solution of 6-(2-fluorophenyl)pyrimidin-4(3H)-one (150 mg, 0.789 mmol), tert-butyl 1-oxa-8-azadispiro[2.0.2⁴.4³]decane-8-carboxylate (208 mg, 0.868 mmol) and cesium carbonate (642 mg, 1.97 mmol) in DMF (4.0 mL) was heated to 80° C. After 2 days, the reaction mixture was allowed to cool to rt, was diluted with water and extracted with EtOAc (×2). The combined organic phase was washed with water (×2) and brine, dried (MgSO4), and the solvents were removed in vacuo. The remaining residue was purified by flash chromatography (0-100% EtOAc in cyclohexane) to give the title compound (229 mg, 68%) as a white solid. LCMS (Method B): R$_T$=1.32 min, m/z=374 [M-butene+H]$^+$.

Step 5: 6-(2-Fluorophenyl)-3-((8-hydroxy-5-azaspiro[2.5]octan-8-yl)methyl)pyrimidin-4(3H)-one: A solution of tert-butyl 8-((4-(2-fluorophenyl)-6-oxopyrimidin-1(6H)-yl)methyl)-8-hydroxy-5-azaspiro[2.5]octane-5-carboxylate (245 mg, 0.570 mmol) in a solution of 4M HCl in 1,4-dioxane) (2 mL, 65.8 mmol) was stirred at rt. After 16 h, the reaction mixture was concentrated to dryness. The residue was loaded onto a pre-equilibrated SCX-2 cartridge, washed with MeOH and eluted using 7N NH$_3$ in MeOH solution. The ammonical fractions were concentrated to dryness to give the crude title compound (212 mg, >100% yield) as a pale yellow powder. LCMS (Method B): R$_T$=0.606 min, m/z=330 [M+H]$^+$.

Step 6: N-Benzyl-8-((4-(2-fluorophenyl)-6-oxopyrimidin-1(6H)-yl)methyl)-8-hydroxy-5-azaspiro[2.5]octane-5-carboxamide: Benzylisocyanate (0.015 mL, 0.121 mmol) was added to a stirred solution of 6-(2-fluorophenyl)-3-((8-hydroxy-5-azaspiro[2.5]octan-8-yl)methyl)pyrimidin-4(3H)-one (20.0 mg, 0.0607 mmol) in DCM (1.4 mL) at rt under nitrogen. After 2 h, the reaction mixture was loaded directly onto a column and purified by flash chromatography (0-100%, EtOAc in cyclohexane) and freeze-dried to give the title compound (7.8 mg, 28%) as a white solid. LCMS (Method A): R$_T$=1.21 min, m/z=463 [M+H]$^+$. $^1$H NMR (500 MHz, DMSO-d$_6$): δ 8.41 (s, 1H), 8.02 (dt, 1H), 7.58-7.50 (m, 1H), 7.41-7.15 (m, 7H), 6.98 (t, 1H), 6.81 (s, 1H), 4.75 (s, 1H), 4.50 (d, 1H), 4.28-4.18 (m, 2H), 3.88 (d, 2H), 3.39-3.19 (m, 3H, overlapping HDO), 1.51-1.40 (m, 2H), 0.74-0.65 (m, 1H), 0.60-0.51 (m, 1H), 0.33-0.19 (m, 2H).

Example 195: N-Benzyl-4-((4-(2-fluorophenyl)-6-oxopyrimidin-1(6H)-yl)methyl)-4-hydroxy-3,3-dimethylpiperidine-1-carboxamide

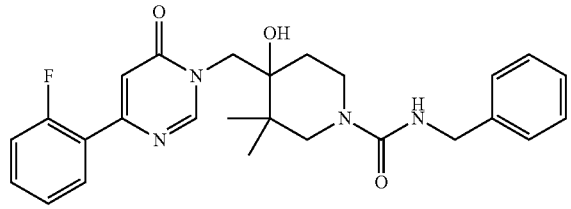 [SMILES: CC1(C)CN(C(=O)NCc2ccccc2)CCC1(O)Cn1cnc(-c2ccccc2F)cc1=O]

Step 1: tert-Butyl 4-((4-(2-fluorophenyl)-6-oxopyrimidin-1(6H)-yl)methyl)-4-hydroxy-3,3-dimethylpiperidine-1-carboxylate: Prepared according to General Procedure 2 using 6-(2-fluorophenyl)pyrimidin-4(3H)-one (1.5 g, 7.89 mmol), Epoxide 1 (2.72 g, 7.89 mmol) and cesium carbonate (3.08 g, 9.47 mmol) in DMF (20 mL). The crude material was suspended in diethyl ether and the resulting solid collected by filtration to give the title compound (1.8 g, 53%). LCMS (Method B): R$_T$=1.39 min, m/z=432 [M+H]$^+$.

Step 2: 6-(2-Fluorophenyl)-3-((4-hydroxy-3,3-dimethylpiperidin-4-yl)methyl)pyrimidin-4(3H)-one: Prepared according to General Procedure 3 using tert-butyl 4-((4-(2-fluorophenyl)-6-oxopyrimidin-1(6H)-yl)methyl)-4-hydroxy-3,3-dimethylpiperidine-1-carboxylate (1.4 g, 3.24 mmol), DCM (10 mL) and TFA (3 mL, 39 mmol) to give the title compound (920 mg, 86%). LCMS (Method B): R$_T$=0.65 min, m/z=332 [M+H]$^+$.

Step 3: N-Benzyl-4-((4-(2-fluorophenyl)-6-oxopyrimidin-1(6H)-yl)methyl)-4-hydroxy-3,3-dimethylpiperidine-1-carboxamide: Benzylisocyanate (0.015 mL, 0.121 mmol) was added to a stirred solution of 6-(2-fluorophenyl)-3-[(4-hydroxy-3,3-dimethyl-4-piperidyl)methyl]pyrimidin-4-one (20.0 mg, 0.0604 mmol) in DCM (1.4 mL) at rt under nitrogen. After 30 min, the reaction mixture was loaded directly onto a column and purified by flash chromatography (0-100%, EtOAc in cyclohexane) and freeze-dried to give the title compound (19.8 mg, 70%) as a white solid. LCMS (Method A): R$_T$=1.23 min, m/z=465 [M+H]$^+$. $^1$H NMR (500 MHz, DMSO-d$_6$): δ 8.44 (s, 1H), 8.03 (dt, 1H), 7.58-7.50 (m, 1H), 7.40-7.16 (m, 7H), 6.94 (t, 1H), 6.80 (s, 1H), 4.77 (s, 1H), 4.42 (d, 1H), 4.23 (d, 2H), 3.77-3.67 (m, 2H), 3.33 (d, 1H), 3.07-2.94 (m, 2H), 1.62 (ddd, 1H), 1.14 (dt, 1H), 1.02 (s, 3H), 0.96 (s, 3H).

Example 196: 10-Hydroxy-10-((6-oxo-4-phenylpyrimidin-1(6H)-yl)methyl)-N-(2,2,2-trifluoroethyl)-7-azaspiro[4.5]decane-7-carboxamide

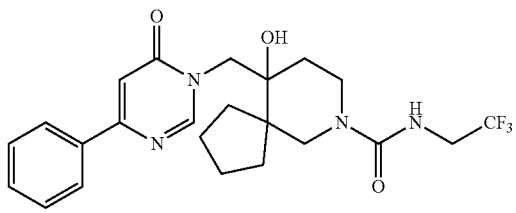 [SMILES: O=C(NCC(F)(F)F)N1CCC(O)(Cn2cnc(-c3ccccc3)cc2=O)C2(CCCC2)C1]

A suspension of 3-((10-hydroxy-7-azaspiro[4.5]decan-10-yl)methyl)-6-phenylpyrimidin-4(3H)-one (15 mg, 0.0442 mmol) and 2,2,2-trifluoroethylisocyanate (8.3 mg, 0.0663 mmol) in DCM (0.45 mL) was stirred at rt for 16 h before the reaction mixture was purified directly by flash chromatography (0-10% MeOH in DCM) to give the title compound (19.8 mg, 92%) as a colourless solid after lyophilisation. LCMS (Method B): $R_T$=1.16 min, m/z=465 [M+H]$^+$. $^1$H NMR (500 MHz, DMSO-d$_6$): δ 8.47 (s, 1H), 8.12-8.05 (m, 2H), 7.55-7.45 (m, 3H), 7.04 (t, J=6.2 Hz, 1H), 6.98 (s, 1H), 4.81 (s, 1H), 4.58 (d, J=13.6 Hz, 1H), 3.85-3.76 (m, 2H), 3.62 (d, J=13.6 Hz, 1H), 3.59-3.53 (m, 1H), 3.28-3.18 (m, 3H), 1.94-1.87 (m, 1H), 1.70-1.59 (m, 4H), 1.57-1.50 (m, 1H), 1.42-1.33 (m, 2H), 1.25-1.14 (m, 2H).

Example 197: 10-Hydroxy-10-((6-oxo-4-phenylpyrimidin-1(6H)-yl)methyl)-N-(pyridin-2-ylmethyl)-7-azaspiro[4.5]decane-7-carboxamide

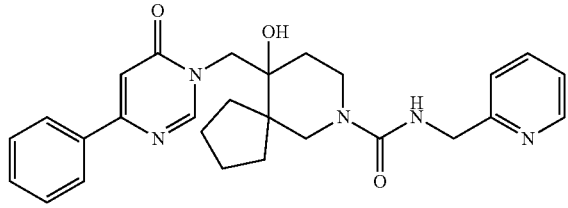 [SMILES: O=C(NCc1ccccn1)N1CCC(O)(Cn2cnc(-c3ccccc3)cc2=O)C2(CCCC2)C1]

Prepared according to General Procedure 10 using 4-nitrophenyl 10-hydroxy-10-((6-oxo-4-phenylpyrimidin-1(6H)-yl)methyl)-7-azaspiro[4.5]decane-7-carboxylate (15 mg, 0.0297 mmol) and 2-(aminomethyl)pyridine (15 μL, 0.149 mmol) in DMA (0.6 mL) for 3 days to give the title compound (2.8 mg, 18%) as an off-white solid after lyophilisation. LCMS (Method B): $R_T$=0.82 min, m/z=474 [M+H]$^+$. $^1$H NMR (500 MHz, DMSO-d$_6$): δ 8.53-8.41 (m, 2H), 8.13-8.04 (m, 2H), 7.74 (td, J=7.7, 1.8 Hz, 1H), 7.57-7.44 (m, 3H), 7.27-7.18 (m, 2H), 7.06 (t, J=5.9 Hz, 1H), 6.99 (s, 1H), 4.81 (s, 1H), 4.60 (d, J=13.6 Hz, 1H), 4.31 (d, J=5.6 Hz, 2H), 3.63 (d, J=13.5 Hz, 1H), 3.60-3.53 (m, 1H), 3.28-3.15 (m, 3H), 1.97-1.88 (m, 1H), 1.77-1.59 (m, 4H), 1.57-1.47 (m, 1H), 1.47-1.33 (m, 2H), 1.23-1.12 (m, 2H).

Example 198: N-Benzyl-10-((4-chloro-6-oxopyrimidin-1(6H)-yl)methyl)-10-hydroxy-7-azaspiro[4.5]decane-7-carboxamide

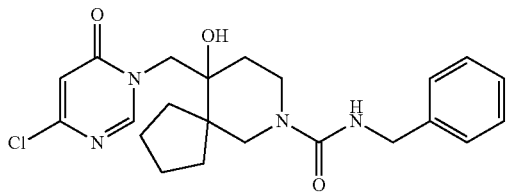 [SMILES: O=C(NCc1ccccc1)N1CCC(O)(Cn2cnc(Cl)cc2=O)C2(CCCC2)C1]

Step 1: 6-Chloro-3-((10-hydroxy-7-azaspiro[4.5]decan-10-yl)methyl)pyrimidin-4(3H)-one hydrochloride: To a solution of tert-butyl 10-((4-chloro-6-oxopyrimidin-1(6H)-yl)methyl)-10-hydroxy-7-azaspiro[4.5]decane-7-carboxylate (276 mg, 0.694 mmol) in 1,4-dioxane (3.5 mL) was added 4 M HCl in 1,4-dioxane (0.486 mL, 14.0 mmol) and the resulting solution was stirred at 50° C. for 2 h. The resulting suspension was diluted with DCM (5 mL) and the precipitate was isolated by filtration. The precipitate was washed with DCM (3×2 mL) and dried in a vacuum oven at 50° C. to give the title compound (227 mg, 97%) as a pale yellow solid. LCMS (Method A): $R_T$=0.29 min, m/z=298, 300 [M–Cl]$^+$.

Step 2: N-Benzyl-10-((4-chloro-6-oxopyrimidin-1(6H)-yl)methyl)-10-hydroxy-7-azaspiro[4.5]decane-7-carboxamide: To a suspension of 6-chloro-3-((10-hydroxy-7-azaspiro[4.5]decan-10-yl)methyl)pyrimidin-4(3H)-one hydrochloride (100 mg, 0.299 mmol) in DCM (3 mL) was added DIPEA (52 μL, 0.299 mmol). After stirring for 5 min, benzyl isocyanate (55 μL, 0.449 mmol) was added and the reaction mixture was stirred for a further 1 h before saturated NaHCO$_{3(aq)}$ (15 mL) was added. The resulting mixture was extracted with DCM (3×10 mL) using a phase separator, the combined organic phases were concentrated under reduced pressure and the residue was purified by flash chromatography (0-100% EtOAc in cyclohexane) to give the title compound (116 mg, 87%) as an off-white foam. LCMS (Method B): $R_T$=1.08 min, m/z=431, 433 [M+H]$^+$. $^1$H NMR (500 MHz, DMSO-d$_6$): δ 8.34 (s, 1H), 7.32-7.26 (m, 2H), 7.25-7.21 (m, 2H), 7.21-7.17 (m, 1H), 6.97 (t, J=5.9 Hz, 1H), 6.61 (s, 1H), 4.75 (s, 1H), 4.52 (d, J=13.4 Hz, 1H), 4.23 (d, J=5.7 Hz, 2H), 3.57 (d, J=13.5 Hz, 1H), 3.55-3.48 (m, 1H), 3.27-3.15 (m, 3H), 1.93-1.84 (m, 1H), 1.68-1.55 (m, 4H), 1.55-1.46 (m, 1H), 1.45-1.35 (m, 1H), 1.35-1.27 (m, 1H), 1.22-1.10 (m, 2H).

Example 199: 10-Hydroxy-10-((6-oxo-4-phenylpyrimidin-1(6H)-yl)methyl)-N-(pyridin-3-ylmethyl)-7-azaspiro[4.5]decane-7-carboxamide

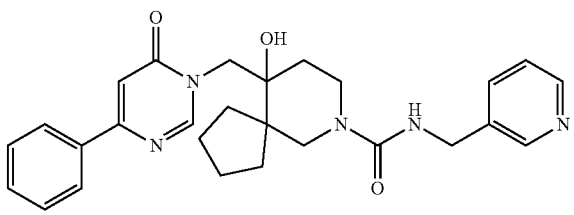 [SMILES: O=C(NCc1cccnc1)N1CCC(O)(Cn2cnc(-c3ccccc3)cc2=O)C2(CCCC2)C1]

Prepared according to General Procedure 10 using 4-nitrophenyl 10-hydroxy-10-((6-oxo-4-phenylpyrimidin-1(6H)-yl)methyl)-7-azaspiro[4.5]decane-7-carboxylate (15 mg, 0.0297 mmol) and 3-(aminomethyl)pyridine (15 μL, 0.149 mmol) in DMA (0.6 mL) for 3 days to give the title compound (6.6 mg, 44%) as a colourless solid after lyophilisation. LCMS (Method B): $R_T$=0.78 min, m/z=474 [M+H]$^+$. $^1$H NMR (500 MHz, DMSO-d$_6$): δ 8.49-8.44 (m, 2H), 8.43-8.39 (m, 1H), 8.12-8.04 (m, 2H), 7.68-7.60 (m, 1H), 7.54-7.45 (m, 3H), 7.34-7.29 (m, 1H), 7.04 (t, J=5.8 Hz, 1H), 6.98 (s, 1H), 4.80 (s, 1H), 4.59 (d, J=13.6 Hz, 1H), 4.24 (d, J=5.6 Hz, 2H), 3.62 (d, J=13.6 Hz, 1H), 3.57-3.50 (m, 1H), 3.27-3.13 (m, 3H), 1.94-1.87 (m, 1H), 1.69-1.58 (m, 4H), 1.57-1.48 (m, 1H), 1.44-1.32 (m, 2H), 1.23-1.13 (m, 2H).

Example 200: N-Benzyl-10-hydroxy-10-((6-oxo-4-(pyridin-3-yl)pyrimidin-1(6H)-yl)methyl)-7-azaspiro[4.5]decane-7-carboxamide

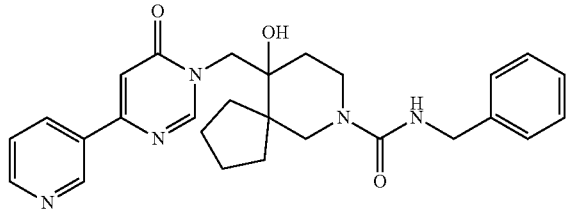 [SMILES: O=C(NCc1ccccc1)N1CCC(O)(Cn2cnc(-c3cccnc3)cc2=O)C2(CCCC2)C1]

Prepared according to General Procedure 5 using N-benzyl-10-((4-chloro-6-oxopyrimidin-1(6H)-yl)methyl)-10-hydroxy-7-azaspiro[4.5]decane-7-carboxamide (15 mg, 0.0348 mmol), pyridin-3-ylboronic acid (8.6 mg, 0.0696 mmol), Pd(dppf)Cl$_2$·DCM (1.5 mg, 1.74 µmol) and sodium carbonate (11.1 mg, 0.104 mmol) in 1,4-dioxane (0.45 mL) and water (0.15 mL) under microwave irradiation at 120° C. for 30 min to give the title compound (15 mg, 85%) as a light beige solid after lyophilisation. LCMS (Method B): $R_T$=0.90 min, m/z=474 [M+H]$^+$. $^1$H NMR (500 MHz, DMSO-d$_6$): δ 9.27-9.21 (m, 1H), 8.68 (d, J=4.4 Hz, 1H), 8.50 (s, 1H), 8.43 (dt, J=8.1, 2.0 Hz, 1H), 7.55-7.50 (m, 1H), 7.29 (t, J=7.5 Hz, 2H), 7.24 (d, J=7.5 Hz, 2H), 7.20 (t, J=7.3 Hz, 1H), 7.12 (s, 1H), 6.97 (t, J=5.9 Hz, 1H), 4.77 (s, 1H), 4.60 (d, J=13.5 Hz, 1H), 4.23 (d, J=5.8 Hz, 2H), 3.63 (d, J=13.5 Hz, 1H), 3.59-3.50 (m, 1H), 3.27-3.12 (m, 3H), 1.97-1.86 (m, 1H), 1.72-1.58 (m, 4H), 1.58-1.48 (m, 1H), 1.46-1.31 (m, 2H), 1.23-1.15 (m, 2H).

Example 201: N-Benzyl-10-hydroxy-10-((6-oxo-4-(pyridin-4-yl)pyrimidin-1(6H)-yl)methyl)-7-azaspiro[4.5]decane-7-carboxamide

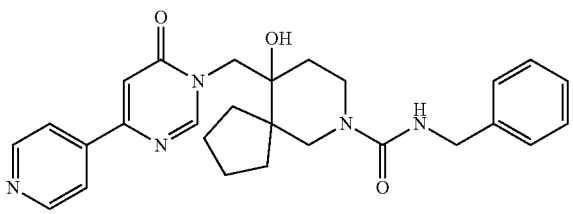 [SMILES: O=C(NCc1ccccc1)N1CCC(O)(Cn2cnc(-c3ccncc3)cc2=O)C2(CCCC2)C1]

Prepared according to General Procedure 5 using N-benzyl-10-((4-chloro-6-oxopyrimidin-1(6H)-yl)methyl)-10-hydroxy-7-azaspiro[4.5]decane-7-carboxamide (15 mg, 0.0348 mmol), pyridin-4-ylboronic acid hydrate (9.8 mg, 0.0696 mmol), Pd(dppf)Cl$_2$·DCM (1.5 mg, 1.74 µmol) and sodium carbonate (11.1 mg, 0.104 mmol) in 1,4-dioxane (0.45 mL) and water (0.15 mL) under microwave irradiation at 120° C. for 30 min to give the title compound (15.6 mg, 88%) as a light beige solid after lyophilisation. LCMS (Method B): $R_T$=0.85 min, m/z=474 [M+H]$^+$. $^1$H NMR (500 MHz, DMSO-d$_6$): δ 8.75-8.68 (m, 2H), 8.51 (s, 1H), 8.05-7.98 (m, 2H), 7.29 (t, J=7.5 Hz, 2H), 7.24 (d, J=7.5 Hz, 2H), 7.22-7.16 (m, 2H), 6.97 (t, J=5.9 Hz, 1H), 4.78 (s, 1H), 4.60 (d, J=13.5 Hz, 1H), 4.23 (d, J=5.8 Hz, 2H), 3.64 (d, J=13.5 Hz, 1H), 3.59-3.50 (m, 1H), 3.28-3.15 (m, 3H), 1.95-1.87 (m, 1H), 1.71-1.58 (m, 4H), 1.58-1.49 (m, 1H), 1.46-1.40 (m, 1H), 1.40-1.32 (m, 1H), 1.23-1.14 (m, 2H).

Example 202: N-Benzyl-10-hydroxy-10-((6-oxo-4-(pyrrolidin-1-yl)pyrimidin-1(6H)-yl)methyl)-7-azaspiro[4.5]decane-7-carboxamide

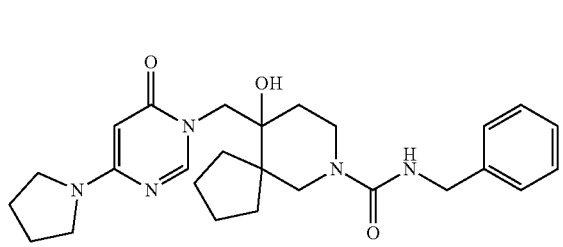 [SMILES: O=C(NCc1ccccc1)N1CCC(O)(Cn2cnc(N3CCCC3)cc2=O)C2(CCCC2)C1]

A solution of N-benzyl-10-((4-chloro-6-oxopyrimidin-1(6H)-yl)methyl)-10-hydroxy-7-azaspiro[4.5]decane-7-carboxamide (15 mg, 0.0348 mmol) and pyrrolidine (29 µL, 0.348 mmol) in 1,4-dioxane (0.5 mL) was heated under microwave irradiation at 150° C. for 30 min before the reaction mixture was directly purified by flash chromatography (0-100% EtOAc in cyclohexane; then 0-20% MeOH in EtOAc) to give the title compound (7.8 mg, 46%) as a colourless solid after lyophilisation. LCMS (Method B): $R_T$=1.09 min, m/z=466 [M+H]$^+$. $^1$H NMR (500 MHz, DMSO-d$_6$): δ 8.12 (s, 1H), 7.29 (t, J=7.5 Hz, 2H), 7.23 (d, J=7.5 Hz, 2H), 7.19 (t, J=7.2 Hz, 1H), 6.95 (t, J=5.9 Hz, 1H), 5.02 (s, 1H), 4.92 (s, 1H), 4.36 (d, J=13.8 Hz, 1H), 4.23 (d, J=5.7 Hz, 2H), 3.57 (d, J=13.9 Hz, 1H), 3.56-3.49 (m, 1H), 3.46-3.11 (m, 7H (signals overlap with HDO)), 1.96-1.78 (m, 5H), 1.68-1.56 (m, 4H), 1.55-1.45 (m, 1H), 1.41-1.26 (m, 2H), 1.20-1.08 (m, 2H).

Example 203: N-Benzyl-10-hydroxy-10-((4-morpholino-6-oxopyrimidin-1(6H)-yl)methyl)-7-azaspiro[4.5]decane-7-carboxamide

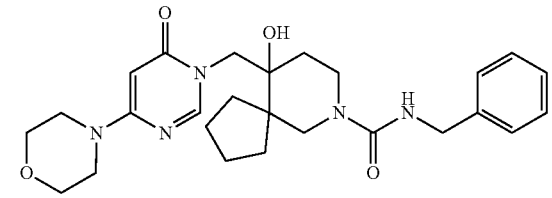 [SMILES: O=C(NCc1ccccc1)N1CCC(O)(Cn2cnc(N3CCOCC3)cc2=O)C2(CCCC2)C1]

A solution of N-benzyl-10-((4-chloro-6-oxopyrimidin-1(6H)-yl)methyl)-10-hydroxy-7-azaspiro[4.5]decane-7-carboxamide (15 mg, 0.0348 mmol) and morpholine (35 µL, 0.348 mmol) in 1,4-dioxane (0.5 mL) was heated under microwave irradiation at 120° C. for 30 min before the reaction mixture was directly purified by flash chromatography (0-100% EtOAc in cyclohexane; then 0-20% MeOH in EtOAc) to give the title compound (13.3 mg, 76%) as a colourless solid after lyophilisation. LCMS (Method B): $R_T$=1.00 min, m/z=482 [M+H]$^+$. $^1$H NMR (500 MHz, DMSO-d$_6$): δ 8.15 (s, 1H), 7.29 (t, J=7.5 Hz, 2H), 7.23 (d, J=7.1 Hz, 2H), 7.19 (t, J=7.1 Hz, 1H), 6.95 (t, J=5.9 Hz, 1H), 5.40 (s, 1H), 4.83 (s, 1H), 4.40 (d, J=13.8 Hz, 1H), 4.23 (d, J=5.7 Hz, 2H), 3.63 (t, J=4.9 Hz, 4H), 3.56-3.41 (m, 6H), 3.28-3.12 (m, 3H), 1.89-1.81 (m, 1H), 1.67-1.56 (m, 4H), 1.54-1.46 (m, 1H), 1.41-1.34 (m, 1H), 1.35-1.28 (m, 1H), 1.20-1.09 (m, 2H).

Example 204: N-Benzyl-10-hydroxy-10-((4-(1-methyl-1H-pyrazol-4-yl)-6-oxopyrimidin-1(6H)-yl)methyl)-7-azaspiro[4.5]decane-7-carboxamide

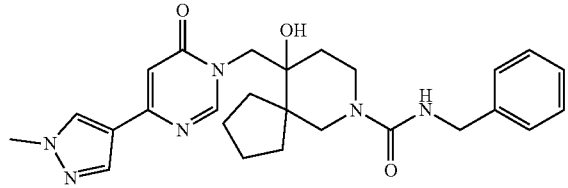 [SMILES: Cn1cc(-c2cc(=O)n(CC3(O)CCN(C(=O)NCc4ccccc4)CC34CCCC4)cn2)cn1]

Prepared according to General Procedure 5 using N-benzyl-10-((4-chloro-6-oxopyrimidin-1(6H)-yl)methyl)-10-hydroxy-7-azaspiro[4.5]decane-7-carboxamide (15 mg, 0.0348 mmol), 1-methyl-4-(4,4,5,5-tetramethyl-1,3,2-dioxaborolan-2-yl)-1H-pyrazole (14.5 mg, 0.0696 mmol), Pd(dppf)Cl$_2$·DCM (1.5 mg, 1.74 μmol) and sodium carbonate (11.1 mg, 0.104 mmol) in 1,4-dioxane (0.45 mL) and water (0.15 mL) under microwave irradiation at 120° C. for 1 h to give the title compound (12.5 mg, 72%) as an off-white solid after lyophilisation. LCMS (Method B): R$_T$=0.97 min, m/z=477 [M+H]$^+$. $^1$H NMR (500 MHz, DMSO-d$_6$): δ 8.33 (s, 1H), 8.29 (s, 1H), 7.99 (s, 1H), 7.29 (t, J=7.5 Hz, 2H), 7.23 (d, J=7.5 Hz, 2H), 7.19 (t, J=7.2 Hz, 1H), 6.96 (t, J=5.9 Hz, 1H), 6.64 (s, 1H), 4.76 (s, 1H), 4.54 (d, J=13.6 Hz, 1H), 4.23 (d, J=5.7 Hz, 2H), 3.87 (s, 3H), 3.58 (d, J=13.7 Hz, 1H), 3.56-3.51 (m, 1H), 3.27-3.15 (m, 3H), 1.93-1.85 (m, 1H), 1.69-1.57 (m, 4H), 1.56-1.48 (m, 1H), 1.45-1.38 (m, 1H), 1.37-1.31 (m, 1H), 1.21-1.13 (m, 2H).

Example 205: N-Benzyl-10-hydroxy-10-((4-(1-methyl-1H-pyrazol-5-yl)-6-oxopyrimidin-1(6H)-yl)methyl)-7-azaspiro[4.5]decane-7-carboxamide

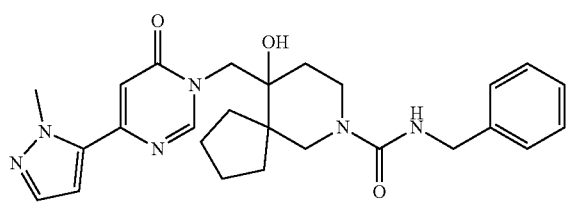 [SMILES: Cn1nccc1-c1cc(=O)n(CC2(O)CCN(C(=O)NCc3ccccc3)CC23CCCC3)cn1]

Prepared according to General Procedure 5 using N-benzyl-10-((4-chloro-6-oxopyrimidin-1(6H)-yl)methyl)-10-hydroxy-7-azaspiro[4.5]decane-7-carboxamide (15 mg, 0.0348 mmol), 1-methyl-5-(4,4,5,5-tetramethyl-1,3,2-dioxaborolan-2-yl)-1H-pyrazole (14.5 mg, 0.0696 mmol), Pd(dppf)Cl$_2$·DCM (1.5 mg, 1.74 μmol) and sodium carbonate (11.1 mg, 0.104 mmol) in 1,4-dioxane (0.45 mL) and water (0.15 mL) under microwave irradiation at 120° C. for 30 min to give the title compound (10.9 mg, 62%) as an off-white solid after lyophilisation. LCMS (Method B): R$_T$=1.03 min, m/z=477 [M+H]$^+$. $^1$H NMR (500 MHz, DMSO-d$_6$): δ 8.46 (s, 1H), 7.48 (d, J=2.0 Hz, 1H), 7.32-7.26 (m, 2H), 7.26-7.22 (m, 2H), 7.22-7.17 (m, 1H), 6.97 (t, J=5.8 Hz, 1H), 6.87 (d, J=2.0 Hz, 1H), 6.80 (s, 1H), 4.76 (s, 1H), 4.59 (d, J=13.5 Hz, 1H), 4.23 (d, J=5.7 Hz, 2H), 4.13 (s, 3H), 3.61 (d, J=13.6 Hz, 1H), 3.58-3.49 (m, 1H), 3.28-3.14 (m, 3H), 1.95-1.86 (m, 1H), 1.72-1.57 (m, 4H), 1.57-1.48 (m, 1H), 1.45-1.32 (m, 2H), 1.26-1.15 (m, 2H).

Example 206: 3-((10-Hydroxy-7-(2-(trifluoromethyl)pyrrolidine-1-carbonyl)-7-azaspiro[4.5]decan-10-yl)methyl)-6-phenylpyrimidin-4(3H)-one

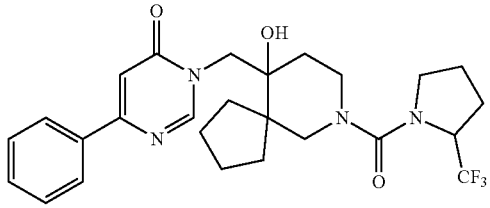 [SMILES: O=C(N1CCC(O)(Cn2cnc(-c3ccccc3)cc2=O)C2(CCCC2)C1)N1CCCC1C(F)(F)F]

A mixture 2-(trifluoromethyl)pyrrolidine (6.2 mg, 0.0442 mmol), triphosgene (4.4 mg, 0.0147 mmol) and DIPEA (21 μL, 0.118 mmol) in DCM (0.3 mL) was stirred at rt for 45 min before 3-((10-hydroxy-7-azaspiro[4.5]decan-10-yl)methyl)-6-phenylpyrimidin-4(3H)-one (10 mg, 0.0295 mmol) was added. The reaction was stirred at rt for 17 h before saturated NaHCO$_{3(aq)}$ (15 mL) was added and the resulting mixture was extracted with DCM (3×10 mL) using a phase separator. The combined organic phases were concentrated under reduced pressure and the residue was purified by flash chromatography (0-100% EtOAc in cyclohexane; then 0-15% MeOH in EtOAc) to give the title compound (11 mg, 72%) as a colourless solid after lyophilisation. LCMS (Method B): R$_T$=1.47 min, m/z=505 [M+H]$^+$. $^1$H NMR (500 MHz, DMSO-d$_6$): δ 8.51-8.44 (m, 1H), 8.15-8.00 (m, 2H), 7.60-7.39 (m, 3H), 7.02-6.95 (m, 1H), 4.92-4.78 (m, 2H), 4.73 (d, J=13.7 Hz, 0.5H), 4.50 (d, J=13.5 Hz, 0.5H), 3.71-3.61 (m, 1H), 3.60-3.50 (m, 1H), 3.42-3.20 (m, 3.5H (signals overlap with HDO)), 3.14 (t, J=12.3 Hz, 1H), 3.03-2.96 (m, 0.5H), 2.21-2.13 (m, 1H), 2.02-1.31 (m, 11H), 1.23-1.12 (m, 2H).

Example 207: 3-((10-Hydroxy-7-((R)-2-methylpiperazine-1-carbonyl)-7-azaspiro[4.5]decan-10-yl)methyl)-6-phenylpyrimidin-4(3H)-one

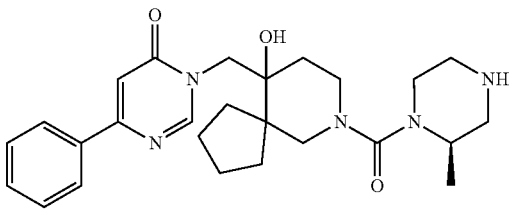 [SMILES: C[C@@H]1CNCCN1C(=O)N1CCC(O)(Cn2cnc(-c3ccccc3)cc2=O)C2(CCCC2)C1]

Step 1: 10-Hydroxy-10-((6-oxo-4-phenylpyrimidin-1(6H)-yl)methyl)-7-azaspiro[4.5]decane-7-carbonyl chloride: To a mixture of 3-((10-hydroxy-7-azaspiro[4.5]decan-10-yl)methyl)-6-phenylpyrimidin-4(3H)-one (130 mg, 0.383 mmol) and pyridine (37 μL, 0.460 mmol) in DCM (3.8 mL) at 0° C. was added triphosgene (45.5 mg, 0.153 mmol). The reaction mixture was stirred at rt for 1 h 45 min before DIPEA (134 μL, 0.766 mmol) was added and the reaction stirred for a further 25 min. The reaction mixture was cooled to 0° C. before DIPEA (134 μL, 0.766 mmol) and triphosgene (45.5 mg, 0.153 mmol) were added and the reaction mixture was stirred at 0° C. for 1 h 35 min before DIPEA (134 μL, 0.766 mmol) and triphosgene (45.5 mg, 0.153 mmol) were added and the reaction mixture was stirred at 0°

C. for 45 min before DIPEA (134 µL, 0.766 mmol) and triphosgene (45.5 mg, 0.153 mmol) were added and the reaction mixture was stirred at 0° C. for 2 h. The reaction mixture was diluted with 1 M HCl$_{(aq)}$ (50 mL) and the resulting mixture was extracted with DCM (3×20 mL) using a phase separator. The combined organic phases were concentrated under reduced pressure and the residue was purified by flash chromatography (0-100% EtOAc in cyclohexane; then flushed with 30% MeOH in DCM; the mixed fractions were repurified, 0-100% EtOAc in DCM) to give the title compound (120 mg, 77%) as an off-white solid. LCMS (Method A): R$_T$=1.46 min, m/z=402, 404 [M+H]$^+$.

Step 2: tert-Butyl (3R)-4-(10-hydroxy-10-((6-oxo-4-phenylpyrimidin-1(6H)-yl)methyl)-7-azaspiro[4.5]decane-7-carbonyl)-3-methylpiperazine-1-carboxylate: A mixture of 10-hydroxy-10-((6-oxo-4-phenylpyrimidin-1(6H)-yl)methyl)-7-azaspiro[4.5]decane-7-carbonyl chloride (10 mg, 0.0249 mmol), tert-butyl (R)-3-methylpiperazine-1-carboxylate (7.5 mg, 0.0373 mmol) and DIPEA (13 µL, 0.0746 mmol) in DCM (0.5 mL) was stirred at rt for 2 h 30 min before tert-butyl (R)-3-methylpiperazine-1-carboxylate (7.5 mg, 0.0373 mmol) and DIPEA (13 µL, 0.0746 mmol) were added. The reaction was stirred for further 18 h 45 min before DMF (0.5 mL) was added and the reaction stirred for a further 23 h. The reaction mixture was diluted with saturated NaHCO$_{3(aq)}$ (15 mL) and the resulting mixture was extracted with DCM (3×10 mL) using a phase separator. The combined organic phases were concentrated under reduced pressure and the residue was purified by flash chromatography (0-100% EtOAc in cyclohexane) to give the title compound (10.2 mg, 72%) as a colourless glass. LCMS (Method A): R$_T$=1.55 min, m/z=566 [M+H]$^+$.

Step 3: 3-((10-Hydroxy-7-((R)-2-methylpiperazine-1-carbonyl)-7-azaspiro[4.5]decan-10-yl)methyl)-6-phenylpyrimidin-4(3H)-one: A solution of tert-butyl (3R)-4-(10-hydroxy-10-((6-oxo-4-phenylpyrimidin-1(6H)-yl)methyl)-7-azaspiro[4.5]decane-7-carbonyl)-3-methylpiperazine-1-carboxylate (10.2 mg, 0.0180 mmol) in TFA (0.2 mL) and DCM (0.4 mL) was stirred at rt for 15 min before the reaction mixture was loaded on to a 2 g SCX-2 cartridge that was pre-equilibrated with 1:1 DCM/MeOH. The cartridge was washed with 1:1 DCM/MeOH (50 mL) before the product was eluted with 1:1 DCM/7 M NH$_3$ in MeOH (30 mL). The basic eluents were concentrated under reduced pressure and the residue was purified by flash chromatography (0-30% MeOH in DCM) to give the title compound (8.3 mg, 96%) as a colourless solid after lyophilisation. LCMS (Method A): R$_T$=0.72 min, m/z=466 [M+H]$^+$. $^1$H NMR (500 MHz, DMSO-d$_6$): δ 8.47 (s, 1H), 8.12-8.03 (m, 2H), 7.56-7.44 (m, 3H), 6.97 (s, 1H), 4.82 (s, 0.5H), 4.80 (s, 0.5H), 4.63 (d, J=13.7 Hz, 0.5H), 4.56 (d, J=13.6 Hz, 0.5H), 3.64 (d, J=13.5 Hz, 0.5H), 3.60 (d, J=13.5 Hz, 0.5H), 3.56-3.46 (m, 1H), 3.42-2.91 (m, 6H (signals overlap HDO)), 2.77-2.67 (m, 2H), 2.58-2.52 (m, 2H), 1.98-1.85 (m, 1H), 1.74-1.50 (m, 5H), 1.49-1.32 (m, 2H), 1.27-1.17 (m, 2H), 1.12 (d, J=7.3 Hz, 1.5H), 1.11 (d, J=7.3 Hz, 1.5H). NH not visible.

Example 208: 3-((10-Hydroxy-7-(2-isopropylpiperazine-1-carbonyl)-7-azaspiro[4.5]decan-10-yl)methyl)-6-phenylpyrimidin-4(3H)-one

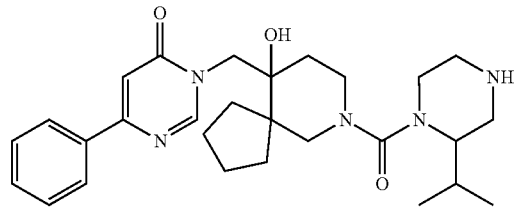 [SMILES: CC(C)C1CNCCN1C(=O)N1CCC(O)(Cn2cnc(-c3ccccc3)cc2=O)C2(CCCC2)C1]

Step 1: tert-Butyl 4-(10-hydroxy-10-((6-oxo-4-phenylpyrimidin-1(6H)-yl)methyl)-7-azaspiro[4.5]decane-7-carbonyl)-3-isopropylpiperazine-1-carboxylate: A mixture of 10-hydroxy-10-((6-oxo-4-phenylpyrimidin-1(6H)-yl)methyl)-7-azaspiro[4.5]decane-7-carbonyl chloride (10 mg, 0.0249 mmol), tert-butyl 3-isopropylpiperazine-1-carboxylate (8.5 mg, 0.0373 mmol) and DIPEA (13 µL, 0.0746 mmol) in DCM (0.5 mL) was stirred at rt for 2 h 30 min before tert-butyl 3-isopropylpiperazine-1-carboxylate (8.5 mg, 0.0373 mmol) and DIPEA (13 µL, 0.0746 mmol) were added. The reaction was stirred for further 18 h 45 min before DMF (0.5 mL) was added and the reaction stirred for a further 6 days. The reaction mixture was diluted with saturated NaHCO$_{3(aq)}$ (15 mL) and the resulting mixture was extracted with DCM (3×10 mL) using a phase separator. The combined organic phases were concentrated under reduced pressure and the residue was purified by flash chromatography (0-100% EtOAc in cyclohexane) to give the title compound (7.7 mg, 52%) as colourless glass. LCMS (Method A): R$_T$=1.70 min, m/z=594 [M+H]$^+$.

Step 2: 3-((10-Hydroxy-7-(2-isopropylpiperazine-1-carbonyl)-7-azaspiro[4.5]decan-10-yl)methyl)-6-phenylpyrimidin-4(3H)-one: A solution of tert-butyl 4-(10-hydroxy-10-((6-oxo-4-phenylpyrimidin-1(6H)-yl)methyl)-7-azaspiro[4.5]decane-7-carbonyl)-3-isopropylpiperazine-1-carboxylate (7.7 mg, 0.0130 mmol) in TFA (0.2 mL) and DCM (0.4 mL) was stirred at rt for 15 min before the reaction mixture was loaded on to a 2 g SCX-2 cartridge that was pre-equilibrated with 1:1 DCM/MeOH. The cartridge was washed with 1:1 DCM/MeOH (50 mL) before the product was eluted with 1:1 DCM/7 M NH$_3$ in MeOH (30 mL). The basic eluents were concentrated under reduced pressure and the residue was purified by flash chromatography (0-30% MeOH in DCM) to give the title compound (4.7 mg, 71%) as a colourless solid after lyophilisation. LCMS (Method A): R$_T$=0.81 min, m/z=494 [M+H]$^+$. $^1$H NMR (500 MHz, DMSO-d$_6$): δ 8.47 (s, 0.5H), 8.47 (s, 0.5H), 8.12-8.02 (m, 2H), 7.56-7.40 (m, 3H), 6.97 (s, 0.5H), 6.97 (s, 0.5H), 4.81 (s, 0.5H), 4.77 (s, 0.5H), 4.68 (d, J=13.6 Hz, 0.5H), 4.52 (d, J=13.5 Hz, 0.5H), 3.66 (d, J=13.5 Hz, 0.5H), 3.57 (d, J=13.6 Hz, 0.5H), 3.40-2.30 (m, 11H (signals overlap with HDO and DMSO)), 2.00-1.89 (m, 1H), 1.77-1.42 (m, 7H), 1.37-1.11 (m, 3H), 0.89-0.82 (m, 3H), 0.80-0.69 (m, 3H). NH not visible.

Example 209: 3-((7-(3-Azabicyclo[3.1.0]hexane-3-carbonyl)-10-hydroxy-7-azaspiro[4.5]decan-10-yl)methyl)-6-phenylpyrimidin-4(3H)-one

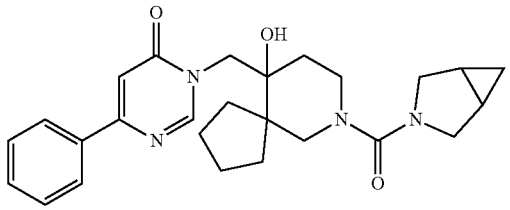 [SMILES: O=C(N1CC2CC2C1)N1CCC(O)(Cn2cnc(-c3ccccc3)cc2=O)C2(CCCC2)C1]

Prepared according to General Procedure 9 using 10-hydroxy-10-((6-oxo-4-phenylpyrimidin-1(6H)-yl)methyl)-7-azaspiro[4.5]decane-7-carbonyl chloride (10 mg, 0.0249 mmol), 3-azabicyclo[3.1.0]hexane hydrochloride (8.9 mg, 0.0746 mmol) and DIPEA (26 μL, 0.149 mmol) in DMF (0.5 mL) for 17 h to give the title compound (6.3 mg, 55%) as a colourless solid after lyophilisation. LCMS (Method A): $R_T$=1.34 min, m/z=449 [M+H]$^+$. $^1$H NMR (500 MHz, DMSO-d$_6$): δ 8.46 (s, 1H), 8.11-8.03 (m, 2H), 7.55-7.42 (m, 3H), 6.97 (s, 1H), 4.79 (s, 1H), 4.59 (d, J=13.6 Hz, 1H), 3.66-3.55 (m, 2H), 3.51 (d, J=10.5 Hz, 1H), 3.36-3.30 (m, 1H), 3.24 (d, J=10.3 Hz, 1H), 3.18 (d, J=10.4 Hz, 1H), 3.14-3.06 (m, 2H), 2.98 (d, J=13.1 Hz, 1H), 1.95-1.86 (m, 1H), 1.71-1.49 (m, 5H), 1.46-1.32 (m, 4H), 1.26-1.14 (m, 2H), 0.56-0.48 (m, 1H), −0.09-−0.17 (m, 1H).

Example 210: 3-(((S)-10-Hydroxy-7-((S)-2-phenylpiperazine-1-carbonyl)-7-azaspiro[4.5]decan-10-yl)methyl)-6-phenylpyrimidin-4(3H)-one

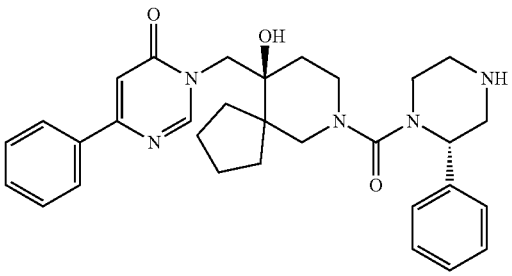 [SMILES: O=C(N1CC[C@@](O)(Cn2cnc(-c3ccccc3)cc2=O)C2(CCCC2)C1)N1CCNC[C@@H]1c1ccccc1]

Step 1: tert-Butyl (S)-10-((4-chloro-6-oxopyrimidin-1(6H)-yl)methyl)-10-hydroxy-7-azaspiro[4.5]decane-7-carboxylate: tert-Butyl 10-((4-chloro-6-oxopyrimidin-1(6H)-yl)methyl)-10-hydroxy-7-azaspiro[4.5]decane-7-carboxylate (8.26 g) was resolved into the single stereoisomers by chiral HPLC using a Lux C4 (30 mm×250 mm, 5 μm) column with isocratic solvent conditions: MeOH. The first eluted material afforded tert-butyl (S)-10-((4-chloro-6-oxopyrimidin-1(6H)-yl)methyl)-10-hydroxy-7-azaspiro[4.5]decane-7-carboxylate (3.67 g, 44% recovery) as an off-white solid. Chiral purity (Method B): $R_T$=2.72 min, 99.1% ee. The second eluted material afforded tert-butyl (R)-10-((4-chloro-6-oxopyrimidin-1(6H)-yl)methyl)-10-hydroxy-7-azaspiro[4.5]decane-7-carboxylate (3.38 g, 41% recovery) as an off-white solid. Chiral purity (Method B): $R_T$=3.68 min, 99.3% ee.

Step 2: tert-Butyl (S)-10-hydroxy-10-((6-oxo-4-phenylpyrimidin-1(6H)-yl)methyl)-7-azaspiro[4.5]decane-7-carboxylate: A suspension of tert-butyl (S)-10-((4-chloro-6-oxopyrimidin-1(6H)-yl)methyl)-10-hydroxy-7-azaspiro[4.5]decane-7-carboxylate (200 mg, 0.503 mmol), phenylboronic acid (123 mg, 1.01 mmol), Pd(dppf)Cl$_2$·DCM (21.3 mg, 0.0251 mmol) and sodium carbonate (160 mg, 1.51 mmol) in 1,4-dioxane (3.6 mL) and water (1.2 mL) in a sealed 2-5 mL microwave vial was purged of O$_2$ by evacuating and refilling the vessel with N$_2$ via a needle through the septa. The reaction mixture was heated under microwave irradiation at 120° C. for 30 min. The reaction mixture was diluted with water (75 mL) and the resulting suspension was stirred vigorously for 10 min before the solids were isolated by filtration. The solids were washed with water (3×25 mL) before being dried in a vacuum oven at 50° C. to give the title compound (230 mg, >100%) as a brown solid. The crude material was used without further purification. LCMS (Method A): $R_T$=1.62 min, m/z=440 [M+H]$^+$.

Step 3: (S)-3-((10-Hydroxy-7-azaspiro[4.5]decan-10-yl)methyl)-6-phenylpyrimidin-4(3H)-one: A solution of tert-butyl (S)-10-hydroxy-10-((6-oxo-4-phenylpyrimidin-1(6H)-yl)methyl)-7-azaspiro[4.5]decane-7-carboxylate (230 mg, 0.523 mmol) in TFA (2.5 mL) and DCM (5 mL) was stirred at rt for 10 min before the reaction mixture was loaded on to a 5 g SCX-2 cartridge that was pre-equilibrated with 1:1 DCM/MeOH. The cartridge was washed with 1:1 DCM/MeOH (100 mL) before the product was eluted with 1:1 DCM/7 M NH$_3$ in MeOH (60 mL). The basic eluents were concentrated under reduced pressure and dried in a vacuum oven at 50° C. to give the title compound (163 mg, 91%) as a beige solid. LCMS (Method A): $R_T$=0.86 min, m/z=340 [M+H]$^+$.

Step 4: (S)-10-Hydroxy-10-((6-oxo-4-phenylpyrimidin-1(6H)-yl)methyl)-7-azaspiro[4.5]decane-7-carbonyl chloride: To a solution of triphosgene (52.5 mg, 0.177 mmol) in DCM (5.9 mL) at 0° C. under N$_2$ was added pyridine (0.119 mL, 1.47 mmol). After stirring for 25 min at 0° C., (S)-3-((10-hydroxy-7-azaspiro[4.5]decan-10-yl)methyl)-6-phenylpyrimidin-4(3H)-one (100 mg, 0.295 mmol) was added and the reaction was stirred at 0° C. for a further 45 min before 0.1 M HCl$_{(aq)}$ (40 mL) was added. After warming to rt, the mixture was extracted with DCM (3×30 mL). The combined organic phases were passed through a phase separator, concentrated under reduced pressure and the residue was purified by flash chromatography (0-100% EtOAc in DCM) to give the title compound (97 mg, 81%) as a peach solid. LCMS (Method A): $R_T$=1.47 min, m/z=402, 404 [M+H]$^+$.

Step 5: tert-Butyl (S)-4-((S)-10-hydroxy-10-((6-oxo-4-phenylpyrimidin-1(6H)-yl)methyl)-7-azaspiro[4.5]decane-7-carbonyl)-3-phenylpiperazine-1-carboxylate: Prepared according to General Procedure 9 using (S)-10-hydroxy-10-((6-oxo-4-phenylpyrimidin-1(6H)-yl)methyl)-7-azaspiro[4.5]decane-7-carbonyl chloride (20 mg, 0.0498 mmol), tert-butyl (S)-3-phenylpiperazine-1-carboxylate (19.6 mg, 0.0746 mmol) [commercially available] and DIPEA (26 μL, 0.149 mmol) in DMF (1.0 mL), except after 24 h, the temperature was increased to 50° C. and the reaction mixture was allowed to stir for a further 24 h to complete the reaction, to give the title compound (16.8 mg, 48%) as a white solid. LCMS (Method A): $R_T$=1.72 min, m/z=628 [M+H]$^+$.

Step 6: 3-(((S)-10-Hydroxy-7-((S)-2-phenylpiperazine-1-carbonyl)-7-azaspiro[4.5]decan-10-yl)methyl)-6-phenylpyrimidin-4(3H)-one: Prepared according to General Procedure 3 using tert-butyl (S)-4-((S)-10-hydroxy-10-((6-oxo-4-phenylpyrimidin-1(6H)-yl)methyl)-7-azaspiro[4.5]decane- 7-carbonyl)-3-phenylpiperazine-1-carboxylate (13.6 mg, 0.0217 mmol), DCM (0.5 mL) and TFA (0.5 mL) to give the title compound (7.9 mg, 69%). LCMS (Method A): $R_T$=0.97 min, m/z=528 [M+H]$^+$. $^1$H NMR (500 MHz, DMSO-d$_6$): δ 8.46 (s, 1H), 8.11-8.04 (m, 2H), 7.54-7.43 (m, 3H), 7.38-7.11 (m, 5H), 6.98 (s, 1H), 4.82 (s, 1H), 4.60 (d, 1H), 4.30 (t, 1H), 3.67-3.50 (m, 2H), 3.44-2.75 (m, 9H, overlapping HDO peak), 1.93-1.78 (m, 1H), 1.76-0.67 (m, 10H).

Example 211: 3-(((S)-10-Hydroxy-7-((R)-3-phenylmorpholine-4-carbonyl)-7-azaspiro[4.5]decan-10-yl)methyl)-6-phenylpyrimidin-4(3H)-one

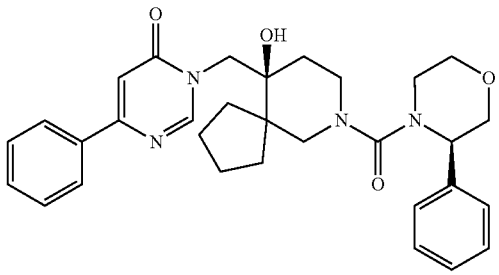 [SMILES: O=C(N1CC[C@@](O)(Cn2cnc(-c3ccccc3)cc2=O)C2(CCCC2)C1)N1CCOC[C@H]1c1ccccc1]

Prepared according to General Procedure 9 using (S)-10-hydroxy-10-((6-oxo-4-phenylpyrimidin-1(6H)-yl)methyl)-7-azaspiro[4.5]decane-7-carbonyl chloride (20 mg, 0.0498 mmol), (R)-3-phenylmorpholine (12.2 mg, 0.0746 mmol) and DIPEA (26 μL, 0.149 mmol) in DMF (0.5 mL) for 24 h to give the title compound (13.6 mg, 51%) as a colourless solid after lyophilisation. LCMS (Method A): $R_T$=1.44 min, m/z=529 [M+H]$^+$. $^1$H NMR (500 MHz, DMSO-d$_6$): δ 8.46 (s, 1H), 8.12-8.04 (m, 2H), 7.55-7.44 (m, 3H), 7.38-7.25 (m, 4H), 7.25-7.20 (m, 1H), 6.97 (s, 1H), 4.83 (s, 1H), 4.55 (d, J=13.6 Hz, 1H), 4.41 (t, J=4.8 Hz, 1H), 3.79-3.55 (m, 6H), 3.26-3.17 (m, 2H), 3.16-3.09 (m, 1H), 3.08-2.98 (m, 2H), 1.94-1.85 (m, 1H), 1.67-1.40 (m, 6H), 1.36-1.28 (m, 1H), 1.24-1.18 (m, 1H), 1.12-1.05 (m, 1H).

Example 212: 3-(((S)-10-Hydroxy-7-((S)-3-phenylmorpholine-4-carbonyl)-7-azaspiro[4.5]decan-10-yl)methyl)-6-phenylpyrimidin-4(3H)-one

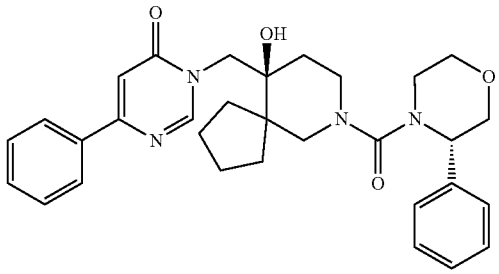 [SMILES: O=C(N1CC[C@@](O)(Cn2cnc(-c3ccccc3)cc2=O)C2(CCCC2)C1)N1CCOC[C@@H]1c1ccccc1]

Prepared according to General Procedure 9 using (S)-10-hydroxy-10-((6-oxo-4-phenylpyrimidin-1(6H)-yl)methyl)-7-azaspiro[4.5]decane-7-carbonyl chloride (20 mg, 0.0498 mmol), (S)-3-phenylmorpholine (12.2 mg, 0.0746 mmol) and DIPEA (26 μL, 0.149 mmol) in DMF (0.5 mL) for 24 h to give the title compound (20.3 mg, 76%) as a colourless solid after lyophilisation. LCMS (Method A): $R_T$=1.44 min, m/z=529 [M+H]$^+$. $^1$H NMR (500 MHz, DMSO-d$_6$): δ 8.46 (s, 1H), 8.12-8.03 (m, 2H), 7.54-7.45 (m, 3H), 7.39-7.27 (m, 4H), 7.27-7.21 (m, 1H), 6.98 (s, 1H), 4.84 (s, 1H), 4.62 (d, J=13.6 Hz, 1H), 4.38 (t, J=5.0 Hz, 1H), 3.79-3.64 (m, 4H), 3.63-3.50 (m, 2H), 3.43-3.33 (m, 1H), 3.21-3.06 (m, 3H), 3.05-2.96 (m, 2H), 1.90-1.80 (m, 1H), 1.66-1.44 (m, 5H), 1.43-1.34 (m, 1H), 1.31-1.24 (m, 2H), 1.14-1.05 (m, 1H).

Example 213: 3-(((S)-10-Hydroxy-7-((S)-2-phenylpyrrolidine-1-carbonyl)-7-azaspiro[4.5]decan-10-yl)methyl)-6-phenylpyrimidin-4(3H)-one

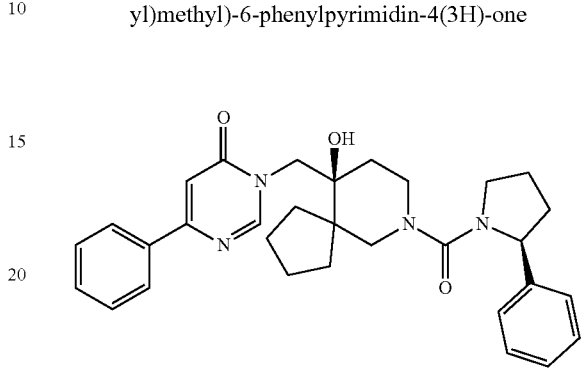

Prepared according to General Procedure 9 using (S)-10-hydroxy-10-((6-oxo-4-phenylpyrimidin-1(6H)-yl)methyl)-7-azaspiro[4.5]decane-7-carbonyl chloride (10 mg, 0.0249 mmol), (S)-2-phenylpyrrolidine (5.5 mg, 0.0373 mmol) and DIPEA (13 μL, 0.0746 mmol) in DMF (0.5 mL) for 1 h 45 min to give the title compound (7.7 mg, 59%) as a colourless solid after lyophilisation. LCMS (Method A): $R_T$=1.58 min, m/z=513 [M+H]$^+$. $^1$H NMR (500 MHz, DMSO-d$_6$): δ 8.45 (s, 1H), 8.10-8.04 (m, 2H), 7.54-7.44 (m, 3H), 7.27 (t, J=7.5 Hz, 2H), 7.22 (d, J=7.3 Hz, 2H), 7.18 (t, J=7.2 Hz, 1H), 6.97 (s, 1H), 4.92-4.87 (m, 1H), 4.76 (s, 1H), 4.46 (d, J=13.5 Hz, 1H), 3.67-3.58 (m, 2H), 3.54 (dt, J=13.3, 4.8 Hz, 1H), 3.41 (t, J=8.7 Hz, 1H), 3.13 (d, J=13.0 Hz, 1H), 3.03 (d, J=13.0 Hz, 1H), 2.97 (t, J=11.6 Hz, 1H), 2.30-2.23 (m, 1H), 1.99-1.92 (m, 1H), 1.92-1.84 (m, 1H), 1.81-1.71 (m, 1H), 1.66-1.41 (m, 7H), 1.29-1.24 (m, 1H), 1.19-1.09 (m, 2H).

Example 214: (S)-10-Hydroxy-10-((6-oxo-4-phenylpyrimidin-1(6H)-yl)methyl)-N-(thiophen-2-ylmethyl)-7-azaspiro[4.5]decane-7-carboxamide

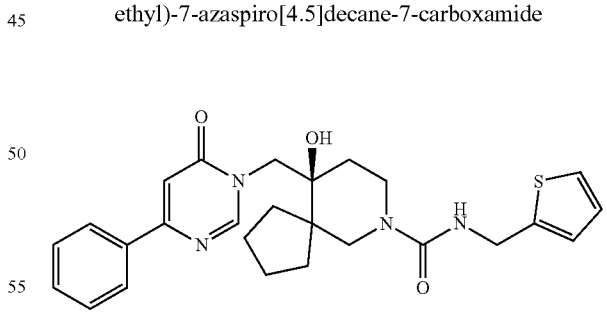

Prepared according to General Procedure 9 using (S)-10-hydroxy-10-((6-oxo-4-phenylpyrimidin-1(6H)-yl)methyl)-7-azaspiro[4.5]decane-7-carbonyl chloride (10 mg, 0.0249 mmol), 2-thiophenemethylamine (4.2 mg, 0.0373 mmol) and DIPEA (13 μL, 0.0746 mmol) in DMF (0.5 mL) for 90 min to give the title compound (11.1 mg, 89%) as a colourless solid after lyophilisation. LCMS (Method A): $R_T$=1.28 min, m/z=479 [M+H]$^+$. $^1$H NMR (500 MHz, DMSO-d$_6$): δ 8.46 (s, 1H), 8.11-8.04 (m, 2H), 7.54-7.43 (m, 3H), 7.32 (dd, J=5.0, 1.3 Hz, 1H), 7.06 (t, J=5.8 Hz, 1H), 6.98 (s, 1H), 6.95-6.87 (m, 2H), 4.78 (s, 1H), 4.58 (d, J=13.5 Hz, 1H), 4.38 (d, J=5.7 Hz, 2H), 3.62 (d, J=13.6 Hz, 1H), 3.57-3.49 (m, 1H), 3.27-3.14 (m, 3H), 1.94-1.86 (m, 1H), 1.71-1.58 (m, 4H), 1.57-1.48 (m, 1H), 1.45-1.40 (m, 1H), 1.40-1.32 (m, 1H), 1.22-1.13 (m, 2H).

Example 215: (S)-N-(4-Cyanobenzyl)-10-hydroxy-10-((6-oxo-4-phenylpyrimidin-1(6H)-yl)methyl)-7-azaspiro[4.5]decane-7-carboxamide

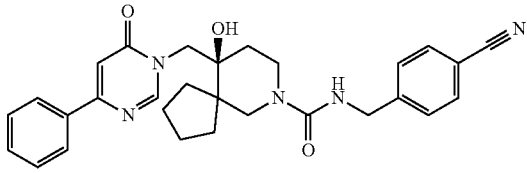 [SMILES: N#Cc1ccc(CNC(=O)N2CC[C@@](O)(Cn3cnc(-c4ccccc4)cc3=O)C3(CCCC3)C2)cc1]

Prepared according to General Procedure 9 using (S)-10-hydroxy-10-((6-oxo-4-phenylpyrimidin-1(6H)-yl)methyl)-7-azaspiro[4.5]decane-7-carbonyl chloride (8 mg, 0.0199 mmol), 4-(aminomethyl)benzonitrile hydrochloride (5 mg, 0.0299 mmol) and DIPEA (10 μL, 0.0597 mmol) in DMF (0.5 mL) for 80 min to give the title compound (6.5 mg, 62%) as a colourless solid after lyophilisation. LCMS (Method A): $R_T$=1.25 min, m/z=498 [M+H]$^+$. $^1$H NMR (500 MHz, DMSO-$d_6$): δ 8.47 (s, 1H), 8.11-8.05 (m, 2H), 7.77 (d, J=8.2 Hz, 2H), 7.54-7.45 (m, 3H), 7.42 (d, J=8.0 Hz, 2H), 7.10 (t, J=5.8 Hz, 1H), 6.98 (s, 1H), 4.79 (s, 1H), 4.59 (d, J=13.6 Hz, 1H), 4.29 (d, J=5.7 Hz, 2H), 3.62 (d, J=13.6 Hz, 1H), 3.59-3.51 (m, 1H), 3.27-3.13 (m, 3H), 1.95-1.88 (m, 1H), 1.71-1.58 (m, 4H), 1.57-1.49 (m, 1H), 1.44-1.33 (m, 2H), 1.23-1.14 (m, 2H).

Example 216: (S)-N-(3-Fluorobenzyl)-10-hydroxy-10-((6-oxo-4-phenylpyrimidin-1(6H)-yl)methyl)-7-azaspiro[4.5]decane-7-carboxamide

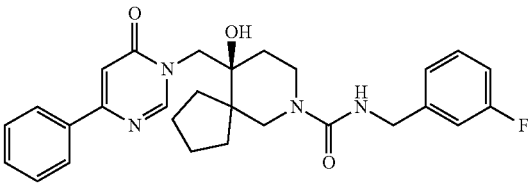 [SMILES: O=C(NCc1cccc(F)c1)N1CC[C@@](O)(Cn2cnc(-c3ccccc3)cc2=O)C2(CCCC2)C1]

Prepared according to General Procedure 9 using (S)-10-hydroxy-10-((6-oxo-4-phenylpyrimidin-1(6H)-yl)methyl)-7-azaspiro[4.5]decane-7-carbonyl chloride (10 mg, 0.0249 mmol), 3-fluorobenzylamine (4.7 mg, 0.0373 mmol) and DIPEA (13 μL, 0.0746 mmol) in DMF (0.5 mL) for 85 min to give the title compound (7.1 mg, 57%) as a colourless solid after lyophilisation. LCMS (Method A): $R_T$=1.34 min, m/z=491 [M+H]$^+$. $^1$H NMR (500 MHz, DMSO-$d_6$): δ 8.47 (s, 1H), 8.11-8.04 (m, 2H), 7.55-7.44 (m, 3H), 7.37-7.31 (m, 1H), 7.08 (d, J=7.7 Hz, 1H), 7.06-6.99 (m, 3H), 6.98 (s, 1H), 4.79 (s, 1H), 4.60 (d, J=13.6 Hz, 1H), 4.24 (d, J=5.7 Hz, 2H), 3.63 (d, J=13.6 Hz, 1H), 3.60-3.51 (m, 1H), 3.28-3.15 (m, 3H), 1.95-1.88 (m, 1H), 1.70-1.59 (m, 4H), 1.57-1.49 (m, 1H), 1.44-1.33 (m, 2H), 1.23-1.14 (m, 2H).

Example 217: (S)-N-(Benzo[d][1,3]dioxol-5-ylmethyl)-10-hydroxy-10-((6-oxo-4-phenylpyrimidin-1(6H)-yl)methyl)-7-azaspiro[4.5]decane-7-carboxamide

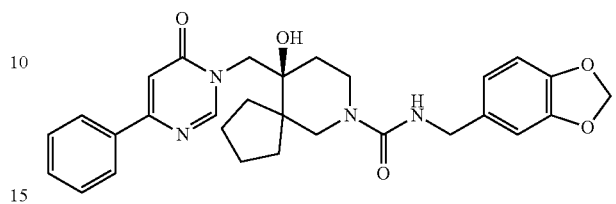

Prepared according to General Procedure 9 using (S)-10-hydroxy-10-((6-oxo-4-phenylpyrimidin-1(6H)-yl)methyl)-7-azaspiro[4.5]decane-7-carbonyl chloride (10 mg, 0.0249 mmol), piperonylamine (5.6 mg, 0.0373 mmol) and DIPEA (13 μL, 0.0746 mmol) in DMF (0.5 mL) for 80 min the title compound (9.3 mg, 71%) as a colourless solid after lyophilisation. LCMS (Method A): $R_T$=1.28 min, m/z=517 [M+H]$^+$. $^1$H NMR (500 MHz, DMSO-$d_6$): δ 8.46 (s, 1H), 8.12-8.03 (m, 2H), 7.56-7.44 (m, 3H), 6.98 (s, 1H), 6.91 (t, J=5.9 Hz, 1H), 6.82 (d, J=7.9 Hz, 1H), 6.80 (s, 1H), 6.70 (d, J=7.8 Hz, 1H), 5.96 (s, 2H), 4.78 (s, 1H), 4.59 (d, J=13.6 Hz, 1H), 4.13 (d, J=5.7 Hz, 2H), 3.62 (d, J=13.6 Hz, 1H), 3.57-3.48 (m, 1H), 3.28-3.13 (m, 3H), 1.93-1.85 (m, 1H), 1.71-1.58 (m, 4H), 1.58-1.49 (m, 1H), 1.45-1.31 (m, 2H), 1.23-1.12 (m, 2H).

Example 218: (S)-N-((5-Cyclopropyl-1,2,4-oxadiazol-3-yl)methyl)-10-hydroxy-10-((6-oxo-4-phenylpyrimidin-1(6H)-yl)methyl)-7-azaspiro[4.5]decane-7-carboxamide

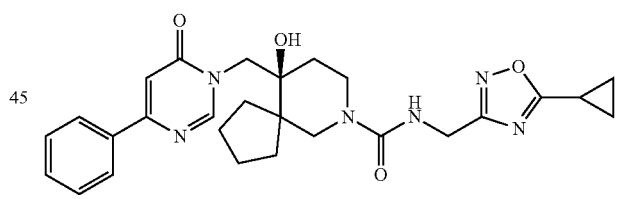

Prepared according to General Procedure 9 using (S)-10-hydroxy-10-((6-oxo-4-phenylpyrimidin-1(6H)-yl)methyl)-7-azaspiro[4.5]decane-7-carbonyl chloride (8 mg, 0.0199 mmol), (5-cyclopropyl-1,2,4-oxadiazol-3-yl)methanamine hydrochloride (5.2 mg, 0.0299 mmol) and DIPEA (10 μL, 0.0597 mmol) in DMF (0.5 mL) for 80 min to give the title compound (3.8 mg, 37%) as a colourless solid after lyophilisation. LCMS (Method A): $R_T$=1.15 min, m/z=505 [M+H]$^+$. $^1$H NMR (500 MHz, DMSO-$d_6$): δ 8.46 (s, 1H), 8.12-8.04 (m, 2H), 7.56-7.43 (m, 3H), 7.01 (t, J=5.8 Hz, 1H), 6.98 (s, 1H), 4.79 (s, 1H), 4.59 (d, J=13.6 Hz, 1H), 4.23 (d, J=5.6 Hz, 2H), 3.62 (d, J=13.6 Hz, 1H), 3.56-3.49 (m, 1H), 3.27-3.13 (m, 3H), 2.29 (tt, J=8.5, 4.7 Hz, 1H), 1.93-1.84 (m, 1H), 1.70-1.58 (m, 4H), 1.56-1.48 (m, 1H), 1.45-1.40 (m, 1H), 1.40-1.31 (m, 1H), 1.23-1.14 (m, 4H), 1.09-1.03 (m, 2H).

Example 219: (S)-N-(Furan-2-ylmethyl)-10-hydroxy-10-(((6-oxo-4-phenylpyrimidin-1(6H)-yl)methyl)-7-azaspiro[4.5]decane-7-carboxamide

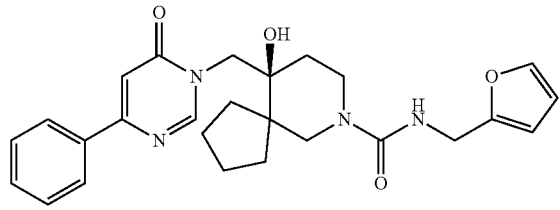 [SMILES: O=C(NCc1ccco1)N1CC[C@@](O)(Cn2cnc(-c3ccccc3)cc2=O)C2(CCCC2)C1]

Prepared according to General Procedure 9 using (S)-10-hydroxy-10-((6-oxo-4-phenylpyrimidin-1(6H)-yl)methyl)-7-azaspiro[4.5]decane-7-carbonyl chloride (10 mg, 0.0249 mmol), furfurylamine (3.6 mg, 0.0373 mmol) and DIPEA (13 μL, 0.0746 mmol) in DMF (0.5 mL) for 70 min to give the title compound (11.6 mg, 99%) as a colourless solid after lyophilisation. LCMS (Method A): $R_T$=1.21 min, m/z=463 [M+H]$^+$. $^1$H NMR (500 MHz, DMSO-d$_6$): δ 8.46 (s, 1H), 8.13-8.02 (m, 2H), 7.52 (dd, J=1.6, 0.8 Hz, 1H), 7.51-7.46 (m, 3H), 6.98 (s, 1H), 6.88 (t, J=5.7 Hz, 1H), 6.36 (dd, J=3.2, 1.8 Hz, 1H), 6.13 (dd, J=3.0, 0.6 Hz, 1H), 4.77 (s, 1H), 4.58 (d, J=13.6 Hz, 1H), 4.20 (d, J=5.5 Hz, 2H), 3.61 (d, J=13.6 Hz, 1H), 3.57-3.47 (m, 1H), 3.28-3.13 (m, 3H), 1.94-1.85 (m, 1H), 1.71-1.56 (m, 4H), 1.56-1.47 (m, 1H), 1.44-1.30 (m, 2H), 1.23-1.12 (m, 2H).

Example 220: 6-Chloro-3-(((S)-10-hydroxy-7-((R)-3-phenylmorpholine-4-carbonyl)-7-azaspiro[4.5]decan-10-yl)methyl)pyrimidin-4(3H)-one

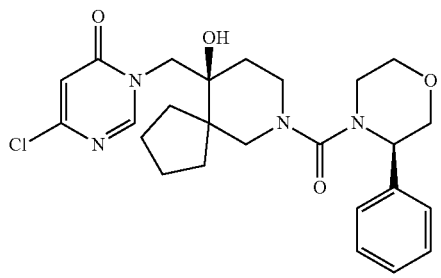 [SMILES: O=C(N1CC[C@@](O)(Cn2cnc(Cl)cc2=O)C2(CCCC2)C1)N1CCOC[C@H]1c1ccccc1]

Step 1: (S)-6-Chloro-3-((10-hydroxy-7-azaspiro[4.5]decan-10-yl)methyl)pyrimidin-4(3H)-one hydrochloride: To a solution of tert-butyl (S)-10-((4-chloro-6-oxopyrimidin-1(6H)-yl)methyl)-10-hydroxy-7-azaspiro[4.5]decane-7-carboxylate (100 mg, 0.251 mmol) in 1,4-dioxane (2.5 mL) was added 4 M HCl in 1,4-dioxane (1.25 mL, 5 mmol) and the resulting solution stirred at rt for 2 h before DCM (2.5 mL) was added and the reaction mixture was stirred for a further 18 h. The reaction mixture was concentrated under reduced pressure to give the title compound (84 mg, quantitative) as an off-white crystalline solid. This material was used in the subsequent step without further purification. LCMS (Method A): $R_T$=0.33 min, m/z=298, 300 [M−Cl]$^+$.

Step 2: (R)-3-Phenylmorpholine-4-carbonyl chloride: A solution of triphosgene (56.4 mg, 0.190 mmol) in DCM (1.9 mL) was added dropwise to a solution of (R)-3-phenylmorpholine (62 mg, 0.380 mmol) and pyridine (46 μL, 0.570 mmol) in DCM (1.9 mL) at 0° C. The resulting yellow solution was stirred at rt for 30 min before 1 M HCl$_{(aq)}$ (15 mL) was added. The resulting mixture was extracted with DCM (3×10 mL) using a phase separator before the combined organic phases were concentrated under reduced pressure to give the title compound (85 mg, 99%) as a yellow oil. This material was used without further purification. LCMS (Method A): $R_T$=1.32 min, m/z=226, 228 [M+H]$^+$.

Step 3: 6-Chloro-3-(((S)-10-hydroxy-7-((R)-3-phenylmorpholine-4-carbonyl)-7-azaspiro[4.5]decan-10-yl)methyl)pyrimidin-4(3H)-one: Prepared according to General Procedure 9 using (S)-6-chloro-3-((10-hydroxy-7-azaspiro[4.5]decan-10-yl)methyl)pyrimidin-4(3H)-one hydrochloride (84 mg, 0.251 mmol), (R)-3-phenylmorpholine-4-carbonyl chloride (85 mg, 0.377 mmol) and DIPEA (0.177 mL, 1.01 mmol) in DCM (2.5 mL) for 16 h give the title compound (115 mg, 89%) as a beige foam. LCMS (Method A): $R_T$=1.24 min, m/z=487, 489 [M+H]$^+$. $^1$H NMR (500 MHz, DMSO-d$_6$): δ 8.33 (s, 1H), 7.36-7.26 (m, 4H), 7.25-7.20 (m, 1H), 6.61 (s, 1H), 4.80 (s, 1H), 4.48 (d, J=13.4 Hz, 1H), 4.41 (t, J=4.7 Hz, 1H), 3.80-3.63 (m, 4H), 3.62-3.51 (m, 2H), 3.25-3.15 (m, 2H), 3.14-3.08 (m, 1H), 3.06-2.96 (m, 2H), 1.91-1.84 (m, 1H), 1.64-1.42 (m, 5H), 1.42-1.35 (m, 1H), 1.33-1.26 (m, 1H), 1.22-1.15 (m, 1H), 1.09-1.02 (m, 1H).

Example 221: (S)-3-((10-Hydroxy-7-(3-(trifluoromethyl)azetidine-1-carbonyl)-7-azaspiro[4.5]decan-10-yl)methyl)-6-phenylpyrimidin-4(3H)-one

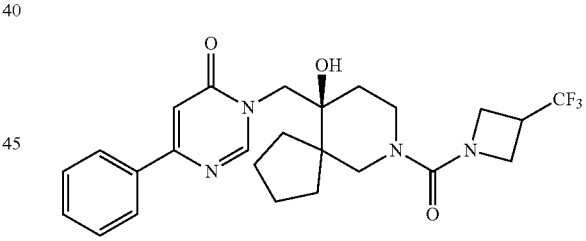

Prepared according to General Procedure 9 using (S)-10-hydroxy-10-((6-oxo-4-phenylpyrimidin-1(6H)-yl)methyl)-7-azaspiro[4.5]decane-7-carbonyl chloride (10 mg, 0.0249 mmol), 3-(trifluoromethyl)azetidine hydrochloride (6 mg, 0.0373 mmol) and DIPEA (13 μL, 0.0746 mmol) in DMF (0.5 mL) for 16 h to give the title compound (8.5 mg, 67%) as a colourless solid after lyophilisation. LCMS (Method A): $R_T$=1.35 min, m/z=491 [M+H]$^+$. $^1$H NMR (500 MHz, DMSO-d$_6$): δ 8.46 (s, 1H), 8.13-8.01 (m, 2H), 7.58-7.42 (m, 3H), 6.97 (s, 1H), 4.84 (s, 1H), 4.58 (d, J=13.6 Hz, 1H), 4.10 (dt, J=14.9, 8.8 Hz, 2H), 3.85 (ddd, J=15.4, 8.9, 5.5 Hz, 2H), 3.63 (d, J=13.6 Hz, 1H), 3.59-3.47 (m, 1H), 3.44-3.37 (m, 1H), 3.21-3.12 (m, 2H), 3.09 (d, J=13.1 Hz, 1H), 1.96-1.88 (m, 1H), 1.70-1.50 (m, 5H), 1.45-1.33 (m, 2H), 1.23-1.14 (m, 2H).

Example 222: 6-Cyclopropyl-3-(((S)-10-hydroxy-7-((R)-3-phenylmorpholine-4-carbonyl)-7-azaspiro[4.5]decan-10-yl)methyl)pyrimidin-4(3H)-one

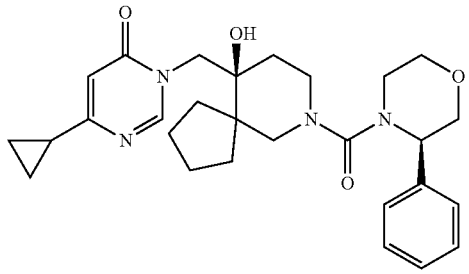 [SMILES: O=C(N1CC[C@@](O)(Cn2cnc(C3CC3)cc2=O)C2(CCCC2)C1)N1CCOC[C@H]1c1ccccc1]

Prepared according to General Procedure 5 using 6-chloro-3-(((S)-10-hydroxy-7-((R)-3-phenylmorpholine-4-carbonyl)-7-azaspiro[4.5]decan-10-yl)methyl)pyrimidin-4(3H)-one (20 mg, 0.0411 mmol), cyclopropylboronic acid MIDA ester (16.2 mg, 0.0821 mmol), tricyclohexylphosphonium tetrafluoroborate (4.5 mg, 12.3 µmol) and palladium(II) acetate (1.4 mg, 6.16 µmol) in toluene (0.3 mL) and water (0.07 mL) heated at 100° C. (oil bath) for 1 h 45 min to give the title compound (13.8 mg, 66%) as a colourless solid after lyophilisation. LCMS (Method A): $R_T$=1.26 min, m/z=493 [M+H]$^+$. $^1$H NMR (500 MHz, DMSO-d$_6$): δ 8.21 (s, 1H), 7.37-7.26 (m, 4H), 7.26-7.18 (m, 1H), 6.31 (s, 1H), 4.75 (s, 1H), 4.45 (d, J=13.6 Hz, 1H), 4.40 (t, J=4.8 Hz, 1H), 3.78-3.64 (m, 4H), 3.60-3.55 (m, 1H), 3.53 (d, J=13.6 Hz, 1H), 3.27-3.15 (m, 2H), 3.15-3.07 (m, 1H), 3.07-2.95 (m, 2H), 1.92-1.80 (m, 2H), 1.65-1.42 (m, 5H), 1.41-1.33 (m, 1H), 1.32-1.25 (m, 1H), 1.18-1.10 (m, 1H), 1.09-1.02 (m, 1H), 0.92 (d, J=6.4 Hz, 4H).

Example 223: 3-(((S)-10-Hydroxy-7-((R)-3-phenylmorpholine-4-carbonyl)-7-azaspiro[4.5]decan-10-yl)methyl)-6-(pyrrolidin-1-yl)pyrimidin-4(3H)-one

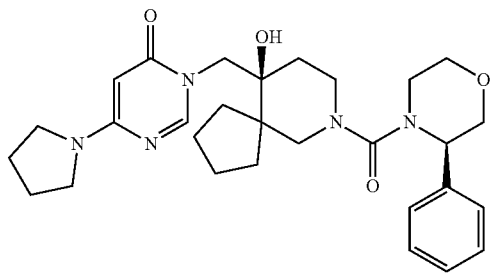 [SMILES: O=C(N1CC[C@@](O)(Cn2cnc(N3CCCC3)cc2=O)C2(CCCC2)C1)N1CCOC[C@H]1c1ccccc1]

A solution of 6-chloro-3-(((S)-10-hydroxy-7-((R)-3-phenylmorpholine-4-carbonyl)-7-azaspiro[4.5]decan-10-yl)methyl)pyrimidin-4(3H)-one (15 mg, 0.0308 mmol) and pyrrolidine (25 µL, 0.308 mmol) in 1,4-dioxane (0.5 mL) was heated under microwave irradiation at 120° C. for 30 min before the reaction mixture was directly purified by flash chromatography (0-10% MeOH in DCM) to give the title compound (15.7 mg, 96%) as a colourless solid after lyophilisation. LCMS (Method A): $R_T$=1.25 min, m/z=522 [M+H]$^+$. $^1$H NMR (500 MHz, DMSO-d$_6$): δ 8.11 (s, 1H), 7.35-7.26 (m, 4H), 7.25-7.20 (m, 1H), 5.02 (s, 1H), 4.99 (s, 1H), 4.39 (t, J=5.0 Hz, 1H), 4.31 (d, J=13.8 Hz, 1H), 3.78-3.64 (m, 4H), 3.63-3.55 (m, 2H), 3.50-3.15 (m, 6H (signals overlap with HDO)), 3.14-3.08 (m, 1H), 3.06-2.95 (m, 2H), 1.98-1.80 (m, 5H), 1.63-1.42 (m, 5H), 1.42-1.34 (m, 1H), 1.31-1.25 (m, 1H), 1.16-1.09 (m, 1H), 1.09-1.02 (m, 1H).

Example 224: 3-(((S)-10-Hydroxy-7-((R)-3-phenylmorpholine-4-carbonyl)-7-azaspiro[4.5]decan-10-yl)methyl)-6-(1-methyl-1H-pyrazol-5-yl)pyrimidin-4(3H)-one

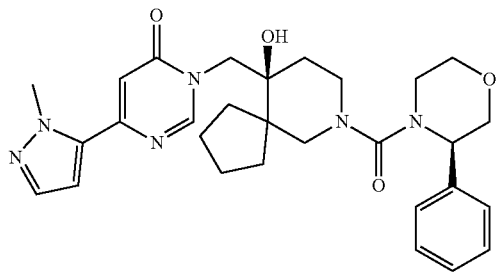 [SMILES: Cn1nccc1-c1cc(=O)n(C[C@]2(O)CCN(C(=O)N3CCOC[C@H]3c3ccccc3)CC23CCCC3)cn1]

Prepared according to General Procedure 5 using 6-chloro-3-(((S)-10-hydroxy-7-((R)-3-phenylmorpholine-4-carbonyl)-7-azaspiro[4.5]decan-10-yl)methyl)pyrimidin-4(3H)-one (15 mg, 0.0308 mmol), 1-methyl-5-(4,4,5,5-tetramethyl-1,3,2-dioxaborolan-2-yl)-1H-pyrazole (12.8 mg, 0.0616 mmol), Pd(dppf)Cl$_2$·DCM (1.3 mg, 1.54 µmol) and sodium carbonate (9.8 mg, 0.0924 mmol) in 1,4-dioxane (0.45 mL) and water (0.15 mL) under microwave irradiation at 120° C. for 30 min to give the title compound (6.6 mg, 39% yield) as a light beige solid after lyophilisation. LCMS (Method A): $R_T$=1.17 min, m/z=533 [M+H]$^+$. $^1$H NMR (500 MHz, DMSO-d$_6$): δ 8.46 (s, 1H), 7.49 (d, J=2.0 Hz, 1H), 7.36-7.27 (m, 4H), 7.26-7.19 (m, 1H), 6.86 (d, J=2.0 Hz, 1H), 6.79 (s, 1H), 4.81 (s, 1H), 4.55 (d, J=13.5 Hz, 1H), 4.41 (t, J=4.8 Hz, 1H), 4.12 (s, 3H), 3.80-3.54 (m, 6H), 3.26-3.16 (m, 2H), 3.16-3.09 (m, 1H), 3.08-2.98 (m, 2H), 1.93-1.84 (m, 1H), 1.65-1.40 (m, 6H), 1.36-1.28 (m, 1H), 1.24-1.18 (m, 1H), 1.12-1.03 (m, 1H).

Example 225: 3-(((S)-10-Hydroxy-7-((R)-3-phenylmorpholine-4-carbonyl)-7-azaspiro[4.5]decan-10-yl)methyl)-6-(1-methyl-1H-pyrazol-4-yl)pyrimidin-4(3H)-one

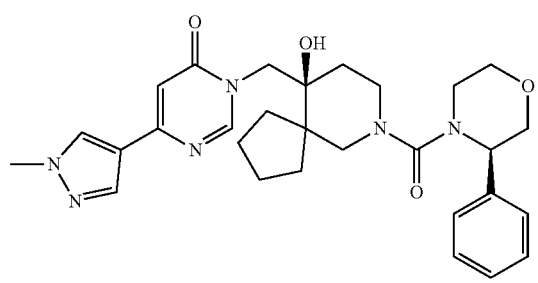 [SMILES: Cn1cc(-c2cc(=O)n(C[C@]3(O)CCN(C(=O)N4CCOC[C@H]4c4ccccc4)CC34CCCC4)cn2)cn1]

Prepared according to General Procedure 5 using 6-chloro-3-(((S)-10-hydroxy-7-((R)-3-phenylmorpholine-4-carbonyl)-7-azaspiro[4.5]decan-10-yl)methyl)pyrimidin-4(3H)-one (15 mg, 0.0308 mmol), 1-methyl-4-(4,4,5,5-tetramethyl-1,3,2-dioxaborolan-2-yl)-1H-pyrazole (12.8 mg, 0.0616 mmol), Pd(dppf)Cl₂·DCM (1.3 mg, 1.54 µmol) and sodium carbonate (9.8 mg, 0.0924 mmol) in 1,4-dioxane (0.45 mL) and water (0.15 mL) under microwave irradiation at 120° C. for 30 min to give the title compound (11 mg, 66%) as a slightly off-white solid after lyophilisation. LCMS (Method A): $R_T$=1.08 min, m/z=533 [M+H]⁺. ¹H NMR (500 MHz, DMSO-d₆): δ 8.32 (s, 1H), 8.29 (s, 1H), 7.99 (s, 1H), 7.35-7.26 (m, 4H), 7.26-7.19 (m, 1H), 6.63 (s, 1H), 4.81 (s, 1H), 4.50 (d, J=13.6 Hz, 1H), 4.40 (t, J=4.9 Hz, 1H), 3.87 (s, 3H), 3.80-3.63 (m, 4H), 3.62-3.53 (m, 2H), 3.26-3.15 (m, 2H), 3.15-3.08 (m, 1H), 3.07-2.96 (m, 2H), 1.91-1.84 (m, 1H), 1.65-1.37 (m, 6H), 1.35-1.27 (m, 1H), 1.22-1.15 (m, 1H), 1.11-1.03 (m, 1H).

Example 226: 6-(Dimethylamino)-3-(((S)-10-hydroxy-7-((R)-3-phenylmorpholine-4-carbonyl)-7-azaspiro[4.5]decan-10-yl)methyl)pyrimidin-4(3H)-one

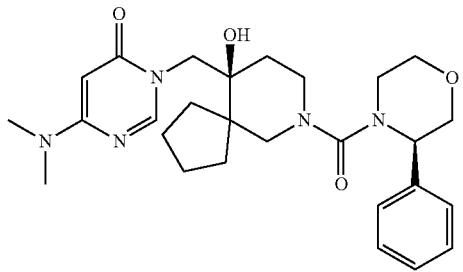 [SMILES: CN(C)c1cc(=O)n(C[C@]2(O)CCN(C(=O)N3CCOC[C@H]3c3ccccc3)CC23CCCC3)cn1]

A solution of 6-chloro-3-(((S)-10-hydroxy-7-((R)-3-phenylmorpholine-4-carbonyl)-7-azaspiro[4.5]decan-10-yl)methyl)pyrimidin-4(3H)-one (11.3 mg, 0.0231 mmol) and dimethylamine (2 M in THF) (0.116 mL, 0.231 mmol) in 1,4-dioxane (0.5 mL) was heated under microwave irradiation at 120° C. for 30 min before the reaction mixture was directly purified by flash chromatography (0-10% MeOH in DCM) to give the title compound (7.2 mg, 62%) as a colourless solid after lyophilisation. LCMS (Method A): $R_T$=1.16 min, m/z=496 [M+H]⁺. ¹H NMR (500 MHz, DMSO-d₆): δ 8.11 (s, 1H), 7.36-7.26 (m, 4H), 7.26-7.19 (m, 1H), 5.17 (s, 1H), 4.97 (s, 1H), 4.39 (t, J=4.9 Hz, 1H), 4.31 (d, J=13.8 Hz, 1H), 3.78-3.64 (m, 4H), 3.62-3.53 (m, 2H), 3.26-3.14 (m, 2H), 3.15-3.08 (m, 1H), 3.07-2.99 (m, 2H), 2.98 (s, 6H), 1.87-1.80 (m, 1H), 1.63-1.43 (m, 5H), 1.42-1.35 (m, 1H), 1.32-1.24 (m, 1H), 1.16-1.09 (m, 1H), 1.09-1.02 (m, 1H).

Example 227: 3-(((10S)-10-Hydroxy-7-(3-(trifluoromethyl)pyrrolidine-1-carbonyl)-7-azaspiro[4.5]decan-10-yl)methyl)-6-phenylpyrimidin-4(3H)-one

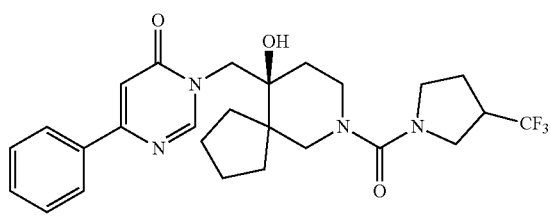 [SMILES: O=C(N1CCC(C(F)(F)F)C1)N1CC[C@@](O)(Cn2cnc(-c3ccccc3)cc2=O)C2(CCCC2)C1]

A solution of triphosgene (3.5 mg, 0.0118 mmol) in DCM (0.3 mL) was added to a mixture 3-(trifluoromethyl)pyrrolidine hydrochloride (6.2 mg, 0.0354 mmol) and DIPEA (21 µL, 0.118 mmol) in DCM (0.3 mL) after 1 h, (S)-3-((10-hydroxy-7-azaspiro[4.5]decan-10-yl)methyl)-6-phenylpyrimidin-4(3H)-one (10 mg, 0.0295 mmol) was added. The reaction was stirred at rt for 18 h before saturated NaHCO₃(aq) (15 mL) was added and the resulting mixture was extracted with DCM (3×10 mL) using a phase separator. The combined organic phases were concentrated under reduced pressure and the residue was purified by flash chromatography (0-100% EtOAc in cyclohexane) to give the title compound (5.2 mg, 34%) as a colourless solid after lyophilisation. LCMS (Method A): $R_T$=1.42 min, m/z=505 [M+H]⁺. ¹H NMR (500 MHz, DMSO-d₆): δ 8.47 (s, 1H), 8.13-8.02 (m, 2H), 7.57-7.42 (m, 3H), 6.97 (s, 1H), 4.82 (s, 1H), 4.60 (d, J=13.6 Hz, 1H), 3.63 (d, J=13.6 Hz, 1H), 3.56-3.45 (m, 1H), 3.44-3.30 (m, 4H), 3.22-3.08 (m, 3H), 3.03 (t, J=13.9 Hz, 1H), 2.13-2.02 (m, 1H), 1.99-1.82 (m, 2H), 1.73-1.50 (m, 5H), 1.50-1.36 (m, 2H), 1.28-1.17 (m, 2H).

Example 228: 3-(((S)-7-((R)-3-(4-Fluorophenyl)morpholine-4-carbonyl)-10-hydroxy-7-azaspiro[4.5]decan-10-yl)methyl)-6-phenylpyrimidin-4(3H)-one

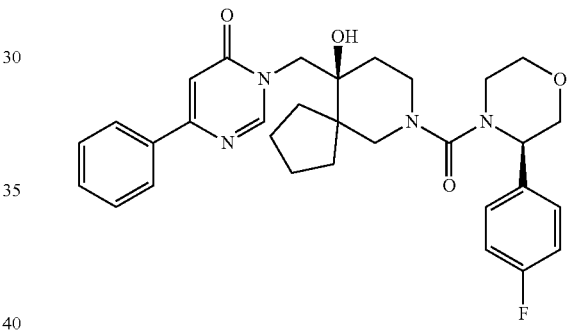

A solution of triphosgene (3.5 mg, 0.0118 mmol) in DCM (0.3 mL) was added to a mixture of (R)-3-(4-fluorophenyl)morpholine hydrochloride (7.7 mg, 0.0354 mmol) [commercially available] and DIPEA (21 µL, 0.118 mmol) in DCM (0.3 mL) after 1 h, (S)-3-((10-hydroxy-7-azaspiro[4.5]decan-10-yl)methyl)-6-phenylpyrimidin-4(3H)-one (10 mg, 0.0295 mmol) was added. The reaction was stirred at rt for 18 h before saturated NaHCO₃(aq) (15 mL) was added and the resulting mixture was extracted with DCM (3×10 mL) using a phase separator. The combined organic phases were concentrated under reduced pressure and the residue was purified by flash chromatography (0-100% EtOAc in cyclohexane) to give the title compound (7.6 mg, 46%) as a colourless solid after lyophilisation. LCMS (Method A): $R_T$=1.46 min, m/z=547 [M+H]⁺. ¹H NMR (500 MHz, DMSO-d₆): δ 8.46 (s, 1H), 8.11-8.03 (m, 2H), 7.57-7.46 (m, 3H), 7.39-7.32 (m, 2H), 7.16-7.08 (m, 2H), 6.97 (s, 1H), 4.83 (s, 1H), 4.55 (d, J=13.5 Hz, 1H), 4.40 (t, J=5.0 Hz, 1H), 3.80-3.53 (m, 6H), 3.27-3.16 (m, 2H), 3.14-3.07 (m, 1H), 3.07-2.95 (m, 2H), 1.93-1.84 (m, 1H), 1.67-1.39 (m, 6H), 1.34-1.26 (m, 1H), 1.25-1.18 (m, 1H), 1.10-1.02 (m, 1H).

The following table of Examples was prepared using parallel synthesis according to General Procedure 13, General Procedure 14, General Procedure 15, or General Procedure 16, as indicated for each Example. Initially, stock solutions of each reagent in DMF were prepared in advance (typically 0.2 M to 1.5 M). Unless stated otherwise, standard 96-well DeepWell 2 mL microtiter plates were used to perform the reaction. All liquid handling operations were performed using TECAN EVO 200 or TECAN EVO 100 Liquid Handlers. Solvents were blown away using stream of nitrogen or evaporated on Savant Speedvac.

| Example (General Procedure) | Structure | Name | LCMS (Method C): $R_T$, m/z |
|---|---|---|---|
| 229 (13) | 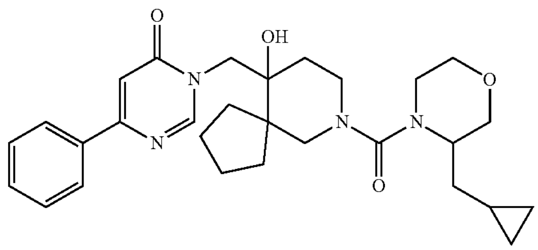 [SMILES: O=C(N1CCC(O)(Cn2cnc(-c3ccccc3)cc2=O)C2(CCCC2)C1)N1CCOCC1CC1CC1] | 3-((7-(3-(Cyclopropylmethyl)morpholine-4-carbonyl)-10-hydroxy-7-azaspiro[4.5]decan-10-yl)methyl)-6-phenylpyrimidin-4(3H)-one | 1.42 min, 507 [M + H]⁺ |
| 230 (13) | 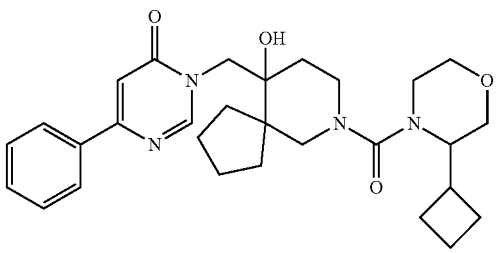 [SMILES: O=C(N1CCC(O)(Cn2cnc(-c3ccccc3)cc2=O)C2(CCCC2)C1)N1CCOCC1C1CCC1] | 3-((7-(3-Cyclobutylmorpholine-4-carbonyl)-10-hydroxy-7-azaspiro[4.5]decan-10-yl)methyl)-6-phenylpyrimidin-4(3H)-one | 1.39 min, 507 [M + H]⁺ |
| 231 (13) | 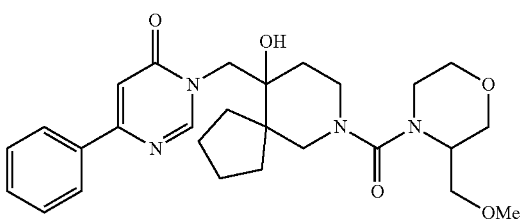 [SMILES: COCC1COCCN1C(=O)N1CCC(O)(Cn2cnc(-c3ccccc3)cc2=O)C2(CCCC2)C1] | 3-((10-Hydroxy-7-(3-(methoxymethyl)morpholine-4-carbonyl)-7-azaspiro[4.5]decan-10-yl)methyl)-6-phenylpyrimidin-4(3H)-one | 1.32 min, 497 [M + H]⁺ |
| 232 (13) | 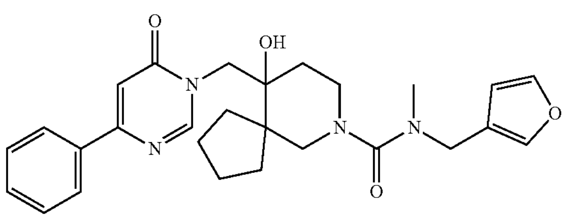 [SMILES: CN(Cc1ccoc1)C(=O)N1CCC(O)(Cn2cnc(-c3ccccc3)cc2=O)C2(CCCC2)C1] | N-(Furan-3-ylmethyl)-10-hydroxy-N-methyl-10-((6-oxo-4-phenylpyrimidin-1(6H)-yl)methyl)-7-azaspiro[4.5]decane-7-carboxamide | 1.43 min, 477 [M + H]⁺ |
| 233 (13) | 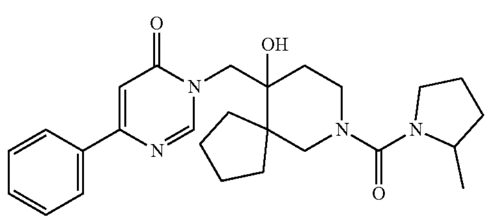 [SMILES: CC1CCCN1C(=O)N1CCC(O)(Cn2cnc(-c3ccccc3)cc2=O)C2(CCCC2)C1] | 3-((10-Hydroxy-7-(2-methylpyrrolidine-1-carbonyl)-7-azaspiro[4.5]decan-10-yl)methyl)-6-phenylpyrimidin-4(3H)-one | 1.35 min, 451 [M + H]⁺ |
| 234 (13) | 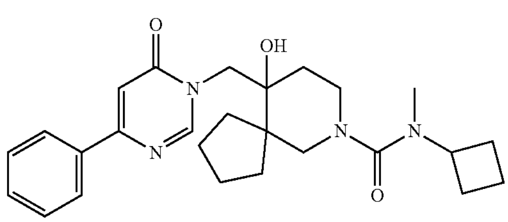 [SMILES: CN(C(=O)N1CCC(O)(Cn2cnc(-c3ccccc3)cc2=O)C2(CCCC2)C1)C1CCC1] | N-Cyclobutyl-10-hydroxy-N-methyl-10-((6-oxo-4-phenylpyrimidin-1(6H)-yl)methyl)-7-azaspiro[4.5]decane-7-carboxamide | 1.43 min, 451 [M + H]⁺ |

| Example (General Procedure) | Structure | Name | LCMS (Method C): $R_T$, m/z |
|---|---|---|---|
| 235 (13) | 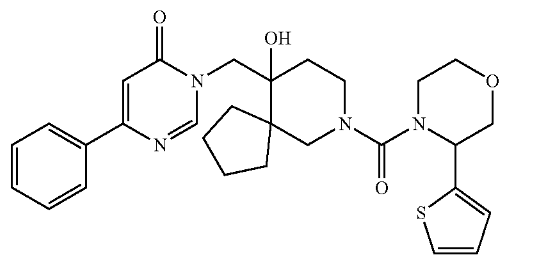 [SMILES: O=C(N1CCC(O)(Cn2cnc(-c3ccccc3)cc2=O)C2(CCCC2)C1)N1CCOCC1c1cccs1] | 3-((10-Hydroxy-7-(3-(thiophen-2-yl)morpholine-4-carbonyl)-7-azaspiro[4.5]decan-10-yl)methyl)-6-phenylpyrimidin-4(3H)-one | 1.34 min, 535 [M + H]$^+$ |
| 236 (13) | 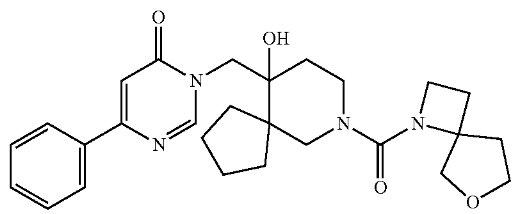 [SMILES: O=C(N1CCC(O)(Cn2cnc(-c3ccccc3)cc2=O)C2(CCCC2)C1)N1CCC12CCOC2] | 3-((10-Hydroxy-7-(6-oxa-1-azaspiro[3.4]octane-1-carbonyl)-7-azaspiro[4.5]decan-10-yl)methyl)-6-phenylpyrimidin-4(3H)-one | 1.26 min, 479 [M + H]$^+$ |
| 237 (13) | 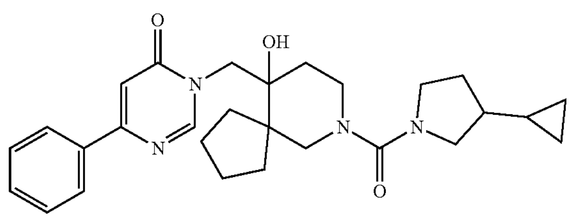 [SMILES: O=C(N1CCC(C2CC2)C1)N1CCC(O)(Cn2cnc(-c3ccccc3)cc2=O)C2(CCCC2)C1] | 3-((7-(3-Cyclopropylpyrrolidine-1-carbonyl)-10-hydroxy-7-azaspiro[4.5]decan-10-yl)methyl)-6-phenylpyrimidin-4(3H)-one | 1.52 min, 477 [M + H]$^+$ |
| 238 (13) | 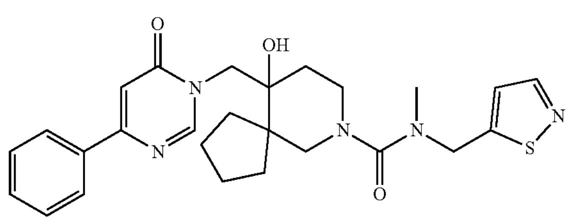 [SMILES: CN(Cc1ccns1)C(=O)N1CCC(O)(Cn2cnc(-c3ccccc3)cc2=O)C2(CCCC2)C1] | 10-Hydroxy-N-(isothiazol-5-ylmethyl)-N-methyl-10-((6-oxo-4-phenylpyrimidin-1(6H)-yl)methyl)-7-azaspiro[4.5]decane-7-carboxamide | 1.27 min, 494 [M + H]$^+$ |
| 239 (13) | 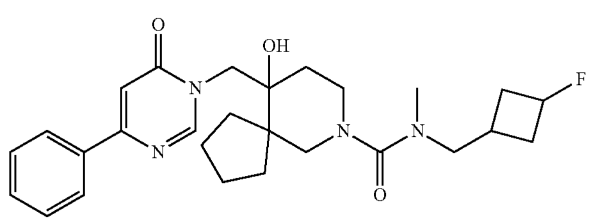 [SMILES: CN(CC1CC(F)C1)C(=O)N1CCC(O)(Cn2cnc(-c3ccccc3)cc2=O)C2(CCCC2)C1] | N-((3-Fluorocyclobutyl)methyl)-10-hydroxy-N-methyl-10-((6-oxo-4-phenylpyrimidin-1(6H)-yl)methyl)-7-azaspiro[4.5]decane-7-carboxamide | 1.39 min, 483 [M + H]$^+$ |
| 240 (13) | 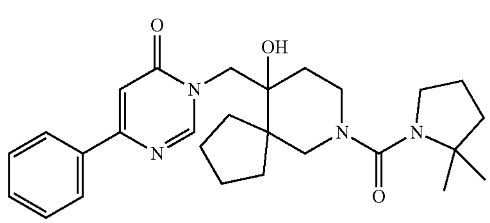 [SMILES: CC1(C)CCCN1C(=O)N1CCC(O)(Cn2cnc(-c3ccccc3)cc2=O)C2(CCCC2)C1] | 3-((7-(2,2-Dimethylpyrrolidine-1-carbonyl)-10-hydroxy-7-azaspiro[4.5]decan-10-yl)methyl)-6-phenylpyrimidin-4(3H)-one | 1.43 min, 465 [M + H]$^+$ |

| Example (General Procedure) | Structure | Name | LCMS (Method C): $R_T$, m/z |
|---|---|---|---|
| 241 (13) | 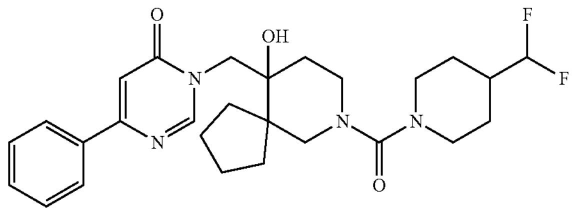 [SMILES: O=C(N1CCC(C(F)F)CC1)N1CCC(O)(Cn2cnc(-c3ccccc3)cc2=O)C2(CCCC2)C1] | 3-((7-(4-(Difluoromethyl)piperidine-1-carbonyl)-10-hydroxy-7-azaspiro[4.5]decan-10-yl)methyl)-6-phenylpyrimidin-4(3H)-one | 1.43 min, 501 [M + H]+ |
| 242 (13) | 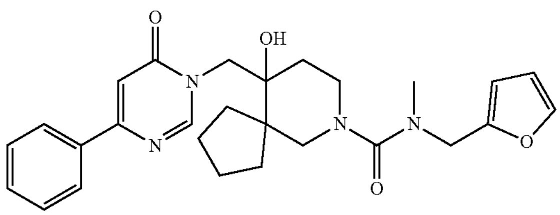 [SMILES: CN(Cc1ccco1)C(=O)N1CCC(O)(Cn2cnc(-c3ccccc3)cc2=O)C2(CCCC2)C1] | N-(Furan-2-ylmethyl)-10-hydroxy-N-methyl-10-((6-oxo-4-phenylpyrimidin-1(6H)-yl)methyl)-7-azaspiro[4.5]decane-7-carboxamide | 1.35 min, 477 [M + H]+ |
| 243 (13) | 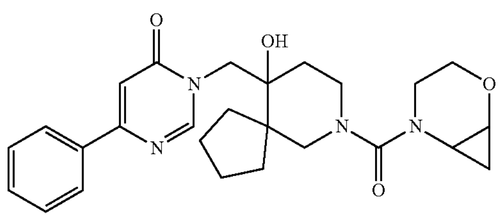 [SMILES: O=C(N1CCC(O)(Cn2cnc(-c3ccccc3)cc2=O)C2(CCCC2)C1)N1CCOC2CC21] | 3-((7-(2-Oxa-5-azabicyclo[4.1.0]heptane-5-carbonyl)-10-hydroxy-7-azaspiro[4.5]decan-10-yl)methyl)-6-phenylpyrimidin-4(3H)-one | 1.23 min, 465 [M + H]+ |
| 244 (13) | 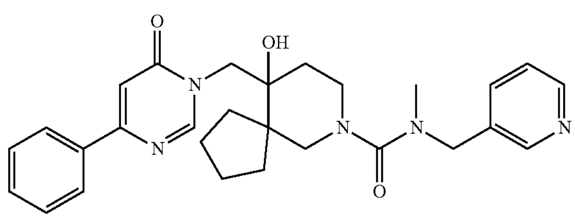 [SMILES: CN(Cc1cccnc1)C(=O)N1CCC(O)(Cn2cnc(-c3ccccc3)cc2=O)C2(CCCC2)C1] | 10-Hydroxy-N-methyl-10-((6-oxo-4-phenylpyrimidin-1(6H)-yl)methyl)-N-(pyridin-3-ylmethyl)-7-azaspiro[4.5]decane-7-carboxamide | 1.00 min, 488 [M + H]+ |
| 245 (13) | 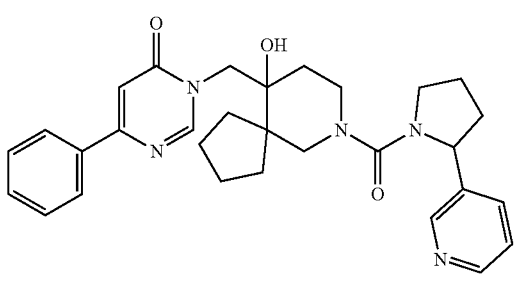 [SMILES: O=C(N1CCC(O)(Cn2cnc(-c3ccccc3)cc2=O)C2(CCCC2)C1)N1CCCC1c1cccnc1] | 3-((10-Hydroxy-7-(2-(pyridin-3-yl)pyrrolidine-1-carbonyl)-7-azaspiro[4.5]decan-10-yl)methyl)-6-phenylpyrimidin-4(3H)-one | 1.07 min, 514 [M + H]+ |
| 246 (13) | 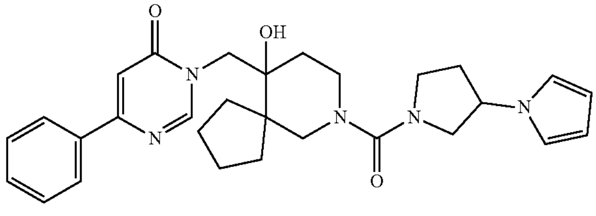 [SMILES: O=C(N1CCC(n2cccc2)C1)N1CCC(O)(Cn2cnc(-c3ccccc3)cc2=O)C2(CCCC2)C1] | 3-((7-(3-(1H-Pyrrol-1-yl)pyrrolidine-1-carbonyl)-10-hydroxy-7-azaspiro[4.5]decan-10-yl)methyl)-6-phenylpyrimidin-4(3H)-one | 1.44 min, 502 [M + H]+ |

| Example (General Procedure) | Structure | Name | LCMS (Method C): $R_T$, m/z |
|---|---|---|---|
| 247 (13) | 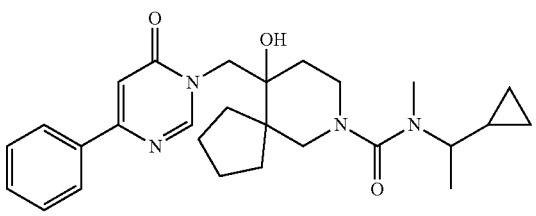 [SMILES: CC(C1CC1)N(C)C(=O)N1CCC(O)(Cn2cnc(-c3ccccc3)cc2=O)C2(CCCC2)C1] | N-(1-Cyclopropylethyl)-10-hydroxy-N-methyl-10-((6-oxo-4-phenylpyrimidin-1(6H)-yl)methyl)-7-azaspiro[4.5]decane-7-carboxamide | 1.40 min, 465 [M + H]+ |
| 248 (13) | 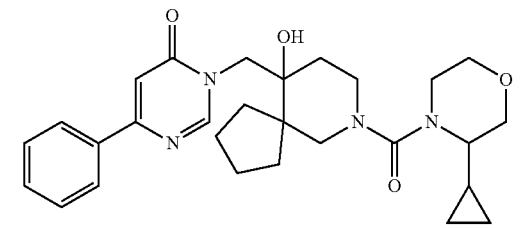 [SMILES: O=C(N1CCC(O)(Cn2cnc(-c3ccccc3)cc2=O)C2(CCCC2)C1)N1CCOCC1C1CC1] | 3-((7-(3-Cyclopropylmorpholine-4-carbonyl)-10-hydroxy-7-azaspiro[4.5]decan-10-yl)methyl)-6-phenylpyrimidin-4(3H)-one | 1.40 min, 493 [M + H]+ |
| 249 (13) | 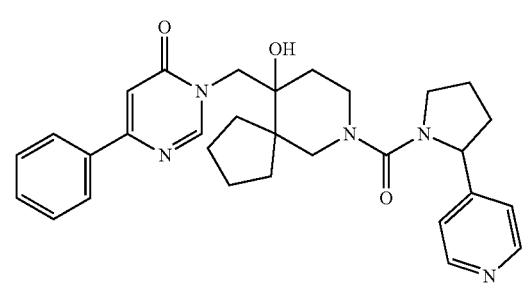 [SMILES: O=C(N1CCC(O)(Cn2cnc(-c3ccccc3)cc2=O)C2(CCCC2)C1)N1CCCC1c1ccncc1] | 3-((10-Hydroxy-7-(2-(pyridin-4-yl)pyrrolidine-1-carbonyl)-7-azaspiro[4.5]decan-10-yl)methyl)-6-phenylpyrimidin-4(3H)-one | 1.02 min, 514 [M + H]+ |
| 250 (13) | 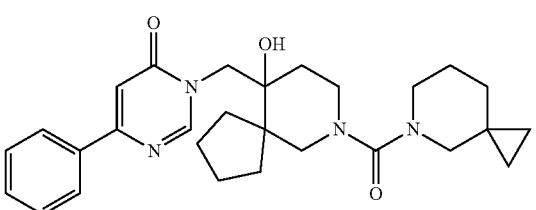 | 3-((10-Hydroxy-7-(5-azaspiro[2.5]octane-5-carbonyl)-7-azaspiro[4.5]decan-10-yl)methyl)-6-phenylpyrimidin-4(3H)-one | 1.53 min, 477 [M + H]+ |
| 251 (13) | 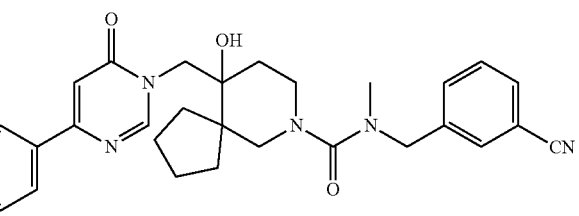 | N-(3-Cyanobenzyl)-10-hydroxy-N-methyl-10-((6-oxo-4-phenylpyrimidin-1(6H)-yl)methyl)-7-azaspiro[4.5]decane-7-carboxamide | 1.39 min, 512 [M + H]+ |
| 252 (13) | 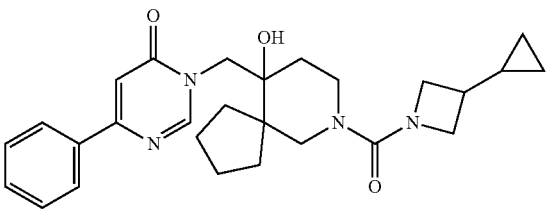 [SMILES: O=C(N1CC(C2CC2)C1)N1CCC(O)(Cn2cnc(-c3ccccc3)cc2=O)C2(CCCC2)C1] | 3-((7-(3-Cyclopropylazetidine-1-carbonyl)-10-hydroxy-7-azaspiro[4.5]decan-10-yl)methyl)-6-phenylpyrimidin-4(3H)-one | 1.38 min, 463 [M + H]+ |

| Example (General Procedure) | Structure | Name | LCMS (Method C): R$_T$, m/z |
|---|---|---|---|
| 253 (13) | 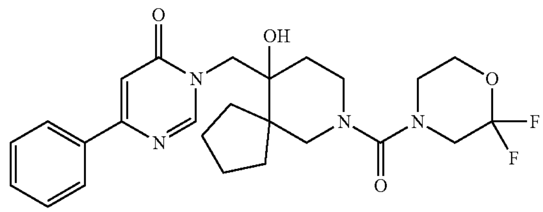 [SMILES: O=C(N1CCOC(F)(F)C1)N1CCC(O)(Cn2cnc(-c3ccccc3)cc2=O)C2(CCCC2)C1] | 3-((7-(2,2-Difluoromorpholine-4-carbonyl)-10-hydroxy-7-azaspiro[4.5]decan-10-yl)methyl)-6-phenylpyrimidin-4(3H)-one | 1.32 min, 489 [M + H]$^+$ |
| 254 (14) | 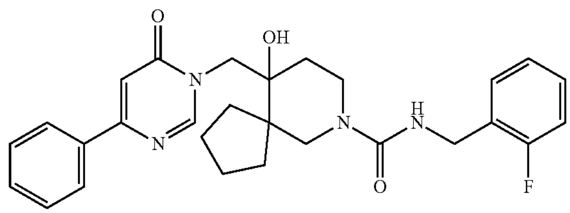 [SMILES: O=C(NCc1ccccc1F)N1CCC(O)(Cn2cnc(-c3ccccc3)cc2=O)C2(CCCC2)C1] | N-(2-Fluorobenzyl)-10-hydroxy-10-((6-oxo-4-phenylpyrimidin-1(6H)-yl)methyl)-7-azaspiro[4.5]decane-7-carboxamide | 1.41 min, 491 [M + H]$^+$ |
| 255 (14) | 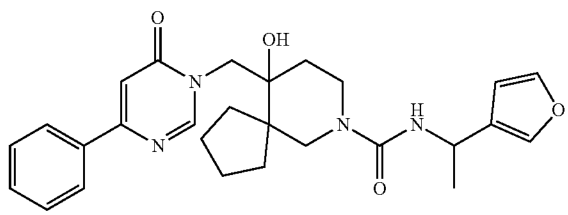 [SMILES: CC(NC(=O)N1CCC(O)(Cn2cnc(-c3ccccc3)cc2=O)C2(CCCC2)C1)c1ccoc1] | N-(1-(Furan-3-yl)ethyl)-10-hydroxy-10-((6-oxo-4-phenylpyrimidin-1(6H)-yl)methyl)-7-azaspiro[4.5]decane-7-carboxamide | 1.35 min, 477 [M + H]$^+$ |
| 256 (14) | 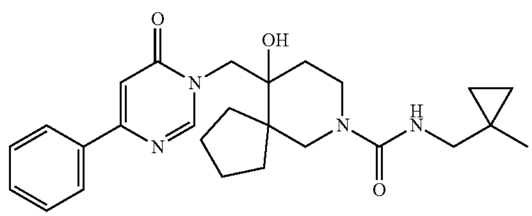 [SMILES: CC1(CNC(=O)N2CCC(O)(Cn3cnc(-c4ccccc4)cc3=O)C3(CCCC3)C2)CC1] | 10-Hydroxy-N-((1-methylcyclopropyl)methyl)-10-((6-oxo-4-phenylpyrimidin-1(6H)-yl)methyl)-7-azaspiro[4.5]decane-7-carboxamide | 1.37 min, 451 [M + H]$^+$ |
| 257 (14) | 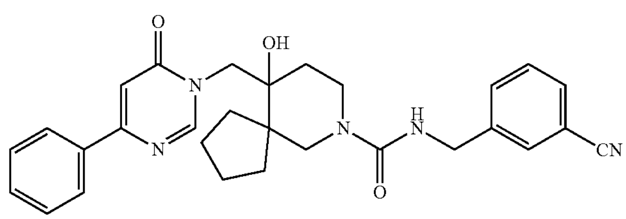 [SMILES: N#Cc1cccc(CNC(=O)N2CCC(O)(Cn3cnc(-c4ccccc4)cc3=O)C3(CCCC3)C2)c1] | N-(3-Cyanobenzyl)-10-hydroxy-10-((6-oxo-4-phenylpyrimidin-1(6H)-yl)methyl)-7-azaspiro[4.5]decane-7-carboxamide | 1.34 min, 498 [M + H]$^+$ |
| 258 (14) | 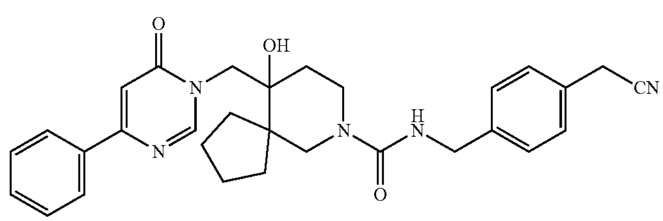 [SMILES: N#CCc1ccc(CNC(=O)N2CCC(O)(Cn3cnc(-c4ccccc4)cc3=O)C3(CCCC3)C2)cc1] | N-(4-(Cyanomethyl)benzyl)-10-hydroxy-10-((6-oxo-4-phenylpyrimidin-1(6H)-yl)methyl)-7-azaspiro[4.5]decane-7-carboxamide | 1.33 min, 512 [M + H]$^+$ |
| 259 (14) | 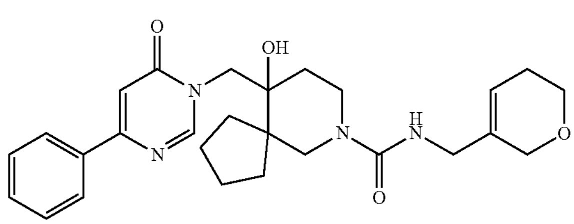 [SMILES: O=C(NCC1=CCCOC1)N1CCC(O)(Cn2cnc(-c3ccccc3)cc2=O)C2(CCCC2)C1] | N-((5,6-Dihydro-2H-pyran-3-yl)methyl)-10-hydroxy-10-((6-oxo-4-phenylpyrimidin-1(6H)-yl)methyl)-7-azaspiro[4.5]decane-7-carboxamide | 1.26 min, 479 [M + H]$^+$ |

-continued

| Example (General Procedure) | Structure | Name | LCMS (Method C): R$_T$, m/z |
|---|---|---|---|
| 260 (14) | 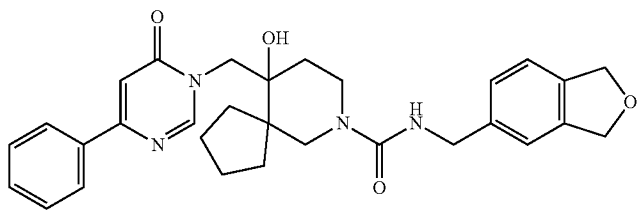 [SMILES: O=C(NCc1ccc2c(c1)COC2)N1CCC(O)(Cn2cnc(-c3ccccc3)cc2=O)C2(CCCC2)C1] | N-((1,3-Dihydroisobenzofuran-5-yl)methyl)-10-hydroxy-10-((6-oxo-4-phenylpyrimidin-1(6H)-yl)methyl)-7-azaspiro[4.5]decane-7-carboxamide | 1.32 min, 515 [M + H]$^+$ |
| 261 (13) | 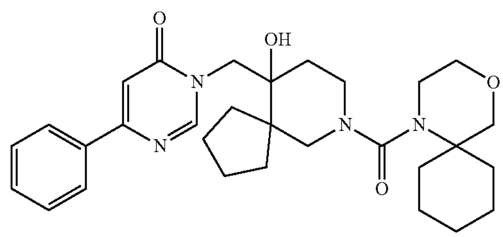 [SMILES: O=C(N1CCC(O)(Cn2cnc(-c3ccccc3)cc2=O)C2(CCCC2)C1)N1CCOCC12CCCCC2] | 3-((10-Hydroxy-7-(4-oxa-1-azaspiro[5.5]undecane-1-carbonyl)-7-azaspiro[4.5]decan-10-yl)methyl)-6-phenylpyrimidin-4(3H)-one | 1.54 min, 521 [M + H]$^+$ |
| 262 (13) | 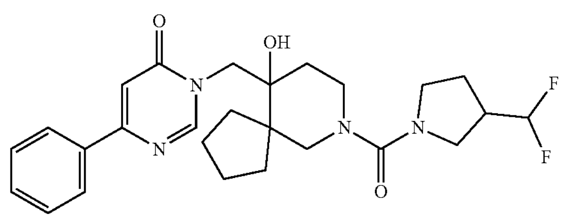 [SMILES: O=C(N1CCC(C(F)F)C1)N1CCC(O)(Cn2cnc(-c3ccccc3)cc2=O)C2(CCCC2)C1] | 3-((7-(3-(Difluoromethyl)pyrrolidine-1-carbonyl)-10-hydroxy-7-azaspiro[4.5]decan-10-yl)methyl)-6-phenylpyrimidin-4(3H)-one | 1.33 min, 487 [M + H]$^+$ |
| 263 (13) | 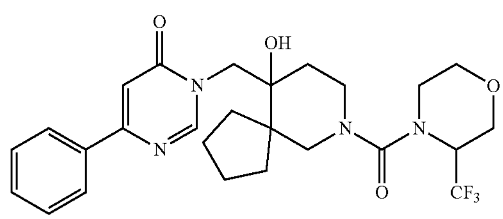 [SMILES: O=C(N1CCC(O)(Cn2cnc(-c3ccccc3)cc2=O)C2(CCCC2)C1)N1CCOCC1C(F)(F)F] | 3-((10-Hydroxy-7-(3-(trifluoromethyl)morpholine-4-carbonyl)-7-azaspiro[4.5]decan-10-yl)methyl)-6-phenylpyrimidin-4(3H)-one | 1.41 min, 521 [M + H]$^+$ |
| 264 (13) | 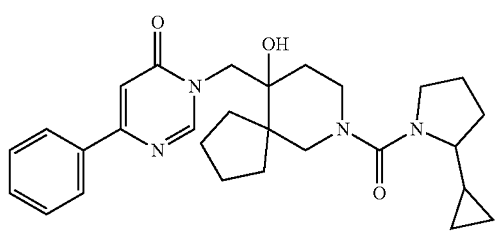 [SMILES: O=C(N1CCC(O)(Cn2cnc(-c3ccccc3)cc2=O)C2(CCCC2)C1)N1CCCC1C1CC1] | 3-((7-(2-Cyclopropylpyrrolidine-1-carbonyl)-10-hydroxy-7-azaspiro[4.5]decan-10-yl)methyl)-6-phenylpyrimidin-4(3H)-one | 1.51 min, 477 [M + H]$^+$ |
| 265 (15) | 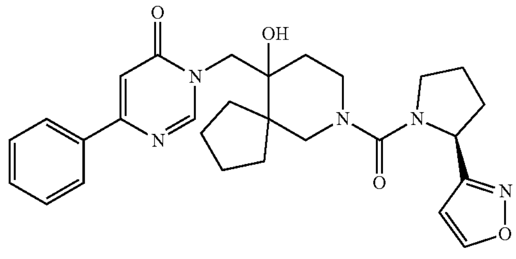 [SMILES: O=C(N1CCC(O)(Cn2cnc(-c3ccccc3)cc2=O)C2(CCCC2)C1)N1CCC[C@H]1c1ccon1] | 3-((10-Hydroxy-7-((S)-2-(isoxazol-3-yl)pyrrolidine-1-carbonyl)-7-azaspiro[4.5]decan-10-yl)methyl)-6-phenylpyrimidin-4(3H)-one | 1.36 min, 504 [M + H]$^+$ |

-continued

| Example (General Procedure) | Structure | Name | LCMS (Method C): $R_T$, m/z |
|---|---|---|---|
| 266 (15) | 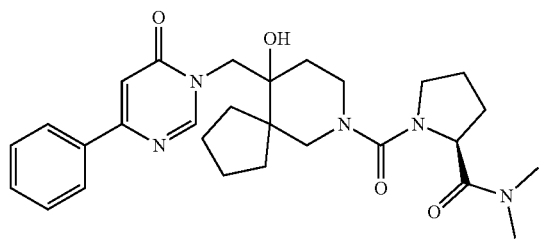 [SMILES: CN(C)C(=O)[C@@H]1CCCN1C(=O)N1CCC(O)(Cn2cnc(-c3ccccc3)cc2=O)C2(CCCC2)C1] | (2S)-1-(10-Hydroxy-10-((6-oxo-4-phenylpyrimidin-1(6H)-yl)methyl)-7-azaspiro[4.5]decane-7-carbonyl)-N,N-dimethylpyrrolidine-2-carboxamide | 1.20 min, 508 [M + H]⁺ |
| 267 (15) | 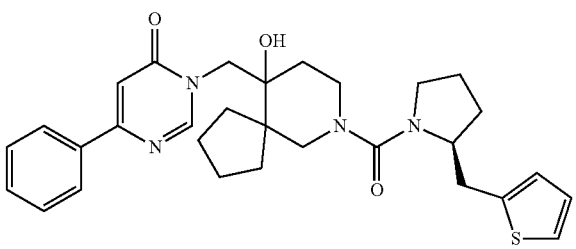 [SMILES: O=C(N1CCC(O)(Cn2cnc(-c3ccccc3)cc2=O)C2(CCCC2)C1)N1CCC[C@H]1Cc1cccs1] | 3-((10-Hydroxy-7-((S)-2-(thiophen-2-ylmethyl)pyrrolidine-1-carbonyl)-7-azaspiro[4.5]decan-10-yl)methyl)-6-phenylpyrimidin-4(3H)-one | 1.55 min, 533 [M + H]⁺ |
| 268 (15) | 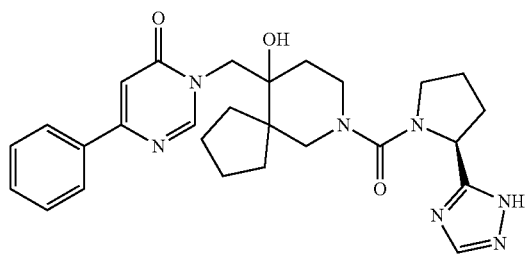 [SMILES: O=C(N1CCC(O)(Cn2cnc(-c3ccccc3)cc2=O)C2(CCCC2)C1)N1CCC[C@H]1c1ncn[nH]1] | 3-((7-((S)-2-(1H-1,2,4-Triazol-5-yl)pyrrolidine-1-carbonyl)-10-hydroxy-7-azaspiro[4.5]decan-10-yl)methyl)-6-phenylpyrimidin-4(3H)-one | 1.11 min, 504 [M + H]⁺ |
| 269 (15) | 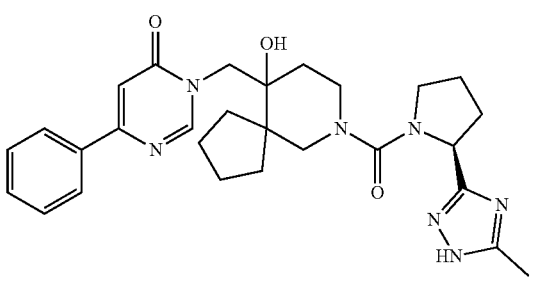 [SMILES: Cc1nc([C@@H]2CCCN2C(=O)N2CCC(O)(Cn3cnc(-c4ccccc4)cc3=O)C3(CCCC3)C2)n[nH]1] | 3-((10-Hydroxy-7-((S)-2-(5-methyl-1H-1,2,4-triazol-3-yl)pyrrolidine-1-carbonyl)-7-azaspiro[4.5]decan-10-yl)methyl)-6-phenylpyrimidin-4(3H)-one | 1.17 min, 518 [M + H]⁺ |
| 270 (15) | 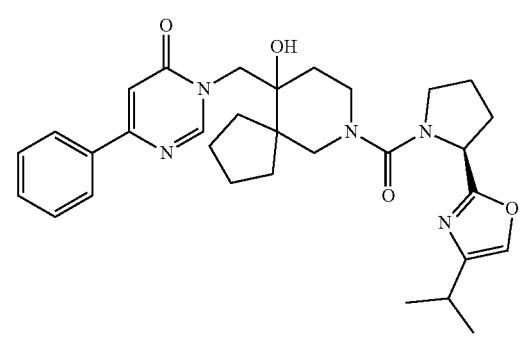 [SMILES: CC(C)c1coc([C@@H]2CCCN2C(=O)N2CCC(O)(Cn3cnc(-c4ccccc4)cc3=O)C3(CCCC3)C2)n1] | 3-((10-Hydroxy-7-((S)-2-(4-isopropyloxazol-2-yl)pyrrolidine-1-carbonyl)-7-azaspiro[4.5]decan-10-yl)methyl)-6-phenylpyrimidin-4(3H)-one | 1.43 min, 546 [M + H]⁺ |

-continued

| Example (General Procedure) | Structure | Name | LCMS (Method C): R_T, m/z |
|---|---|---|---|
| 271 (16) | 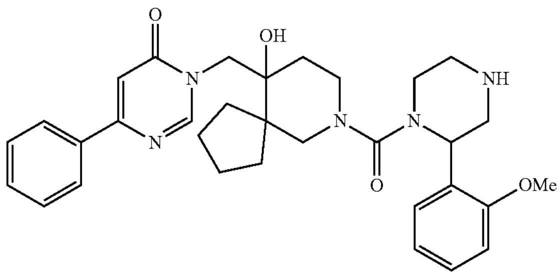 [SMILES: COc1ccccc1C1CNCCN1C(=O)N1CCC(O)(Cn2cnc(-c3ccccc3)cc2=O)C2(CCCC2)C1] | 3-((10-Hydroxy-7-(2-(2-methoxyphenyl)piperazine-1-carbonyl)-7-azaspiro[4.5]decan-10-yl)methyl)-6-phenylpyrimidin-4(3H)-one | 1.16 min, 558 [M + H]⁺ |
| 272 (16) | 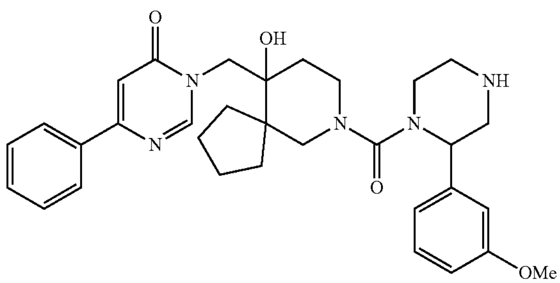 [SMILES: COc1cccc(C2CNCCN2C(=O)N2CCC(O)(Cn3cnc(-c4ccccc4)cc3=O)C3(CCCC3)C2)c1] | 3-((10-Hydroxy-7-(2-(3-methoxyphenyl)piperazine-1-carbonyl)-7-azaspiro[4.5]decan-10-yl)methyl)-6-phenylpyrimidin-4(3H)-one | 1.11 min, 558 [M + H]⁺ |
| 273 (16) | 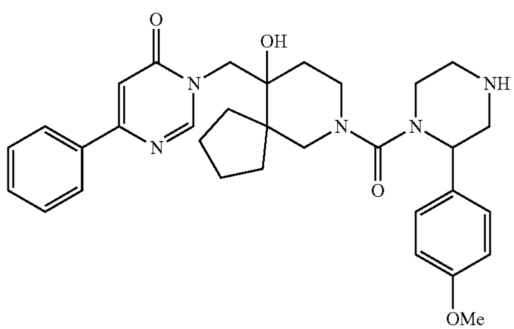 [SMILES: COc1ccc(C2CNCCN2C(=O)N2CCC(O)(Cn3cnc(-c4ccccc4)cc3=O)C3(CCCC3)C2)cc1] | 3-((10-Hydroxy-7-(2-(4-methoxyphenyl)piperazine-1-carbonyl)-7-azaspiro[4.5]decan-10-yl)methyl)-6-phenylpyrimidin-4(3H)-one | 1.12 min, 558 [M + H]⁺ |
| 274 (16) | 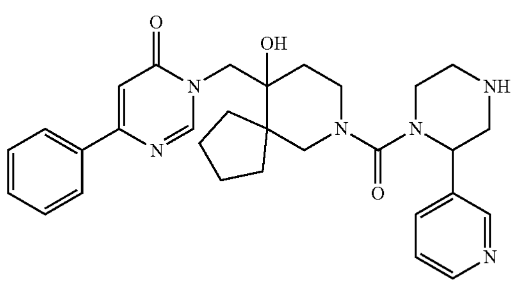 [SMILES: O=C(N1CCC(O)(Cn2cnc(-c3ccccc3)cc2=O)C2(CCCC2)C1)N1CCNCC1c1cccnc1] | 3-((10-Hydroxy-7-(2-(pyridin-3-yl)piperazine-1-carbonyl)-7-azaspiro[4.5]decan-10-yl)methyl)-6-phenylpyrimidin-4(3H)-one | 0.97 min, 529 [M + H]⁺ |
| 275 (16) | 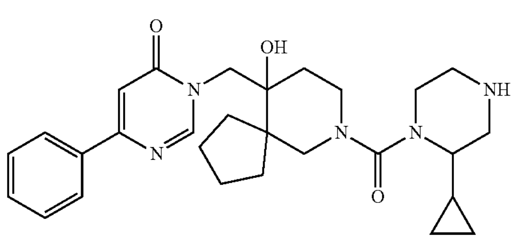 [SMILES: O=C(N1CCC(O)(Cn2cnc(-c3ccccc3)cc2=O)C2(CCCC2)C1)N1CCNCC1C1CC1] | 3-((7-(2-Cyclopropylpiperazine-1-carbonyl)-10-hydroxy-7-azaspiro[4.5]decan-10-yl)methyl)-6-phenylpyrimidin-4(3H)-one | 1.06 min, 492 [M + H]⁺ |

| Example (General Procedure) | Structure | Name | LCMS (Method C): $R_T$, m/z |
|---|---|---|---|
| 276 (16) | 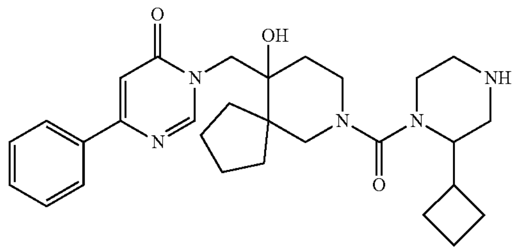 [SMILES: O=C(N1CCC(O)(Cn2cnc(-c3ccccc3)cc2=O)C2(CCCC2)C1)N1CCNCC1C1CCC1] | 3-((7-(2-Cyclobutylpiperazine-1-carbonyl)-10-hydroxy-7-azaspiro[4.5]decan-10-yl)methyl)-6-phenylpyrimidin-4(3H)-one | 1.10 min, 506 [M + H]$^+$ |
| 277 (16) | 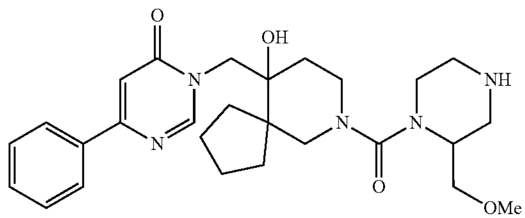 [SMILES: COCC1CNCCN1C(=O)N1CCC(O)(Cn2cnc(-c3ccccc3)cc2=O)C2(CCCC2)C1] | 3-((10-Hydroxy-7-(2-(methoxymethyl)piperazine-1-carbonyl)-7-azaspiro[4.5]decan-10-yl)methyl)-6-phenylpyrimidin-4(3H)-one | 1.04 min, 496 [M + H]$^+$ |

Example 278: 3-(((S)-10-Hydroxy-7-((R)-2-phenylpiperazine-1-carbonyl)-7-azaspiro[4.5]decan-10-yl)methyl)-6-phenylpyrimidin-4(3H)-one

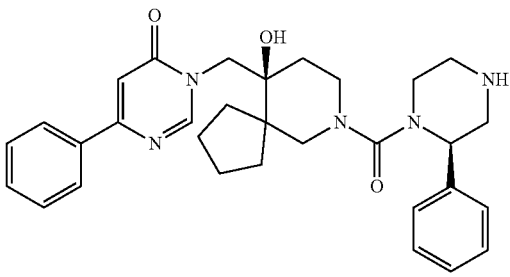 [SMILES: O=C(N1CC[C@@](O)(Cn2cnc(-c3ccccc3)cc2=O)C2(CCCC2)C1)N1CCNC[C@H]1c1ccccc1]

Step 1: tert-Butyl (R)-4-((S)-10-hydroxy-10-((6-oxo-4-phenylpyrimidin-1(6H)-yl)methyl)-7-azaspiro[4.5]decane-7-carbonyl)-3-phenylpiperazine-1-carboxylate: Prepared according to General Procedure 9 using (S)-3-((10-hydroxy-7-azaspiro[4.5]decan-10-yl)methyl)-6-phenylpyrimidin-4(3H)-one (50 mg, 0.147 mmol), tert-butyl (R)-4-(chlorocarbonyl)-3-phenylpiperazine-1-carboxylate (57.4 mg, 0.177 mmol), DIPEA (103 μL, 0.589 mmol) and DCM (2 mL), stirring at rt for 1 h to give the title compound (41 mg, 44%). LCMS (Method A): $R_T$=1.72 min, m/z=628 [M+H]$^+$; 572 [M-butene+H]$^+$.

Step 2: 3-(((S)-10-Hydroxy-7-((R)-2-phenylpiperazine-1-carbonyl)-7-azaspiro[4.5]decan-10-yl)methyl)-6-phenylpyrimidin-4(3H)-one: Prepared according to General Procedure 3 using tert-butyl (R)-4-((S)-10-hydroxy-10-((6-oxo-4-phenylpyrimidin-1(6H)-yl)methyl)-7-azaspiro[4.5]decane-7-carbonyl)-3-phenylpiperazine-1-carboxylate (50 mg, 79.6 μmol), TFA (1 mL) and DCM (2 mL), stirred at rt for 1 h to give the title compound (39 mg, 92%). LCMS (Method A): $R_T$=0.88 min, m/z=528 [M+H]$^+$. $^1$H NMR (500 MHz, DMSO-d$_6$): δ 8.46 (s, 1H), 8.10-8.04 (m, 2H), 7.52-7.48 (m, 3H), 7.28 (d, J=6.5 Hz, 4H), 7.18 (t, J=6.2 Hz, 1H), 6.97 (s, 1H), 4.81 (s, 1H), 4.55 (d, J=13.7 Hz, 1H), 4.31 (t, J=4.9 Hz, 1H), 3.62 (d, J=13.6 Hz, 1H), 3.60-3.53 (m, 1H), 3.28-3.16 (m, 2H), 3.04 (dt, J=10.6, 5.5 Hz, 2H), 2.99-2.92 (m, 1H), 2.90 (d, J=4.9 Hz, 2H), 2.78 (t, J=4.5 Hz, 2H), 1.92-1.82 (m, 1H), 1.67-1.18 (m, 8H), 1.07 (dt, J=12.4, 6.2 Hz, 1H). NH signal not observed.

Example 279: 3-(((S)-7-((R)-4-Acetyl-2-phenylpiperazine-1-carbonyl)-10-hydroxy-7-azaspiro[4.5]decan-10-yl)methyl)-6-phenylpyrimidin-4(3H)-one

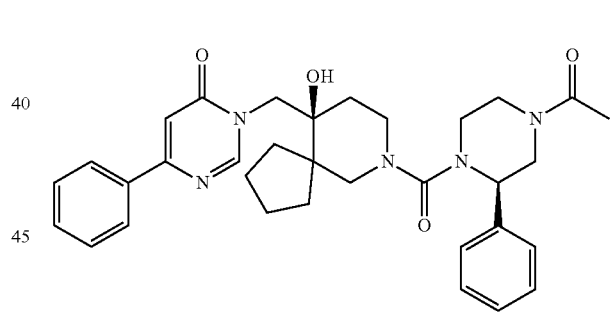

To a stirring solution of 3-(((S)-10-hydroxy-7-((R)-2-phenylpiperazine-1-carbonyl)-7-azaspiro[4.5]decan-10-yl)methyl)-6-phenylpyrimidin-4(3H)-one (13 mg, 24.6 μmol) and DIPEA (13 μL, 73.9 μmol) in DCM (0.5 mL) was added acetic anhydride (2.8 μL, 29.6 μmol). The resulting solution was stirred at rt for 1 h before quenching with saturated NaHCO$_{3(aq)}$. The resulting mixture was extracted with DCM (×3) using a phase separator and the combined organic phases were concentrated in vacuo. The crude material was purified by flash chromatography to give the title compound (13.1 mg, 93%). LCMS (Method A): $R_T$=1.24 min, m/z=570 [M+H]$^+$. $^1$H NMR (500 MHz, DMSO-d$_6$): δ 8.46 (d, J=1.8 Hz, 1H), 8.08 (dd, J=6.5, 2.7 Hz, 2H), 7.53-7.47 (m, 3H), 7.28 (ddd, J=31.1, 18.1, 7.5 Hz, 5H), 6.97 (s, 1H), 4.82 (d, J=5.3 Hz, 1H), 4.67-4.60 (m, 1H), 4.55 (d, J=13.3 Hz, 1H), 3.95-3.50 (m, 5H), 3.49-3.40 (m, 1H), 3.27-3.11 (m, 4H), 3.02 (dd, J=12.1, 7.0 Hz, 1H), 1.94 (d, J=18.7 Hz, 4H), 1.66-1.03 (m, 9H).

221

Example 280: 2-((10-Hydroxy-7-((R)-3-phenylmorpholine-4-carbonyl)-7-azaspiro[4.5]decan-10-yl)methyl)-5-phenylpyridazin-3(2H)-one

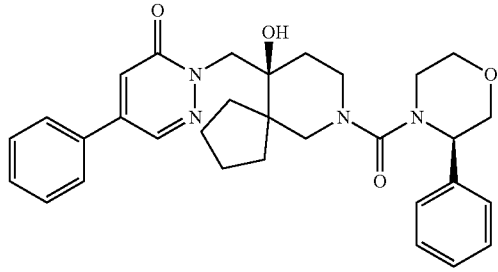 [SMILES: O=C(N1CC[C@@](O)(Cn2ncc(-c3ccccc3)cc2=O)C2(CCCC2)C1)N1CCOC[C@H]1c1ccccc1]

Step 1: tert-Butyl 10-hydroxy-10-((6-oxo-4-phenylpyridazin-1(6H)-yl)methyl)-7-azaspiro[4.5]decane-7-carboxylate: Prepared according to General procedure 2 using 5-phenylpyridazin-3(2H)-one (0.20 g, 1.2 mmol), Epoxide 2 (0.47 g, 1.7 mmol), cesium carbonate (0.57 g, 1.7 mmol) in DMF (2 mL), heated to 80° C. for 24 h to give the title compound (0.10 g, 20%). LCMS (Method C): $R_T$=1.65 min, m/z=384 [M-butene+H]$^+$.

Step 2: 2-((10-Hydroxy-7-azaspiro[4.5]decan-10-yl)methyl)-5-phenylpyridazin-3(2H)-one: A solution of tert-butyl 10-hydroxy-10-((6-oxo-4-phenylpyridazin-1(6H)-yl)methyl)-7-azaspiro[4.5]decane-7-carboxylate (46 mg, 0.105 mmol) in TFA (0.5 mL) and DCM (1 mL) was stirred at rt for 10 min before the reaction mixture was loaded on to a 2 g SCX-2 cartridge that was pre-equilibrated with 1:1 DCM/MeOH. The cartridge was washed with 1:1 DCM/MeOH (40 mL) before the product was eluted with 1:1 DCM/7 M NH$_3$ in MeOH (30 mL). The basic eluents were concentrated under reduced pressure to give the title compound (31.5 mg, 88%) as an off-white solid. LCMS (Method A): $R_T$=0.69 min, m/z=340 [M+H]$^+$.

Step 3: 2-((10-Hydroxy-7-((R)-3-phenylmorpholine-4-carbonyl)-7-azaspiro[4.5]decan-10-yl)methyl)-5-phenylpyridazin-3(2H)-one: A solution of triphosgene (4.4 mg, 0.0147 mmol) in DCM (0.3 mL) was added to a mixture of (R)-3-phenylmorpholine (7.2 mg, 0.0442 mmol) and DIPEA (21 µL, 0.118 mmol) in DCM (0.3 mL) after 1 h, 2-((10-hydroxy-7-azaspiro[4.5]decan-10-yl)methyl)-5-phenylpyridazin-3(2H)-one (10 mg, 0.0295 mmol) was added. The reaction was stirred at rt for 15 h 15 min before saturated NaHCO$_{3(aq)}$ (15 mL) was added and the resulting mixture was extracted with DCM (3×10 mL) using a phase separator. The combined organic phases were concentrated under reduced pressure and the residue was purified by flash chromatography (0-100% EtOAc in cyclohexane) to give the title compound (8.7 mg, 55%) as a colourless solid after lyophilisation. LCMS (Method A): $R_T$=1.56 min, m/z=529 [M+H]$^+$. $^1$H NMR (500 MHz, DMSO-d$_6$): δ 8.46-8.40 (m, 1H), 7.91-7.81 (m, 2H), 7.61-7.45 (m, 3H), 7.42-7.14 (m, 6H), 4.76-4.66 (m, 1H), 4.45-4.25 (m, 3H), 3.85-3.63 (m, 4H), 3.61-3.50 (m, 1H), 3.43-2.94 (m, 5H (signals overlap with HDO)), 1.96-1.85 (m, 1H), 1.66-1.25 (m, 8H), 1.15-1.04 (m, 1H).

222

Example 281: 3-(((S)-10-Hydroxy-7-((R)-4-methyl-2-phenylpiperazine-1-carbonyl)-7-azaspiro[4.5]decan-10-yl)methyl)-6-phenylpyrimidin-4(3H)-one

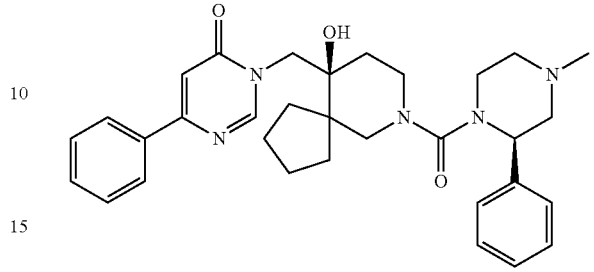

A solution of 3-(((S)-10-hydroxy-7-((R)-2-phenylpiperazine-1-carbonyl)-7-azaspiro[4.5]decan-10-yl)methyl)-6-phenylpyrimidin-4(3H)-one (13 mg, 24.6 µmol) and 37% formaldehyde in water solution (24.8 µL, 0.123 mmol) in MeCN (0.5 mL) and MeOH (0.5 mL) was stirred at rt for 30 min before adding sodium triacetoxyhydroborate (26.1 mg, 0.123 mmol). The resulting reaction was stirred at rt for 1 h. The reaction mixture was purified by SCX-2 and further purified by flash chromatography to give the title compound (8.6 mg, 63%). LCMS (Method A): $R_T$=0.91 min, m/z=542 [M+H]$^+$. $^1$H NMR (500 MHz, DMSO-d$_6$): δ 8.46 (s, 1H), 8.12-8.02 (m, 2H), 7.57-7.42 (m, 3H), 7.40-7.22 (m, 4H), 7.22-7.16 (m, 1H), 6.97 (s, 1H), 4.82 (s, 1H), 4.59-4.47 (m, 2H), 3.63 (d, J=13.6 Hz, 1H), 3.57-3.51 (m, 1H), 3.25-3.14 (m, 2H), 3.13-2.98 (m, 3H), 2.74-2.65 (m, 1H), 2.48-2.40 (m, 2H), 2.34-2.26 (m, 1H), 2.17 (s, 3H), 1.93-1.86 (m, 1H), 1.66-1.40 (m, 6H), 1.37-1.31 (m, 1H), 1.25-1.18 (m, 1H), 1.13-1.05 (m, 1H).

Example 282: 6-Chloro-3-(((S)-7-((R)-3-(4-fluorophenyl)morpholine-4-carbonyl)-10-hydroxy-7-azaspiro[4.5]decan-10-yl)methyl)pyrimidin-4(3H)-one

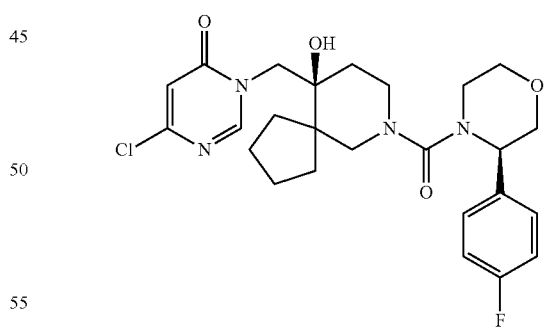

Step 1: (R)-3-(4-Fluorophenyl)morpholine-4-carbonyl chloride: A solution of triphosgene (56.4 mg, 0.190 mmol) in DCM (1.9 mL) was added dropwise to a solution of (R)-3-(4-fluorophenyl)morpholine hydrochloride (82.6 mg, 0.380 mmol) and pyridine (77 µL, 0.950 mmol) in DCM (1.9 mL) at 0° C. The resulting yellow solution was stirred at rt for 1 h before 1 M HCl$_{(aq)}$ (15 mL) was added. The resulting mixture was extracted with DCM (3×10 mL) using a phase separator before the combined organic phases were concentrated under reduced pressure to give the title compound (91.8 mg, 99%) as a yellow oil. This material was used without further purification. LCMS (Method A): R$_T$=1.36 min, m/z=244, 246 [M+H]$^+$.

Step 2: 6-Chloro-3-(((S)-7-((R)-3-(4-fluorophenyl)morpholine-4-carbonyl)-10-hydroxy-7-azaspiro[4.5]decan-10-yl)methyl)pyrimidin-4(3H)-one: Prepared according to General Procedure 9 using (S)-6-chloro-3-((10-hydroxy-7-azaspiro[4.5]decan-10-yl)methyl)pyrimidin-4(3H)-one hydrochloride (84 mg, 0.251 mmol), (R)-3-(4-fluorophenyl) morpholine-4-carbonyl chloride (91.8 mg, 0.377 mmol) and DIPEA (0.176 mL, 1.01 mmol) in DCM (2.5 mL) for 1 h 20 min to give the title compound (109 mg, 85%) as an off-white foam. LCMS (Method A): R$_T$=1.27 min, m/z=505, 507 [M+H]$^+$. $^1$H NMR (500 MHz, DMSO-d$_6$): δ 8.33 (s, 1H), 7.35 (dd, J=8.4, 5.5 Hz, 2H), 7.12 (t, J=8.7 Hz, 2H), 6.61 (s, 1H), 4.80 (s, 1H), 4.47 (d, J=13.4 Hz, 1H), 4.40 (t, J=5.0 Hz, 1H), 3.81-3.62 (m, 4H), 3.62-3.50 (m, 1H), 3.26-3.13 (m, 2H), 3.12-3.07 (m, 1H), 3.06-2.93 (m, 2H), 1.90-1.82 (m, 1H), 1.65-1.42 (m, 5H), 1.41-1.34 (m, 1H), 1.31-1.24 (m, 1H), 1.21-1.15 (m, 1H), 1.07-1.00 (m, 1H).

Example 283: 1-(((S)-4-Hydroxy-3,3-dimethyl-1-((R)-3-phenylmorpholine-4-carbonyl)piperidin-4-yl)methyl)-N,N-dimethyl-6-oxo-4-phenyl-1,6-dihydropyridine-3-carboxamide

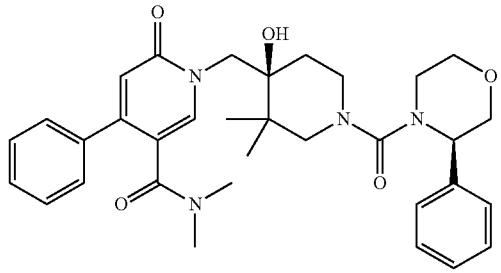 [SMILES: CN(C)C(=O)c1cn(C[C@]2(O)CCN(C(=O)N3CCOC[C@H]3c3ccccc3)CC2(C)C)c(=O)cc1-c1ccccc1]

Step 1: Ethyl 4-chloro-6-oxo-1,6-dihydropyridine-3-carboxylate: A mixture of ethyl 4,6-dichloronicotinate (25 g, 114 mmol) and sodium acetate (46.6 g, 568 mmol) in acetic acid (325 mL, 5.68 mol) was heated at reflux for 3 days. Upon cooling to rt the reaction mixture was diluted with water (650 mL) and the resulting precipitate was isolated by filtration. The precipitate was washed with water (6×100 mL) and dried in a vacuum oven at 50° C. to give the title compound (18.7 g, 81%) as a light beige solid. LCMS (Method A): R$_T$=0.73 min, m/z=202, 204 [M+H]$^+$. $^1$H NMR (500 MHz, DMSO-d$_6$): δ 12.40 (br. s, 1H), 8.11 (s, 1H), 6.55 (s, 1H), 4.22 (q, J=7.1 Hz, 2H), 1.27 (t, J=7.1 Hz, 3H).

Step 2: Ethyl 1-((1-(tert-butoxycarbonyl)-4-hydroxy-3,3-dimethylpiperidin-4-yl)methyl)-4-chloro-6-oxo-1,6-dihydropyridine-3-carboxylate: Prepared according to General Procedure 2 using ethyl 4-chloro-6-oxo-1,6-dihydropyridine-3-carboxylate (4.00 g, 19.8 mmol), Epoxide 1 (6.22 g, 25.8 mmol) and cesium carbonate (8.40 g, 25.8 mmol) (dried at 120° C. under high vacuum for 5 h) in DMF (66 mL) heated at 90° C. for 19 h to give the title compound (3.31 g, 37%) as a pale yellow foam. LCMS (Method A): R$_T$=1.54 min, m/z=443, 445 [M+H]$^+$. $^1$H NMR (500 MHz, DMSO-d$_6$): δ 8.44 (s, 1H), 6.64 (s, 1H), 4.84 (s, 1H), 4.49 (d, J=13.4 Hz, 1H), 4.27 (q, J=7.1 Hz, 2H), 3.74-3.60 (m, 2H), 3.30-2.85 (m, 3H), 1.62-1.48 (m, 1H), 1.38 (s, 9H), 1.29 (t, J=7.1 Hz, 3H), 1.08-0.99 (m, 1H), 0.97 (s, 3H), 0.92 (s, 3H). Ethyl 1-((1-(tert-butoxycarbonyl)-4-hydroxy-3,3-dimethylpiperidin-4-yl)methyl)-4-chloro-6-oxo-1,6-dihydropyridine-3-carboxylate (9.89 g) was resolved into the single stereoisomers by chiral supercritical fluid chromatography using an AmyC (20 mm×250 mm, 5 μm) column with isocratic solvent conditions: 20:80 IPA/CO$_2$ (0.1% v/v NH$_3$). The first eluted material afforded ethyl (R)-1-((1-(tert-butoxycarbonyl)-4-hydroxy-3,3-dimethylpiperidin-4-yl)methyl)-4-chloro-6-oxo-1,6-dihydropyridine-3-carboxylate (4.55 g, 46% recovery) as an orange solid. Chiral purity (Method C): R$_T$=1.85 min, 100% ee. The second eluted material afforded ethyl (S)-1-((1-(tert-butoxycarbonyl)-4-hydroxy-3,3-dimethylpiperidin-4-yl)methyl)-4-chloro-6-oxo-1,6-dihydropyridine-3-carboxylate (4.36 g, 44% recovery) as an orange solid. Chiral purity (Method C): R$_T$=2.18 min, 99.4% ee.

Step 3: Ethyl (S)-1-((1-(tert-butoxycarbonyl)-4-hydroxy-3,3-dimethylpiperidin-4-yl)methyl)-6-oxo-4-phenyl-1,6-dihydropyridine-3-carboxylate: Prepared according to General Procedure 5 using ethyl (S)-1-((1-(tert-butoxycarbonyl)-4-hydroxy-3,3-dimethylpiperidin-4-yl)methyl)-4-chloro-6-oxo-1,6-dihydropyridine-3-carboxylate (200 mg, 0.452 mmol), phenylboronic acid (82.5 mg, 0.677 mmol), Pd(dppf)Cl$_2$·DCM (19 mg, 22.6 μmol), sodium carbonate (96 mg, 0.903 mmol), 1,4-dioxane (1.5 mL) and water (0.5 mL). The reaction was heated under microwave irradiation at 120° C. for 30 min to give the title compound (220 mg, quantitative) as a light yellow foam. LCMS (Method A): R$_T$=1.68 min, m/z=485 [M+H]$^+$.

Step 4: (S)-1-((1-(tert-Butoxycarbonyl)-4-hydroxy-3,3-dimethylpiperidin-4-yl)methyl)-6-oxo-4-phenyl-1,6-dihydropyridine-3-carboxylic acid: A solution of ethyl (S)-1-((1-(tert-butoxycarbonyl)-4-hydroxy-3,3-dimethylpiperidin-4-yl)methyl)-6-oxo-4-phenyl-1,6-dihydropyridine-3-carboxylate (220 mg, 0.454 mmol) in 1 M NaOH$_{(aq)}$ (0.910 mL, 0.910 mmol) and 1,4-dioxane (2.2 mL) was stirred at 50° C. for 5 h. Upon cooling to rt the pH was adjusted to pH 3 by the addition of 1 M HCl$_{(aq)}$ and the mixture was extracted with DCM (3×20 mL) using a phase separator. The combined organic phases were concentrated under reduced pressure to give the title compound (193 mg, 93%) as a colourless foam. LCMS (Method A): R$_T$=1.31 min, m/z=457 [M+H]$^+$.

Step 5: tert-Butyl (S)-4-((5-(dimethylcarbamoyl)-2-oxo-4-phenylpyridin-1(2H)-yl)methyl)-4-hydroxy-3,3-dimethylpiperidine-1-carboxylate: Prepared according to General Procedure 4 using (S)-1-((1-(tert-butoxycarbonyl)-4-hydroxy-3,3-dimethylpiperidin-4-yl)methyl)-6-oxo-4-phenyl-1,6-dihydropyridine-3-carboxylic acid (193 mg, 0.423 mmol), dimethylamine (2 M in THF, 0.254 mL, 0.507 mmol), DIPEA (0.295 mL, 1.69 mmol), HATU (193 mg, 0.507 mmol) and DCM (8.5 mL) to give the title compound (241 mg, >100%) as a pale yellow foam. This material was used without further purification. LCMS (Method A): R$_T$=1.29 min, m/z=484 [M+H]$^+$.

Step 6: (S)-1-((4-Hydroxy-3,3-dimethylpiperidin-4-yl)methyl)-N,N-dimethyl-6-oxo-4-phenyl-1,6-dihydropyridine-3-carboxamide: Prepared according to General Procedure 3 using tert-butyl (S)-4-((5-(dimethylcarbamoyl)-2-oxo-4-phenylpyridin-1(2H)-yl)methyl)-4-hydroxy-3,3-dimethylpiperidine-1-carboxylate (204 mg, 0.422 mmol), TFA (1 mL) and DCM (2 mL) to give the title compound (157 mg, 97%) as a colourless solid. LCMS (Method A): R$_T$=0.46 min, m/z=384 [M+H]$^+$. $^1$H NMR (500 MHz, DMSO-d$_6$): δ 7.79 (s, 1H), 7.50-7.40 (m, 3H), 7.40-7.32 (m, 2H), 6.43 (s, 1H), 4.59 (s, 1H), 4.46 (d, J=13.3 Hz, 1H), 3.72 (d, J=13.3 Hz, 1H), 3.17 (s, 1H), 2.74 (s, 3H), 2.71-2.64 (m, 3H), 2.62 (s, 3H), 2.20 (d, J=12.5 Hz, 1H), 1.59-1.46 (m, 1H), 1.13-0.97 (m, 1H), 1.05 (s, 3H), 0.89 (s, 3H).

Step 7: 1-(((S)-4-Hydroxy-3,3-dimethyl-1-((R)-3-phenylmorpholine-4-carbonyl)piperidin-4-yl)methyl)-N,N-dimethyl-6-oxo-4-phenyl-1,6-dihydropyridine-3-carboxamide: A solution of triphosgene (5.8 mg, 0.0196 mmol) in DCM (0.4 mL) was added to a mixture of (R)-3-phenylmorpholine (9.6 mg, 0.0587 mmol) and DIPEA (27 µL, 0.157 mmol) in DCM (0.4 mL) after 1 h, (S)-1-((4-hydroxy-3,3-dimethylpiperidin-4-yl)methyl)-N,N-dimethyl-6-oxo-4-phenyl-1,6-dihydropyridine-3-carboxamide (15 mg, 0.0391 mmol) in DCM (0.4 mL) was added. The reaction was stirred at rt for 3 days before saturated NaHCO$_{3(aq)}$, (15 mL) was added and the resulting mixture was extracted with DCM (3×10 mL) using a phase separator. The combined organic phases were concentrated under reduced pressure and the residue was purified by flash chromatography twice (0-100% EtOAc in cyclohexane; then 0-10% MeOH in EtOAc; followed by 0-8% MeOH in DCM) to give the title compound (12.4 mg, 54%) as a colourless solid after lyophilisation. LCMS (Method A): R$_T$=1.18 min, m/z=573 [M+H]$^+$. $^1$H NMR (500 MHz, DMSO-d$_6$): δ 7.80 (s, 1H), 7.48-7.41 (m, 3H), 7.40-7.35 (m, 2H), 7.35-7.26 (m, 4H), 7.24-7.20 (m, 1H), 6.44 (s, 1H), 4.86 (s, 1H), 4.46 (t, J=4.7 Hz, 1H), 4.41 (d, J=13.4 Hz, 1H), 3.83-3.77 (m, 2H), 3.77-3.70 (m, 2H), 3.69-3.60 (m, 2H), 3.18-3.11 (m, 1H), 3.11-2.98 (m, 4H), 2.75 (s, 3H), 2.62 (s, 3H), 1.78-1.69 (m, 1H), 1.19-1.12 (m, 1H), 0.97 (s, 3H), 0.92 (s, 3H).

Example 284: 3-(((S)-7-((R)-3-(4-Fluorophenyl)morpholine-4-carbonyl)-10-hydroxy-7-azaspiro[4.5]decan-10-yl)methyl)-6-(1-methyl-1H-pyrazol-5-yl)pyrimidin-4(3H)-one

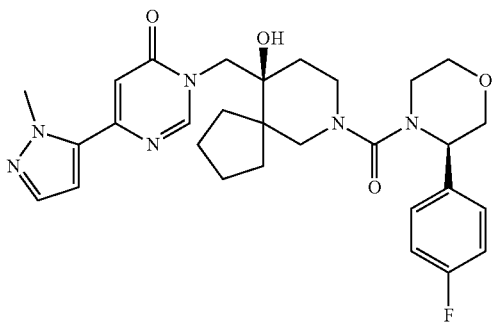 [SMILES: Cn1nccc1-c1cc(=O)n(C[C@]2(O)CCN(C(=O)N3CCOC[C@H]3c3ccc(F)cc3)CC23CCCC3)cn1]

Prepared according to General Procedure 5 using 6-chloro-3-(((S)-7-((R)-3-(4-fluorophenyl)morpholine-4-carbonyl)-10-hydroxy-7-azaspiro[4.5]decan-10-yl)methyl)pyrimidin-4(3H)-one (15 mg, 0.0297 mmol), 1-methyl-5-(4,4,5,5-tetramethyl-1,3,2-dioxaborolan-2-yl)-1H-pyrazole (12.4 mg, 0.0594 mmol), Pd(dppf)Cl$_2$·DCM (1.3 mg, 1.49 µmol) and sodium carbonate (9.4 mg, 0.0891 mmol) in 1,4-dioxane (0.45 mL) and water (0.15 mL) under microwave irradiation at 120° C. for 30 min to give the title compound (10.9 mg, 65%) as colourless solid after lyophilisation. LCMS (Method A): R$_T$=1.20 min, m/z=551 [M+H]$^+$. $^1$H NMR (500 MHz, DMSO-d$_6$): δ 8.45 (s, 1H), 7.51-7.46 (m, 1H), 7.36 (dd, J=8.4, 5.5 Hz, 2H), 7.12 (t, J=8.6 Hz, 2H), 6.88-6.84 (m, 1H), 6.79 (s, 1H), 4.81 (s, 1H), 4.54 (d, J=13.5 Hz, 1H), 4.41 (t, J=5.0 Hz, 1H), 4.13 (s, 3H), 3.79-3.65 (m, 4H), 3.65-3.53 (m, 2H), 3.27-3.16 (m, 2H), 3.14-3.07 (m, 1H), 3.07-2.96 (m, 2H), 1.92-1.84 (m, 1H), 1.66-1.39 (m, 6H), 1.32-1.26 (m, 1H), 1.23-1.17 (m, 1H), 1.10-1.02 (m, 1H).

Example 285: 3-(((S)-7-((R)-3-(4-Fluorophenyl)morpholine-4-carbonyl)-10-hydroxy-7-azaspiro[4.5]decan-10-yl)methyl)-6-(1-methyl-1H-pyrazol-4-yl)pyrimidin-4(3H)-one

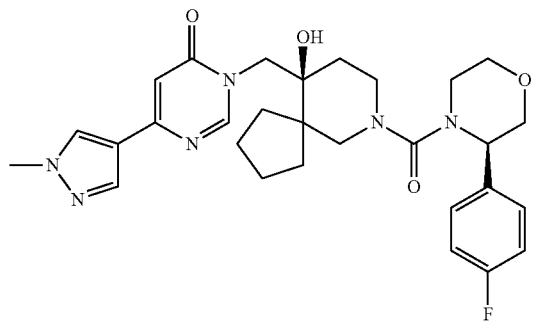 [SMILES: Cn1cc(-c2cc(=O)n(C[C@]3(O)CCN(C(=O)N4CCOC[C@H]4c4ccc(F)cc4)CC34CCCC4)cn2)cn1]

Prepared according to General Procedure 5 using 6-chloro-3-(((S)-7-((R)-3-(4-fluorophenyl)morpholine-4-carbonyl)-10-hydroxy-7-azaspiro[4.5]decan-10-yl)methyl)pyrimidin-4(3H)-one (15 mg, 0.0297 mmol), 1-methyl-4-(4,4,5,5-tetramethyl-1,3,2-dioxaborolan-2-yl)-1H-pyrazole (12.4 mg, 0.0594 mmol), Pd(dppf)Cl$_2$·DCM (1.3 mg, 1.49 µmol) and sodium carbonate (9.4 mg, 0.0891 mmol) in 1,4-dioxane (0.45 mL) and water (0.15 mL) under microwave irradiation at 120° C. for 30 min to give the title compound (11.2 mg, 67%) as a colourless solid after lyophilisation. LCMS (Method A): R$_T$=1.11 min, m/z=551 [M+H]$^+$. $^1$H NMR (500 MHz, DMSO-d$_6$): δ 8.32 (s, 1H), 8.29 (s, 1H), 7.99 (s, 1H), 7.35 (dd, J=8.5, 5.7 Hz, 2H), 7.12 (t, J=8.7 Hz, 2H), 6.63 (s, 1H), 4.81 (s, 1H), 4.49 (d, J=13.6 Hz, 1H), 4.39 (t, J=5.1 Hz, 1H), 3.87 (s, 3H), 3.80-3.62 (m, 4H), 3.62-3.52 (m, 2H), 3.26-3.15 (m, 2H), 3.14-3.07 (m, 1H), 3.06-2.94 (m, 2H), 1.90-1.82 (m, 1H), 1.66-1.36 (m, 6H), 1.32-1.26 (m, 1H), 1.21-1.14 (m, 1H), 1.08-1.01 (m, 1H).

Example 286: 1-(((S)-4-Hydroxy-3,3-dimethyl-1-((R)-3-phenylmorpholine-4-carbonyl)piperidin-4-yl)methyl)-4-phenylpyridin-2(1H)-one

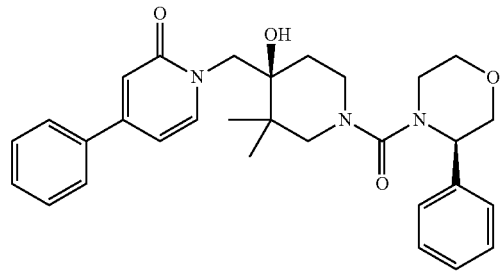 [SMILES: CC1(C)CN(C(=O)N2CCOC[C@H]2c2ccccc2)CC[C@@]1(O)Cn1ccc(-c2ccccc2)cc1=O]

Step 1: (S)-1-((1-(tert-Butoxycarbonyl)-4-hydroxy-3,3-dimethylpiperidin-4-yl)methyl)-4-chloro-6-oxo-1,6-dihydropyridine-3-carboxylic acid: A suspension of ethyl (S)-1-((1-(tert-butoxycarbonyl)-4-hydroxy-3,3-dimethylpiperidin-4-yl)methyl)-4-chloro-6-oxo-1,6- dihydropyridine-3-carboxylate (400 mg, 0.903 mmol) in 1 M NaOH$_{(aq)}$ (1.81 mL, 1.81 mmol) and 1,4-dioxane (3.6 mL) was stirred at 50° C. for 1 h. Upon cooling to rt, DCM (20 mL) was added to the reaction mixture and the pH of aqueous phase was adjusted to <pH 2 before the phases were separated using a phase separator. The aqueous phase was further extracted with DCM (2×20 mL) using the phase separator. The combined organic phases were concentrated under reduced pressure and the residue was dried in a vacuum oven at 50° C. to give the title compound (374 mg, quantitative) as a slightly yellow foam. This material was used without further purification. LCMS (Method A): R$_T$=1.16 min, m/z=359, 361 [M-butene+H]$^+$.

Step 2: tert-Butyl (S)-4-((4-chloro-2-oxopyridin-1(2H)-yl)methyl)-4-hydroxy-3,3-dimethylpiperidine-1-carboxylate: A suspension of (S)-1-((1-(tert-butoxycarbonyl)-4-hydroxy-3,3-dimethylpiperidin-4-yl)methyl)-4-chloro-6-oxo-1,6-dihydropyridine-3-carboxylic acid (375 mg, 0.903 mmol) and copper(I) oxide (32.3 mg, 0.226 mmol) in quinoline (4.5 mL) was heated at 140° C. for 15 h 30 min. Upon cooling to rt, 1 M HCl$_{(aq)}$ (80 mL) was added and the resulting mixture was extracted with DCM (3×20 mL) using a phase separator. The combined organic phases were concentrated under reduced pressure and the residue was purified by flash chromatography (0%; then 20%; then 30% EtOAc in cyclohexane (isocratic)) to give the title compound (141.5 mg, 42%) as a yellow solid. LCMS (Method A): R$_T$=1.35 min, m/z=371, 373 [M+H]$^+$. $^1$H NMR (500 MHz, DMSO-d$_6$): δ 7.69 (d, J=7.4 Hz, 1H), 6.55 (d, J=1.1 Hz, 1H), 6.38 (dd, J=7.0, 1.4 Hz, 1H), 4.75 (s, 1H), 4.37 (d, J=13.4 Hz, 1H), 3.75-3.62 (m, 2H), 3.26-3.14 (m, 1H), 3.09-2.89 (m, 2H), 1.63-1.52 (m, 1H), 1.39 (s, 9H), 1.08-1.01 (m, 1H), 0.97 (s, 3H), 0.92 (s, 3H).

Step 3: tert-Butyl (S)-4-hydroxy-3,3-dimethyl-4-((2-oxo-4-phenylpyridin-1(2H)-yl)methyl)piperidine-1-carboxylate: Prepared according to General Procedure 5 using tert-butyl (S)-4-((4-chloro-2-oxopyridin-1(2H)-yl)methyl)-4-hydroxy-3,3-dimethylpiperidine-1-carboxylate (60 mg, 0.162 mmol), phenylboronic acid (39.5 mg, 0.324 mmol), Pd(dppf)Cl$_2$·DCM (6.9 mg, 8.09 μmol) and sodium carbonate (51.4 mg, 0.485 mmol) in 1,4-dioxane (1.2 mL) and water (0.4 mL) under microwave irradiation at 120° C. for 30 min to give the title compound (66 mg, 98%) as an off-white solid. LCMS (Method A): R$_T$=1.54 min, m/z=413 [M+H]$^+$.

Step 4: (S)-1-((4-Hydroxy-3,3-dimethylpiperidin-4-yl)methyl)-4-phenylpyridin-2(1H)-one: A solution of tert-butyl (S)-4-hydroxy-3,3-dimethyl-4-((2-oxo-4-phenylpyridin-1(2H)-yl)methyl)piperidine-1-carboxylate (66 mg, 0.1600 mmol) in TFA (0.75 mL) and DCM (1.5 mL) was stirred at rt for 20 min before the reaction mixture was loaded on to a 2 g SCX-2 cartridge that was pre-equilibrated with 1:1 DCM/MeOH. The cartridge was washed with 1:1 DCM/MeOH (60 mL) before the product was eluted with 1:1 DCM/7 M NH$_3$ in MeOH (30 mL). The basic eluents were concentrated under reduced pressure to give the title compound (50 mg, quantitative) as an off-white solid. LCMS (Method A): R$_T$=0.69 min, m/z=313 [M+H]$^+$.

Step 5: 1-(((S)-4-Hydroxy-3,3-dimethyl-1-((R)-3-phenylmorpholine-4-carbonyl)piperidin-4-yl)methyl)-4-phenylpyridin-2(1H)-one: A solution of triphosgene (7.1 mg, 0.0240 mmol) in DCM (0.4 mL) was added to a mixture of (R)-3-phenylmorpholine (11.8 mg, 0.0720 mmol) and DIPEA (34 μL, 0.192 mmol) in DCM (0.4 mL) and after 1 h, (S)-1-((4-hydroxy-3,3-dimethylpiperidin-4-yl)methyl)-4-phenylpyridin-2(1H)-one (15 mg, 0.0480 mmol) in DCM (0.4 mL) was added. The reaction was stirred at rt for 3 days before saturated NaHCO$_{3(aq)}$ (15 mL) was added and the resulting mixture was extracted with DCM (3×10 mL) using a phase separator. The combined organic phases were concentrated under reduced pressure and the residue was purified by flash chromatography twice (0-100% EtOAc in cyclohexane; then 0-10% MeOH in EtOAc; followed by 0-8% MeOH in DCM) to give the title compound (12.6 mg, 52%) as a colourless solid after lyophilisation. LCMS (Method A): R$_T$=1.38 min, m/z=502 [M+H]$^+$. $^1$H NMR (500 MHz, DMSO-d$_6$): δ 7.81-7.69 (m, 3H), 7.54-7.42 (m, 3H), 7.38-7.25 (m, 4H), 7.24-7.20 (m, 1H), 6.72 (d, J=2.1 Hz, 1H), 6.64 (dd, J=7.2, 2.1 Hz, 1H), 5.02 (s, 1H), 4.45 (t, J=4.7 Hz, 1H), 4.33 (d, J=13.5 Hz, 1H), 3.88 (d, J=13.5 Hz, 1H), 3.81-3.70 (m, 3H), 3.69-3.60 (m, 2H), 3.14 (ddd, J=13.0, 6.8, 3.1 Hz, 1H), 3.11-2.96 (m, 4H), 1.77-1.70 (m, 1H), 1.14-1.08 (m, 1H), 0.98 (s, 3H), 0.94 (s, 3H).

Example 287: 1-(((S)-10-Hydroxy-7-((R)-2-phenylpiperazine-1-carbonyl)-7-azaspiro[4.5]decan-10-yl)methyl)-4-phenylpyridin-2(1H)-one

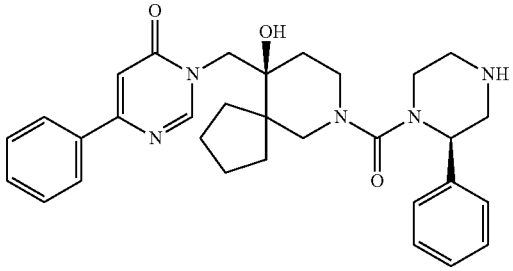 [SMILES: O=C(N1CC[C@@](O)(Cn2cnc(-c3ccccc3)cc2=O)C2(CCCC2)C1)N1CCNC[C@H]1c1ccccc1]

Step 1: tert-Butyl (S)-10-((4-chloro-2-oxopyridin-1(2H)-yl)methyl)-10-hydroxy-7-azaspiro[4.5]decane-7-carboxylate: tert-Butyl 10-((4-chloro-2-oxopyridin-1(2H)-yl)methyl)-10-hydroxy-7-azaspiro[4.5]decane-7-carboxylate (1.13 g) was resolved into the single stereoisomers by chiral supercritical fluid chromatography using an Chiralpak IG (20 mm×250 mm, 5 μm) column with isocratic solvent conditions: 50:50 MeOH/CO$_2$. The first eluted material afforded tert-butyl (S)-10-((4-chloro-2-oxopyridin-1(2H)-yl)methyl)-10-hydroxy-7-azaspiro[4.5]decane-7-carboxylate (525 mg, 46% recovery) as a white solid. Chiral purity (Method D): R$_T$=2.16 min, 99.9% ee. The second eluted material afforded tert-butyl (R)-10-((4-chloro-2-oxopyridin-1(2H)-yl)methyl)-10-hydroxy-7-azaspiro[4.5]decane-7-carboxylate (523 mg, 46% recovery) as a white solid. Chiral purity (Method D): R$_T$=3.38 min, 99.8% ee.

Step 2: tert-Butyl (S)-10-hydroxy-10-((2-oxo-4-phenylpyridin-1(2H)-yl)methyl)-7-azaspiro[4.5]decane-7-carboxylate: Prepared according to General Procedure 5 using tert-butyl (S)-10-((4-chloro-2-oxopyridin-1(2H)-yl)methyl)-10-hydroxy-7-azaspiro[4.5]decane-7-carboxylate (250 mg, 0.630 mmol), phenylboronic acid (154 mg, 1.26 mmol), Pd(dppf)Cl$_2$·DCM (26.7 mg, 0.0315 mmol) and sodium carbonate (200 mg, 1.89 mmol) in 1,4-dioxane (3 mL) and water (1 mL) under microwave irradiation at 120° C. for 30 min to give the title compound (269 mg, 97%) as an off-white solid. LCMS (Method A): R$_T$=1.65 min, m/z=439 [M+H]$^+$.

Step 3: (S)-1-((10-Hydroxy-7-azaspiro[4.5]decan-10-yl)methyl)-4-phenylpyridin-2(1H)-one: A solution of tert-butyl (S)-10-hydroxy-10-((2-oxo-4-phenylpyridin-1(2H)-yl)methyl)-7-azaspiro[4.5]decane-7-carboxylate (269 mg, 0.613 mmol) in TFA (3 mL) and DCM (6 mL) was stirred at rt for 10 min before the reaction mixture was loaded on to a 5 g SCX-2 cartridge that was pre-equilibrated with 1:1 DCM/MeOH. The cartridge was washed with 1:1 DCM/MeOH (90 mL) before the product was eluted with 1:1 DCM/7 M $NH_3$ in MeOH (60 mL). The basic eluents were concentrated under reduced pressure to give the title compound (201 mg, 96%) as a very pale yellow crystalline solid. LCMS (Method A): $R_T$=0.59 min, m/z=339 [M+H]$^+$.

Step 4: tert-Butyl (R)-4-((S)-10-hydroxy-10-((2-oxo-4-phenylpyridin-1(2H)-yl)methyl)-7-azaspiro[4.5]decane-7-carbonyl)-3-phenylpiperazine-1-carboxylate: A solution of triphosgene (21.9 mg, 0.0739 mmol) in THF (1.1 mL) was added to a mixture of tert-butyl (R)-3-phenylpiperazine-1-carboxylate (58.1 mg, 0.222 mmol) and DIPEA (77 µL, 0.443 mmol) in THF (1.1 mL) at 0° C. After 65 min, the reaction mixture was allowed to warm to rt before being added via syringe to a solution of (S)-1-((10-hydroxy-7-azaspiro[4.5]decan-10-yl)methyl)-4-phenylpyridin-2(1H)-one (50 mg, 0.148 mmol) in DCM (1.5 mL). The reaction was stirred at rt for 17 h before saturated $NaHCO_{3(aq)}$ (15 mL) was added and the resulting mixture was extracted with DCM (3×10 mL) using a phase separator. The combined organic phases were concentrated under reduced pressure and the residue was purified by flash chromatography (0-100% EtOAc in cyclohexane) to give the title compound (71.2 mg, 76%) as an off-white foam. LCMS (Method A): $R_T$=1.75 min, m/z=627 [M+H]$^+$.

Step 5: 1-(((S)-10-Hydroxy-7-((R)-2-phenylpiperazine-1-carbonyl)-7-azaspiro[4.5]decan-10-yl)methyl)-4-phenylpyridin-2(1H)-one: A solution of tert-butyl (R)-4-((S)-10-hydroxy-10-((2-oxo-4-phenylpyridin-1(2H)-yl)methyl)-7-azaspiro[4.5]decane-7-carbonyl)-3-phenylpiperazine-1-carboxylate (71.2 mg, 0.114 mmol) in TFA (0.5 mL) and DCM (1 mL) was stirred at rt for 15 min before the reaction mixture was loaded on to a 2 g SCX-2 cartridge that was pre-equilibrated with 1:1 DCM/MeOH. The cartridge was washed with 1:1 DCM/MeOH (60 mL) before the product was eluted with 1:1 DCM/7 M $NH_3$ in MeOH (30 mL). The basic eluents were concentrated under reduced pressure and the residue purified by flash chromatography (0-20% MeOH in DCM) to give the title compound (54.5 mg, 90%) as a colourless solid after lyophilisation. LCMS (Method A): $R_T$=1.02 min, m/z=527 [M+H]$^+$. $^1$H NMR (500 MHz, DMSO-d$_6$): δ 7.79 (d, J=7.1 Hz, 1H), 7.77-7.69 (m, 2H), 7.55-7.43 (m, 3H), 7.36-7.23 (m, 4H), 7.22-7.16 (m, 1H), 6.73 (d, J=1.6 Hz, 1H), 6.64 (dd, J=7.1, 1.8 Hz, 1H), 5.00 (s, 1H), 4.50 (d, J=13.5 Hz, 1H), 4.31 (t, J=5.2 Hz, 1H), 3.77 (d, J=13.5 Hz, 1H), 3.60 (dt, J=13.2, 5.0 Hz, 1H), 3.27-3.14 (m, 2H), 3.11-2.99 (m, 2H), 2.98-2.91 (m, 1H), 2.90 (d, J=5.2 Hz, 2H), 2.77 (t, J=5.0 Hz, 2H), 2.40 (br. s, 1H), 1.92-1.83 (m, 1H), 1.69-1.41 (m, 6H), 1.36-1.27 (m, 1H), 1.22-1.15 (m, 1H), 1.12-1.03 (m, 1H).

Example 288: 1-(((S)-4-Hydroxy-3,3-dimethyl-1-((R)-2-phenylpiperazine-1-carbonyl)piperidin-4-yl)methyl)-4-phenylpyridin-2(1H)-one

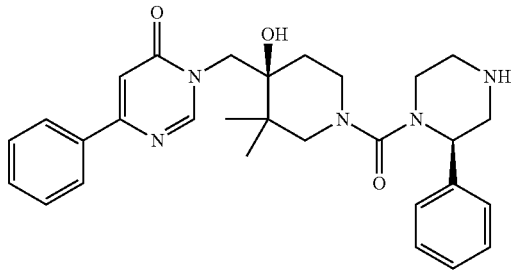 [SMILES: CC1(C)CN(C(=O)N2CCNC[C@H]2c2ccccc2)CC[C@@]1(O)Cn1cnc(-c2ccccc2)cc1=O]

Step 1: tert-Butyl (R)-4-((S)-4-hydroxy-3,3-dimethyl-4-((2-oxo-4-phenylpyridin-1(2H)-yl)methyl)piperidine-1-carbonyl)-3-phenylpiperazine-1-carboxylate: A solution of triphosgene (9.5 mg, 0.0320 mmol) in THF (0.5 mL) was added to a mixture of tert-butyl (R)-3-phenylpiperazine-1-carboxylate (25.2 mg, 0.0960 mmol) and DIPEA (34 µL, 0.192 mmol) in THF (0.5 mL) at 0° C. After 10 min, the reaction mixture was allowed to warm to rt before being added via syringe to a solution of (S)-1-((4-hydroxy-3,3-dimethylpiperidin-4-yl)methyl)-4-phenylpyridin-2(1H)-one (20 mg, 0.0640 mmol) in DCM (0.64 mL). The reaction was stirred at rt for 3 days before saturated $NaHCO_{3(aq)}$ (15 mL) was added and the resulting mixture was extracted with DCM (3×10 mL) using a phase separator. The combined organic phases were concentrated under reduced pressure and the residue was purified by flash chromatography (0-100% EtOAc in cyclohexane) to give the title compound (28 mg, 72%) as an off-white foam. LCMS (Method A): $R_T$=1.67 min, m/z=601 [M+H]$^+$.

Step 2: 1-(((S)-4-Hydroxy-3,3-dimethyl-1-((R)-2-phenylpiperazine-1-carbonyl)piperidin-4-yl)methyl)-4-phenylpyridin-2(1H)-one: A solution of tert-butyl (R)-4-((S)-4-hydroxy-3,3-dimethyl-4-((2-oxo-4-phenylpyridin-1(2H)-yl)methyl)piperidine-1-carbonyl)-3-phenylpiperazine-1-carboxylate (28 mg, 0.0466 mmol) in TFA (0.25 mL) and DCM (0.5 mL) was stirred at rt for 15 min before the reaction mixture was loaded on to a 2 g SCX-2 cartridge that was pre-equilibrated with 1:1 DCM/MeOH. The cartridge was washed with 1:1 DCM/MeOH (60 mL) before the product was eluted with 1:1 DCM/7 M $NH_3$ in MeOH (30 mL). The basic eluents were concentrated under reduced pressure and the residue was purified by flash chromatography (0-20% MeOH in DCM) to give the title compound (18.9 mg, 80%) as a colourless solid after lyophilisation. LCMS (Method A): $R_T$=0.98 min, m/z=501 [M+H]$^+$. $^1$H NMR (500 MHz, DMSO-d$_6$): δ 7.76 (d, J=7.2 Hz, 1H), 7.75-7.67 (m, 2H), 7.57-7.42 (m, 3H), 7.37-7.20 (m, 4H), 7.20-7.15 (m, 1H), 6.72 (d, J=1.5 Hz, 1H), 6.64 (dd, J=7.2, 2.1 Hz, 1H), 5.00 (s, 1H), 4.40-4.29 (m, 2H), 3.87 (d, J=13.5 Hz, 1H), 3.62 (dt, J=13.2, 4.3 Hz, 1H), 3.14-2.84 (m, 7H), 2.82-2.72 (m, 2H), 1.76-1.68 (m, 1H), 1.14-1.08 (m, 1H), 0.97 (s, 3H), 0.92 (s, 3H). NH signal not observed.

Example 289: 3-(((S)-10-Hydroxy-7-((R)-2-phenylpiperazine-1-carbonyl)-7-azaspiro[4.5]decan-10-yl)methyl)-6-(1-methyl-1H-pyrazol-5-yl)pyrimidin-4(3H)-one

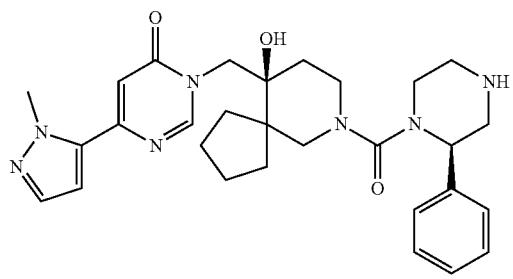 [SMILES: Cn1nccc1-c1cc(=O)n(C[C@]2(O)CCN(C(=O)N3CCNC[C@H]3c3ccccc3)CC23CCCC3)cn1]

Step 1: tert-Butyl (R)-4-((S)-10-((4-chloro-6-oxopyrimidin-1(6H)-yl)methyl)-10-hydroxy-7-azaspiro[4.5]decane-7-carbonyl)-3-phenylpiperazine-1-carboxylate: To a solution of bis(trichloromethyl)carbonate (75 mg, 0.25 mmol) in DCM (9 mL) at −10° C. under nitrogen was added pyridine (0.15 mL, 1.89 mmol), followed by dropwise addition of tert-butyl (3R)-3-phenylpiperazine-1-carboxylate hydrochloride (188 mg, 0.63 mmol) [commercially available] in DCM (9 mL). The reaction mixture was warmed to rt and stirred for 2 h. Additional pyridine (0.05 mL) was added and the reaction was continued for 1 h. Further pyridine (0.05 mL) was added and the reaction was continued for a further 1 h. To the resultant mixture was added (S)-6-chloro-3-((10-hydroxy-7-azaspiro[4.5]decan-10-yl)methyl)pyrimidin-4(3H)-one hydrochloride (168 mg, 0.50 mmol) in DCM (6 mL) followed by DIPEA (0.26 mL, 1.51 mmol). The reaction mixture was stirred under nitrogen at rt for 3 days. The volatiles were evaporated under reduced pressure and the residue was purified by flash chromatography (5-100% EtOAc in cyclohexane) to give the title compound (151 mg, 51%) as a clear glass. LCMS (Method B): $R_T$=1.43 min, m/z=530, 532 [M-butene+H]$^+$.

Step 2: tert-Butyl (R)-4-((S)-10-hydroxy-10-((4-(1-methyl-1H-pyrazol-5-yl)-6-oxopyrimidin-1(6H)-yl)methyl)-7-azaspiro[4.5]decane-7-carbonyl)-3-phenylpiperazine-1-carboxylate: Prepared according to General Procedure 5 using tert-butyl (R)-4-((S)-10-((4-chloro-6-oxopyrimidin-1(6H)-yl)methyl)-10-hydroxy-7-azaspiro[4.5]decane-7-carbonyl)-3-phenylpiperazine-1-carboxylate (15 mg, 0.026 mmol), 1-methyl-5-(4,4,5,5-tetramethyl-1,3,2-dioxaborolan-2-yl)-1H-pyrazole (11 mg, 0.051 mmol), Pd(dppf)Cl$_2$ DCM complex (1.1 mg, 0.0013 mmol) and Na$_2$CO$_3$ (8.0 mg, 0.077 mmol) in 1,4-dioxane (0.45 mL) and water (0.15 mL). The reaction mixture was heated using microwave irradiation at 120° C. for 30 min to give the title compound (12 mg, 74%) as clear glass. LCMS (Method A): $R_T$=1.48 min, m/z=632 [M+H]$^+$.

Step 3: 3-(((S)-10-Hydroxy-7-((R)-2-phenylpiperazine-1-carbonyl)-7-azaspiro[4.5]decan-10-yl)methyl)-6-(1-methyl-1H-pyrazol-5-yl)pyrimidin-4(3H)-one: Prepared according to General Procedure 3 using tert-butyl (R)-4-((S)-10-hydroxy-10-((4-(1-methyl-1H-pyrazol-5-yl)-6-oxopyrimidin-1(6H)-yl)methyl)-7-azaspiro[4.5]decane-7-carbonyl)-3-phenylpiperazine-1-carboxylate (12 mg, 0.019 mmol), TFA (1.0 mL) and DCM (2.0 mL), and stirred at rt for 30 min to give the title compound (10 mg, 99%) as off-white solid. LCMS (Method A): $R_T$=0.77 min, m/z=532 [M+H]$^+$. $^1$H NMR (500 MHz, DMSO-d$_6$): δ 8.45 (s, 1H), 7.49 (d, J=2.0 Hz, 1H), 7.32-7.25 (m, 4H), 7.24-7.18 (m, 1H), 6.86 (d, J=2.0 Hz, 1H), 6.79 (s, 1H), 4.80 (s, 1H), 4.55 (d, J=13.6 Hz, 1H), 4.35 (t, J=5.6 Hz, 1H), 4.12 (s, 3H), 3.66-3.52 (m, 2H), 3.27-3.16 (m, 2H), 3.12-2.82 (m, 7H), 2.47-2.38 (m, 1H, overlap with DMSO), 1.90-1.81 (m, 1H), 1.67-1.37 (m, 6H), 1.33-1.27 (m, 1H), 1.24-1.19 (m, 1H), 1.09-1.01 (m, 1H).

Example 290: 3-(((S)-10-Hydroxy-7-((R)-2-phenylpiperazine-1-carbonyl)-7-azaspiro[4.5]decan-10-yl)methyl)-6-(pyrrolidin-1-yl)pyrimidin-4(3H)-one

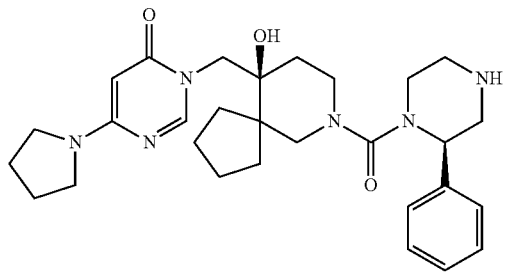 [SMILES: O=C(N1CC[C@@](O)(Cn2cnc(N3CCCC3)cc2=O)C2(CCCC2)C1)N1CCNC[C@H]1c1ccccc1]

Step 1: tert-Butyl (R)-4-((S)-10-hydroxy-10-((6-oxo-4-(pyrrolidin-1-yl)pyrimidin-1(6H)-yl)methyl)-7-azaspiro[4.5]decane-7-carbonyl)-3-phenylpiperazine-1-carboxylate: In a microwave vial tert-butyl (R)-4-((S)-10-((4-chloro-6-oxopyrimidin-1(6H)-yl)methyl)-10-hydroxy-7-azaspiro[4.5]decane-7-carbonyl)-3-phenylpiperazine-1-carboxylate (10 mg, 0.017 mmol) was suspended in dioxane (0.5 mL) and pyrrolidine (14 µL, 0.17 mmol) was added. The vessel was sealed and the reaction mixture was heated under microwave irradiation at 120° C. for 30 min. The volatiles were evaporated under reduced pressure and the residue was purified by flash chromatography (5-100% EtOAc in cyclohexane; then 0-20% MeOH in EtOAc). The product containing fractions were evaporated under reduced pressure to give the title compound (10 mg, 94%) as clear glass. LCMS (Method A): $R_T$=1.56 min, m/z=621 [M+H]$^+$.

Step 2: 3-(((S)-10-Hydroxy-7-((R)-2-phenylpiperazine-1-carbonyl)-7-azaspiro[4.5]decan-10-yl)methyl)-6-(pyrrolidin-1-yl)pyrimidin-4(3H)-one: Prepared according to General Procedure 3 using tert-butyl (R)-4-((S)-10-hydroxy-10-((6-oxo-4-(pyrrolidin-1-yl)pyrimidin-1(6H)-yl)methyl)-7-azaspiro[4.5]decane-7-carbonyl)-3-phenylpiperazine-1-carboxylate (10 mg, 0.016 mmol), TFA (1.0 mL) and DCM (2.0 mL), and stirred at rt for 30 min to give the title compound (7 mg, 84%) as an off-white solid. LCMS (Method A): $R_T$=0.80 min, m/z=521 [M+H]$^+$. $^1$H NMR (500 MHz, DMSO-d$_6$): δ 8.10 (s, 1H), 7.32-7.24 (m, 4H), 7.25-7.15 (m, 1H), 5.01 (s, 1H), 4.96 (s, 1H), 4.36-4.28 (m, 2H), 3.62-3.52 (m, 2H), 3.47-3.13 (m, 6H, overlap with HDO), 3.11-2.78 (m, 7H), 1.96-1.77 (m, 5H), 1.64-1.43 (m, 5H), 1.39-1.32 (m, 1H), 1.31-1.25 (m, 1H), 1.17-1.09 (m, 1H), 1.06-0.98 (m, 1H).

Example 291: 3-(((S)-10-Hydroxy-7-((R)-2-phenylpiperazine-1-carbonyl)-7-azaspiro[4.5]decan-10-yl)methyl)-6-(1-methyl-1H-pyrazol-4-yl)pyrimidin-4(3H)-one

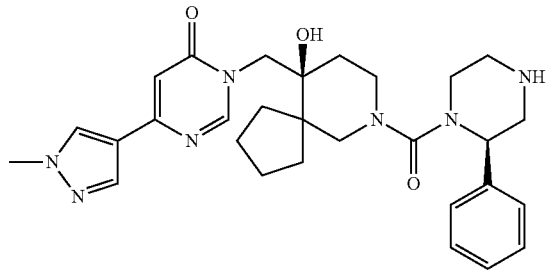 [SMILES: Cn1cc(-c2cc(=O)n(C[C@]3(O)CCN(C(=O)N4CCNC[C@H]4c4ccccc4)CC34CCCC4)cn2)cn1]

Step 1: tert-Butyl (R)-4-((S)-10-hydroxy-10-((4-(1-methyl-1H-pyrazol-4-yl)-6-oxopyrimidin-1(6H)-yl)methyl)-7-azaspiro[4.5]decane-7-carbonyl)-3-phenylpiperazine-1-carboxylate: Prepared according to General Procedure 5 using tert-butyl (R)-4-((S)-10-((4-chloro-6-oxopyrimidin-1(6H)-yl)methyl)-10-hydroxy-7-azaspiro[4.5]decane-7-carbonyl)-3-phenylpiperazine-1-carboxylate (14 mg, 0.024 mmol), 1-methyl-4-(4,4,5,5-tetramethyl-1,3,2-dioxaborolan-2-yl)-1H-pyrazole (9.9 mg, 0.048 mmol), Pd(dppf)Cl$_2$ DCM complex (1.0 mg, 0.0011 mmol) and Na$_2$CO$_3$ (7.6 mg, 0.072 mmol) in 1,4-dioxane (0.45 mL) and water (0.15 mL). The reaction mixture was heated using microwave irradiation at 120° C. for 30 min to give the title compound (10 mg, 66%) as clear glass. LCMS (Method B): R$_T$=1.29 min, m/z=632 [M+H]$^+$.

Step 2: 3-(((S)-10-Hydroxy-7-((R)-2-phenylpiperazine-1-carbonyl)-7-azaspiro[4.5]decan-10-yl)methyl)-6-(1-methyl-1H-pyrazol-4-yl)pyrimidin-4(3H)-one: Prepared according to General Procedure 3 using tert-butyl (R)-4-((S)-10-hydroxy-10-((4-(1-methyl-1H-pyrazol-4-yl)-6-oxopyrimidin-1(6H)-yl)methyl)-7-azaspiro[4.5]decane-7-carbonyl)-3-phenylpiperazine-1-carboxylate (10 mg, 0.016 mmol), TFA (1.0 mL) and DCM (2.0 mL), stirred at rt for 30 min to give the title compound (8 mg, 95%) as white solid. LCMS (Method A): R$_T$=0.47 min, m/z=532 [M+H]$^+$. $^1$H NMR (500 MHz, DMSO-d$_6$): δ 8.32 (s, 1H), 8.29 (s, 1H), 7.99 (s, 1H), 7.31-7.24 (m, 4H), 7.22-7.16 (m, 1H), 6.63 (s, 1H), 4.80 (s, 1H), 4.50 (d, J=13.6 Hz, 1H), 4.31 (t, J=5.3 Hz, 1H), 3.87 (s, 3H), 3.64-3.50 (m, 2H), 3.27-3.14 (m, 2H), 3.08-2.88 (m, 5H), 2.84-2.74 (m, 2H), 1.90-1.78 (m, 1H), 1.66-1.27 (m, 8H), 1.22-1.16 (m, 1H), 1.10-1.01 (m, 1H).

Example 292: 6-Cyclopropyl-3-(((S)-10-hydroxy-7-((R)-2-phenylpiperazine-1-carbonyl)-7-azaspiro[4.5]decan-10-yl)methyl)pyrimidin-4(3H)-one

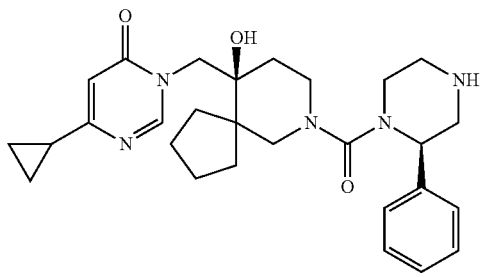 [SMILES: O=C(N1CC[C@@](O)(Cn2cnc(C3CC3)cc2=O)C2(CCCC2)C1)N1CCNC[C@H]1c1ccccc1]

Step 1: tert-Butyl (R)-4-((S)-10-((4-cyclopropyl-6-oxopyrimidin-1(6H)-yl)methyl)-10-hydroxy-7-azaspiro[4.5]decane-7-carbonyl)-3-phenylpiperazine-1-carboxylate: A suspension of tert-butyl (R)-4-((S)-10-((4-chloro-6-oxopyrimidin-1(6H)-yl)methyl)-10-hydroxy-7-azaspiro[4.5]decane-7-carbonyl)-3-phenylpiperazine-1-carboxylate (15 mg, 0.026 mmol), cyclopropylboronic acid MIDA ester (10 mg, 0.051 mmol), tricyclohexylphosphonium tetrafluoroborate (2.8 mg, 0.0077 mmol) and Pd(OAc)$_2$ (0.9 mg, 0.0038 mmol) in toluene (0.45 mL) and water (0.05 mL) in a sealed vial was 'degassed' by evacuating and backfilling the vessel with nitrogen. The reaction mixture was heated at 100° C. (sand bath) for 6 h. The volatiles were evaporated under reduced pressure and the residue was dry loaded onto silica and purified by flash chromatography (5-100% EtOAc in cyclohexane) to give the title compound (10 mg, 66%) as a white solid. LCMS (Method A): R$_T$=1.58 min, m/z=592 [M+H]$^+$.

Step 2: 6-Cyclopropyl-3-(((S)-10-hydroxy-7-((R)-2-phenylpiperazine-1-carbonyl)-7-azaspiro[4.5]decan-10-yl)methyl)pyrimidin-4(3H)-one: Prepared according to General Procedure 3 using tert-butyl (R)-4-((S)-10-((4-cyclopropyl-6-oxopyrimidin-1(6H)-yl)methyl)-10-hydroxy-7-azaspiro[4.5]decane-7-carbonyl)-3-phenylpiperazine-1-carboxylate (10 mg, 0.017 mmol), TFA (1.0 mL) and DCM (2.0 mL), stirred at rt for 30 min, and purified by preparative HPLC (basic conditions) to give the title compound (3 mg, 36%) as off-white solid. LCMS (Method A): R$_T$=0.79 min, m/z=492 [M+H]$^+$. $^1$H NMR (500 MHz, DMSO-d$_6$): δ 8.21 (s, 1H), 7.32-7.23 (m, 4H), 7.22-7.14 (m, 1H), 6.31 (s, 1H), 4.73 (s, 1H), 4.45 (d, J=13.6 Hz, 1H), 4.30 (t, J=5.5 Hz, 1H), 3.60-3.49 (m, 2H), 3.28-3.12 (m, 2H), 3.05-2.85 (m, 5H), 2.76 (d, J=5.4 Hz, 2H), 2.27-2.14 (m, 1H), 1.92-1.78 (m, 2H), 1.62-1.44 (m, 5H), 1.38-1.26 (m, 2H), 1.18-1.10 (m, 1H), 1.09-1.00 (m, 1H), 0.92 (d, J=6.4 Hz, 4H).

Example 293: 3-(((S)-7-((R)-3-(1H-Benzo[d]imidazol-2-yl)morpholine-4-carbonyl)-10-hydroxy-7-azaspiro[4.5]decan-10-yl)methyl)-6-phenylpyrimidin-4(3H)-one

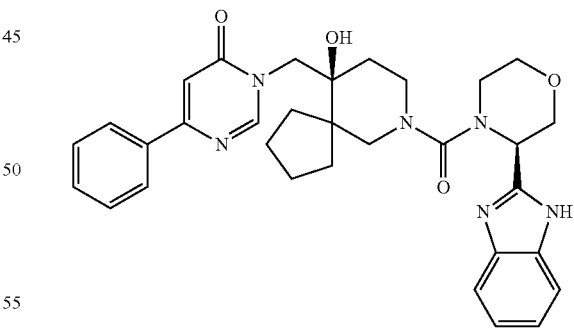

Step 1: (R)-3-(1H-Benzo[d]imidazol-2-yl)morpholine: A solution of tert-butyl (R)-3-(1H-benzo[d]imidazol-2-yl)morpholine-4-carboxylate (86 mg, 0.284 mmol) [prepared according to Angew. Chem. Int. Ed., 2017, 56, 1294-1297] in TFA (0.7 mL) and DCM (1.4 mL) was stirred at rt for 15 min before the reaction mixture was loaded on to a 2 g SCX-2 cartridge that was pre-equilibrated with 1:1 DCM/MeOH. The cartridge was washed with 1:1 DCM/MeOH (60 mL) before the product was eluted with 1:1 DCM/7 M NH$_3$ in MeOH (30 mL). The basic eluents were concentrated under reduced pressure to give the title compound (54.7 mg, 94%) as an off-white solid. LCMS (Method A): $R_T$=0.28 min, m/z=204 [M+H]$^+$.

Step 2: 3-(((S)-7-((R)-3-(1H-Benzo[d]imidazol-2-yl)morpholine-4-carbonyl)-10-hydroxy-7-azaspiro[4.5]decan-10-yl)methyl)-6-phenylpyrimidin-4(3H)-one: To a solution of triphosgene (6.6 mg, 0.0221 mmol) and pyridine (11 μL, 0.133 mmol) in DCM (0.8 mL) at 0° C. was added (R)-3-(1H-benzo[d]imidazol-2-yl)morpholine (13.5 mg, 0.0663 mmol). After 30 min, (S)-3-((10-hydroxy-7-azaspiro[4.5]decan-10-yl)methyl)-6-phenylpyrimidin-4(3H)-one (15 mg, 0.0442 mmol) and DIPEA (15 μL, 0.0884 mmol) were added. The reaction was stirred at rt for 3 days before saturated NaHCO$_{3(aq)}$ (15 mL) was added and the resulting mixture was extracted with DCM (3×10 mL) using a phase separator. The combined organic phases were concentrated under reduced pressure and the residue was purified by flash chromatography (0-100% EtOAc in cyclohexane; then 0-10% MeOH in EtOAc) and preparative HPLC to give the title compound (2 mg, 7%) as colourless solid after lyophilisation. LCMS (Method A): $R_T$=0.99 min, m/z=569 [M+H]$^+$. $^1$H NMR (500 MHz, DMSO-d$_6$): δ 12.12 (br. s, 1H), 8.46 (s, 1H), 8.12-8.02 (m, 2H), 7.60-7.35 (m, 5H), 7.12 (s, 2H), 6.97 (s, 1H), 4.89 (s, 1H), 4.83 (s, 1H), 4.58 (d, J=13.5 Hz, 1H), 4.30 (dd, J=11.6, 2.6 Hz, 1H), 3.80 (dd, J=11.6, 3.4 Hz, 1H), 3.72 (d, J=10.8 Hz, 1H), 3.62 (d, J=13.5 Hz, 1H), 3.58-3.52 (m, 1H), 3.51-3.43 (m, 2H), 3.35-3.32 (m, 1H), 3.25-3.17 (m, 2H), 3.10 (d, J=12.9 Hz, 1H), 1.95-1.87 (m, 1H), 1.70-1.40 (m, 7H), 1.28-1.17 (m, 2H).

Example 294: (S)-10-Hydroxy-10-((6-oxo-4-phenylpyrimidin-1(6H)-yl)methyl)-N-((R)-2,2,2-trifluoro-1-phenylethyl)-7-azaspiro[4.5]decane-7-carboxamide

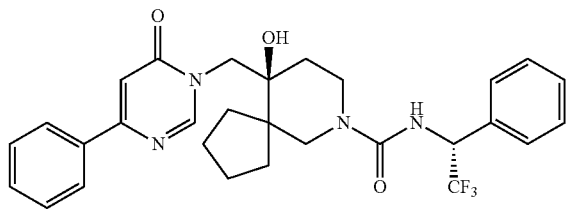 [SMILES: O=C(N[C@H](c1ccccc1)C(F)(F)F)N1CC[C@@](O)(Cn2cnc(-c3ccccc3)cc2=O)C2(CCCC2)C1]

A solution of (R)-2,2,2-trifluoro-1-phenylethan-1-amine (11.6 mg, 0.0663 mmol) in DCM (0.4 mL) was added to a mixture of triphosgene (6.6 mg, 0.0221 mmol) and pyridine (11 μL, 0.133 mmol) in DCM (0.4 mL) at 0° C. After 15 min, (S)-3-((10-hydroxy-7-azaspiro[4.5]decan-10-yl)methyl)-6-phenylpyrimidin-4(3H)-one (15 mg, 0.0442 mmol) and DIPEA (15 μL, 0.0884 mmol) were added. The reaction was stirred at rt for 18 h before saturated NaHCO$_{3(aq)}$ (15 mL) was added and the resulting mixture was extracted with DCM (3×10 mL) using a phase separator. The combined organic phases were concentrated under reduced pressure and the residue was purified by flash chromatography twice (0%; then 2%; then 4% MeOH in DCM (isocratic); followed by 0%; then 1%; then 2%; then 4% MeOH in DCM (isocratic)) to give the title compound (21 mg, 87%) as an off-white solid after lyophilisation. LCMS (Method A): $R_T$=1.52 min, m/z=541 [M+H]$^+$. $^1$H NMR (500 MHz, DMSO-d$_6$): δ 8.46 (s, 1H), 8.11-8.04 (m, 2H), 7.60-7.54 (m, 2H), 7.53-7.45 (m, 3H), 7.43-7.35 (m, 3H), 7.30 (d, J=9.6 Hz, 1H), 6.98 (s, 1H), 5.70 (p, J=9.2 Hz, 1H), 4.82 (s, 1H), 4.59 (d, J=13.6 Hz, 1H), 3.68-3.58 (m, 2H), 3.40-3.25 (m, 3H (signals overlap with HDO)), 1.93-1.86 (m, 1H), 1.70-1.56 (m, 4H), 1.55-1.47 (m, 1H), 1.40-1.31 (m, 2H), 1.23-1.11 (m, 2H).

Example 295: (R)-3-((4-Hydroxy-1-(3-phenylmorpholine-4-carbonyl)piperidin-4-yl)methyl)-6-phenylpyrimidin-4(3H)-one

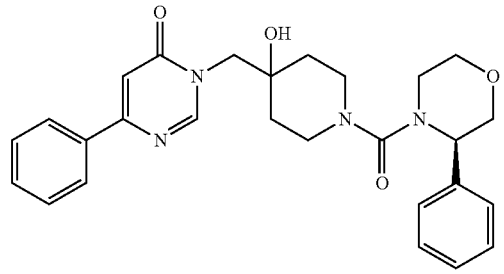 [SMILES: O=C(N1CCC(O)(Cn2cnc(-c3ccccc3)cc2=O)CC1)N1CCOC[C@H]1c1ccccc1]

Step 1: tert-Butyl 4-hydroxy-4-((6-oxo-4-phenylpyrimidin-1(6H)-yl)methyl)piperidine-1-carboxylate: Prepared according to General Procedure 5 using tert-butyl 4-((4-chloro-6-oxopyrimidin-1(6H)-yl)methyl)-4-hydroxypiperidine-1-carboxylate (300 mg, 0.873 mmol) [ACS Med. Chem. Lett., 2018, 9, p 238-243], phenylboronic acid (213 mg, 1.75 mmol), sodium carbonate (277 mg, 2.62 mmol) and Pd(dppf)Cl$_2$·DCM (36.9 mg, 43.6 μmol) in 1,4-dioxane (6 mL) and water (2 mL). The reaction was heated under microwave irradiation at 120° C. for 1 h to give the title compound (174 mg, 51%). LCMS (Method A): $R_T$=1.26 min, m/z=386 [M+H]$^+$.

Step 2: 3-((4-Hydroxypiperidin-4-yl)methyl)-6-phenylpyrimidin-4(3H)-one: Prepared according to General Procedure 3 using tert-butyl 4-hydroxy-4-((6-oxo-4-phenylpyrimidin-1(6H)-yl)methyl)piperidine-1-carboxylate (174 mg, 0.451 mmol), TFA (3 mL) and DCM (6 mL), stirred at rt for 1 h to give the title compound (120 mg, 93%). LCMS (Method A): $R_T$=0.43 min, m/z=286 [M+H]$^+$.

Step 3: (R)-3-((4-Hydroxy-1-(3-phenylmorpholine-4-carbonyl)piperidin-4-yl)methyl)-6-phenylpyrimidin-4(3H)-one: Prepared according to General Procedure 9 using 3-((4-hydroxypiperidin-4-yl)methyl)-6-phenylpyrimidin-4(3H)-one (25 mg, 87.6 μmol), (R)-3-phenylmorpholine-4-carbonyl chloride (23.7 mg, 0.105 mmol) and DIPEA (61 μL, 0.351 mmol) in DCM (1.5 mL), stirring at rt for 1 h to give the title compound (27.7 mg, 65%). LCMS (Method A): $R_T$=1.15 min, m/z=475 [M+H]$^+$. $^1$H NMR (500 MHz, DMSO-d$_6$): δ 8.42 (s, 1H), 8.10-8.05 (m, 2H), 7.53-7.47 (m, 3H), 7.35-7.28 (m, 4H), 7.19 (t, J=6.8 Hz, 1H), 6.97 (s, 1H), 4.98 (s, 1H), 4.50 (t, J=4.5 Hz, 1H), 3.96 (s, 2H), 3.84 (dd, J=11.8, 5.5 Hz, 1H), 3.77-3.61 (m, 3H), 3.51 (ddt, J=12.9, 8.7, 4.3 Hz, 2H), 3.19-3.03 (m, 4H), 1.52 (ddd, J=16.7, 10.9, 4.7 Hz, 2H), 1.40 (dd, J=24.6, 13.5 Hz, 2H).

Example 296: 3-((5-Hydroxy-2-((R)-3-phenylmorpholine-4-carbonyl)-2-azaspiro[5.5]undecan-5-yl)methyl)-6-phenylpyrimidin-4(3H)-one

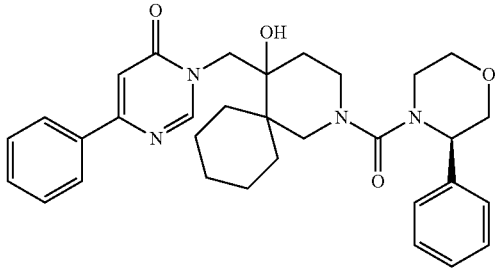

Step 1: tert-Butyl 5-oxo-2-azaspiro[5.5]undecane-2-carboxylate: Potassium tert-butoxide (2.48 g, 22.1 mmol) was added portionwise to a solution of tert-butyl 4-oxopiperidine-1-carboxylate (2 g, 10 mmol) in toluene (20 mL) in a 3-necked RBF fitted with a reflux condenser under $N_2$ at rt. After 1 h, 1,5-dibromopentane (1.37 mL, 10 mmol) was added dropwise over 10 min and the reaction heated at reflux for 3 h. The reaction was allowed to cool to rt, diluted with 1:1 saturated $NH_4Cl_{(aq)}$/water and extracted using EtOAc (×3). The combined organic phases were washed with brine, passed through a phase separator and concentrated in vacuo. The crude product was purified by flash chromatography to give the title compound (500 mg, 19%). $^1$H NMR (500 MHz, $CDCl_3$): δ 3.77-3.61 (br s, 2H), 3.60-3.46 (br s, 2H), 2.48 (t, J=6.5 Hz, 2H), 1.77-1.29 (m, 10H (signal obscured by HDO)), 1.50 (s, 9H).

Step 2: tert-Butyl 1-oxa-11-azadispiro[2.0.5$^4$.4$^3$]tridecane-11-carboxylate: Prepared according to General Procedure 1 using trimethylsulfonium iodide (572 mg, 2.81 mmol), sodium hydride (60% dispersion in mineral oil, 112 mg, 2.81 mmol) and tert-butyl 5-oxo-2-azaspiro[5.5]undecane-2-carboxylate (500 mg, 1.87 mmol) in DMF (9 mL) at rt to give the title compound (440 mg, 83%). $^1$H NMR (500 MHz, $CDCl_3$): δ 3.73-3.51 (m, 2H), 3.51-3.29 (m, 2H), 2.92 (d, J=4.4 Hz, 1H), 2.42 (d, J=4.4 Hz, 1H), 1.48 (s, 9H), 1.72-1.33 (m, 9H (signal obscured by HDO)), 1.23-1.02 (m, 3H).

Step 3: tert-Butyl 5-hydroxy-5-((6-oxo-4-phenylpyrimidin-1(6H)-yl)methyl)-2-azaspiro[5.5]undecane-2-carboxylate: Prepared according to General Procedure 2 using tert-butyl 1-oxa-11-azadispiro[2.0.5$^4$.4$^3$]tridecane-11-carboxylate (400 mg, 1.42 mmol), 6-phenylpyrimidin-4(3H)-one (490 mg, 2.84 mmol), cesium carbonate (926 mg, 2.84 mmol) and DMF (4 mL), stirred at 80° C. for 17 h to give the title compound (40 mg, 6.2%). LCMS (Method A): $R_T$=1.73 min, m/z=454 $[M+H]^+$; 398 $[M-butene+H]^+$.

Step 4: 3-((5-Hydroxy-2-azaspiro[5.5]undecan-5-yl)methyl)-6-phenylpyrimidin-4(3H)-one: Prepared according to General Procedure 3 using tert-butyl 5-hydroxy-5-((6-oxo-4-phenylpyrimidin-1(6H)-yl)methyl)-2-azaspiro[5.5]undecane-2-carboxylate (40 mg, 88.2 μmol), TFA (0.5 mL) and DCM (1 mL), stirred at rt for 0.5 h to give the title compound (27 mg, 86%). LCMS (Method A): $R_T$=0.80 min, m/z=354 $[M+H]^+$.

Step 5: 3-((5-Hydroxy-2-((R)-3-phenylmorpholine-4-carbonyl)-2-azaspiro[5.5]undecan-5-yl)methyl)-6-phenylpyrimidin-4(3H)-one: Prepared according to General Procedure 9 using 3-((5-hydroxy-2-azaspiro[5.5]undecan-5-yl)methyl)-6-phenylpyrimidin-4(3H)-one (15 mg, 42.4 μmol), (R)-3-phenylmorpholine-4-carbonyl chloride (11.5 mg, 50.9 mmol) and DIPEA (30 μL, 0.170 mmol) in DCM (1 mL), stirring at rt for 1 h to give the title compound (7.7 mg, 31%). LCMS (Method A): $R_T$=1.54 min, m/z=543 $[M+H]^+$. $^1$H NMR (500 MHz, DMSO-$d_6$): δ 8.42 (s, 1H), 8.10-8.04 (m, 2H), 7.53-7.48 (m, 3H), 7.36-7.26 (m, 4H), 7.22 (dt, J=10.0, 7.0 Hz, 1H), 6.97 (d, J=4.6 Hz, 1H), 4.77 (s, 1H), 4.52 (dd, J=13.6, 6.7 Hz, 1H), 4.34 (dt, J=33.7, 4.6 Hz, 1H), 3.80-3.52 (m, 7H), 3.27-2.93 (m, 4H), 1.64-0.96 (m, 12H).

Example 297: (R)-3-((4-Hydroxy-1-(2-phenylpiperazine-1-carbonyl)piperidin-4-yl)methyl)-6-phenylpyrimidin-4(3H)-one

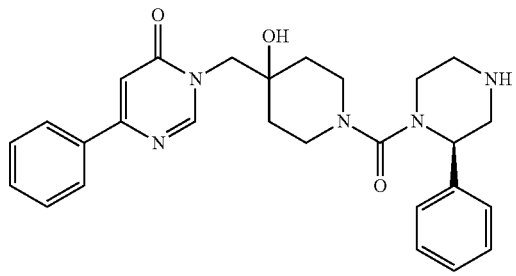 [SMILES: O=C(N1CCC(O)(Cn2cnc(-c3ccccc3)cc2=O)CC1)N1CCNC[C@H]1c1ccccc1]

Step 1: tert-Butyl (R)-4-(4-hydroxy-4-((6-oxo-4-phenylpyrimidin-1(6H)-yl)methyl)piperidine-1-carbonyl)-3-phenylpiperazine-1-carboxylate: Prepared according to General Procedure 9 using 3-((4-hydroxypiperidin-4-yl)methyl)-6-phenylpyrimidin-4(3H)-one (25 mg, 87.6 μmol), tert-butyl (R)-4-(chlorocarbonyl)-3-phenylpiperazine-1-carboxylate (34.1 mg, 0.105 mmol), DIPEA (61 μL, 0.351 mmol) and DCM (2 mL), stirring at rt for 1 h to give the title compound (40 mg, 80%). LCMS (Method B): $R_T$=1.45 min, m/z=574 $[M+H]^+$; 518 $[M-butene+H]^+$.

Step 2: (R)-3-((4-Hydroxy-1-(2-phenylpiperazine-1-carbonyl)piperidin-4-yl)methyl)-6-phenylpyrimidin-4(3H)-one: Prepared according to General Procedure 3 using tert-butyl (R)-4-(4-hydroxy-4-((6-oxo-4-phenylpyrimidin-1(6H)-yl)methyl)piperidine-1-carbonyl)-3-phenylpiperazine-1-carboxylate (40 mg, 69.7 μmol), TFA (1 mL) and DCM (2 mL), stirred at rt for 40 min to give the title compound (32.6 mg, quantitative). LCMS (Method A): $R_T$=0.69 min, m/z=474 $[M+H]^+$. $^1$H NMR (500 MHz, DMSO-$d_6$): δ 8.41 (s, 1H), 8.07 (dd, J=6.8, 3.0 Hz, 2H), 7.52-7.48 (m, 3H), 7.32-7.25 (m, 4H), 7.15 (tt, J=5.7, 2.6 Hz, 1H), 6.97 (s, 1H), 4.96 (s, 1H), 4.43 (dd, J=5.8, 3.9 Hz, 1H), 3.95 (s, 2H), 3.50 (dq, J=14.1, 4.6 Hz, 2H), 3.16-3.01 (m, 4H), 2.98 (dd, J=12.6, 5.9 Hz, 1H), 2.90 (dd, J=12.6, 3.9 Hz, 1H), 2.81-2.71 (m, 2H), 1.50 (tt, J=11.0, 3.8 Hz, 2H), 1.39 (dd, J=21.5, 13.5 Hz, 2H). NH signal not observed.

Example 298: 3-((5-Hydroxy-2-((R)-2-phenylpiperazine-1-carbonyl)-2-azaspiro[5.5]undecan-5-yl)methyl)-6-phenylpyrimidin-4(3H)-one

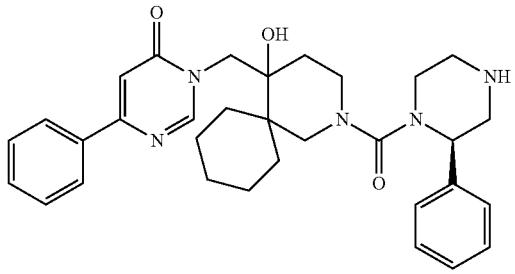

Step 1: tert-Butyl (3R)-4-(5-hydroxy-5-((6-oxo-4-phenylpyrimidin-1(6H)-yl)methyl)-2-azaspiro[5.5]undecane-2-carbonyl)-3-phenylpiperazine-1-carboxylate: Prepared according to General Procedure 9 using 3-((5-hydroxy-2-azaspiro[5.5]undecan-5-yl)methyl)-6-phenylpyrimidin-4(3H)-one (15 mg, 42.4 µmol), tert-butyl (R)-4-(chlorocarbonyl)-3-phenylpiperazine-1-carboxylate (16.5 mg, 50.9 µmol), DIPEA (30 µL, 0.170 mmol) and DCM (1 mL), stirring at rt for 1 h to give the title compound (15 mg, 57%). LCMS (Method A): $R_T$=1.85 min, m/z=642 [M+H]$^+$; 586 [M-butene+H]$^+$.

Step 2: 3-((5-Hydroxy-2-((R)-2-phenylpiperazine-1-carbonyl)-2-azaspiro[5.5]undecan-5-yl)methyl)-6-phenylpyrimidin-4(3H)-one: Prepared according to General Procedure 3 using tert-butyl (3R)-4-(5-hydroxy-5-((6-oxo-4-phenylpyrimidin-1(6H)-yl)methyl)-2-azaspiro[5.5]undecane-2-carbonyl)-3-phenylpiperazine-1-carboxylate (15 mg, 23.4 µmol), TFA (0.5 mL) and DCM (1 mL), stirred at rt for 1 h to give the title compound (7.6 mg, 57%). LCMS (Method A): $R_T$=1.01 min, m/z=542 [M+H]$^+$. $^1$H NMR (500 MHz, DMSO-d$_6$): δ 8.41 (s, 1H), 8.08 (dd, J=6.5, 2.9 Hz, 2H), 7.53-7.48 (m, 3H), 7.32-7.23 (m, 4H), 7.23-7.15 (m, 1H), 6.97 (d, J=3.2 Hz, 1H), 4.75 (d, J=4.2 Hz, 1H), 4.51 (d, J=12.9 Hz, 1H), 4.30-4.18 (m, 1H), 3.77-3.47 (m, 3H), 3.27-2.73 (m, 9H), 1.64-0.96 (m, 11H). NH signal not observed.

Example 299: (S)-3-((10-Hydroxy-7-(2-phenylpyrazolidine-1-carbonyl)-7-azaspiro[4.5]decan-10-yl)methyl)-6-phenylpyrimidin-4(3H)-one

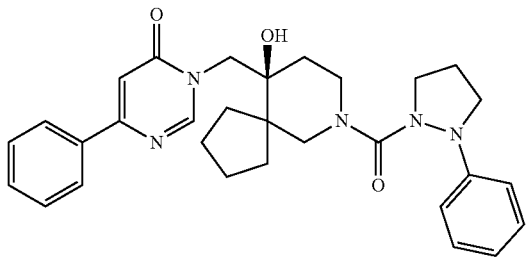 [SMILES: O=C(N1CC[C@@](O)(Cn2cnc(-c3ccccc3)cc2=O)C2(CCCC2)C1)N1CCCN1c1ccccc1]

Step 1: 1-Phenylpyrazolidine: [Prepared according to Chem. Commun., 2015, 51, p 10435-10438] To a stirred suspension of lithium aluminium hydride (468 mg, 12.3 mmol) in dry THF (6 mL) was added a solution of 1-phenylpyrazolidin-3-one (500 mg, 3.08 mmol) in dry THF (6 mL). The resulting mixture was stirred at 75° C. for 20 h before being allowed to cool to rt. Et$_2$O (30 mL) was added to the reaction mixture which was then added portionwise to water (30 mL). The resulting mixture was filtered and the filtrate extracted with Et$_2$O (×3). The combined organic phases were passed through a phase separator and concentrated in vacuo. The crude material was purified by flash chromatography to give the title compound (140 mg, 30%). $^1$H NMR (500 MHz, CDCl$_3$): δ 7.19-7.13 (m, 2H), 6.96 (dt, J=7.7, 1.2 Hz, 2H), 6.80-6.70 (m, 1H), 3.30 (t, J=7.2 Hz, 2H), 2.97 (t, J=6.8 Hz, 2H), 2.05 (p, J=7.0 Hz, 2H). NH signal not observed.

Step 2: 2-Phenylpyrazolidine-1-carbonyl chloride: Prepared according to General Procedure 8 using 1-phenylpyrazolidine (50 mg, 0.337 mmol), triphosgene (50.1 mg, 0.169 mmol), pyridine (41 µL, 0.506 mmol) and DCM (4 mL), stirred at 0° C. for 30 min, warmed to rt and stirred at rt for 1 h to give the title compound (60 mg, 84%). Material was used in the next step without further purification.

Step 3: (S)-3-((10-Hydroxy-7-(2-phenylpyrazolidine-1-carbonyl)-7-azaspiro[4.5]decan-10-yl)methyl)-6-phenylpyrimidin-4(3H)-one: Prepared according to General Procedure 9 using (S)-3-((10-hydroxy-7-azaspiro[4.5]decan-10-yl)methyl)-6-phenylpyrimidin-4(3H)-one (16 mg, 47.1 µmol), 2-phenylpyrazolidine-1-carbonyl chloride (14.9 mg, 70.7 µmol), DIPEA (33 µL, 0.187 mmol) and DCM (2 mL), stirring at rt for 1 h to give the title compound (13.1 mg, 53%). LCMS (Method A): $R_T$=1.53 min, m/z=514 [M+H]$^+$. $^1$H NMR (500 MHz, DMSO-d$_6$): δ 8.44 (s, 1H), 8.06 (dd, J=6.7, 2.9 Hz, 2H), 7.49 (dd, J=5.0, 1.9 Hz, 3H), 7.27-7.20 (m, 2H), 6.99 (d, J=8.1 Hz, 2H), 6.95 (s, 1H), 6.86 (t, J=7.3 Hz, 1H), 4.80 (s, 1H), 4.58 (d, J=13.6 Hz, 1H), 4.01-2.83 (m, 9H (signal obscured by HDO)), 1.88 (dt, J=13.9, 7.4 Hz, 3H), 1.70-1.10 (m, 9H).

Example 300: 3-(((S)-10-Hydroxy-7-((R)-2-phenylpiperazine-1-carbonyl)-7-azaspiro[4.5]decan-10-yl)methyl)-6-methylpyrimidin-4(3H)-one

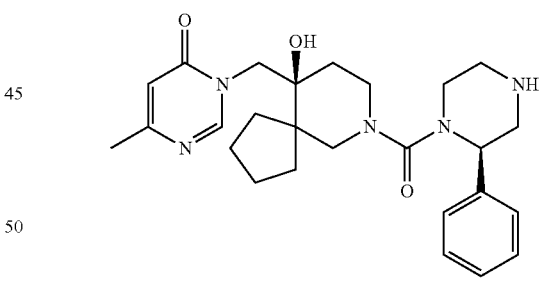

Step 1: tert-Butyl (R)-4-((S)-10-hydroxy-10-((4-methyl-6-oxopyrimidin-1(6H)-yl)methyl)-7-azaspiro[4.5]decane-7-carbonyl)-3-phenylpiperazine-1-carboxylate: To a pre-degassed suspension of tert-butyl (R)-4-((S)-10-((4-chloro-6-oxopyrimidin-1(6H)-yl)methyl)-10-hydroxy-7-azaspiro[4.5]decane-7-carbonyl)-3-phenylpiperazine-1-carboxylate (13 mg, 0.022 mmol), Pd$_2$(dba)$_3$ (1.0 mg, 0.0011 mmol) and XPhos (1.1 mg, 0.0022 mmol) in THF (2 mL) under nitrogen in a capped 10 mL vial was added bis(trimethylaluminum)-1,4-diazabicyclo[2.2.2]octane adduct (DABAL-Me$_3$) (4.6 mg, 0.018 mmol) suspension in THF (1 mL). The reaction mixture was then heated at 65° C. (conventional) for 2 h. Additional DABAL-Me$_3$ (9 mg, 0.035 mmol) in THF (1 mL) and Pd$_2$(dba)$_3$ (5.0 mg, 0.055 mmol) in THF (0.3 mL)

were added. The temperature was increased to 85° C. After 4 h, the reaction mixture cooled, dry loaded onto silica and purified by flash chromatography (2-100% EtOAc in cyclohexane; then 0-15% MeOH in EtOAc) to give the title compound (8 mg, 64%) as a clear glass. LCMS (Method A): $R_T$=1.38 min, m/z=566 [M+H]⁺.

Step 2: 3-(((S)-10-Hydroxy-7-((R)-2-phenylpiperazine-1-carbonyl)-7-azaspiro[4.5]decan-10-yl)methyl)-6-methylpyrimidin-4(3H)-one: Prepared according to General Procedure 3 using tert-butyl (R)-4-((S)-10-hydroxy-10-((4-methyl-6-oxopyrimidin-1(6H)-yl)methyl)-7-azaspiro[4.5]decane-7-carbonyl)-3-phenylpiperazine-1-carboxylate (8 mg, 0.014 mmol), TFA (1.0 mL) and DCM (2.0 mL), and stirred at rt for 30 min to give the title compound (5 mg, 76%) as a white solid. LCMS (Method A): $R_T$=0.59 min, m/z=466 [M+H]⁺. ¹H NMR (500 MHz, DMSO-d₆): δ 8.26 (s, 1H), 7.33-7.24 (m, 4H), 7.23-7.14 (m, 1H), 6.25 (s, 1H), 4.74 (s, 1H), 4.48 (d, J=13.6 Hz, 1H), 4.31 (s, 1H), 3.54 (d, J=13.6 Hz, 2H), 3.24-3.13 (m, 2H), 3.07-2.88 (m, 5H), 2.81-2.74 (m, 2H), 2.19 (s, 3H), 1.87-1.79 (m, 1H), 1.64-1.42 (m, 5H), 1.39-1.26 (m, 2H), 1.17-1.10 (m, 1H), 1.08-1.00 (m, 1H).

Example 301: (S)-N-(2,3-Difluorobenzyl)-10-hydroxy-10-((6-oxo-4-phenylpyrimidin-1(6H)-yl)methyl)-7-azaspiro[4.5]decane-7-carboxamide

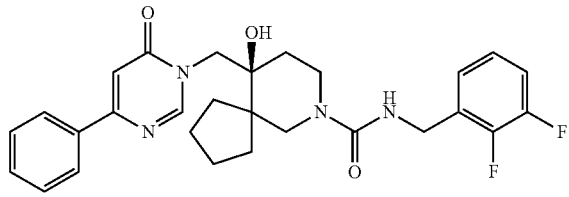 [SMILES: O=C(NCc1cccc(F)c1F)N1CC[C@@](O)(Cn2cnc(-c3ccccc3)cc2=O)C2(CCCC2)C1]

A solution of 2,3-difluorobenzylamine (9.5 mg, 0.0663 mmol) in DCM (0.4 mL) was added to a mixture of triphosgene (6.6 mg, 0.0221 mmol) and pyridine (11 µL, 0.133 mmol) in DCM (0.4 mL) at 0° C. After 5 min, the ice bath was removed and (S)-3-((10-hydroxy-7-azaspiro[4.5]decan-10-yl)methyl)-6-phenylpyrimidin-4(3H)-one (15 mg, 0.0442 mmol) and DIPEA (15 µL, 0.0884 mmol) were added. The reaction was stirred at rt for 19 h before saturated NaHCO₃(aq) (8 mL) was added and the resulting mixture was extracted with DCM (3×7 mL) using a phase separator. The combined organic phases were concentrated under reduced pressure and the residue was purified by flash chromatography three times (0-6% MeOH in DCM; followed by 0-100% EtOAc in cyclohexane; followed by 0-6% MeOH in DCM) to give the title compound (16.4 mg, 72%) as an off-white solid after lyophilisation. LCMS (Method A): $R_T$=1.37 min, m/z=509 [M+H]⁺. ¹H NMR (500 MHz, DMSO-d₆): δ 8.47 (s, 1H), 8.13-8.02 (m, 2H), 7.58-7.42 (m, 3H), 7.30-7.24 (m, 1H), 7.19-7.13 (m, 1H), 7.13-7.09 (m, 1H), 7.02 (t, J=5.8 Hz, 1H), 6.98 (s, 1H), 4.79 (s, 1H), 4.59 (d, J=13.6 Hz, 1H), 4.30 (d, J=5.5 Hz, 2H), 3.62 (d, J=13.6 Hz, 1H), 3.58-3.49 (m, 1H), 3.28-3.13 (m, 3H), 1.94-1.86 (m, 1H), 1.72-1.57 (m, 4H), 1.57-1.49 (m, 1H), 1.44-1.33 (m, 2H), 1.26-1.13 (m, 2H).

Example 302: (S)-N-(2,6-Difluorobenzyl)-10-hydroxy-10-((6-oxo-4-phenylpyrimidin-1(6H)-yl)methyl)-7-azaspiro[4.5]decane-7-carboxamide

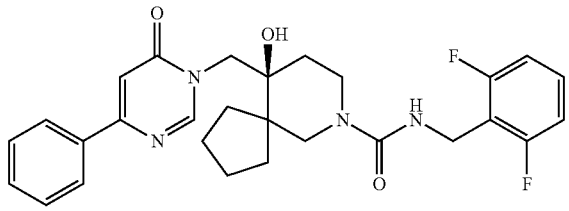 [SMILES: O=C(NCc1c(F)cccc1F)N1CC[C@@](O)(Cn2cnc(-c3ccccc3)cc2=O)C2(CCCC2)C1]

A solution of 2,6-difluorobenzylamine (9.5 mg, 0.0663 mmol) in DCM (0.4 mL) was added to a mixture of triphosgene (6.6 mg, 0.0221 mmol) and pyridine (11 µL, 0.133 mmol) in DCM (0.4 mL) at 0° C. After 5 min, the ice bath was removed and (S)-3-((10-hydroxy-7-azaspiro[4.5]decan-10-yl)methyl)-6-phenylpyrimidin-4(3H)-one (15 mg, 0.0442 mmol) and DIPEA (15 µL, 0.0884 mmol) were added. The reaction was stirred at rt for 3 days before saturated NaHCO₃(aq) (8 mL) was added and the resulting mixture was extracted with DCM (3×7 mL) using a phase separator. The combined organic phases were concentrated under reduced pressure and the residue was purified by flash chromatography twice (0-100% EtOAc in cyclohexane; followed by 0-6% MeOH in DCM) to give the title compound (15.4 mg, 67%) as a very light beige solid after lyophilisation. LCMS (Method A): $R_T$=1.34 min, m/z=509 [M+H]⁺. ¹H NMR (500 MHz, DMSO-d₆): δ 8.45 (s, 1H), 8.11-8.03 (m, 2H), 7.55-7.43 (m, 3H), 7.37-7.30 (m, 1H), 7.07-6.99 (m, 2H), 6.97 (s, 1H), 6.76 (t, J=5.2 Hz, 1H), 4.75 (s, 1H), 4.56 (d, J=13.6 Hz, 1H), 4.27 (d, J=5.0 Hz, 2H), 3.60 (d, J=13.6 Hz, 1H), 3.52-3.45 (m, 1H), 3.24-3.09 (m, 3H), 1.90-1.83 (m, 1H), 1.66-1.54 (m, 4H), 1.53-1.46 (m, 1H), 1.40-1.28 (m, 2H), 1.20-1.09 (m, 2H).

Example 303: (S)-N-(2,4-Difluorobenzyl)-10-hydroxy-10-((6-oxo-4-phenylpyrimidin-1(6H)-yl)methyl)-7-azaspiro[4.5]decane-7-carboxamide

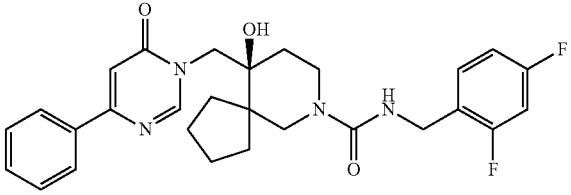 [SMILES: O=C(NCc1ccc(F)cc1F)N1CC[C@@](O)(Cn2cnc(-c3ccccc3)cc2=O)C2(CCCC2)C1]

A mixture of (S)-3-((10-hydroxy-7-azaspiro[4.5]decan-10-yl)methyl)-6-phenylpyrimidin-4(3H)-one (15 mg, 0.0442 mmol) and 2,4-difluoro-1-(isocyanatomethyl)benzene (11.2 mg, 0.0663 mmol) in DCM (0.44 mL) were stirred at rt for 15 min before the reaction mixture was purified directly by flash chromatography three times (0%; then 2%; then 4% MeOH in DCM (isocratic); followed by 0-100% EtOAc in cyclohexane; followed by 0-6% MeOH in DCM) to give the title compound (19.2 mg, 84%) as a colourless solid after lyophilisation. LCMS (Method A): $R_T$=1.38 min, m/z=509 [M+H]⁺. ¹H NMR (500 MHz, DMSO-d₆): δ 8.47 (s, 1H), 8.11-8.04 (m, 2H), 7.53-7.45 (m, 3H), 7.33 (td, J=8.6, 6.7 Hz, 1H), 7.15 (td, J=9.9, 2.6 Hz, 1H), 7.04 (td, J=8.5, 2.6 Hz, 1H), 7.00-6.93 (m, 2H), 4.79 (s, 1H), 4.59 (d, J=13.6 Hz, 1H), 4.23 (d, J=5.5 Hz, 2H), 3.62 (d, J=13.6 Hz, 1H), 3.59-3.50 (m, 1H), 3.28-3.13 (m, 3H), 1.95-1.86 (m, 1H), 1.71-1.58 (m, 4H), 1.57-1.49 (m, 1H), 1.44-1.32 (m, 2H), 1.23-1.14 (m, 2H).

Example 304: (S)-N-(3,4-Difluorobenzyl)-10-hydroxy-10-((6-oxo-4-phenylpyrimidin-1(6H)-yl)methyl)-7-azaspiro[4.5]decane-7-carboxamide

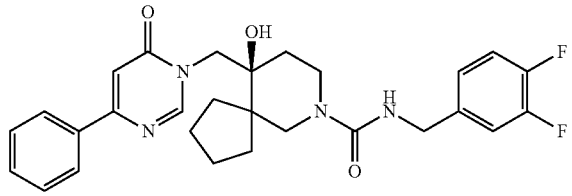 [SMILES: O=C(NCc1ccc(F)c(F)c1)N1CC[C@@](O)(Cn2cnc(-c3ccccc3)cc2=O)C2(CCCC2)C1]

A mixture of (S)-3-((10-hydroxy-7-azaspiro[4.5]decan-10-yl)methyl)-6-phenylpyrimidin-4(3H)-one (15 mg, 0.0442 mmol) and 1,2-difluoro-4-(isocyanatomethyl)benzene (11.2 mg, 0.0663 mmol) in DCM (0.44 mL) were stirred at rt for 40 min before the reaction mixture was purified directly by flash chromatography twice (0-100% EtOAc in cyclohexane; followed by 0-6% MeOH in DCM) to give the title compound (16.2 mg, 71%) as a colourless solid after lyophilisation. LCMS (Method A): $R_T$=1.38 min, m/z=509 [M+H]$^+$. $^1$H NMR (500 MHz, DMSO-d$_6$): δ 8.47 (s, 1H), 8.11-8.04 (m, 2H), 7.53-7.45 (m, 3H), 7.35 (dt, J=10.9, 8.5 Hz, 1H), 7.24 (ddd, J=11.9, 7.9, 2.1 Hz, 1H), 7.10-7.06 (m, 1H), 7.03 (t, J=5.9 Hz, 1H), 6.98 (s, 1H), 4.79 (s, 1H), 4.59 (d, J=13.6 Hz, 1H), 4.20 (d, J=5.6 Hz, 2H), 3.62 (d, J=13.6 Hz, 1H), 3.59-3.49 (m, 1H), 3.28-3.14 (m, 3H), 1.95-1.87 (m, 1H), 1.71-1.58 (m, 4H), 1.57-1.50 (m, 1H), 1.43-1.33 (m, 2H), 1.24-1.15 (m, 2H).

Example 305: 3-((9-Hydroxy-6-((R)-3-phenylmorpholine-4-carbonyl)-6-azaspiro[3.5]nonan-9-yl)methyl)-6-phenylpyrimidin-4(3H)-one

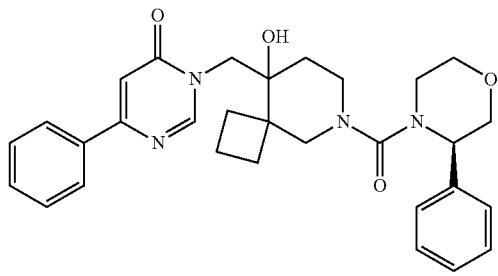 [SMILES: O=C(N1CCC(O)(Cn2cnc(-c3ccccc3)cc2=O)C2(CCC2)C1)N1CCOC[C@H]1c1ccccc1]

Step 1: tert-Butyl 9-((4-chloro-6-oxopyrimidin-1(6H)-yl)methyl)-9-hydroxy-6-azaspiro[3.5]nonane-6-carboxylate: Prepared according to General Procedure 2 using tert-butyl 1-oxa-9-azadispiro[2.0.3$^4$.4$^3$]undecane-9-carboxylate (500 mg, 1.97 mmol), 6-chloropyrimidin-4(3H)-one (258 mg, 1.97 mmol), potassium tert-butoxide (244 mg, 2.17 mmol) and DMSO (2 mL), stirred at 90° C. for 16 h under N$_2$ atmosphere to give the title compound (200 mg, 26%). LCMS (Method A): $R_T$=1.32 min, m/z=328 [M-butene+H]$^+$.

Step 2: tert-Butyl 9-hydroxy-9-((6-oxo-4-phenylpyrimidin-1(6H)-yl)methyl)-6-azaspiro[3.5]nonane-6-carboxylate: Prepared according to General Procedure 5 using tert-butyl 9-((4-chloro-6-oxopyrimidin-1(6H)-yl)methyl)-9-hydroxy-6-azaspiro[3.5]nonane-6-carboxylate (200 mg, 0.521 mmol), phenylboronic acid (127 mg, 1.04 mmol), sodium carbonate (166 mg, 1.56 mmol) and Pd(dppf)Cl$_2$·DCM (22.1 mg, 26.1 μmol) in 1,4-dioxane (3 mL) and water (1 mL). The reaction was heated under microwave irradiation at 120° C. for 1 h to give the title compound (213 mg, quantitative). LCMS (Method A): $R_T$=1.52 min, m/z=426 [M+H]$^+$.

Step 3: 3-((9-Hydroxy-6-azaspiro[3.5]nonan-9-yl)methyl)-6-phenylpyrimidin-4(3H)-one: Prepared according to General Procedure 3 using tert-butyl 9-hydroxy-9-((6-oxo-4-phenylpyrimidin-1(6H)-yl)methyl)-6-azaspiro[3.5]nonane-6-carboxylate (210 mg, 0.494 mmol), TFA (2 mL) and DCM (4 mL), stirred at rt for 1 h to give the title compound (150 mg, 93%). LCMS (Method B): $R_T$=0.65 min, m/z=326 [M+H]$^+$.

Step 4: 3-((9-Hydroxy-6-((R)-3-phenylmorpholine-4-carbonyl)-6-azaspiro[3.5]nonan-9-yl)methyl)-6-phenylpyrimidin-4(3H)-one: Prepared according to General Procedure 9 using 3-((9-hydroxy-6-azaspiro[3.5]nonan-9-yl)methyl)-6-phenylpyrimidin-4(3H)-one (20 mg, 61.5 μmol), (R)-3-phenylmorpholine-4-carbonyl chloride (16.6 mg, 73.8 mmol) and DIPEA (43 μL, 0.246 mmol) in DCM (2 mL), stirring at rt for 0.5 h to give the title compound (14.5 mg, 45%). LCMS (Method B): $R_T$=1.27 min, m/z=515 [M+H]$^+$. $^1$H NMR (500 MHz, DMSO-d$_6$): δ 8.47 (s, 1H), 8.10-8.05 (m, 2H), 7.50 (p, J=3.9 Hz, 3H), 7.37-7.27 (m, 4H), 7.23 (q, J=7.4 Hz, 1H), 6.96 (s, 1H), 4.96 (d, J=11.5 Hz, 1H), 4.56 (dd, J=13.7, 2.2 Hz, 1H), 4.44 (dt, J=47.0, 4.6 Hz, 1H), 3.87-3.33 (m, 8H), 3.28-3.02 (m, 3H), 2.27-2.12 (m, 2H), 1.81 (dtt, J=26.8, 18.4, 8.9 Hz, 1H), 1.68 (dqd, J=19.8, 10.2, 9.3, 3.3 Hz, 1H), 1.43-1.15 (m, 4H).

Example 306: 3-((9-Hydroxy-6-((R)-2-phenylpiperazine-1-carbonyl)-6-azaspiro[3.5]nonan-9-yl)methyl)-6-phenylpyrimidin-4(3H)-one

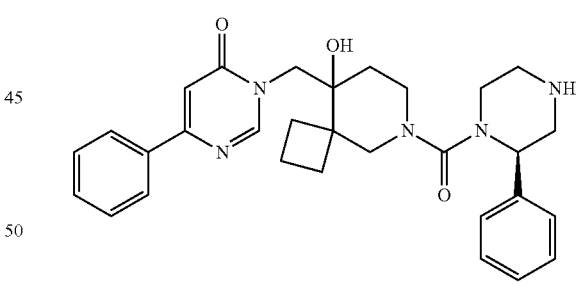

Step 1: tert-Butyl (3R)-4-(9-hydroxy-9-((6-oxo-4-phenylpyrimidin-1(6H)-yl)methyl)-6-azaspiro[3.5]nonane-6-carbonyl)-3-phenylpiperazine-1-carboxylate: Prepared according to General Procedure 9 using 3-((9-hydroxy-6-azaspiro[3.5]nonan-9-yl)methyl)-6-phenylpyrimidin-4(3H)-one (20 mg, 61.5 μmol), tert-butyl (R)-4-(chlorocarbonyl)-3-phenylpiperazine-1-carboxylate (24.0 mg, 73.8 μmol), DIPEA (43 μL, 0.246 mmol) and DCM (2 mL), stirring at rt for 30 min to give the title compound (27 mg, 71%). LCMS (Method B): $R_T$=1.53 min, m/z=558 [M-butene+H]$^+$.

Step 2: 3-((9-Hydroxy-6-((R)-2-phenylpiperazine-1-carbonyl)-6-azaspiro[3.5]nonan-9-yl)methyl)-6-phenylpyrimidin-4(3H)-one: Prepared according to General Procedure 3 using tert-butyl (3R)-4-(9-hydroxy-9-((6-oxo-4-phenylpyrimidin-1(6H)-yl)methyl)-6-azaspiro[3.5]nonane-6-carbonyl)-3-phenylpiperazine-1-carboxylate (27 mg, 44.0 µmol), TFA (0.5 mL) and DCM (1 mL), stirred at rt for 1 h to give the title compound (16 mg, 70%). LCMS (Method B): $R_T$=0.83 min, m/z=514 [M+H]⁺. ¹H NMR (500 MHz, DMSO-d₆): δ 8.47 (s, 1H), 8.10-8.04 (m, 2H), 7.53-7.46 (m, 3H), 7.37-7.15 (m, 5H), 6.96 (s, 1H), 4.94 (d, J=7.7 Hz, 1H), 4.55 (dd, J=13.7, 3.6 Hz, 1H), 4.35 (dt, J=56.6, 5.0 Hz, 1H), 3.79-3.20 (m, 5H (signal obscured by HDO)), 3.14-2.72 (m, 6H), 2.19 (dt, J=26.7, 9.2 Hz, 2H), 1.89-1.59 (m, 2H), 1.42-1.14 (m, 4H). NH signal not observed.

Example 307: (S)-N-((3,3-Difluorocyclobutyl)methyl)-10-hydroxy-10-((6-oxo-4-phenylpyrimidin-1(6H)-yl)methyl)-7-azaspiro[4.5]decane-7-carboxamide

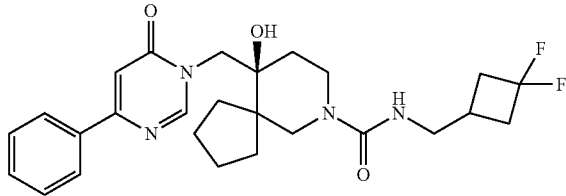 [SMILES: O=C(NCC1CC(F)(F)C1)N1CC[C@@](O)(Cn2cnc(-c3ccccc3)cc2=O)C2(CCCC2)C1]

To a solution of triphosgene (6.6 mg, 0.0221 mmol) and pyridine (14 µL, 0.177 mmol) in DCM (0.44 mL) at 0° C. was added (3,3-difluorocyclobutyl)methanamine hydrochloride (10.5 mg, 0.0663 mmol) after 1 h the reaction was allowed to warm to rt and (S)-3-((10-hydroxy-7-azaspiro[4.5]decan-10-yl)methyl)-6-phenylpyrimidin-4(3H)-one (15 mg, 0.0442 mmol) and DIPEA (15 µL, 0.0884 mmol) were added. The reaction was stirred at rt for 3 h before saturated NaHCO₃(aq) (8 mL) was added and the resulting mixture was extracted with DCM (3×7 mL) using a phase separator. The combined organic phases were concentrated under reduced pressure and the residue was purified by flash chromatography twice (0-100% EtOAc in cyclohexane; followed by 0-6% MeOH in DCM) to give the title compound (8 mg, 37%) as a colourless solid after lyophilisation. LCMS (Method A): $R_T$=1.28 min, m/z=487 [M+H]⁺. ¹H NMR (500 MHz, DMSO-d₆): δ 8.46 (s, 1H), 8.14-8.01 (m, 2H), 7.59-7.40 (m, 3H), 6.98 (s, 1H), 6.55 (t, J=5.7 Hz, 1H), 4.77 (s, 1H), 4.58 (d, J=13.6 Hz, 1H), 3.61 (d, J=13.6 Hz, 1H), 3.51 (dt, J=11.9, 5.1 Hz, 1H), 3.28-3.18 (m, 2H), 3.18-3.01 (m, 3H), 2.59-2.52 (m, 2H (signal overlaps with DMSO)), 2.35-2.19 (m, 3H), 1.93-1.86 (m, 1H), 1.73-1.56 (m, 4H), 1.57-1.47 (m, 1H), 1.43-1.30 (m, 2H), 1.22-1.12 (m, 2H).

Example 308: (S)-N-(1,1,1,3,3,3-Hexafluoropropan-2-yl)-10-hydroxy-10-((6-oxo-4-phenylpyrimidin-1(6H)-yl)methyl)-7-azaspiro[4.5]decane-7-carboxamide

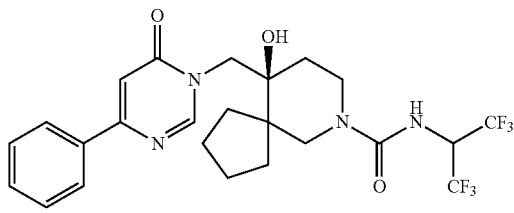 [SMILES: O=C(NC(C(F)(F)F)C(F)(F)F)N1CC[C@@](O)(Cn2cnc(-c3ccccc3)cc2=O)C2(CCCC2)C1]

To a solution of triphosgene (6.6 mg, 0.0221 mmol) in DCM (0.88 mL) at 0° C. was added pyridine (18 µL, 0.221 mmol). After stirring for 20 min, (S)-3-((10-hydroxy-7-azaspiro[4.5]decan-10-yl)methyl)-6-phenylpyrimidin-4(3H)-one (15 mg, 0.0442 mmol) was added. After stirring for 40 min at 0° C., a solution of 1,1,1,3,3,3-hexafluoroisopropylamine (14.8 mg, 0.0884 mmol) in DCM (0.44 mL) was added and the reaction was allowed to warm to rt. The reaction was stirred at rt for 30 min before DIPEA (23 µL, 0.133 mmol) was added. The reaction was stirred at rt for 15 min before 1,1,1,3,3,3-hexafluoroisopropylamine (40 mg, 0.239 mmol) was added and the reaction was stirred at rt for 5 days before saturated NaHCO₃(aq) (8 mL) was added and the resulting mixture was extracted with DCM (3×7 mL) using a phase separator. The combined organic phases were concentrated under reduced pressure and the residue was purified by flash chromatography twice (0-100% EtOAc in cyclohexane; then 0-10% MeOH in EtOAc; followed by 0%; then 20%; then 30% EtOAc in cyclohexane (isocratic)) to give the title compound (2.4 mg, 10%) as a colourless solid after lyophilisation. LCMS (Method B): $R_T$=1.36 min, m/z=533 [M+H]⁺. ¹H NMR (500 MHz, DMSO-d₆): δ 8.47 (s, 1H), 8.14-8.03 (m, 2H), 7.68 (d, J=9.8 Hz, 1H), 7.57-7.42 (m, 3H), 6.99 (s, 1H), 5.73-5.63 (m, 1H), 4.86 (s, 1H), 4.59 (d, J=13.6 Hz, 1H), 3.71-3.60 (m, 2H), 3.40-3.29 (m, 3H), 1.96-1.88 (m, 1H), 1.71-1.50 (m, 5H), 1.43-1.33 (m, 2H), 1.22-1.10 (m, 2H).

Example 309: (S)-10-Hydroxy-10-((2-oxo-4-phenylpyridin-1(2H)-yl)methyl)-N-((R)-2,2,2-trifluoro-1-phenylethyl)-7-azaspiro[4.5]decane-7-carboxamide

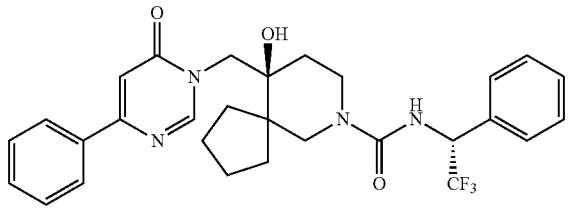 [SMILES: O=C(N[C@H](c1ccccc1)C(F)(F)F)N1CC[C@@](O)(Cn2cnc(-c3ccccc3)cc2=O)C2(CCCC2)C1]

A solution of (R)-2,2,2-trifluoro-1-phenylethan-1-amine (11.6 mg, 0.0665 mmol) in DCM (0.44 mL) was added to a mixture of triphosgene (6.6 mg, 0.0222 mmol) and pyridine (11 µL, 0.133 mmol) in DCM (0.44 mL) at 0° C. After 20 min, (S)-1-((10-hydroxy-7-azaspiro[4.5]decan-10-yl)methyl)-4-phenylpyridin-2(1H)-one (15 mg, 0.0443 mmol) and DIPEA (15 µL, 0.0886 mmol) were added, and the reaction was allowed to warm to rt. The reaction was stirred at rt for 1 h before saturated NaHCO₃(aq) (15 mL) was added and the resulting mixture was extracted with DCM (3×10 mL) using a phase separator. The combined organic phases were concentrated under reduced pressure and the residue was purified by flash chromatography (0%; then 1%; then 2%; then 4% MeOH in DCM (isocratic)) to give the title compound (22.6 mg, 93%) as a very pale yellow solid after lyophilisation. LCMS (Method A): $R_T$=1.55 min, m/z=540 [M+H]⁺. ¹H NMR (500 MHz, DMSO-d₆): δ 7.79 (d, J=7.1 Hz, 1H), 7.76-7.71 (m, 2H), 7.59-7.54 (m, 2H), 7.53-7.44 (m, 3H), 7.43-7.34 (m, 3H), 7.29 (d, J=9.6 Hz, 1H), 6.73 (d, J=2.1 Hz, 1H), 6.64 (dd, J=7.1, 2.1 Hz, 1H), 5.70 (p, J=9.2 Hz, 1H), 5.00 (s, 1H), 4.53 (d, J=13.5 Hz, 1H), 3.75 (d, J=13.6 Hz, 1H), 3.66 (dt, J=11.5, 5.1 Hz, 1H), 3.36-3.30 (m, 3H), 1.88 (dt, J=13.7, 7.2 Hz, 1H), 1.68-1.48 (m, 5H), 1.40 (ddd, J=13.2, 8.8, 4.2 Hz, 1H), 1.35-1.29 (m, 1H), 1.21-1.12 (m, 2H).

Example 310: 3-(((S)-4-Hydroxy-3,3-dimethyl-1-((R)-3-phenylmorpholine-4-carbonyl)piperidin-4-yl)methyl)-6-phenylpyrimidin-4(3H)-one

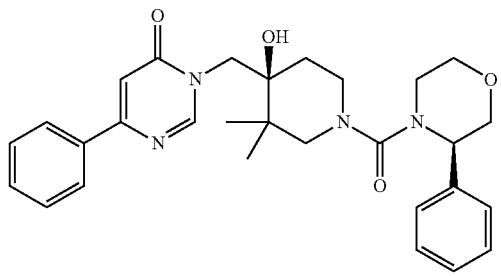

Step 1: tert-Butyl 4-((4-chloro-6-oxopyrimidin-1(6H)-yl)methyl)-4-hydroxy-3,3-dimethylpiperidine-1-carboxylate: Prepared according to General Procedure 2 using 6-chloropyrimidin-4(3H)-one (1.60 g, 12.2 mmol), Epoxide 1 (2.95 g, 12.2 mmol) and potassium tert-butoxide (1.51 g, 13.4 mmol) in NMP (12.2 mL) at 110° C. for 16 h to give the title compound (800 mg, 17%) as an off-white foam. LCMS (Method A): $R_T$=1.27 min, m/z=316, 318 [M-butene+H]$^+$. $^1$H NMR (500 MHz, DMSO-d$_6$): δ 8.30 (s, 1H), 6.61 (s, 1H), 4.80 (s, 1H), 4.33 (d, J=13.4 Hz, 1H), 3.71-3.59 (m, 2H), 3.26-3.17 (m, 1H), 3.12-2.85 (m, 2H), 1.58-1.49 (m, 1H), 1.39 (s, 9H), 1.14-1.03 (m, 1H), 0.97 (s, 3H), 0.93 (s, 3H).

Step 2: tert-Butyl (S)-4-((4-chloro-6-oxopyrimidin-1(6H)-yl)methyl)-4-hydroxy-3,3-dimethylpiperidine-1-carboxylate: tert-Butyl 4-((4-chloro-6-oxopyrimidin-1(6H)-yl)methyl)-4-hydroxy-3,3-dimethylpiperidine-1-carboxylate (1.05 g) was resolved into the single stereoisomers by chiral HPLC using a Lux A1 (21.2 mm×250 mm, 5 μm) column with isocratic solvent conditions: MeOH. The first eluted material afforded tert-butyl (S)-4-((4-chloro-6-oxopyrimidin-1(6H)-yl)methyl)-4-hydroxy-3,3-dimethylpiperidine-1-carboxylate (446 mg, 42% recovery). Chiral purity (Method E): $R_T$=2.20 min, 100% ee. The second eluted material afforded tert-butyl (R)-4-((4-chloro-6-oxopyrimidin-1(6H)-yl)methyl)-4-hydroxy-3,3-dimethylpiperidine-1-carboxylate (496 mg, 47% recovery). Chiral purity (Method E): $R_T$=3.26 min, 99.4% ee.

Step 3: tert-Butyl (S)-4-hydroxy-3,3-dimethyl-4-((6-oxo-4-phenylpyrimidin-1(6H)-yl)methyl)piperidine-1-carboxylate: Prepared according to General Procedure 5 using tert-butyl (S)-4-((4-chloro-6-oxopyrimidin-1(6H)-yl)methyl)-4-hydroxy-3,3-dimethylpiperidine-1-carboxylate (50 mg, 0.135 mmol), phenylboronic acid (32.8 mg, 0.269 mmol), sodium carbonate (42.7 mg, 0.403 mmol) and Pd(dppf)Cl$_2$·DCM (5.7 mg, 6.7 μmol) in 1,4-dioxane (0.9 mL) and water (0.3 mL). The reaction was heated under microwave irradiation at 120° C. for 1 h to give the title compound (55 mg, quantitative). LCMS (Method A): $R_T$=1.49 min, m/z=414 [M+H]$^+$.

Step 4: (S)-3-((4-Hydroxy-3,3-dimethylpiperidin-4-yl)methyl)-6-phenylpyrimidin-4(3H)-one: Prepared according to General Procedure 3 using tert-butyl (S)-4-hydroxy-3,3-dimethyl-4-((6-oxo-4-phenylpyrimidin-1(6H)-yl)methyl)piperidine-1-carboxylate (55 mg, 0.133 mmol), TFA (0.5 mL) and DCM (1 mL), stirred at rt for 2 h to give the title compound (40 mg, 96%). LCMS (Method A): $R_T$=0.57 min, m/z=314 [M+H]$^+$.

Step 5: 3-(((S)-4-Hydroxy-3,3-dimethyl-1-((R)-3-phenylmorpholine-4-carbonyl)piperidin-4-yl)methyl)-6-phenylpyrimidin-4(3H)-one: Prepared according to General Procedure 9 using (S)-3-((4-hydroxy-3,3-dimethylpiperidin-4-yl)methyl)-6-phenylpyrimidin-4(3H)-one (17 mg, 54.2 μmol), (R)-3-phenylmorpholine-4-carbonyl chloride (14.7 mg, 65.1 μmol) and DIPEA (38 μL, 0.217 mmol) in DCM (2 mL), stirring at rt for 0.5 h to give the title compound (16 mg, 58%). LCMS (Method A): $R_T$=1.34 min, m/z=503 [M+H]$^+$. $^1$H NMR (500 MHz, DMSO-d$_6$): δ 8.43 (s, 1H), 8.08 (dd, J=6.8, 3.0 Hz, 2H), 7.50 (p, J=3.8 Hz, 3H), 7.36-7.27 (m, 4H), 7.25-7.19 (m, 1H), 6.97 (s, 1H), 4.82 (s, 1H), 4.46 (dd, J=5.7, 3.8 Hz, 1H), 4.40 (d, J=13.5 Hz, 1H), 3.84-3.57 (m, 6H), 3.18-2.96 (m, 5H), 1.71 (ddd, J=16.5, 12.3, 4.7 Hz, 1H), 1.14 (dt, J=14.2, 3.5 Hz, 1H), 0.97 (s, 3H), 0.94 (s, 3H).

Example 311: (S)-N-((1-Fluorocyclopropyl)methyl)-10-hydroxy-10-((6-oxo-4-phenylpyrimidin-1(6H)-yl)methyl)-7-azaspiro[4.5]decane-7-carboxamide

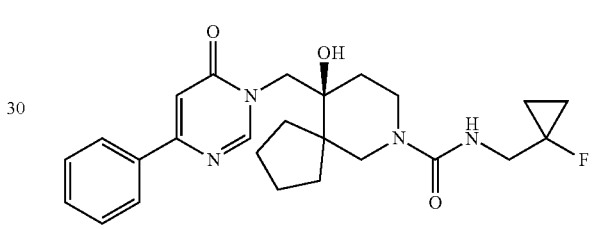

Prepared according to General Procedure 9 using (S)-10-hydroxy-10-((6-oxo-4-phenylpyrimidin-1(6H)-yl)methyl)-7-azaspiro[4.5]decane-7-carbonyl chloride (10 mg, 0.0249 mmol), (1-fluorocyclopropyl)methanamine hydrochloride (4.7 mg, 0.0373 mmol) and DIPEA (13 μL, 0.149 mmol) in DMF (0.5 mL) for 3 days to give the title compound (6.7 mg, 56%) as a colourless solid after lyophilisation. LCMS (Method A): $R_T$=1.20 min, m/z=455 [M+H]$^+$. $^1$H NMR (500 MHz, DMSO-d$_6$): δ 8.47 (s, 1H), 8.12-8.04 (m, 2H), 7.55-7.44 (m, 3H), 6.98 (s, 1H), 6.68 (t, J=5.9 Hz, 1H), 4.77 (s, 1H), 4.59 (d, J=13.6 Hz, 1H), 3.62 (d, J=13.6 Hz, 1H), 3.53 (dt, J=12.0, 5.0 Hz, 1H), 3.47 (dd, J=19.8, 5.7 Hz, 2H), 3.27-3.14 (m, 3H), 1.93-1.86 (m, 1H), 1.70-1.58 (m, 4H), 1.57-1.49 (m, 1H), 1.44-1.31 (m, 2H), 1.23-1.13 (m, 2H), 0.93-0.85 (m, 2H), 0.74-0.66 (m, 2H).

Example 312: (S)-N-((1-Fluorocyclobutyl)methyl)-10-hydroxy-10-((6-oxo-4-phenylpyrimidin-1(6H)-yl)methyl)-7-azaspiro[4.5]decane-7-carboxamide

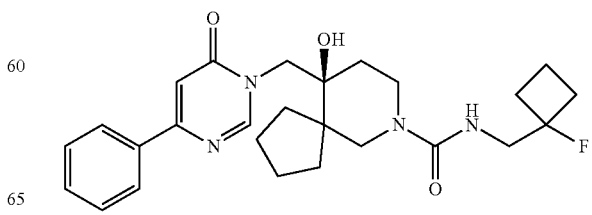

Prepared according to General Procedure 9 using (S)-10-hydroxy-10-(((6-oxo-4-phenylpyrimidin-1(6H)-yl)methyl)-7-azaspiro[4.5]decane-7-carbonyl chloride (10 mg, 0.0249 mmol), (1-fluorocyclobutyl)methanamine hydrochloride (5.2 mg, 0.0373 mmol) and DIPEA (13 µL, 0.149 mmol) in DMF (0.5 mL) for 3 days to give the title compound (9.9 mg, 83%) as a colourless solid after lyophilisation. LCMS (Method A): $R_T$=1.28 min, m/z=469 [M+H]$^+$. $^1$H NMR (500 MHz, DMSO-d$_6$): δ 8.46 (d, J=0.9 Hz, 1H), 8.12-8.04 (m, 2H), 7.54-7.44 (m, 3H), 6.98 (d, J=0.9 Hz, 1H), 6.57 (t, J=6.0 Hz, 1H), 4.77 (s, 1H), 4.59 (d, J=13.6 Hz, 1H), 3.61 (d, J=13.6 Hz, 1H), 3.55 (dt, J=11.8, 5.4 Hz, 1H), 3.37 (dd, J=23.1, 5.9 Hz, 2H), 3.28-3.15 (m, 3H), 2.20-2.03 (m, 4H), 1.93-1.86 (m, 1H), 1.77-1.58 (m, 5H), 1.57-1.49 (m, 1H), 1.46-1.38 (m, 2H), 1.38-1.31 (m, 1H), 1.23-1.14 (m, 2H).

Example 313: (S)-N-(Cyclopropylmethyl)-10-hydroxy-N-methyl-10-(((6-oxo-4-phenylpyrimidin-1(6H)-yl)methyl)-7-azaspiro[4.5]decane-7-carboxamide

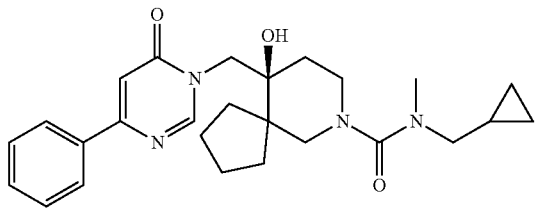 [SMILES: CN(CC1CC1)C(=O)N1CC[C@@](O)(Cn2cnc(-c3ccccc3)cc2=O)C2(CCCC2)C1]

Prepared according to General Procedure 9 using (S)-10-hydroxy-10-(((6-oxo-4-phenylpyrimidin-1(6H)-yl)methyl)-7-azaspiro[4.5]decane-7-carbonyl chloride (10 mg, 0.0249 mmol), 1-cyclopropyl-N-methylmethanamine (3.2 mg, 0.0373 mmol) and DIPEA (13 µL, 0.149 mmol) in DMF (0.5 mL) for 3 days to give the title compound (10.7 mg, 94%) as an off-white solid after lyophilisation. LCMS (Method A): $R_T$=1.40 min, m/z=451 [M+H]$^+$. $^1$H NMR (500 MHz, DMSO-d$_6$): δ 8.47 (s, 1H), 8.13-8.02 (m, 2H), 7.55-7.44 (m, 3H), 6.98 (s, 1H), 4.79 (s, 1H), 4.60 (d, J=13.6 Hz, 1H), 3.62 (d, J=13.6 Hz, 1H), 3.34-3.29 (m, 1H), 3.17-3.04 (m, 2H), 2.98-2.89 (m, 3H), 2.78 (s, 3H), 1.97-1.87 (m, 1H), 1.72-1.50 (m, 5H), 1.47-1.38 (m, 2H), 1.28-1.18 (m, 2H), 0.96-0.88 (m, 1H), 0.48-0.41 (m, 2H), 0.19-0.09 (m, 2H).

Example 314: 6-(2-Fluorophenyl)-3-(((S)-10-hydroxy-7-((R)-2-phenylpiperazine-1-carbonyl)-7-azaspiro[4.5]decan-10-yl)methyl)pyrimidin-4(3H)-one

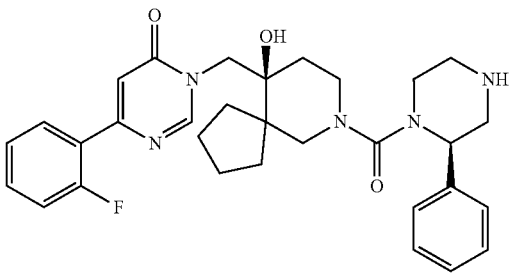 [SMILES: O=C(N1CC[C@@](O)(Cn2cnc(-c3ccccc3F)cc2=O)C2(CCCC2)C1)N1CCNC[C@H]1c1ccccc1]

Step 1: tert-Butyl (R)-4-((S)-10-((4-(2-fluorophenyl)-6-oxopyrimidin-1(6H)-yl)methyl)-10-hydroxy-7-azaspiro[4.5]decane-7-carbonyl)-3-phenylpiperazine-1-carboxylate: Prepared according to General Procedure 5 using tert-butyl (R)-4-((S)-10-((4-chloro-6-oxopyrimidin-1(6H)-yl)methyl)-10-hydroxy-7-azaspiro[4.5]decane-7-carbonyl)-3-phenylpiperazine-1-carboxylate (15 mg, 0.026 mmol), 2-fluorobenzeneboronic acid (7.2 mg, 0.051 mmol), Pd(dppf)Cl$_2$·DCM (1.1 mg, 0.0013 mmol) and Na$_2$CO$_3$ (8.0 mg, 0.077 mmol) in 1,4-dioxane (0.45 mL) and water (0.15 mL). The reaction mixture was heated using microwave irradiation at 120° C. for 30 min to give the title compound (12 mg, 73%) as clear glass. LCMS (Method B): $R_T$=1.58 min, m/z=646 [M+H]$^+$.

Step 2: 6-(2-Fluorophenyl)-3-(((S)-10-hydroxy-7-((R)-2-phenylpiperazine-1-carbonyl)-7-azaspiro[4.5]decan-10-yl)methyl)pyrimidin-4(3H)-one: Prepared according to General Procedure 3 using tert-butyl (R)-4-((S)-10-((4-(2-fluorophenyl)-6-oxopyrimidin-1(6H)-yl)methyl)-10-hydroxy-7-azaspiro[4.5]decane-7-carbonyl)-3-phenylpiperazine-1-carboxylate (12 mg, 0.019 mmol), TFA (1.0 mL) and DCM (2.0 mL), stirred at rt for 30 min to give the title compound (9 mg, 89%) as white solid. LCMS (Method B): $R_T$=0.89 min, m/z=546 [M+H]$^+$. $^1$H NMR (500 MHz, DMSO-d$_6$): δ 8.47 (s, 1H), 8.03 (t, J=7.8 Hz, 1H), 7.58-7.51 (m, 1H), 7.38-7.32 (m, 2H), 7.32-7.24 (m, 4H), 7.22-7.14 (m, 2H), 6.80 (s, 1H), 4.81 (s, 1H), 4.56 (d, J=13.5 Hz, 1H), 4.35-4.27 (m, 1H), 3.62 (d, J=13.5 Hz, 1H), 3.60-3.52 (m, 1H), 3.27-3.15 (m, 2H), 3.08-2.99 (m, 2H), 2.98-2.92 (m, 1H), 2.90 (d, J=5.5 Hz, 2H), 2.78 (t, J=5.3 Hz, 2H), 1.93-1.81 (m, 1H), 1.67-1.38 (m, 6H), 1.37-1.28 (m, 1H), 1.28-1.22 (m, 1H), 1.12-1.01 (m, 1H).

Example 315: 6-(3-Fluorophenyl)-3-(((S)-10-hydroxy-7-((R)-2-phenylpiperazine-1-carbonyl)-7-azaspiro[4.5]decan-10-yl)methyl)pyrimidin-4(3H)-one

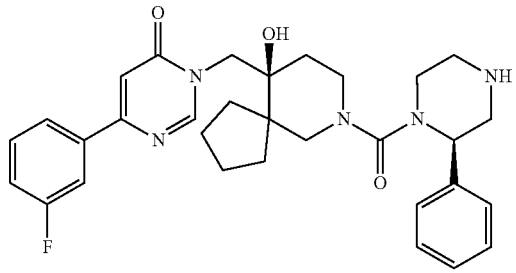 [SMILES: O=C(N1CC[C@@](O)(Cn2cnc(-c3cccc(F)c3)cc2=O)C2(CCCC2)C1)N1CCNC[C@H]1c1ccccc1]

Step 1: tert-Butyl (R)-4-((S)-10-((4-(3-fluorophenyl)-6-oxopyrimidin-1(6H)-yl)methyl)-10-hydroxy-7-azaspiro[4.5]decane-7-carbonyl)-3-phenylpiperazine-1-carboxylate: Prepared according to General Procedure 5 using tert-butyl (R)-4-((S)-10-((4-chloro-6-oxopyrimidin-1(6H)-yl)methyl)-10-hydroxy-7-azaspiro[4.5]decane-7-carbonyl)-3-phenylpiperazine-1-carboxylate (15 mg, 0.026 mmol), 3-fluorobenzeneboronic acid (7.2 mg, 0.051 mmol), Pd(dppf)Cl$_2$·DCM (1.1 mg, 0.0013 mmol) and Na$_2$CO$_3$ (8.0 mg, 0.077 mmol) in 1,4-dioxane (0.45 mL) and water (0.15 mL). The reaction mixture was heated using microwave irradiation at 120° C. for 30 min to give the title compound (12 mg, 73%) as clear glass. LCMS (Method B): $R_T$=1.60 min, m/z=646 [M+H]$^+$.

Step 2: 6-(3-Fluorophenyl)-3-(((S)-10-hydroxy-7-((R)-2-phenylpiperazine-1-carbonyl)-7-azaspiro[4.5]decan-10-yl)methyl)pyrimidin-4(3H)-one: Prepared according to General Procedure 3 using tert-butyl (R)-4-((S)-10-((4-(3-fluorophenyl)-6-oxopyrimidin-1(6H)-yl)methyl)-10-hydroxy-7-azaspiro[4.5]decane-7-carbonyl)-3-phenylpiperazine-1-carboxylate (12 mg, 0.019 mmol), TFA (1.0 mL) and DCM (2.0 mL), stirred at rt for 30 min to give the title compound (9 mg, 89%) as white solid. LCMS (Method B): $R_T$=0.91 min, m/z=546 [M+H]$^+$. $^1$H NMR (500 MHz, DMSO-$d_6$): δ 8.46 (s, 1H), 7.95 (d, J=7.8 Hz, 1H), 7.89 (d, J=10.5 Hz, 1H), 7.54 (q, J=7.4 Hz, 1H), 7.37-7.31 (m, 1H), 7.31-7.25 (m, 4H), 7.22-7.17 (m, 1H), 7.06 (s, 1H), 4.81 (s, 1H), 4.56 (d, J=13.6 Hz, 1H), 4.39-4.28 (m, 1H), 3.62 (d, J=13.5 Hz, 1H), 3.60-3.53 (m, 1H), 3.26-3.16 (m, 2H), 3.10-2.90 (m, 5H), 2.88-2.80 (m, 2H), 1.93-1.82 (m, 1H), 1.67-1.36 (m, 6H), 1.35-1.27 (m, 1H), 1.26-1.18 (m, 1H), 1.11-0.99 (m, 1H).

Example 316: 6-(4-Fluorophenyl)-3-(((S)-10-hydroxy-7-((R)-2-phenylpiperazine-1-carbonyl)-7-azaspiro[4.5]decan-10-yl)methyl)pyrimidin-4(3H)-one

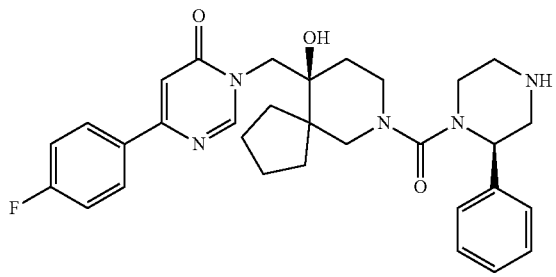 [SMILES: O=C(N1CC[C@@](O)(Cn2cnc(-c3ccc(F)cc3)cc2=O)C2(CCCC2)C1)N1CCNC[C@H]1c1ccccc1]

Step 1: tert-Butyl (R)-4-((S)-10-((4-(4-fluorophenyl)-6-oxopyrimidin-1(6H)-yl)methyl)-10-hydroxy-7-azaspiro[4.5]decane-7-carbonyl)-3-phenylpiperazine-1-carboxylate: Prepared according to General Procedure 5 using tert-butyl (R)-4-((S)-10-((4-chloro-6-oxopyrimidin-1(6H)-yl)methyl)-10-hydroxy-7-azaspiro[4.5]decane-7-carbonyl)-3-phenylpiperazine-1-carboxylate (15 mg, 0.026 mmol), 4-fluorobenzeneboronic acid (7.2 mg, 0.051 mmol), Pd(dppf)Cl$_2$·DCM (1.1 mg, 0.0013 mmol) and Na$_2$CO$_3$ (8.0 mg, 0.077 mmol) in 1,4-dioxane (0.45 mL) and water (0.15 mL). The reaction mixture was heated using microwave irradiation at 120° C. for 30 min to give the title compound (11 mg, 67%) as clear glass. LCMS (Method B): $R_T$=1.59 min, m/z=590 [M-butene+H]$^+$.

Step 2: 6-(4-Fluorophenyl)-3-(((S)-10-hydroxy-7-((R)-2-phenylpiperazine-1-carbonyl)-7-azaspiro[4.5]decan-10-yl)methyl)pyrimidin-4(3H)-one: Prepared according to General Procedure 3 using tert-butyl (R)-4-((S)-10-((4-(4-fluorophenyl)-6-oxopyrimidin-1(6H)-yl)methyl)-10-hydroxy-7-azaspiro[4.5]decane-7-carbonyl)-3-phenylpiperazine-1-carboxylate (11 mg, 0.017 mmol), TFA (1.0 mL) and DCM (2.0 mL), stirred at rt for 30 min to give the title compound (9 mg, 97%) as white solid. LCMS (Method B): $R_T$=0.92 min, m/z=546 [M+H]$^+$. $^1$H NMR (500 MHz, DMSO-$d_6$): δ 8.45 (s, 1H), 8.19-8.12 (m, 2H), 7.38-7.23 (m, 6H), 7.21-7.15 (m, 1H), 6.98 (s, 1H), 4.80 (s, 1H), 4.55 (d, J=13.6 Hz, 1H), 4.31 (t, J=5.5 Hz, 1H), 3.61 (d, J=13.6 Hz, 1H), 3.59-3.52 (m, 1H), 3.27-3.15 (m, 2H), 3.09-2.99 (m, 2H), 2.99-2.87 (m, 3H), 2.84-2.74 (m, 2H), 1.92-1.81 (m, 1H), 1.67-1.37 (m, 6H), 1.36-1.28 (m, 1H), 1.23-1.18 (m, 1H), 1.11-1.02 (m, 1H).

Example 317: 3-(((S)-10-Hydroxy-7-((R)-2-phenylpiperazine-1-carbonyl)-7-azaspiro[4.5]decan-10-yl)methyl)-6-(2-methoxyphenyl)pyrimidin-4(3H)-one

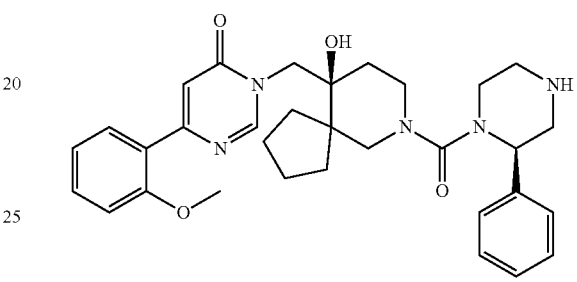

Step 1: tert-Butyl (R)-4-((S)-10-hydroxy-10-((4-(2-methoxyphenyl)-6-oxopyrimidin-1(6H)-yl)methyl)-7-azaspiro[4.5]decane-7-carbonyl)-3-phenylpiperazine-1-carboxylate: Prepared according to General Procedure 5 using tert-butyl (R)-4-((S)-10-((4-chloro-6-oxopyrimidin-1(6H)-yl)methyl)-10-hydroxy-7-azaspiro[4.5]decane-7-carbonyl)-3-phenylpiperazine-1-carboxylate (15 mg, 0.026 mmol), (2-methoxyphenyl)boronic acid (7.8 mg, 0.051 mmol), Pd(dppf)Cl$_2$·DCM (1.1 mg, 0.0013 mmol) and Na$_2$CO$_3$ (8.0 mg, 0.077 mmol) in 1,4-dioxane (0.45 mL) and water (0.15 mL). The reaction mixture was heated using microwave irradiation at 120° C. for 30 min to give the title compound (14 mg, 83%) as clear glass. LCMS (Method B): $R_T$=1.59 min, m/z=658 [M+H]$^+$.

Step 2: 3-(((S)-10-Hydroxy-7-((R)-2-phenylpiperazine-1-carbonyl)-7-azaspiro[4.5]decan-10-yl)methyl)-6-(2-methoxyphenyl)pyrimidin-4(3H)-one: Prepared according to General Procedure 3 using tert-butyl (R)-4-((S)-10-hydroxy-10-((4-(2-methoxyphenyl)-6-oxopyrimidin-1(6H)-yl)methyl)-7-azaspiro[4.5]decane-7-carbonyl)-3-phenylpiperazine-1-carboxylate (14 mg, 0.021 mmol), TFA (1.0 mL) and DCM (2.0 mL), stirred at rt for 30 min to give the title compound (10 mg, 84%) as white solid. LCMS (Method B): $R_T$=0.88 min, m/z=558 [M+H]$^+$. $^1$H NMR (500 MHz, DMSO-$d_6$): δ 8.42 (s, 1H), 8.02-7.96 (m, 1H), 7.49-7.42 (m, 1H), 7.33-7.24 (m, 4H), 7.22-7.15 (m, 2H), 7.07 (t, J=7.5 Hz, 1H), 7.02 (s, 1H), 4.81 (s, 1H), 4.53 (d, J=13.5 Hz, 1H), 4.36-4.27 (m, 1H), 3.89 (s, 3H), 3.61 (d, J=13.7 Hz, 1H), 3.59-3.54 (m, 1H), 3.27-3.16 (m, 2H), 3.09-2.89 (m, 5H), 2.83-2.76 (m, 2H), 1.94-1.81 (m, 1H), 1.67-1.37 (m, 6H), 1.38-1.26 (m, 1H), 1.24-1.20 (m, 1H), 1.10-1.01 (m, 1H).

Example 318: 6-(Dimethylamino)-3-(((S)-10-hydroxy-7-((R)-2-phenylpiperazine-1-carbonyl)-7-azaspiro[4.5]decan-10-yl)methyl)pyrimidin-4(3H)-one

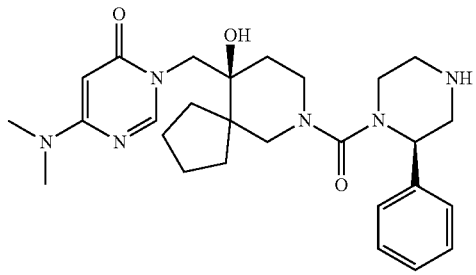 [SMILES: CN(C)c1cc(=O)n(C[C@]2(O)CCN(C(=O)N3CCNC[C@H]3c3ccccc3)CC23CCCC3)cn1]

Step 1: tert-Butyl (R)-4-((S)-10-((4-(dimethylamino)-6-oxopyrimidin-1(6H)-yl)methyl)-10-hydroxy-7-azaspiro[4.5]decane-7-carbonyl)-3-phenylpiperazine-1-carboxylate: A solution of tert-butyl (R)-4-((S)-10-((4-chloro-6-oxopyrimidin-1(6H)-yl)methyl)-10-hydroxy-7-azaspiro[4.5]decane-7-carbonyl)-3-phenylpiperazine-1-carboxylate (15.0 mg, 0.026 mmol) and 2 M dimethylamine in THF (0.19 mL, 0.38 mmol) in 1,4-dioxane (0.45 mL) was heated under microwave irradiation at 100° C. for 30 min. The volatiles were evaporated under reduced pressure and the residue was purified by flash chromatography (5-100% EtOAc in cyclohexane; then 0-20% MeOH in EtOAc) to give the title compound (14 mg, 92%) as clear glass. LCMS (Method B): $R_T$=1.38 min, m/z=595 [M+H]$^+$.

Step 2: 6-(Dimethylamino)-3-(((S)-10-hydroxy-7-((R)-2-phenylpiperazine-1-carbonyl)-7-azaspiro[4.5]decan-10-yl)methyl)pyrimidin-4(3H)-one: Prepared according to General Procedure 3 using tert-butyl (R)-4-((S)-10-((4-(dimethylamino)-6-oxopyrimidin-1(6H)-yl)methyl)-10-hydroxy-7-azaspiro[4.5]decane-7-carbonyl)-3-phenylpiperazine-1-carboxylate (14 mg, 0.021 mmol), TFA (1.0 mL) and DCM (2.0 mL), stirred at rt for 30 min to give the title compound (11 mg, 94%) as white solid. LCMS (Method B): $R_T$=0.75 min, m/z=495 [M+H]$^+$. $^1$H NMR (500 MHz, DMSO-d$_6$): δ 8.11 (s, 1H), 7.37-7.23 (m, 4H), 7.24-7.09 (m, 1H), 5.17 (s, 1H), 4.94 (s, 1H), 4.39-4.26 (m, 2H), 3.63-3.50 (m, 2H), 3.27-3.13 (m, 3H), 3.08-2.86 (m, 10H), 2.85-2.74 (m, 2H), 1.88-1.76 (m, 1H), 1.65-1.42 (m, 5H), 1.41-1.32 (m, 1H), 1.30-1.23 (m, 1H), 1.18-1.09 (m, 1H), 1.09-0.99 (m, 1H).

Example 319: 3-(((S)-10-Hydroxy-7-((R)-2-phenylpiperazine-1-carbonyl)-7-azaspiro[4.5]decan-10-yl)methyl)-6-(methylamino)pyrimidin-4(3H)-one

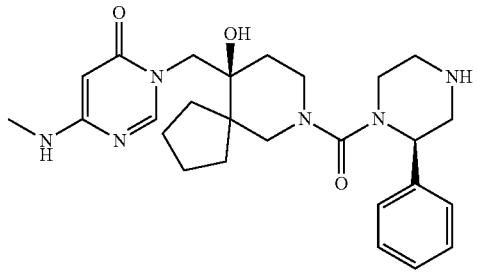 [SMILES: CNc1cc(=O)n(C[C@]2(O)CCN(C(=O)N3CCNC[C@H]3c3ccccc3)CC23CCCC3)cn1]

Step 1: tert-Butyl (R)-4-((S)-10-hydroxy-10-((4-(methylamino)-6-oxopyrimidin-1(6H)-yl)methyl)-7-azaspiro[4.5]decane-7-carbonyl)-3-phenylpiperazine-1-carboxylate: A suspension of tert-butyl (R)-4-((S)-10-((4-chloro-6-oxopyrimidin-1(6H)-yl)methyl)-10-hydroxy-7-azaspiro[4.5]decane-7-carbonyl)-3-phenylpiperazine-1-carboxylate (15 mg, 0.026 mmol) and 2 M methylamine in THF (0.19 mL, 0.38 mmol) in 1,4-dioxane (0.45 mL) was heated under microwave irradiation at 100° C. for 30 min. Additional methylamine in THF (0.2 mL) was added and the heating was continued for 1 h. Further 2 M methylamine in THF (0.2 mL) was added and the heating was continued for a further 1 h. The volatiles were evaporated under reduced pressure and the residue was purified by flash chromatography (5-100% EtOAc in cyclohexane; then 0-20% MeOH in EtOAc) to give the title compound (11 mg, 74%) as clear glass. LCMS (Method B): $R_T$=1.28 min, m/z=581 [M+H]$^+$.

Step 2: 3-(((S)-10-Hydroxy-7-((R)-2-phenylpiperazine-1-carbonyl)-7-azaspiro[4.5]decan-10-yl)methyl)-6-(methylamino)pyrimidin-4(3H)-one: Prepared according to General Procedure 3 using tert-butyl (R)-4-((S)-10-hydroxy-10-((4-(methylamino)-6-oxopyrimidin-1(6H)-yl)methyl)-7-azaspiro[4.5]decane-7-carbonyl)-3-phenylpiperazine-1-carboxylate (11 mg, 0.019 mmol), TFA (1.0 mL) and DCM (2.0 mL), stirred at rt for 30 min to give the title compound (7 mg, 77%) as white solid. LCMS (Method B): $R_T$=0.66 min, m/z=481 [M+H]$^+$. $^1$H NMR (500 MHz, DMSO-d$_6$) δ 8.03 (s, 1H), 7.33-7.25 (m, 4H), 7.22-7.15 (m, 1H), 6.98-6.91 (m, 1H), 4.99 (s, 1H), 4.95 (s, 1H), 4.39-4.23 (m, 2H), 3.62-3.49 (m, 2H), 3.28-3.13 (m, 3H), 3.09-2.98 (m, 2H), 2.97-2.88 (m, 3H), 2.85-2.76 (m, 2H), 2.70-2.64 (m, 2H), 1.86-1.77 (m, 1H), 1.63-1.41 (m, 5H), 1.40-1.33 (m, 1H), 1.32-1.24 (m, 1H), 1.18-1.09 (m, 1H), 1.08-0.98 (m, 1H).

Example 320: 3-(((S)-7-((R)-2-(3-Fluorophenyl)piperazine-1-carbonyl)-10-hydroxy-7-azaspiro[4.5]decan-10-yl)methyl)-6-phenylpyrimidin-4(3H)-one

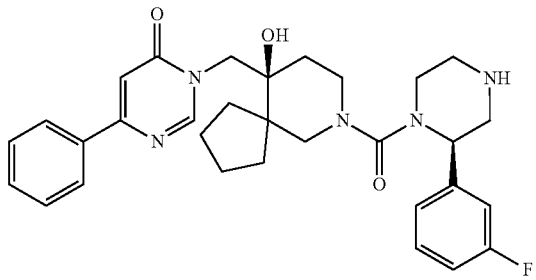 [SMILES: O=C(N1CC[C@@](O)(Cn2cnc(-c3ccccc3)cc2=O)C2(CCCC2)C1)N1CCNC[C@H]1c1cccc(F)c1]

Step 1: tert-Butyl (R)-3-(3-fluorophenyl)piperazine-1-carboxylate: tert-Butyl 3-(3-fluorophenyl)piperazine-1-carboxylate (1.00 g) [commercially available] was resolved into the single stereoisomers by chiral preparative HPLC using a Chiralpak AD-H (20 mm×250 mm, 5 μm) column with isocratic solvent conditions: 90:5:5 hexane/isopropyl alcohol/MeOH. The first eluted material afforded tert-butyl (S)-3-(3-fluorophenyl)piperazine-1-carboxylate (412 mg, 41% recovery) as a white solid. Chiral purity: $R_T$=10.14 min, 100% ee. [α]$_D^{20}$=−35.7 (c 0.5, MeOH). The second eluted material afforded tert-butyl (R)-3-(3-fluorophenyl)piperazine-1-carboxylate (429 mg, 43% recovery) as a white solid. Chiral purity: $R_T$=11.64 min, 99.7% ee. [α]$_D^{20}$=+32.0 (c 0.5, MeOH). LCMS (Method C): $R_T$=0.99 min, m/z=225 [M-butene+H]$^+$.

Step 2: tert-Butyl (R)-3-(3-fluorophenyl)-4-((S)-10-hydroxy-10-((6-oxo-4-phenylpyrimidin-1(6H)-yl)methyl)-7-azaspiro[4.5]decane-7-carbonyl)piperazine-1-carboxylate: To a solution of bis(trichloromethyl)carbonate (8 mg, 0.027 mmol) in DCM (1 mL) at −10° C. under nitrogen was added pyridine (0.013 mL, 0.16 mmol) followed by dropwise addition of tert-butyl (R)-3-(3-fluorophenyl)piperazine-1-carboxylate (15 mg, 0.054 mmol) in DCM (1 mL). The reaction mixture was warmed to rt and stirred for 2 h. Additional pyridine (0.05 mL) was added and the reaction was continued for 1 h. Further pyridine (0.05 mL) was added and the reaction was continued for a further 1 h. (S)-3-((10-Hydroxy-7-azaspiro[4.5]decan-10-yl)methyl)-6-phenylpyrimidin-4(3H)-one (10 mg, 0.030 mmol) in DCM (1 mL) was added then followed by DIPEA (0.026 mL, 0.147 mmol). The reaction mixture was stirred under nitrogen at rt for 3 days. The volatiles were evaporated then and the residue was purified by flash chromatography (5-100% EtOAc in cyclohexane). The product containing fractions were evaporated under reduced pressure yielding the title compound (14 mg, 74%) as a clear glass. LCMS (Method B): $R_T$=1.57 min, m/z=590 [M-butene+H]$^+$.

Step 3: 3-(((S)-7-((R)-2-(3-Fluorophenyl)piperazine-1-carbonyl)-10-hydroxy-7-azaspiro[4.5]decan-10-yl)methyl)-6-phenylpyrimidin-4(3H)-one: Prepared according to General Procedure 3 using tert-butyl (R)-3-(3-fluorophenyl)-4-((S)-10-hydroxy-10-((6-oxo-4-phenylpyrimidin-1(6H)-yl)methyl)-7-azaspiro[4.5]decane-7-carbonyl)piperazine-1-carboxylate (14 mg, 0.022 mmol), TFA (1.0 mL) and DCM (2.0 mL), stirred at rt for 30 min to give the title compound (6 mg, 51%) as white solid. LCMS (Method B): $R_T$=0.89 min, m/z=546 [M+H]$^+$. $^1$H NMR (500 MHz, DMSO-$d_6$): δ 8.46 (s, 1H), 8.12-8.04 (m, 2H), 7.53-7.46 (m, 3H), 7.31 (q, J=7.4 Hz, 1H), 7.15-7.06 (m, 2H), 7.03-6.97 (m, 2H), 4.83 (s, 1H), 4.56 (d, J=13.5 Hz, 1H), 4.36-4.28 (m, 1H), 3.67-3.52 (m, 2H), 3.28-3.17 (m, 2H), 3.09-2.99 (m, 2H), 2.99-2.85 (m, 3H), 2.81-2.72 (m, 2H), 1.94-1.83 (m, 1H), 1.68-1.38 (m, 6H), 1.35-1.29 (m, 1H), 1.23-1.17 (m, 1H), 1.11-1.03 (m, 1H).

Example 321: 3-((5-Hydroxy-2-((R)-2-phenylpiperazine-1-carbonyl)-9-oxa-2-azaspiro[5.5]undecan-5-yl)methyl)-6-phenylpyrimidin-4(3H)-one

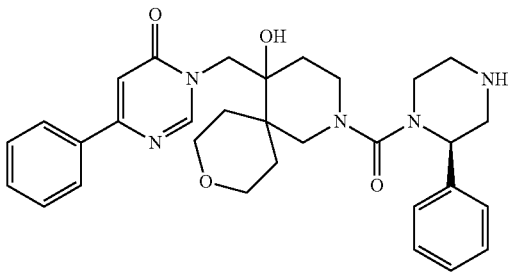 [SMILES: O=C(N1CCC(O)(Cn2cnc(-c3ccccc3)cc2=O)C2(CCOCC2)C1)N1CCNC[C@H]1c1ccccc1]

Step 1: tert-Butyl 5-oxo-9-oxa-2-azaspiro[5.5]undecane-2-carboxylate: To a solution of tert-butyl 4-oxopiperidine-1-carboxylate (3.98 g, 20.0 mmol) in toluene (40 mL) in a 3-necked 250 mL RBF fitted with a reflux condenser under $N_2$ at rt was added potassium tert-butoxide (4.94 g, 44.0 mmol) portionwise. After stirring for 1 h, bis(2-bromoethyl) ether (2.51 mL, 20.0 mmol) was added dropwise over 5 min and the reaction heated at reflux for 2 h. Upon cooling to rt, 1:1 saturated NH$_4$Cl$_{(aq)}$/water (40 mL) was added and the resulting mixture was extracted with EtOAc (3×40 mL). The combined organic phases were washed with brine (100 mL), passed through a phase separator, concentrated under reduced pressure and the residue was purified by flash chromatography (0-15% EtOAc in cyclohexane) to give the title compound (458 mg, 8.5%) as a pale yellow solid. LCMS (Method A): $R_T$=1.13 min, m/z=214 [M-butene+H]$^+$. $^1$H NMR (500 MHz, CDCl$_3$): δ 3.82-3.65 (m, 6H), 3.57 (s, 2H), 2.49 (t, J=6.4 Hz, 2H), 1.94 (dt, J=13.9, 5.1 Hz, 2H), 1.49 (s, 9H), 1.47-1.43 (m, 2H). $^{13}$C NMR (126 MHz, CDCl$_3$): δ 211.13, 154.71, 80.70, 63.96, 52.48 (br.), 48.00, 43.92 (br.), 38.13, 30.85, 28.52.

Step 2: tert-Butyl 1,7-dioxa-11-azadispiro[2.0.5$^4$.4$^3$]tridecane-11-carboxylate: Sodium hydride (60% dispersion in mineral oil, 98 mg, 2.45 mmol) was added to a stirred suspension of trimethylsulfonium iodide (500 mg, 2.45 mmol) in DMF (4 mL) at rt. After 1 h, a solution of tert-butyl 5-oxo-9-oxa-2-azaspiro[5.5]undecane-2-carboxylate (440 mg, 1.63 mmol) in DMF (4 mL) was added dropwise. After 16 h, the reaction was diluted with 1:1 water/saturated NH$_4$Cl$_{(aq)}$ (40 mL) and the mixture was extracted using EtOAc (3×20 mL). The combined organic phases were washed with water (20 mL) and brine (20 mL) before being passed through a phase separator. The resulting solution was concentrated under reduced pressure and the residue was purified by flash chromatography (0-30% EtOAc in cyclohexane) to give the title compound (355 mg, 76%) as colourless oil. LCMS (Method A): $R_T$=1.18 min, m/z=228 [M-butene+H]$^+$. $^1$H NMR (500 MHz, CDCl$_3$): δ 3.86-3.74 (m, 2H), 3.73-3.42 (m, 6H), 2.92 (d, J=4.1 Hz, 1H), 2.46 (d, J=4.2 Hz, 1H), 1.72-1.55 (m, 4H), 1.48 (s, 9H), 1.42-1.36 (m, 1H), 1.32-1.24 (m, 1H).

Step 3: tert-Butyl 5-hydroxy-5-((6-oxo-4-phenylpyrimidin-1(6H)-yl)methyl)-9-oxa-2-azaspiro[5.5]undecane-2-carboxylate: Prepared according to General Procedure 2 using 6-phenylpyrimidin-4(3H)-one (60.8 mg, 0.353 mmol), tert-butyl 1,7-dioxa-11-azadispiro[2.0.5$^4$.4$^3$]tridecane-11-carboxylate (100 mg, 0.353 mmol) and cesium carbonate (138 mg, 0.424 mmol) in DMF (1.8 mL) at 90° C. for 15 h 40 min to give the title compound (124 mg, 77%) as an off-white solid. This material was used in the next step without further purification. LCMS (Method A): $R_T$=1.34 min, m/z=456 [M+H]$^+$.

Step 4: 3-((5-Hydroxy-9-oxa-2-azaspiro[5.5]undecan-5-yl)methyl)-6-phenylpyrimidin-4(3H)-one: A solution of tert-butyl 5-hydroxy-5-((6-oxo-4-phenylpyrimidin-1(6H)-yl)methyl)-9-oxa-2-azaspiro[5.5]undecane-2-carboxylate (124 mg, 0.272 mmol) in TFA (1.35 mL) and DCM (2.7 mL) was stirred at rt for 15 min before the reaction mixture was loaded on to a 2 g SCX-2 cartridge that was pre-equilibrated with 1:1 DCM/MeOH. The cartridge was washed with 1:1 DCM/MeOH (60 mL) before the product was eluted with 1:1 DCM/7 M NH$_3$ in MeOH (30 mL). The basic eluents were concentrated under reduced pressure and the residue was purified by flash chromatography (Biotage KP-NH 28 g cartridge, 0-100% DCM in cyclohexane; then 0-20% MeOH in DCM) to give the title compound (72.9 mg, 75%) as a colourless solid. LCMS (Method A): $R_T$=0.49 min, m/z=356 [M+H]$^+$.

Step 5: tert-Butyl (3R)-4-(5-hydroxy-5-((6-oxo-4-phenylpyrimidin-1(6H)-yl)methyl)-9-oxa-2-azaspiro[5.5]undecane-2-carbonyl)-3-phenylpiperazine-1-carboxylate: To a solution of triphosgene (12.5 mg, 0.0422 mmol) in THF (0.85 mL) at 0° C. was added pyridine (34 µL, 0.422 mmol). After 30 min, a solution of tert-butyl (R)-3-phenylpiperazine-1-carboxylate (33.2 mg, 0.127 mmol) in THF (0.85 mL) was added and the reaction mixture was stirred at 0° C.

for a further 20 min before being allowed to warm to rt. After 2 h, 3-((5-hydroxy-9-oxa-2-azaspiro[5.5]undecan-5-yl)methyl)-6-phenylpyrimidin-4(3H)-one (30 mg, 0.0844 mmol) and DIPEA (44 µL, 0.253 mmol) were added. The reaction was stirred at rt for 16 h before saturated NaHCO$_{3(aq)}$ (15 mL) was added and the resulting mixture was extracted with DCM (3×10 mL) using a phase separator. The combined organic phases were concentrated under reduced pressure and the residue was purified by flash chromatography (0-100% EtOAc in cyclohexane; then 0-10% MeOH in EtOAc) to give the title compound (45 mg, 82%) as a yellow solid. LCMS (Method A): R$_T$=1.51 min, m/z=644 [M+H]$^+$.

Step 6: 3-((5-Hydroxy-2-((R)-2-phenylpiperazine-1-carbonyl)-9-oxa-2-azaspiro[5.5]undecan-5-yl)methyl)-6-phenylpyrimidin-4(3H)-one: A solution of tert-butyl (3R)-4-(5-hydroxy-5-((6-oxo-4-phenylpyrimidin-1(6H)-yl)methyl)-9-oxa-2-azaspiro[5.5]undecane-2-carbonyl)-3-phenylpiperazine-1-carboxylate (45 mg, 0.0699 mmol) in TFA (0.35 mL) and DCM (0.7 mL) was stirred at rt for 20 min before the reaction mixture was concentrated under reduced pressure. The residue was dissolved in DCM (10 mL) and saturated NaHCO$_{3(aq)}$ (10 mL) was added before the mixture was shaken and the layers separated using a phase separator. The organic phase was concentrated under reduced pressure and the residue was purified by flash chromatography (0-20% MeOH in DCM) to give the title compound (32.8 mg, 85%) as an off-white solid after lyophilisation. LCMS (Method B): R$_T$=0.78 min, m/z=544 [M+H]$^+$. $^1$H NMR (500 MHz, DMSO-d$_6$): δ 8.43 (s, 0.5H), 8.43 (s, 0.5H), 8.13-8.02 (m, 2H), 7.59-7.43 (m, 3H), 7.37-7.23 (m, 4H), 7.23-7.14 (m, 1H), 6.98 (s, 0.5H), 6.97 (s, 0.5H), 4.94 (s, 0.5H), 4.92 (s, 0.5H), 4.58 (d, J=13.6 Hz, 0.5H), 4.52 (d, J=13.5 Hz, 0.5H), 4.24 (dd, J=7.2, 3.9 Hz, 0.5H), 4.20 (dd, J=7.6, 3.8 Hz, 0.5H), 3.75-3.34 (m, 9H (signal overlaps with HDO)), 3.09-3.01 (m, 1H), 2.99-2.74 (m, 5H), 1.84-1.69 (m, 1.5H), 1.61-1.51 (m, 0.5H), 1.45-1.32 (m, 1H), 1.31-1.18 (m, 2H), 1.01 (d, J=13.5 Hz, 0.5H), 0.89 (d, J=13.4 Hz, 0.5H). NH not visible.

Example 322: 3-(((S)-4-Hydroxy-3,3-dimethyl-1-((R)-2-phenylpiperazine-1-carbonyl)piperidin-4-yl)methyl)-6-phenylpyrimidin-4(3H)-one

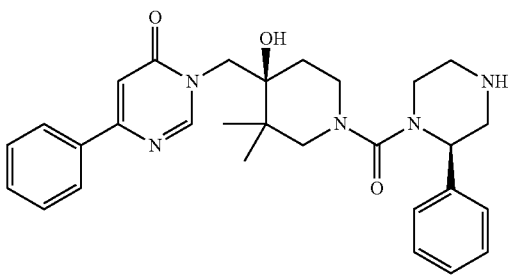 [SMILES: CC1(C)CN(C(=O)N2CCNC[C@H]2c2ccccc2)CC[C@@]1(O)Cn1cnc(-c2ccccc2)cc1=O]

Step 1: tert-Butyl (R)-4-((S)-4-hydroxy-3,3-dimethyl-4-((6-oxo-4-phenylpyrimidin-1(6H)-yl)methyl)piperidine-1-carbonyl)-3-phenylpiperazine-1-carboxylate: Prepared according to General Procedure 9 using (S)-3-((4-hydroxy-3,3-dimethylpiperidin-4-yl)methyl)-6-phenylpyrimidin-4(3H)-one (20 mg, 63.8 µmol), tert-butyl (R)-4-(chlorocarbonyl)-3-phenylpiperazine-1-carboxylate (24.8 mg, 76.6 µmol), DIPEA (45 µL, 0.255 mmol) and DCM (2 mL), stirring at rt for 1.5 h to give the title compound (15 mg, 39%). LCMS (Method B): R$_T$=1.49 min, m/z=602 [M+H]$^+$; 546 [M-butene+H]$^+$.

Step 2: 3-(((S)-4-Hydroxy-3,3-dimethyl-1-((R)-2-phenylpiperazine-1-carbonyl)piperidin-4-yl)methyl)-6-phenylpyrimidin-4(3H)-one: Prepared according to General Procedure 3 using tert-butyl (R)-4-((S)-4-hydroxy-3,3-dimethyl-4-((6-oxo-4-phenylpyrimidin-1(6H)-yl)methyl)piperidine-1-carbonyl)-3-phenylpiperazine-1-carboxylate (15 mg, 24.9 µmol), TFA (0.5 mL) and DCM (1 mL), stirred at rt for 1.5 h to give the title compound (10.3 mg, 79%). LCMS (Method B): R$_T$=0.79 min, m/z=502 [M+H]$^+$. $^1$H NMR (500 MHz, DMSO-d$_6$): δ 8.43 (d, J=0.8 Hz, 1H), 8.10-8.05 (m, 2H), 7.52-7.48 (m, 3H), 7.32-7.24 (m, 4H), 7.20-7.15 (m, 1H), 6.97 (d, J=0.8 Hz, 1H), 4.80 (s, 1H), 4.43-4.35 (m, 2H), 3.72 (d, J=13.6 Hz, 1H), 3.59 (dt, J=13.2, 4.3 Hz, 1H), 3.10-2.87 (m, 7H), 2.82-2.73 (m, 2H), 1.75-1.64 (m, 1H), 1.14 (dt, J=14.1, 3.4 Hz, 1H), 0.97 (s, 3H), 0.93 (s, 3H). NH signal not observed.

Example 323: 3-(((S)-10-Hydroxy-7-((R)-2-phenyl-4-(2,2,2-trifluoroethyl)piperazine-1-carbonyl)-7-azaspiro[4.5]decan-10-yl)methyl)-6-phenylpyrimidin-4(3H)-one

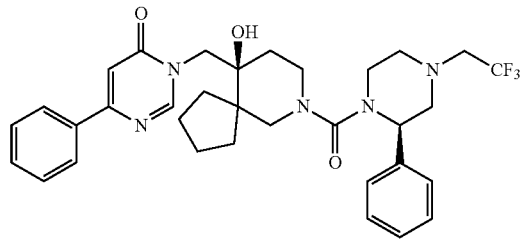 [SMILES: O=C(N1CC[C@@](O)(Cn2cnc(-c3ccccc3)cc2=O)C2(CCCC2)C1)N1CCN(CC(F)(F)F)C[C@H]1c1ccccc1]

To an oven dried 5 mL RBF was added 3-(((S)-10-hydroxy-7-((R)-2-phenylpiperazine-1-carbonyl)-7-azaspiro[4.5]decan-10-yl)methyl)-6-phenylpyrimidin-4(3H)-one (9.5 mg, 0.018 mmol) and THF (0.5 mL). The solution was heated to 70° C. before phenylsilane (6.7 µL, 0.054 mmol) and then TFA (6.9 µL, 0.090 mmol) were added and the reaction was stirred at reflux under nitrogen. After 1 h, further phenylsilane (6.7 µL, 0.054 mmol) and TFA (6.9 µL, 0.090 mmol) were added. After a further 3 h, the reaction mixture was diluted with EtOAc and washed using saturated NaHCO$_{3(aq)}$ (×2). The aqueous phase was extracted using EtOAc (×2) and the combined organics were dried (phase separator) and concentrated in vacuo. The residue was purified using flash chromatography (0-10% MeOH in DCM) to give the title compound (4.7 mg, 39%) as a white solid after lyophilisation. LCMS (Method A): R$_T$=1.53 min, m/z=610 [M+H]$^+$. $^1$H NMR (500 MHz, DMSO-d$_6$) δ 8.46 (s, 1H), 8.12-8.03 (m, 2H), 7.51-7.48 (m, 3H), 7.35-7.19 (m, 5H), 6.97 (s, 1H), 4.83 (s, 1H), 4.56-4.47 (m, 2H), 3.63 (d, J=13.6 Hz, 1H), 3.57-3.52 (m, 1H), 3.26-3.15 (m, 4H), 3.10-2.96 (m, 4H), 2.81 (dd, J=11.8, 3.7 Hz, 1H), 2.77-2.72 (m, 1H), 2.70-2.64 (m, 1H), 1.93-1.86 (m, 1H), 1.64-1.39 (m, 6H), 1.37-1.31 (m, 1H), 1.23-1.18 (m, 1H), 1.13-1.05 (m, 1H).

259

Example 324: 3-(((S)-10-Hydroxy-7-((R)-2-phenylpiperazine-1-carbonyl)-7-azaspiro[4.5]decan-10-yl)methyl)-6-methoxypyrimidin-4(3H)-one

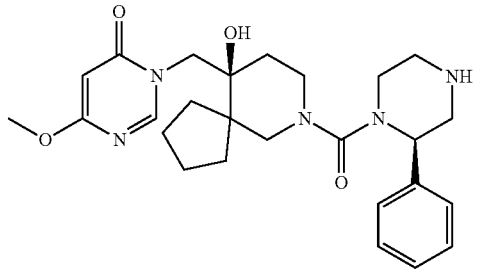 [SMILES: COc1cc(=O)n(C[C@]2(O)CCN(C(=O)N3CCNC[C@H]3c3ccccc3)CC23CCCC3)cn1]

Step 1: tert-Butyl (R)-4-((S)-10-hydroxy-10-((4-methoxy-6-oxopyrimidin-1(6H)-yl)methyl)-7-azaspiro[4.5]decane-7-carbonyl)-3-phenylpiperazine-1-carboxylate: MeOH (0.5 mL) was added to sodium hydride (60% dispersion in oil, 5.1 mg, 0.128 mmol) under nitrogen. The resultant mixture was stirred for 10 min before tert-butyl (R)-4-((S)-10-((4-chloro-6-oxopyrimidin-1(6H)-yl)methyl)-10-hydroxy-7-azaspiro[4.5]decane-7-carbonyl)-3-phenylpiperazine-1-carboxylate (15 mg, 0.026 mmol) in MeOH (0.5 mL) was added and the reaction mixture was stirred at rt. After 6 h, the reaction mixture was quenched using AcOH and evaporated under reduced pressure. The residue was purified by flash chromatography (20-100% EtOAc in cyclohexane; then 0-20% MeOH in EtOAc) to give the title compound (14 mg, 94%) as a clear glass. LCMS (Method B): $R_T$=1.32 min, m/z=582 [M+H]$^+$.

Step 2: 3-(((S)-10-Hydroxy-7-((R)-2-phenylpiperazine-1-carbonyl)-7-azaspiro[4.5]decan-10-yl)methyl)-6-methoxypyrimidin-4(3H)-one: Prepared according to General Procedure 3 using tert-butyl (R)-4-((S)-10-hydroxy-10-((4-methoxy-6-oxopyrimidin-1(6H)-yl)methyl)-7-azaspiro[4.5]decane-7-carbonyl)-3-phenylpiperazine-1-carboxylate (14 mg, 0.024 mmol), TFA (1.0 mL) and DCM (2.0 mL), stirred at rt for 30 min to give the title compound (8 mg, 78%) as white solid. LCMS (Method B): $R_T$=0.67 min, m/z=482 [M+H]$^+$. $^1$H NMR (500 MHz, DMSO-d$_6$): δ 8.26 (s, 1H), 7.33-7.24 (m, 4H), 7.23-7.16 (m, 1H), 5.64 (s, 1H), 4.76 (s, 1H), 4.47 (d, J=13.6 Hz, 1H), 4.31 (t, J=5.3 Hz, 1H), 3.80 (s, 3H), 3.55 (d, J=13.6 Hz, 2H), 3.26-3.14 (m, 2H), 3.09-2.88 (m, 5H), 2.88-2.76 (m, 2H), 1.90-1.75 (m, 1H), 1.66-1.41 (m, 5H), 1.41-1.20 (m, 3H), 1.20-1.12 (m, 1H), 1.09-0.99 (m, 1H).

Example 325: 3-((5-Hydroxy-2-((R)-3-phenylmorpholine-4-carbonyl)-9-oxa-2-azaspiro[5.5]undecan-5-yl)methyl)-6-phenylpyrimidin-4(3H)-one

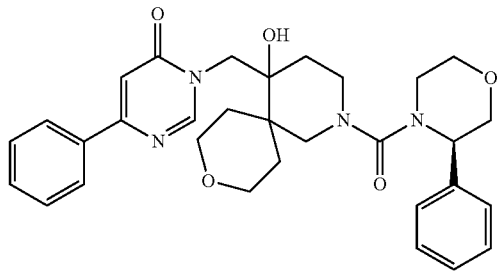 [SMILES: O=C(N1CCC(O)(Cn2cnc(-c3ccccc3)cc2=O)C2(CCOCC2)C1)N1CCOC[C@H]1c1ccccc1]

260

To a solution of triphosgene (6.3 mg, 0.0211 mmol) in DCM (0.42 mL) at 0° C. was added pyridine (17 μL, 0.211 mmol) and after stirring for 20 min, a solution of (R)-3-phenylmorpholine (10.3 mg, 0.0633 mmol) in DCM (0.42 mL) was added. After 1 h, the reaction was allowed to warm to rt before 3-((5-hydroxy-9-oxa-2-azaspiro[5.5]undecan-5-yl)methyl)-6-phenylpyrimidin-4(3H)-one (15 mg, 0.0422 mmol) and DIPEA (22 μL, 0.127 mmol) were added. The reaction was stirred at rt for 21 h 20 min before saturated sodium hydrogen carbonate (aq) solution (15 mL) was added and the resulting mixture was extracted with DCM (3×10 mL) using a phase separator. The combined organic phases were concentrated under reduced pressure and the residue was purified by flash chromatography three times (0-100% EtOAc in cyclohexane; then 0-10% MeOH in EtOAc; followed by 0-8% MeOH in DCM; followed by Biotage KP-NH 11 g cartridge, 0-100% EtOAc in cyclohexane; then 0-10% MeOH in EtOAc) to give the title compound (6.3 mg, 27%) as a colourless solid after lyophilisation. LCMS (Method B): $R_T$=1.15 min, m/z=545 [M+H]$^+$. $^1$H NMR (500 MHz, DMSO-d$_6$): δ 8.42 (s, 1H), 8.19-7.97 (m, 2H), 7.67-7.39 (m, 3H), 7.46-7.05 (m, 5H), 6.99 (s, 0.5H), 6.97 (s, 0.5H), 4.95 (s, 0.5H), 4.93 (s, 0.5H), 4.58 (d, J=13.7 Hz, 0.5H), 4.55 (d, J=13.3 Hz, 0.5H), 4.35 (dd, J=6.0, 4.1 Hz, 0.5H), 4.31 (dd, J=6.6, 3.9 Hz, 0.5H), 3.89-3.29 (m, 13H), 3.16-3.06 (m, 1H), 3.03-2.91 (m, 1H), 1.87-1.71 (m, 1.5H), 1.65-1.57 (m, 0.5H), 1.46-1.35 (m, 1H), 1.32-1.18 (m, 2H), 1.08 (d, J=12.9 Hz, 0.5H), 0.98 (d, J=12.3 Hz, 0.5H).

Example 326: 4-Chloro-1-(((S)-10-hydroxy-7-((R)-2-phenylpiperazine-1-carbonyl)-7-azaspiro[4.5]decan-10-yl)methyl)pyridin-2(1H)-one

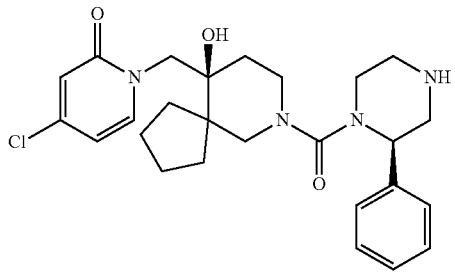 [SMILES: O=C(N1CC[C@@](O)(Cn2ccc(Cl)cc2=O)C2(CCCC2)C1)N1CCNC[C@H]1c1ccccc1]

Step 1: (S)-4-Chloro-1-((10-hydroxy-7-azaspiro[4.5]decan-10-yl)methyl)pyridin-2(1H)-one hydrochloride: To a solution of tert-butyl (S)-10-((4-chloro-2-oxopyridin-1(2H)-yl)methyl)-10-hydroxy-7-azaspiro[4.5]decane-7-carboxylate (100 mg, 0.252 mmol) in DCM (2.5 mL) was added 4 M HCl in 1,4-dioxane (1.26 mL, 5.04 mmol) and the resulting solution was stirred at rt for 17 h before the resulting suspension was concentrated under reduced pressure to give the title compound (84 mg, quantitative) as an off-white crystalline solid. This material was used in the next step without further purification. LCMS (Method A): $R_T$=0.35 min, m/z=297, 299 [M−Cl]$^+$.

Step 2: tert-Butyl (R)-4-((S)-10-((4-chloro-2-oxopyridin-1(2H)-yl)methyl)-10-hydroxy-7-azaspiro[4.5]decane-7-carbonyl)-3-phenylpiperazine-1-carboxylate: To a solution triphosgene (37.4 mg, 0.126 mmol) in DCM (2.5 mL) at 0° C. was added pyridine (0.102 mL, 1.26 mmol). After 20 min, a solution of tert-butyl (R)-3-phenylpiperazine-1-carboxylate (99.2 mg, 0.378 mmol) in DCM (2.5 mL) was added and the reaction mixture was stirred at 0° C. for a further 20 min before being allowed to warm to rt. After 3 h, the reaction mixture was transferred via syringe to flask containing (S)-4-chloro-1-((10-hydroxy-7-azaspiro[4.5]decan-10-yl)methyl)pyridin-2(1H)-one hydrochloride (84 mg, 0.252 mmol) before DIPEA (0.132 mL, 0.756 mmol) was added. After stirring at rt for 4 days, the reaction had not reached full conversion so to a solution of triphosgene (18.7 mg, 0.063 mmol) in DCM (1.25 mL) at 0° C. in a separate flask was added pyridine (51 µL, 0.630 mmol). After 20 min, a solution of tert-butyl (R)-3-phenylpiperazine-1-carboxylate (49.6 mg, 0.189 mmol) in DCM (1.25 mL) was added to the new reaction and the reaction mixture was stirred at 0° C. for a further 20 min before being allowed to warm to rt. After stirring at rt for 3 h, the resulting solution was added into the first reaction. After a further 16 h, saturated NaHCO$_{3(aq)}$ (15 mL) was added and the resulting mixture was extracted with DCM (3×10 mL) using a phase separator. The combined organic phases were concentrated under reduced pressure and the residue was purified by flash chromatography twice (0-100% EtOAc in cyclohexane; followed by 0%; then 25%; then 50% EtOAc in cyclohexane (isocratic)) to give the title compound (133 mg, 90%) as bright yellow foam. LCMS (Method A): R$_T$=1.62 min, m/z=585, 587 [M+H]$^+$.

Step 3: 4-Chloro-1-(((S)-10-hydroxy-7-((R)-2-phenylpiperazine-1-carbonyl)-7-azaspiro[4.5]decan-10-yl)methyl)pyridin-2(1H)-one: To a solution of tert-butyl (R)-4-((S)-10-((4-chloro-2-oxopyridin-1(2H)-yl)methyl)-10-hydroxy-7-azaspiro[4.5]decane-7-carbonyl)-3-phenylpiperazine-1-carboxylate (10 mg, 0.0171 mmol) in DCM (0.5 mL) was added 4 M HCl in 1,4-dioxane (0.25 mL, 1 mmol) and the resulting solution was stirred at rt for 18 h before the reaction mixture was concentrated under reduced pressure. To the HCl salt was added DCM (10 mL) and saturated sodium hydrogen carbonate(aq) (2 mL). The mixture was shaken, and the phases were separated using a phase separator. The aqueous phase was further extracted with DCM (2×10 mL) using the phase separator. The combined organic phases were concentrated under reduced pressure and the residue was purified by flash chromatography twice (0-20% MeOH in DCM; followed by Biotage KP-NH 11 g cartridge, 0-100% EtOAC in cyclohexane; then 0-10% MeOH in EtOAc) to give the title compound (6.4 mg, 73%) as a colourless solid after lyophilisation. LCMS (Method A): R$_T$=0.66 min, m/z=485, 487 [M+H]$^+$. $^1$H NMR (500 MHz, DMSO-d$_6$): δ 7.72 (d, J=7.4 Hz, 1H), 7.34-7.20 (m, 4H), 7.20-7.14 (m, 1H), 6.55 (d, J=2.4 Hz, 1H), 6.38 (dd, J=7.4, 2.4 Hz, 1H), 4.73 (s, 1H), 4.52 (d, J=13.4 Hz, 1H), 4.30 (t, J=5.2 Hz, 1H), 3.58 (d, J=13.4 Hz, 1H), 3.57-3.49 (m, 1H), 3.25-3.12 (m, 2H), 3.05-2.97 (m, 2H), 2.96-2.91 (m, 1H), 2.91-2.85 (m, 2H), 2.80-2.71 (m, 2H), 1.83 (dt, J=13.0, 6.6 Hz, 1H), 1.63-1.43 (m, 5H), 1.42-1.35 (m, 1H), 1.31-1.25 (m, 1H), 1.14 (dt, J=14.0, 4.7 Hz, 1H), 1.04 (dt, J=13.5, 6.7 Hz, 1H). NH not visible.

Example 327: 4-Cyclopropyl-1-(((S)-10-hydroxy-7-((R)-2-phenylpiperazine-1-carbonyl)-7-azaspiro[4.5]decan-10-yl)methyl)pyridin-2(1H)-one

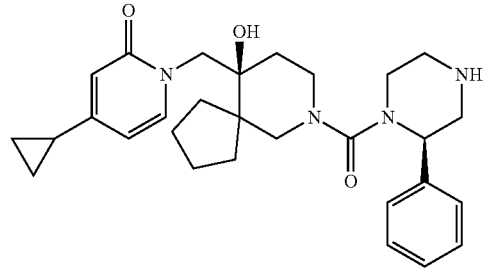 [SMILES: O=C(N1CC[C@@](O)(Cn2ccc(C3CC3)cc2=O)C2(CCCC2)C1)N1CCNC[C@H]1c1ccccc1]

Step 1: tert-Butyl (R)-4-((S)-10-((4-cyclopropyl-2-oxopyridin-1(2H)-yl)methyl)-10-hydroxy-7-azaspiro[4.5]decane-7-carbonyl)-3-phenylpiperazine-1-carboxylate: Prepared according to General Procedure 5 using tert-butyl (R)-4-((S)-10-((4-chloro-2-oxopyridin-1(2H)-yl)methyl)-10-hydroxy-7-azaspiro[4.5]decane-7-carbonyl)-3-phenylpiperazine-1-carboxylate (20 mg, 0.0342 mmol), cyclopropylboronic acid M IDA ester (13.5 mg, 0.0684 mmol), tricyclohexylphosphonium tetrafluoroborate (3.8 mg, 10.3 µmol) and palladium(II) acetate (1.2 mg, 5.13 µmol) in toluene (0.3 mL) and water (0.06 mL) heated at 100° C. (oil bath) for 17 h 35 min to give the title compound (18.6 mg, 92%) as colourless glass. LCMS (Method A): R$_T$=1.47 min, m/z=591 [M+H]$^+$.

Step 2: 4-Cyclopropyl-1-(((S)-10-hydroxy-7-((R)-2-phenylpiperazine-1-carbonyl)-7-azaspiro[4.5]decan-10-yl)methyl)pyridin-2(1H)-one: A solution of tert-butyl (R)-4-((S)-10-((4-cyclopropyl-2-oxopyridin-1(2H)-yl)methyl)-10-hydroxy-7-azaspiro[4.5]decane-7-carbonyl)-3-phenylpiperazine-1-carboxylate (18.6 mg, 0.0315 mmol) in TFA (0.15 mL) and DCM (0.3 mL) was stirred at rt for 10 min before the reaction mixture was concentrated under reduced pressure. To the TFA salt was added DCM (10 mL) and saturated NaHCO$_{3(aq)}$ (5 mL) and the mixture was shaken. The phases were separated using a phase separator and aqueous phase was further extracted with DCM (2×10 mL) using the phase separator. The combined organic phases were concentrated under reduced pressure and the residue was purified by flash chromatography (0-20% MeOH in DCM) to give the title compound (15.2 mg, 96%) as an off-white solid after lyophilisation. LCMS (Method A): R$_T$=0.70 min, m/z=491 [M+H]$^+$. $^1$H NMR (500 MHz, DMSO-d$_6$): δ 7.56 (d, J=7.1 Hz, 1H), 7.33-7.21 (m, 4H), 7.21-7.17 (m, 1H), 6.18 (d, J=2.0 Hz, 1H), 5.94 (dd, J=7.1, 2.1 Hz, 1H), 5.06 (s, 1H), 4.36-4.28 (m, 2H), 3.73 (d, J=13.6 Hz, 1H), 3.60-3.53 (m, 1H), 3.25-3.12 (m, 2H), 3.11-3.00 (m, 2H), 2.99-2.89 (m, 3H), 2.87-2.78 (m, 2H), 1.85-1.74 (m, 2H), 1.62-1.43 (m, 5H), 1.42-1.34 (m, 1H), 1.30-1.25 (m, 1H), 1.13-0.96 (m, 4H), 0.78-0.73 (m, 2H). NH not visible.

Example 328: 1-(((S)-10-Hydroxy-7-((R)-2-phenylpiperazine-1-carbonyl)-7-azaspiro[4.5]decan-10-yl)methyl)-4-(1-methyl-1H-pyrazol-5-yl)pyridin-2(1H)-one

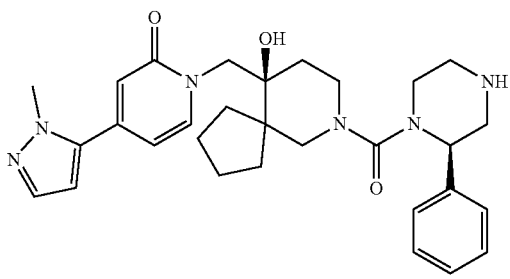 [SMILES: Cn1nccc1-c1ccn(C[C@]2(O)CCN(C(=O)N3CCNC[C@H]3c3ccccc3)CC23CCCC3)c(=O)c1]

Step 1: tert-Butyl (R)-4-((S)-10-hydroxy-10-((4-(1-methyl-1H-pyrazol-5-yl)-2-oxopyridin-1(2H)-yl)methyl)-7-azaspiro[4.5]decane-7-carbonyl)-3-phenylpiperazine-1-carboxylate: Prepared according to General Procedure 5 using tert-butyl (R)-4-((S)-10-((4-chloro-2-oxopyridin-1(2H)-yl)methyl)-10-hydroxy-7-azaspiro[4.5]decane-7-carbonyl)-3-phenylpiperazine-1-carboxylate (20 mg, 0.0342 mmol), 1-methyl-5-(4,4,5,5-tetramethyl-1,3,2-dioxaborolan-2-yl)-1H-pyrazole (14.2 mg, 0.0684 mmol), Pd(dppf)Cl$_2$·DCM (1.5 mg, 1.71 μmol) and sodium carbonate (10.9 mg, 0.103 mmol) in 1,4-dioxane (0.3 mL) and water (0.1 mL) under microwave irradiation at 120° C. for 30 min to give the title compound (19.2 mg, 89%) as a light beige foam. LCMS (Method B): R$_T$=1.35 min, m/z=631 [M+H]$^+$.

Step 2: 1-(((S)-10-Hydroxy-7-((R)-2-phenylpiperazine-1-carbonyl)-7-azaspiro[4.5]decan-10-yl)methyl)-4-(1-methyl-1H-pyrazol-5-yl)pyridin-2(1H)-one: A solution of tert-butyl (R)-4-((S)-10-hydroxy-10-((4-(1-methyl-1H-pyrazol-5-yl)-2-oxopyridin-1(2H)-yl)methyl)-7-azaspiro[4.5]decane-7-carbonyl)-3-phenylpiperazine-1-carboxylate (19.2 mg, 0.0304 mmol) in TFA (0.15 mL) and DCM (0.3 mL) was stirred at rt for 10 min before the reaction mixture was concentrated under reduced pressure. To the TFA salt, were added DCM (1 mL) and triethylamine (1 mL) and the resulting solution was directly purified by flash chromatography (Biotage KP-NH 11 g cartridge, 0-100% EtOAc in cyclohexane; then 0-20% MeOH in EtOAc) to give the title compound (14.4 mg, 87%) as a colourless solid after lyophilisation. LCMS (Method A): R$_T$=0.62 min, m/z=531 [M+H]$^+$. $^1$H NMR (500 MHz, DMSO-d$_6$): δ 7.78 (d, J=7.1 Hz, 1H), 7.50 (d, J=1.9 Hz, 1H), 7.31-7.20 (m, 4H), 7.20-7.16 (m, 1H), 6.60 (d, J=1.9 Hz, 1H), 6.59 (d, J=2.1 Hz, 1H), 6.46 (dd, J=7.1, 2.1 Hz, 1H), 4.90 (s, 1H), 4.52 (d, J=13.5 Hz, 1H), 4.31 (t, J=5.2 Hz, 1H), 3.94 (s, 3H), 3.71 (d, J=13.5 Hz, 1H), 3.59 (dt, J=13.2, 5.0 Hz, 1H), 3.26-3.14 (m, 2H), 3.08-2.99 (m, 2H), 2.97-2.85 (m, 3H), 2.81-2.71 (m, 2H), 2.27 (br. s, 1H), 1.89-1.83 (m, 1H), 1.65-1.40 (m, 6H), 1.34-1.28 (m, 1H), 1.22-1.16 (m, 1H), 1.07 (dt, J=13.8, 7.3 Hz, 1H).

Example 329: 1-(((S)-10-Hydroxy-7-((R)-2-phenylpiperazine-1-carbonyl)-7-azaspiro[4.5]decan-10-yl)methyl)-4-(1-methyl-1H-pyrazol-4-yl)pyridin-2(1H)-one

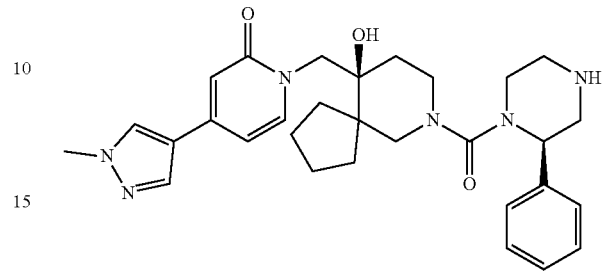

Step 1: tert-Butyl (R)-4-((S)-10-hydroxy-10-((4-(1-methyl-1H-pyrazol-4-yl)-2-oxopyridin-1(2H)-yl)methyl)-7-azaspiro[4.5]decane-7-carbonyl)-3-phenylpiperazine-1-carboxylate: Prepared according to General Procedure 5 using tert-butyl (R)-4-((S)-10-((4-chloro-2-oxopyridin-1(2H)-yl)methyl)-10-hydroxy-7-azaspiro[4.5]decane-7-carbonyl)-3-phenylpiperazine-1-carboxylate (20 mg, 0.0342 mmol), 1-methyl-4-(4,4,5,5-tetramethyl-1,3,2-dioxaborolan-2-yl)-1H-pyrazole (14.2 mg, 0.0684 mmol), Pd(dppf)Cl$_2$·DCM (1.5 mg, 1.71 μmol) and sodium carbonate (10.9 mg, 0.103 mmol) in 1,4-dioxane (0.3 mL) and water (0.1 mL) under microwave irradiation at 120° C. for 30 min to give the title compound (20.3 mg, 94%) as a light beige foam. LCMS (Method B): R$_T$=1.32 min, m/z=631 [M+H]$^+$.

Step 2: 1-(((S)-10-Hydroxy-7-((R)-2-phenylpiperazine-1-carbonyl)-7-azaspiro[4.5]decan-10-yl)methyl)-4-(1-methyl-1H-pyrazol-4-yl)pyridin-2(1H)-one: A solution of tert-butyl (R)-4-((S)-10-hydroxy-10-((4-(1-methyl-1H-pyrazol-4-yl)-2-oxopyridin-1(2H)-yl)methyl)-7-azaspiro[4.5]decane-7-carbonyl)-3-phenylpiperazine-1-carboxylate (20.3 mg, 0.0322 mmol) in TFA (0.15 mL) and DCM (0.3 mL) was stirred at rt for 10 min before the reaction mixture was concentrated under reduced pressure. To the TFA salt, were added DCM (1 mL) and triethylamine (1 mL) and the resulting solution was directly purified by flash chromatography (Biotage KP-NH 11 g cartridge, 0-100% EtOAc in cyclohexane; then 0-20% MeOH in EtOAc) to give the title compound (15 mg, 86%) as a colourless solid after lyophilisation. LCMS (Method A): R$_T$=0.59 min, m/z=531 [M+H]$^+$. $^1$H NMR (500 MHz, DMSO-d$_6$): δ 8.30 (s, 1H), 7.98 (d, J=0.6 Hz, 1H), 7.67 (d, J=7.1 Hz, 1H), 7.30-7.20 (m, 4H), 7.20-7.15 (m, 1H), 6.63 (d, J=2.0 Hz, 1H), 6.53 (dd, J=7.1, 2.0 Hz, 1H), 5.09 (s, 1H), 4.37 (d, J=13.6 Hz, 1H), 4.30 (t, J=5.2 Hz, 1H), 3.86 (s, 3H), 3.77 (d, J=13.6 Hz, 1H), 3.61-3.53 (m, 1H), 3.26-3.13 (m, 2H), 3.08-2.99 (m, 2H), 2.97-2.85 (m, 3H), 2.80-2.71 (m, 2H), 2.31 (br. s, 1H), 1.90-1.81 (m, 1H), 1.63-1.40 (m, 6H), 1.33-1.25 (m, 1H), 1.19-1.12 (m, 1H), 1.06 (dt, J=13.7, 6.8 Hz, 1H).

Example 330: 1-(((S)-10-Hydroxy-7-((R)-2-phenylpiperazine-1-carbonyl)-7-azaspiro[4.5]decan-10-yl)methyl)-4-(pyrrolidin-1-yl)pyridin-2(1H)-one

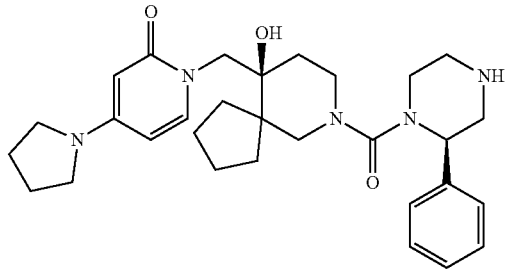 [SMILES: O=C(N1CC[C@@](O)(Cn2ccc(N3CCCC3)cc2=O)C2(CCCC2)C1)N1CCNC[C@H]1c1ccccc1]

Step 1: tert-Butyl (R)-4-((S)-10-hydroxy-10-((2-oxo-4-(pyrrolidin-1-yl)pyridin-1(2H)-yl)methyl)-7-azaspiro[4.5]decane-7-carbonyl)-3-phenylpiperazine-1-carboxylate: A solution of tert-butyl (R)-4-((S)-10-((4-chloro-2-oxopyridin-1(2H)-yl)methyl)-10-hydroxy-7-azaspiro[4.5]decane-7-carbonyl)-3-phenylpiperazine-1-carboxylate (20 mg, 0.0342 mmol) and pyrrolidine (28 µL, 0.342 mmol) in 1,4-dioxane (0.34 mL) was heated under microwave irradiation at 120° C. for 30 min before pyrrolidine (28 µL, 0.342 mmol) was added and the reaction mixture was heated under microwave irradiation at 120° C. for a further 2 h. The reaction mixture was directly purified by flash chromatography (0-100% EtOAc in cyclohexane; then 0-20% MeOH in EtOAc) to give the title compound (19.6 mg, 92%) as a light beige foam. LCMS (Method B): $R_T$=1.43 min, m/z=620 [M+H]$^+$.

Step 2: 1-(((S)-10-Hydroxy-7-((R)-2-phenylpiperazine-1-carbonyl)-7-azaspiro[4.5]decan-10-yl)methyl)-4-(pyrrolidin-1-yl)pyridin-2(1H)-one: A solution of tert-butyl (R)-4-((S)-10-hydroxy-10-((2-oxo-4-(pyrrolidin-1-yl)pyridin-1(2H)-yl)methyl)-7-azaspiro[4.5]decane-7-carbonyl)-3-phenylpiperazine-1-carboxylate (19.6 mg, 0.0316 mmol) in TFA (0.15 mL) and DCM (0.3 mL) was stirred at rt for 10 min before the reaction mixture was concentrated under reduced pressure. To the TFA salt, were added DCM (1 mL) and triethylamine (1 mL) and the resulting solution was directly purified by flash chromatography (Biotage KP-NH 11 g cartridge, 0-100% EtOAc in cyclohexane; then 0-20% MeOH in EtOAc) to give the title compound (14 mg, 84%) as a colourless solid after lyophilisation. LCMS (Method A): $R_T$=0.69 min, m/z=520 [M+H]$^+$. $^1$H NMR (500 MHz, DMSO-d$_6$): δ 7.47 (d, J=7.6 Hz, 1H), 7.32-7.19 (m, 4H), 7.19-7.14 (m, 1H), 5.86 (dd, J=7.6, 2.7 Hz, 1H), 5.82 (s, 1H), 5.20 (d, J=2.6 Hz, 1H), 4.28 (t, J=5.3 Hz, 1H), 4.04-3.90 (m, 2H), 3.58-3.51 (m, 1H), 3.28-3.09 (m, 6H), 3.07-2.99 (m, 2H), 2.95-2.84 (m, 3H), 2.80-2.71 (m, 2H), 2.28 (br. s, 1H), 1.99-1.88 (m, 4H), 1.88-1.79 (m, 1H), 1.63-1.43 (m, 5H), 1.42-1.35 (m, 1H), 1.28-1.21 (m, 1H), 1.13-1.00 (m, 2H).

Example 331: 5-Fluoro-1-((10-hydroxy-7-((R)-2-phenylpiperazine-1-carbonyl)-7-azaspiro[4.5]decan-10-yl)methyl)-4-phenylpyridin-2(1H)-one

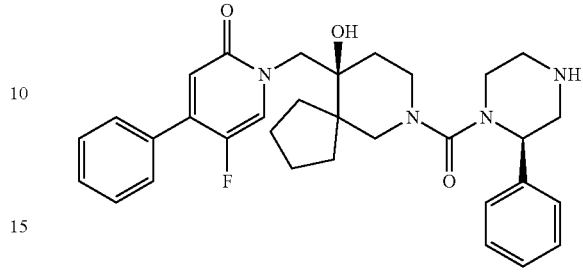

Step 1: 2-Chloro-5-fluoro-4-phenylpyridine: Prepared according to General Procedure 5 using 2-chloro-5-fluoro-4-iodopyridine (1.03 g, 4.00 mmol), phenylboronic acid (512 mg, 4.20 mmol), Pd(dppf)Cl$_2$·DCM (169 mg, 0.200 mmol) and sodium carbonate (848 mg, 8.00 mmol) in 1,4-dioxane (15 mL) and water (5 mL) stirred at 80° C. for 16 h 40 min using flash chromatography twice (0% then 5% EtOAc in cyclohexane; followed by 0-100% DCM in cyclohexane) to give the title compound (725 mg, 87%) as an off-white solid. LCMS (Method A): $R_T$=1.64 min, m/z=208, 210 [M+H]$^+$.

Step 2: 5-Fluoro-4-phenylpyridin-2(1H)-one: A solution of 2-chloro-5-fluoro-4-phenylpyridine (100 mg, 0.482 mmol) and sodium acetate (198 mg, 2.41 mmol) in acetic acid (1.6 mL) in a screw cap sealed tube was stirred at 140° C. for 2 h. Water (0.8 mL) was added and the reaction was stirred at 140° C. for 4 h. The reaction mixture was transferred to a 2-5 mL microwave vial and was heated under microwave irradiation at 160° C. for 16 h. The reaction was heated under microwave irradiation at 180° C. for 1 h. The reaction mixture was heated under microwave irradiation at 200° C. for 20 h. After standing for 20 min, the product began to precipitate and water (2 mL) was added. After stirring for 30 min, the product was isolated by filtration. The product was washed with water (3×5 mL) and dried in a vacuum oven at 50° C. to give the title compound (71 mg, 77%) as a colourless crystalline solid. LCMS (Method B): $R_T$=0.85 min, m/z=190 [M+H]$^+$. $^1$H NMR (500 MHz, DMSO-d$_6$): δ 11.29 (s, 1H), 7.81 (d, J=4.4 Hz, 1H), 7.60-7.54 (m, 2H), 7.54-7.46 (m, 3H), 6.55 (d, J=6.4 Hz, 1H).

Step 3: tert-Butyl 10-((5-fluoro-2-oxo-4-phenylpyridin-1(2H)-yl)methyl)-10-hydroxy-7-azaspiro[4.5]decane-7-carboxylate: Prepared according to General Procedure 2 using 5-fluoro-4-phenylpyridin-2(1H)-one (66.8 mg, 0.353 mmol), Epoxide 2 (113 mg, 0.424 mmol) and cesium carbonate (126 mg, 0.388 mmol) in DMF (1.8 mL) at 90° C. for 16 h to give the title compound (63 mg, 39%) as colourless glass. LCMS (Method B): $R_T$=1.51 min, m/z=401 [M-butene+H]$^+$. $^1$H NMR (500 MHz, DMSO-d$_6$): δ 7.95 (d, J=6.9 Hz, 1H), 7.63-7.56 (m, 2H), 7.55-7.47 (m, 3H), 6.54 (d, J=7.7 Hz, 1H), 4.93 (s, 1H), 4.54 (d, J=13.5 Hz, 1H), 3.66 (d, J=13.5 Hz, 1H), 3.62-3.55 (m, 1H), 3.27-3.12 (m, 3H), 1.90 (dt, J=13.4, 6.9 Hz, 1H), 1.71-1.50 (m, 5H), 1.39 (s, 9H), 1.40-1.35 (m, 2H), 1.18 (t, J=15.4 Hz, 2H).

Step 4: 5-Fluoro-1-((10-hydroxy-7-azaspiro[4.5]decan-10-yl)methyl)-4-phenylpyridin-2(1H)-one: A solution of tert-butyl 10-((5-fluoro-2-oxo-4-phenylpyridin-1(2H)-yl)methyl)-10-hydroxy-7-azaspiro[4.5]decane-7-carboxylate (92 mg, 0.202 mmol) in TFA (1 mL) and DCM (2 mL) was stirred at rt for 25 min before the reaction mixture was loaded on to a 2 g SCX-2 cartridge that was pre-equilibrated with 1:1 DCM/MeOH. The cartridge was washed with 1:1 DCM/MeOH (60 mL) before the product was eluted with 1:1 DCM/7 M NH$_3$ in MeOH (30 mL). The basic eluents were concentrated under reduced pressure to give the title compound (41.2 mg, 57%) as beige solid. LCMS (Method B): R$_T$=0.74 min, m/z=357 [M+H]$^+$.

Step 5: tert-Butyl (3R)-4-(10-((5-fluoro-2-oxo-4-phenylpyridin-1(2H)-yl)methyl)-10-hydroxy-7-azaspiro[4.5]decane-7-carbonyl)-3-phenylpiperazine-1-carboxylate: To a solution triphosgene (6.2 mg, 0.0209 mmol) in THF (0.42 mL) at 0° C. was added pyridine (17 µL, 0.210 mmol). After 30 min, a solution of tert-butyl (R)-3-phenylpiperazine-1-carboxylate (16.6 mg, 0.0633 mmol) in THF (0.42 mL) was added and the reaction mixture was stirred at 0° C. for a further 20 min before being allowed to warm to rt. After stirring for 4 h, 5-fluoro-1-((10-hydroxy-7-azaspiro[4.5]decan-10-yl)methyl)-4-phenylpyridin-2(1H)-one (8 mg, 0.0224 mmol) and DIPEA (37 µL, 0.211 mmol) were added. The reaction was stirred at rt for 17 h before saturated sodium hydrogen carbonate (aq) solution (15 mL) was added and the resulting mixture was extracted with DCM (3×10 mL) using a phase separator. The combined organic phases were concentrated under reduced pressure and the residue was purified by flash chromatography (0-100% EtOAc in cyclohexane; then 0-10% MeOH in EtOAc) to give the title compound (13.4 mg, 92%) as a light beige foam. LCMS (Method A): R$_T$=1.77 min, m/z=645 [M+H]$^+$.

Step 6: 5-Fluoro-1-((10-hydroxy-7-((R)-2-phenylpiperazine-1-carbonyl)-7-azaspiro[4.5]decan-10-yl)methyl)-4-phenylpyridin-2(1H)-one: A solution of tert-butyl (3R)-4-(10-((5-fluoro-2-oxo-4-phenylpyridin-1(2H)-yl)methyl)-10-hydroxy-7-azaspiro[4.5]decane-7-carbonyl)-3-phenylpiperazine-1-carboxylate (13.4 mg, 0.0208 mmol) in TFA (0.1 mL) and DCM (0.2 mL) was stirred at rt for 30 min before the reaction mixture was concentrated under reduced pressure. To the TFA salt, were added DCM (1 mL) and triethylamine (1 mL) and the resulting solution was directly purified by flash chromatography (Biotage KP-NH 11 g cartridge, 0-100% EtOAc in cyclohexane; then 0-20% MeOH in EtOAc) to give the title compound (10.4 mg, 88%) as an off-white solid after lyophilisation. LCMS (Method B): R$_T$=0.91 min, m/z=545 [M+H]$^+$. $^1$H NMR (500 MHz, DMSO-d$_6$): δ 7.96 (s, 0.5H), 7.95 (s, 0.5H), 7.63-7.55 (m, 2H), 7.54-7.43 (m, 3H), 7.33-7.22 (m, 4H), 7.22-7.15 (m, 1H), 6.55 (d, J=1.9 Hz, 0.5H), 6.53 (d, J=1.9 Hz, 0.5H), 4.91 (s, 0.5H), 4.90 (s, 0.5H), 4.58 (d, J=13.4 Hz, 0.5H), 4.52 (d, J=13.5 Hz, 0.5H), 4.31 (t, J=5.2 Hz, 0.5H), 4.28 (t, J=5.2 Hz, 0.5H), 3.69-3.54 (m, 2H), 3.38-2.98 (m, 4H (signals overlap with HDO)), 2.97-2.86 (m, 3H), 2.80-2.71 (m, 2H), 1.91-1.80 (m, 1H), 1.65-1.40 (m, 6H), 1.34-1.19 (m, 2H), 1.14-1.04 (m, 1H). NH not visible.

Example 332: 3-Fluoro-1-((10-hydroxy-7-((R)-2-phenylpiperazine-1-carbonyl)-7-azaspiro[4.5]decan-10-yl)methyl)-4-phenylpyridin-2(1H)-one

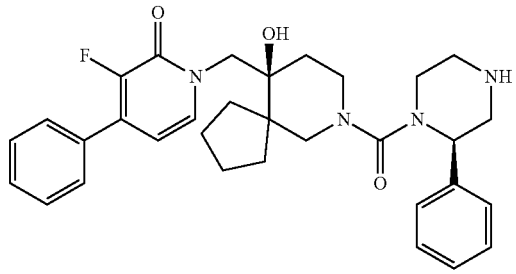 [SMILES: O=C(N1CC[C@@](O)(Cn2ccc(-c3ccccc3)c(F)c2=O)C2(CCCC2)C1)N1CCNC[C@H]1c1ccccc1]

Step 1: 2-Chloro-3-fluoro-4-phenylpyridine: Prepared according to General Procedure 5 using 2-chloro-3-fluoro-4-iodopyridine (980 mg, 3.80 mmol), phenylboronic acid (487 mg, 3.99 mmol), Pd(dppf)Cl$_2$·DCM (161 mg, 0.190 mmol) and sodium carbonate (806 mg, 7.61 mmol) in 1,4-dioxane (15 mL) and water (5 mL), stirred at 80° C. for 19 h 30 min, and using flash chromatography (0-100% DCM in cyclohexane) to give the title compound (722 mg, 91%) as a beige crystalline solid. LCMS (Method A): R$_T$=1.59 min, m/z=208, 210 [M+H]$^+$.

Step 2: 3-Fluoro-4-phenylpyridin-2(1H)-one: A suspension of 2-chloro-3-fluoro-4-phenylpyridine (100 mg, 0.482 mmol) in acetic acid (1.2 mL) and water (1.2 mL) was heated under microwave irradiation at 220° C. for 1 h. To the resulting suspension was added water (5 mL) and the product was isolated by filtration. The product was washed with water (3×5 mL) and dried in a vacuum oven at 50° C. to give the title compound (79.3 mg, 87%) as a colourless solid. LCMS (Method A): R$_T$=0.80 min, m/z=190 [M+H]$^+$.

Step 3: tert-Butyl 10-((3-fluoro-2-oxo-4-phenylpyridin-1(2H)-yl)methyl)-10-hydroxy-7-azaspiro[4.5]decane-7-carboxylate: Prepared according to General Procedure 2 using 3-fluoro-4-phenylpyridin-2(1H)-one (79.3 mg, 0.419 mmol), Epoxide 2 (134 mg, 0.503 mmol) and cesium carbonate (150 mg, 0.461 mmol) in DMF (2.1 mL) at 90° C. for 16 h 35 min to give the title compound (183.6 mg, 95%) as a light beige foam. LCMS (Method A): R$_T$=1.67 min, m/z=457 [M+H]$^+$.

Step 4: 3-Fluoro-1-((10-hydroxy-7-azaspiro[4.5]decan-10-yl)methyl)-4-phenylpyridin-2(1H)-one: A solution of tert-butyl 10-((3-fluoro-2-oxo-4-phenylpyridin-1(2H)-yl)methyl)-10-hydroxy-7-azaspiro[4.5]decane-7-carboxylate (183.6 mg, 0.402 mmol) in TFA (2 mL) and DCM (4 mL) was stirred at rt for 15 min before the reaction mixture was loaded on to a 2 g SCX-2 cartridge that was pre-equilibrated with 1:1 DCM/MeOH. The cartridge was washed with 1:1 DCM/MeOH (60 mL) before the product was eluted with 1:1 DCM/7 M NH$_3$ in MeOH (30 mL). The basic eluents were concentrated under reduced pressure to give the title compound (133.5 mg, 93%) as a beige solid. LCMS (Method A): R$_T$=0.63 min, m/z=357 [M+H]$^+$.

Step 5: tert-Butyl (3R)-4-(10-((3-fluoro-2-oxo-4-phenylpyridin-1(2H)-yl)methyl)-10-hydroxy-7-azaspiro[4.5]decane-7-carbonyl)-3-phenylpiperazine-1-carboxylate: To a solution of triphosgene (6.2 mg, 0.0210 mmol) in MeCN (0.42 mL) at 0° C. was added pyridine (17 µL, 0.210 mmol). After 30 min, a solution of tert-butyl (R)-3-phenylpiperazine-1-carboxylate (16.6 mg, 0.0631 mmol) in MeCN (0.42 mL) was added and the reaction mixture was stirred at 0° C.

for a further 20 min before being allowed to warm to rt. After stirring for 4 h, 3-fluoro-1-((10-hydroxy-7-azaspiro[4.5]decan-10-yl)methyl)-4-phenylpyridin-2(1H)-one (15 mg, 0.0421 mmol) and DIPEA (37 µL, 0.210 mmol) were added. The reaction was stirred at rt for 16 h before saturated NaHCO$_{3(aq)}$ (15 mL) was added and the resulting mixture was extracted with DCM (3×10 mL) using a phase separator. The combined organic phases were concentrated under reduced pressure and the residue was purified by flash chromatography (0-100% EtOAc in cyclohexane) to give title compound (22.9 mg, 84%) as an off-white foam. LCMS (Method A): R$_T$=1.77 min, m/z=645 [M+H]$^+$.

Step 6: 3-Fluoro-1-((10-hydroxy-7-((R)-2-phenylpiperazine-1-carbonyl)-7-azaspiro[4.5]decan-10-yl)methyl)-4-phenylpyridin-2(1H)-one: A solution of tert-butyl (3R)-4-(10-((3-fluoro-2-oxo-4-phenylpyridin-1(2H)-yl)methyl)-10-hydroxy-7-azaspiro[4.5]decane-7-carbonyl)-3-phenylpiperazine-1-carboxylate (22.9 mg, 0.0355 mmol) in TFA (0.18 mL) and DCM (0.36 mL) was stirred at rt for 35 min before the reaction mixture was concentrated under reduced pressure. To the TFA salt, were added DCM (1 mL) and triethylamine (1 mL) and the resulting solution was directly purified by flash chromatography (Biotage KP-NH 11 g cartridge, 0-100% EtOAc in cyclohexane; then 0-20% MeOH in EtOAc) to give the title compound (17.4 mg, 87%) as an off-white solid after lyophilisation. LCMS (Method B): R$_T$=0.90, 0.91 min (2 diastereoisomers), m/z=545 [M+H]$^+$. $^1$H NMR (500 MHz, DMSO-d$_6$): δ 7.65-7.46 (m, 5H), 7.37-7.22 (m, 5H), 7.22-7.16 (m, 1H), 6.41 (t, J=6.9 Hz, 1H), 4.76 (s, 0.5H), 4.75 (s, 0.5H), 4.66 (d, J=13.5 Hz, 0.5H), 4.61 (d, J=13.5 Hz, 0.5H), 4.31 (t, J=5.2 Hz, 0.5H), 4.27 (t, J=5.3 Hz, 0.5H), 3.70 (d, J=13.5 Hz, 0.5H), 3.66 (d, J=13.5 Hz, 0.5H), 3.63-3.54 (m, 1H), 3.39-2.55 (m, 9H signals overlap with HDO), 1.92-1.80 (m, 1H), 1.66-1.39 (m, 6H), 1.36-1.19 (m, 2H), 1.16-1.03 (m, 1H). NH not visible.

Example 333: (S)-3-((10-Hydroxy-7-(3-phenylthiomorpholine-4-carbonyl)-7-azaspiro[4.5]decan-10-yl)methyl)-6-phenylpyrimidin-4(3H)-one

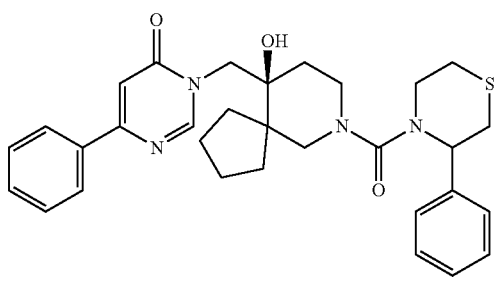 [SMILES: O=C(N1CC[C@@](O)(Cn2cnc(-c3ccccc3)cc2=O)C2(CCCC2)C1)N1CCSCC1c1ccccc1]

A mixture of (S)-10-Hydroxy-10-((6-oxo-4-phenylpyrimidin-1(6H)-yl)methyl)-7-azaspiro[4.5]decane-7-carbonyl chloride (24 mg, 0.060 mmol), 2-phenylthiomorpholine (32 mg, 0.180 mmol) and DIPEA (31 µL, 0.180 mmol) in DMF (1 mL) was stirred at rt. After 48 h, the volatiles were evaporated under reduced pressure and the residue was purified by flash chromatography (10-100% EtOAc in cyclohexane) to give the title compound (17 mg, 52%) as clear glass. LCMS (Method A): R$_T$=1.58 min, m/z=545 [M+H]$^+$. $^1$H NMR (500 MHz, DMSO-d$_6$): δ 8.46 (s, 1H), 8.11-8.04 (m, 2H), 7.53-7.47 (m, 3H), 7.39-7.29 (m, 4H), 7.27-7.20 (m, 1H), 6.97 (s, 1H), 4.89-4.77 (m, 2H), 4.58 (d, J=13.6 Hz, 1H), 3.61 (d, J=13.6 Hz, 1H), 3.56-3.42 (m, 2H), 3.27-2.92 (m, 6H), 2.79-2.70 (m, 1H), 1.93-1.84 (m, 1H), 1.63-1.24 (m, 9H), 1.15-1.07 (m, 1H).

Example 334: 3-(((10S)-10-Hydroxy-7-(1-imino-1-oxido-3-phenyl-1λ$^6$-thiomorpholine-4-carbonyl)-7-azaspiro[4.5]decan-10-yl)methyl)-6-phenylpyrimidin-4(3H)-one

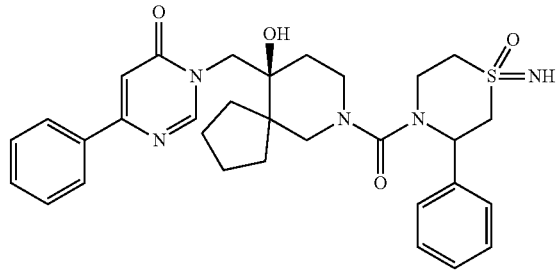 [SMILES: N=S1(=O)CCN(C(=O)N2CC[C@@](O)(Cn3cnc(-c4ccccc4)cc3=O)C3(CCCC3)C2)C(c2ccccc2)C1]

To a mixture of (S)-3-((10-Hydroxy-7-(3-phenylthiomorpholine-4-carbonyl)-7-azaspiro[4.5]decan-10-yl)methyl)-6-phenylpyrimidin-4(3H)-one (5 mg, 0.0092 mmol) and ammonium carbamate (1.4 mg, 0.018 mmol) in MeOH (0.5 mL) was added (diacetoxyiodo)benzene (7.4 mg, 0.029 mmol). The reaction mixture was stirred in an open flask for 2 h. Additional ammonium carbamate (6 equiv.) and (diacetoxyiodo)benzene (7.5 equiv.) were added and the reaction was continued for a further 2 h. The volatiles were evaporated under reduced pressure and the residue was dry loaded onto silica and purified by flash chromatography (20-100% EtOAc in cyclohexane; then 0-20% MeOH in DCM) to give the title compound (5 mg, 95%) as a white solid after lyophilisation. LCMS (Method A): R$_T$=1.1 min, m/z=576 [M+H]$^+$. $^1$H NMR (500 MHz, DMSO-d$_6$): δ 8.45 (s, 1H), 8.14-8.01 (m, 2H), 7.57-7.43 (m, 3H), 7.39-7.16 (m, 5H), 6.97 (d, J=5.4 Hz, 1H), 4.82 (s, 1H), 4.65-4.46 (m, 2H), 3.82-3.38 (m, 6H), 3.24-3.01 (m, 4H), 1.92-1.66 (m, 2H), 1.64-1.24 (m, 7H), 1.22-1.12 (m, 1H), 1.07-0.82 (m, 2H).

Example 335: (S)-3-((7-(1,1-Dioxido-3-phenylthiomorpholine-4-carbonyl)-10-hydroxy-7-azaspiro[4.5]decan-10-yl)methyl)-6-phenylpyrimidin-4(3H)-one

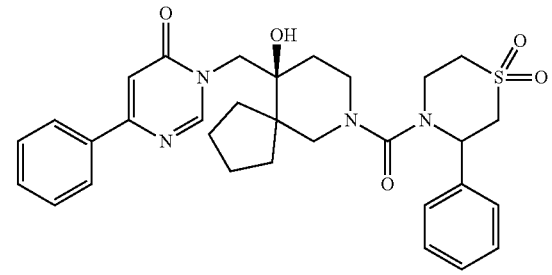 [SMILES: O=C(N1CC[C@@](O)(Cn2cnc(-c3ccccc3)cc2=O)C2(CCCC2)C1)N1CCS(=O)(=O)CC1c1ccccc1]

(S)-3-((10-Hydroxy-7-(3-phenylthiomorpholine-4-carbonyl)-7-azaspiro[4.5]decan-10-yl)methyl)-6-phenylpyrimidin-4(3H)-one (9 mg, 0.017 mmol) was dissolved in DCM (2 mL) and mCPBA (<77% pure) (9 mg, 0.036 mmol) was added to the stirred solution at rt. After 2 h, the reaction mixture was loaded onto a silica column and purified by flash chromatography (20-100% EtOAc in cyclohexane) to give the title compound (6 mg, 63%) as a white solid after lyophilisation. LCMS (Method B): $R_T$=1.24 min, m/z=577 [M+H]$^+$. $^1$H NMR (500 MHz, DMSO-d$_6$): δ 8.44 (s, 1H), 8.11-8.04 (m, 2H), 7.54-7.46 (m, 3H), 7.40-7.22 (m, 5H), 6.97 (d, J=4.5 Hz, 1H), 4.82 (s, 1H), 4.71 (ddd, J=24.3, 9.2, 3.8 Hz, 1H), 4.55 (dd, J=38.6, 13.6 Hz, 1H), 3.84-3.69 (m, 2H), 3.63-3.35 (m, 5H), 3.27-3.04 (m, 4H), 1.90-1.72 (m, 1H), 1.63-1.27 (m, 6H), 1.23-1.14 (m, 1H), 1.09-0.87 (m, 2H).

Example 336: 3-(((10S)-10-Hydroxy-7-(2-(4-(trifluoromethyl)phenyl)piperazine-1-carbonyl)-7-azaspiro[4.5]decan-10-yl)methyl)-6-phenylpyrimidin-4(3H)-one

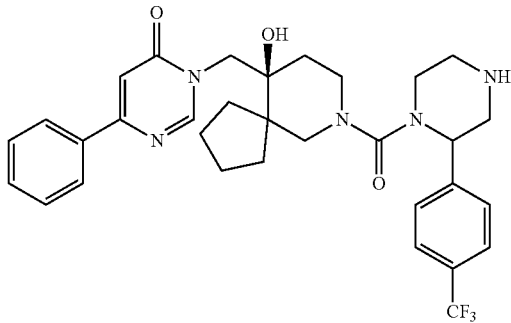 [SMILES: O=C(N1CC[C@@](O)(Cn2cnc(-c3ccccc3)cc2=O)C2(CCCC2)C1)N1CCNCC1c1ccc(C(F)(F)F)cc1]

Step 1: tert-Butyl 4-((S)-10-hydroxy-10-((6-oxo-4-phenylpyrimidin-1(6H)-yl)methyl)-7-azaspiro[4.5]decane-7-carbonyl)-3-(4-(trifluoromethyl)phenyl)piperazine-1-carboxylate: Prepared according to General Procedure 9 using (S)-10-hydroxy-10-((6-oxo-4-phenylpyrimidin-1(6H)-yl)methyl)-7-azaspiro[4.5]decane-7-carbonyl chloride (7.3 mg, 0.0180 mmol), tert-butyl 3-(4-(trifluoromethyl)phenyl)piperazine-1-carboxylate (8.9 mg, 0.0271 mmol) and DIPEA (9.5 μL, 0.0541 mmol) in DMF (0.5 mL) for 40 h to give the title compound (3.2 mg, 25%) as colourless film. LCMS (Method A): $R_T$=1.84 min, m/z=696 [M+H]$^+$.

Step 2: 3-(((10S)-10-Hydroxy-7-(2-(4-(trifluoromethyl)phenyl)piperazine-1-carbonyl)-7-azaspiro[4.5]decan-10-yl)methyl)-6-phenylpyrimidin-4(3H)-one: A solution of tert-butyl 4-((S)-10-hydroxy-10-((6-oxo-4-phenylpyrimidin-1(6H)-yl)methyl)-7-azaspiro[4.5]decane-7-carbonyl)-3-(4-(trifluoromethyl)phenyl)piperazine-1-carboxylate (3.2 mg, 0.00460 mmol) in TFA (0.25 mL) and DCM (0.5 mL) was stirred for 10 min before the reaction mixture was concentrated under reduced pressure. To the TFA salt, were added DCM (1 mL) and triethylamine (1 mL) and the resulting solution was directly purified by flash chromatography (Biotage KP-NH 11 g cartridge, 0-100% EtOAc in cyclohexane then 0-20% MeOH in EtOAc) to give the title compound (2.6 mg, 91%) as a colourless solid after lyophilisation. LCMS (Method B): $R_T$=0.97, 0.98 min (2 diastereoisomers), m/z=596 [M+H]$^+$. $^1$H NMR (500 MHz, DMSO-d$_6$): δ 8.46 (s, 1H), 8.13-8.02 (m, 2H), 7.70-7.59 (m, 2H), 7.58-7.32 (m, 5H), 6.98 (s, 0.5H), 6.98 (s, 0.5H), 4.83 (s, 0.5H), 4.82 (s, 0.5H), 4.59 (d, J=13.6 Hz, 0.5H), 4.56 (d, J=14.9 Hz, 0.5H), 4.35 (dd, J=6.2, 4.1 Hz, 0.5H), 4.32 (dd, J=6.5, 4.0 Hz, 0.5H), 3.67-3.52 (m, 2H), 3.38-2.99 (m, 4H (signals overlap with HDO)), 2.97-2.83 (m, 3H), 2.83-2.73 (m, 2H), 1.91-1.79 (m, 1H), 1.65-1.37 (m, 6H), 1.29-1.17 (m, 2H), 1.11-0.99 (m, 1H). NH not visible.

Example 337: 3-(((10S)-10-Hydroxy-7-(1-oxido-3-phenylthiomorpholine-4-carbonyl)-7-azaspiro[4.5]decan-10-yl)methyl)-6-phenylpyrimidin-4(3H)-one

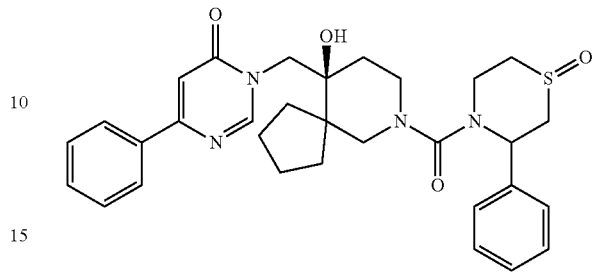

(S)-3-((10-Hydroxy-7-(3-phenylthiomorpholine-4-carbonyl)-7-azaspiro[4.5]decan-10-yl)methyl)-6-phenylpyrimidin-4(3H)-one (9.0 mg, 0.016 mmol) was dissolved in DCM (2 mL) and mCPBA (<77% pure) (4.1 mg, 0.016 mmol) in DCM (1 mL) was added dropwise. The reaction mixture was stirred at rt for 1 h. The reaction mixture was loaded directly onto a column and was purified by flash chromatography (20-100% EtOAc in cyclohexane; then 0-20% MeOH in EtOAc) and freeze-dried to give the title compound (3 mg, 32%) as a white solid. LCMS (Method B): $R_T$=1.12 min, m/z=561 [M+H]+. 1H NMR (500 MHz, DMSO-d$_6$): δ 8.46 (s, 1H), 8.11-8.04 (m, 2H), 7.52-7.47 (m, 3H), 7.37-7.29 (m, 4H), 7.28-7.20 (m, 1H), 6.97 (d, J=3.2 Hz, 1H), 4.95-4.85 (m, 1H), 4.83 (s, 1H), 4.57 (dd, J=21.7, 13.6 Hz, 1H), 3.74-3.54 (m, 3H), 3.45-3.37 (m, 1H), 3.27-3.01 (m, 5H), 2.94-2.86 (m, 1H), 2.81-2.74 (m, 1H), 1.92-1.76 (m, 1H), 1.65-1.27 (m, 6H), 1.16-0.93 (m, 3H).

The invention claimed is:
1. A compound of formula (I):

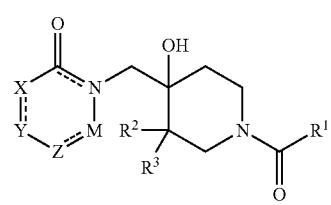

(I)

wherein
R$^1$ is NR$^a$R$^b$ or NR$^a$CH2R$^b$, wherein R$^a$ and R$^b$ are independently selected from H, methyl, ethyl, propyl, CF3, optionally substituted cyclopropyl, optionally substituted cyclobutyl, optionally substituted cyclopentyl, optionally substituted cyclohexyl, optionally substituted phenyl, optionally substituted benzyl, optionally substituted pyridinyl, pyrazole, imidazole, furan, benzodioxol, optionally substituted oxadiazole, thiazole, and thiophene, wherein the optionally substituents are independently selected from halo, methyl, cyclopropyl and CN,
when R$^1$ is NR$^a$CH2R$^b$, the methylene group is substituted with CF3; or
when R$^1$ is NR$^a$R$^b$, R$^a$ and R$^b$ together form an optionally substituted C3-C9 heterocycle together with the N to which they are attached;
R$^2$ and R$^3$ are independently selected from H, and C1-C6 alkyl, or together form an optionally substituted C3-C6 cycloalkyl or an optionally substituted C3-C6 heterocycloalkyl with the carbon to which they attached;

X is $CR^{4a}$,
wherein $R^{4a}$ is selected from H, optionally substituted C1-C6 alkyl and halo;

Y is $CR^5$,
wherein $R^5$ is selected from H, halo, optionally substituted C1-C6 alkyl, optionally substituted C3-C6 cycloalkyl, optionally substituted C5-C8 aryl, optionally substituted C6-C9 arylalkyl, optionally substituted C3-C8 heteroaryl, CH2OH, NR'R', NS(O)R'R", SO2R', C(O)R', C(O)OR', C(O)NR'R", and OR', wherein R' and R" are independently selected from H, C1-C6 alkyl, C5-C8 aryl, C6-C9 arylalkyl, and C3-C8 heteroaryl, Z is N or $CR^7$,
wherein $R^7$ and is selected from H, halo, C1-C6 alkyl, C2-C6 alkene, C2-C6 alkyne, C3-C6 cycloalkyl, optionally substituted C3-C6 heterocycloalkyl, C5-C8 aryl, C6-C9 arylalkyl, C3-C8 heteroaryl, CN, C(O)OR$^c$, CONR$^c$R$^d$, NR$^c$R$^d$, NS(O)R$^c$R$^d$, S(O)(R$^c$)NR$^d$, SOR$^c$, SO2R$^c$, and SR$^c$, wherein R$^c$ and R$^d$ are independently H, C1-C6 alkyl, C3-C6 cycloalkyl, C5-C6 aryl, C6-C9 arylalkyl, C3-C6 heteroaryl, CN, COOH, or COCH3 or R$^c$ and R$^d$ together form an optionally substituted C3-C7 heterocycle together with the heteroatom to which they are attached;

M is CH or C—CH3;
and
the ring including X, Y and Z is aliphatic or aromatic;
or a stereoisomer, tautomer, hydrate, N-oxide derivative or pharmaceutically acceptable salt thereof.

2. The compound, stereoisomer, tautomer, hydrate, N-oxide derivative or pharmaceutically acceptable salt of claim 1, wherein $R^1$ is NR$^a$R$^b$ and R$^a$ and R$^b$ form a heterocycle together with the N to which they are attached, wherein the heterocycle is selected from pyrrolidinyl, pyrimidinyl, morpholino, piperazinyl, and thiomorpholino,
wherein the heterocycle is optionally substituted with one or more substituents independently selected from CH2CF3, oxo, thiophene, and phenyl optionally substituted with F or CF3;
or R$^a$ and R$^b$ together with the N to which they are attached form a morpholino group or a piperazinyl group, wherein the morpholino group or piperazinyl group is substituted with phenyl or fluoro-phenyl.

3. The compound, stereoisomer, tautomer, hydrate, N-oxide derivative or pharmaceutically acceptable salt of claim 1, wherein $R^1$ is NR$^a$CH2R$^b$, wherein R$^a$ is H or methyl and R$^b$ is selected from cyclobutyl optionally substituted with F, cyclohexyl, phenyl optionally substituted with F, furan and thiophene,
optionally wherein the methylene group is substituted with CF3.

4. The compound, stereoisomer, tautomer, hydrate, N-oxide derivative or pharmaceutically acceptable salt of claim 1, wherein $R^2$ and $R^3$ are independently selected from H, methyl and ethyl, or together with the carbon to which they are attached form an optionally substituted cyclopropyl, optionally substituted cyclobutyl, optionally substituted cyclopentyl, optionally substituted cyclohexyl, optionally substituted pyrrolidine, optionally substituted tetrahydropyran or optionally substituted tetrahydrofuran.

5. The compound, stereoisomer, tautomer, hydrate, N-oxide derivative or pharmaceutically acceptable salt of claim 1, wherein:
X is $CR^{4a}$, wherein $R^{4a}$ is H or C1-C6 alkyl.

6. The compound, stereoisomer, tautomer, hydrate, N-oxide derivative or pharmaceutically acceptable salt of claim 1, wherein:
X is $CR^{4a}$, wherein $R^{4a}$ is as defined in claim 1;
Y is $CR^5$, wherein $R^5$ is selected from H, halo, C1-C6 alkyl, C3-C6 cycloalkyl, optionally halo-substituted phenyl, optionally halo-substituted benzyl, pyridinyl, pyrazole, imidazole, CH2OH, NR'R", C(O)OR', C(O)NR'R", and OR', wherein R' and R" are independently selected from C1-C6 alkyl, and phenyl, benzyl, pyridinyl, pyrazole, and imidazole;
Z is $CR^7$, wherein $R^7$ is as defined in claim 1;
M is CH;
and the ring including X, Y and Z is aliphatic or aromatic.

7. The compound, stereoisomer, tautomer, hydrate, N-oxide derivative or pharmaceutically acceptable salt according to claim 1 wherein:
Z is $CR^7$ and $R^7$ is selected from NS(O)R$^c$R$^d$, S(O)(R$^c$)NR$^d$, SO2R$^c$, and SR$^c$, wherein R$^c$ is H or methyl;
and wherein R$^d$ is selected from H, C1-C6 alkyl, C5-C6 aryl, C6-C9 arylalkyl, C3-C6 heteroaryl, CN, COOH, or COCH3.

8. A compound according to formula (I) selected from:
N-Benzyl-4-((4-(2-fluorophenyl)-6-oxopyrimidin-1(6H)-yl)methyl)-4-hydroxy-N-methylpiperidine-1-carboxamide N-(Cyclohexylmethyl)-10-((5-(dimethylcarbamoyl)-2-oxo-4-phenylpyridin-1(2H)-yl)methyl)-10-hydroxy-N-methyl-7-azaspiro[4.5]decane-7-carboxamide N-Benzyl-10-((5-(dimethylcarbamoyl)-2-oxo-4-phenylpyridin-1(2H)-yl)methyl)-10-hydroxy-7-azaspiro[4.5]decane-7-carboxamide 10-((5-(Dimethylcarbamoyl)-2-oxo-4-phenylpyridin-1(2H)-yl)methyl)-10-hydroxy-N,N-dimethyl-7-azaspiro[4.5]decane-7-carboxamide N-Benzyl-10-((5-(dimethylcarbamoyl)-2-oxo-4-phenylpyridin-1(2H)-yl)methyl)-10-hydroxy-N-methyl-7-azaspiro[4.5]decane-7-carboxamide 1-((10-Hydroxy-7-(3-(trifluoromethyl)pyrrolidine-1-carbonyl)-7-azaspiro[4.5]decan-10-yl)methyl)-N,N-dimethyl-6-oxo-4-phenyl-1,6-dihydropyridine-3-carboxamide N-Cyclohexyl-10-((5-(dimethylcarbamoyl)-2-oxo-4-phenylpyridin-1(2H)-yl)methyl)-10-hydroxy-N-methyl-7-azaspiro[4.5]decane-7-carboxamide 1-((10-Hydroxy-7-((R)-3-phenylmorpholine-4-carbonyl)-7-azaspiro[4.5]decan-10-yl)methyl)pyrazin-2(1H)-one 1-((10-Hydroxy-7-((R)-2-phenylpiperazine-1-carbonyl)-7-azaspiro[4.5]decan-10-yl)methyl)pyrazin-2(1H)-one 1-((10-Hydroxy-7-((R)-2-phenylpiperazine-1-carbonyl)-7-azaspiro[4.5]decan-10-yl)methyl)-5-methylpyrazin-2(1H)-one 1-((10-Hydroxy-7-((R)-2-phenylpiperazine-1-carbonyl)-7-azaspiro[4.5]decan-10-yl)methyl)-3-methylpyrazin-2(1H)-one 10-((4-Benzoyl-2-oxopiperazin-1-yl)methyl)-N-benzyl-10-hydroxy-7-azaspiro[4.5]decane-7-carboxamide N-Benzyl-10-hydroxy-10-((2-oxo-4-phenylpiperazin-1-yl)methyl)-7-azaspiro[4.5]decane-7-carboxamide 10-((4-Acetyl-2-oxopiperazin-1-yl)methyl)-N-benzyl-10-hydroxy-7-azaspiro[4.5]decane-7-carboxamide N-Benzyl-10-((4-(4,4-dimethylcyclohexyl)-2-oxopiperazin-1-yl)methyl)-10-hydroxy-7-azaspiro[4.5]decane-7-carboxamide 4-((10-Hydroxy-7-((R)-3-phenylmorpholine-4-carbonyl)-7-azaspiro[4.5]decan-10-yl)methyl)morpholin-3-one 4-((10-Hydroxy-7-((R)-2-phenylpiperazine-1-carbonyl)-7-azaspiro[4.5]decan-10-yl)methyl)morpholin-3-one 7-((10-Hydroxy-7-((R)-2-phenylpiperazine-1-carbonyl)-7-azaspiro[4.5]decan-10-yl)methyl)-7,8-dihydroimidazo[1,2-a]pyrazin-6(5H)-one 6-Fluoro-3-((10-Hydroxy-7-((R)-3-phenylmorpholine-4-carbonyl)-7-azaspiro[4.5]decan-10-yl)methyl)quinazolin-4(3H)-one 6,7-Difluoro-3-((10-hydroxy-7-((R)-3-phenylmorpholine-4-carbonyl)-7-azaspiro[4.5]decan-10-yl)methyl)quinazolin-4(3H)-one 2-((10-Hydroxy-7-((R)-3-phenylmorpholine-4-carbonyl)-7-azaspiro[4.5]decan-10-yl)methyl)-2,7-naphthyridin-1(2H)-one 1-Benzyl-5-((10-hydroxy-7-((R)-3-phenylmorpholine-4-carbonyl)-7-azaspiro[4.5]decan-10-yl)methyl)-1,5-dihydro-4H-pyrazolo[3,4-d]pyrimidin-4-one 6-Fluoro-3-((10-hydroxy-7-((R)-2-phenylpiperazine-1-carbonyl)-7-azaspiro[4.5]decan-10-yl)methyl)quinazolin-4(3H)-one 6,7-Difluoro-3-((10-hydroxy-7-((R)-2-phenylpiperazine-1-carbonyl)-7-azaspiro[4.5]decan-10-yl)methyl)quinazolin-4(3H)-one 2-((10-Hydroxy-7-((R)-2-phenylpiperazine-1-carbonyl)-7-azaspiro[4.5]decan-10-yl)methyl)-2,7-naphthyridin-1(2H)-one 1-Benzyl-5-((10-hydroxy-7-((R)-2-phenylpiperazine-1-carbonyl)-7-azaspiro[4.5]decan-10-yl)methyl)-1,5-dihydro-4H-pyrazolo[3,4-d]pyrimidin-4-one 2-((10-Hydroxy-7-((R)-2-phenylpiperazine-1-carbonyl)-7-azaspiro[4.5]decan-10-yl)methyl)-1-methyl-1,2-dihydro-3H-pyrazolo[3,4-d]pyrimidin-3-one 5-((10-Hydroxy-7-((R)-2-phenylpiperazine-1-carbonyl)-7-azaspiro[4.5]decan-10-yl)methyl)-1-phenyl-1,5-dihydro-4H-pyrazolo[3,4-d]pyrimidin-4-one 6-((10-Hydroxy-7-((R)-2-phenylpiperazine-1-carbonyl)-7-azaspiro[4.5]decan-10-yl)methyl)-2-methyl-2,6-dihydro-7H-pyrazolo[4,3-d]pyrimidin-7-one 5-((10-Hydroxy-7-((R)-2-phenylpiperazine-1-carbonyl)-7-azaspiro[4.5]decan-10-yl)methyl)-1-methyl-1,5-dihydro-4H-pyrazolo[3,4-d]pyrimidin-4-one 1-Cyclopropyl-5-((10-hydroxy-7-((R)-2-phenylpiperazine-1-carbonyl)-7-azaspiro[4.5]decan-10-yl)methyl)-1,5-dihydro-4H-pyrazolo[3,4-d]pyrimidin-4-one 6-(((S)-10-Hydroxy-7-((R)-2-phenylpiperazine-1-carbonyl)-7-azaspiro[4.5]decan-10-yl)methyl)-2-(methylthio)pyrido[4,3-d]pyrimidin-5(6H)-one 6-(((S)-10-Hydroxy-7-((R)-2-phenylpiperazine-1-carbonyl)-7-azaspiro[4.5]decan-10-yl)methyl)pyrido[4,3-d]pyrimidin-5(6H)-one 1-((10-Hydroxy-7-((R)-2-phenylpiperazine-1-carbonyl)-7-azaspiro[4.5]decan-10-yl)methyl)-5-(methylthio)-4-phenylpyridin-2(1H)-one 1-((10-Hydroxy-7-((R)-2-phenylpiperazine-1-carbonyl)-7-azaspiro[4.5]decan-10-yl)methyl)-5-(methylsulfinyl)-4-phenylpyridin-2(1H)-one 1-((10-Hydroxy-7-((R)-2-phenylpiperazine-1-carbonyl)-7-azaspiro[4.5]decan-10-yl)methyl)-5-(methylsulfonyl)-4-phenylpyridin-2(1H)-one 1-((10-Hydroxy-7-((R)-2-phenylpiperazine-1-carbonyl)-7-azaspiro[4.5]decan-10-yl)methyl)-5-(S-methylsulfonimidoyl)-4-phenylpyridin-2(1H)-one 1-((10-Hydroxy-7-((R)-3-phenylmorpholine-4-carbonyl)-7-azaspiro[4.5]decan-10-yl)methyl)-5-(S-methylsulfonimidoyl)-4-phenylpyridin-2(1H)-one 5-((Dimethyl(oxo)-$\lambda^6$-sulfaneylidene)amino)-1-((10-hydroxy-7-((R)-2-phenylpiperazine-1-carbonyl)-7-azaspiro[4.5]decan-10-yl)methyl)-4-phenylpyridin-2(1H)-one N-Benzyl-10-hydroxy-10-((2-oxo-4-phenylpyridin-1(2H)-yl)methyl)-7-azaspiro[4.5]decane-7-carboxamide N-Benzyl-10-hydroxy-10-((6-oxo-4-phenylpyrimidin-1(6H)-yl)methyl)-7-azaspiro[4.5]decane-7-carboxamide N-Benzyl-8-((4-(2-fluorophenyl)-6-oxopyrimidin-1(6H)-yl)methyl)-8-hydroxy-5-azaspiro[2.5]octane-5-carboxamide N-Benzyl-4-((4-(2-fluorophenyl)-6-oxopyrimidin-1(6H)-yl)methyl)-4-hydroxy-3,3-dimethylpiperidine-1-carboxamide 10-Hydroxy-10-((6-oxo-4-phenylpyrimidin-1(6H)-yl)methyl)-N-(2,2,2-trifluoroethyl)-7-azaspiro[4.5]decane-7-carboxamide 10-Hydroxy-10-((6-oxo-4-phenylpyrimidin-1(6H)-yl)methyl)-N-(pyridin-2-ylmethyl)-7-azaspiro[4.5]decane-7-carboxamide N-Benzyl-10-((4-chloro-6-oxopyrimidin-1(6H)-yl)methyl)-10-hydroxy-7-azaspiro[4.5]decane-7-carboxamide 10-Hydroxy-10-((6-oxo-4-phenylpyrimidin-1(6H)-yl)methyl)-N-(pyridin-3-ylmethyl)-7-azaspiro[4.5]decane-7-carboxamide N-Benzyl-10-hydroxy-10-((6-oxo-4-(pyridin-3-yl)pyrimidin-1(6H)-yl)methyl)-7-azaspiro[4.5]decane-7-carboxamide N-Benzyl-10-hydroxy-10-((6-oxo-4-(pyridin-4-yl)pyrimidin-1(6H)-yl)methyl)-7-azaspiro[4.5]decane-7-carboxamide N-Benzyl-10-hydroxy-10-((6-oxo-4-(pyrrolidin-1-yl)pyrimidin-1(6H)-yl)methyl)-7-azaspiro[4.5]decane-7-carboxamide N-Benzyl-10-hydroxy-10-((4-morpholino-6-oxopyrimidin-1(6H)-yl)methyl)-7-azaspiro[4.5]decane-7-carboxamide N-Benzyl-10-hydroxy-10-((4-(1-methyl-1H-pyrazol-4-yl)-6-oxopyrimidin-1(6H)-yl)methyl)-7-azaspiro[4.5]decane-7-carboxamide N-Benzyl-10-hydroxy-10-((4-(1-methyl-1H-pyrazol-5-yl)-6-oxopyrimidin-1(6H)-yl)methyl)-7-azaspiro[4.5]decane-7-carboxamide 3-((10-Hydroxy-7-(2-(trifluoromethyl)pyrrolidine-1-carbonyl)-7-azaspiro[4.5]decan-10-yl)methyl)-6-phenylpyrimidin-4(3H)-one 3-((10-Hydroxy-7-((R)-2-methylpiperazine-1-carbonyl)-7-azaspiro[4.5]decan-10-yl)methyl)-6-phenylpyrimidin-4(3H)-one 3-((10-Hydroxy-7-(2-isopropylpiperazine-1-carbonyl)-7-azaspiro[4.5]decan-10-yl)methyl)-6-phenylpyrimidin-4(3H)-one 3-((7-(3-Azabicyclo[3.1.0]hexane-3-carbonyl)-10-hydroxy-7-azaspiro[4.5]decan-10-yl)methyl)-6-phenylpyrimidin-4(3H)-one 3-(((S)-10-Hydroxy-7-((S)-2-phenylpiperazine-1-carbonyl)-7-azaspiro[4.5]decan-10-yl)methyl)-6-phenylpyrimidin-4(3H)-one 3-(((S)-10-Hydroxy-7-((R)-3-phenylmorpholine-4-carbonyl)-7-azaspiro[4.5]decan-10-yl)methyl)-6-phenylpyrimidin-4(3H)-one 3-(((S)-10-Hydroxy-7-((S)-3-phenylmorpholine-4-carbonyl)-7-azaspiro[4.5]decan-10-yl)methyl)-6-phenylpyrimidin-4(3H)-one 3-(((S)-10-Hydroxy-7-((S)-2-phenylpyrrolidine-1-carbonyl)-7-azaspiro[4.5]decan-10-yl)methyl)-6-phenylpyrimidin-4(3H)-one (S)-10-Hydroxy-10-((6-oxo-4-phenylpyrimidin-1(6H)-yl)methyl)-N-(thiophen-2-ylmethyl)-7-azaspiro[4.5]decane-7-carboxamide (S)-N-(4-Cyanobenzyl)-10-hydroxy-10-((6-oxo-4-phenylpyrimidin-1(6H)-yl)methyl)-7-azaspiro[4.5]decane-7-carboxamide (S)-N-(3-Fluorobenzyl)-10-hydroxy-10-((6-oxo-4-phenylpyrimidin-1(6H)-yl)methyl)-7-azaspiro[4.5]decane-7-carboxamide (S)-N-(Benzo[d][1,3]dioxol-5-ylmethyl)-10-hydroxy-10-((6-oxo-4-phenylpyrimidin-1(6H)-yl)methyl)-7-azaspiro[4.5]decane-7-carboxamide (S)-N-((5-Cyclopropyl-1,2,4-oxadiazol-3-yl)methyl)-10-hydroxy-10-((6-oxo-4-phenylpyrimidin-1 (6H)-yl)methyl)-7-azaspiro[4.5]decane-7-carboxamide (S)-N-(Furan-2-ylmethyl)-10-hydroxy-10-((6-oxo-4-phenylpyrimidin-1(6H)-yl)methyl)-7-azaspiro[4.5]decane-7-carboxamide 6-Chloro-3-(((S)-10-hydroxy-7-((R)-3-phenylmorpholine-4-carbonyl)-7-azaspiro[4.5]decan-10-yl)methyl)pyrimidin-4(3H)-one (S)-3-((10-Hydroxy-7-(3-(trifluoromethyl)azetidine-1-carbonyl)-7-azaspiro[4.5]decan-10-yl)methyl)-6-phenylpyrimidin-4(3H)-one 6-Cyclopropyl-3-(((S)-10-hydroxy-7-((R)-3-phenylmorpholine-4-carbonyl)-7-azaspiro[4.5]decan-10-yl)methyl)pyrimidin-4(3H)-one 3-(((S)-10-Hydroxy-7-((R)-3-phenylmorpholine-4-carbonyl)-7-azaspiro[4.5]decan-10-yl)methyl)-6-(pyrrolidin-1H)pyrimidin-4(3H)-one 3-(((S)-10-Hydroxy-7-((R)-3-phenylmorpholine-4-carbonyl)-7-azaspiro[4.5]decan-10-yl)methyl)-6-(1-methyl-1H-pyrazol-5-yl)pyrimidin-4(3H)-one 3-(((S)-10-Hydroxy-7-((R)-3-phenylmorpholine-4-carbonyl)-7-azaspiro[4.5]decan-10-yl)methyl)-6-(1-methyl-1H-pyrazol-4-yl)pyrimidin-4(3H)-one 6-(Dimethylamino)-3-(((S)-10-hydroxy-7-((R)-3-phenylmorpholine-4-carbonyl)-7-azaspiro[4.5]decan-10-yl)methyl)pyrimidin-4(3H)-one 3-(((10S)-10-Hydroxy-7-(3-(trifluoromethyl)pyrrolidine-1-carbonyl)-7-azaspiro[4.5]decan-10-yl)methyl)-6-phenylpyrimidin-4(3H)-one 3-(((S)-7-((R)-3-(4-Fluorophenyl)morpholine-4-carbonyl)-10-hydroxy-7-azaspiro[4.5]decan-10-yl)methyl)-6-phenylpyrimidin-4(3H)-one 3-((7-(3-(Cyclopropylmethyl)morpholine-4-carbonyl)-10-hydroxy-7-azaspiro[4.5]decan-10-yl)methyl)-6-phenylpyrimidin-4(3H)-one 3-((7-(3-Cyclobutylmorpholine-4-carbonyl)-10-hydroxy-7-azaspiro[4.5]decan-10-yl)methyl)-6-phenylpyrimidin-4(3H)-one 3-((10-Hydroxy-7-(3-(methoxymethyl)morpholine-4-carbonyl)-7-azaspiro[4.5]decan-10-yl)methyl)-6-phenylpyrimidin-4(3H)-one N-(Furan-3-ylmethyl)-10-hydroxy-N-methyl-10-((6-oxo-4-phenylpyrimidin-1(6H)-yl)methyl)-7-azaspiro[4.5]decane-7-carboxamide 3-((10-Hydroxy-7-(2-methylpyrrolidine-1-carbonyl)-7-azaspiro[4.5]decan-10-yl)methyl)-6-phenylpyrimidin-4(3H)-one N-Cyclobutyl-10-hydroxy-N-methyl-10-((6-oxo-4-phenylpyrimidin-1(6H)-yl)methyl)-7-azaspiro[4.5]decane-7-carboxamide 3-((10-Hydroxy-7-(3-(thiophen-2-yl)morpholine-4-carbonyl)-7-azaspiro[4.5]decan-10-yl)methyl)-6-phenylpyrimidin-4(3H)-one 3-((10-Hydroxy-7-(6-oxa-1-azaspiro[3.4]octane-1-carbonyl)-7-azaspiro[4.5]decan-10-yl)methyl)-6-phenylpyrimidin-4(3H)-one 3-((7-(3-Cyclopropylpyrrolidine-1-carbonyl)-10-hydroxy-7-azaspiro[4.5]decan-10-yl)methyl)-6-phenylpyrimidin-4(3H)-one 10-Hydroxy-N-(isothiazol-5-ylmethyl)-N-methyl-10-((6-oxo-4-phenylpyrimidin-1(6H)-yl)methyl)-7-azaspiro[4.5]decane-7-carboxamide N-((3-Fluorocyclobutyl)methyl)-10-hydroxy-N-methyl-10-((6-oxo-4-phenylpyrimidin-1(6H)-yl)methyl)-7-azaspiro[4.5]decane-7-carboxamide 3-((7-(2,2-Dimethylpyrrolidine-1-carbonyl)-10-hydroxy-7-azaspiro[4.5]decan-10-yl)methyl)-6-phenylpyrimidin-4(3H)-one 3-((7-(4-(Difluoromethyl)piperidine-1-carbonyl)-10-hydroxy-7-azaspiro[4.5]decan-10-yl)methyl)-6-phenylpyrimidin-4(3H)-one N-(Furan-2-ylmethyl)-10-hydroxy-N-methyl-10-((6-oxo-4-phenylpyrimidin-1(6H)-yl)methyl)-7-azaspiro[4.5]decane-7-carboxamide 3-((7-(2-Oxa-5-azabicyclo[4.1.0]heptane-5-carbonyl)-10-hydroxy-7-azaspiro[4.5]decan-10-yl)methyl)-6-phenylpyrimidin-4(3H)-one 10-Hydroxy-N-methyl-10-((6-oxo-4-phenylpyrimidin-1(6H)-yl)methyl)-N-(pyridin-3-ylmethyl)-7-azaspiro[4.5]decane-7-carboxamide 3-((10-Hydroxy-7-(2-(pyridin-3-yl)pyrrolidine-1-carbonyl)-7-azaspiro[4.5]decan-10-yl)methyl)-6-phenylpyrimidin-4(3H)-one 3-((7-(3-(1H-Pyrrol-1-yl)pyrrolidine-1-carbonyl)-10-hydroxy-7-azaspiro[4.5]decan-10-yl)methyl)-6-phenylpyrimidin-4(3H)-one N-(1-Cyclopropylethyl)-10-hydroxy-N-methyl-10-((6-oxo-4-phenylpyrimidin-1(6H)-yl)methyl)-7-azaspiro[4.5]decane-7-carboxamide 3-((7-(3-Cyclopropylmorpholine-4-carbonyl)-10-hydroxy-7-azaspiro[4.5]decan-10-yl)methyl)-6-phenylpyrimidin-4(3H)-one 3-((10-Hydroxy-7-(2-(pyridin-4-yl)pyrrolidine-1-carbonyl)-7-azaspiro[4.5]decan-10-yl)methyl)-6-phenylpyrimidin-4(3H)-one 3-((10-Hydroxy-7-(5-azaspiro[2.5]octane-5-carbonyl)-7-azaspiro[4.5]decan-10-yl)methyl)-6-phenylpyrimidin-4(3H)-one N-(3-Cyanobenzyl)-10-hydroxy-N-methyl-10-((6-oxo-4-phenylpyrimidin-1(6H)-yl)methyl)-7-azaspiro[4.5]decane-7-carboxamide 3-((7-(3-Cyclopropylazetidine-1-carbonyl)-10-hydroxy-7-azaspiro[4.5]decan-10-yl)methyl)-6-phenylpyrimidin-4(3H)-one 3-((7-(2,2-Difluoromorpholine-4-carbonyl)-10-hydroxy-7-azaspiro[4.5]decan-10-yl)methyl)-6-phenylpyrimidin-4(3H)-one N-(2-Fluorobenzyl)-10-hydroxy-10-((6-oxo-4-phenylpyrimidin-1(6H)-yl)methyl)-7-azaspiro[4.5]decane-7-carboxamide N-(1-(Furan-3-yl)ethyl)-10-hydroxy-10-((6-oxo-4-phenylpyrimidin-1(6H)-yl)methyl)-7-azaspiro[4.5]decane-7-carboxamide 10-Hydroxy-N-((1-methylcyclopropyl)methyl)-10-((6-oxo-4-phenylpyrimidin-1(6H)-yl)methyl)-7-azaspiro[4.5]decane-7-carboxamide N-(3-Cyanobenzyl)-10-hydroxy-10-((6-oxo-4-phenylpyrimidin-1(6H)-yl)methyl)-7-azaspiro[4.5]decane-7-carboxamide N-(4-(Cyanomethyl)benzyl)-10-hydroxy-10-((6-oxo-4-phenylpyrimidin-1(6H)-yl)methyl)-7-azaspiro[4.5]decane-7-carboxamide N-((5,6-Dihydro-2H-pyran-3-yl)methyl)-10-hydroxy-10-((6-oxo-4-phenylpyrimidin-1(6H)-yl)methyl)-7-azaspiro[4.5]decane-7-carboxamide N-((1,3-Dihydroisobenzofuran-5-yl)methyl)-10-hydroxy-10-((6-oxo-4-phenylpyrimidin-1(6H)-yl)methyl)-7-azaspiro[4.5]decane-7-carboxamide 3-((10-Hydroxy-7-(4-oxa-1-azaspiro[5.5]undecane-1-carbonyl)-7-azaspiro[4.5]decan-10-yl)methyl)-6-phenylpyrimidin-4(3H)-one 3-((7-(3-(Difluoromethyl)pyrrolidine-1-carbonyl)-10-hydroxy-7-azaspiro[4.5]decan-10-yl)methyl)-6-phenylpyrimidin-4(3H)-one 3-((10-Hydroxy-7-(3-(trifluoromethyl)morpholine-4-carbonyl)-7-azaspiro[4.5]decan-10-yl)methyl)-6-phenylpyrimidin-4(3H)-one 3-((7-(2-Cyclopropylpyrrolidine-1-carbonyl)-10-hydroxy-7-azaspiro[4.5]decan-10-yl)methyl)-6-phenylpyrimidin-4(3H)-one 3-((10-Hydroxy-7-((S)-2-(isoxazol-3-yl)pyrrolidine-1-carbonyl)-7-azaspiro[4.5]decan-10-yl)methyl)-6-phenylpyrimidin-4(3H)-one (2S)-1-(10-Hydroxy-10-((6-oxo-4-phenylpyrimidin-1(6H)-yl)methyl)-7-azaspiro[4.5]decane-7-carbonyl)-N,N-dimethylpyrrolidine-2-carboxamide 3-((10-Hydroxy-7-((S)-2-(thiophen-2-ylmethyl)pyrrolidine-1-carbonyl)-7-azaspiro[4.5]decan-10-yl)methyl)-6-phenylpyrimidin-4(3H)-one 3-((7-((S)-2-(1H-1,2,4-Triazol-5-yl)pyrrolidine-1-carbonyl)-10-hydroxy-7-azaspiro[4.5]decan-10-yl)methyl)-6-phenylpyrimidin-4(3H)-one 3-((10-Hydroxy-7-((S)-2-(5-methyl-1H-1,2,4-triazol-3H)pyrrolidine-1-carbonyl)-7-azaspiro[4.5]decan-10-yl)methyl)-6-phenylpyrimidin-4(3H)-one 3-((10-Hydroxy-7-((S)-2-(4-isopropyloxazol-2-yl)pyrrolidine-1-carbonyl)-7-azaspiro[4.5]decan-10-yl)methyl)-6-phenylpyrimidin-4(3H)-one 3-((10-Hydroxy-7-(2-(2-methoxyphenyl)piperazine-1-carbonyl)-7-azaspiro[4.5]decan-10-yl)methyl)-6-phenylpyrimidin-4(3H)-one 3-((10-Hydroxy-7-(2-(3-methoxyphenyl)piperazine-1-carbonyl)-7-azaspiro[4.5]decan-10-yl)methyl)-6-phenylpyrimidin-4(3H)-one 3-((10-Hydroxy-7-(2-(4-methoxyphenyl)piperazine-1-carbonyl)-7-azaspiro[4.5]decan-10-yl)methyl)-6-phenylpyrimidin-4(3H)-one 3-((10-Hydroxy-7-(2-(pyridin-3-yl)piperazine-1-carbonyl)-7-azaspiro[4.5]decan-10-yl)methyl)-6-phenylpyrimidin-4(3H)-one 3-((7-(2-Cyclopropylpiperazine-1-carbonyl)-10-hydroxy-7-azaspiro[4.5]decan-10-yl)methyl)-6-phenylpyrimidin-4(3H)-one 3-((7-(2-Cyclobutylpiperazine-1-carbonyl)-10-hydroxy-7-azaspiro[4.5]decan-10-yl)methyl)-6-phenylpyrimidin-4(3H)-one 3-((10-Hydroxy-7-(2-(methoxymethyl)piperazine-1-carbonyl)-7-azaspiro[4.5]decan-10-yl)methyl)-6-phenylpyrimidin-4(3H)-one 3-(((S)-10-Hydroxy-7-((R)-2-phenylpiperazine-1-carbonyl)-7-azaspiro[4.5]decan-10-yl)methyl)-6-phenylpyrimidin-4(3H)-one 3-(((S)-7-((R)-4-Acetyl-2-phenylpiperazine-1-carbonyl)-10-hydroxy-7-azaspiro[4.5]decan-10-yl)methyl)-6-phenylpyrimidin-4(3H)-one 2-((10-Hydroxy-7-((R)-3-phenylmorpholine-4-carbonyl)-7-azaspiro[4.5]decan-10-yl)methyl)-5-phenylpyridazin-3(2H)-one 3-(((S)-10-Hydroxy-7-((R)-4-methyl-2-phenylpiperazine-1-carbonyl)-7-azaspiro[4.5]decan-10-yl)methyl)-6-phenylpyrimidin-4(3H)-one 6-Chloro-3-(((S)-7-((R)-3-(4-fluorophenyl)morpholine-4-carbonyl)-10-hydroxy-7-azaspiro[4.5]decan-10-yl)methyl)pyrimidin-4(3H)-one 1-(((S)-4-Hydroxy-3,3-dimethyl-1-((R)-3-phenylmorpholine-4-carbonyl)piperidin-4Il)methyl)-N,N-dimethyl-6-oxo-4-phenyl-1,6-dihydropyridine-3-carboxamide 3-(((S)-7-((R)-3-(4-Fluorophenyl)morpholine-4-carbonyl)-10-hydroxy-7-azaspiro[4.5]decan-10-yl)methyl)-6-(1-methyl-1H-pyrazol-5-yl)pyrimidin-4(3H)-one 3-(((S)-7-((R)-3-(4-Fluorophenyl)morpholine-4-carbonyl)-10-hydroxy-7-azaspiro[4.5]decan-10-yl)methyl)-6-(1-methyl-1H-pyrazol-4-yl)pyrimidin-4(3H)-one 1-(((S)-4-Hydroxy-3,3-dimethyl-1-((R)-3-phenylmorpholine-4-carbonyl)piperidin-4-yl)methyl)-4-phenylpyridin-2(1H)-one 1-(((S)-10-Hydroxy-7-((R)-2-phenylpiperazine-1-carbonyl)-7-azaspiro[4.5]decan-10-yl)methyl)-4-phenylpyridin-2(1H)-one 1-(((S)-4-Hydroxy-3,3-dimethyl-1-((R)-2-phenylpiperazine-1-carbonyl)piperidin-4-yl)methyl)-4-phenylpyridin-2(1H)-one 3-(((S)-10-Hydroxy-7-((R)-2-phenylpiperazine-1-carbonyl)-7-azaspiro[4.5]decan-10-yl)methyl)-6-(1-methyl-1H-pyrazol-5-yl)pyrimidin-4(3H)-one 3-(((S)-10-Hydroxy-7-((R)-2-phenylpiperazine-1-carbonyl)-7-azaspiro[4.5]decan-10-yl)methyl)-6-(pyrrolidin-1-yl)pyrimidin-4(3H)-one 3-(((S)-10-Hydroxy-7-((R)-2-phenylpiperazine-1-carbonyl)-7-azaspiro[4.5]decan-10-yl)methyl)-6-(1-methyl-1H-pyrazol-4-yl)pyrimidin-4(3H)-one 6-Cyclopropyl-3-(((S)-10-hydroxy-7-((R)-2-phenylpiperazine-1-carbonyl)-7-azaspiro[4.5]decan-10-yl)methyl)pyrimidin-4(3H)-one 3-(((S)-7-((R)-3-(1H-Benzo[d]imidazol-2-yl)morpholine-4-carbonyl)-10-hydroxy-7-azaspiro[4.5]decan-10-yl)methyl)-6-phenylpyrimidin-4(3H)-one (S)-10-Hydroxy-10-((6-oxo-4-phenylpyrimidin-1(6H)-yl)methyl)-N-((R)-2,2,2-trifluoro-1-phenylethyl)-7-azaspiro[4.5]decane-7-carboxamide (R)-3-((4-Hydroxy-1-(3-phenylmorpholine-4-carbonyl)piperidin-4-yl)methyl)-6-phenylpyrimidin-4(3H)-one 3-((5-Hydroxy-2-((R)-3-phenylmorpholine-4-carbonyl)-2-azaspiro[5.5]undecan-5-yl)methyl)-6-phenylpyrimidin-4(3H)-one (R)-3-((4-Hydroxy-1-(2-phenylpiperazine-1-carbonyl)piperidin-4-yl)methyl)-6-phenylpyrimidin-4(3H)-one 3-((5-Hydroxy-2-((R)-2-phenylpiperazine-1-carbonyl)-2-azaspiro[5.5]undecan-5-yl)methyl)-6-phenylpyrimidin-4(3H)-one (S)-3-((10-Hydroxy-7-(2-phenylpyrazolidine-1-carbonyl)-7-azaspiro[4.5]decan-10-yl)methyl)-6-phenylpyrimidin-4(3H)-one 3-(((S)-10-Hydroxy-7-((R)-2-phenylpiperazine-1-carbonyl)-7-azaspiro[4.5]decan-10-yl)methyl)-6-methylpyrimidin-4(3H)-one (S)-N-(2,3-Difluorobenzyl)-10-hydroxy-10-((6-oxo-4-phenylpyrimidin-1(6H)-yl)methyl)-7-azaspiro[4.5]decane-7-carboxamide (S)-N-(2,6-Difluorobenzyl)-10-hydroxy-10-((6-oxo-4-phenylpyrimidin-1(6H)-yl)methyl)-7-azaspiro[4.5]decane-7-carboxamide (S)-N-(2,4-Difluorobenzyl)-10-hydroxy-10-((6-oxo-4-phenylpyrimidin-1(6H)-yl)methyl)-7-azaspiro[4.5]decane-7-carboxamide (S)-N-(3,4-Difluorobenzyl)-10-hydroxy-10-((6-oxo-4-phenylpyrimidin-1(6H)-yl)methyl)-7-azaspiro[4.5]decane-7-carboxamide 3-((9-Hydroxy-6-((R)-3-phenylmorpholine-4-carbonyl)-6-azaspiro[3.5]nonan-9-yl)methyl)-6-phenylpyrimidin-4(3H)-one 3-((9-Hydroxy-6-((R)-2-phenylpiperazine-1-carbonyl)-6-azaspiro[3.5]nonan-9-yl)methyl)-6-phenylpyrimidin-4(3H)-one (S)-N-((3,3-Difluorocyclobutyl)methyl)-10-hydroxy-10-((6-oxo-4-phenylpyrimidin-1(6H)-yl)methyl)-7-azaspiro[4.5]decane-7-carboxamide (S)-N-(1,1,1,3,3,3-Hexafluoropropan-2-yl)-10-hydroxy-10-((6-oxo-4-phenylpyrimidin-1(6H)-yl)methyl)-7-azaspiro[4.5]decane-7-carboxamide (S)-10-Hydroxy-10-((2-oxo-4-phenylpyridin-1(2H)-yl)methyl)-N-((R)-2,2,2-trifluoro-1-phenylethyl)-7-azaspiro[4.5]decane-7-carboxamide 3-(((S)-4-Hydroxy-3,3-dimethyl-1-((R)-3-phenylmorpholine-4-carbonyl)piperidin-4-yl)methyl)-6-phenylpyrimidin-4(3H)-one (S)-N-((1-Fluorocyclopropyl)methyl)-10-hydroxy-10-((6-oxo-4-phenylpyrimidin-1(6H)-yl)methyl)-7-azaspiro[4.5]decane-7-carboxamide (S)-N-((1-Fluorocyclobutyl)methyl)-10-hydroxy-10-((6-oxo-4-phenylpyrimidin-1(6H)-yl)methyl)-7-azaspiro[4.5]decane-7-carboxamide (S)-N-(Cyclopropylmethyl)-10-hydroxy-N-methyl-10-((6-oxo-4-phenylpyrimidin-1(6H)-yl)methyl)-7-azaspiro[4.5]decane-7-carboxamide 6-(2-Fluorophenyl)-3-(((S)-10-hydroxy-7-((R)-2-phenylpiperazine-1-carbonyl)-7-azaspiro[4.5]decan-10-yl)methyl)pyrimidin-4(3H)-one 6-(3-Fluorophenyl)-3-(((S)-10-hydroxy-7-((R)-2-phenylpiperazine-1-carbonyl)-7-azaspiro[4.5]decan-10-yl)methyl)pyrimidin-4(3H)-one 6-(4-Fluorophenyl)-3-(((S)-10-hydroxy-7-((R)-2-phenylpiperazine-1-carbonyl)-7-azaspiro[4.5]decan-10-yl)methyl)pyrimidin-4(3H)-one 3-(((S)-10-Hydroxy-7-((R)-2-phenylpiperazine-1-carbonyl)-7-azaspiro[4.5]decan-10-yl)methyl)-6-(2-methoxyphenyl)pyrimidin-4(3H)-one 6-(Dimethylamino)-3-(((S)-10-hydroxy-7-((R)-2-phenylpiperazine-1-carbonyl)-7-azaspiro[4.5]decan-10-yl)methyl)pyrimidin-4(3H)-one 3-(((S)-10-Hydroxy-7-((R)-2-phenylpiperazine-1-carbonyl)-7-azaspiro[4.5]decan-10-yl)methyl)-6-(methylamino)pyrimidin-4(3H)-one 3-(((S)-7-((R)-2-(3-Fluorophenyl)piperazine-1-carbonyl)-10-hydroxy-7-azaspiro[4.5]decan-10-yl)methyl)-6-phenylpyrimidin-4(3H)-one 3-((5-Hydroxy-2-((R)-2-phenylpiperazine-1-carbonyl)-9-oxa-2-azaspiro[5.5]undecan-5-yl)methyl)-6-phenylpyrimidin-4(3H)-one 3-(((S)-4-Hydroxy-3,3-dimethyl-1-((R)-2-phenylpiperazine-1-carbonyl)piperidin-4-yl)methyl)-6-phenylpyrimidin-4(3H)-one 3-(((S)-10-Hydroxy-7-((R)-2-phenyl-4-(2,2,2-trifluoroethyl)piperazine-1-carbonyl)-7-azaspiro[4.5]decan-10-yl)methyl)-6-phenylpyrimidin-4(3H)-one 3-(((S)-10-Hydroxy-7-((R)-2-phenylpiperazine-1-carbonyl)-7-azaspiro[4.5]decan-10-yl)methyl)-6-methoxypyrimidin-4(3H)-one 3-((5-Hydroxy-2-((R)-3-phenylmorpholine-4-carbonyl)-9-oxa-2-azaspiro[5.5]undecan-5-yl)methyl)-6-phenylpyrimidin-4(3H)-one 4-Chloro-1-(((S)-10-hydroxy-7-((R)-2-phenylpiperazine-1-carbonyl)-7-azaspiro[4.5]decan-10-yl)methyl)pyridin-2(1H)-one 4-Cyclopropyl-1-(((S)-10-hydroxy-7-((R)-2-phenylpiperazine-1-carbonyl)-7-azaspiro[4.5]decan-10-yl)methyl)pyridin-2(1H)-one 1-(((S)-10-Hydroxy-7-((R)-2-phenylpiperazine-1-carbonyl)-7-azaspiro[4.5]decan-10-yl)methyl)-4-(1-methyl-1H-pyrazol-5-yl)pyridin-2(1H)-one 1-(((S)-10-Hydroxy-7-((R)-2-phenylpiperazine-1-carbonyl)-7-azaspiro[4.5]decan-10-yl)methyl)-4-(1-methyl-1H-pyrazol-4-yl)pyridin-2(1H)-one 1-(((S)-10-Hydroxy-7-((R)-2-phenylpiperazine-1-carbonyl)-7-azaspiro[4.5]decan-10-yl)methyl)-4-(pyrrolidin-1-yl)pyridin-2(1H)-one 5-Fluoro-1-((10-hydroxy-7-((R)-2-phenylpiperazine-1-carbonyl)-7-azaspiro[4.5]decan-10-yl)methyl)-4-phenylpyridin-2(1H)-one 3-Fluoro-1-((10-hydroxy-7-((R)-2-phenylpiperazine-1-carbonyl)-7-azaspiro[4.5]decan-10-yl)methyl)-4-phenylpyridin-2(1H)-one (S)-3-((10-Hydroxy-7-(3-phenylthiomorpholine-4-carbonyl)-7-azaspiro[4.5]decan-10-yl)methyl)-6-phenylpyrimidin-4(3H)-one 3-(((10S)-10-Hydroxy-7-(1-imino-1-oxido-3-phenyl-1$\lambda^6$-thiomorpholine-4-carbonyl)-7-azaspiro[4.5]decan-10-yl)methyl)-6-phenylpyrimidin-4(3H)-one (S)-3-((7-(1,1-Dioxido-3-phenylthiomorpholine-4-carbonyl)-10-hydroxy-7-azaspiro[4.5]decan-10-yl)methyl)-6-phenylpyrimidin-4(3H)-one 3-(((10S)-10-Hydroxy-7-(2-(4-(trifluoromethyl)phenyl)piperazine-1-carbonyl)-7-azaspiro[4.5]decan-10-yl)methyl)-6-phenylpyrimidin-4(3H)-one, and 3-(((10S)-10-Hydroxy-7-(1-oxido-3-phenylthiomorpholine-4-carbonyl)-7-azaspiro[4.5]decan-10-yl)methyl)-6-phenylpyrimidin-4(3H)-one, or a stereoisomer, tautomer, hydrate, N-oxide derivative or pharmaceutically acceptable salt thereof.

9. A pharmaceutical composition comprising a compound according to claim 1 or a stereoisomer, tautomer, hydrate, N-oxide derivative or pharmaceutically acceptable salt thereof, and a pharmaceutically acceptable carrier or diluent.

10. The compound according to claim 1, wherein the compound of formula (I) is 3-(((S)-10-hydroxy-7-((R)-2-phenylpiperazine-1-carbonyl)-7-azaspiro[4.5]decan-10-yl)methyl)-6-phenylpyrimidin-4(3H)-one, or a stereoisomer, tautomer, hydrate, N-oxide derivative or pharmaceutically acceptable salt thereof.

11. The compound, stereoisomer, tautomer, hydrate, N-oxide derivative or pharmaceutically acceptable salt of claim 1, wherein:

$R^{4a}$ is H;

$R^5$ is Cl or phenyl optionally substituted with fluoro; and

Z is N or $CR^7$.

12. The compound, stereoisomer, tautomer, hydrate, N-oxide derivative or pharmaceutically acceptable salt of claim 4, wherein $R^2$ and $R^3$ are independently selected from H and methyl.

13. The compound, stereoisomer, tautomer, hydrate, N-oxide derivative or pharmaceutically acceptable salt of claim 4, wherein $R^2$ and $R^3$ together with the carbon to which they are attached form cyclohexyl, cyclopentyl or cyclobutyl.

14. The compound, stereoisomer, tautomer, hydrate, N-oxide derivative or pharmaceutically acceptable salt of claim 7, wherein X is CH, Y is $CR^5$, and wherein $R^5$ is phenyl or halo.

15. The compound, stereoisomer, tautomer, hydrate, N-oxide derivative or pharmaceutically acceptable salt of claim 14, wherein $R^5$ is Cl.

* * * * *